(12) United States Patent
Li et al.

(10) Patent No.: US 8,426,402 B2
(45) Date of Patent: Apr. 23, 2013

(54) BENZODIAZEPINE DERIVATIVES

(75) Inventors: Wei Li, Acton, MA (US); Nathan Fishkin, Weymouth, MA (US); Robert Zhao, Lexington, MA (US); Michael Miller, Framingham, MA (US); Ravi Chari, Newton, MA (US)

(73) Assignee: ImmunoGen, Inc., Waltham, MA (US)

( * ) Notice: Subject to any disclaimer, the term of this patent is extended or adjusted under 35 U.S.C. 154(b) by 369 days.

(21) Appl. No.: 12/700,131

(22) Filed: Feb. 4, 2010

(65) Prior Publication Data

US 2010/0203007 A1    Aug. 12, 2010

Related U.S. Application Data

(60) Provisional application No. 61/150,201, filed on Feb. 5, 2009.

(51) Int. Cl.
| | |
|---|---|
| *C07D 519/00* | (2006.01) |
| *A61K 31/5517* | (2006.01) |
| *A61K 31/55* | (2006.01) |
| *A61P 35/00* | (2006.01) |

(52) U.S. Cl.
USPC .......................................... 514/219; 540/494

(58) Field of Classification Search .................. 540/494; 514/219
See application file for complete search history.

(56) References Cited

U.S. PATENT DOCUMENTS

| | | | |
|---|---|---|---|
| 3,860,600 | A | 1/1975 | Carabateas |
| 2009/0036431 | A1 | 2/2009 | Gauzy et al. |
| 2010/0316656 | A1 | 12/2010 | Bouchard et al. |
| 2011/0256157 | A1 | 10/2011 | Howard et al. |

FOREIGN PATENT DOCUMENTS

| | | |
|---|---|---|
| EP | 0 219 292 A2 | 4/1987 |
| EP | 2 019 104 A1 | 1/2009 |
| WO | 2011/130613 A1 | 10/2011 |
| WO | 2011/130616 A1 | 10/2011 |

OTHER PUBLICATIONS

Wei Li, et al.. "Design, Synthesis and Evaluation of a Novel DNA-Interactive Agent: A Promising New Class of Cytotoxic Molecules for Use in Antibody-Drug Conjugates", 239th ACS National Meeting, San Francisco, CA, Mar. 21-25, 2010 [MEDI 251].
International Search Report and Written Opinion dated Mar. 31, 2010, as issued in International Application No. PCT/US10/23150.

*Primary Examiner* — Bruck Kifle
(74) *Attorney, Agent, or Firm* — McCarter & English, LLP; Steven G. Davis; Yu Lu

(57) ABSTRACT

The invention relates to novel benzodiazepine derivatives with antiproliferative activity and more specifically to novel benzodiazepines of formula (I) and (II), in which the diazepine ring (B) is fused with a heterocyclic ring (CD), wherein the heterocyclic ring is bicyclic or a compound of formula (III), in which the diazepine ring (B) is fused with a heterocyclic ring (C), wherein the heterocyclic ring is monocyclic. The invention provides cytotoxic dimers of these compounds. The invention also provides conjugates of the monomers and the dimers. The invention further provides compositions and methods useful for inhibiting abnormal cell growth or treating a proliferative disorder in a mammal using the compounds or conjugates of the invention. The invention further relates to methods of using the compounds or conjugates for in vitro, in situ, and in vivo diagnosis or treatment of mammalian cells, or associated pathological conditions.

23 Claims, 41 Drawing Sheets

Figure 1. Synthetic scheme of IBD monomer 8
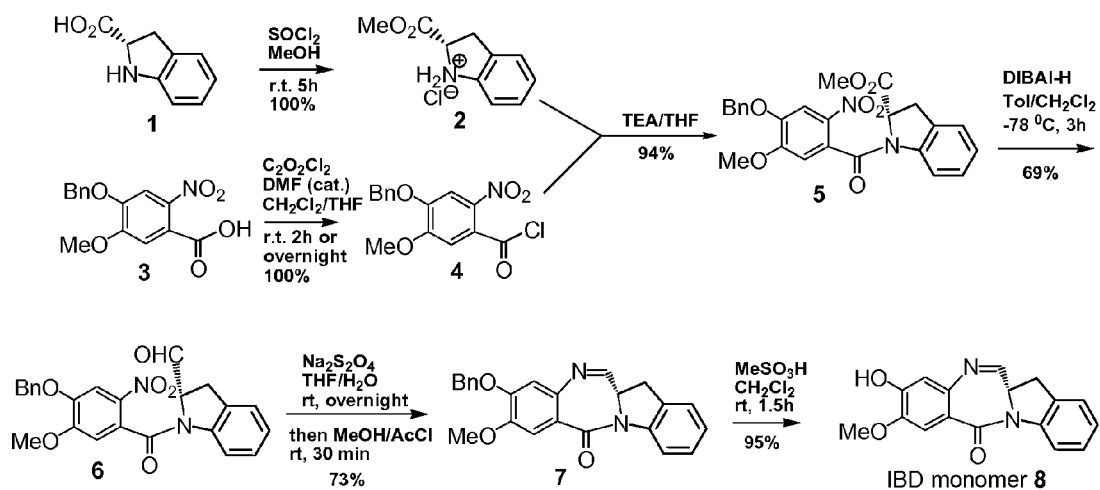
Figure 2. Synthetic scheme of OBD monomer 14
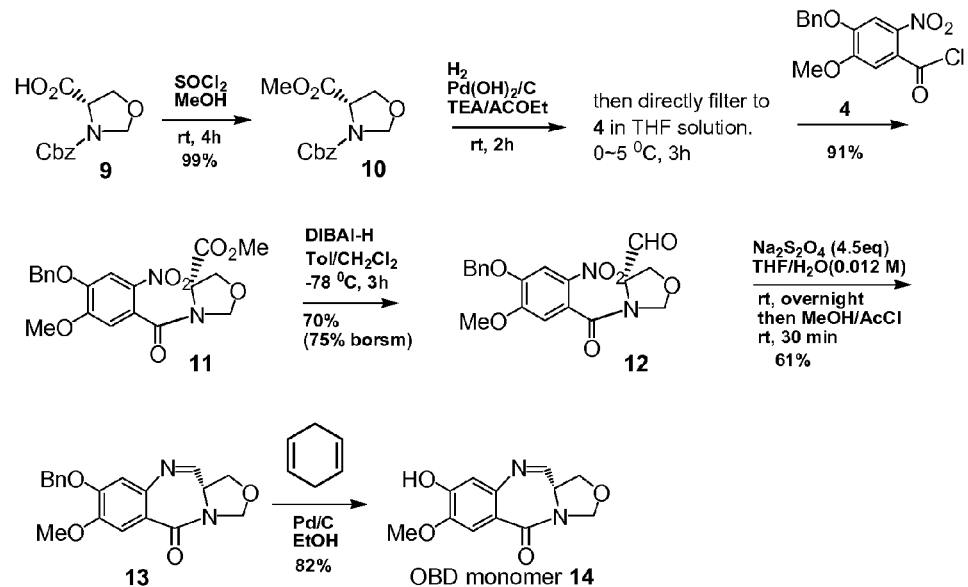

Figure 3. Synthetic scheme of dimer 15 (IGN-09)
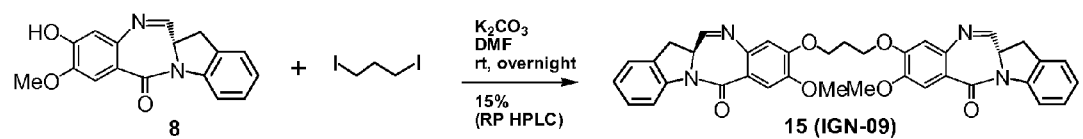
Figure 4. Synthetic scheme of dimer 18 (IGN-01)
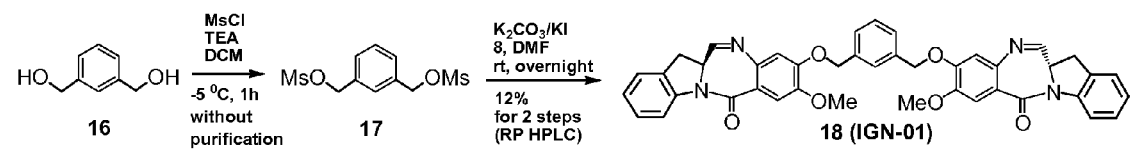
Figure 5. Synthetic scheme of dimer 19 (IGN-02)
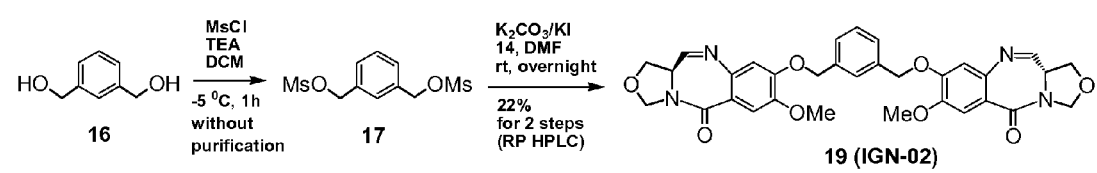

Figure 6. Synthetic scheme of the linkers
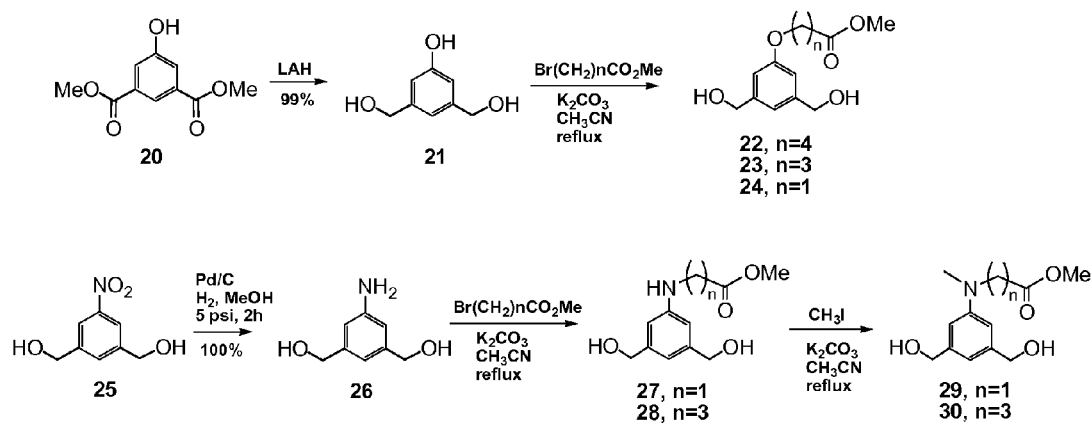
Figure 7. Synthetic scheme of dimers 34, 35, 36, 39 and 40 (IGN-03~07)
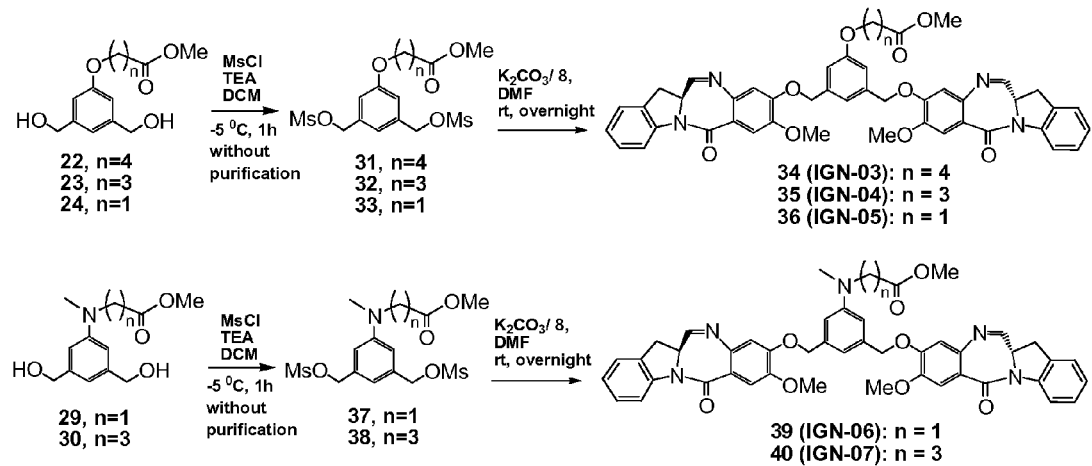

Figure 8. Synthetic scheme of the NHS esters 43, 44 and 46
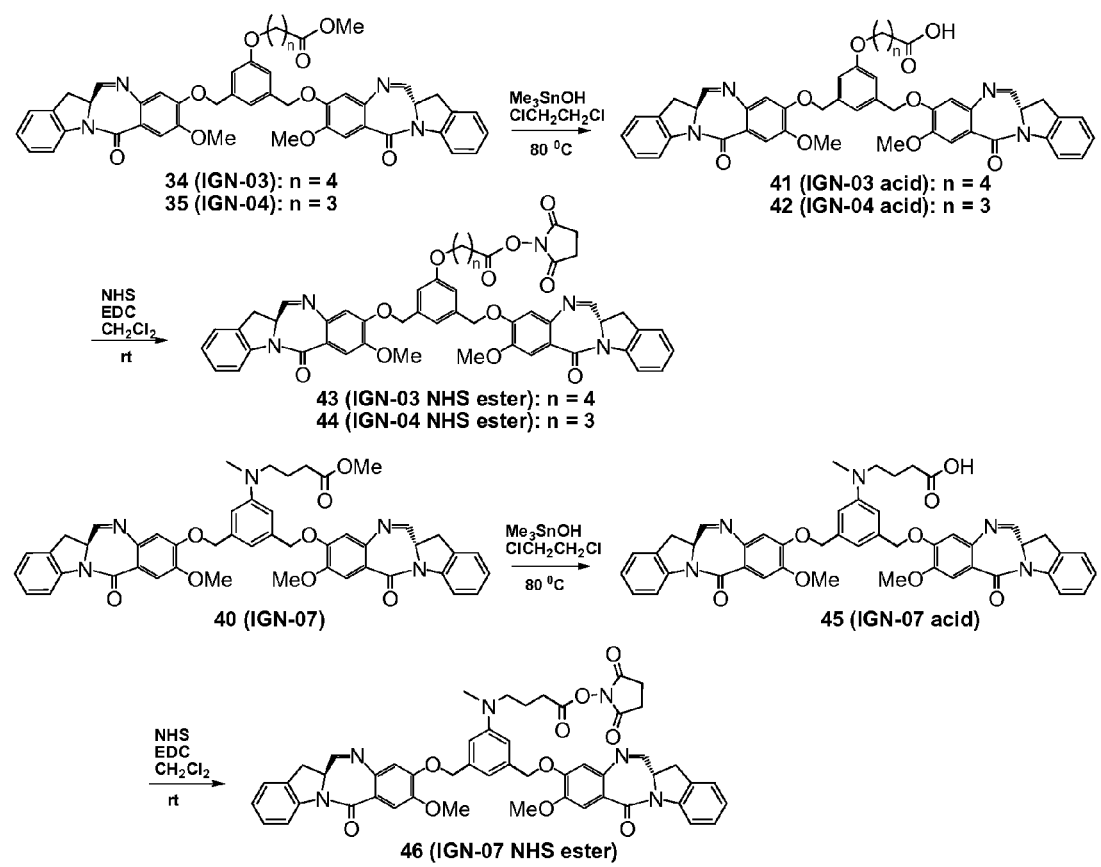

Figure 9. Synthetic scheme of thiol 49
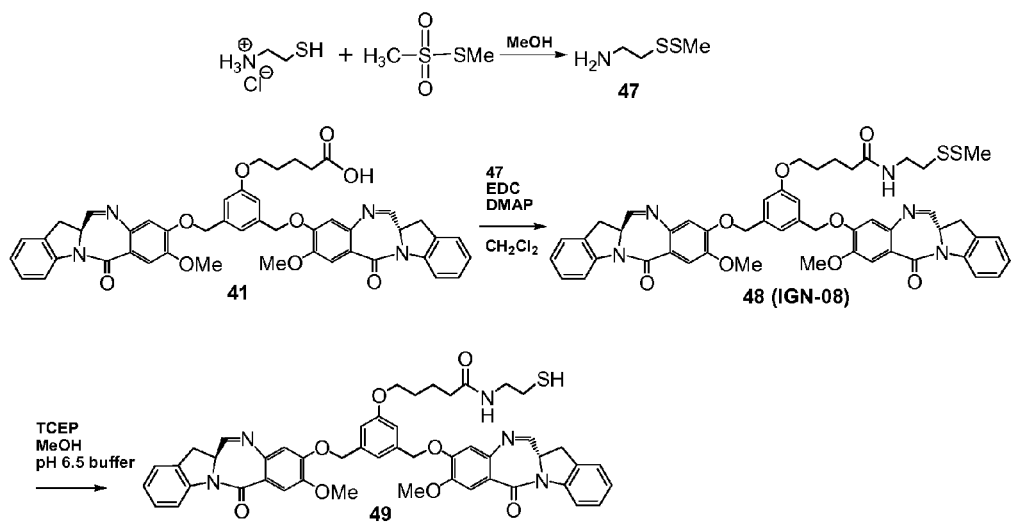
Figure 10. Synthetic scheme of disulfide 51
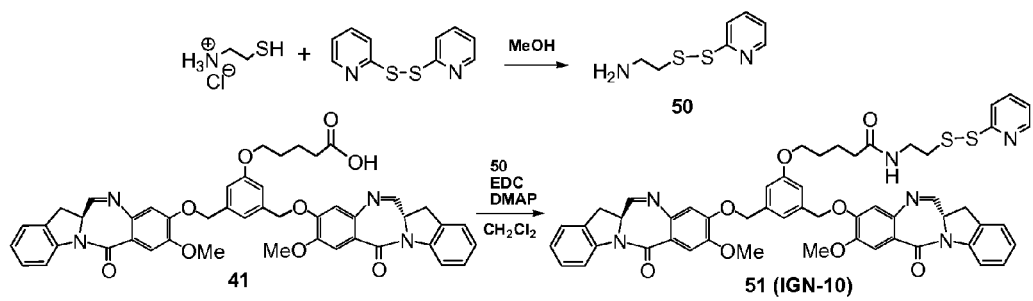

Figure 11. Synthetic scheme of B-ring modified monomer 58
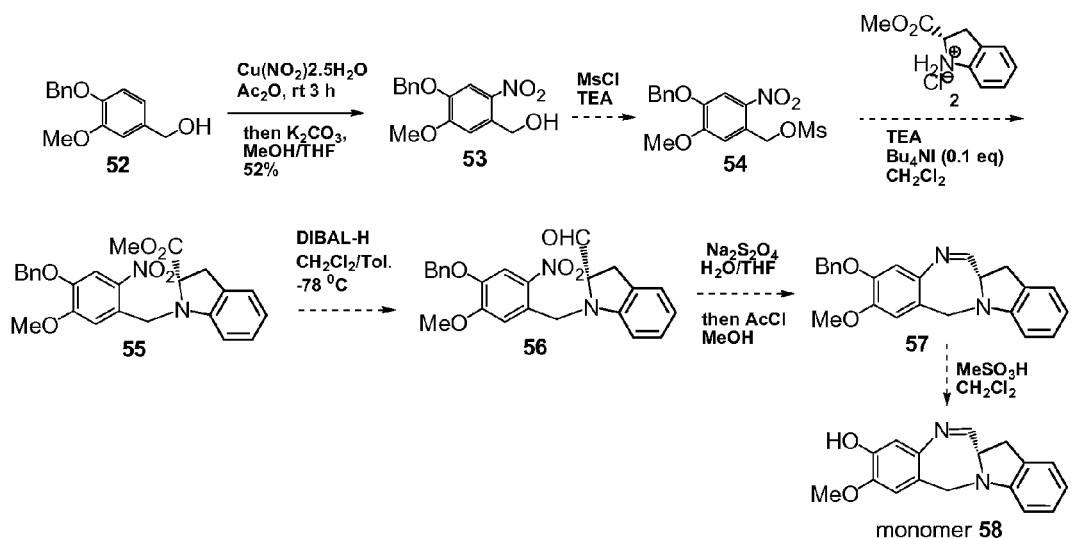
Figure 12. Synthetic scheme of isoindolinobenzodiazepine monomer 66
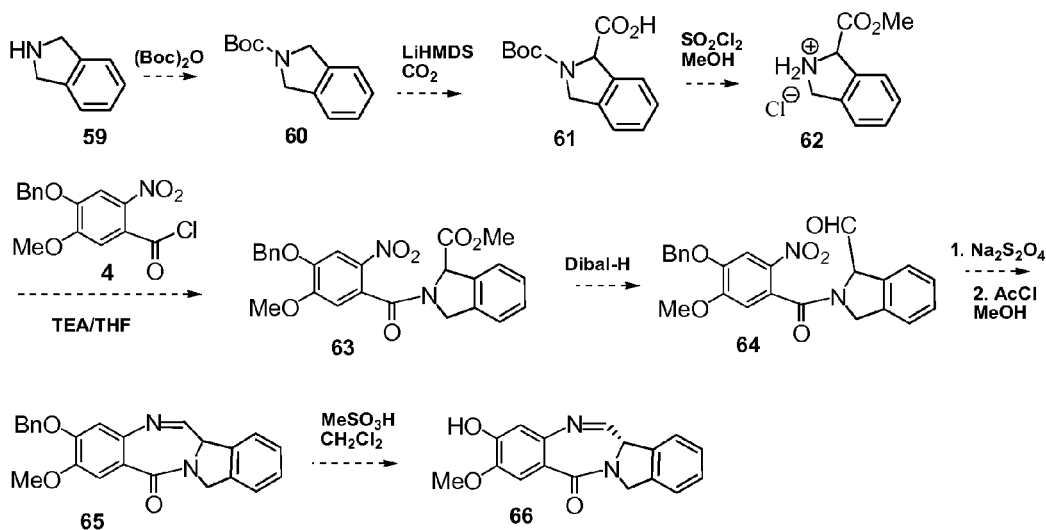

Figure 13. Synthetic scheme of compound 82 with linker attached to the Indoline moiety
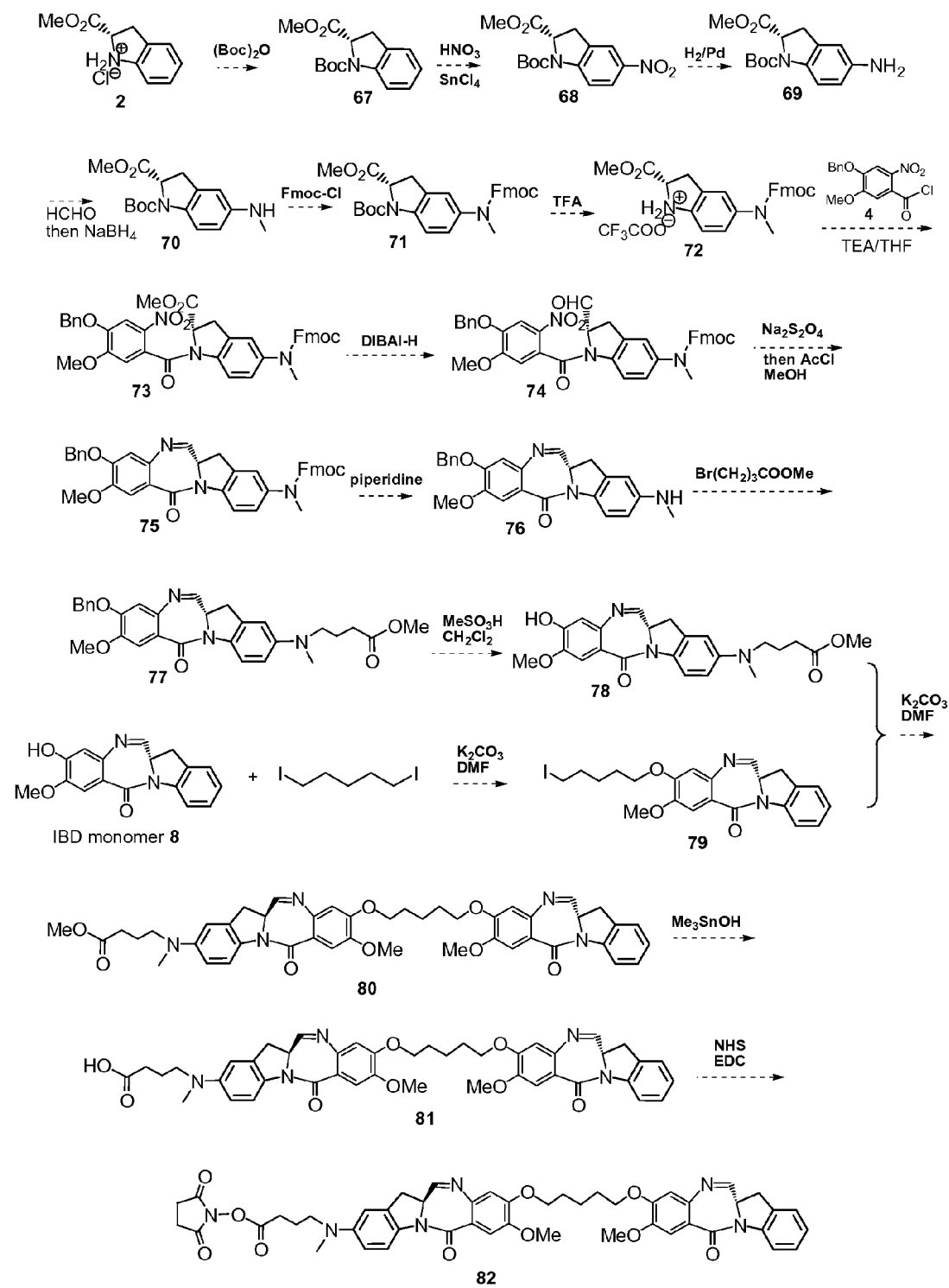

Figure 14. Synthetic schemes of dimers 87, 88, 92, 96 and 100 containing (PEG)$_n$ moiety on the linear linkers
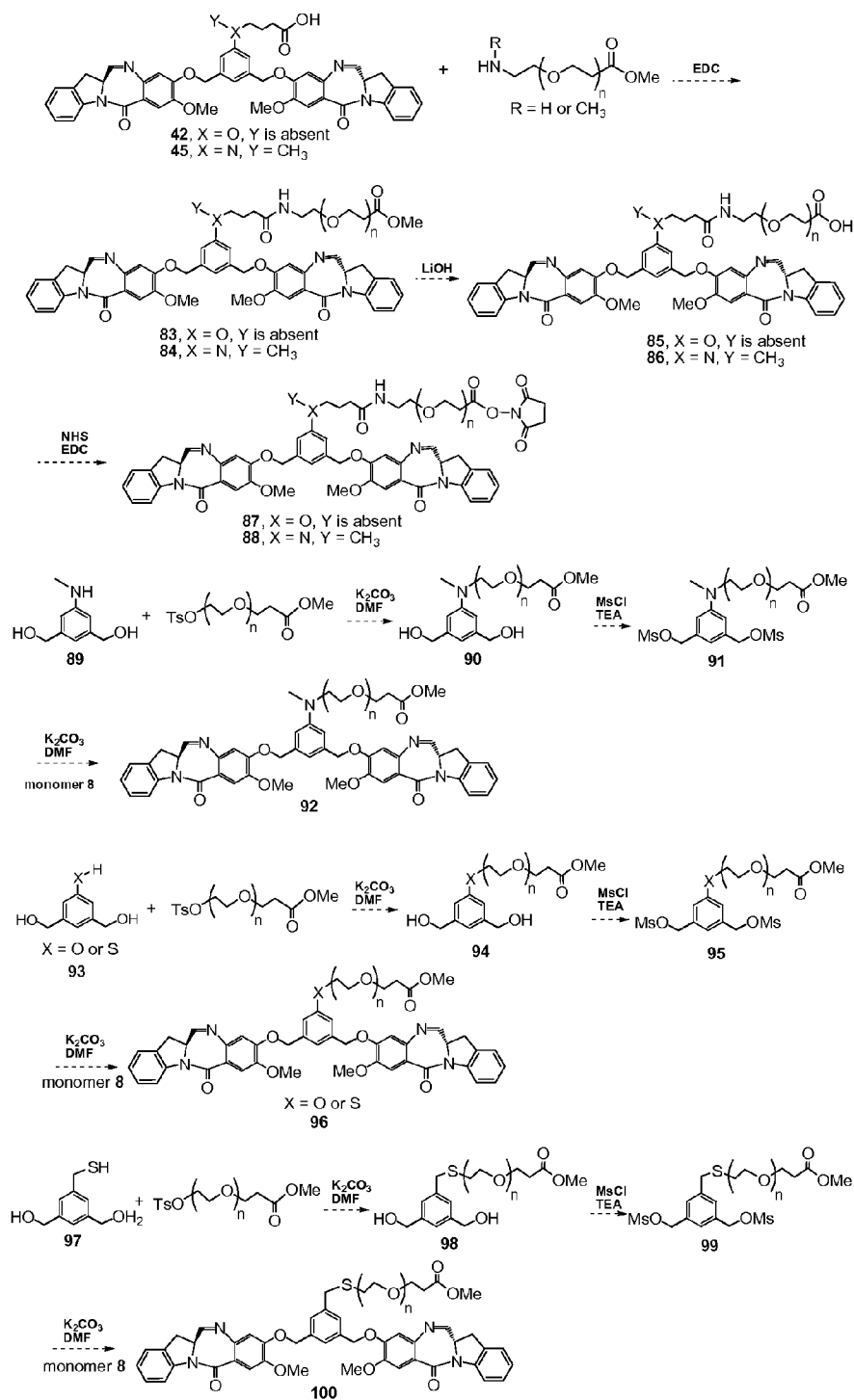

Figure 15. Synthetic schemes of dimers 105 and 110 containing (PEG)$_n$ moiety on the branched linkers
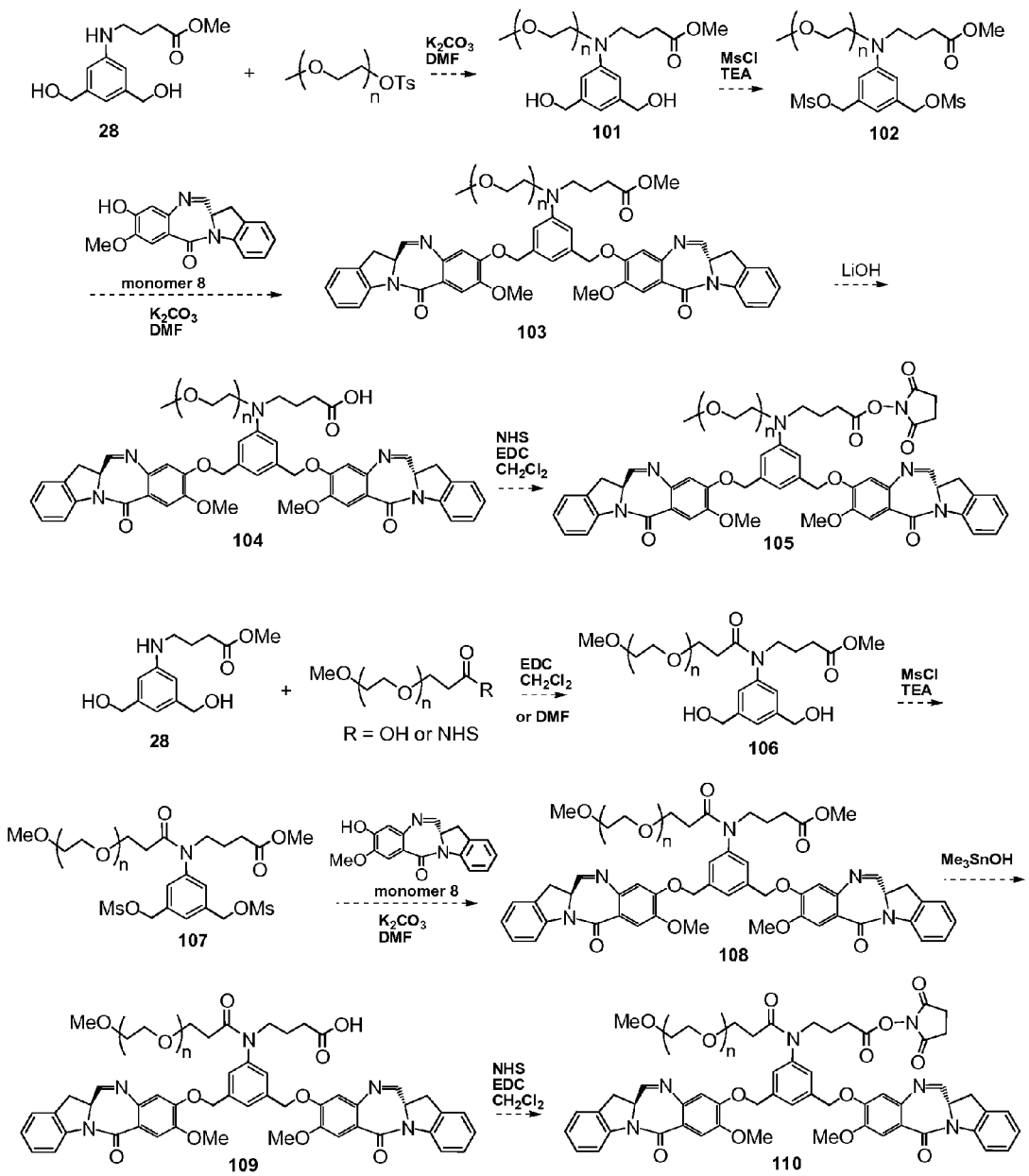

Figure 16. Synthetic schemes of compounds 115, 119 and 121
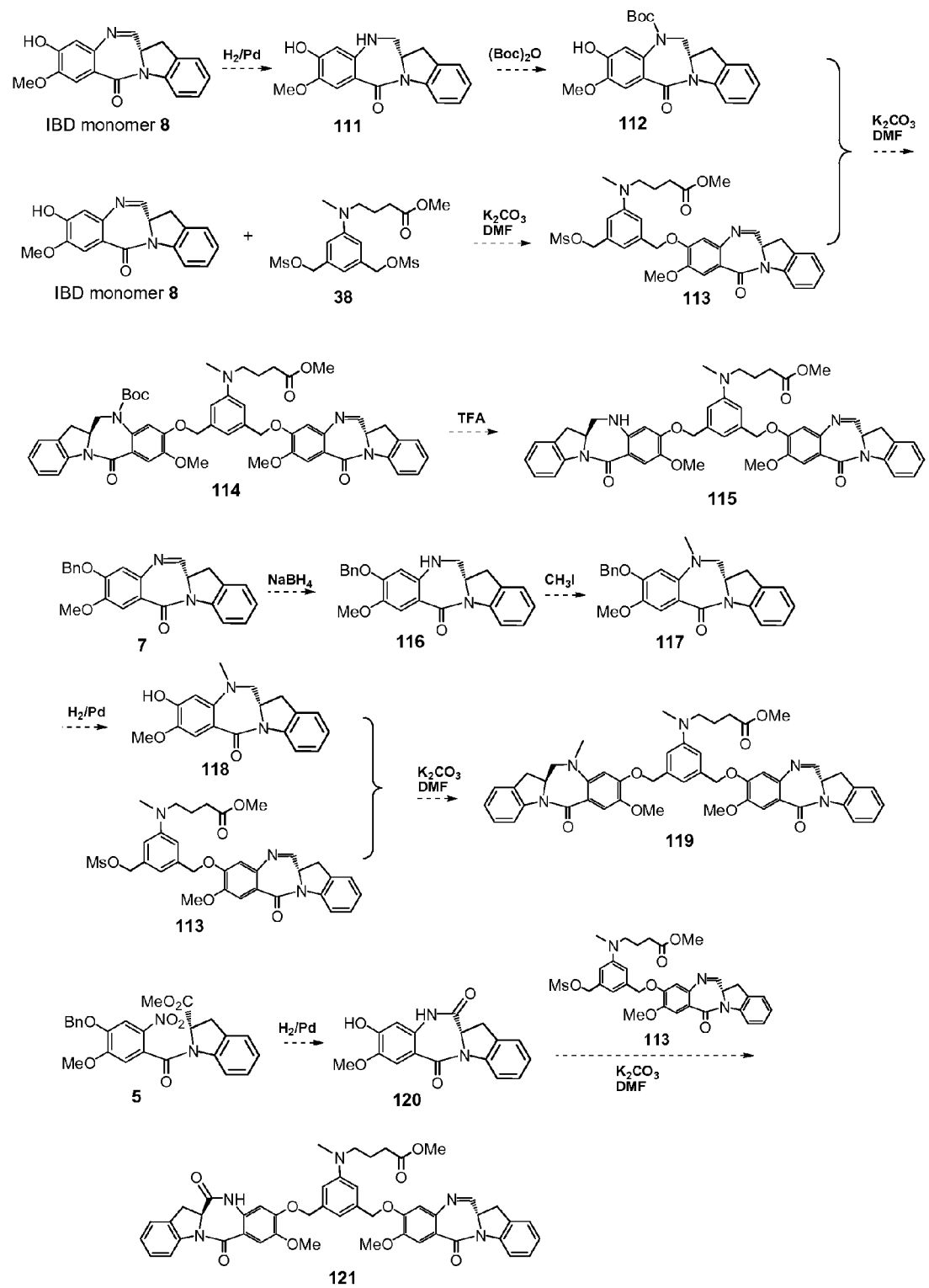

Figure 17. Synthetic scheme of compound 127 (IGN-11)
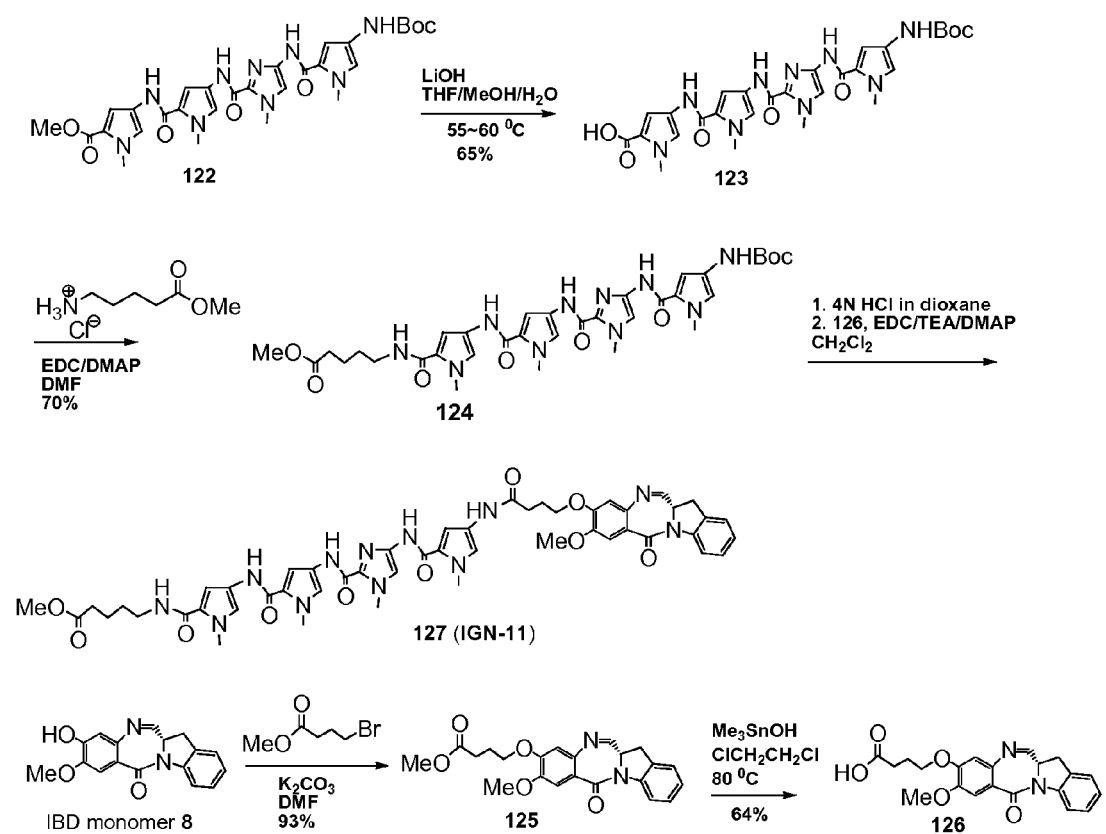

Figure 18. The assembling of polypyrroles/polyimidazoles
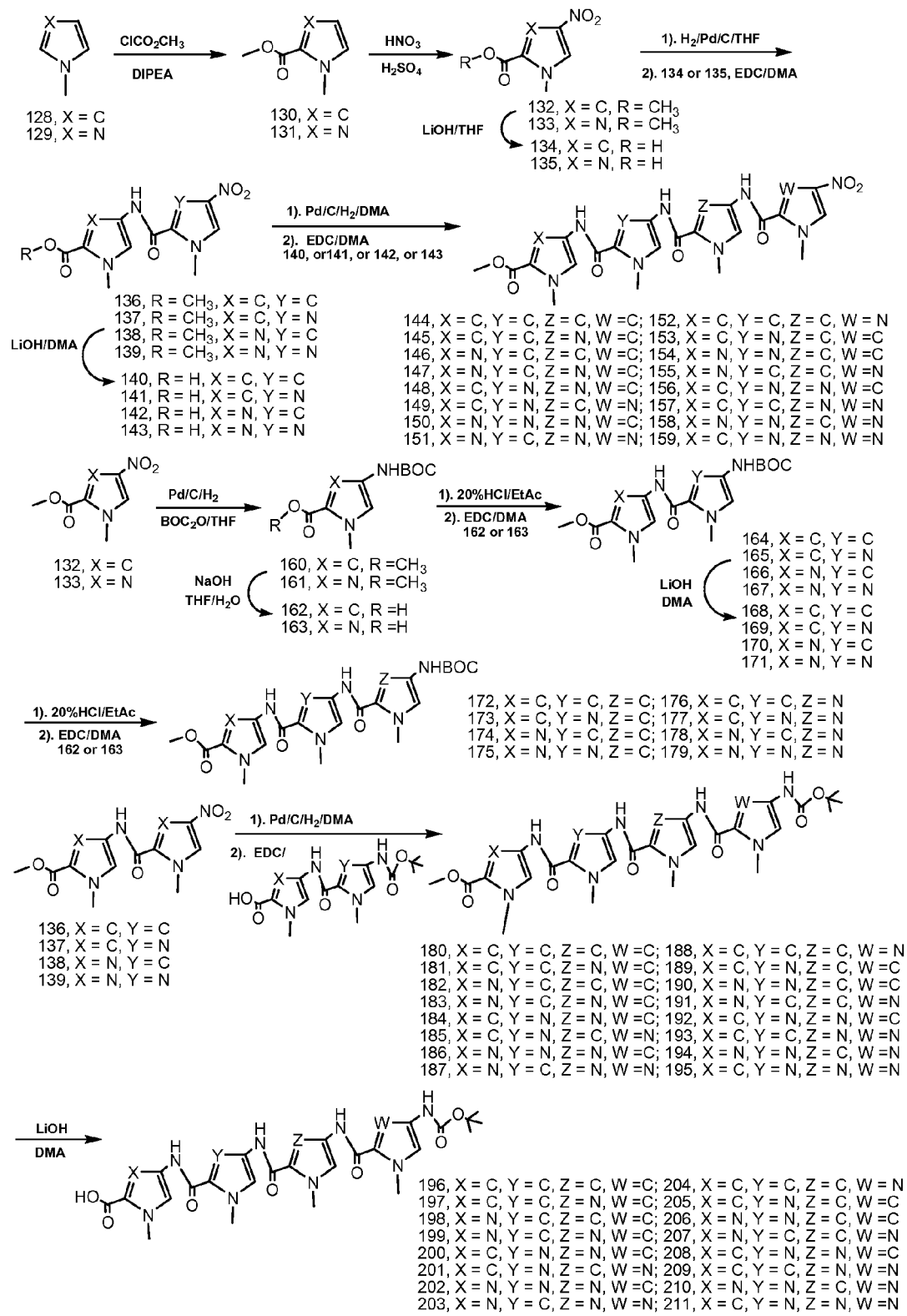

Figure 19. The synthesis of IBD-polypyrrole-imidazole analogs
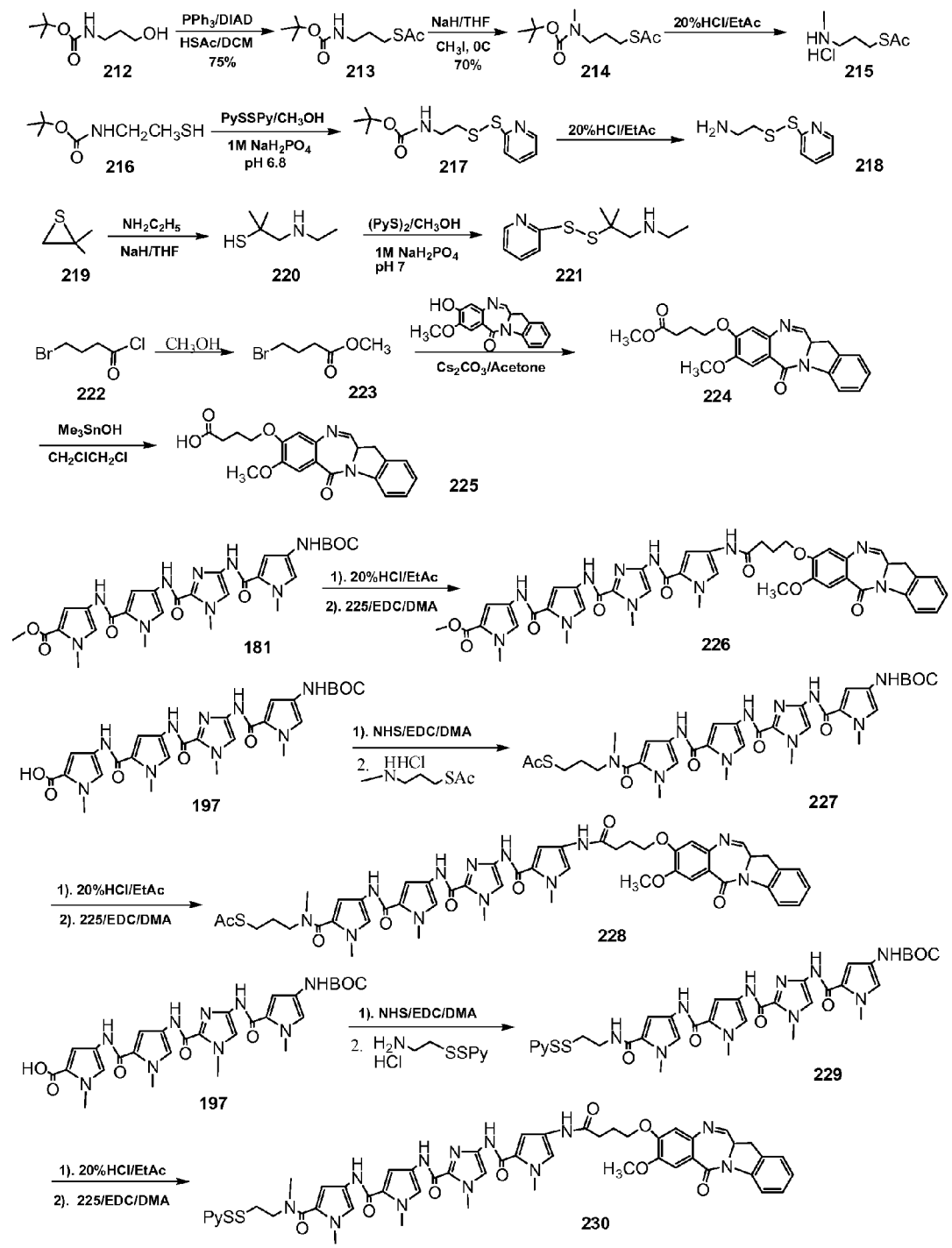

Figure 20. The synthesis of piperidinobenzodiazepine conjugated to antibody through a hydrazone linkage
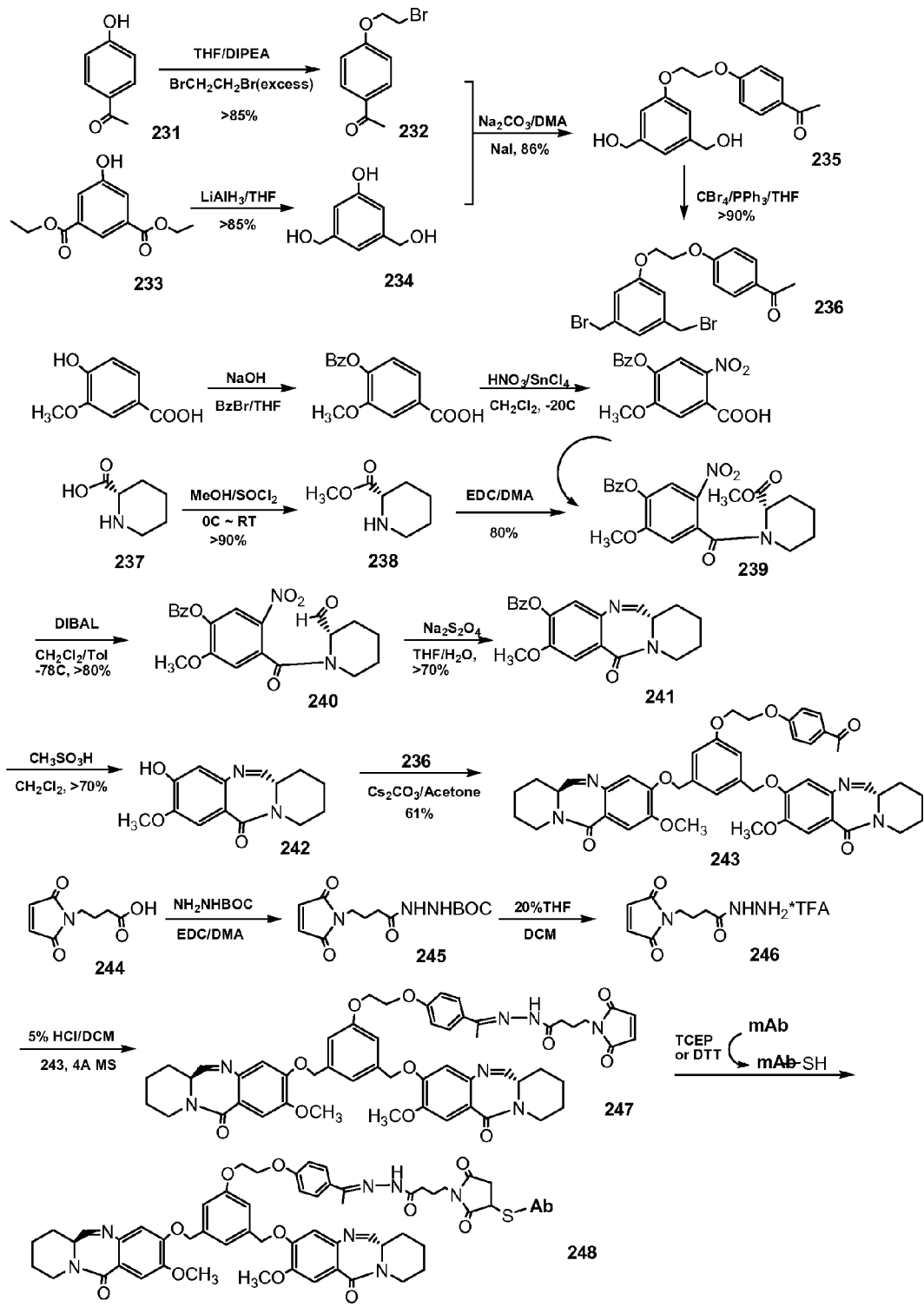

Figure 21. Antiproliferative activity of muB38.1-IGN-03 against COLO205 (Ag+), COLO205 MDR (Ag+), and Namalwa cells (Ag-).
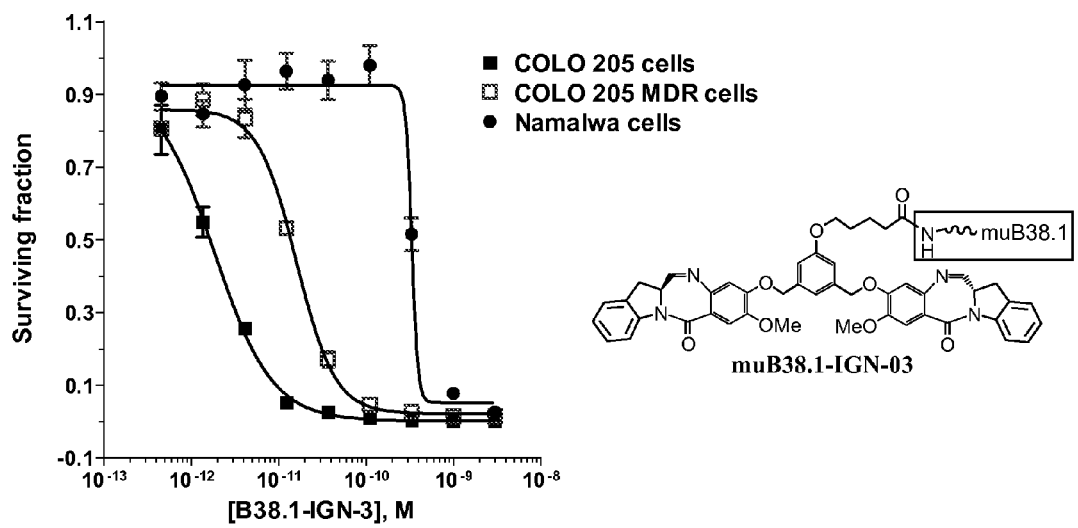
Figure 22. Antiproliferative activity of huN901-IGN-03 against RH-30 (Ag+) cells with and without blocking of antigen binding sites using 1 μM huN901.
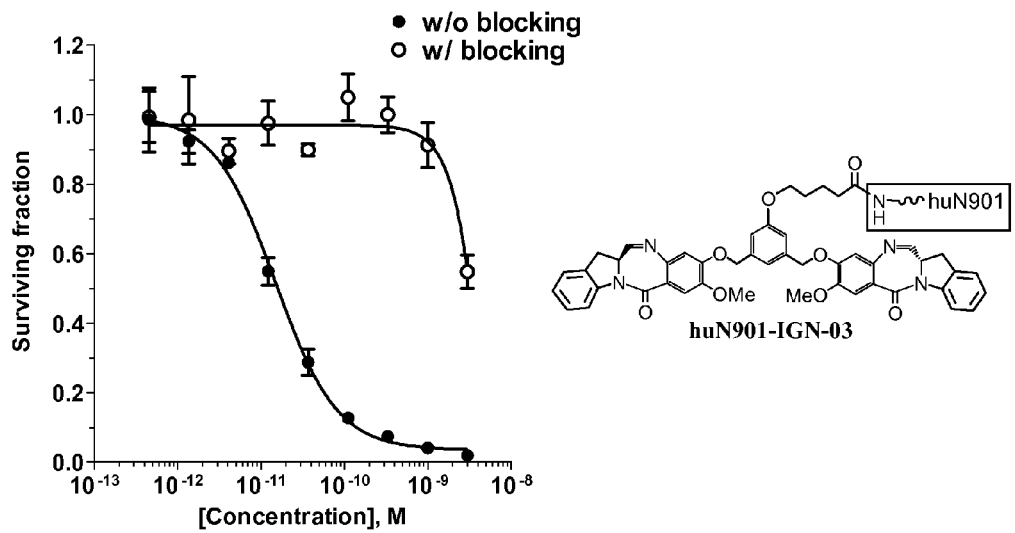

Figure 23. Antiproliferative activity of huN901-IGN-07 against RH-30 (Ag+) cells. Conjugates were tested at three different ratios of cytotoxic agent per antibody (D/A).
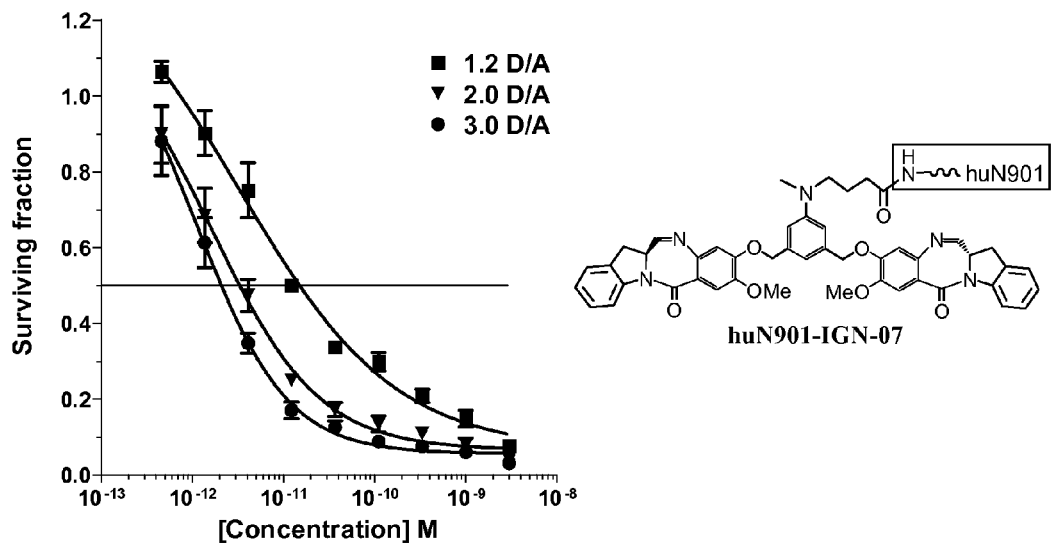
Figure 24. Antiproliferative activity of huN901-IGN-07 (1.2-3.0 D/A) and huN901-IGN-03 (1.7 D/A) against Molp-8 (Ag+) cells.
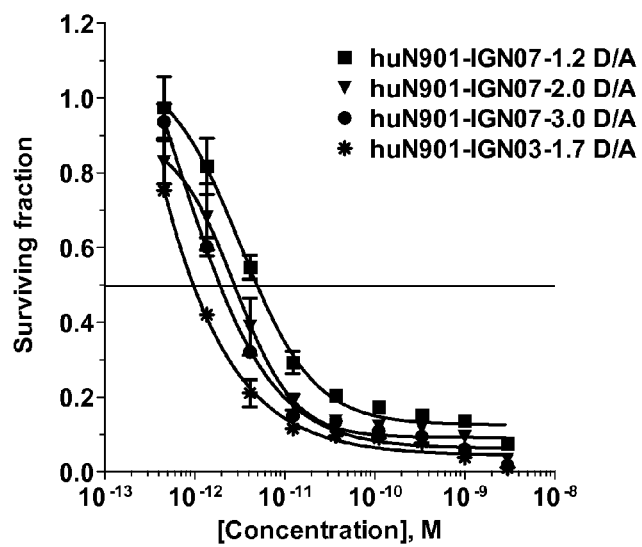

Figure 25. Antiproliferative activity of huN901-IGN-07 (1.2-3.0 D/A) and huN901-IGN-03 (1.7 D/A) against Namalwa (Ag-) cells.
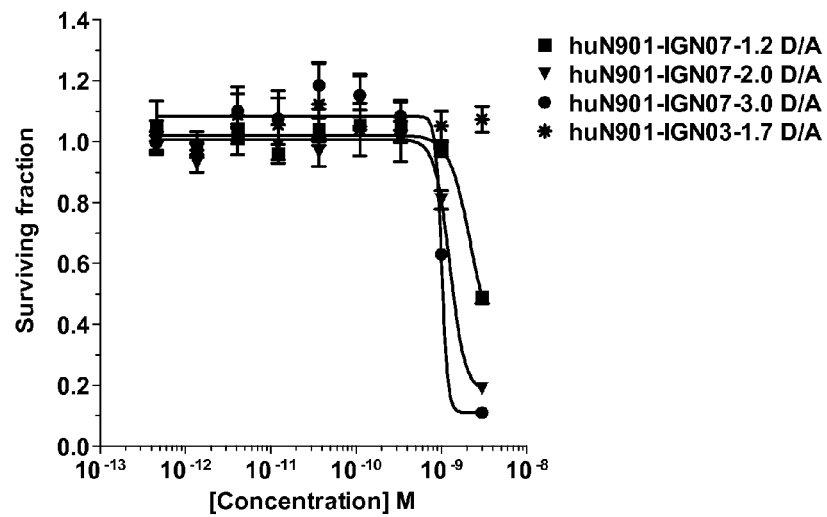
Figure 26. Antiproliferative activity of muB38.1-IGN-10 against COLO 205 (Ag+) and Ramos (Ag-) cells.
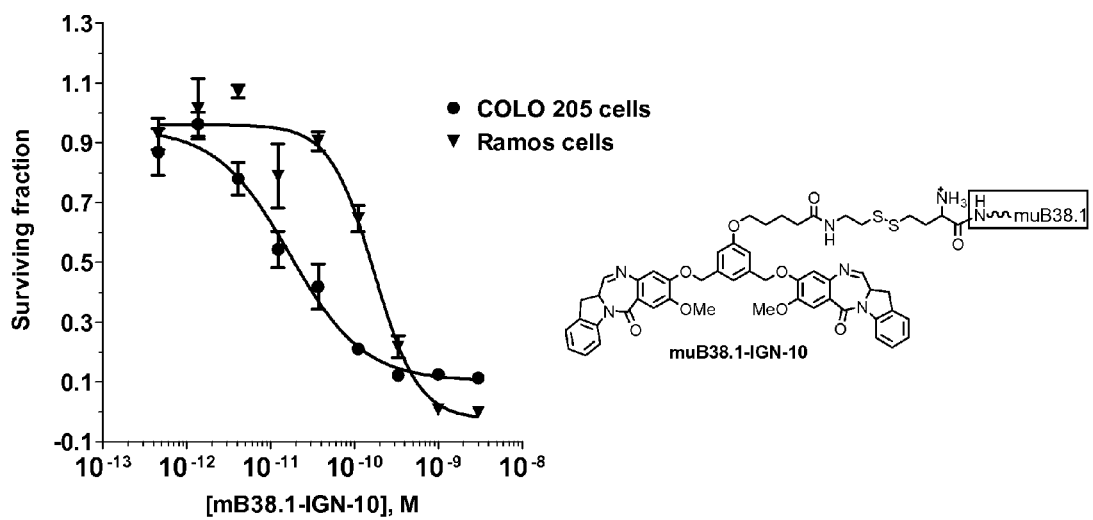

Figure 27. Tumor regression data for single iv dosing of huN901-IGN-07 in nude mice bearing Molp-8 tumors.
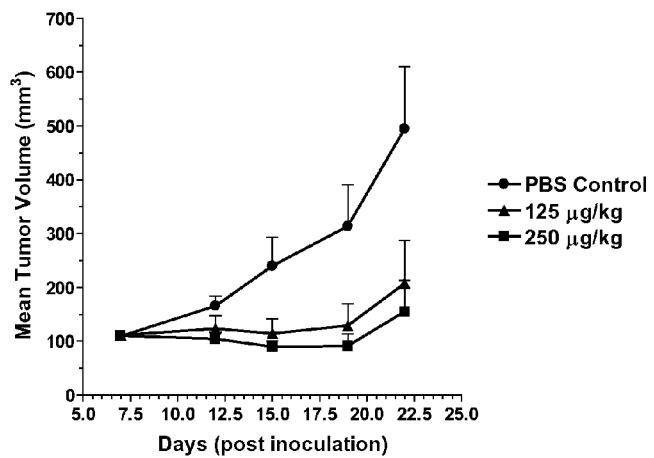
Figure 28. A) Reverse phase ion pair chromatography showing time dependent formation of a covalent adduct between IGN-1 and a 12 base pair duplex DNA probe containing guanines on opposite strands. B) UV-Vis spectra of DNA probe and IGN-1-DNA adduct.
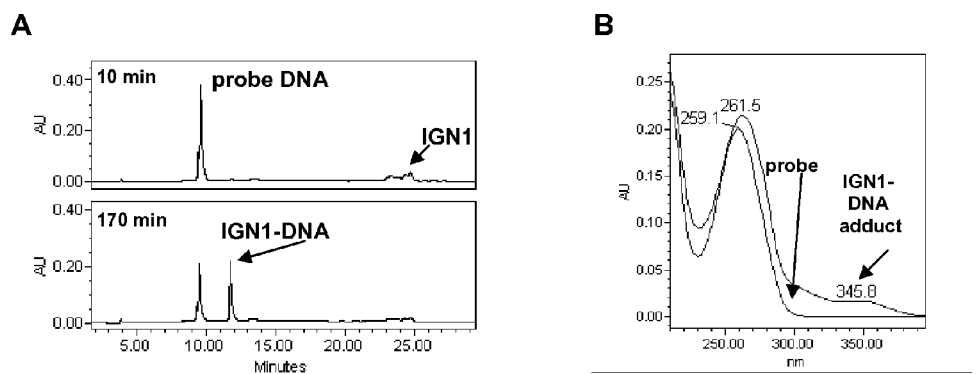

Figure 29. Initial rate of IGN1-DNA adduct formation is dependent on DNA sequence. IGN1 binds faster to DNA containing an internal GATC motif than DNA with a GTAC sequence. DNA probe substituted with deoxyInosine (I) (containing no C-2 amino group) in place of guanine (G) showed no reaction with IGN-1.
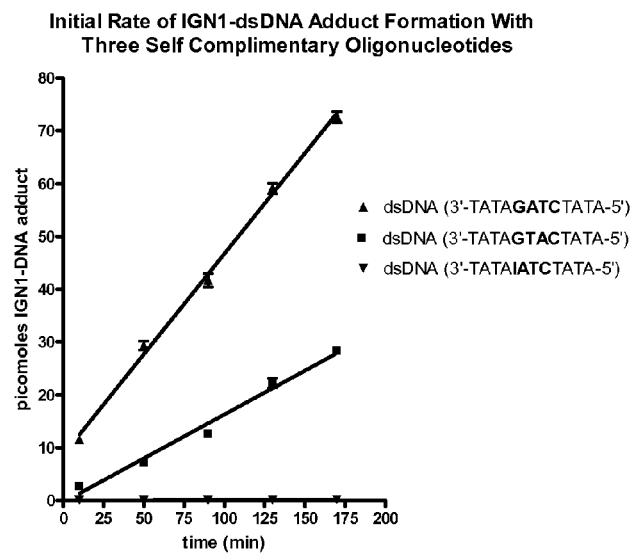

Figure 30. IGN-01, IGN-02 and IGN-09 tested for binding and crosslinking to double stranded self-complimentary probe DNA.
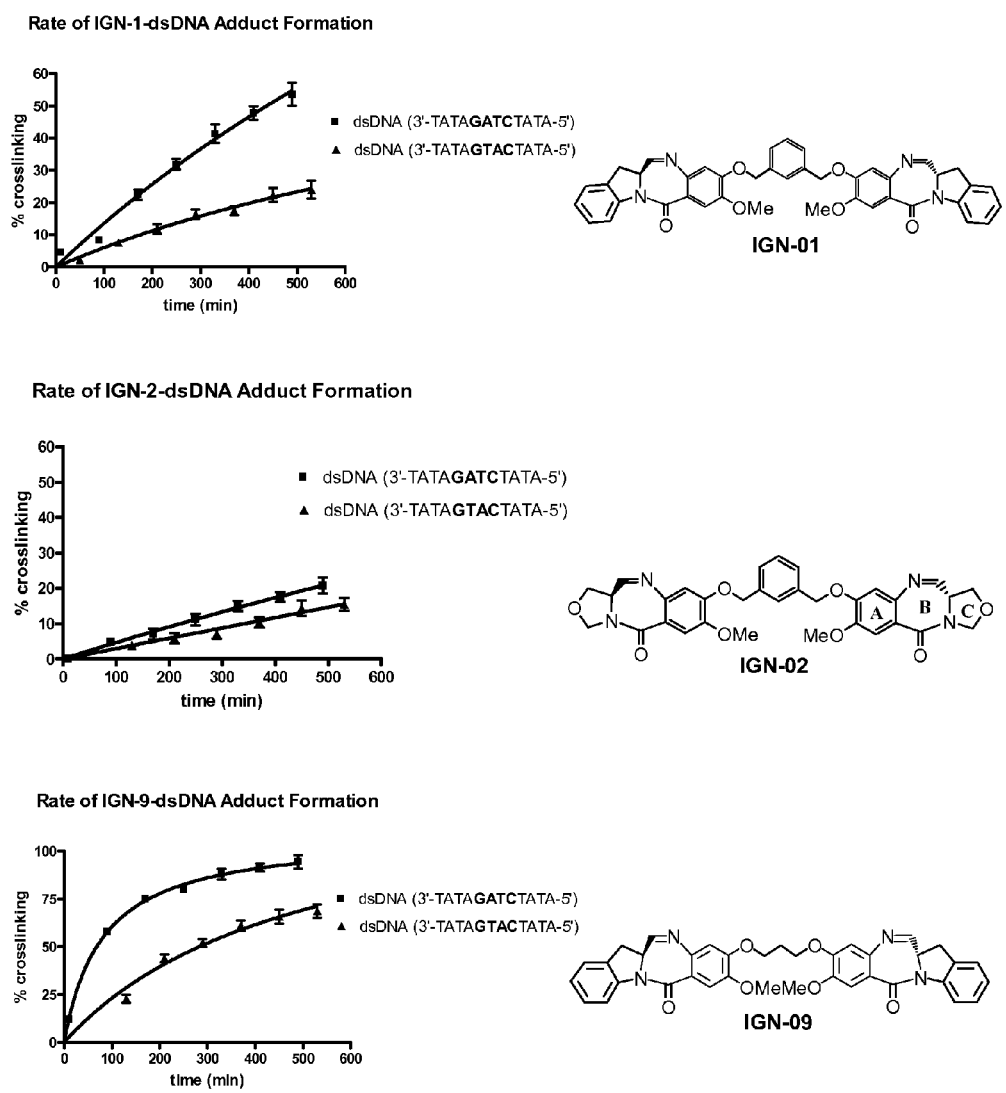

Figure 31

Table 1. Indolinobenzodiazepine dimers and oxazoloidinobenzodiazepine dimer antiproliferative activity on a variety of cancer cell lines. IC50 values (pM) are shown for each compound tested in a 5 day continuous exposure assay.

| Dimers | IC50s (pM) | | | | | | | | | | |
|---|---|---|---|---|---|---|---|---|---|---|---|
| | HL60/ATCC | Ramos | MDA-MB-231 | SK-MEL-28 | BJAB | Molt-4 | RH-30 | COLO 205 | COLO 205-MDR | Namalwa | Namalwa-MDR |
| IGN-01 | <0.46 | <0.46 | 1.4 | 44 | | | | | | | |
| IGN-02 | 450 | 67 | 1400 | 4700 | | | | | | | |
| IGN-03 | 3.2 | 0.64 | 16 | 14 | | | | | | | |
| IGN-04 | | | | | 1.9 | 2.7 | | | | | |
| IGN-05 | | 0.65 | | | 1.0 | | 3.9 | | | | |
| IGN-06 | | 1.5 | | | | | 3.7 | | | 4.2 | |
| IGN-07 | | 1.9 | | | | | 5.9 | | | 4.7 | |
| IGN-08 | | 5.8 | | | | | 22 | | | 7.0 | |
| IGN-09 | | <0.46 | | | | | 7.8 | 14 | 61 | 1.4 | 13 |

Figure 32

Table 2. Comparison of the IC50s for the dimers with and without linkers

| Dimers | IC50s (pM) |
|---|---|
| | Ramos cells |
| IGN-01 | <0.46 |
| IGN-09 | <0.46 |
| IGN-03 | 0.64 |
| IGN-05 | 0.65 |

Figure 33. Synthetic scheme for indolinobenzodiazepine (IBD) dimers
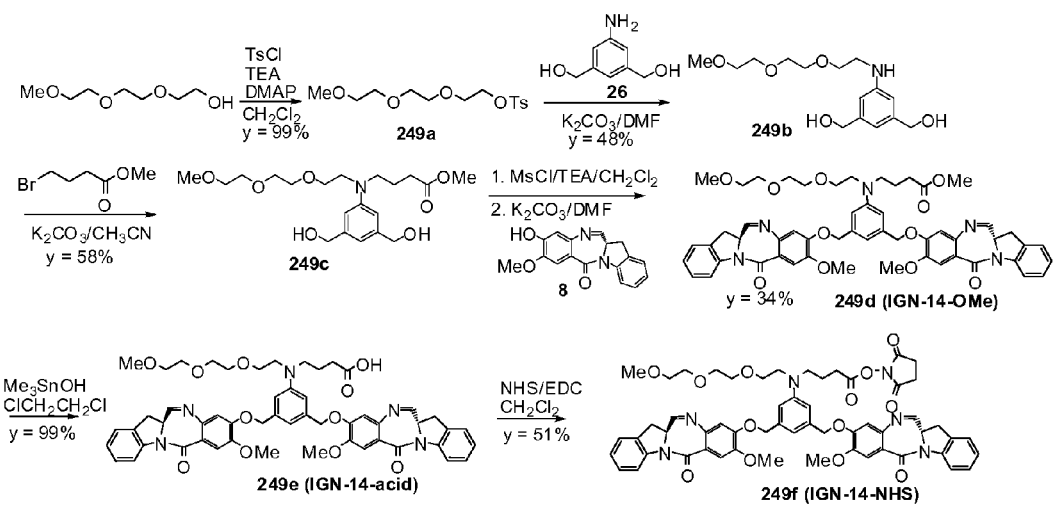
Figure 34. Synthetic scheme of esters of IBD dimers
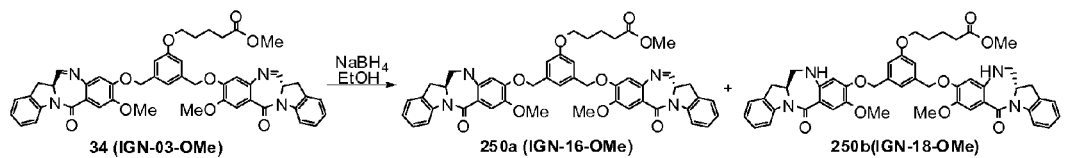

Figure 35. Synthetic scheme of dimer 251b (IGN-17-OMe).
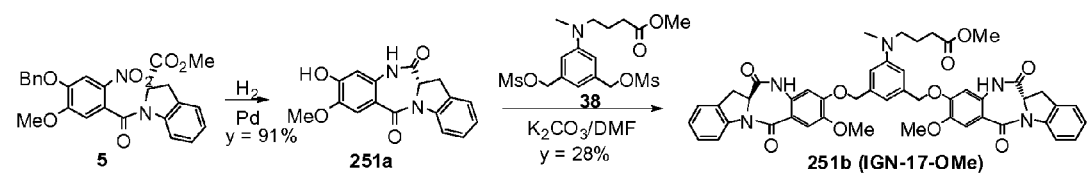
Figure 36. Synthetic scheme for dimer 252b (IGN-19-OMe).
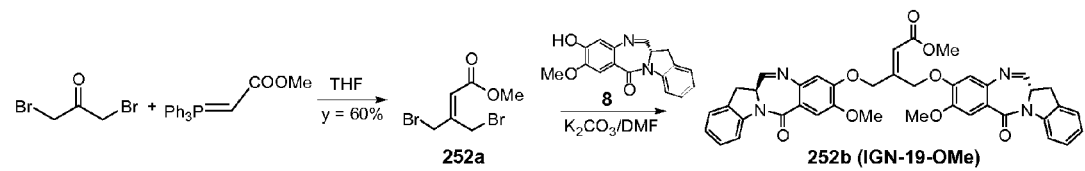

Figure 37. Synthetic scheme for linkable dimer
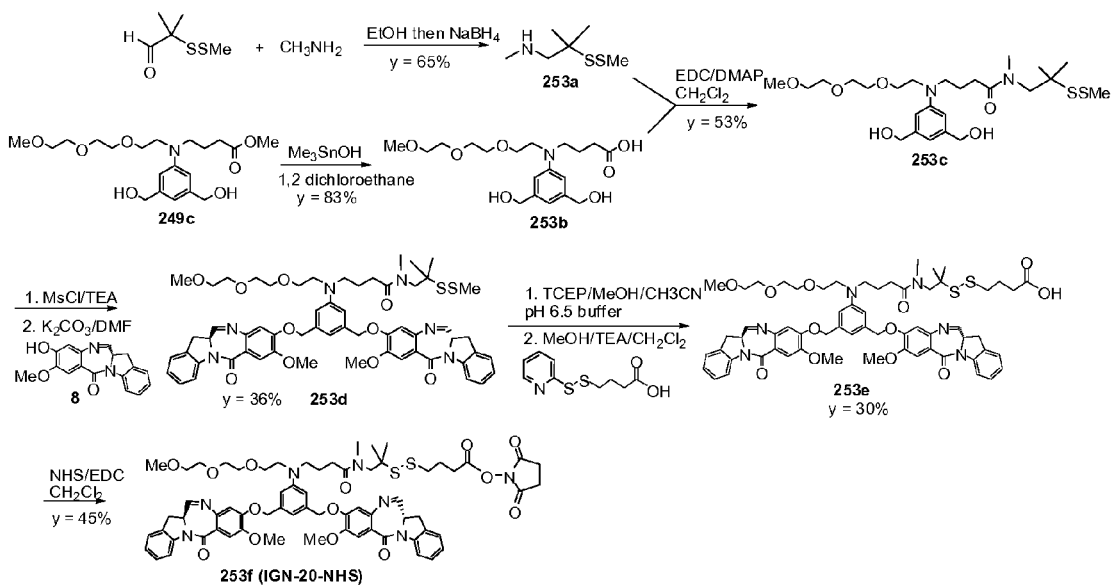

Figure 38. Synthetic scheme of linkable compounds 254d (IGN-23-NHS) and 254f (IGN-24-NHS).
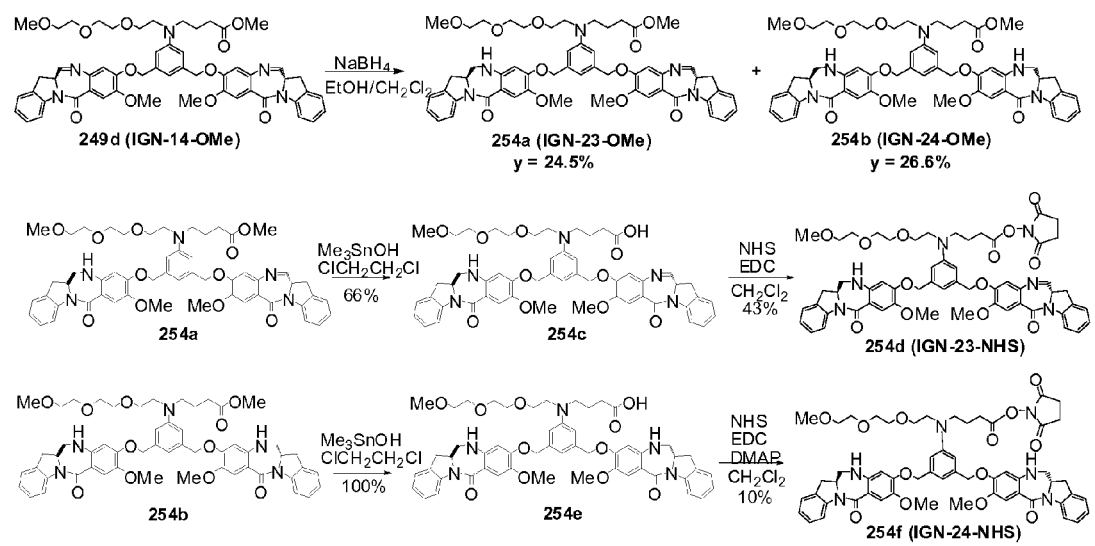
Figure 39. Synthetic scheme of IBD dimer 255c (IGN-26-OMe).
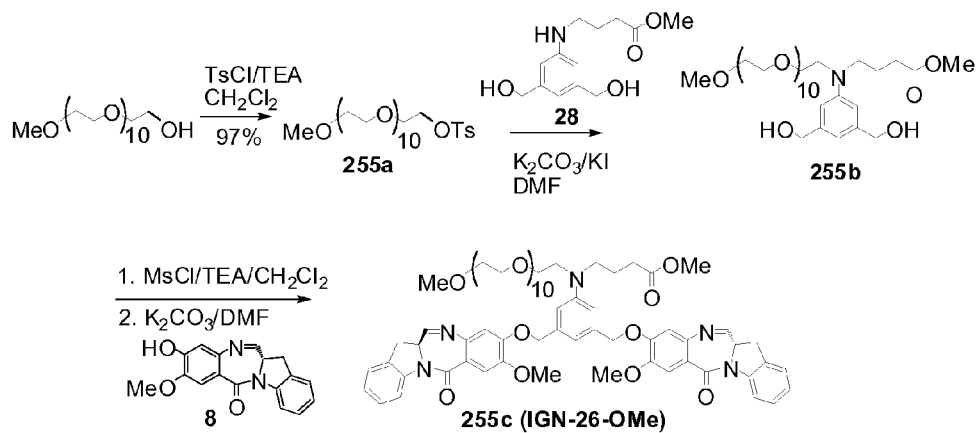

Figure 40. Synthetic scheme of compound 256g (IGN-29-NHS).
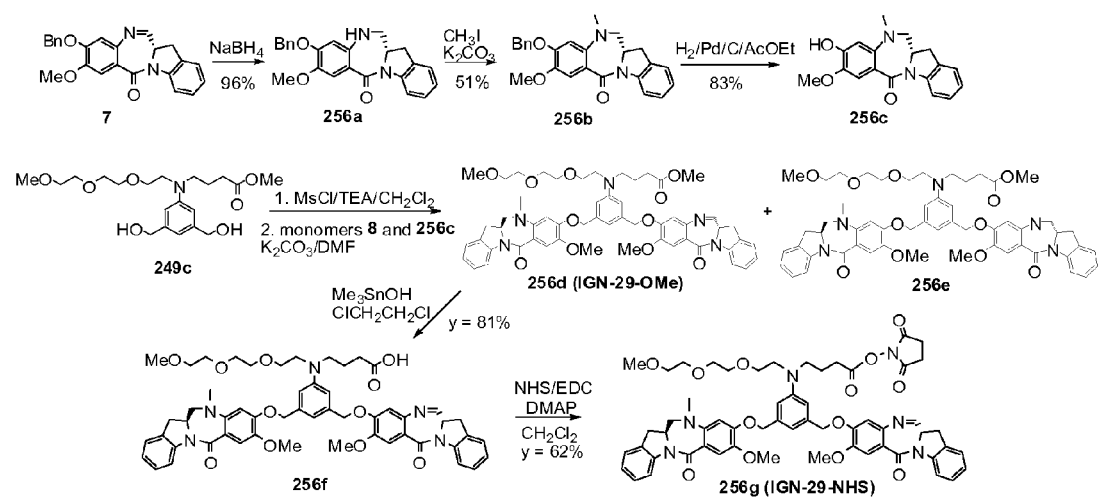

Figure 41. Synthetic scheme of compound 257e (IGN-33-NHS).
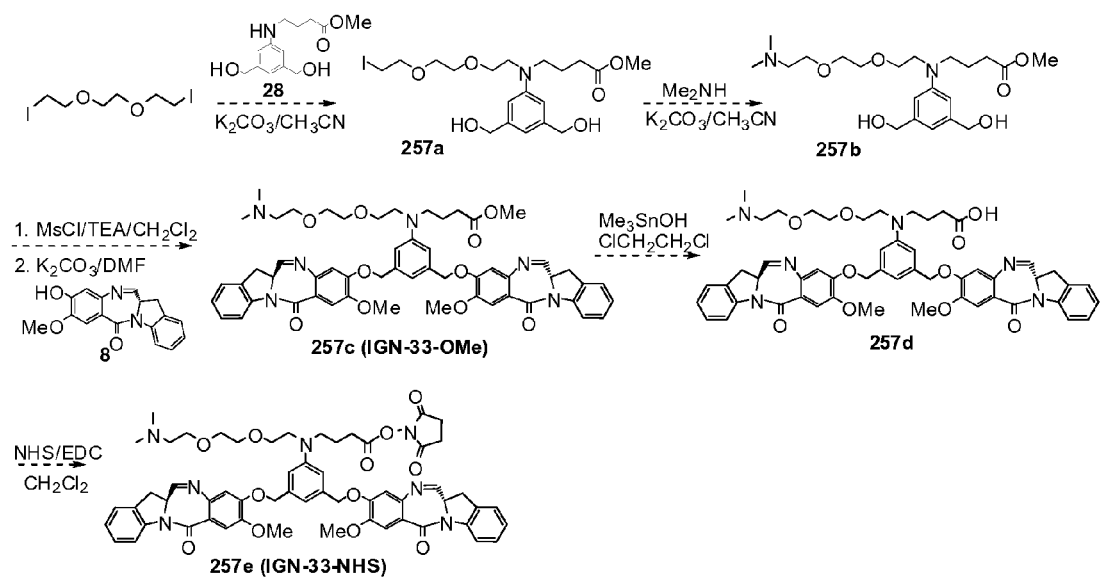

Figure 42. Synthetic scheme of compounds 258h (IGN-15-SMe) and 259b (IGN-21-SMe).
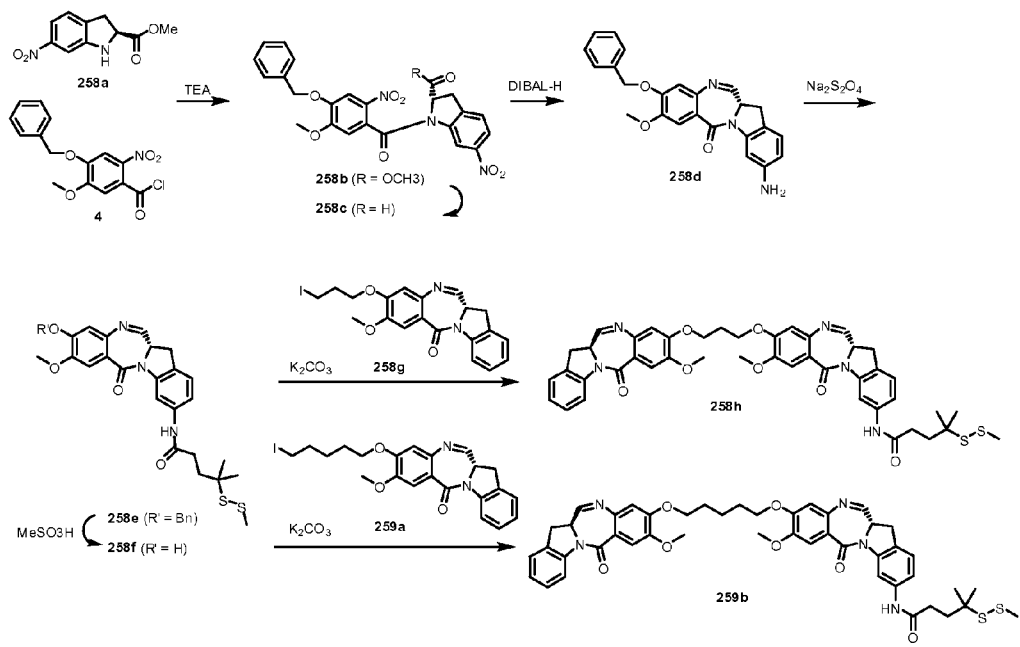

Figure 43. Synthetic scheme of compound 260c (IGN-25-OMe).
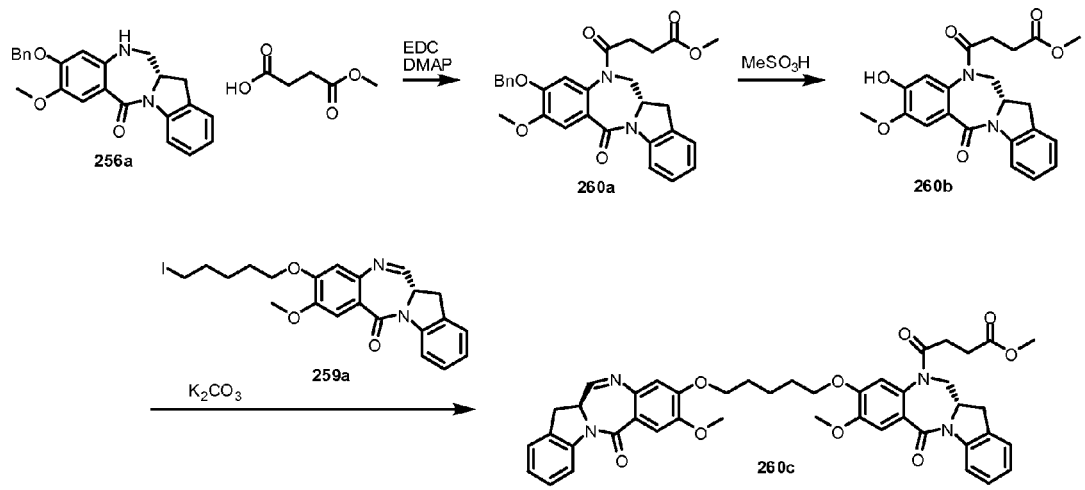
Figure 44. Synthetic scheme of compounds 261e (TBD monomer) and 262 (IGN-30-OMe).
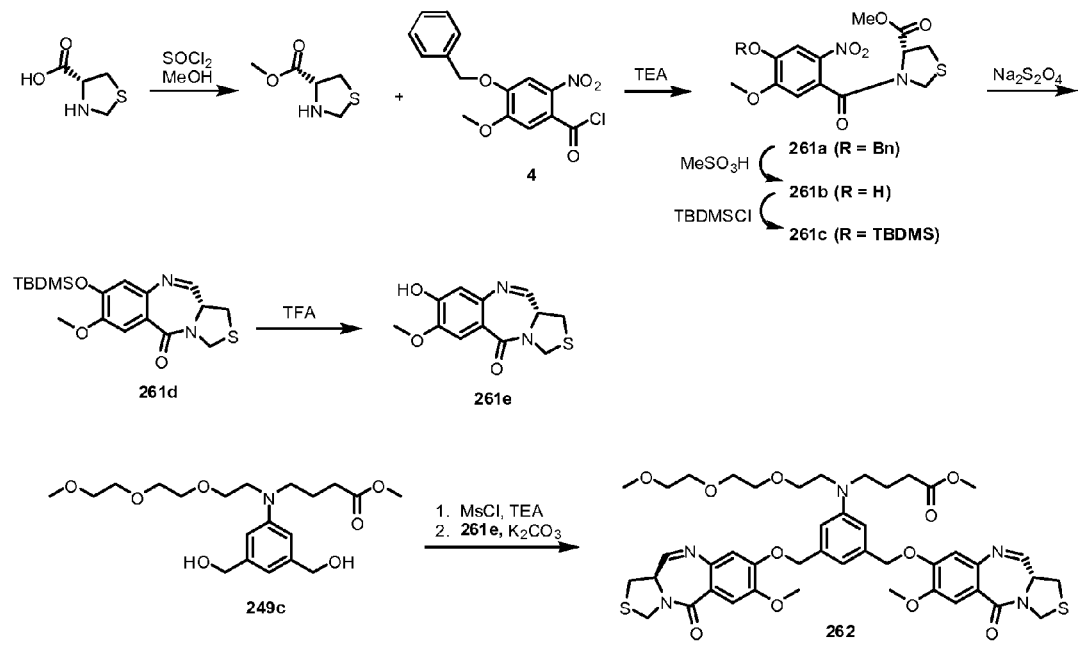

Figure 45. Synthetic scheme of dimer 263e (IGN-13-NHS).
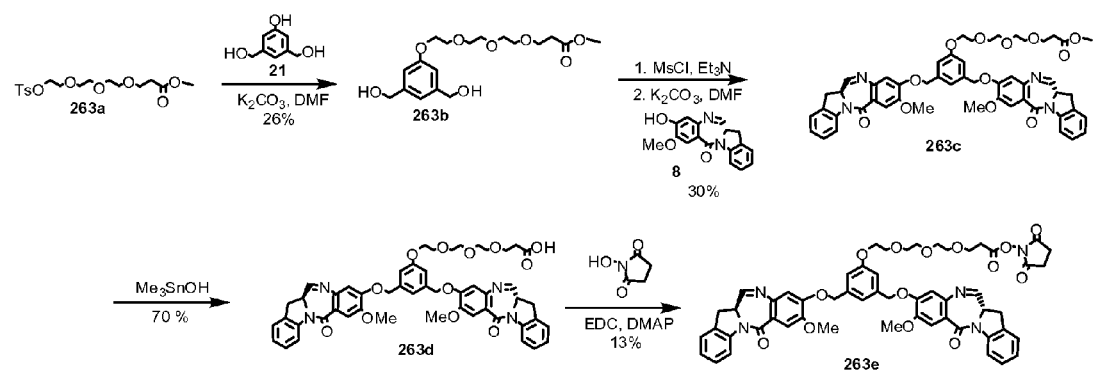
Figure 46. Synthetic scheme of dimer 264e (IGN-27-NHS).
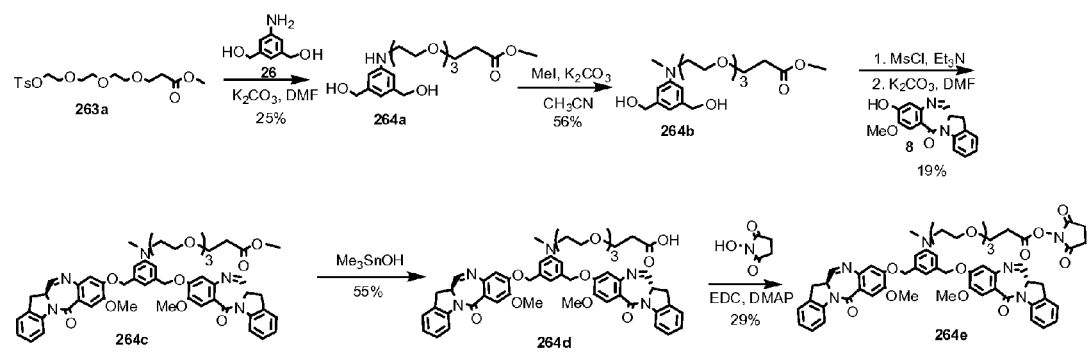

Figure 47. Synthetic scheme of dimer 265g (IGN-28-NHS).
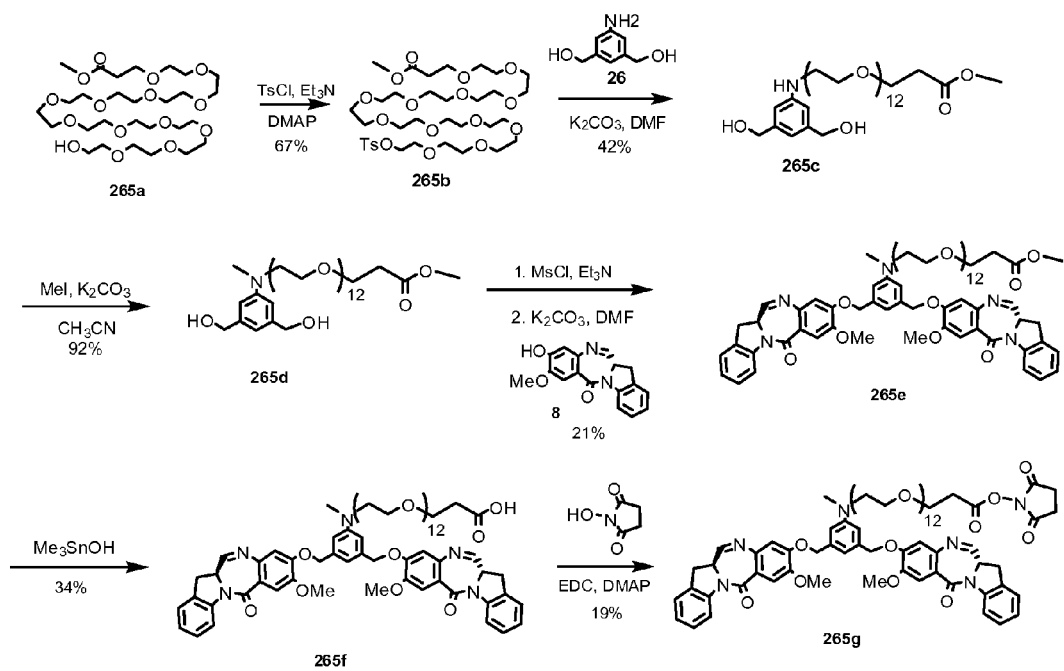
Figure 48. Synthetic scheme of dimer 266c (IGN-22-OMe).
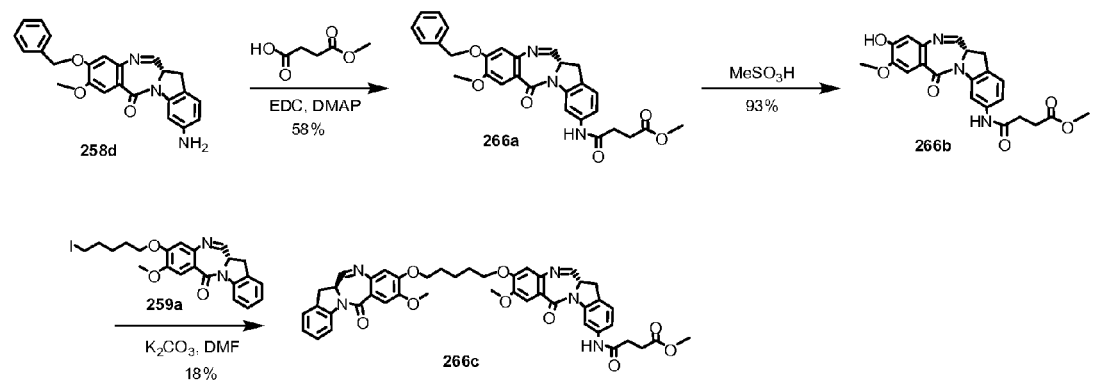

Figure 49. Synthetic scheme of dimer 267d (IGN-31-SMe).
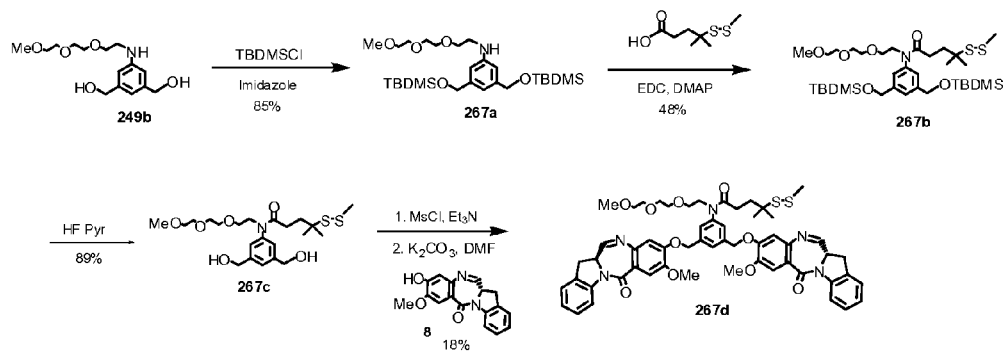
Figure 50. Synthetic scheme of dimer 268b (IGN-32-OtBu).
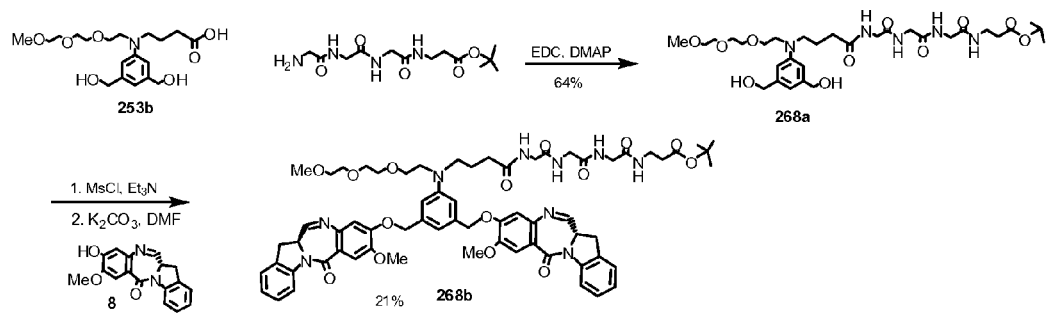

Figure 51. In Vitro Cytotoxicity of IGN Compounds

| IGN | IC50 (nM) | | | | | |
| --- | --- | --- | --- | --- | --- | --- |
| | Ramos | COLO205 | RH-30 | Namalwa | KB | LoVo |
| IGN13-OMe | 0.003 | 0.031 | 0.009 | 0.005 | 0.005 | |
| IGN14-OMe | 0.005 | 0.079 | 0.025 | 0.017 | 0.020 | |
| IGN15-SMe | 0.048 | 3.000 | 0.520 | 0.410 | | |
| IGN16-OMe | 0.003 | | | | 0.009 | 0.012 |
| IGN17-OMe | 3.000 | 3.000 | 0.048 | 3.000 | | |
| IGN18-OMe | 0.037 | | | | 0.890 | 0.570 |
| IGN19-OMe | 0.047 | | | | 0.350 | 0.800 |
| IGN20-SMe | | | | | 1.160 | |
| IGN21-SMe | | | | | 0.146 | |
| IGN23-OMe | | | | | 0.138 | |
| IGN24-OMe | | | | | 0.789 | |
| IGN25-OMe | | | | | | |
| IGN26-OMe | | 3.800 | | 0.200 | | |
| IGN27-OMe | | 0.210 | | 0.015 | | |
| IGN28-OMe | | 1.000 | | 0.130 | | |
| IGN30-OMe | | 2.900 | | 0.320 | 1.500 | |

Figure 52. Antiproliferative activity of chB38.1-IGN13 against (A) COLO 205 (Ag+) cells with and without blocking of antigen binding sites and (B) against LOVO (Ag+) cells.
A)
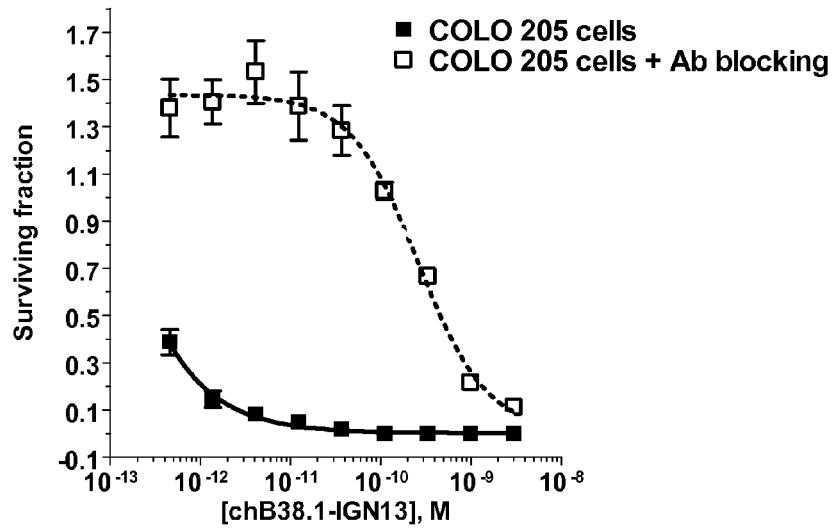
B)
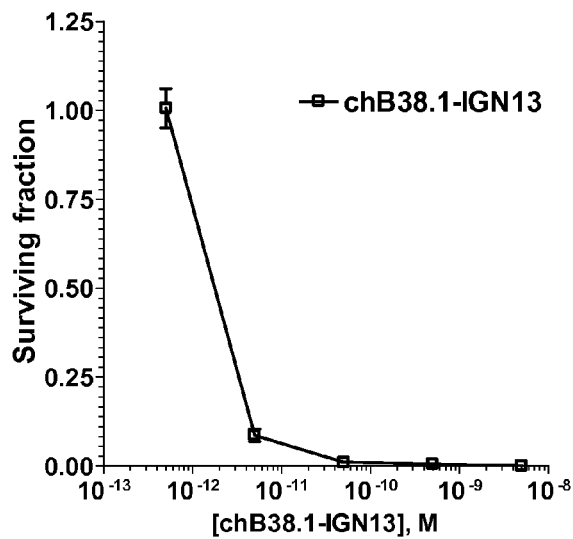

Figure 53. Antiproliferative activity of huMy9-6-IGN13 against NB-4 (Ag+) cells with and without blocking of antigen binding sites.
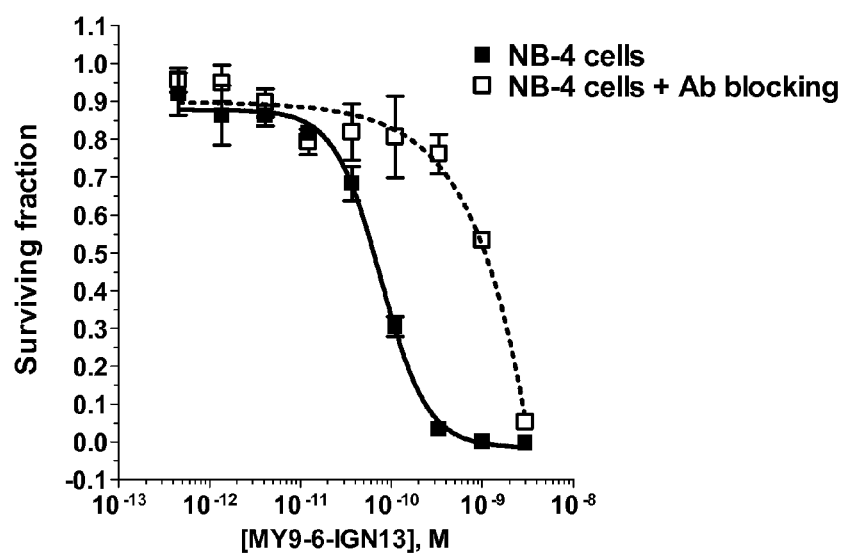

Figure 54. Antiproliferative activity of chB38.1-IGN14 against (A) COLO205 (Ag+) cells and (B) LOVO (Ag+) cells and Namalwa (Ag-) cells
A)
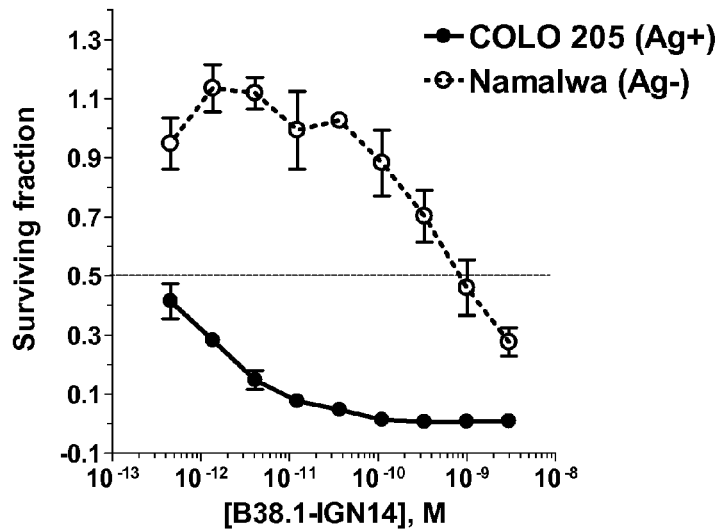
B)
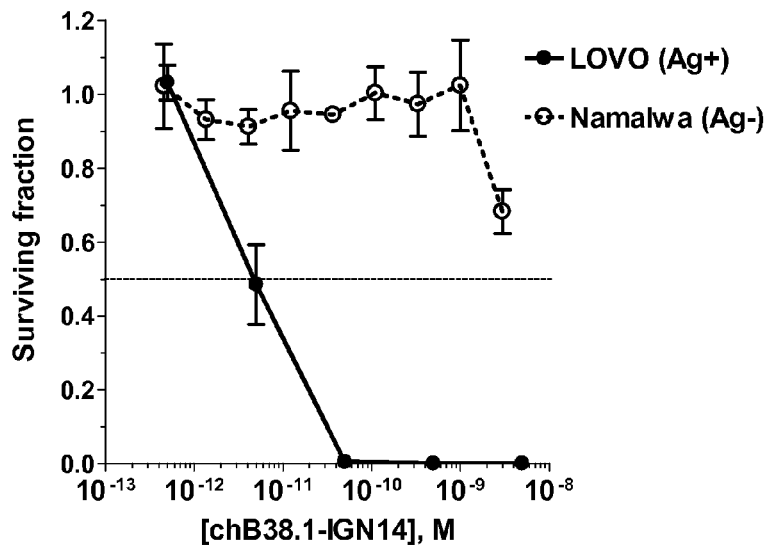

Figure 55. Antiproliferative activity of huMY9-6-IGN14 against NB-4 (Ag+) cells using Namalwa (Ag-) cells as a control.
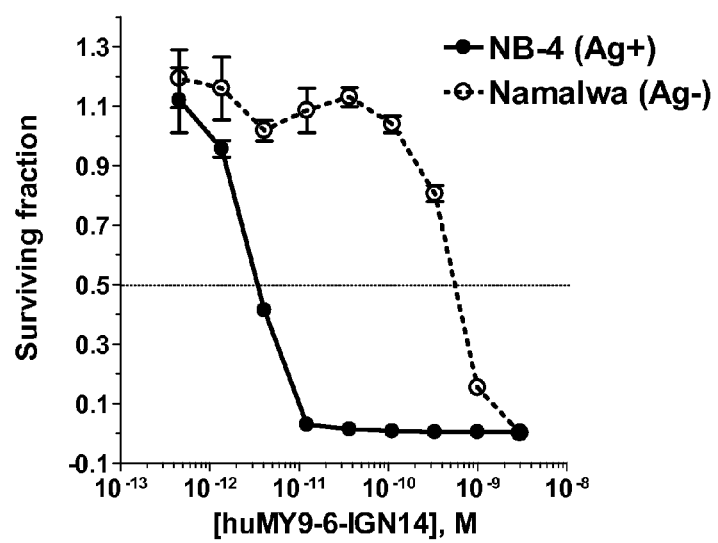

Figure 56. Antiproliferative activity of chB38.1-IGN23 (A) against LOVO (Ag+) cells using Namalwa (Ag-) cells as a control; and (B) against COLO205 (Ag+) cells with and without blocking antigen binding sites.
A)
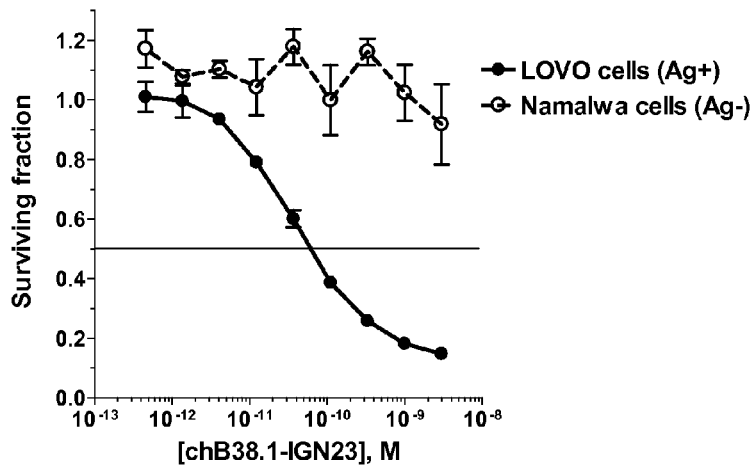
B)
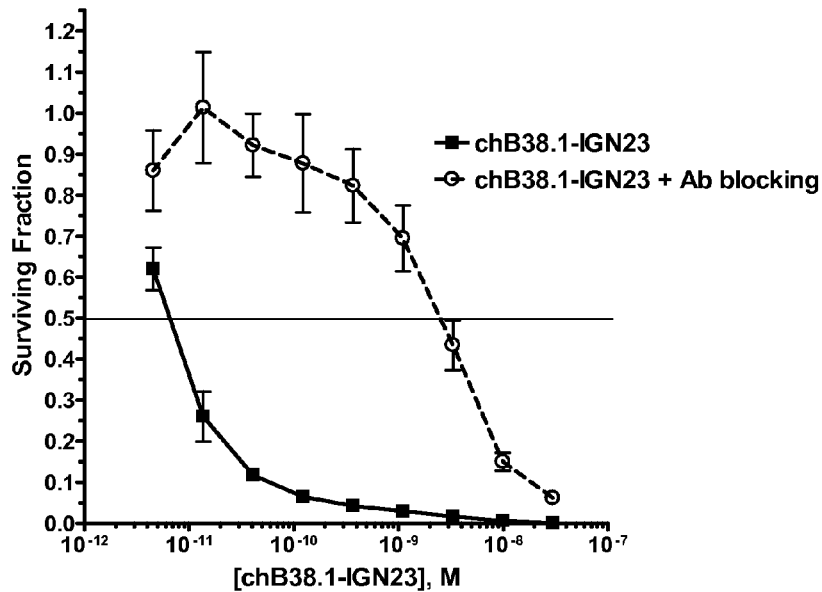

Figure 57. Antiproliferative activity of chB38.1-IGN29 against COLO205 (Ag+) cells with and without blocking antigen binding sites.
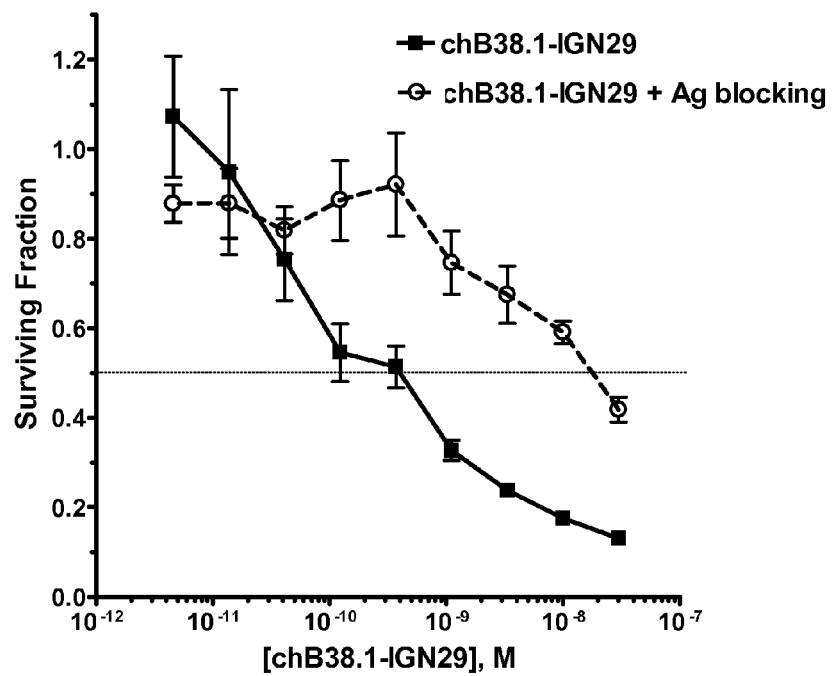

Figure 58. In vivo efficacy of chB38.1-IGN14 in COLO205 tumor bearing nude mice
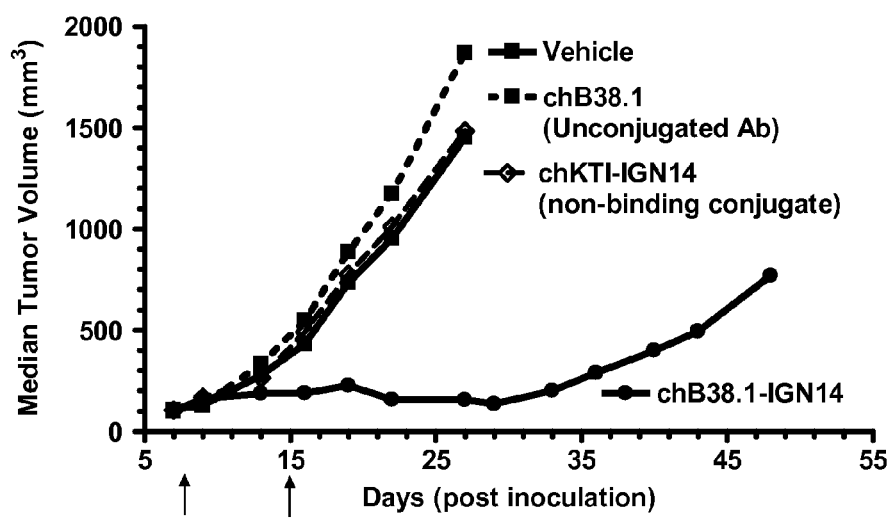

Figure 59. MS analysis of chB38.1-IGN14 conjugate
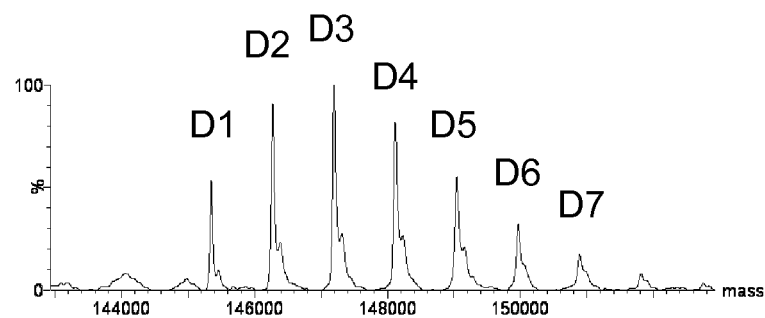

BENZODIAZEPINE DERIVATIVES

FIELD OF THE INVENTION

The present invention relates to novel cytotoxic compounds and cytotoxic conjugates comprising these cytotoxic compounds and cell-binding agents. More specifically, this invention relates to novel benzodiazepine compounds (e.g., indolinobenzodiazepines or oxazolidinobenzodiazepines), derivatives thereof, intermediates thereof, conjugates thereof, and pharmaceutically acceptable salts thereof, which are useful as medicaments, in particular as anti-proliferative agents.

BACKGROUND OF THE INVENTION

Benzodiazepine derivatives are useful compounds for treating various disorders, and include medicaments such as, antiepileptics (imidazo [2,1-b][1,3,5]benzothiadiazepines, U.S. Pat. No. 4,444,688; U.S. Pat. No. 4,062,852), antibacterials (pyrimido[1,2-c][1,3,5]benzothiadiazepines, GB 1476684), diuretics and hypotensives (pyrrolo(1,2-b)[1,2,5] benzothiadiazepine 5,5 dioxide, U.S. Pat. No. 3,506,646), hypolipidemics (WO 03091232), anti-depressants (U.S. Pat. No. 3,453,266); osteoporosis (JP 2138272).

Recently, it has been shown in animal tumor models that benzodiazepine derivatives, such as pyrrolobenzodiazepines (PBDs), act as anti-tumor agents (N-2-imidazolyl alkyl substituted 1,2,5-benzothiadiazepine-1,1-dioxide, U.S. Pat. No. 6,156,746), benzo-pyrido or dipyrido thiadiazepine (WO 2004/069843), pyrrolo [1,2-b][1,2,5]benzothiadiazepines and pirrole [1,2-b][1,2,5]benzodiazepine derivatives (WO2007/015280),tomaymycin derivatives (e.g., pyrrolo[1, 4]benzodiazepines), such as those described in WO 00/12508, WO2005/085260, WO2007/085930, and EP 2019104. Benzodiazepines are also known to affect cell growth and differentiation (Kamal A., et al., Bioorg Med Chem. 2008 Aug. 15;16(16):7804-10 (and references cited therein); Kumar R, Mini Rev Med Chem. 2003 Jun.;3(4):323-39 (and references cited therein); Bednarski J J, et al., 2004; Sutter A. P, et al., 2002; Blatt N B, et al., 2002), Kamal A. et al., Current Med. Chem., 2002; 2; 215-254, Wang J-J., J. Med. Chem., 2206; 49:1442-1449, Alley M. C. et al., Cancer Res. 2004; 64:6700-6706, Pepper C. J., Cancer Res 2004; 74:6750-6755, Thurston D. E. and Bose D. S., Chem Rev 1994; 94:433-465; and Tozuka, Z., et al., Journal of Antibiotics, (1983) 36; 1699-1708. General structure of PBDs is described in US Publication Number 20070072846. The PBDs differ in the number, type and position of substituents, in both their aromatic A rings and pyrrolo C rings, and in the degree of saturation of the C ring. Their ability to form an adduct in the minor groove enables them to interfere with DNA processing, hence their potential for use as antiproliferative agents.

There still exists a need for novel benzodiazepine derivatives as effective and safe therapeutics for treating a variety of proliferative disease states, such as cancer.

SUMMARY OF THE INVENTION

One object of the invention is to provide novel benzodiazepines of formula (I) and (II), in which the diazepine ring (B) is fused with a heterocyclic ring (CD), wherein the heterocyclic ring is bicyclic,

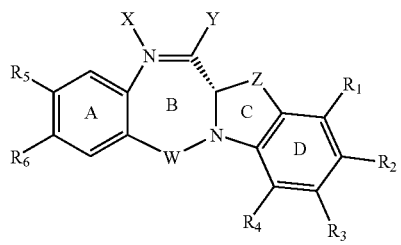

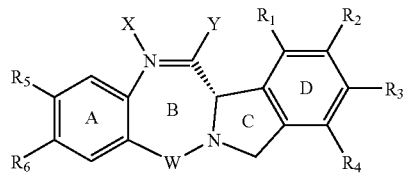

wherein:
the double line == between N and C represents a single bond or a double bond, provided that when it is a double bond X is absent and Y is H, and when it is a single bond, X is H, or an amine protecting moiety that converts the compound into a prodrug that can be transformed into the free amine in vitro or in vivo;

Y is selected from —OR, an ester represented by —OCOR', a carbonate represented by —OCOOR', a carbamate represented by —OCONR'R", an amine or a hydroxyl amine represented by NR'R", amide represented by —NRCOR', a peptide represented by NRCOP, wherein P is an amino acid or a polypeptide containing between 2 to 20 amino acid units, a thioether represented by SR', a sulfoxide represented by SOR', a sulfone represented by —SO$_2$R', a sulfite —SO$_3$, a bisulfite —OSO$_3$, a halogen, cyano, an azido, or a thiol, wherein R, R' and R" are same or different and are selected from H, substituted or unsubstituted linear, branched or cyclic alkyl, alkenyl or alkynyl having from 1 to 20 carbon atoms a polyethylene glycol unit (—OCH$_2$CH$_2$)$_n$, wherein n is an integer from 1 to 2000, a 5- or 6-membered heteroaryl ring containing one or more heteroatoms independently selected from nitrogen, oxygen, and sulfur, a 5 to 18 membered fused ring system, wherein at least one of the rings is aromatic, containing one or more heteroatoms independently selected from nitrogen, oxygen, and sulfur, aryl having from 6 to 18 carbon atoms, a 3 to 18-membered heterocyclic ring having 1 to 6 heteroatoms selected from O, S, N and P wherein the substituent is selected from halogen, OR$_7$, NR$_8$R$_9$, NO$_2$, NRCOR', SR$_{10}$, a sulfoxide represented by SOR', a sulfone represented by —SO$_2$R', a sulfite —SO$_3$, a bisulfite —OSO$_3$, a sulfonamide represented by SO$_2$NRR', cyano, an azido, —COR$_{11}$, OCOR$_{11}$ or OCONR$_{11}$R$_{12}$, wherein R$_7$, R$_8$, R$_9$, R$_{10}$, R$_{11}$ and R$_{12}$ are each independently selected from H, linear, branched or cyclic alkyl, alkenyl or alkynyl having from 1 to 10 carbon atoms, a polyethylene glycol unit (—OCH$_2$CH$_2$)$_n$, wherein n is an integer from 1 to 2000, a 5- or 6-membered heteroaryl ring containing one or more heteroatoms independently selected from nitrogen, oxygen, and sulfur a 5 to 18 membered fused ring system, wherein at least one of the rings is aromatic containing one or more heteroatoms independently selected from nitrogen, oxygen, and sulfur, aryl having from 6 to 18 carbon atoms 3 to 18-membered heterocyclic ring having 1 to 6 heteroatoms selected from O, S, N and P and R$_{10}$ optionally is SR$_{13}$ or COR$_{13}$, wherein R$_{13}$ is selected from linear, branched or cyclic alkyl, alkenyl or alkynyl having from 1 to 10 carbon atoms, a polyethylene glycol unit (—OCH$_2$CH$_2$)$_n$, wherein n is an integer from 1 to 2000, a 5- or 6-membered heteroaryl ring containing one or more heteroatoms independently selected from nitrogen, oxygen, and sulfur, a 5 to 18 membered fused ring system, wherein at least one of the rings is aromatic, containing one or more heteroatoms independently selected from nitrogen, oxygen, and sulfur, 3 to 18-membered heterocyclic ring having 1 to 6 heteroatoms selected from O, S, N and P and R$_{11}$ can also be OR$_{14}$, wherein R$_{14}$ is H or has the same definition as R, optionally, R" is an OH;

W is C=O, C=S, CH$_2$, BH (B=Boron), SO or SO$_2$;

R$_1$, R$_2$, R$_3$, R$_4$, are each independently selected from H, substituted or unsubstituted linear, branched or cyclic alkyl, alkenyl or alkynyl having from 1 to 10 carbon atoms, a polyethylene glycol unit (—OCH$_2$CH$_2$)$_n$, wherein n is an integer from 1 to 2000, or a substituent selected from a halogen, OR$_7$, NR$_8$R$_9$, NO$_2$, NRCOR', SR$_1$O, a sulfoxide represented by SOR', a sulfone represented by —SO$_2$R', a sulfite —SO$_3$, a bisulfite —OSO$_3$, a sulfonamide represented by SO$_2$NRR', cyano, an azido, guanidinium [—NH(C=NH)NH$_2$], —COR$_{11}$, —OCOR$_{11}$ or —OCONR$_{11}$R$_{12}$ wherein R$_7$, R$_8$, R$_9$, R$_{10}$, R$_{11}$ and R$_{12}$ have the same definitions as given above, optionally, any one of R$_1$, R$_2$, R$_3$, R$_4$ is a linking group that enables linkage to a cell binding agent via a covalent bond or is selected from a polypyrrolo, poly-indolyl, poly-imidazolyl, polypyrrolo-imidazolyl, poly-pyrrolo-indolyl or polyimidazolo-indolyl unit optionally bearing a linking group that enables linkage to a cell binding agent;

R$_5$ is selected from OR$_{15}$, CRR'OH, SH, CRR'SH, NHR$_{15}$ or CRR'NHR$_{15}$, wherein R$_{15}$ has the same definition as R., R and R' have the same definition as given above; optionally, R$_5$ is a linking group that enables linkage to a cell binding agent via a covalent bond or is selected from a polypyrrolo, poly-indolyl, poly-imidazolyl, polypyrrollo-imidazolyl, poly-pyrrolo-indolyl or polyimidazolo-indolyl unit optionally bearing a linking group that enables linkage to a cell binding agent;;

R$_6$ is OR, SR, NRR', wherein R and R' have the same definition as given above, or optionally R$_6$ is a linking group;

Z is selected from (CH$_2$)$_n$, wherein n is 1, 2 or 3, CR$_{15}$R$_{16}$, NR$_{17}$, O or S, wherein R$_{15}$R$_{16}$ and R$_{17}$ are each independently selected from H, linear, branched or cyclic alkyl having from 1 to 10 carbon atoms, a polyethylene glycol unit (—OCH$_2$CH$_2$)$_n$, wherein n is an integer from 1 to 2000; or their pharmaceutically acceptable solvates, salts, hydrates or hydrated salts, their optical isomers, racemates, diastereomers, enantiomers of these compounds provided that the compound has no more than one linking group that enables linkage to a cell binding agent via a covalent bond.

A second object of the invention is to provide novel benzodiazepines of formula (III), in which the diazepine ring (B) is fused with a heterocyclic ring (C), wherein the heterocyclic ring is monocyclic,

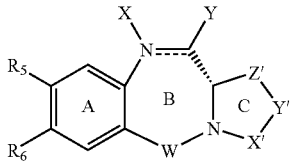

(III)

wherein:

the double line == between N and C represents a single bond or a double bond, provided that when it is a double bond X is absent and Y is H, and when it is a single bond, X is H or an amine protecting moiety that converts the compound into a prodrug;

Y is selected from —OR, an ester represented by —OCOR', a carbonate represented by —OCOOR', a carbamate represented by —OCONR'R", an amine or a hydroxyl amine represented by NR'R", amide represented by —NRCOR', a peptide represented by NRCOP, wherein P is an amino acid or a polypeptide containing between 2 to 20 amino acid units, a thioether represented by SR', a sulfoxide represented by SOR', a sulfone represented by —SO$_2$R', a sulfite —SO$_3$, a bisulfite —OSO$_3$, a halogen, cyano, an azido, or a thiol, wherein R, R' and R" are same or different and selected from H, substituted or unsubstituted linear, branched or cyclic alkyl, alkenyl or alkynyl having from 1 to 10 carbon atoms, a polyethylene glycol unit (—OCH$_2$CH$_2$)$_n$, wherein n is an integer from 1 to 2000, a 5- or 6-membered heteroaryl ring containing one or more heteroatoms independently selected from nitrogen, oxygen, and sulfur, a 5 to 18 membered fused ring system, wherein at least one of the rings is aromatic, containing one or more heteroatoms independently selected from nitrogen, oxygen, and sulfur, aryl having from 6 to 18 carbon atoms 3 to 18-membered heterocyclic ring having 1 to 6 heteroatoms selected from O, S, N and P, wherein the substituent is selected from halogen, OR$_7$, NR$_8$R$_9$, NO$_2$, NRCOR', SR$_{10}$, a sulfoxide represented by SOR', a sulfone represented by —SO$_2$R', a sulfite —SO$_3$, a bisulfite —OSO$_3$, a sulfonamide represented by SO$_2$NRR', cyano, an azido, —COR$_{11}$, OCOR$_{11}$ or OCONR$_{11}$R$_{12}$, wherein R$_7$, R$_8$, R$_9$, R$_{10}$, R$_{11}$ and R$_{12}$ are each independently selected from H, linear, branched or cyclic alkyl, alkenyl or alkynyl having from 1 to 10 carbon atoms, a polyethylene glycol unit (—OCH$_2$CH$_2$)$_n$, wherein n is an integer from 1 to 2000, a 5- or 6-membered heteroaryl ring containing one or more heteroatoms independently selected from nitrogen, oxygen, and sulfur, a 5 to 18 membered fused ring system, wherein at least one of the rings is aromatic, containing one or more heteroatoms independently selected from nitrogen, oxygen, and sulfur, aryl having from 6 to 18 carbon atoms 3 to 18-membered heterocyclic ring having 1 to 6 heteroatoms selected from O, S, N and P and R$_{10}$ optionally is SR$_{13}$ or COR$_{13}$, herein R$_{13}$ is selected from linear, branched or cyclic alkyl, alkenyl or alkynyl having from 1 to 10 carbon atoms, a polyethylene glycol unit (—OCH$_2$CH$_2$)$_n$, wherein n is an integer from 1 to 2000, a 5- or 6-membered heteroaryl ring containing one or more heteroatoms independently selected from nitrogen, oxygen, and sulfur, a 5 to 18 membered fused ring system, wherein at least one of the rings is aromatic, containing one or more heteroatoms independently selected from nitrogen, oxygen, and sulfur, aryl having from 6 to 18 carbon atoms, 3 to 18-membered heterocyclic ring having 1 to 6 heteroatoms selected from O, S, N and P and R$_{11}$ can also be OR$_{14}$, wherein R$_{14}$ is H or has the same definition as R, optionally R" is OH;

W is C=O, C=S, CH$_2$, BH, SO or SO$_2$;

R$_5$ is selected from OR$_{15}$, CRR'OH, SH, CRR'SH, NHR$_{15}$ or CRR'NHR$_{15}$, wherein R$_{15}$ has the same definition as R. or is a linking group that enables linkage to a cell binding agent via a covalent bond or is selected from a polypyrrolo, poly-indolyl, poly-imidazolyl, polypyrrollo-imidazolyl, poly-pyrollo-indolyl or polyimidazolo-indolyl unit optionally bearing a linking group that enables linkage to a cell binding agent;;

$R_6$ is OR, SR or NRR', wherein R and R' have the same definition as given above, optionally $R_6$ is a linking group;

X' is $CH_2$, NR, CO, BH, SO or $SO_2$;

Y' is O, $CH_2$, NR or S;

Z' is $CH_2$ or $(CH_2)_n$, wherein n is 2, 3 or 4; or their pharmaceutically acceptable solvates, salts, hydrates or hydrated salts, their optical isomers, racemates, diastereomers, enantiomers or the polymorphic crystalline structures of these compounds; provided that the compound has no more than one linking group that enables linkage to a cell binding agent via a covalent bond.

A third object of the invention is to provide cytotoxic dimers (IV), (V) and (VI)

heteroatoms independently selected from nitrogen, oxygen, and sulfur, a 5 to 18 membered fused ring system, wherein at least one of the rings is aromatic, containing one or more heteroatoms independently selected from nitrogen, oxygen, and sulfur, aryl having from 6 to 18 carbon atoms, 3 to 18-membered heterocyclic ring having 1 to 6 heteroatoms selected from O, S, N and P wherein the substituent is selected from halogen, $OR_7$, $NR_8R_9$, $NO_2$, NRCOR', $SR_{10}$, a sulfoxide represented by SOR', a sulfone represented by $—SO_2R'$, a sulfite $—SO_3$, a bisulfite $—OSO_3$, a sulfonamide represented by $SO_2NRR'$, cyano, an azido, $—COR_{11}$, $OCOR_{11}$ or $OCONR_{11}R_{12}$, wherein of $R_7$, $R_8$, $R_9$, $R_{10}$, $R_{11}$ and $R_{12}$ are each independently selected from H, linear, branched or cyclic alkyl, alkenyl or alkynyl having from 1 to 10 carbon atoms, a polyethylene glycol unit $(—OCH_2CH_2)_n$, wherein n is an integer from 1

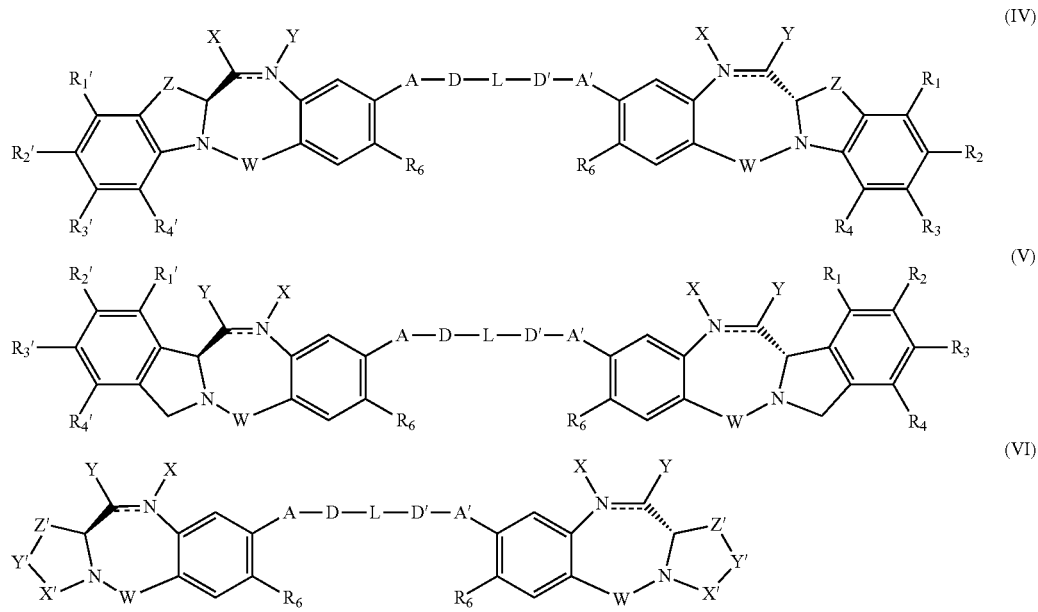

of the benzodiazepine monomers of formulas (I) and (II) and (III), respectively, in which the dimer compounds optionally bear a linking group that allows for linkage to cell binding agents, wherein:

the double line == between N and C represents a single bond or a double bond, provided that when it is a double bond X is absent and Y is H, and when it is a single bond, X is H or an amine protecting moiety that converts the compound into a prodrug;

Y is selected from —OR, an ester represented by —OCOR', a carbonate represented by —OCOOR', a carbamate represented by —OCONR'R", an amine or a hydroxyl amine represented by NR'R", amide represented by —NRCOR', a peptide represented by NRCOP, wherein P is an amino acid or a polypeptide containing between 2 to 20 amino acid units, a thioether represented by SR', a sulfoxide represented by SOR', a sulfone represented by —$SO_2R'$, a sulfite —$SO_3$, a bisulfite —$OSO_3$, a halogen, cyano, an azido, or a thiol, wherein R, R' and R" are same or different and are selected from H, substituted or unsubstituted linear, branched or cyclic alkyl, alkenyl or alkynyl having from 1 to 10 carbon atoms, a polyethylene glycol unit $(—OCH_2CH_2)n$, wherein n is an integer from 1 to 2000, a 5- or 6-membered heteroaryl ring containing one or more to 2000, a 5- or 6-membered heteroaryl ring containing one or more heteroatoms independently selected from nitrogen, oxygen, and sulfur, a 5 to 18 membered fused ring system, wherein at least one of the rings is aromatic, containing one or more heteroatoms independently selected from nitrogen, oxygen, and sulfur, aryl having from 6 to 18 carbon atoms, 3 to 10-membered heterocyclic ring having 3 to 18-membered heterocyclic ring having 1 to 6 heteroatoms selected from O, S, N and P and $R_{10}$ is optionally $SR_{13}$ or $COR_{13}$, wherein $R_{13}$ is selected from linear, branched or cyclic alkyl, alkenyl or alkynyl having from 1 to 10 carbon atoms, a 5- or 6-membered heteroaryl ring containing one or more heteroatoms independently selected from nitrogen, oxygen, and sulfur, a 5 to 18 membered fused ring system, wherein at least one of the rings is aromatic, containing one or more heteroatoms independently selected from nitrogen, oxygen, and sulfur, aryl having from 6 to 18 carbon atoms, 3 to 18-membered heterocyclic ring having 1 to 6 heteroatoms selected from O, S, N and P, optionally $R_{11}$ is $OR_{14}$, wherein $R_{14}$ has the same definition as R, optionally R" is OH;

W is C=O, C=S, $CH_2$, BH, SO or $SO_2$;

$R_1$, $R_2$, $R_3$, $R_4$, $R_1'$, $R_2'$, $R_3'$ and $R_4'$ are each independently selected from H, substituted or unsubstituted linear, branched or cyclic alkyl, alkenyl or alkynyl having from 1 to 10 carbon atoms, a polyethylene glycol unit (—OCH$_2$CH$_2$)n, wherein n is an integer from 1 to 2000, or a substituent selected from a halogen, guanidinium [—NH(C=NH)NH$_2$], OR$_7$, NR$_8$R$_9$, NO$_2$, NRCOR', SR$_{10}$, a sulfoxide represented by SOR', a sulfone represented by —SO$_2$R', a sulfite —SO$_3$, a bisulfite —OSO$_3$, a sulfonamide represented by SO$_2$NRR', cyano, an azido, —COR$_{11}$, OCOR$_{11}$ or OCONR$_{11}$R$_{12}$ wherein R$_7$, R$_8$, R$_9$, R$_{10}$, R$_{11}$ and R$_{12}$ are as defined aboveoptionally, any one of R$_1$, R$_2$, R$_3$, R$_4$, R$_1$', R$_2$', R$_3$', or R$_4$' is a linking group that enables linkage to a cell binding agent via a covalent bond or is selected from a polypyrrolo, poly-indolyl, poly-imidazolyl, polypyrrolo-imidazolyl, poly-pyrrolo-indolyl or polyimidazolo-indolyl unit optionally bearing a linking group that enables linkage to a cell binding agent, Z is selected from (CH$_2$)$_n$, wherein n is 1, 2 or 3, CR$_{15}$R$_{16}$, NR$_{17}$, O or S, wherein R$_{15}$, R$_{16}$ and R$_{17}$ are each independently selected from H, linear, branched or cyclic alkyl having from 1 to 10 carbon atoms, a polyethylene glycol unit (—OCH$_2$CH$_2$)$_n$, wherein n is an integer from 1 to 2000;

R$_6$ is OR, SR or NRR', wherein R and R' have the same definition as given above, optionally R$_6$ is a linking group;

X' is selected from CH$_2$, NR, CO, BH, SO or SO$_2$ wherein R has the same definition as given above;

Y' is O, CH$_2$, NR or S, wherein R has the same definition as given above;

Z' is CH$_2$ or (CH$_2$)$_n$, wherein n is 2, 3 or 4, provided that X', Y' and Z' are not all CH$_2$ at the same time;

A and A' are the same or different and are selected from O, —CRR'O, S, —CRR'S, —NR$_{15}$ or CRR'NHR$_{15}$, wherein R and R' have the same definition as given above and wherein R$_{15}$ has the same definition as R.

D and D' are same or different and independently selected from linear, branched or cyclic alkyl, alkenyl or alkynyl having 1 to 10 carbon atoms, optionally substituted with any one of halogen, OR$_7$, NR$_8$R$_9$, NO$_2$, NRCOR', SR$_{10}$, a sulfoxide represented by SOR', a sulfone represented by —SO$_2$R', a sulfite —SO$_3$, a bisulfite —OSO$_3$, a sulfonamide represented by SO$_2$NRR', cyano, an azido, —COR$_{11}$, OCOR$_{11}$ or OCONR$_{11}$R$_{12}$, wherein the definitions of R$_7$, R$_8$, R$_9$, R$_{10}$, R$_{11}$ and R$_{12}$ are as defined above, or a polyethylene glycol unit (—OCH$_2$CH$_2$)$_n$, wherein n is an integer from 1 to 2000;

L is an optional phenyl group or 3 to 18-membered heterocyclic ring having 1 to 6 heteroatoms selected from O, S, N and P that is optionally substituted, wherein the substituent is a linking group that enables linkage to a cell binding agent via a covalent bond, or is selected from linear, branched or cyclic alkyl, alkenyl or alkynyl having 1 to 10 carbon atoms, optionally substituted with any one of halogen, OR$_7$, NR$_8$R$_9$, NO$_2$, NRCOR', SR$_{10}$, a sulfoxide represented by SOR', a sulfone represented by —SO$_2$R', a sulfite —SO$_3$, a bisulfite —OSO$_3$, a sulfonamide represented by SO$_2$NRR', cyano, an azido, —COR$_{11}$, OCOR$_{11}$ or OCONR$_{11}$R$_{12}$, wherein R$_7$, R$_8$, R$_9$, R$_{10}$, R$_{11}$ and R$_{12}$ have the same definitions as given above, a polyethylene glycol unit (—OCH$_2$CH$_2$)n, wherein n is an integer from 1 to 2000; optionally, L itself is a linking group that enables linkage to a cell binding agent via a covalent bond; or their pharmaceutically acceptable solvates, salts, hydrates or hydrated salts, their optical isomers, racemates, diastereomers, enantiomers or the polymorphic crystalline structures of these compounds; provided that the compound has no more than one linking group that enables linkage to a cell binding agent via a covalent bond.

A fourth object of the invention is to provide conjugates of cell binding agents with the novel benzodiazepine compounds or derivatives thereof of the present invention. These conjugates are useful as therapeutic agents, which are delivered specifically to target cells and are cytotoxic.

The present invention includes a composition (e.g., a pharmaceutical composition) comprising novel benzodiazepine compounds, derivatives thereof, or conjugates thereof, (and/or solvates, hydrates and/or salts thereof) and a carrier (a pharmaceutically acceptable carrier). The present invention also includes a composition (e.g., a pharmaceutical composition) comprising novel benzodiazepine compounds, derivatives thereof, or conjugates thereof, (and/or solvates, hydrates and/or salts thereof) and a carrier (a pharmaceutically acceptable carrier), further comprising a second therapeutic agent. The present compositions are useful for inhibiting abnormal cell growth or treating a proliferative disorder in a mammal (e.g., human). The present compositions are also useful for treating depression, anxiety, stress, phobias, panic, dysphoria, psychiatric disorders, pain, and inflammatory diseases in a mammal (e.g., human).

The present invention includes a method of inhibiting abnormal cell growth or treating a proliferative disorder in a mammal (e.g., human) comprising administering to said mammal a therapeutically effective amount of novel benzodiazepine compounds, derivatives thereof, or conjugates thereof, (and/or solvates and salts thereof) or a composition thereof, alone or in combination with a second therapeutic agent.

The present invention includes a method of synthesizing and using novel benzodiazepine compounds, derivatives thereof, and conjugates thereof for in vitro, in situ, and in vivo diagnosis or treatment of mammalian cells, organisms, or associated pathological conditions.

The compounds of this invention, derivatives thereof, or conjugates thereof, and compositions comprising them, are useful for treating or lessening the severity of disorders, such as, characterized by abnormal growth of cells (e.g., cancer). Other applications for compounds and conjugates of this invention include, but are not limited to, treating osteoporosis, depression, anxiety, stress, phobias, panic, dysphoria, psychiatric disorders, and pain or as antiepileptics, antibacterials, diuretics and hypotensives, hypolipidemics, and antidepressants.

BRIEF DESCRIPTION OF THE FIGURES

FIGS. 1-10 show the schemes for the synthesis of indolinobenzodiazepine and oxazolidinobenzodiazepine monomers, the representative linkers and the dimers in the present invention.

FIG. 11 shows the scheme for the synthesis of the representative B-ring modified indolinobenzodiazepine monomer.

FIG. 12 shows the scheme for the synthesis of the representative isoindolinobenzodiazepine monomer.

FIG. 13 shows the scheme for the synthesis of the representative dimer with the linker directly attached on the indolinobenzodiazepine moiety in the present invention.

FIGS. 14 and 15 show the schemes for the synthesis of the representative dimers containing (PEG). moieties on the linkers.

FIG. 16 shows the schemes for the synthesis of the representative mixed imine-amine and imine-amide indolinobenzodiazepine dimers.

FIG. 17 shows the scheme for the synthesis of the representative IBD-poly(N-methylpyrrole-imidazole) conjugates.

FIGS. 18-19 show the synthetic scheme for the preparation of polypyrrolo and polypyrrolo-imidazolo derivatives of the monomers.

FIG. 20 shows a scheme for the synthesis of piperidinyl-benzodiazepines bearing a hydrazone linker.

FIGS. 21-26 show the dose dependent in vitro antiproliferative activity of muB38.1-IGN-03, huN901-IGN-03, huN901-IGN-07, and muB38.1-IGN-10 conjugates on antigen positive and antigen negative cancer cell lines.

FIG. 27 shows in vivo efficacy of huN901-IGN-07 conjugate in mice bearing Molp-8 tumors.

FIGS. 28-30 show data that demonstrate that IGN-01, IGN-02, and IGN-09 bind and covalently adduct to double stranded DNA containing guanine residues on opposite strands.

FIG. 31 contains TABLE 1, which shows the $IC_{50}$ values for in vitro antiproliferative activity of indolinobenzodiazepine dimers and oxazolidinobenzodiazepine dimer on several cancer cell lines.

FIG. 32 contains TABLE 2, which shows the comparison of the $IC_{50}$ values for in vitro antiproliferative activity of indolinobenzodiazepine dimers with and without linkers.

FIGS. 33-36, 39, 42, 43, 44, 48, 49 and 50 show synthetic schemes for the preparation of compounds of the present invention.

FIGS. 37, 38, 40 and 41, 45, 46, and 47 show synthetic schemes for the preparation of linkable compounds of the present invention.

FIG. 51 shows the in vitro cytotoxicity of compounds of the present invention.

FIGS. 52, 54, 56 57 and 58 show the in vitro cytotoxicity and specificity of chB38.1 conjugates.

FIGS. 53 and 55 show the in vitro cytotoxicity and specificity of huMy9-6 conjugates.

FIG. 59 shows the in vivo anti-tumor activity of chB38.1 conjugate

DETAILED DESCRIPTION OF THE INVENTION

Reference will now be made in detail to certain embodiments of the invention, examples of which are illustrated in the accompanying structures and formulas. While the invention will be described in conjunction with the enumerated embodiments, it will be understood that they are not intended to limit the invention to those embodiments. On the contrary, the invention is intended to cover all alternatives, modifications, and equivalents which may be included within the scope of the present invention as defined by the claims. One skilled in the art will recognize many methods and materials similar or equivalent to those described herein, which could be used in the practice of the present invention.

Definitions

"Linear or branched alkyl" as used herein refers to a saturated linear or branched-chain monovalent hydrocarbon radical of one to twenty carbon atoms. Examples of alkyl include, but are not limited to, methyl, ethyl, 1-propyl, 2-propyl, 1-butyl, 2-methyl-1-propyl, —CH$_2$CH(CH$_3$)$_2$), 2-butyl, 2-methyl-2-propyl, 1-pentyl, 2-pentyl 3-pentyl, 2-methyl-2-butyl, 3-methyl-2-butyl, 3-methyl-1-butyl, 2-methyl-1-butyl, 1-hexyl), 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, 1-heptyl, 1-octyl, and the like.

"Linear or branched alkenyl" refers to linear or branched-chain monovalent hydrocarbon radical of two to twenty carbon atoms with at least one site of unsaturation, i.e., a carbon-carbon, double bond, wherein the alkenyl radical includes radicals having "cis" and "trans" orientations, or alternatively, "E" and "Z" orientations. Examples include, but are not limited to, ethylenyl or vinyl (—CH═CH$_2$), allyl (—CH$_2$CH═CH$_2$), and the like.

"Linear or branched alkynyl" refers to a linear or branched monovalent hydrocarbon radical of two to twenty carbon atoms with at least one site of unsaturation, i.e., a carbon-carbon, triple bond. Examples include, but are not limited to, ethynyl, propynyl, 1-butynyl, 2-butynyl, 1-pentynyl, 2-pentynyl, 3-pentynyl, hexynyl, and the like.

The terms "cyclic alkyl", "cyclic alkenyl", "cyclic alkynyl", "carbocycle", "carbocyclyl", "carbocyclic ring" and "cycloalkyl" refer to a monovalent non-aromatic, saturated or partially unsaturated ring having 3 to 12 carbon atoms as a monocyclic ring or 7 to 12 carbon atoms as a bicyclic ring. Bicyclic carbocycles having 7 to 12 atoms can be arranged, for example, as a bicyclo [4,5], [5,5], [5,6] or [6,6] system, and bicyclic carbocycles having 9 or 10 ring atoms can be arranged as a bicyclo [5,6] or [6,6] system, or as bridged systems such as bicyclo[2.2.1]heptane, bicyclo[2.2.2]octane and bicyclo[3.2.2]nonane. Examples of monocyclic carbocycles include, but are not limited to, cyclopropyl, cyclobutyl, cyclopentyl, 1-cyclopent-I-enyl, 1-cyclopent-2-enyl, 1-cyclopent-3-enyl, cyclohexyl, 1-cyclohex-I-enyl, 1-cyclohex-2-enyl, 1-cyclohex-3-enyl, cyclohexadienyl, cycloheptyl, cyclooctyl, cyclononyl, cyclodecyl, cycloundecyl, cyclododecyl, and the like.

"Aryl" means a monovalent aromatic hydrocarbon radical of 6-18 carbon atoms derived by the removal of one hydrogen atom from a single carbon atom of a parent aromatic ring system. Some aryl groups are represented in the exemplary structures as "Ar". Aryl includes bicyclic radicals comprising an aromatic ring fused to a saturated, partially unsaturated ring, or aromatic carbocyclic or heterocyclic ring. Typical aryl groups include, but are not limited to, radicals derived from benzene (phenyl), substituted benzenes, naphthalene, anthracene, indenyl, indanyl, 1,2-dihydronapthalene, 1,2,3,4-tetrahydronapthyl, and the like.

The terms "heterocycle," "heterocyclyl" and "heterocyclic ring" are used interchangeably herein and refer to a saturated or a partially unsaturated (i.e., having one or more double and/or triple bonds within the ring) carbocyclic radical of 3 to 18 ring atoms in which at least one ring atom is a heteroatom selected from nitrogen, oxygen, phosphorus, and sulfur, the remaining ring atoms being C, where one or more ring atoms is optionally substituted independently with one or more substituents described below. A heterocycle may be a monocycle having 3 to 7 ring members (2 to 6 carbon atoms and 1 to 4 heteroatoms selected from N, O, P, and S) or a bicycle having 7 to 10 ring members (4 to 9 carbon atoms and 1 to 6 heteroatoms selected from N, O, P, and S), for example: a bicyclo [4,5], [5,5], [5,6], or [6,6] system. Heterocycles are described in Paquette, Leo A.; "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and J. Am. Chem. Soc. (1960) 82:5566. "Heterocyclyl" also includes radicals where heterocycle radicals are fused with a saturated, partially unsaturated ring, or aromatic carbocyclic or heterocyclic ring. Examples of heterocyclic rings include, but are not limited to, pyrrolidinyl, tetrahydrofuranyl, dihydrofuranyl, tetrahydrothienyl, tetrahydropyranyl, dihydropyranyl, tetrahydrothiopyranyl, piperidino, morpholino, thiomorpholino, thioxanyl, piperazinyl, homopiperazinyl, azetidinyl, oxetanyl, thietanyl, homopiperidinyl, oxepanyl, thiepanyl, oxazepinyl, diazepinyl, thiazepinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinylimidazolinyl, imidazolidinyl, 3-azabicyco[3.1.0]hexanyl, 3-azabicyclo[4.1.0]heptanyl, and azabicyclo[2.2.2]hexanyl. Spiro moieties are also included within the scope of this definition. Examples of a heterocyclic group wherein ring atoms are substituted with oxo (═O) moieties are pyrimidinonyl and 1,1-dioxo-thiomorpholinyl.

The term "heteroaryl" refers to a monovalent aromatic radical of 5- or 6-membered rings, and includes fused ring systems (at least one of which is aromatic) of 5-18 atoms, containing one or more heteroatoms independently selected from nitrogen, oxygen, and sulfur. Examples of heteroaryl groups are pyridinyl (including, for example, 2-hydroxypyridinyl), imidazolyl, imidazopyridinyl, pyrimidinyl (including, for example, 4-hydroxypyrimidinyl), pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, triazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl.

The heterocycle or heteroaryl groups may be carbon (carbon-linked) or nitrogen (nitrogen-linked) attached where such is possible. By way of example and not limitation, carbon bonded heterocycles or heteroaryls are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline.

By way of example and not limitation, nitrogen bonded heterocycles or heteroaryls are bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, 1H-indazole, position 2 of a isoindole, or isoindoline, position 4 of a morpholine, and position 9 of a carbazole, or O-carboline.

The heteroatoms present in heteroaryl or heterocycicyl include the oxidized forms such as NO, SO, and $SO_2$.

The term "halo" or "halogen" refers to F, Cl, Br or I.

The term "compound" or "cytotoxic compound" or "cytotoxic agent" as used herein is intended to include compounds for which a structure or formula or any derivative thereof has been disclosed in the present invention or a structure or formula or any derivative thereof that has been incorporated by reference. The term also includes, stereoisomers, geometric isomers, tautomers, solvates, metabolites, salts (e.g., pharmaceutically acceptable salts) and prodrugs, and prodrug salts of a compound of all the formulae disclosed in the present invention. The term also includes any solvates, hydrates, and polymorphs of any of the foregoing. The specific recitation of "stereoisomers", "geometric isomers", "tautomers", "solvates", "metabolites", "salt" "prodrug," "prodrug salt," "conjugates," "conjugates salt," "solvate," "hydrate," or "polymorph" in certain aspects of the invention described in this application shall not be interpreted as an intended omission of these forms in other aspects of the invention where the term "compound" is used without recitation of these other forms.

The term "conjugate" as used herein refers to a compound or a derivative thereof that is linked to a cell binding agent and is defined by a generic formula: C-L-CBA, wherein C=compound, L=linker, and CBA=cell binding agent.

The term "linkable to a cell binding agent" as used herein referes to the novel benzodiazepine compounds (e.g., indolinobenzodiazepine or oxazolidinobenzodiazepine), derivates thereof or dimers thereof comprising at least one linking group or a precursor thereof suitable to bond these compounds, derivatives thereof or dimers thereof to a cell binding agent.

The term "precursor" of a given group refers to any group which may lead to that group by any deprotection, a chemical modification, or a coupling reaction.

The term "linked to a cell binding agent" refers to a conjugate molecule comprising at least one the novel benzodiazepine compounds (e.g., indolinobenzodiazepine or oxazolidinobenzodiazepine), derivates thereof or dimers thereof bound to a cell binding agent via a suitable linking group or a precursor thereof.

The term "chiral" refers to molecules which have the property of non-superimposability of the mirror image partner, while the term "achiral" refers to molecules which are superimposable on their mirror image partner.

The term "stereoisomer" refers to compounds which have identical chemical constitution and connectivity, but different orientations of their atoms in space that cannot be interconverted by rotation about single bonds.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as crystallization, electrophoresis and chromatography.

"Enantiomers" refer to two stereoisomers of a compound which are non-superimposable mirror images of one another.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and I or (+) and (−) are employed to designate the sign of rotation of plane-polarized light by the compound, with (−) or 1 meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

A substituent is "substitutable" if it comprises at least one carbon, sulfur, oxygen or nitrogen atom that is bonded to one or more hydrogen atoms. Thus, for example, hydrogen, halogen, and cyano do not fall within this definition.

If a substituent is described as being "substituted," a non-hydrogen substituent is in the place of a hydrogen substituent on a carbon, oxygen, sulfur or nitrogen of the substituent. Thus, for example, a substituted alkyl substituent is an alkyl substituent wherein at least one non-hydrogen substituent is in the place of a hydrogen substituent on the alkyl substituent. To illustrate, monofluoroalkyl is alkyl substituted with a fluoro substituent, and difluoroalkyl is alkyl substituted with two fluoro substituents. It should be recognized that if there is more than one substitution on a substituent, each non-hydrogen substituent may be identical or different (unless otherwise stated).

If a substituent is described as being "optionally substituted," the substituent may be either (1) not substituted, or (2) substituted. If a carbon of a substituent is described as being optionally substituted with one or more of a list of substituents, one or more of the hydrogens on the carbon (to the extent there are any) may separately and/or together be replaced with an independently selected optional substituent. If a nitrogen of a substituent is described as being optionally substituted with one or more of a list of substituents, one or more of the hydrogens on the nitrogen (to the extent there are any) may each be replaced with an independently selected optional substituent. One exemplary substituent may be depicted as —NR'R,' wherein R' and R" together with the nitrogen atom to which they are attached, may form a heterocyclic ring. The heterocyclic ring formed from R' and R" together with the nitrogen atom to which they are attached may be partially or fully saturated. In one embodiment, the heterocyclic ring consists of 3 to 7 atoms. In another embodiment, the heterocyclic ring is selected from the group consisting of pyrrolyl, imidazolyl, pyrazolyl, triazolyl, tetrazolyl, isoxazolyl, pyridyl and thiazolyl.

This specification uses the terms "substituent," "radical," and "group" interchangeably.

If a group of substituents are collectively described as being optionally substituted by one or more of a list of substituents, the group may include: (1) unsubstitutable substituents, (2) substitutable substituents that are not substituted by the optional substituents, and/or (3) substitutable substituents that are substituted by one or more of the optional substituents.

If a substituent is described as being optionally substituted with up to a particular number of non-hydrogen substituents, that substituent may be either (1) not substituted; or (2) substituted by up to that particular number of non-hydrogen substituents or by up to the maximum number of substitutable positions on the substituent, whichever is less. Thus, for example, if a substituent is described as a heteroaryl optionally substituted with up to 3 non-hydrogen substituents, then any heteroaryl with less than 3 substitutable positions would be optionally substituted by up to only as many non-hydrogen substituents as the heteroaryl has substitutable positions. Such substituents, in non-limiting examples, can be selected from a linear, branched or cyclic alkyl, alkenyl or alkynyl having from 1 to 10 carbon atoms, halogen, guanidinium [—NH(C=NH)NH$_2$], OR$_7$, NR$_8$R$_9$, NO$_2$, NRCOR', SR10, a sulfoxide represented by SOR', a sulfone represented by —SO$_2$R', a sulfite —SO$_3$, a bisulfite —OSO$_3$, a sulfonamide represented by SO$_2$NRR', cyano, an azido, —COR$_{11}$, OCOR$_{11}$ or OCONR$_{11}$R$_{12}$ wherein R$_7$, R$_8$, R$_9$, R$_{10}$, R$_{11}$ and R$_{12}$ are each independently selected from H, linear, branched or cyclic alkyl, alkenyl or alkynyl having from 1 to 10 carbon atoms, a polyethylene glycol unit (—OCH$_2$CH$_2$)$_n$, wherein n is an integer from 1 to 2000, aryl having from 6 to 10 carbon atoms, heterocyclic ring having from 3 to 10 carbon atoms.

The term "prodrug" as used in this application refers to a precursor or derivative form of a compound of the invention that is capable of being enzymatically or hydrolytically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). The prodrugs of this invention include, but are not limited to, ester-containing prodrugs, phosphate-containing prodrugs, thiophosphate-containing prodrugs, sulfate-containing prodrugs, peptide-containing prodrugs, D-amino acid-modified prodrugs, glycosylated prodrugs, .beta.-lactam-containing prodrugs, optionally substituted phenoxyacetamide-containing prodrugs, optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, compounds of the invention and chemotherapeutic agents such as described above.

The term "prodrug" is also meant to include a derivative of a compound that can hydrolyze, oxidize, or otherwise react under biological conditions (in vitro or in vivo) to provide a compound of this invention. Prodrugs may only become active upon such reaction under biological conditions, or they may have activity in their unreacted forms. Examples of prodrugs contemplated in this invention include, but are not limited to, analogs or derivatives of compounds of any one of the formulae disclosed herein that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of any one of the formulae disclosed herein that comprise —NO, —NO$_2$, —ONO, or —ONO$_2$ moieties. Prodrugs can typically be prepared using well-known methods, such as those described by Burger's Medicinal Chemistry and Drug Discovery (1995) 172-178, 949-982 (Manfred E. Wolff ed., 5th ed); see also Goodman and Gilman's, The Pharmacological basis of Therapeutics, 8th ed., McGraw-Hill, Int. Ed. 1992, "Biotransformation of Drugs".

As used herein and unless otherwise indicated, the terms "biohydrolyzable amide", "biohydrolyzable ester", "biohydrolyzable carbamate", "biohydrolyzable carbonate", "biohydrolyzable ureide" and "biohydrolyzable phosphate analogue" mean an amide, ester, carbamate, carbonate, ureide, or phosphate analogue, respectively, that either: 1) does not destroy the biological activity of the compound and confers upon that compound advantageous properties in vivo, such as uptake, duration of action, or onset of action; or 2) is itself biologically inactive but is converted in vivo to a biologically active compound. Examples of biohydrolyzable amides include, but are not limited to, lower alkyl amides, .alpha.-amino acid amides, alkoxyacyl amides, and alkylaminoalkylcarbonyl amides. Examples of biohydrolyzable esters include, but are not limited to, lower alkyl esters, alkoxyacyloxy esters, alkyl acylamino alkyl esters, and choline esters. Examples of biohydrolyzable carbamates include, but are not limited to, lower alkylamines, substituted ethylenediamines, amino acids, hydroxyalkylamines, heterocyclic and heteroaromatic amines, and polyether amines. Particularly favored prodrugs and prodrug salts are those that increase the bioavailability of the compounds of this invention when such compounds are administered to a mammal.

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

As used herein, the term "solvate" means a compound which further includes a stoichiometric or non-stoichiometric amount of solvent such as water, isopropanol, acetone, ethanol, methanol, DMSO, ethyl acetate, acetic acid, and ethanolamine dichloromethane, 2-propanol, or the like, bound by non-covalent intermolecular forces. Solvates or hydrates of the compounds are readily prepared by addition of at least one molar equivalent of a hydroxylic solvent such as methanol, ethanol, 1-propanol, 2-propanol or water to the compound to result in solvation or hydration of the imine moiety.

The terms "abnormal cell growth" and "proliferative disorder" are used interchangeably in this application. "Abnormal cell growth", as used herein, unless otherwise indicated, refers to cell growth that is independent of normal regulatory mechanisms (e.g., loss of contact inhibition). This includes, for example, the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (3) any tumors that proliferate by receptor tyrosine kinases; (4) any tumors that proliferate by aberrant serine/threonine kinase activation; and (5) benign and malignant cells of other proliferative diseases in which aberrant serine/threonine kinase activation occurs.

The terms "cancer" and "cancerous" refer to or describe the physiological condition in mammals that is typically characterized by unregulated cell growth. A "tumor" comprises one or more cancerous cells. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, acute leukemia, as well as head/brain and neck cancer.

A "therapeutic agent" encompasses both a biological agent such as an antibody, a peptide, a protein, an enzyme or a chemotherapeutic agent. A "chemotherapeutic agent" is a chemical compound useful in the treatment of cancer. Examples of chemotherapeutic agents include Erlotinib (TARCEVA®, Genentech/OSI Pharm.), Bortezomib (VELCADE®, Millennium Pharm.), Fulvestrant (FASLODEX®, AstraZeneca), Sutent (SU11248, Pfizer), Letrozole (FEMARA®, Novartis), Imatinib mesylate (GLEEVEC®, Novartis), PTK787/ZK 222584 (Novartis), Oxaliplatin (Eloxatin®, Sanofi), 5-FU (5-fluorouracil), Leucovorin, Rapamycin (Sirolimus, RAPAMUNEO, Wyeth), Lapatinib (TYKERB®, GSK572016, Glaxo Smith Kline), Lonafarnib (SCH 66336), Sorafenib (BAY43-9006, Bayer Labs), and Gefitinib (IRESSA®, AstraZeneca), AG1478, AG1571 (SU 5271; Sugen), alkylating agents such as thiotepa and CYTOXAN® cyclophosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gammaII and calicheamicin omegaII (Angew Chem. Intl. Ed. Engl. (1994) 33:183-186); dynemicin, including dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCINO (doxorubicin), morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamniprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® (paclitaxel; Bristol-Myers Squibb Oncology, Princeton, N.J.), ABRAXANE® (Cremophor-free), albumin-engineered nanoparticle formulations of paclitaxel (American Pharmaceutical Partners, Schaumberg, Ill.), and TAXOTERE® (doxetaxel; Rhone-Poulenc Rorer, Antony, France); chloranmbucil; GEMZAR® (gemcitabine); 6-thioguanine; mercaptopurine; methotrexate; platinum analogs such as cisplatin and carboplatin; vinblastine; etoposide (VP-16); ifosfamide; mitoxantrone; vincristine; NAVELBINEO (vinorelbine); novantrone; teniposide; edatrexate; daunomycin; aminopterin; capecitabine (XELODA®); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASINO (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors; (v) lipid kinase inhibitors; (vi) antisense oligonucleotides, particularly those which inhibit expression of genes in signaling pathways implicated in aberrant cell proliferation, such as, for example, PKC-alpha, Ralf and H-Ras; (vii) ribozymes such as VEGF expression inhibitors (e.g., ANGIOZYME®) and HER2 expression inhibitors; (viii) vaccines such as gene therapy vaccines, for example, ALLOVECTINO, LEUVECTINO., and VAXID®.; PROLEUKINO rIL-2; a topoisomerase 1 inhibitor such as LURTOTECAN®; ABARELIX® rmRH; (ix) anti-angiogenic agents such as bevacizumab (AVASTINO, Genentech); and (x) pharmaceutically acceptable salts, acids and derivatives of any of the above. Other anti-angiogenic agents include MMP-2 (matrix-metalloproteinase 2) inhibitors, MMP-9 (matrix-metalloproteinase 9) inhibitors, COX-II (cyclooxygenase II) inhibitors, and VEGF receptor tyrosine kinase inhibitors. Examples of such useful matrix metalloproteinase inhibitors that can be used in combination with the present compounds/compositions are described in WO 96/33172, WO 96/27583, EP 818442, EP 1004578, WO 98/07697, WO 98/03516, WO 98/34918, WO 98/34915, WO 98/33768, WO 98/30566, EP 606,046, EP 931,788, WO 90/05719, WO 99/52910, WO 99/52889, WO 99/29667, WO 99/07675, EP 945864, U.S. Pat. Nos. 5,863,949, 5,861,510, and EP 780, 386, all of which are incorporated herein in their entireties by reference. Examples of VEGF receptor tyrosine kinase inhibitors include 4-(4-bromo-2-fluoroanilino)-6-methoxy-7-(1-methylpiperidin-4-ylmethoxy)qu- inazoline (ZD6474; Example 2 within WO 01/32651), 4-(4-fluoro-2-methylindo1-5-yloxy)-6-methoxy-7-(3-pyrrolidin-1-ylpropoxy)--quinazoline (AZD2171; Example 240 within WO 00/47212), vatalanib (PTK787; WO 98/35985) and SU11248 (sunitinib; WO 01/60814), and compounds such as those disclosed in PCT Publication Nos. WO 97/22596, WO 97/30035, WO 97/32856, and WO 98/13354).

Other examples of chemotherapeutic agents that can be used in combination with the present compounds include inhibitors of PI3K (phosphoinositide-3 kinase), such as those reported in Yaguchi et al (2006) Jour. of the Nat. Cancer Inst. 98(8):545-556; U.S. Pat. Nos. 7,173,029; 7,037,915; 6,608, 056; 6,608,053; 6,838,457; 6,770,641; 6,653,320; 6,403,588; WO 2006/046031; WO 2006/046035; WO 2006/046040; WO 2007/042806; WO 2007/042810; WO 2004/017950; US 2004/092561; WO 2004/007491; WO 2004/006916; WO 2003/037886; US 2003/149074; WO 2003/035618; WO 2003/034997; US 2003/158212; EP 1417976; US 2004/053946; JP 2001247477; JP 08175990; JP 08176070; U.S. Pat. No. 6,703,414; and WO 97/15658, all of which are incorporated herein in their entireties by reference. Specific examples of such PI3K inhibitors include SF-1126 (PI3K inhibitor, Semafore Pharmaceuticals), BEZ-235 (PI3K inhibitor, Novartis), XL-147 (PI3K inhibitor, Exelixis, Inc.).

A "metabolite" is a product produced through metabolism in the body of a specified compound, a derivative thereof, or a conjugate thereof, or salt thereof. Metabolites of a compound, a derivative thereof, or a conjugate thereof, may be identified using routine techniques known in the art and their activities determined using tests such as those described herein. Such products may result for example from the oxidation, hydroxylation, reduction, hydrolysis, amidation, deamidation, esterification, deesterification, enzymatic cleavage, and the like, of the administered compound. Accordingly, the invention includes metabolites of compounds, a derivative thereof, or a conjugate thereof, of the invention, including compounds, a derivative thereof, or a conjugate thereof, produced by a process comprising contacting a compound, a derivative thereof, or a conjugate thereof, of this invention with a mammal for a period of time sufficient to yield a metabolic product thereof The phrase "pharmaceutically acceptable" indicates that the substance or composition must be compatible chemically and/or toxicologically, with the other ingredients comprising a formulation, and/or the mammal being treated therewith.

The term "protecting group" or "protecting moiety" refers to a substituent that is commonly employed to block or protect a particular functionality while reacting other functional groups on the compound, a derivative thereof, or a conjugate thereof. For example, an "amino-protecting group" or an "amino-protecting moiety" is a substituent attached to an amino group that blocks or protects the amino functionality in the compound. Suitable amino-protecting groups include acetyl, trifluoroacetyl, t-butoxycarbonyl (BOC), benzyloxycarbonyl (CBZ) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include phenylsulfonylethyl, cyanoethyl, 2-(trimethylsilyl) ethyl, 2-(trimethylsilyl)ethoxymethyl, 2-(p-toluenesulfonyl) ethyl, 2-(p-nitrophenylsulfenyl)ethyl, 2-(diphenylphosphino)-ethyl, nitroethyl and the like. Common thiol-protecting groups include those that convert the thiol into a thioester, such as acetyl, benzoyl or trifluoroacetyl, into a thioether, such as benzyl, t-butyl, triphenylmethyl, 9-fluorenylmetyl, methoxymethyl, 2-tetrahydropyranyl or silyl, into a disulfide, such as methyl, benzyl, t-butyl, pyridyl, nitropyridyl, phenyl, nitrophenyl or dinitrophenyl, into a thiocarbonate, such as t-butoxycarbonyl, into a thiocarbamate, such as N-ethyl. For a general description of protecting groups and their use, see P. G. M. Wuts & T. W. Greene, Protective Groups in Organic Synthesis, John Wiley & Sons, New York, 2007.

For novel benzodiazepines of formula (I) and (II),

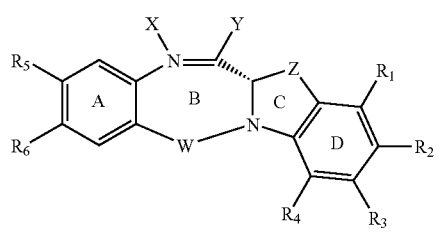

(I)

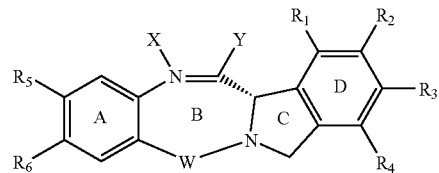

(II)

wherein:

the double line = between N and C represents a single bond or a double bond, provided that when it is a double bond X is absent and Y is H, and when it is a single bond, X is H, or an amine protecting moiety that converts the compound into a prodrug that can be transformed into the free amine in vitro or in vivo;

Y is selected from —OR, an ester represented by —OCOR', a carbonate represented by —OCOOR', a carbamate represented by —OCONR'R", an amine or a hydroxyl amine represented by NR'R", amide represented by —NRCOR', a peptide represented by NRCOP, wherein P is an amino acid or a polypeptide containing between 2 to 20 amino acid units, a thioether represented by SR', a sulfoxide represented by SOR', a sulfone represented by —SO$_2$R', a sulfite —SO$_3$, a bisulfite —OSO$_3$, a halogen, cyano, an azido, or a thiol, wherein R, R' and R" are same or different and are selected from H, substituted or unsubstituted linear, branched or cyclic alkyl, alkenyl or alkynyl having from 1 to 20 carbon atoms a polyethylene glycol unit (—OCH$_2$CH$_2$)$_2$, wherein n is an integer from 1 to 2000, a 5- or 6-membered heteroaryl ring containing one or more heteroatoms independently selected from nitrogen, oxygen, and sulfur, a 5 to 18 membered fused ring system, wherein at least one of the rings is aromatic, containing one or more heteroatoms independently selected from nitrogen, oxygen, and sulfur, aryl having from 6 to 18 carbon atoms, a 3 to 18-membered heterocyclic ring having 1 to 6 heteroatoms selected from O, S, N and P wherein the substituent is selected from halogen, OR$_7$, NR$_8$R$_9$, NO$_2$, NRCOR', SR$_{10}$, a sulfoxide represented by SOR', a sulfone represented by —SO$_2$R', a sulfite —SO$_3$, a bisulfite —OSO$_3$, a sulfonamide represented by SO$_2$NRR', cyano, an azido, —COR$_{11}$, OCOR$_{11}$ or OCONR$_{11}$R$_{12}$, wherein R$_7$, R$_8$, R$_9$, R$_{10}$, R$_{11}$ and R$_{12}$ are each independently selected from H, linear, branched or cyclic alkyl, alkenyl or alkynyl having from 1 to 10 carbon atoms, a polyethylene glycol unit (—OCH$_2$CH$_2$)$_n$, wherein n is an integer from 1 to 2000, a 5- or 6-membered heteroaryl ring containing one or more heteroatoms independently selected from nitrogen, oxygen, and sulfur, a 5 to 18 membered fused ring system, wherein at least one of the rings is aromatic.containing one or more heteroatoms independently selected from nitrogen, oxygen, and sulfur, aryl having from 6 to 18 carbon atoms 3 to 18-membered heterocyclic ring having 1 to 6 heteroatoms selected from O, S, N and P and R$_{10}$ optionally is SR$_{13}$ or COR$_{13}$, wherein R$_{13}$ is selected from linear, branched or cyclic alkyl, alkenyl or alkynyl having from 1 to 10 carbon atoms, a polyethylene glycol unit (—OCH$_2$CH$_2$)$_n$, wherein n is an integer from 1 to 2000, a 5- or 6-membered heteroaryl ring containing one or more heteroatoms independently selected from nitrogen, oxygen, and sulfur, a 5 to 18 membered fused ring system, wherein at least one of the rings is aromatic, containing one or more heteroatoms independently selected from nitrogen, oxygen, and sulfur, 3 to 18-membered heterocyclic ring having 1 to 6 heteroatoms selected from O, S, N and P and $R_{11}$ can also be $OR_{14}$, wherein $R_{14}$ is H or has the same definition as R, optionally, R" is an OH;

W is C=O, C=S, $CH_2$, BH (B=Boron), SO or $SO_2$;

$R_1$, $R_2$, $R_3$, $R_4$, are each independently selected from H, substituted or unsubstituted linear, branched or cyclic alkyl, alkenyl or alkynyl having from 1 to 10 carbon atoms, a polyethylene glycol unit ($-OCH_2CH_2)_n$, wherein n is an integer from 1 to 2000, or a substituent selected from a halogen, $OR_7$, $NR_8R_9$, $NO_2$, $NRCOR'$, $SR_1O$, a sulfoxide represented by $SOR'$, a sulfone represented by $-SO_2R'$, a sulfite $-SO_{3}$, a bisulfite $-OSO_3$, a sulfonamide represented by $SO_2NRR'$, cyano, an azido, guanidinium [$-NH(C=NH)NH_2$], $-COR_{11}$, $-OCOR_{11}$ or $-OCONR_{11}R_{12}$ wherein $R_7$, $R_8$, $R_9$, $R_{10}$, $R_{11}$ and $R_{12}$ are as defined above, optionally, any one of $R_1$, $R_2$, $R_3$, $R_4$ is a linking group that enables linkage to a cell binding agent via a covalent bond or is selected from a polypyrrolo, poly-indolyl, poly-imidazolyl, polypyrollo-imidazolyl, poly-pyrrolo-indolyl or polyimidazolo-indolyl unit optionally bearing a linking group that enables linkage to a cell binding agent;

$R_5$ is selected from $OR_{15}$, CRR'OH, SH, CRR'SH, $NHR_{15}$ or $CRR'NHR_{15}$, wherein $R_{15}$ has the same definition as R., R and R' have the same definition as given above; optionally, $R_5$ is a linking group that enables linkage to a cell binding agent via a covalent bond or is selected from a polypyrrolo, poly-indolyl, poly-imidazolyl, polypyrollo-imidazolyl, poly-pyrrolo-indolyl or polyimidazolo-indolyl unit optionally bearing a linking group that enables linkage to a cell binding agent;;

$R_6$ is OR, SR, NRR', wherein R and R' have the same definition as given above, or optionally $R_6$ is a linking group;

Z is selected from $(CH_2)_n$, wherein n is 1, 2 or 3, $CR_{15}R_{16}$, $NR_{17}$, O or S, wherein $R_{15}$, $R_{16}$ and $R_{17}$ are each independently selected from H, linear, branched or cyclic alkyl having from 1 to 10 carbon atoms, a polyethylene glycol unit ($-OCH_2CH_2)_n$, wherein n is an integer from 1 to 2000; or their pharmaceutically acceptable solvates, salts, hydrates or hydrated salts, their optical isomers, racemates, diastereomers, enantiomers of these compounds.

provided that the compound has no more than one linking group that enables linkage to a cell binding agent via a covalent bond.

In one preferred embodiment, the double line = between N and C represents a double bond and X is absent and Y is H, or the double line = between N and C represents a single bond wherein X is H and Y is selected from $-OR$, a sulfite $-SO_3$, or an amine protecting moiety that converts the compound into a prodrug;

W is C=O, $CH_2$, or $SO_2$;

$R_1$, $R_2$, $R_3$, $R_4$, are each H; optionally, independently, any one of $R_1$, $R_2$, $R_3$ and $R_4$ can be a linking group that enables linkage to a cell binding agent via a covalent bond;

$R_5$ is selected from $OR_{15}$, CRR'OH, SH, CRR'SH, $NHR_{15}$ or $CRR'NHR_{15}$, wherein $R_{15}$ is H or has the same definition as given above for R, or is selected from a polypyrrolo, poly-indolyl, poly-imidazolyl, polypyrollo-imidazolyl, poly-pyrrolo-indolyl or polyimidazolo-indolyl unit optionally bearing a linking group that enables linkage to a cell binding agent, R and R' have the same definition as given above;

$R_6$ is $OCH_3$;

Z is selected from $(CH_2)_n$., wherein n is 1 or 2, NH, $NCH_3$ or S; or their pharmaceutically acceptable solvates, salts, hydrates or hydrated salts, their optical isomers, racemates, diastereomers, enantiomers or the polymorphic crystalline structures of these compounds.

In a preferred embodiment, compounds of formula (I) and (II) are compounds of formulae (VII), (VIII) or (IX):

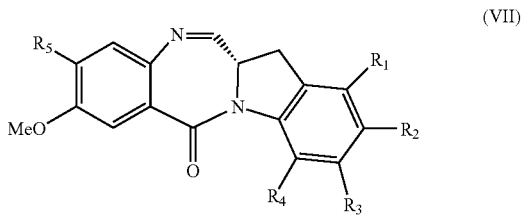

(VII)

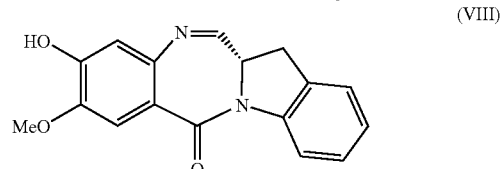

(VIII)

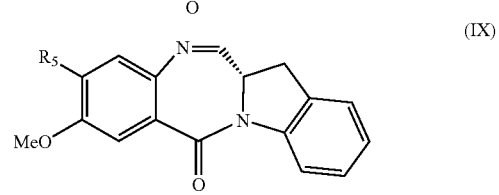

(IX)

wherein the substituents are described as above; or their pharmaceutically acceptable solvates, salts, hydrates or hydrated salts, their optical isomers, racemates, diastereomers, enantiomers or the polymorphic crystalline structures of these compounds.

For the novel benzodiazepines of formula (III), in which the diazepine ring (B) is fused with a heterocyclic ring (C), wherein the heterocyclic ring is monocyclic,

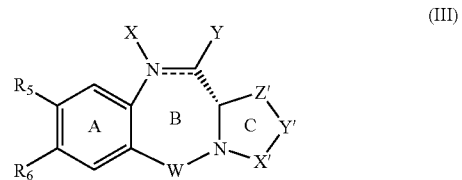

(III)

wherein:
the double line = between N and C represents a single bond or a double bond, provided that when it is a double bond X is absent and Y is H, and when it is a single bond, X is H or an amine protecting moiety that converts the compound into a prodrug;

Y is selected from $-OR$, an ester represented by $-OCOR'$, a carbonate represented by $-OCOOR'$, a carbamate represented by $-OCONR'R''$, an amine or a hydroxyl amine represented by $NR'R''$, amide represented by $-NRCOR'$, a peptide represented by NRCOP, wherein P is an amino acid or a polypeptide containing between 2 to 20 amino acid units, a thioether represented by SR', a sulfoxide represented by SOR', a sulfone represented by —SO$_2$R', a sulfite —SO$_3$, a bisulfite —OSO$_3$, a halogen, cyano, an azido, or a thiol, wherein R, R' and R" are same or different and selected from H, substituted or unsubstituted linear, branched or cyclic alkyl, alkenyl or alkynyl having from 1 to 10 carbon atoms, a polyethylene glycol unit (—OCH$_2$CH$_2$)$_n$, wherein n is an integer from 1 to 2000, a 5- or 6-membered heteroaryl ring containing one or more heteroatoms independently selected from nitrogen, oxygen, and sulfur, a 5 to 18 membered fused ring system, wherein at least one of the rings is aromatic, containing one or more heteroatoms independently selected from nitrogen, oxygen, and sulfur, aryl having from 6 to 18 carbon atoms, 3 to 18-membered heterocyclic ring having 1 to 6 heteroatoms selected from O, S, N and P, wherein the substituent is selected from halogen, OR$_7$, NR$_8$R$_9$, NO$_2$, NRCOR', SR$_{10}$, a sulfoxide represented by SOR', a sulfone represented by —SO$_2$R', a sulfite —SO$_3$, a bisulfite—OSO$_3$, a sulfonamide represented by SO$_2$NRR', cyano, an azido, —COR$_{11}$, OCOR$_{11}$ or OCONR$_{11}$R$_{12}$, wherein R$_7$, R$_8$, R$_9$, R$_{10}$, R$_{11}$ and R$_{12}$ are each independently selected from H, linear, branched or cyclic alkyl, alkenyl or alkynyl having from 1 to 10 carbon atoms, a polyethylene glycol unit (—OCH$_2$CH$_2$)$_n$, wherein n is an integer from 1 to 2000, a 5- or 6-membered heteroaryl ring containing one or more heteroatoms independently selected from nitrogen, oxygen, and sulfur, a 5 to 18 membered fused ring system, wherein at least one of the rings is aromatic, containing one or more heteroatoms independently selected from nitrogen, oxygen, and sulfur, aryl having from 6 to 18 carbon atoms 3 to 18-membered heterocyclic ring having 1 to 6 heteroatoms selected from O, S, N and P and R$_{10}$ optionally is SR$_{13}$ or COR$_{13}$, wherein R$_{13}$ is selected from linear, branched or cyclic alkyl, alkenyl or alkynyl having from 1 to 10 carbon atoms, a polyethylene glycol unit (—OCH$_2$CH$_2$)$_n$, wherein n is an integer from 1 to 2000, a 5- or 6-membered heteroaryl ring containing one or more heteroatoms independently selected from nitrogen, oxygen, and sulfur, a 5 to 18 membered fused ring system, wherein at least one of the rings is aromatic, containing one or more heteroatoms independently selected from nitrogen, oxygen, and sulfur, aryl having from 6 to 18 carbon atoms, 3 to 18-membered heterocyclic ring having 1 to 6 heteroatoms selected from O, S, N and P and R$_{11}$ can also be OR$_{14}$, wherein R$_{14}$ is H or has the same definition as R, optionally R" is OH;

W is C=O, C=S, CH$_2$, BH, SO or SO$_2$;

R$_5$ is selected from OR$_{15}$, CRR'OH, SH, CRR'SH, NHR$_{15}$ or CRR'NHR$_{15}$, wherein R$_{15}$ is H or has the same definition as R. or is a linking group that enables linkage to a cell binding agent via a covalent bond or is selected from a polypyrrolo, poly-indolyl, poly-imidazolyl, polypyrrollo-imidazolyl, poly-pyrrollo-indolyl or polyimidazolo-indolyl unit optionally bearing a linking group that enables linkage to a cell binding agent;is selected from a poly-pyrrolo, poly-indolyl, poly-imidazolyl, polypyrrollo-imidazolyl, poly-pyrrollo-indolyl or polyimidazolo-indolyl unit optionally bearing a linking group that enables linkage to a cell binding agent, optionally, R$_5$ is a linking group that enables linkage to a cell binding agent via a covalent bond;

R$_6$ is OR, SR or NRR', wherein R and R' have the same definition as given above, optionally R$_6$ is a linking group;

X' is CH$_2$, NR, CO, BH, SO or SO$_2$;

Y' is O, CH$_2$, NR or S;

Z' is CH$_2$ or (CH$_2$)$_n$, wherein n is 2, 3 or 4; or their pharmaceutically acceptable solvates, salts, hydrates or hydrated salts, their optical isomers, racemates, diastereomers, enantiomers or the polymorphic crystalline structures of these compounds;

provided that the compound has no more than one linking group that enables linkage to a cell binding agent via a covalent bond.

In one preferred embodiment, the double line ═ between N and C represents a double bond and X is absent and Y═H, or the double line ═ between N and C represents a single bond wherein X is H and Y is selected from —OR, a sulfite —SO$_3$, or an amine protecting moiety that converts the compound into a prodrug;

W is C=O, CH$_2$, or SO$_2$;

R$_5$ is selected from OR$_{15}$, CRR'OH, SH, CRR'SH, NHR$_1$5 or CRR'NHR$_{15}$, wherein R$_{15}$ is H or has the same definition as given above for R, or is selected from a polypyrrolo, poly-indolyl, poly-imidazolyl, polypyrrollo-imidazolyl, poly-pyrrolloindolyl or polyimidazoloindolyl unit optionally bearing a linking group that enables linkage to a cell binding agent;

R$_6$ is OCH$_3$;

X' is selected from CH$_2$, or C=O;

Y' is O, CH$_2$, NR or S;

Z' is (CH$_2$)$_n$, wherein n is 1 or 2, provided that X', Y' and Z' are not all CH$_2$ at the same time; or their pharmaceutically acceptable solvates, salts, hydrates or hydrated salts, their optical isomers, racemates, diastereomers, enantiomers or the polymorphic crystalline structures of these compounds.

In a preferred embodiment, compound of formula III is represented by a compound of formula (X) or (XI),

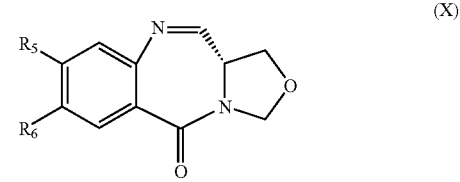

(X)

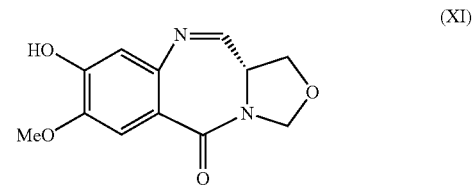

(XI)

wherein the substituents are described as above; or their pharmaceutically acceptable solvates, salts, hydrates or hydrated salts, their optical isomers, racemates, diastereomers, enantiomers or the polymorphic crystalline structures of these compounds.

For the cytotoxic dimers represented by formulas (IV), (V) and (VI)

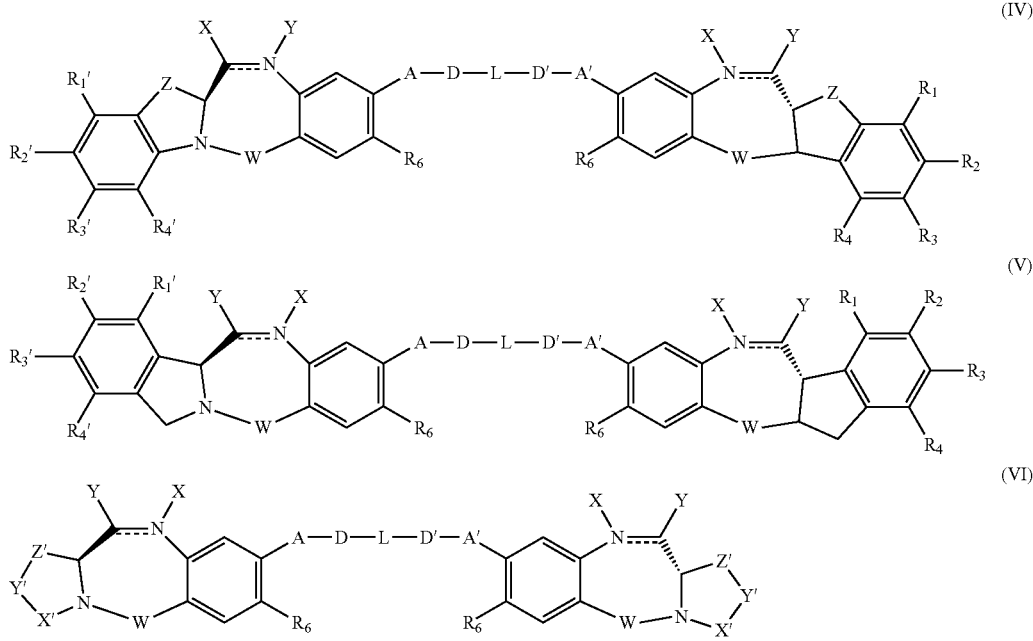

(IV)

(V)

(VI)

the double line == between N and C represents a single bond or a double bond, provided that when it is a double bond X is absent and Y is H, and when it is a single bond, X is H or an amine protecting moiety that converts the compound into a prodrug;

Y is selected from —OR, an ester represented by —OCOR', a carbonate represented by —OCOOR', a carbamate represented by —OCONR'R", an amine or a hydroxyl amine represented by NR'R", amide represented by —NRCOR', a peptide represented by NRCOP, wherein P is an amino acid or a polypeptide containing between 2 to 20 amino acid units, a thioether represented by SR', a sulfoxide represented by SOR', a sulfone represented by —SO$_2$R', a sulfite —SO$_3$, a bisulfite —OSO$_3$, a halogen, cyano, an azido, or a thiol, wherein R, R' and R" are same or different and are selected from H, substituted or unsubstituted linear, branched or cyclic alkyl, alkenyl or alkynyl having from 1 to 10 carbon atoms, a polyethylene glycol unit (—OCH$_2$CH$_2$)n, wherein n is an integer from 1 to 2000, a 5- or 6-membered heteroaryl ring containing one or more heteroatoms independently selected from nitrogen, oxygen, and sulfur, a 5 to 18 membered fused ring system, wherein at least one of the rings is aromatic, containing one or more heteroatoms independently selected from nitrogen, oxygen, and sulfur, aryl having from 6 to 18 carbon atoms, 3 to 18-membered heterocyclic ring having 1 to 6 heteroatoms selected from O, S, N and P wherein the substituent is selected from halogen, OR$_7$, NR$_8$R$_9$, NO$_2$, NRCOR', SR$_{10}$, a sulfoxide represented by SOR', a sulfone represented by —SO$_2$R', a sulfite —SO$_3$, a bisulfite —OSO$_3$, a sulfonamide represented by SO$_2$NRR', cyano, an azido, —COR$_{11}$, OCOR$_{11}$ or OCONR$_{11}$R$_{12}$, wherein R$_7$, R$_8$, R$_9$, R$_{10}$, R$_{11}$ and R$_{12}$ are each independently selected from H, linear, branched or cyclic alkyl, alkenyl or alkynyl having from 1 to 10 carbon atoms, a polyethylene glycol unit (—OCH$_2$CH$_2$)$_n$, wherein n is an integer from 1 to 2000, a 5- or 6-membered heteroaryl ring containing one or more heteroatoms independently selected from nitrogen, oxygen, and sulfur, a 5 to 18 membered fused ring system, wherein at least one of the rings is aromatic, containing one or more heteroatoms independently selected from nitrogen, oxygen, and sulfur, aryl having from 6 to 18 carbon atoms, 3 to 10-membered heterocyclic ring having 3 to 18-membered heterocyclic ring having 1 to 6 heteroatoms selected from O, S, N and P and R$_{10}$ is optionally SR$_{13}$ or COR$_{13}$, wherein R$_{13}$ is selected from linear, branched or cyclic alkyl, alkenyl or alkynyl having from 1 to 10 carbon atoms, a 5- or 6-membered heteroaryl ring containing one or more heteroatoms independently selected from nitrogen, oxygen, and sulfur, a 5 to 18 membered fused ring system, wherein at least one of the rings is aromatic, containing one or more heteroatoms independently selected from nitrogen, oxygen, and sulfur, aryl having from 6 to 18 carbon atoms, 3 to 18-membered heterocyclic ring having 1 to 6 heteroatoms selected from O, S, N and P, optionally R$_{11}$ is OR$_{14}$, wherein R$_{14}$ has the same definition as R, optionally R" is OH;

W is C=O, C=S, CH$_2$, BH, SO or SO$_2$;

R$_1$, R$_2$, R$_3$, R$_4$, R$_1$', R$_2$', R$_3$' and R$_4$' are each independently selected from H, substituted or unsubstituted linear, branched or cyclic alkyl, alkenyl or alkynyl having from 1 to 10 carbon atoms, a polyethylene glycol unit (—OCH$_2$CH$_2$)n, wherein n is an integer from 1 to 2000, or a substituent selected from a halogen, guanidinium [—NH (C=NH)NH$_2$], OR$_S$, NR$_8$R$_9$, NO$_2$, NRCOR', SR$_{10}$, a sulfoxide represented by SOR', a sulfone represented by —SO$_2$R', a sulfite —SO$_3$, a bisulfite —OSO$_3$, a sulfonamide represented by SO$_2$NRR', cyano, an azido, —COR$_{11}$, OCOR$_{11}$ or OCONR$_{11}$R$_{12}$ wherein R$_7$, R$_8$, R$_9$, R$_{10}$, R$_{11}$ and R$_{12}$ are as defined above, optionally, any one of R$_1$, R$_2$, R$_3$, R$_4$, R$_1$', R$_2$', R$_3$', or R$_4$' is a linking group that enables linkage to a cell binding agent via a covalent bond or is selected from a polypyrrolo, poly-indolyl, poly-imidazolyl, polypyrrolo-imidazolyl, poly-pyrrolo-indolyl or polyimidazolo-indolyl unit optionally bearing a linking group that enables linkage to a cell binding agent, Z is selected from $(CH_2)_n$, wherein n is 1, 2 or 3, $CR_{15}R_{16}$, $NR_{17}$, O or S, wherein $R_{15}$, $R_{16}$ and $R_{17}$ are each independently selected from H, linear, branched or cyclic alkyl having from 1 to 10 carbon atoms, a polyethylene glycol unit $(-OCH_2CH_2)_n$, wherein n is an integer from 1 to 2000;

$R_6$ is OR, SR or NRR', wherein R and R' have the same definition as given above, optionally $R_6$ is a linking group;

X' is selected from $CH_2$, NR, CO, BH, SO or $SO_2$ wherein R has the same definition as given above;

Y' is O, $CH_2$, NR or S, wherein R has the same definition as given above;

Z' is $CH_2$ or $(CH_2)_n$, wherein n is 2, 3 or 4, provided that X', Y' and Z' are not all $CH_2$ at the same time;

A and A' are the same or different and are selected from O, —CRR'O, S, —CRR'S, —$NR_{15}$ or CRR'$NHR_{15}$, wherein R and R' have the same definition as given above and wherein $R_{15}$ has the same definition as R.

D and D' are same or different and independently selected from linear, branched or cyclic alkyl, alkenyl or alkynyl having 1 to 10 carbon atoms, optionally substituted with any one of halogen, $OR_7$, $NR_8R_9$, $NO_2$, NRCOR', $SR_{10}$, a sulfoxide represented by SOR', a sulfone represented by —$SO_2R'$, a sulfite —$SO_3$, a bisulfite —$OSO_3$, a sulfonamide represented by $SO_2NRR'$, cyano, an azido, —$COR_{11}$, $OCOR_{11}$ or $OCONR_{11}R_{12}$, wherein the definitions of $R_7$, $R_8$, $R_9$, $R_{10}$, $R_{11}$ and $R_{12}$ are as defined above, or a polyethylene glycol unit $(-OCH_2CH_2)_n$, wherein n is an integer from 1 to 2000;

L is an optional phenyl group or 3 to 18-membered heterocyclic ring having 1 to 6 heteroatoms selected from O, S, N and P that is optionally substituted, wherein the substituent is a linking group that enables linkage to a cell binding agent via a covalent bond, or is selected from linear, branched or cyclic alkyl, alkenyl or alkynyl having from 1 to 10 carbon atoms, optionally substituted with any one of halogen, $OR_7$, $NR_8R_9$, $NO_2$, NRCOR', $SR_{10}$, a sulfoxide represented by SOR', a sulfone represented by —$SO_2R'$, a sulfite —$SO_3$, a bisulfite —$OSO_3$, a sulfonamide represented by $SO_2NRR'$, cyano, an azido, —$COR_{11}$, $OCOR_{11}$ or $OCONR_{11}R_{12}$, wherein the definitions of $R_7$, $R_8$, $R_9$, $R_{10}$, $R_{11}$ and $R_{12}$ are as defined above, a polyethylene glycol unit $(-OCH_2CH_2)n$, wherein n is an integer from 1 to 2000; optionally, L itself is a linking group that enables linkage to a cell binding agent via a covalent bond; or their pharmaceutically acceptable solvates, salts, hydrates or hydrated salts, their optical isomers, racemates, diastereomers, enantiomers or the polymorphic crystalline structures of these compounds; provided that the compound has no more than one linking group that enables linkage to a cell binding agent via a covalent bond.

In one preferred embodiment, the double line == between N and C represents a single bond or a double bond, provided that when it is a double bond X is absent and Y is H, and when it is a single bond, X is H or an amine protecting group that converts the compound into a prodrug;

Y is selected from —OR, NR'R", a sulfite —$SO_3$, or a bisulfite —$OSO_3$, wherein R is selected from H, linear, branched or cyclic alkyl, alkenyl or alkynyl having from 1 to 10 carbon atoms, a polyethylene glycol unit $(-OCH_2CH_2)_n$, wherein n is an integer from 1 to 2000, aryl having from 6 to 10 carbon atoms, heterocyclic ring having from 3 to 10 carbon atoms;

W is C=O, $CH_2$ or $SO_2$;

$R_1$, $R_2$, $R_3$, $R_4$, $R_1'$, $R_2'$, $R_3'$ and $R_4'$ are each independently selected from H, $NO_2$ or a linking group that enables linkage to a cell binding agent via a covalent bond;

$R_6$ is $OR_{18}$, wherein $R_{18}$ has the same definition as R;

Z is selected from $(CH_2)_n$, wherein n is 1, 2 or 3, $CR_{15}R_{16}$, $NR_{17}$, O or S, wherein $R_{15}$, $R_{16}$ and $R_{17}$ are each independently selected from H, linear, branched or cyclic alkyl having from 1 to 10 carbon atoms, a polyethylene glycol unit $(-OCH_2CH_2)_n$, wherein n is an integer from 1 to 2000;

X' is selected from $CH_2$, or C=O;

Y' is O, NR, or S, wherein R is defined as above;

Z' is $CH_2$ or $(CH_2)_2$;

A and A' are each O;

D and D' are same or different and independently selected from linear, branched or cyclic alkyl, alkenyl or alkynyl having from 1 to 10 carbon atoms;

L is an optional phenyl group or a heterocycle ring having from 3 to 10 carbon atoms that is optionally substituted, wherein the substituent is a linking group that enables linkage to a cell binding agent via a covalent bond, or is selected from linear, branched or cyclic alkyl, alkenyl or alkynyl having from 1 to 10 carbon atoms, optionally substituted with any one of halogen, $OR_7$, $NR_8R_9$, $NO_2$, NRCOR', $SR_{10}$, a sulfoxide represented by SOR', a sulfone represented by —$SO_2R'$, a sulfite —$SO_3$, a bisulfite —$OSO_3$, a sulfonamide represented by $SO_2NRR'$, cyano, an azido, —$COR_{11}$, $OCOR_{11}$ or $OCONR_{11}R_{12}$, a polyethylene glycol unit $(-OCH_2CH_2)n$, wherein n is an integer from 1 to 2000; optionally, L itself is a linking group that enables linkage to a cell binding agent via a covalent bond; or their pharmaceutically acceptable solvates, salts, hydrates or hydrated salts, their optical isomers, racemates, diastereomers, enantiomers or the polymorphic crystalline structures of these compounds.

In another preferred embodiment, the compound of formula (IV), (V) or (VI) is represented by compounds of formulae (XII) and (XIII):

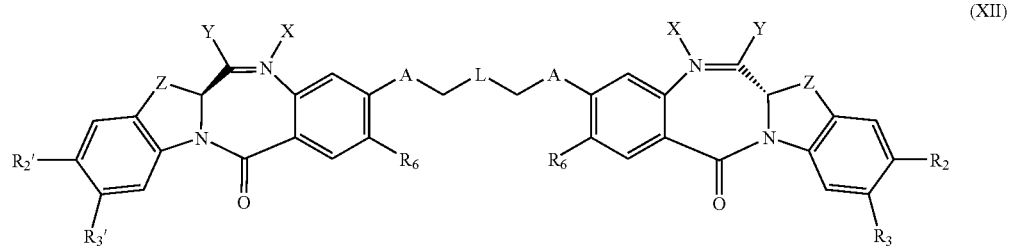

(XII)

(XIII)

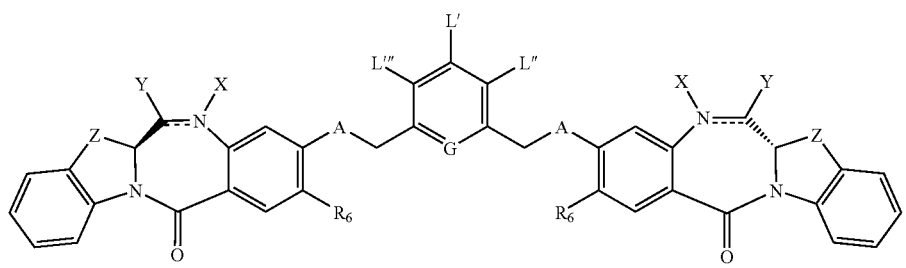

wherein the double line ═ between N and C represents a single bond or a double bond, provided that when it is a double bond X is absent and Y is H, and when it is a single bond, X is H or an amine protecting group that converts the compound into a prodrug; Y is selected from OH, an ether represented by —OR, NR'R", a sulfite —SO$_3$, or a bisulfite —OSO$_3$, wherein R, R' and R" are selected from linear, branched or cyclic alkyl, alkenyl or alkynyl having from 1 to 10 carbon atoms;

one of $R_2$, $R_3$, $R_2$' and $R_3$' is a linking group that enables linkage to a cell binding agent via a covalent bond and the others are H, NRCOR' or NO$_2$;

ally, L itself is a linking group that enables linkage to a cell binding agent via a covalent bond;

one of L', L" or L'" is a linking group that enables linkage to a cell binding agent, while the others are H; preferably L' is the linking group; and G is CH or N or their pharmaceutically acceptable solvates, salts, hydrates or hydrated salts, their optical isomers, racemates, diastereomers, enantiomers or the polymorphic crystalline structures of these compounds.

In yet another preferred embodiment, the compound of formula (IV), (V) or (VI) is represented by compounds of formulae from formulae (XIV) and (XV):

(XIV)

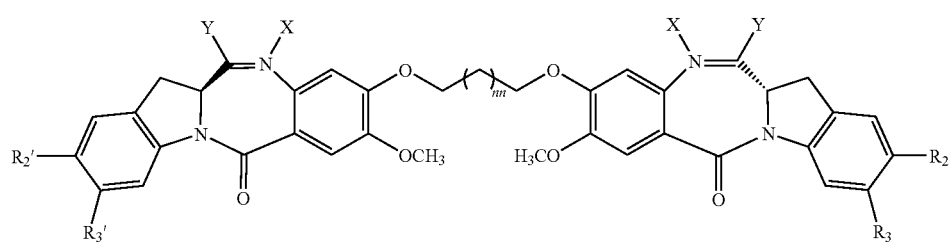

(XV)

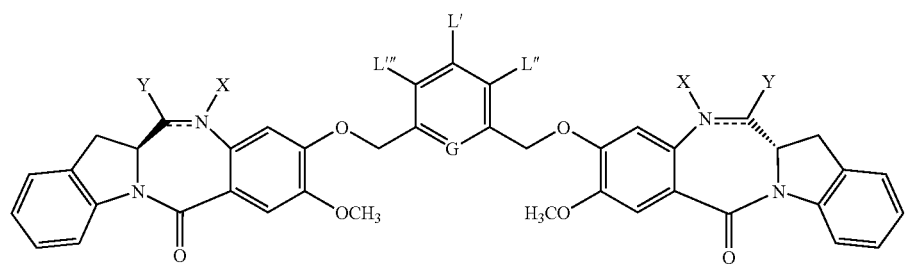

$R_6$ is OR, wherein R has the same definition as above;

Z is CH$_2$ or NR, wherein R has the same definition as above;

A is O or NR$_{15}$;

L is (CH$_2$)$_{nn}$, wherein nn is O or an integer between 1 and 5, or a substituted or unsubstituted alkyl or alkenyl having from 2 to 4 carbon atoms, wherein the substituent is selected from halogen, OR$_7$, NR$_8$R$_9$, NO$_2$, NRCOR', SR$_{10}$, a sulfoxide represented by SOR', a sulfone represented by —SO$_2$R', a sulfite —SO$_3$, a bisulfite —OSO$_3$, a sulfonamide represented by SO$_2$NRR', cyano, an azido, —COR$_{11}$, OCOR$_{11}$ or OCONR$_{11}$R$_{12}$, wherein R$_7$, R$_8$, R$_9$, R$_{10}$, R$_{11}$, R$_{12}$ and R$_{15}$ has the same definition as given above, optionwherein the double line ═ between N and C represents a single bond or a double bond, provided that when it is a double bond X is absent and Y is H, and when it is a single bond, X is H or an amine protecting group that converts the compound into a prodrug; Y is selected from OH, an ether represented by —OR, a sulfite —SO$_3$, or a bisulfite —OSO$_3$, wherein R is selected from linear, branched or cyclic alkyl, alkenyl or alkynyl having from 1 to 10 carbon atoms;

nn is O or an integer from 1 to 5;

One of $R_2$, $R_3$, $R_2$' and $R_3$' is a linking group that enables linkage to a cell binding agent via a covalent bond and the others are H, NRCOR', or NO$_2$;

one of L', L" or L'" is a linking group that enables linkage to a cell binding agent, provided that when one of L', L" or L'" is a linking group others are H (e.g., if L' is a linker, then L" and L'" are H)

G is CH or N or their pharmaceutically acceptable solvates, salts, hydrates or hydrated salts, their optical isomers, racemates, diastereomers, enantiomers or the polymorphic crystalline structures of these compounds.

In order to link the cytotoxic compounds (e.g., indolinobenzodiazepine or oxazolidinobenzodiazepine), derivatives thereof, or dimers thereof of the present invention to the cell-binding agent, the cytotoxic compound comprises a linking moiety. While a linker that connects two moieties is bifunctional, one end of the linker moiety can be first reacted with the cytotoxic compound to provide the compound bearing a monofunctional linking group, which can then react with a cell binding agent. Alternatively, one end of the linker moiety can be first reacted with the cell binding agent to provide the cell binding agent bearing a monofunctional linking group, which can then react with a cytotoxic compound. The linking moiety contains a chemical bond that allows for the release of the cytotoxic moiety at a particular site. Suitable chemical bonds are well known in the art and include disulfide bonds, thioether bonds, acid labile bonds, photolabile bonds, peptidase labile bonds and esterase labile bonds (see for example U.S. Pat. Nos. 5,208,020; 5,475,092; 6,441,163; 6,716,821; 6,913,748; 7,276,497; 7,276,499; 7,368,565; 7,388,026 and 7,414,073). Preferred are disulfide bonds, thioether and peptidase labile bonds. Other linkers that can be used in the present invention include non-cleavable linkers, such as those described in are described in detail in U.S. publication number 20050169933, or charged linkers or hydrophilic linkers and are described in provisional patent application No., 61/049,291, filed Apr. 30, 2008, 61/147,966, filed Jan. 28, 2009, and 61/049,289, filed Apr. 30. 2008, each of which is expressly incorporated herein by reference.

The compounds of formula (1), (II), and (III) (i.e., monomers) can be linked through $R_1$, $R_2$, $R_3$, $R_4$ or $R_5$. Of these, preferred linkable groups are $R_2$, $R_3$, and $R_5$, and the most preferred linkable group is $R_5$. Examples of suitable substituents at $R_1$, $R_2$, $R_3$, $R_4$ and $R_5$ for compounds of formula (I), (II) and (III) include, but are not limited to:

—OH,
—O$(CR_{20}R_{21})_m(CR_{22}R_{23})_n(OCH_2CH_2)_p(CR_{40}R_{41})_{p''}Y''(CR_{24}R_{25})_q(CO)_rX''$,
—O$(CR_{20}R_{21})_m(CR_{26}=CR_{27})_m(CR_{22}R_{23})_n(OCH_2CH_2)_p(CR_{40}R_{41})_{p''}Y''(CR_{24}R_{25})_q(CO)_rX''$,
—O$(CR_{20}R_{21})_m(alkynyl)_n(CR_{22}R_{23})_n(OCH_2CH_2)_p(CR_{40}R_{41})_{p''}Y''(CR_{24}R_{25})_q(CO)_rX''$,
—O$(CR_{20}R_{21})_m(indolo)_p(CR_{22}R_{23})_n(OCH_2CH_2)_p(CR_{40}R_{41})_{p''}Y''(CR_{24}R_{25})_q(CO)_rX''$
—O$(CR_{20}R_{21})_m(pyrrolo)_q(CR_{22}R_{23})_n(OCH_2CH_2)_p(CR_{40}R_{41})_{p''}Y''(CR_{24}R_{25})_q(CO)_rX''$,
—O$(CR_{20}R_{21})_m(pyrrolo)_q(imidazolo)_{q''}(CR_{22}R_{23})_n(OCH_2CH_2)_p(CR_{40}R_{41})_{p''}Y''(CR_{24}R_{25})_q(CO)_rX''$,
—O$(CR_{20}R_{21})_m(imidazolo)_{q''}(CR_{22}R_{23})_n(OCH_2CH_2)_p(CR_{40}R_{41})_{p''}Y''(CR_{24}R_{25})_q(CO)_rX''$,
—O$(CR_{20}R_{21})_m(pyrrolo)_q(indolo)_{q''}(CR_{22}R_{23})_n(OCH_2CH_2)_p(CR_{40}R_{41})_{p''}Y''(CR_{24}R_{25})_q(CO)_rX''$,
—O$(CR_{20}R_{21})_m(indolo)_{q'}(imidazolo)_{q''}(CR_{22}R_{23})_n(OCH_2CH_2)_p(CR_{40}R_{41})_{p''}YΔ(CR_{24}R_{25})_q(CO)_rX''$,
—O$(CR_{20}R_{21})_m(piperazino)_t(CR_{22}R_{23})_n(OCH_2CH_2)_p(CR_{40}R_{41})_{p''}Y''(CR_{24}R_{25})_q(CO)_rX''$,
—O$(CR_{20}R_{21})_mA''_{m''}(CR_{22}R_{23})_n(OCH_2CH_2)_p(CR_{40}R_{41})_{p''}Y''(CR_{24}R_{25})_q(CO)_rX''$,
—SH,
—S$(CR_{20}R_{21})_m(CR_{22}R_{23})_n(OCH_2CH_2)_p(CR_{40}R_{41})_{p''}Y''(CR_{24}R_{25})_q(CO)_rX''$,
—S$(CR_{20}R_{21})_m(CR_{26}=CR_{27})_m(CR_{22}R_{23})_n(OCH_2CH_2)_p(CR_{40}R_{41})_{p''}Y''(CR_{24}R_{25})_q(CO)_rX''$,
—S$(CR_{20}R_{21})_m(alkynyl)_n(CR_{22}R_{23})_n(OCH_2CH_2)_p(CR_{40}R_{41})_{p''}Y''(CR_{24}R_{25})_q(CO)_rX''$,
S$(CR_{20}R_{21})_m(indolo)_p(CR_{22}R_{23})_n(OCH_2CH_2)_p(CR_{40}R_{41})_{p''}Y''(CR_{24}R_{25})_q(CO)_rX''$,
—S$(CR_{20}R_{21})_m(pyrrolo)_q(CR_{22}R_{23})_n(OCH_2CH_2)_p(CR_{40}R_{41})_{p''}Y''(CR_{24}R_{25})_q(CO)_rX''$,
—S$(CR_{20}R_{21})_m(imidazolo)_{q''}(CR_{22}R_{23})_n(OCH_2CH_2)_p(CR_{40}R_{41})_{p''}Y''(CR_{24}R_{25})_q(CO)_rX''$,
—S$(CR_{20}R_{21})_m(pyrrolo)_q(indolo)_{q''}(CR_{22}R_{23})_n(OCH_2CH_2)_p(CR_{40}R_{41})_{p''}Y''(CR_{24}R_{25})_q(CO)_rX''$,
—S$(CR_{20}R_{21})_m(pyrrolo)_q(indolo)_{q''}(CR_{22}R_{23})_n(OCH_2CH_2)_p(CR_{40}R_{41})_{p''}Y''(CR_{24}R_{25})_q(CO)_rX''$,
—S$(CR_{20}R_{21})_m(indolo)_{q'}(imidazolo)_{q''}(CR_{22}R_{23})_n(OCH_2CH_2)_p(CR_{40}R_{41})_{p''}Y''(CR_{24}R_{25})_q(CO)_rX''$,
—S$(CR_{20}R_{21})_m(piperazino)_t(CR_{22}R_{23})_n(OCH_2CH_2)_p(CR_{40}R_{41})_{p''}Y''(CR_{24}R_{25})_q(CO)_rX''$,
—S$(CR_{20}R_{21})_mA''_{m''}(CR_{22}R_{23})_n(OCH_2CH_2)_p(CR_{40}R_{41})_{p''}Y''(CR_{24}R_{25})_q(CO)_rX''$,
—NH$_2$,
—NR$_{28}(CR_{20}R_{21})_m(CR_{22}R_{23})_n(OCH_2CH_2)_p(CR_{40}R_{41})_{p''}Y''(CR_{24}R_{25})_q(CO)_rX''$, —NR$_{28}(CR_{20}R_{21})_m(CR_{26}=CR_{27})_m(CR_{22}R_{23})_n(OCH_2CH_2)_p(CR_{40}R_{41})_{p''}Y''(CR_{24}R_{25})_q(CO)_rY''$,
—NR$_{28}(CR_{20}R_{21})_m(alkynyl)_n(CR_{22}R_{23})_n(OCH_2CH_2)_p(CR_{40}R_{41})_{p''}Y''(CR_{24}R_{25})_q(CO)_rX''$,
—NR$_{28}(CR_{20}R_{21})_m(indolo)_p(CR_{22}R_{23})_n(OCH_2CH_2)_p(CR_{40}R_{41})_{p''}Y''(CR_{24}R_{25})_q(CO)_rX''$,
—NR$_{28}(CR_{20}R_{21})_m(pyrrolo)_q(CR_{22}R_{23})_n(OCH_2CH_2)_p(CR_{40}R_{41})_{p''}Y''(CR_{24}R_{25})_q(CO)_rX''$,
—NR$_{28}(CR_{20}R_{21})_m(imidazole)_{q''}(CR_{22}R_{23})_n(OCH_2CH_2)_p(CR_{40}R_{41})_{p''}Y''(CR_{24}R_{25})_q(CO)_rX''$,
—NR$_{28}(CR_{20}R_{21})_m(pyrrolo)_q(imidazolo)_{q''}(CR_{22}R_{23})_n(OCH_2CH_2)_p(CR_{40}R_{41})_{p''}Y''—(CR_{24}R_{25})_q(CO)_rX''$,
—NR$_{28}(CR_{20}R_{21})_m(pyrrolo)_q(indolo)_{q'}(CR_{22}R_{23})_n(OCH_2CH_2)_p(CR_{40}R_{41})_{p''}Y''—(CR_{24}R_{25})_q(CO)_rX''$,
—NR$_{28}(CR_{20}R_{21})_m(indolo)_{q'}(imidazolo)_{q''}(CR_{22}R_{23})_m(OCH_2CH_2)_p(CR_{40}R_{41})_{p''}Y''—(CR_{24}R_{25})_q(CO)_rX''$,
—NR$_{28}(CR_{20}R_{21})_m(piperazino)_t(CR_{22}R_{23})_n(OCH_2CH_2)_p(CR_{40}R_{41})_{p''}Y''(CR_{24}R_{25})_q(CO)_rX''$,
—NR$_{28}(CR_{20}R_{21})_mA''_{m''}(CR_{22}R_{23})_n(OCH_2CH_2)_p(CR_{40}R_{41})_{p''}Y''(CR_{24}R_{25})_q(CO)_rX''$,
—$(CR_{20}R_{21})_m(CR_{22}R_{23})_n(OCH_2CH_2)_p(CR_{40}R_{41})_{p''}Y''(CR_{24}R_{25})_q(CO)_rX''$,
—$(CR_{20}R_{21})_m(CR_{26}=CR_{27})_m(CR_{22}R_{23})_n(OCH_2CH_2)_p(CR_{40}R_{41})_{p''}Y''(CR_{24}R_{25})_q(CO)_rX''$,
—$(CR_{20}R_{21})_m(alkynyl)_n(CR_{22}R_{23})_n(OCH_2CH_2)_p(CR_{40}R_{41})_{p''}Y''(CR_{24}R_{25})_q(CO)_rX''$,
—$(CR_{20}R_{21})_m(indolo)_p(CR_{22}R_{23})_n(OCH_2CH_2)_p(CR_{40}R_{41})_{p''}Y''(CR_{24}R_{25})_q(CO)_rX''$,
—$(CR_{20}R_{21})_m(pyrrolo)_q(CR_{22}R_{23})_n(OCH_2CH_2)_p(CR_{40}R_{41})_{p''}Y''(CR_{24}R_{25})_q(CO)_rX''$,
—$(CR_{20}R_{21})_m(piperazino)_t(CR_{22}R_{23})_n(OCH_2CH_2)_p(CR_{40}R_{41})_{p''}Y''(CR_{24}R_{25})_q(CO)_rX''$,
—$(CR_{20}R_{21})_m(pyrrolo)_q(indolo)_{q''}(CR_{22}R_{23})_n(OCH_2CH_2)_p(CR_{40}R_{41})_{p''}Y''—(CR_{24}R_{25})_q(CO)_rX''$,
—$(CR_{20}R_{21})_m(pyrrolo)_q(CR_{22}R_{23})_n(OCH_2CH_2)_p(CR_{40}R_{41})_{p''}Y''—(CR_{24}R_{25})_q(CO)_rX''$,
$(CR_{20}R_{21})_m(pyrrolo)_q(imidazolo)_{q''}(CR_{22}R_{23})_n(OCH_2CH_2)_p(CR_{40}R_{41})_{p''}Y''—(CR_{24}R_{25})_q(CO)_rX''$,
—$(CR_{20}R_{21})_m(imidazolo)_q(indolo)_{q''}(CR_{22}R_{23})_n(OCH_2CH_2)_p(CR_{40}R_{41})_{p''}Y''—(CR_{24}R_{25})_q(CO)_rX''$,
—$(CR_{20}R_{21})_mA''_{m''}(CR_{22}R_{23})_n(OCH_2CH_2)_p(CR_{40}R_{41})_{p''}Y''(CR_{24}R_{25})_q(CO)_rX''$, —$(CR_{20}R_{21})_m(CR_{29}=N-NR_{30})_{n''}(CR_{22}R_{23})_n(OCH_2CH_2)_p$—$Y''(CR_{24}R_{25})_q(CO)_tX''$, —$(CR_{20}R_{21})_m(CR_{29}=N-NR_{30})_{n''}(CR_{26}=CR_{27})_{m'}(CR_{22}R_{23})_n(OCH_2CH_2)_p(CR_{40}R_{41})_{p''}Y''(CR_{24}R_{25})_q(CO)_tX''$, —$(CR_{20}R_{21})_m(CR_{29}=N-NR_{30})_{n''}(\text{alkynyl})_{n'}(CR_{22}R_{23})_n(OCH_2CH_2)_p(CR_{40}R_{41})_{p''}Y''(CR_{24}R_{25})_q(CO)_tX''$, —$(CR_{20}R_{21})_m(CR_{29}=N-NR_{30})_{n''}A''_{m''}(CR_{22}R_{23})_n(OCH_2CH_2)_{p(CR_{40}}R_{41})_{p''}Y''(CR_{24}R_{25})_q(CO)_tX''$, wherein:

m, n, p, q, m', n', p', q', q", are integer from 1 to 10 and can be 0;

t, m", n" and p" are 0 or 1;

X" is selected from $OR_{36}$, $SR_{37}$, $NR_{38}R_{39}$, wherein $R_{36}$, $R_{37}$, $R_{38}$, $R_{39}$ are H, or linear, branched or cyclic alkyl, alkenyl or alkynyl having from 1 to 20 carbon atoms and, or, a polyethylene glycol unit —$(OCH_2CH_2)_n$, optionally $R_{37}$ is a thiol protecting group, or when t=1, COX" forms a reactive ester selected from N-hydroxysuccinimide esters, N-hydroxyphthalimide esters, N-hydroxy sulfo-succinimide esters, para-nitrophenyl esters, dinitrophenyl esters, pentafluorophenyl esters and their derivatives, wherein said derivatives facilitate amide formation;

Y" is absent or is selected from O, S, S—S or $NR_{32}$, wherein $R_{32}$ has the same definition as given above for R, or when Y" is not S—S and t=O, X" is selected from a maleimido group, a haloacetyl group or $SR_{37}$, wherein $R_{37}$ has the same definition as above;

A" is an amino acid selected from glycine, alanine, leucine, valine, lysine, citrulline and glutamate or a polypeptide containing between 2 to 20 amino acid units;

$R_{20}$, $R_{21}$, $R_{22}$, $R_{23}$, $R_{24}$, $R_{25}$, $R_{26}$, $R_{27}$ are the same or different and are H or a linear or branched alkyl having from 1 to 5 carbon atoms;

$R_{28}$ is H or alkyl;

$R_{29}$ and $R_{30}$ are the same or different and are H or alkyl from 1 to 5 carbon atoms;

optionally, one of $R_{40}$ and $R_{41}$ is a negatively or positively charged functional group and the other is H or alkyl, alkenyl, alkynyl having 1 to 4 carbon atoms.

The compounds of formula (IV), (V), (VI), (VII), (XII) and (XIII) (i.e., dimers) can be linked through $R_1$, $R_2$, $R_3$, $R_4$, $R_1'$, $R_2'$, $R_3'$, $R_4'$, L', L", L'". Of these, preferred linkable groups are $R_2'$, $R_3'$, $R_4'$, L', L", L'" and most preferred linkable groups are $R_2'$, $R_3'$ and L'. Examples of linking groups for compounds of formula (IV), (V), (VI), (VII), (XII) and (XIII) include, but are not limited to:

—$O(CR_{20}R_{21})_m(CR_{22}R_{23})_n(OCH_2CH_2)_p(CR_{40}R_{41})_{p''}Y''(CR_{24}R_{25})_q(CO)_tX''$,

—$O(CR_{20}R_{21})_m(CR_{26}=CR_{27})_{m'}(CR_{22}R_{23})_n(OCH_2CH_2)_p(CR_{40}R_{41})_{p''}Y''(CR_{24}R_{25})_q(CO)_tX''$,

—$O(CR_{20}R_{21})_m(\text{alkynyl})_{n'}(CR_{22}R_{23})_n(OCH_2CH_2)_p(CR_{40}R_{41})_{p''}Y''(CR_{24}R_{25})_q(CO)_tX''$, —$O(CR_{20}R_{21})_m(\text{piperazino})_t(CR_{22}R_{23})_n(OCH_2CH_2)_p(CR_{40}R_{41})_{p''}Y''(CR_{24}R_{25})_q(CO)_tX''$, —$O(CR_{20}R_{21})_m(\text{pyrrolo})_t(CR_{22}R_{23})_n(OCH_2CH_2)_p(CR_{40}R_{41})_{p''}Y''(CR_{24}R_{25})_q(CO)_tX''$, —$O(CR_{20}R_{21})_mA''_{m''}(CR_{22}R_{23})_n(OCH_2CH_2)_p(CR_{40}R_{41})_{p''}Y''(CR_{24}R_{25})_q(CO)_tX''$, —$S(CR_{20}R_{21})_m(CR_{22}R_{23})_n(OCH_2CH_2)_p(CR_{40}R_{41})_{p''}Y''(CR_{24}R_{25})_q(CO)_tX''$, —$S(CR_{20}R_{21})_m(CR_{26}=CR_{27})_{m'}(CR_{22}R_{23})_n(OCH_2CH_2)_p(CR_{40}R_{41})_{p''}Y''(CR_{24}R_{25})_q(CO)_tX''$, —$S(CR_{20}R_{21})_m(\text{alkynyl})_{n'}(CR_{22}R_{23})_n(OCH_2CH_2)_p(CR_{40}R_{41})_{p''}Y''(CR_{24}R_{25})_q(CO)_tX''$, —$S(CR_{20}R_{21})_m(\text{piperazino})_t(CR_{22}R_{23})_n(OCH_2CH_2)_p(CR_{40}R_{41})_{p''}Y''(CR_{24}R_{25})_q(CO)_tX''$, —$S(CR_{20}R_{21})_m(\text{pyrrolo})_t(CR_{22}R_{23})_n(OCH_2CH_2)_p(CR_{40}R_{41})_{p''}Y''(CR_{24}R_{25})_q(CO)_tX''$, —$S(CR_{20}R_{21})_mA''_{m''}(CR_{22}R_{23})_n(OCH_2CH_2)_p(CR_{40}R_{41})_{p''}Y''(CR_{24}R_{25})_q(CO)_tX''$, —$NR_{33}(C=O)_{p''}(CR_{20}R_{21})_m(CR_{22}R_{23})_n(OCH_2CH_2)_p(CR_{40}R_{41})_{p''}Y''(CR_{24}R_{25})_q(CO)_tX''$, —$NR_{33}(C=O)_{p''}(CR_{20}R_{21})_m(CR_{26}=CR_{27})_{m'}(CR_{22}R_{23})_n(OCH_2CH_2)_p(CR_{40}R_{41})_{p''}Y''(CR_{24}R_{25})_q(CO)_tX''$, —$NR_{33}(C=O)_{p''}(CR_{20}R_{21})_m(\text{alkynyl})_{n'}(CR_{22}R_{23})_n(OCH_2CH_2)_p(CR_{40}R_{41})_{p''}Y''(CR_{24}R_{25})_q(CO)_tX''$, —$NR_{33}(C=O)_{p''}(CR_{20}R_{21})_m(\text{piperazino})_t(CR_{22}R_{23})_n(OCH_2CH_2)_p(CR_{40}R_{41})_{p''}Y''(CR_{24}R_{25})_q(CO)_tX''$, —$NR_{33}(C=O)_{p''}(CR_{20}R_{21})_m(\text{pyrrolo})_t(CR_{22}R_{23})_n(OCH_2CH_2)_p(CR_{40}R_{41})_{p''}Y''(CR_{24}R_{25})_q(CO)_tX''$, —$NR_{33}(C=O)_{p''}(CR_{20}R_{21})_mA''_{m''}(CR_{22}R_{23})_n(OCH_2CH_2)_p(CR_{40}R_{41})_{p''}Y''(CR_{24}R_{25})_q(CO)_tX''$, —$(CR_{20}R_{21})_m(CR_{22}R_{23})_n(OCH_2CH_2)_p(CR_{40}R_{41})_{p''}Y''(CR_{24}R_{25})_q(CO)_tX''$, —$(CR_{20}R_{21})_m(CR_{26}=CR_{27})_{m'}(CR_{22}R_{23})_n(OCH_2CH_2)_p(CR_{40}R_{41})_{p''}Y''(CR_{24}R_{25})_q(CO)_tX''$, —$(CR_{20}R_{21})_m(\text{alkynyl})_{n'}(CR_{22}R_{23})_n(OCH_2CH_2)_p(CR_{40}R_{41})_{p''}Y''(CR_{24}R_{25})_q(CO)_tX''$, —$(CR_{20}R_{21})_m(\text{piperazino})_t(CR_{22}R_{23})_n(OCH_2CH_2)_p(CR_{40}R_{41})_{p''}Y''(CR_{24}R_{25})_q(CO)_tX''$, —$(CR_{20}R_{21})_mA''_{m''}(CR_{22}R_{23})_n(OCH_2CH_2)_p(CR_{40}R_{41})_{p''}Y''(CR_{24}R_{25})_q(CO)_tX''$, —$(CR_{20}R_{21})_m(CR_{29}=N-NR_{30})_{n''}(CR_{22}R_{23})_n(OCH_2CH_2)_p(CR_{40}R_{41})_{p''}Y''(CR_{24}R_{25})_q(CO)_tX''$, —$(CR_{20}R_{21})_m(CR_{29}=N-NR_{30})_{n''}(CR_{26}=CR_{27})_{m'}(CR_{22}R_{23})_n(OCH_2CH_2)_p(CR_{40}R_{41})_{p''}Y''(CR_{24}R_{25})_q(CO)_tX''$, —$(CR_{20}R_{21})_m(CR_{29}=N-NR_{30})_{n''}(\text{alkynyl})_{n'}(CR_{22}R_{23})_n(OCH_2CH_2)_p(CR_{40}R_{41})_{p''}Y''(CR_{24}R_{25})_q(CO)_tX''$, —$(CR_{20}R_{21})_m(CR_{29}'N-NR_{30})_{n''}A''_{m''}(CR_{22}R_{23})_n(OCH_2CH_2)_p(CR_{40}R_{41})_{p''}Y''(CR_{24}R_{25})_q(CO)_tX''$, wherein:

m, n, p, q, m', n', t' are integer from 1 to 10, or are optionally 0;

t, m", n" and p" are 0 or 1;

X" is selected from $OR_{36}$, $SR_{37}$, $NR_{38}R_{39}$, wherein $R_{36}$, $R_{37}$, $R_{38}$, $R_{39}$ are H, or linear, branched or cyclic alkyl, alkenyl or alkynyl having from 1 to 20 carbon atoms and, or, a polyethylene glycol unit —$(OCH_2CH_2)_n$, $R_{37}$, optionally, is a thiol protecting group when t=1, COX" forms a reactive ester selected from N-hydroxysuccinimide esters, N-hydroxyphthalimide esters, N-hydroxy sulfo-succinimide esters, para-nitrophenyl esters, dinitrophenyl esters, pentafluorophenyl esters and their derivatives, wherein said derivatives facilitate amide bond formation;

Y" is absent or is selected from O, S, S—S or $NR_{32}$, wherein $R_{32}$ has the same definition as given above for R, or when Y" is not S—S and t=O, X" is selected from a maleimido group, a haloacetyl group or $SR_{37}$, wherein $R_{37}$ has the same definition as above;

A" is an amino acid selected from glycine, alanine, leucine, valine, lysine, citrulline and glutamate or a polypeptide containing between 2 to 20 amino acid units;

$R_{20}$, $R_{21}$, $R_{22}$, $R_{23}$, $R_{24}$, $R_{25}$, $R_{26}$, and $R_{27}$ are the same or different and are H or a linear or branched alkyl having from 1 to 5 carbon atoms;

$R_{29}$ and $R_{30}$ are the same or different and are H or alkyl from 1 to 5 carbon atoms;

$R_{33}$ is H or linear, branched or cyclic alkyl, alkenyl or alkynyl having from 1 to 12 carbon atoms, a polyethylene glycol unit —$(OCH_2CH_2)_n$, or $R_{33}$ is —$COR_{34}$, —$CSR_{34}$, —SOR₃₄, or —SO₂R₃₄, wherein R₃₄ is H or linear, branched or cyclic alkyl, alkenyl or alkynyl having from 1 to 20 carbon atoms or, a polyethylene glycol unit —(OCH₂CH₂)ₙ; and one of $R_{40}$ and $R_{41}$ is optionally a negatively or positively charged functional group and the other is H or alkyl, alkenyl, alkynyl having 1 to 4 carbon atoms.

Further, while the synthesis of cytotoxic compounds (e.g., indolinobenzodiazepine or oxazolidinobenzodiazepine), derivatives thereof, or dimers thereof bearing a linking moiety is described below in terms of an amide, thioether or disulfide bond containing linking moieties at the L' (in the compound of formula XIII) or $R_3$ (in the compound of formula XII) positions, one of skill in the art will understand that linking moieties at other positions and with other chemical bonds, as described above, can also be used with the present invention.

The structures of representative compounds, representative conjugates and claimed compounds in the examples of the present invention are shown in Tables 3~9:

TABLE 3

Structures of representative compounds of the present invention.

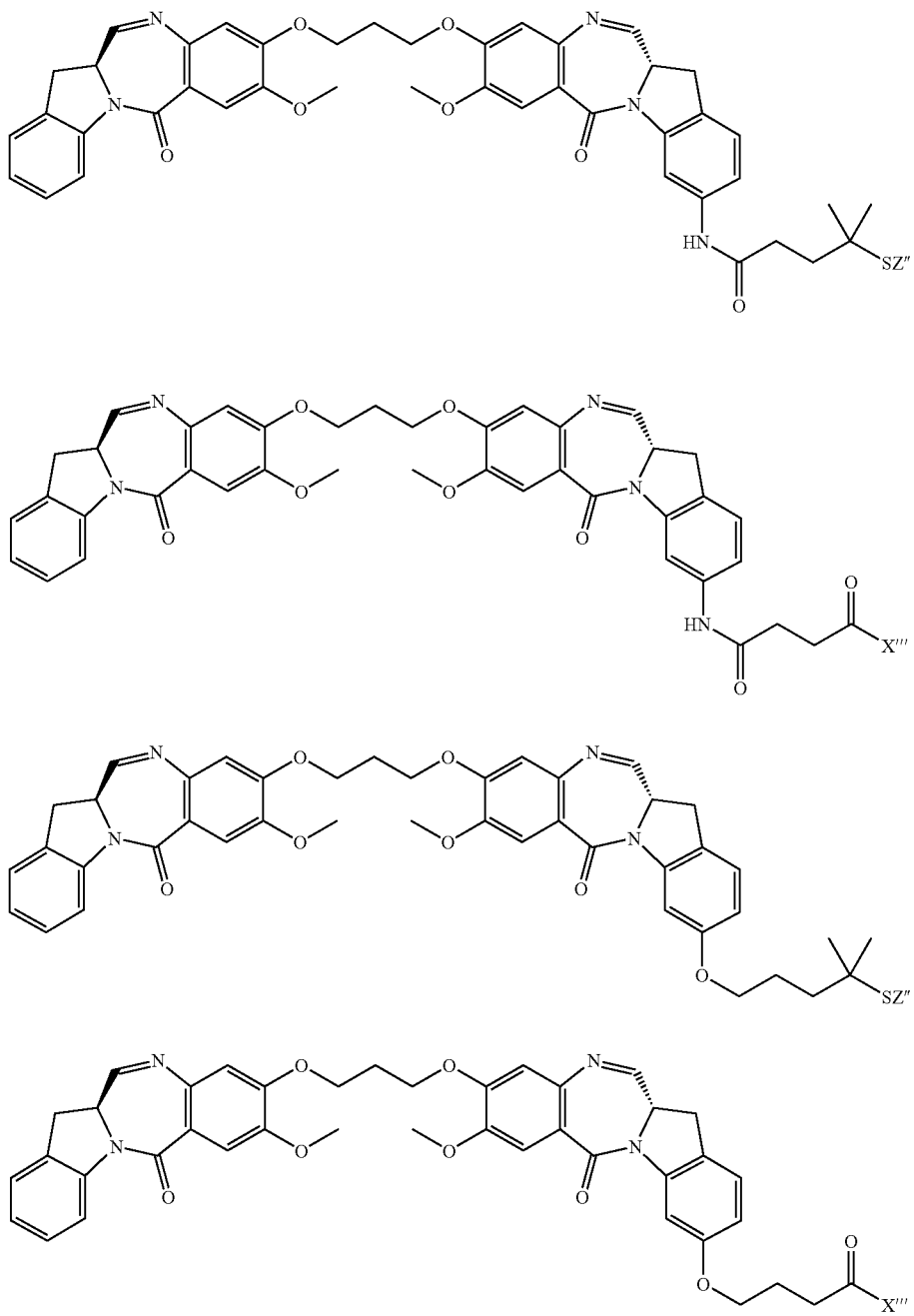

TABLE 3-continued
Structures of representative compounds of the present invention.
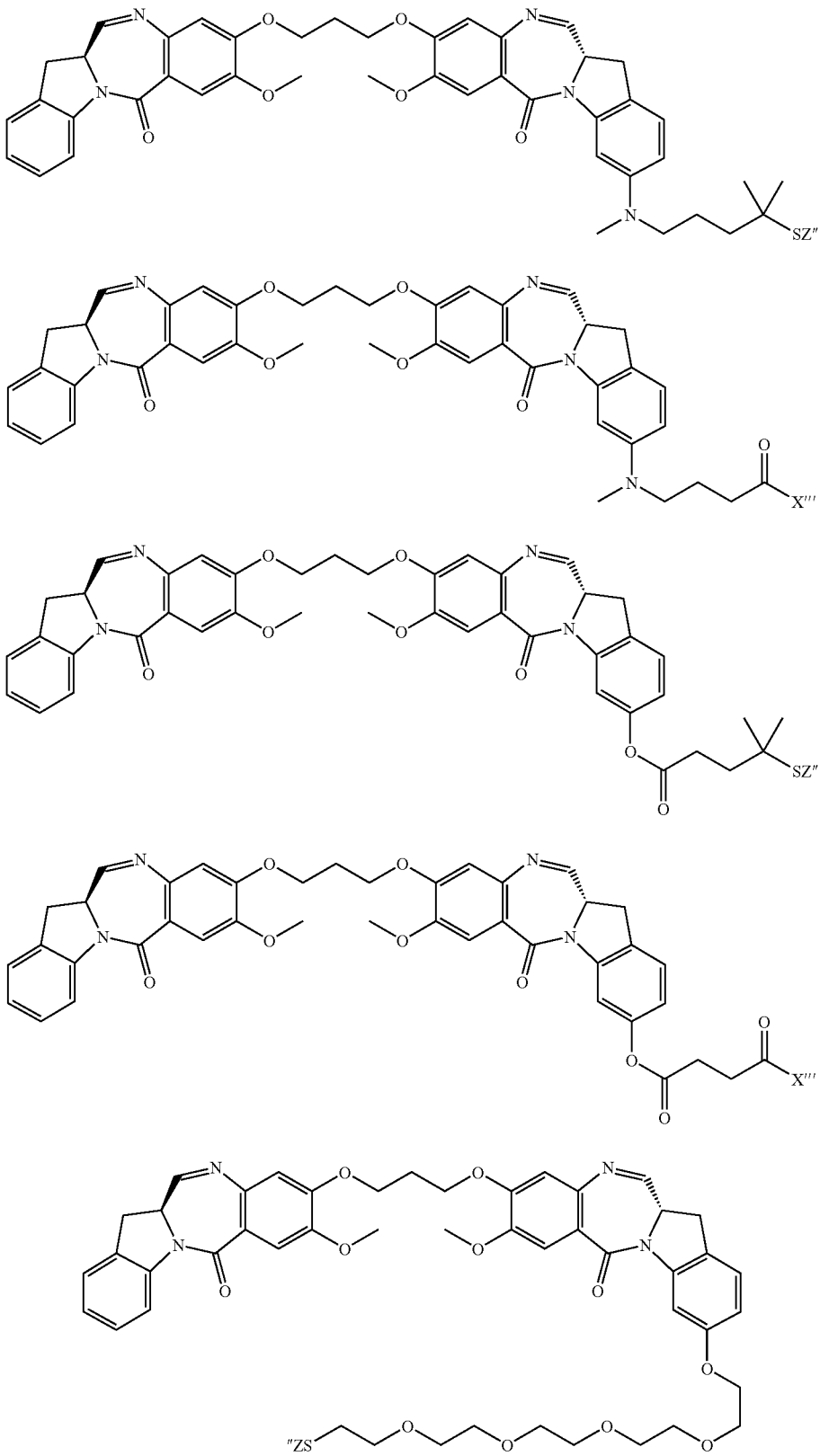

TABLE 3-continued
Structures of representative compounds of the present invention.
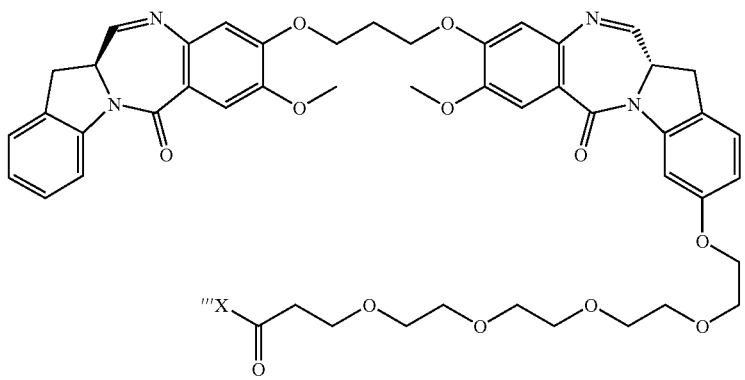
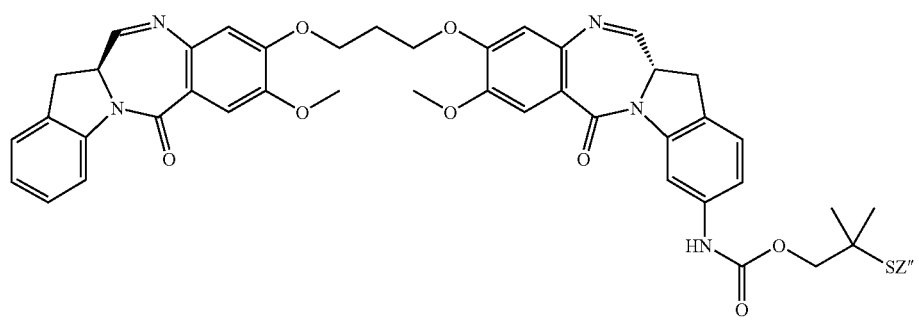
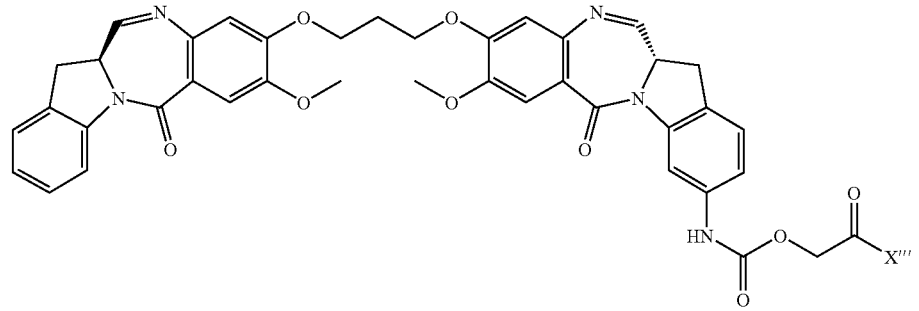
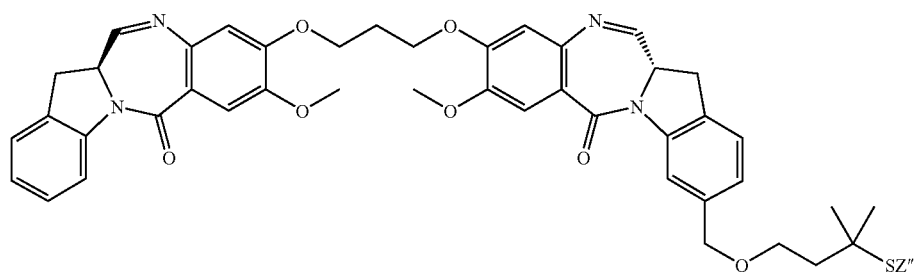
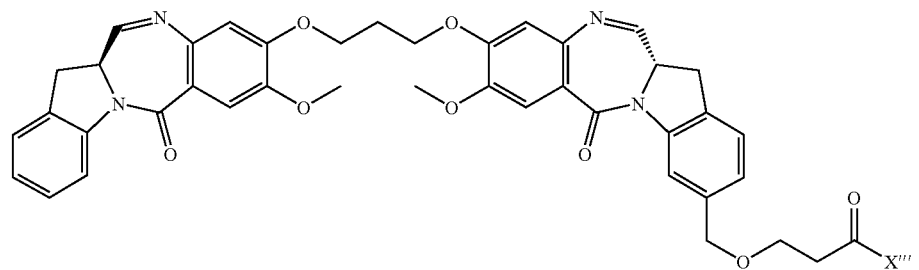

TABLE 3-continued
Structures of representative compounds of the present invention.
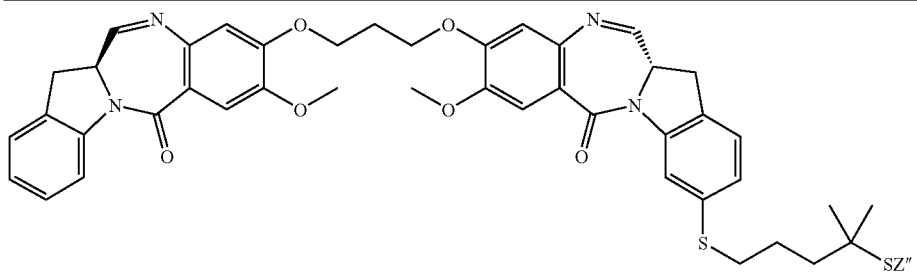
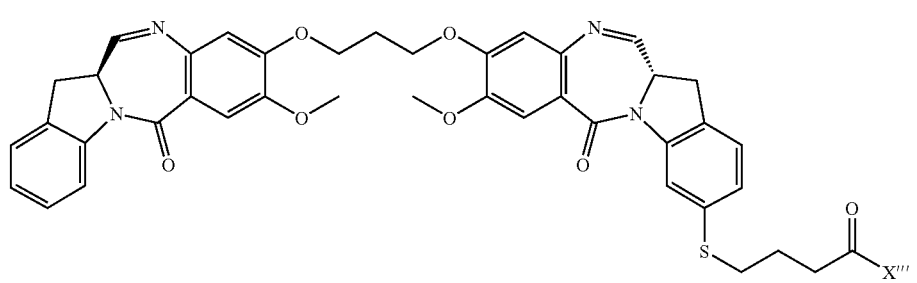
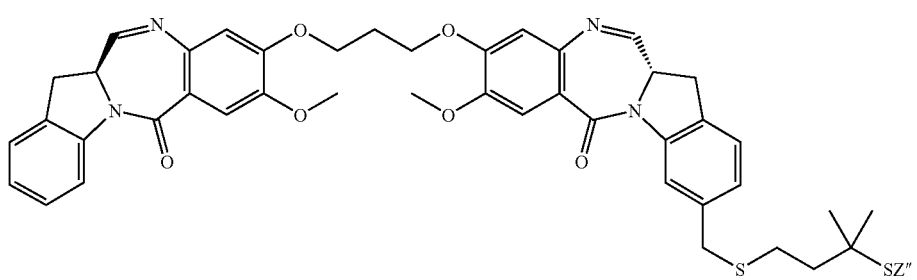
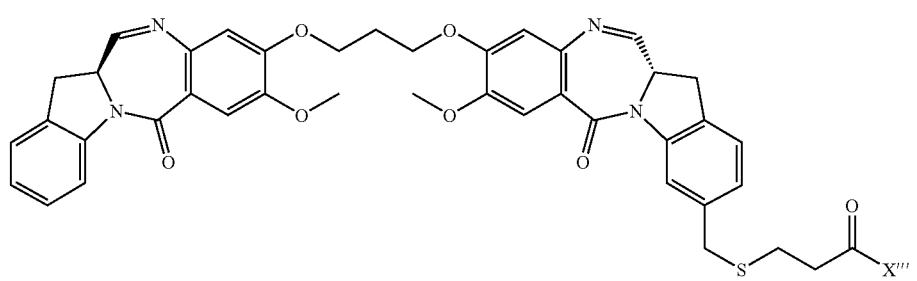
Note:
Z" = H, SMe, SPy, SPy-NO$_2$, Ac; X''' = NHS;
TABLE 4
Structures of representative compounds of the present invention (Continued).
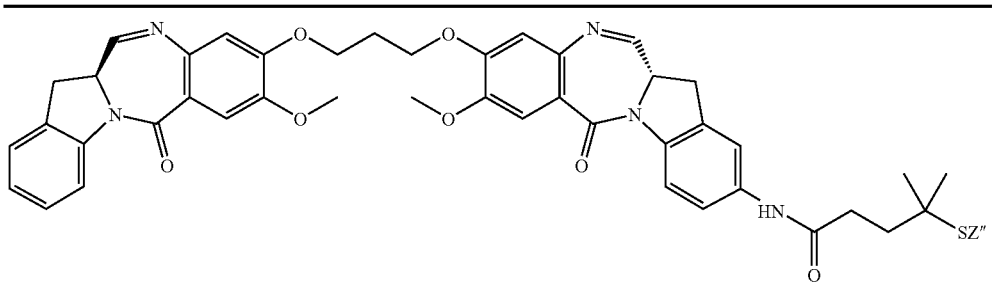

TABLE 4-continued
Structures of representative compounds of the present invention (Continued).
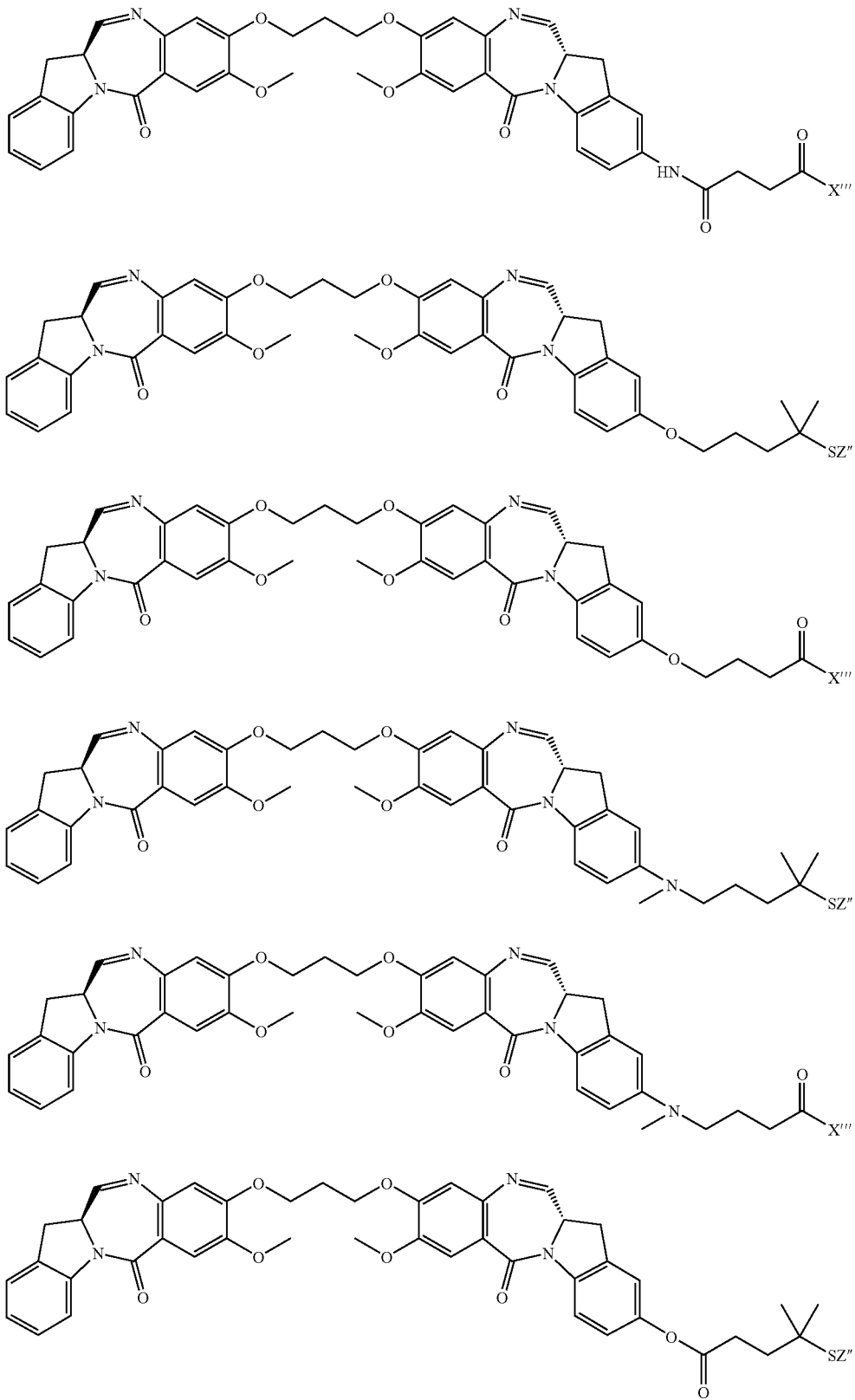

TABLE 4-continued
Structures of representative compounds of the present invention (Continued).
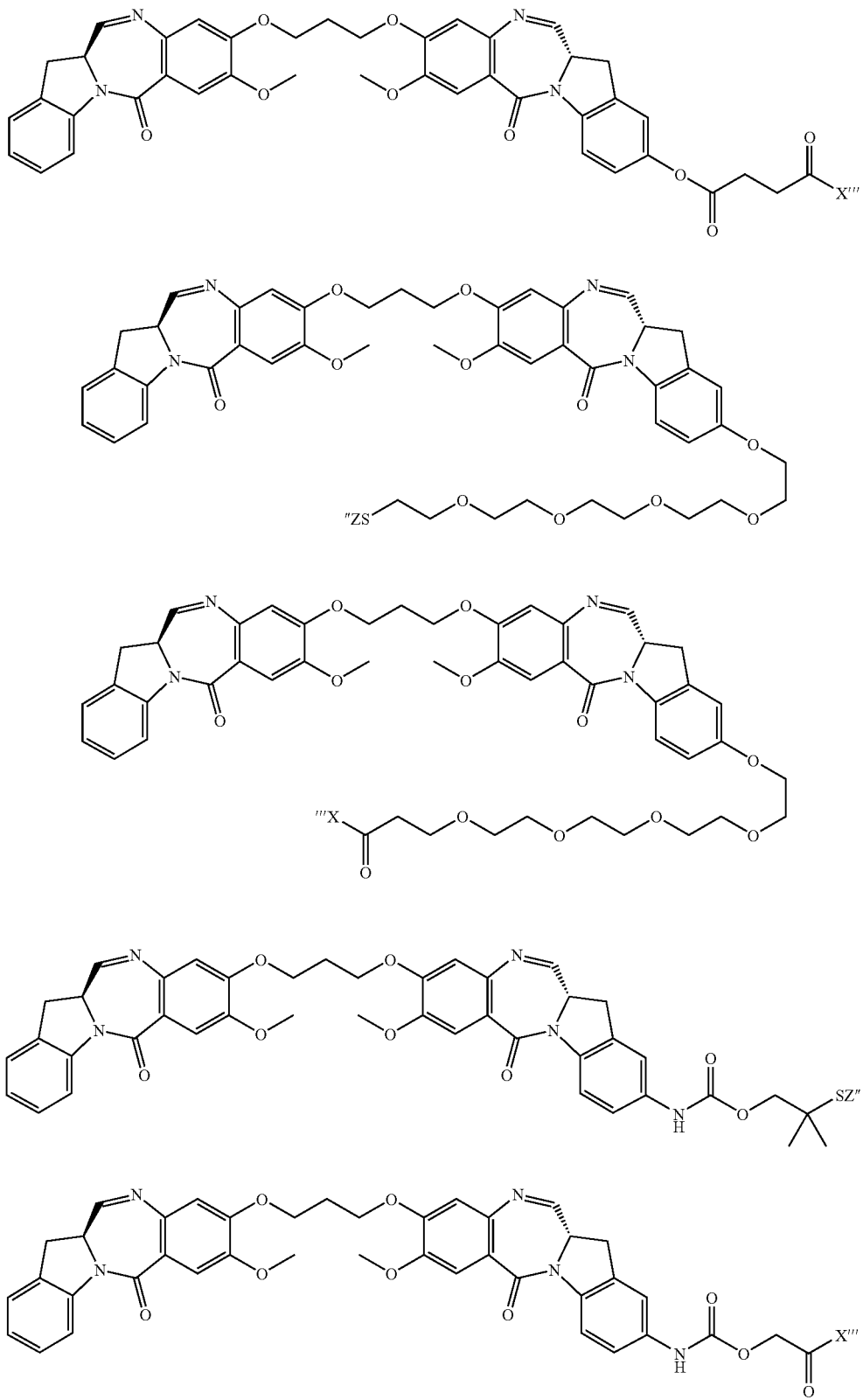

TABLE 4-continued
Structures of representative compounds of the present invention (Continued).
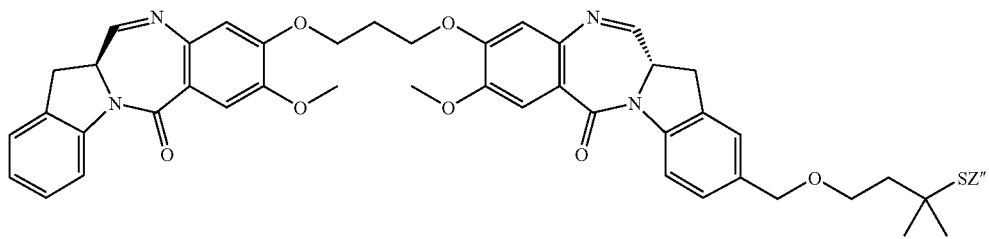
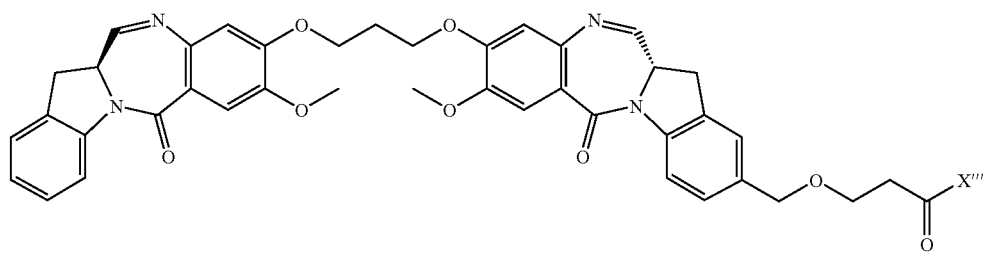
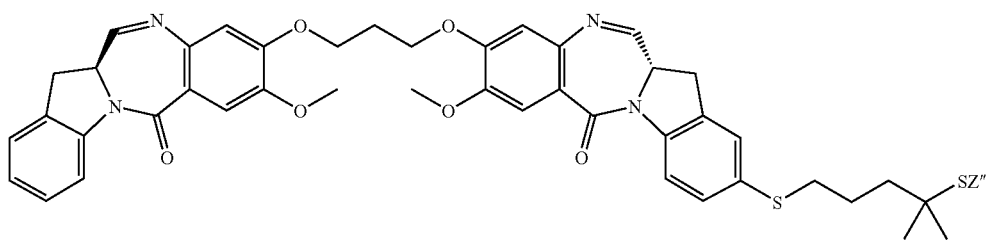
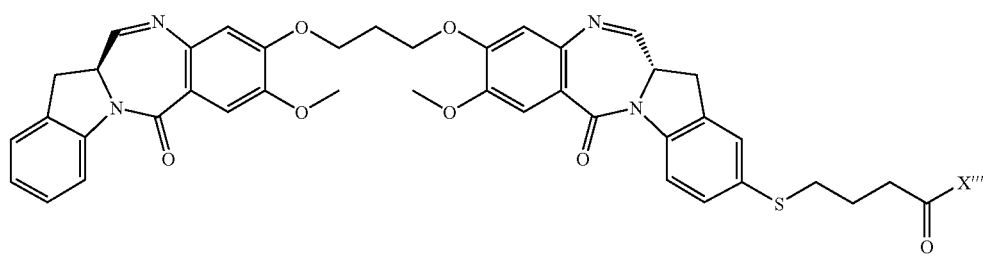
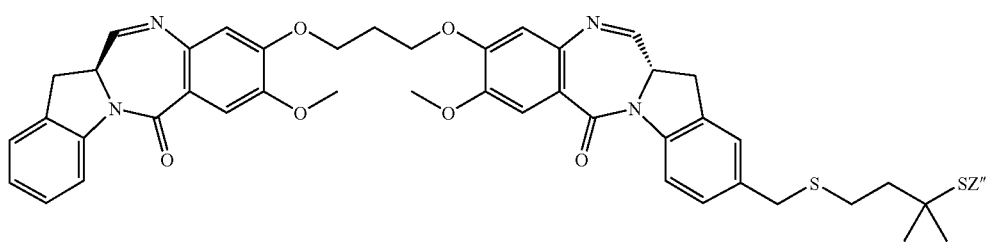
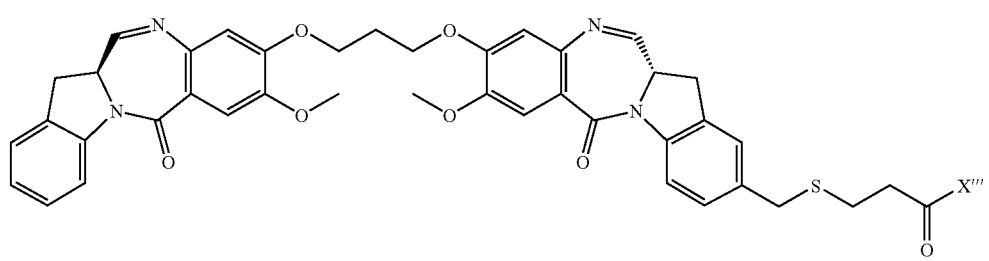
Note:
Z" = H, SMe, SPy, SPy-NO$_2$, Ac; X'" = NHS;

TABLE 5
Structures of representative compounds of the present invention (Continued).
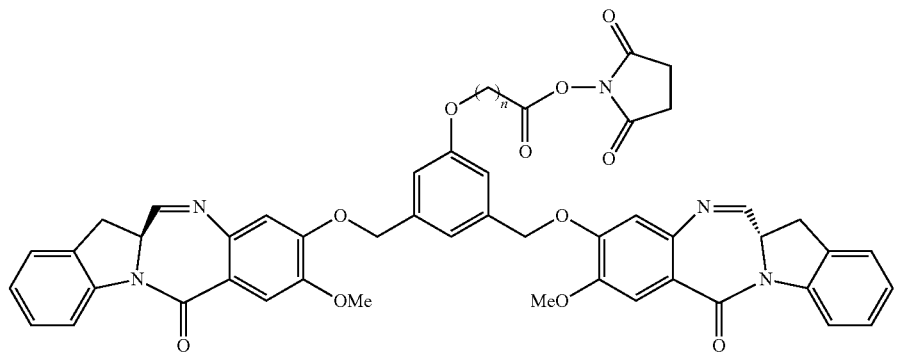
n = 3, 4
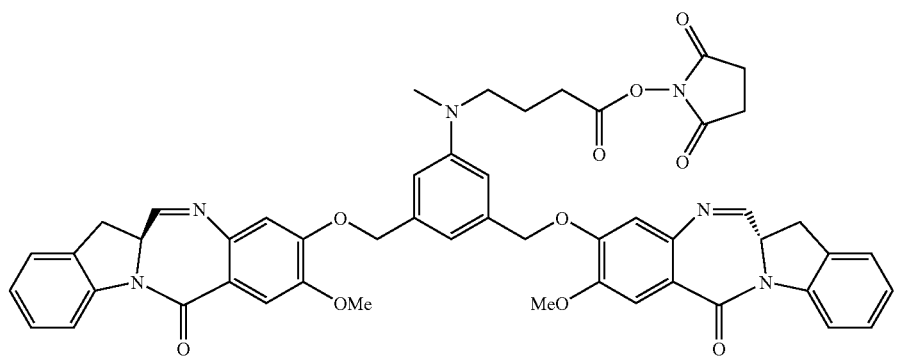 [SMILES: COc1cc2c(cc1OCc1cc(COc3cc4c(cc3OC)C(=O)N3c5ccccc5C[C@H]3C=N4)cc(N(C)CCCC(=O)ON3C(=O)CCC3=O)c1)N=C[C@@H]1Cc3ccccc3N1C2=O]
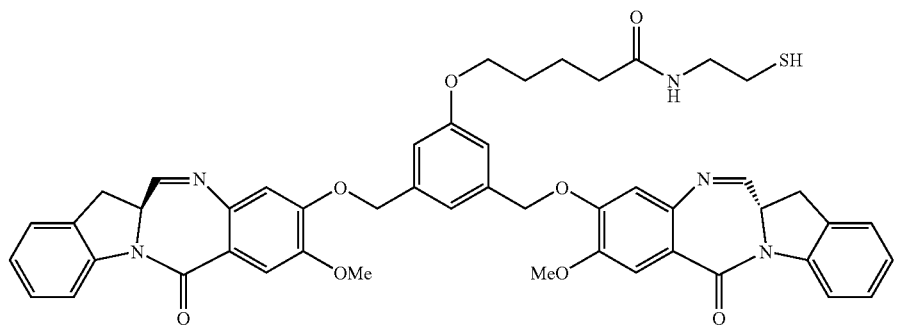 [SMILES: COc1cc2c(cc1OCc1cc(COc3cc4c(cc3OC)C(=O)N3c5ccccc5C[C@H]3C=N4)cc(OCCCCC(=O)NCCS)c1)N=C[C@@H]1Cc3ccccc3N1C2=O]
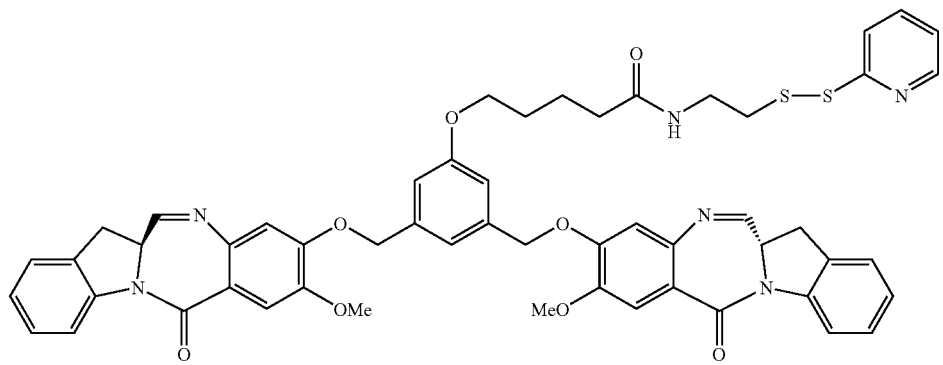 [SMILES: COc1cc2c(cc1OCc1cc(COc3cc4c(cc3OC)C(=O)N3c5ccccc5C[C@H]3C=N4)cc(OCCCCC(=O)NCCSSc3ccccn3)c1)N=C[C@@H]1Cc3ccccc3N1C2=O]

TABLE 5-continued
Structures of representative compounds of the present invention (Continued).
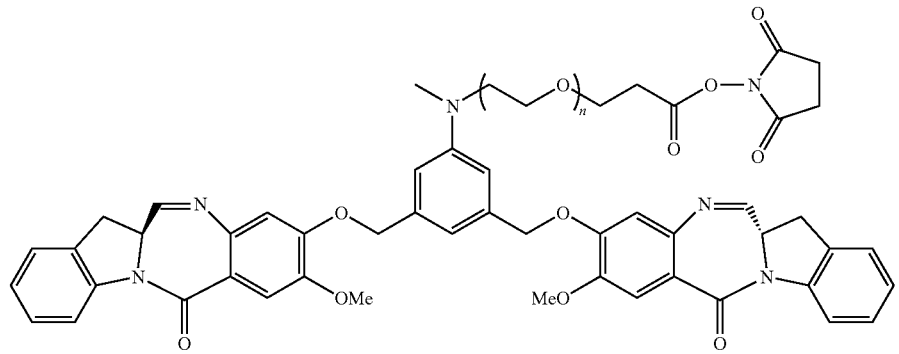
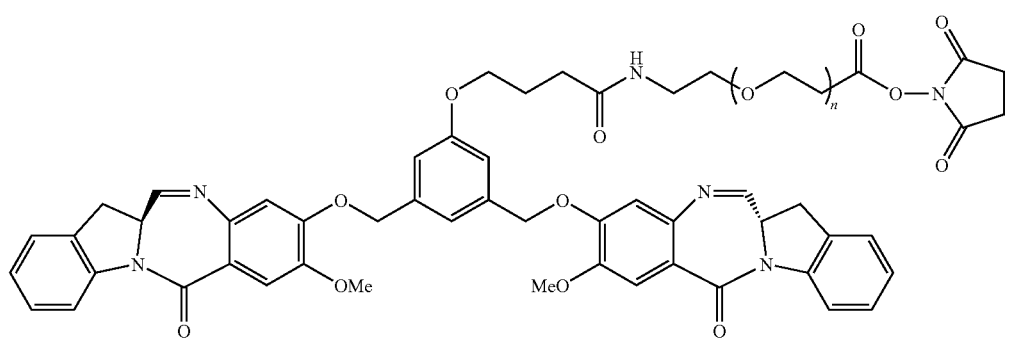
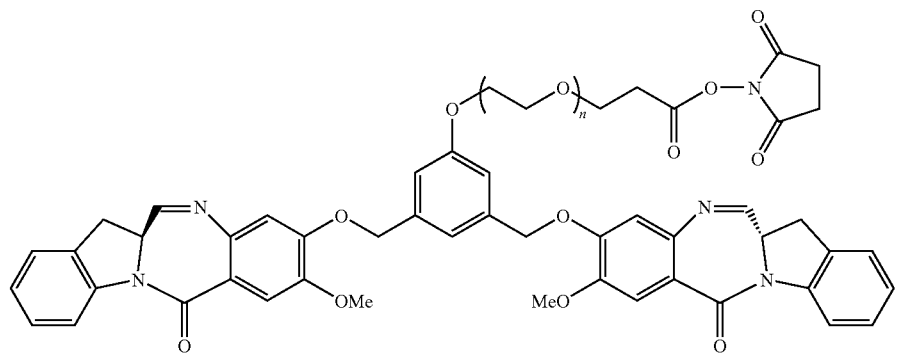
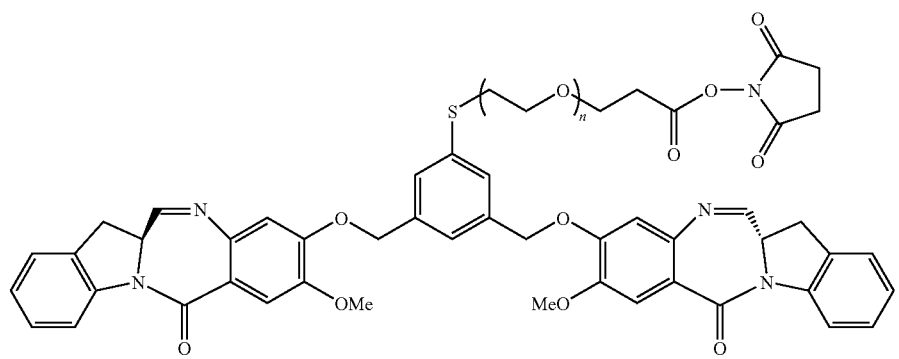

TABLE 5-continued
Structures of representative compounds of the present invention (Continued).
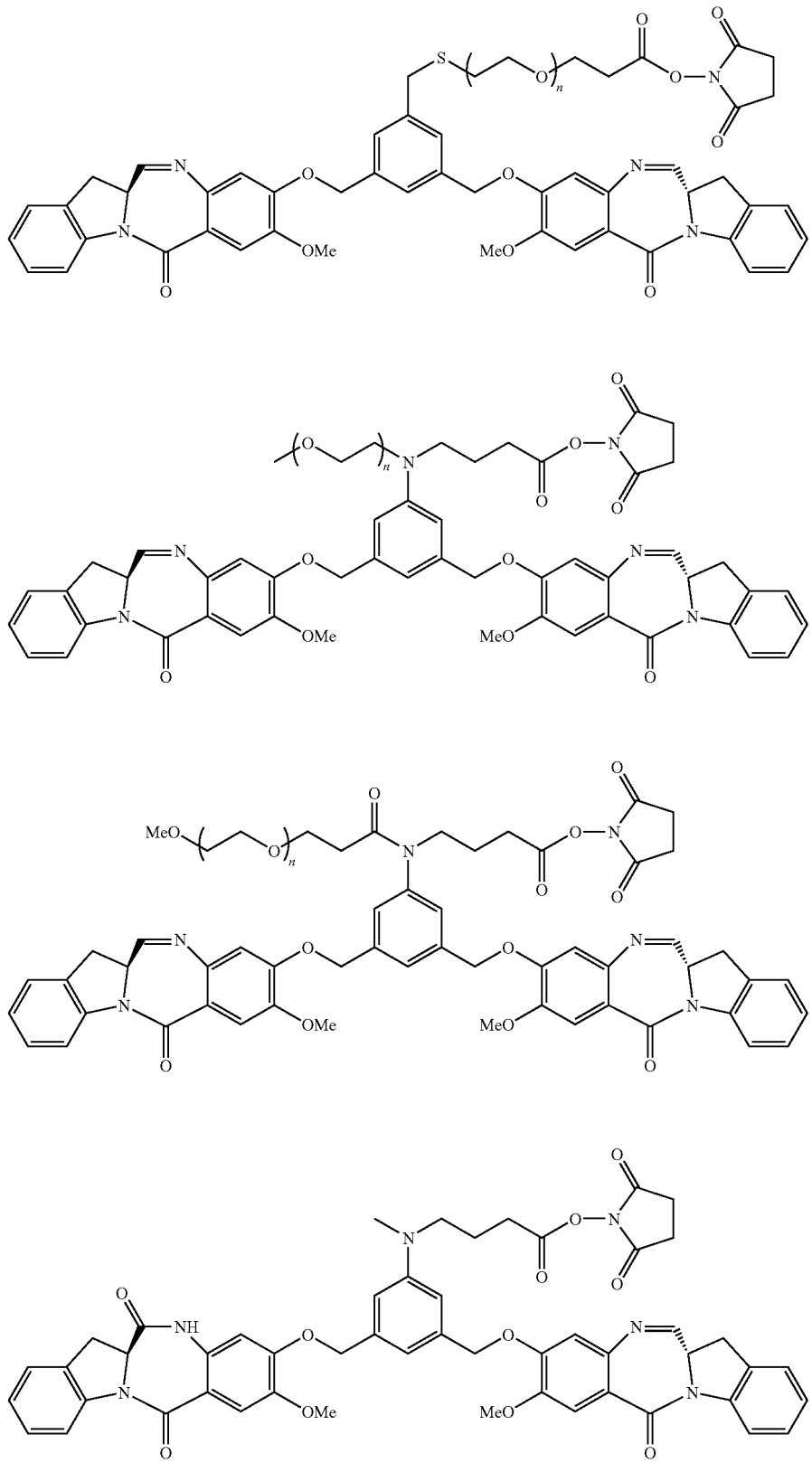

TABLE 5-continued
Structures of representative compounds of the present invention (Continued).
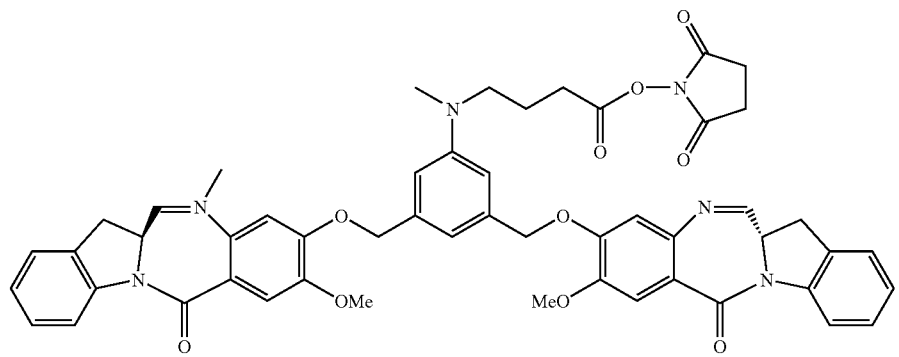
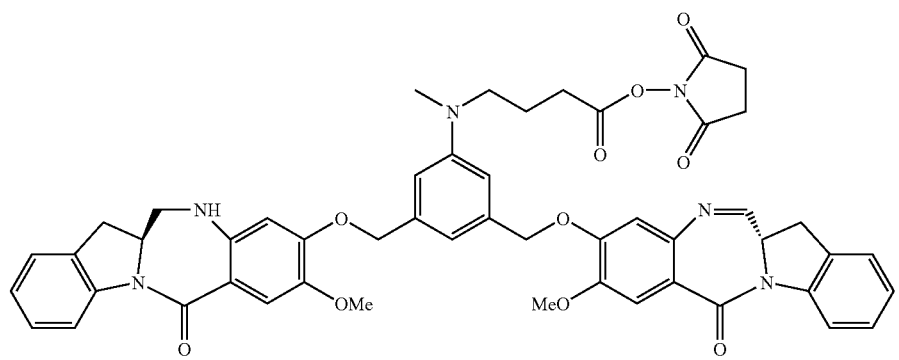 [SMILES: COc1cc2c(cc1OCc1cc(COc3cc4c(cc3OC)C(=O)N3c5ccccc5C[C@H]3CN4)cc(N(C)CCCC(=O)ON3C(=O)CCC3=O)c1)N=C[C@@H]1Cc3ccccc3N1C2=O]
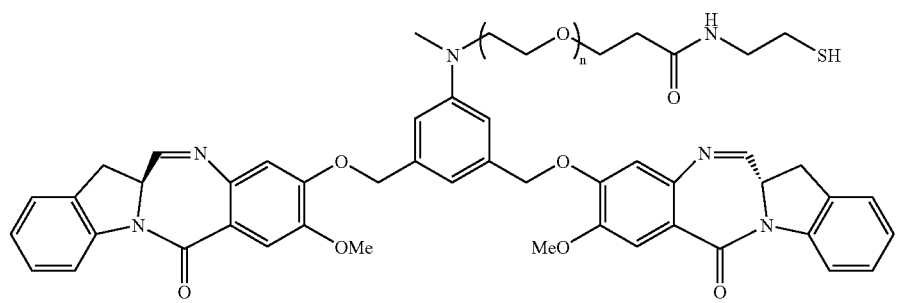
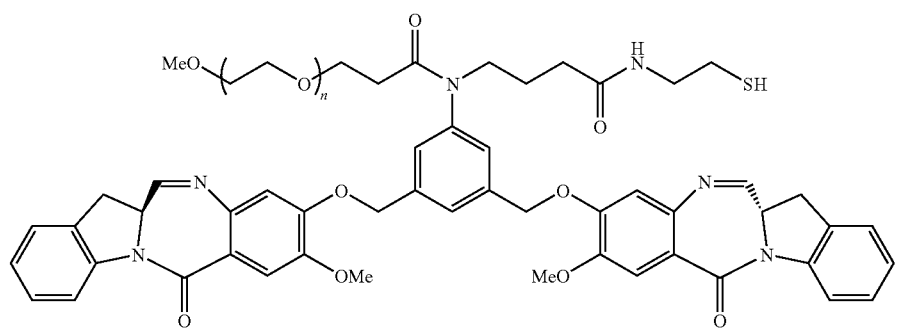 [SMILES: COCCOCCC(=O)N(CCCC(=O)NCCS)c1cc(COc2cc3c(cc2OC)C(=O)N2c4ccccc4C[C@H]2C=N3)cc(COc2cc3c(cc2OC)C(=O)N2c4ccccc4C[C@H]2C=N3)c1]

TABLE 5-continued
Structures of representative compounds of the present invention (Continued).
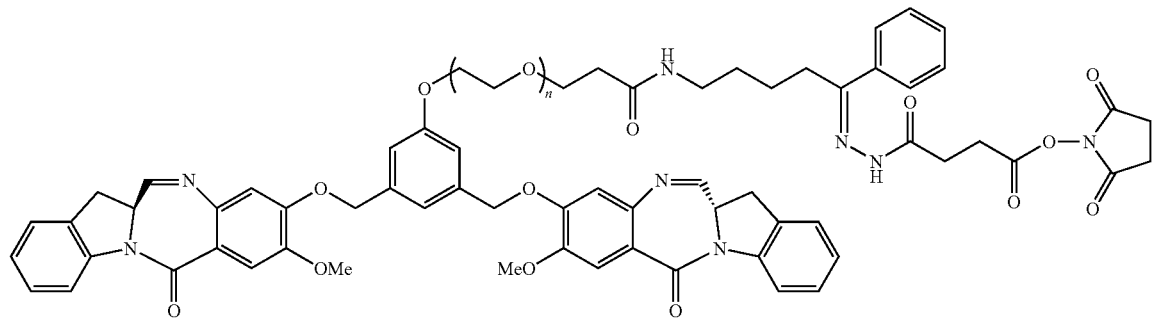
TABLE 6
Structures of representative conjugates of the present invention.
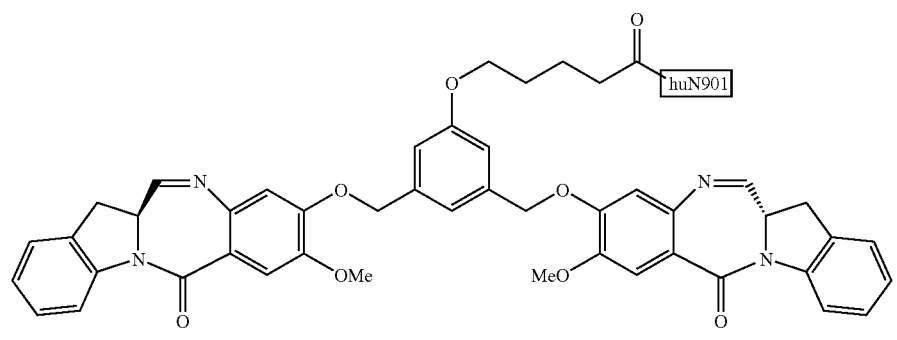
N901-IGN-03
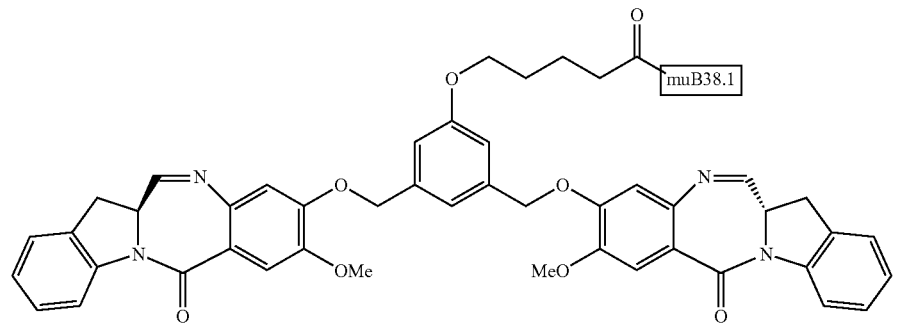
B38.1-IGN-03
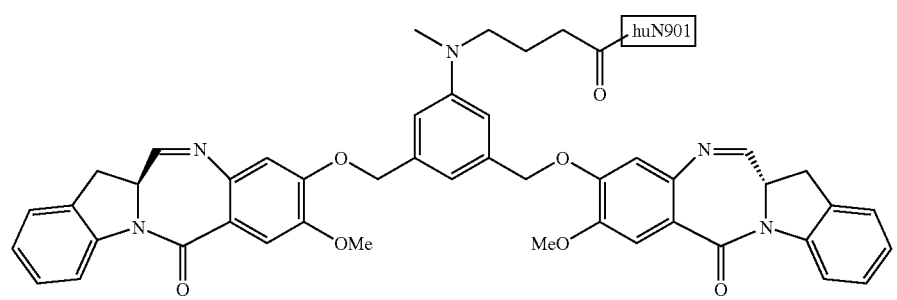
huN901-IGN-07

TABLE 6-continued
Structures of representative conjugates of the present invention.
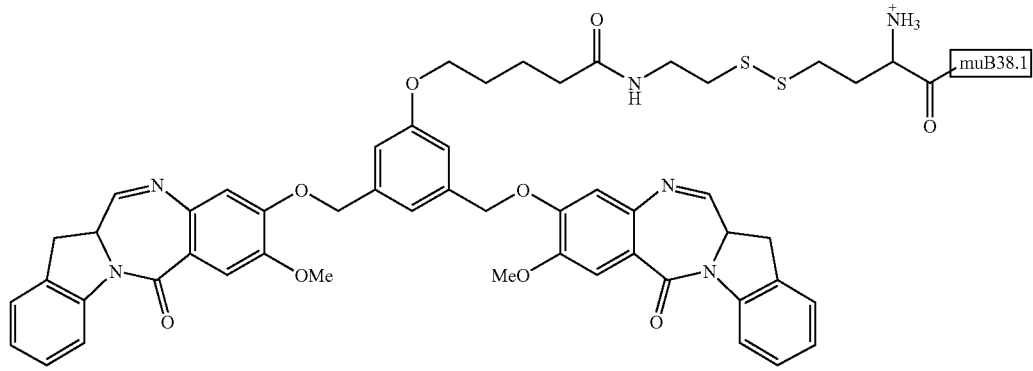
B38.1-IGN-10
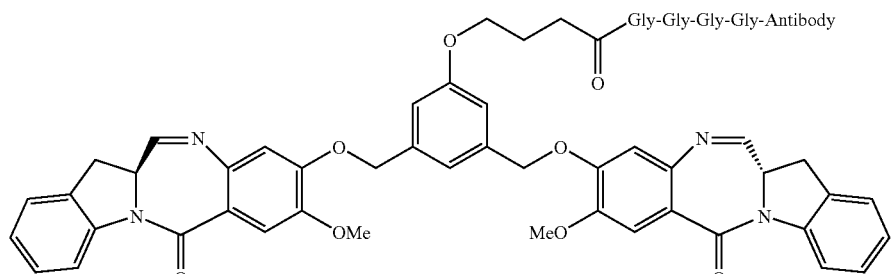
Dimer 1
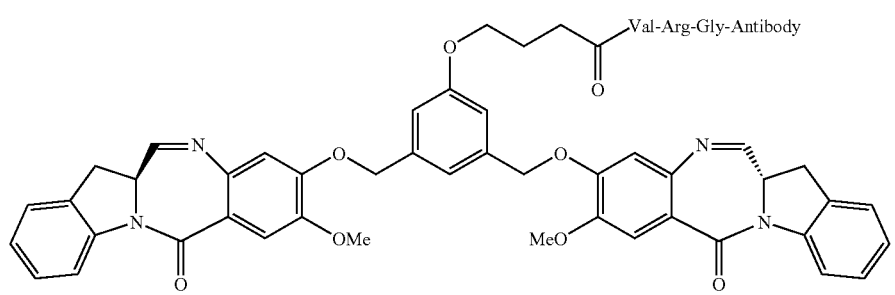
Dimer 2
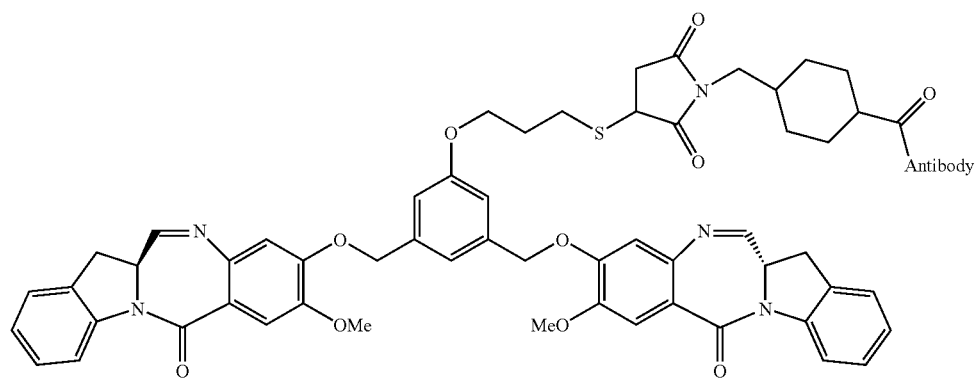
Dimer 3

TABLE 6-continued
Structures of representative conjugates of the present invention.
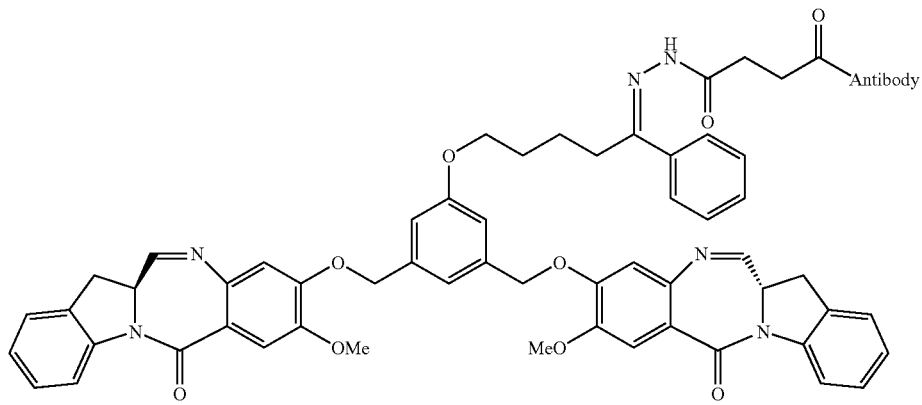
Dimer 4
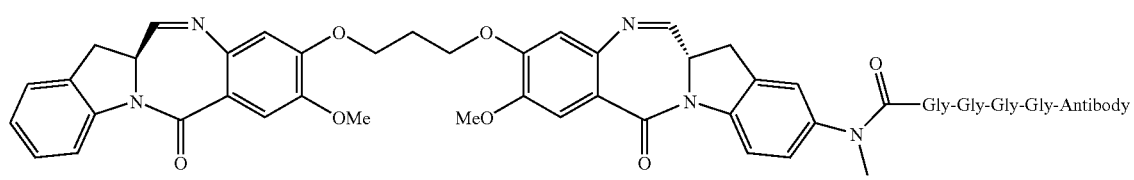
Dimer 5
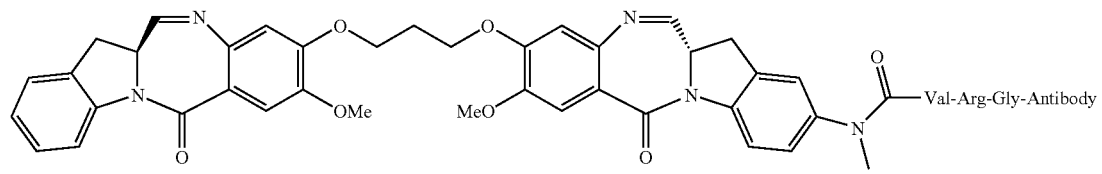
Dimer 6
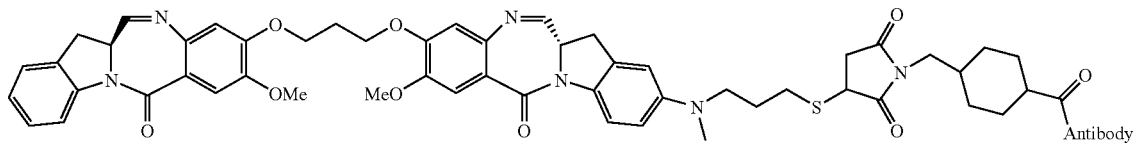
Dimer 7
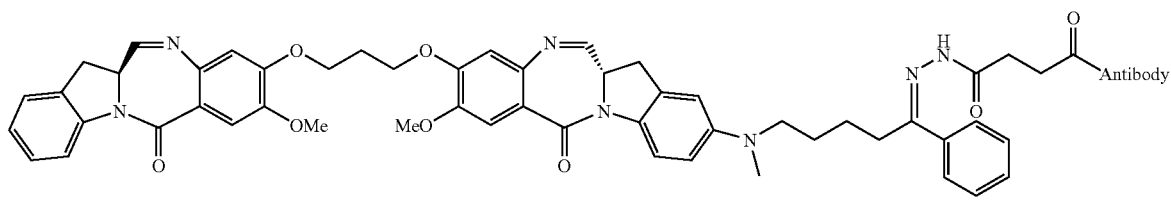
Dimer 8

TABLE 7

Structures of compounds from the examples of the present invention.

| Structure | Compound No. | Example No. |
|---|---|---|
| 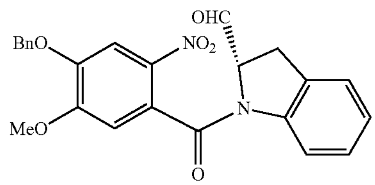 [SMILES: COc1cc(C(=O)N2c3ccccc3C[C@H]2C=O)c([N+](=O)[O-])cc1OCc1ccccc1] | 6 | 1 |
| 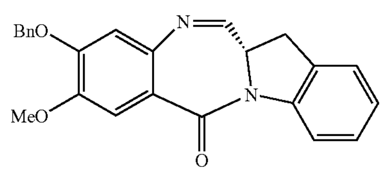 [SMILES: COc1cc2c(cc1OCc1ccccc1)N=C[C@@H]1Cc3ccccc3N1C2=O] | 7 | 1 |
| 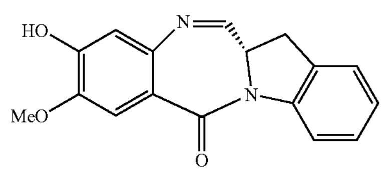 [SMILES: COc1cc2c(cc1O)N=C[C@@H]1Cc3ccccc3N1C2=O] | 8 | 1 |
| 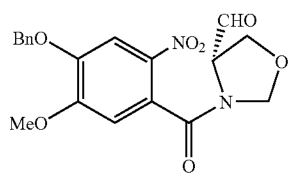 | 12 | 2 |
| 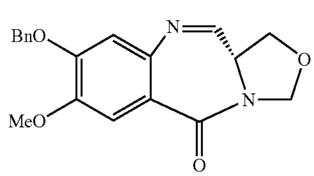 [SMILES: COc1cc2c(cc1OCc1ccccc1)N=C[C@@H]1COCN1C2=O] | 13 | 2 |
| 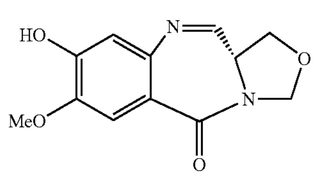 [SMILES: COc1cc2c(cc1O)N=C[C@@H]1COCN1C2=O] | 14 | 2 |
| 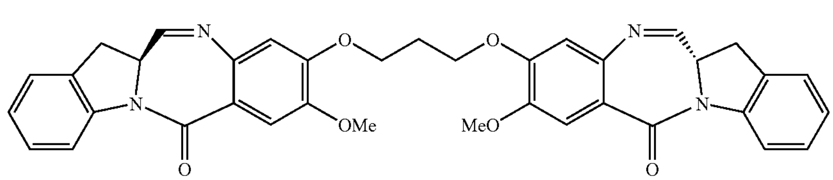 [SMILES: COc1cc2c(cc1OCCCOc1cc3c(cc1OC)C(=O)N1c4ccccc4C[C@H]1C=N3)N=C[C@@H]1Cc3ccccc3N1C2=O] | 15 | 3 |
| 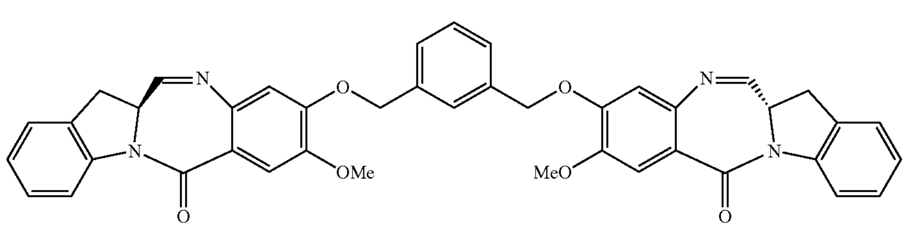 [SMILES: COc1cc2c(cc1OCc1cccc(COc3cc4c(cc3OC)C(=O)N3c5ccccc5C[C@H]3C=N4)c1)N=C[C@@H]1Cc3ccccc3N1C2=O] | 18 | 4 |

TABLE 7-continued
Structures of compounds from the examples of the present invention.
| Structure | Compound No. | Example No. |
|---|---|---|
| 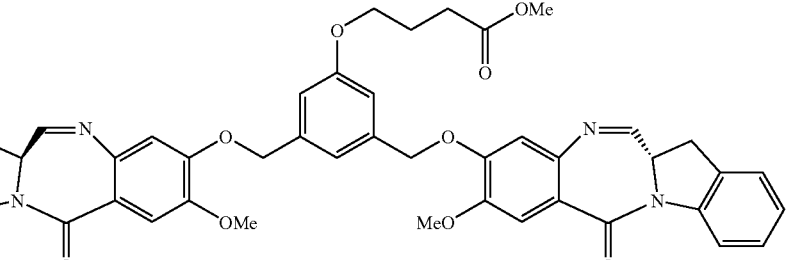 | 19 | 5 |
| 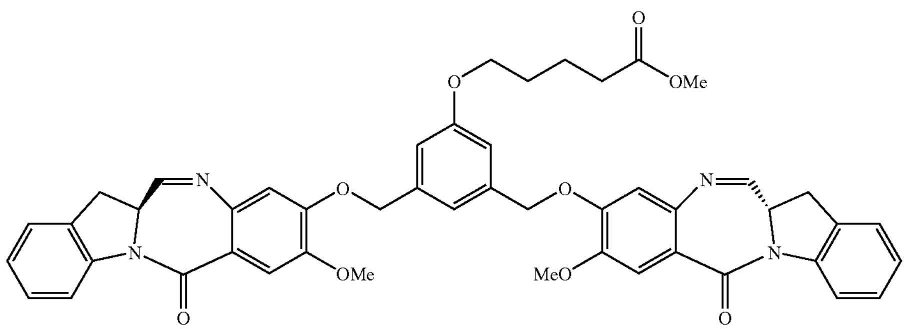 [SMILES: COC(=O)CCCCOc1cc(COc2cc3c(cc2OC)C(=O)N2c4ccccc4C[C@H]2C=N3)cc(COc2cc3c(cc2OC)C(=O)N2c4ccccc4C[C@H]2C=N3)c1] | 34 | 6 |
TABLE 8
Structures of compounds from the examples of the present invention (Continued).
| Structure | Compound No. | Example No. |
|---|---|---|
| 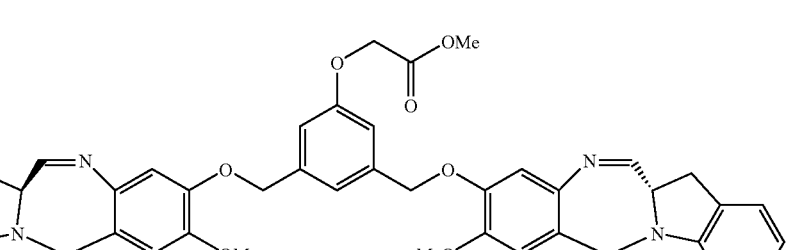 | 35 | 6 |
| 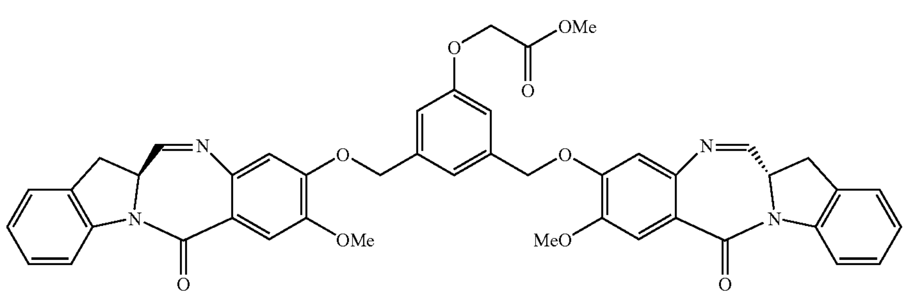 [SMILES: COC(=O)COc1cc(COc2cc3c(cc2OC)C(=O)N2c4ccccc4C[C@H]2C=N3)cc(COc2cc3c(cc2OC)C(=O)N2c4ccccc4C[C@H]2C=N3)c1] | 36 | 6 |

TABLE 8-continued

Structures of compounds from the examples of the present invention (Continued).

| Structure | Compound No. | Example No. |
|---|---|---|
| 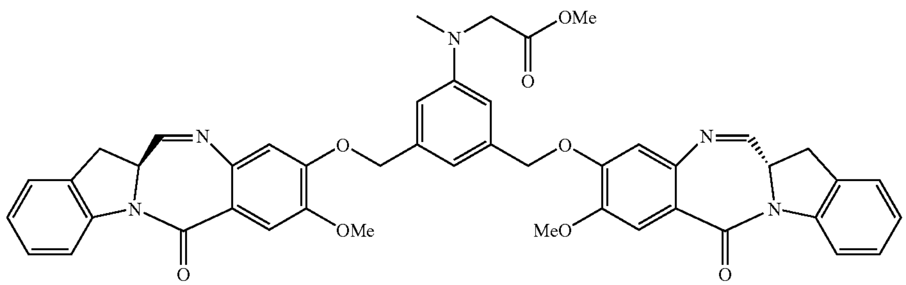 [SMILES: COC(=O)CN(C)c1cc(COc2cc3c(cc2OC)C(=O)N2c4ccccc4C[C@H]2C=N3)cc(COc2cc3c(cc2OC)C(=O)N2c4ccccc4C[C@H]2C=N3)c1] | 39 | 6 |
| 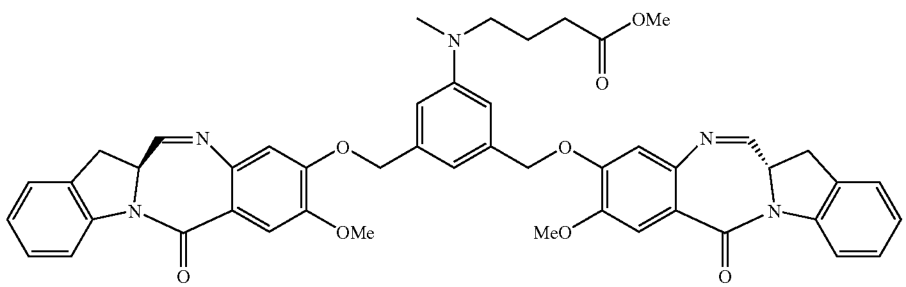 [SMILES: COC(=O)CCCN(C)c1cc(COc2cc3c(cc2OC)C(=O)N2c4ccccc4C[C@H]2C=N3)cc(COc2cc3c(cc2OC)C(=O)N2c4ccccc4C[C@H]2C=N3)c1] | 40 | 6 |
| 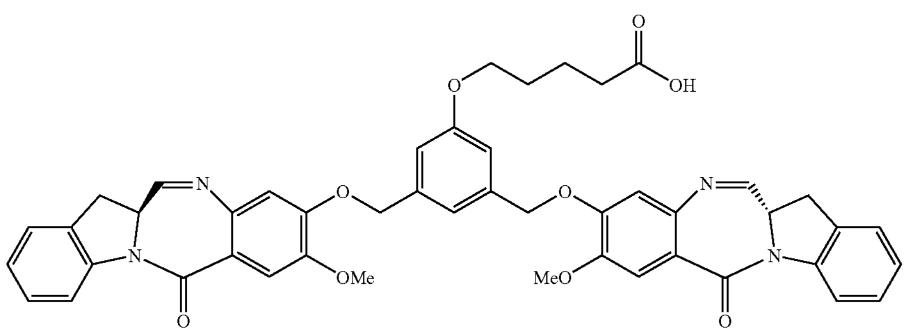 [SMILES: COc1cc2c(cc1OCc1cc(COc3cc4c(cc3OC)C(=O)N3c5ccccc5C[C@H]3C=N4)cc(OCCCCC(=O)O)c1)N=C[C@@H]1Cc3ccccc3N1C2=O] | 41 | 7 |
| 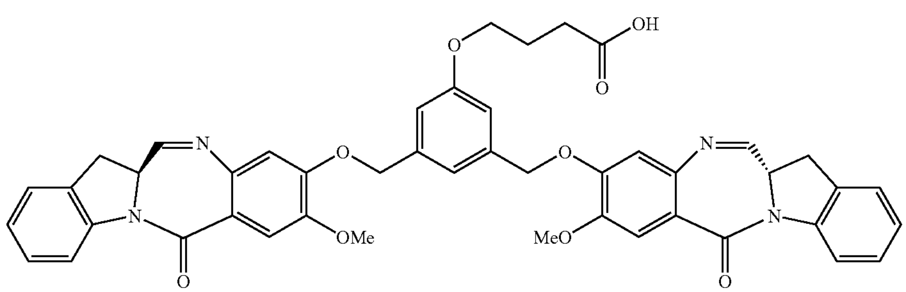 [SMILES: COc1cc2c(cc1OCc1cc(COc3cc4c(cc3OC)C(=O)N3c5ccccc5C[C@H]3C=N4)cc(OCCCC(=O)O)c1)N=C[C@@H]1Cc3ccccc3N1C2=O] | 42 | 7 |
| 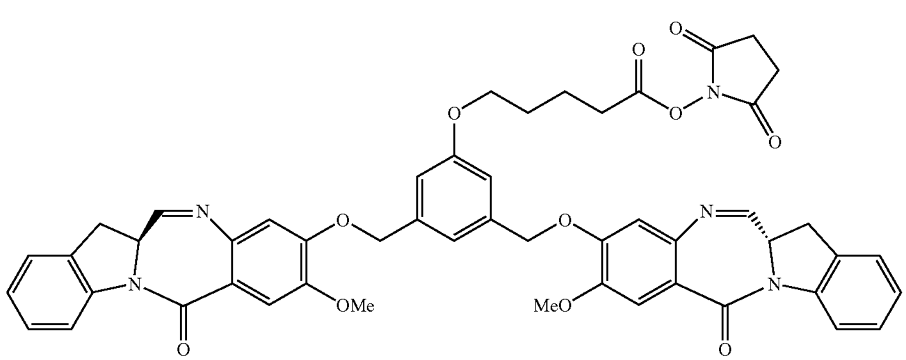 [SMILES: COc1cc2c(cc1OCc1cc(COc3cc4c(cc3OC)C(=O)N3c5ccccc5C[C@H]3C=N4)cc(OCCCCC(=O)ON3C(=O)CCC3=O)c1)N=C[C@@H]1Cc3ccccc3N1C2=O] | 43 | 7 |

TABLE 8-continued

Structures of compounds from the examples of the present invention (Continued).

| Structure | Compound No. | Example No. |
|---|---|---|
| 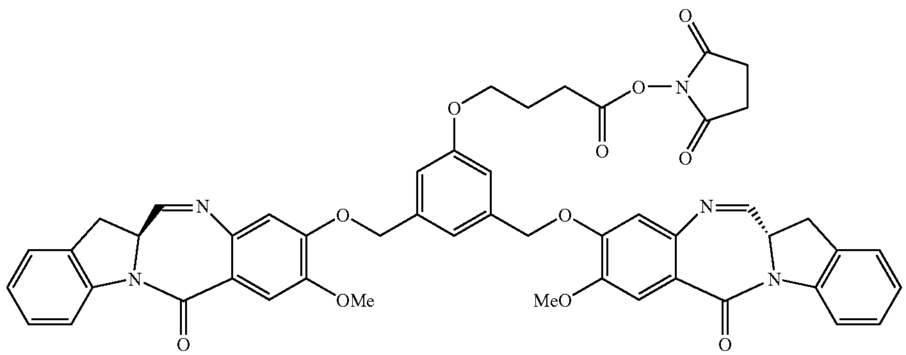 [SMILES: COc1cc2c(cc1OCc1cc(COc3cc4c(cc3OC)C(=O)N3c5ccccc5C[C@H]3C=N4)cc(OCCCC(=O)ON3C(=O)CCC3=O)c1)N=C[C@@H]1Cc3ccccc3N1C2=O] | 44 | 7 |
| 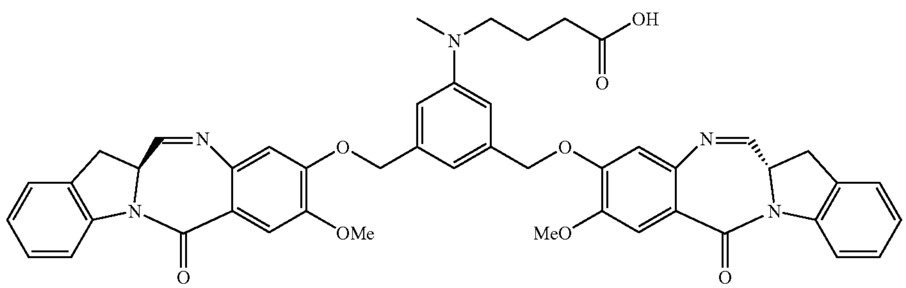 [SMILES: COc1cc2c(cc1OCc1cc(COc3cc4c(cc3OC)C(=O)N3c5ccccc5C[C@H]3C=N4)cc(N(C)CCCC(=O)O)c1)N=C[C@@H]1Cc3ccccc3N1C2=O] | 45 | 7 |

TABLE 9

Structures of compounds from the examples of the present invention (Continued).

| Structure | Compound No. | Example No. |
|---|---|---|
| 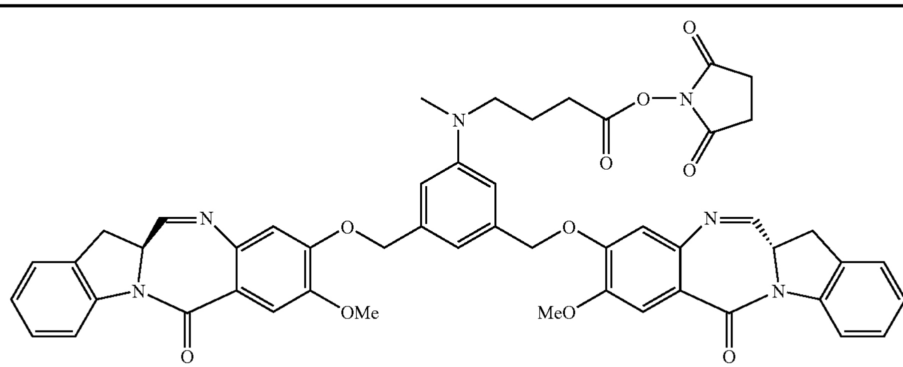 | 46 | 7 |
| 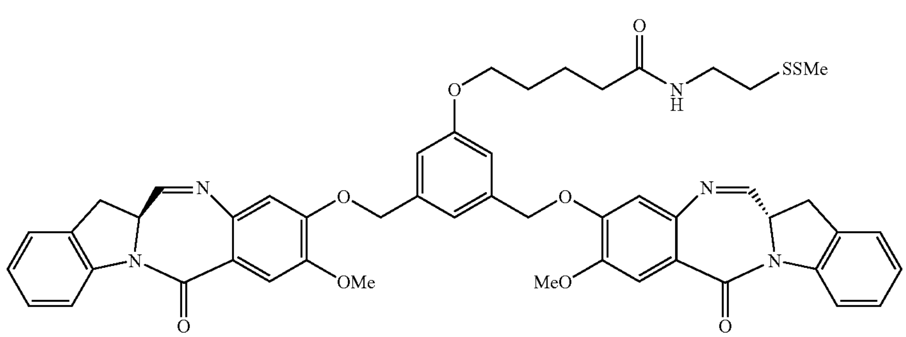 | 48 | 8 |

TABLE 9-continued

Structures of compounds from the examples of the present invention (Continued).

| Structure | Compound No. | Example No. |
|---|---|---|
| 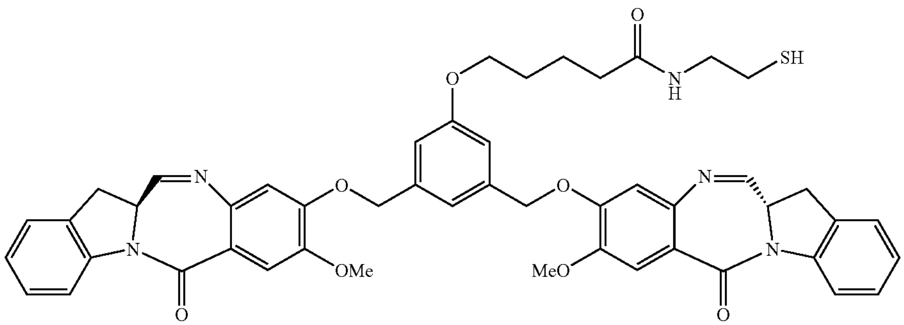 [SMILES: COc1cc2c(cc1OCc1cc(COc3cc4c(cc3OC)C(=O)N3c5ccccc5C[C@H]3C=N4)cc(OCCCCC(=O)NCCS)c1)N=C[C@@H]1Cc3ccccc3N1C2=O] | 49 | 8 |
| 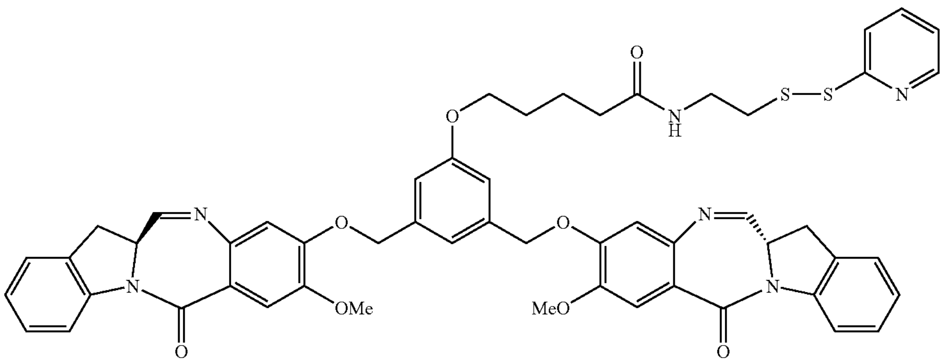 [SMILES: COc1cc2c(cc1OCc1cc(COc3cc4c(cc3OC)C(=O)N3c5ccccc5C[C@H]3C=N4)cc(OCCCCC(=O)NCCSSc3ccccn3)c1)N=C[C@@H]1Cc3ccccc3N1C2=O] | 51 | 9 |
| 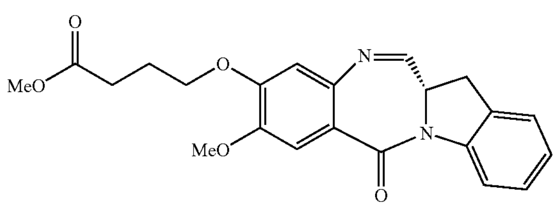 [SMILES: COC(=O)CCCOc1cc2c(cc1OC)C(=O)N1c3ccccc3C[C@H]1C=N2] | 125 | 10 |
| 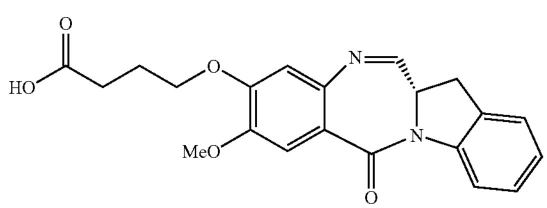 [SMILES: COc1cc2c(cc1OCCCC(=O)O)N=C[C@@H]1Cc3ccccc3N1C2=O] | 126 | 10 |
| 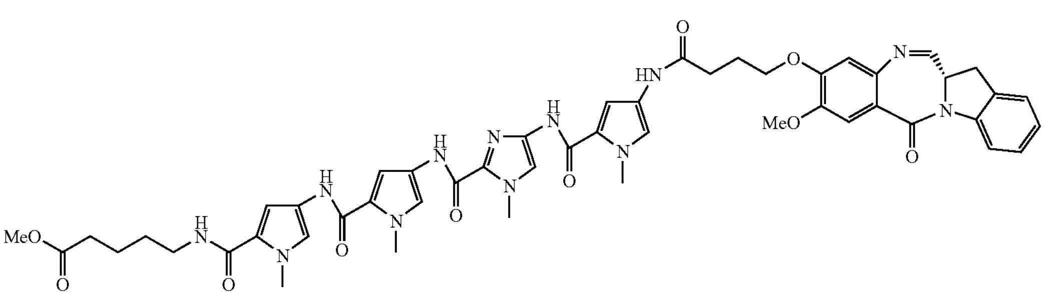 [SMILES: COC(=O)CCCCNC(=O)c1cc(NC(=O)c2cc(NC(=O)c3nc(NC(=O)c4cc(NC(=O)CCCOc5cc6c(cc5OC)C(=O)N5c7ccccc7C[C@H]5C=N6)cn4C)cn3C)cn2C)cn1C] | 127 | 10 |

Synthesis of Cytotoxic Compounds

The process of preparation of a representative monomer compound of the present invention, exemplified by indolinobenzodiazepine compound 8, is shown in FIG. 1. Starting from commercially available indoline-2-carboxylic acid 1, its methyl ester 2 was prepared in quantitative yield by reaction with thionyl chloride in methanol. Methyl indoline-2-carboxylate 2 was coupled with the acid chloride 4, or directly with acid 3, to furnish the amide 5, which was further reduced with diisobutylaluminum hydride (DIBAL) to the aldehyde 6. While, many methods can be used to reduce the nitro functional group of formula 5 to the corresponding amino group, in this example sodium dithionite was used to conveniently convert to aldehyde 6 to the ring closed compound 7 after further treatment with methanol under acidic conditions. The benzyl protecting group was removed to furnish monomer 8.

The process of preparation of the oxazolidinobenzodiazepine monomer compound of formula 14 of the invention is shown in FIG. 2. Starting from commercially available compound 9, its methyl ester 10 was prepared in quantitative yield by treatment with thionyl chloride in methanol. Compound 10 was deprotected followed by coupling with the acetyl chloride 4 or directly with acid 3 to furnish the amide 11, which was further converted to the aldehyde 12. Reduction of the nitro group was accomplished by treatment with sodium dithionite followed by efficient conversion to the ring closed compound 13 after further treatment with methanol under acidic conditions. The benzyl protecting group was removed to furnish monomer 14.

The process of preparation of representative dimer compounds of the present invention is shown in FIGS. 3-5 and 7. The dimers were prepared by reacting of the monomers of formula 8 or formula 14 with compounds which possesses two leaving groups such as Br, I, triflate, mesylate or tosylate.

Dimers which possess linkers that can react with antibodies are prepared by converting the methyl esters to the corresponding reactive esters of a leaving group such as, but not limited to, N-hydroxysuccinimide esters, N-hydroxyphtalimide esters, N-hydroxy sulfo-succinimide esters, para-nitrophenyl esters, dinitrophenyl esters, pentafluorophenyl esters. Representative examples for the synthesis of the linkable dimers are shown in FIGS. 8. Synthesis of dimers that bear a thiol or disulfide moiety to enable linkage to cell binding agents via reducible or non-reducible bonds is shown in FIGS. 9 and 10. The B ring modified monomer 58 devoid of a carbonyl group is achieved from the benzyl acohol compound 52 by the steps shown in FIG. 11. The isoindolino monomer 66 can be prepared from isoindole 59 as outlined in FIG. 12. The linker can also be attached directly to the indolino moiety. Methyl indolino-2-carboxylate can be converted into the linkable dimer 82 via the synthetic steps shown in FIG. 13. The synthesis of linkable dimers bearing a PEG moiety is shown in FIGS. 14 and 15.

Thus in one aspect, the invention provides a process for the preparation of the indolinobenzodiazepine (IBD) monomer of formula (I) (FIG. 1), the process comprising the steps of:

a) coupling compound of formula (1) and compound of formula (2) to give compound of formula (3);

b) converting compound of formula (3) into aldehyde of formula (4); and c) converting compound of formula (4) into compound of formula (I),

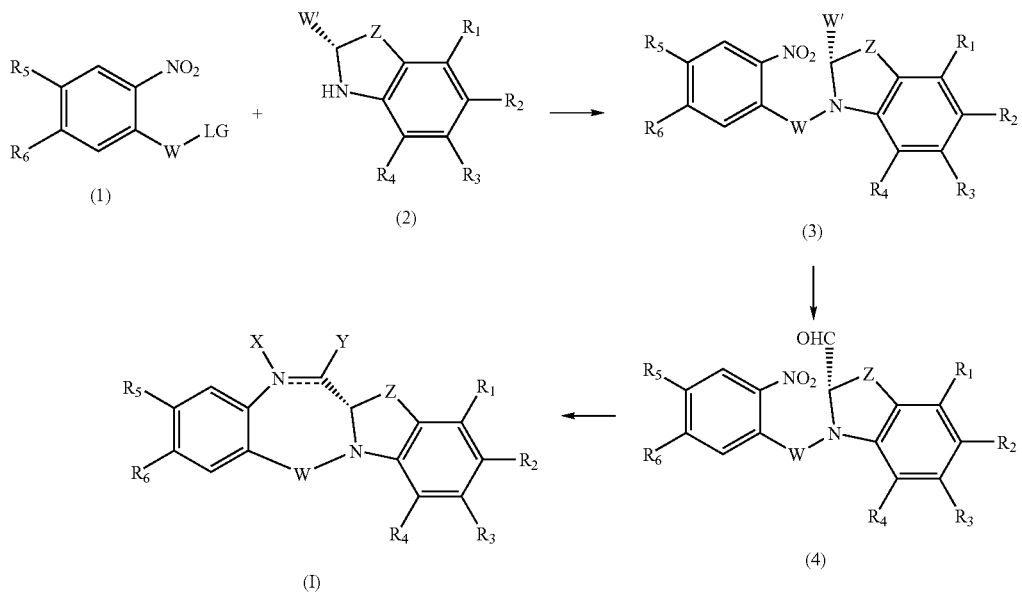

(1)

(2)

(3)

(4)

(I)

wherein LG is a leaving group; W' is COOR or CH$_2$OW", wherein R has the same definition as above and W" is a protecting group; R$_1$, R$_2$, R$_3$, R$_4$, R$_5$, R$_6$, W, Z, X, Y and == have the same definition as described above.

Another aspect of the invention provides a process for the preparation of compound of formula (II) comprising the steps of:

a) coupling compound of formula (1) and compound of formula (5) to give compound of formula (6);

b) converting compound of formula (6) into aldehyde of formula (7); and c) converting compound of formula (7) into compound of formula (II),

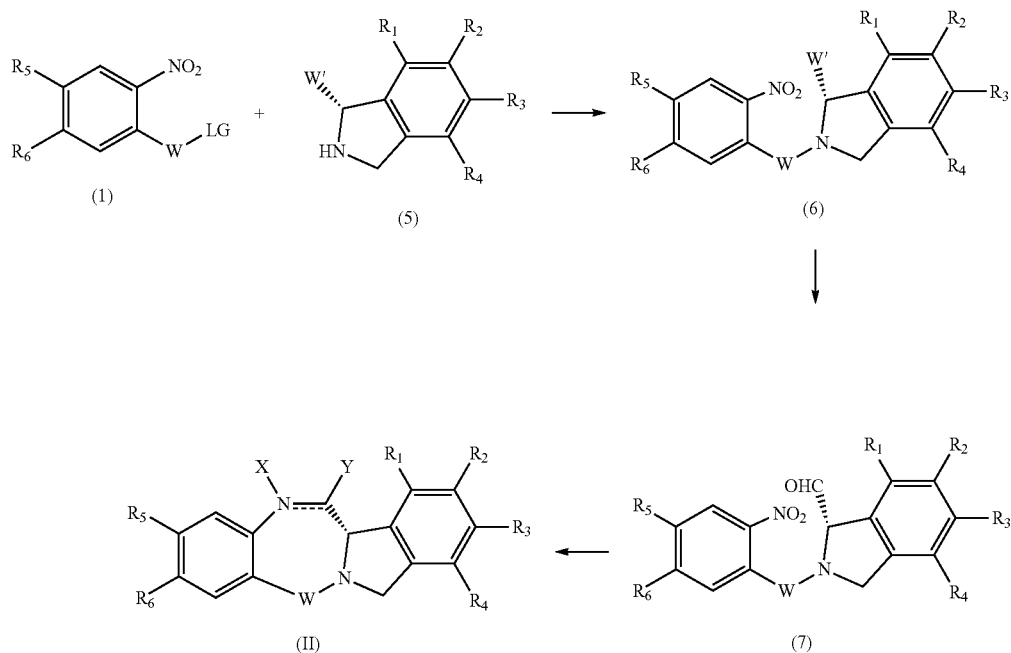

wherein LG is a leaving group; W' is COOR or CH$_2$OW'', wherein R has the same definition as above and W'' is a protecting group; R$_1$, R$_2$, R$_3$, R$_4$, R$_5$, R$_6$, W, X, Y and == have the same definition as above.

Another aspect of the invention provides a process for the preparation of compound of formula (III) comprising steps of:
a) coupling compound of formula (1) and compound of formula (8) to give compound of formula (9);
b) converting compound of formula (9) into aldehyde of formula (10); and
c) converting compound of formula (10) into compound of formula (II), wherein LG is a leaving group; W' is COOR or CH$_2$OW'', wherein R has the same definition as above and W'' is a protecting group; R$_5$, R$_6$, W, X, Y, X', Y', Z' and == have the same definition as above.

Another aspect of the invention provides a process for the preparation of compound of formula (Another aspect of the invention provides a process for the preparation of compound of formula (IV) comprising the steps of:

coupling compound of formula (11), compound of formula (11)' and compound of formula (12) to give compound of formula (IV),

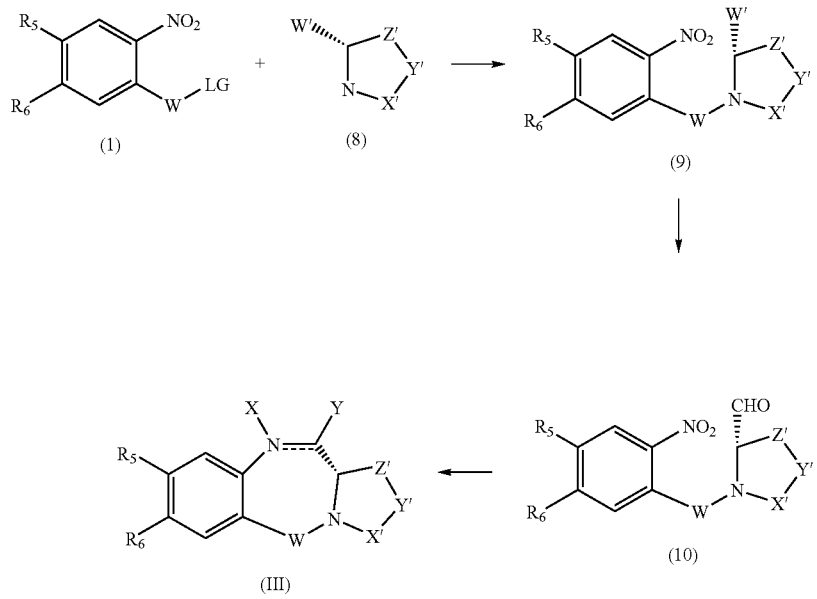

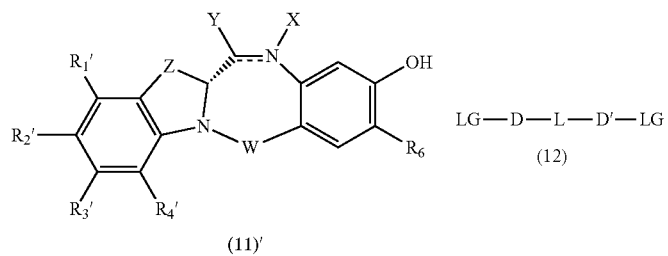

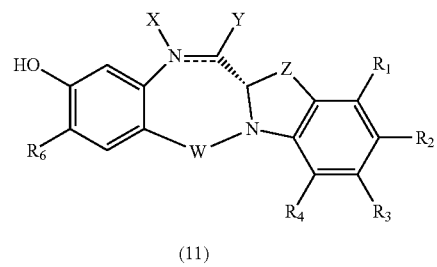

(11)'  LG—D—L—D'—LG  (11)
             (12)

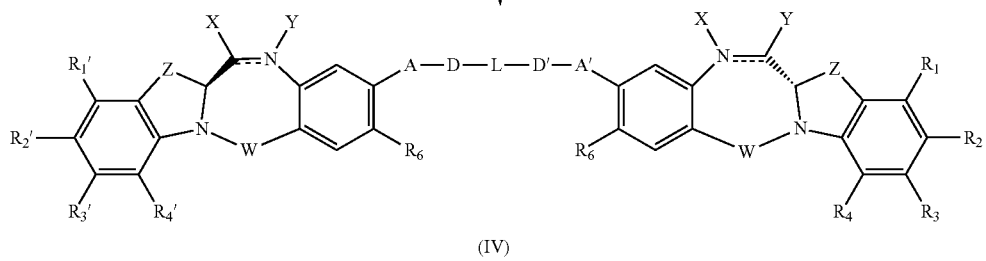

(IV)

wherein LG is a leaving group; $R_1$, $R_2$, $R_3$, $R_4$, $R_1'$, $R_2'$, $R_3'$, $R_4'$, $R_6$, W, X, Y, Z, A, A', D, D', L and -- have the same definition as above.

Another aspect of the invention provides an alternative process for the preparation of compound of formula (IV) of the present invention comprising steps of:

a) converting compound of formula (15) into aldehyde of formula (16); and b) converting compound of formula (16) into compound of formula (IV),

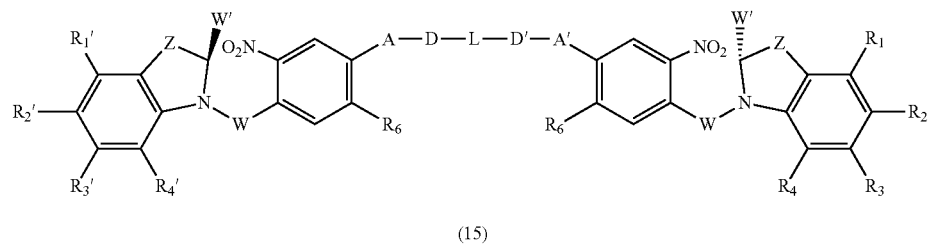

(15)

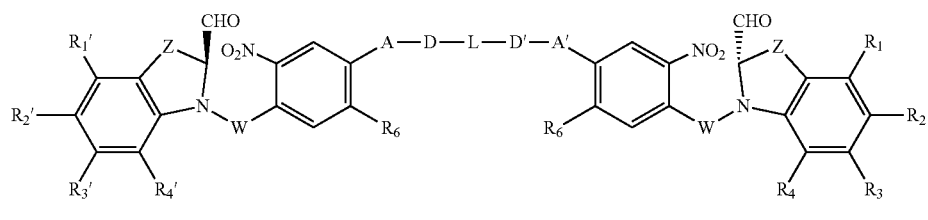

(16)

-continued

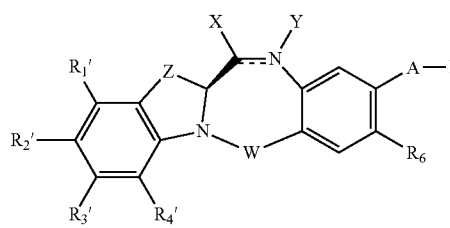
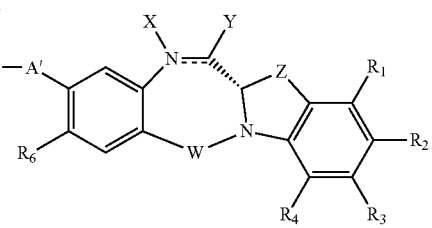

(IV)

wherein W' is COOR or CH$_2$OW", wherein R has the same definition as above and W" is a protecting group; R$_1$, R$_2$, R$_3$, R$_4$, R$_1$', R$_2$', R$_3$', R$_4$', R$_6$, W, X, Y, Z, A, A', D, D', L and ═ have the same definition as above.

Another aspect of the invention provides a process for the preparation of compound of formula (V) comprising the step of coupling compound of formula (13), compound of formula (13)' and compound of formula (12) to give compound of formula (V), Another aspect of the invention provides an alternative process for the preparation of compound of formula (V) of the invention comprising the steps of:

a) converting compound of formula (17) into aldehyde of formula (18); and b) converting compound of formula (18) into compound of formula (V),

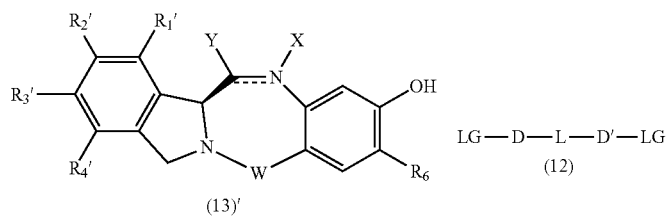
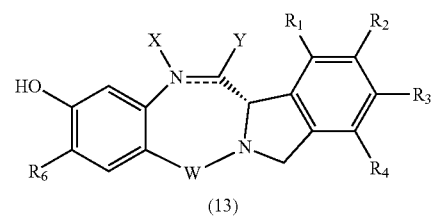

(13)'    (12)    (13)

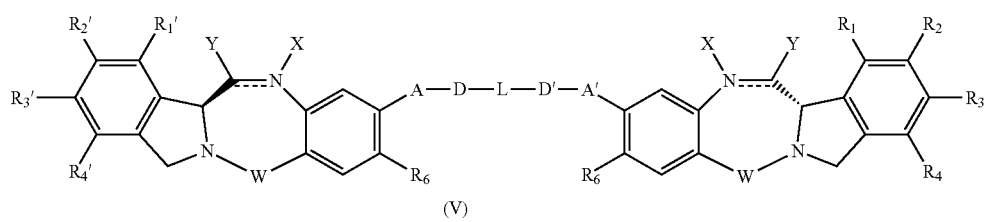

(V)

wherein LG is a leaving group; R$_1$, R$_2$, R$_3$, R$_4$, R$_1$', R$_2$', R$_3$', R$_4$', R$_6$, W, X, Y, A, A', D, D', L and ═ have the same definition as above.

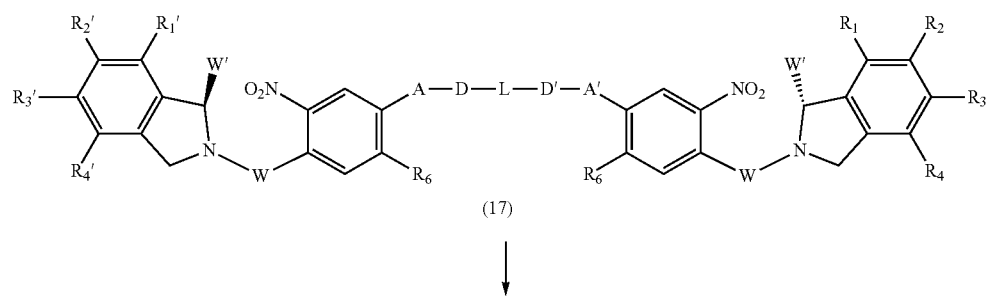

(17)

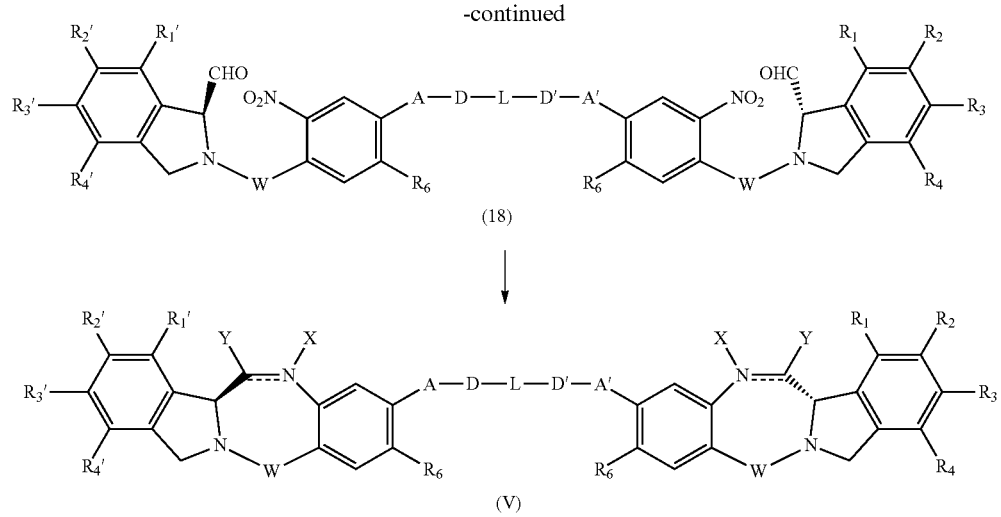

(18)

(V)

wherein W' is COOR or CH$_2$OW'', wherein R has the same definition as above and W'' is a protecting group; R$_1$, R$_2$, R$_3$, R$_4$, R$_1$', R$_2$', R$_3$', R$_4$', R$_6$, W, X, Y, A, A', D, D', L and ═ have the same definition as above.

Another aspect of the invention provides a process for the preparation of compound of formula (VI) of the invention comprising the step of coupling compound of formula (14), compound of formula (14)∝ and compound of formula (12) to give compound of formula (VI), Another aspect of the invention provides a process for the preparation of compound of formula (VI) of the invention comprising the steps of:

a) converting compound of formula (19) into aldehyde of formula (20); and b) converting compound of formula (20) into compound of formula (VI),

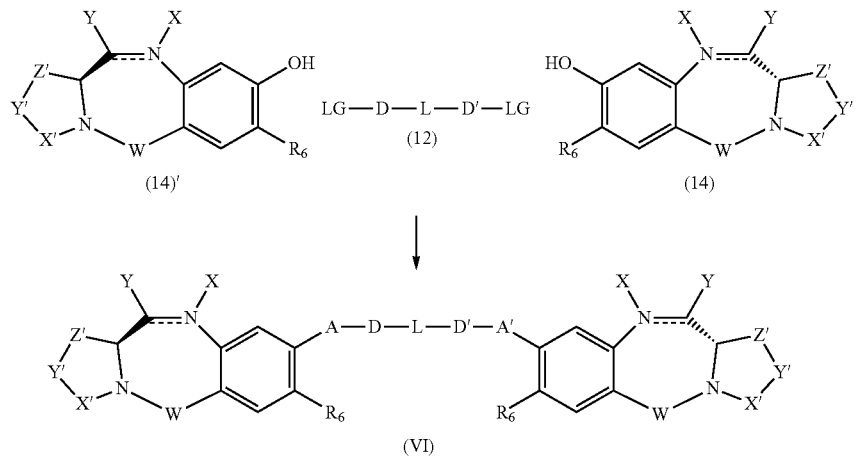

wherein LG is a leaving group; R$_6$, W, X, Y, X', Y', Z' A, A', D, D', L and ═ have the same definition as above.

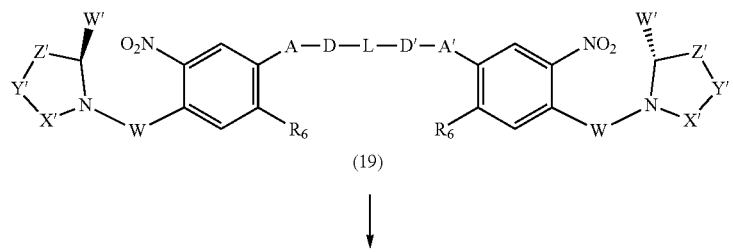

(19)

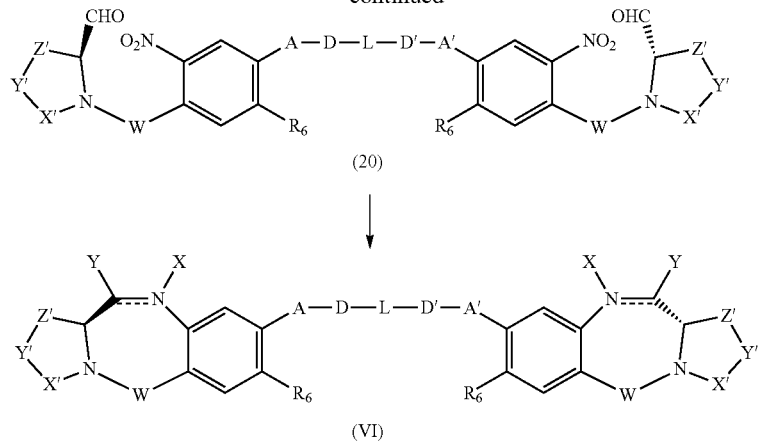

(20)

(VI)

wherein W' is COOR or $CH_2OW''$, wherein R has the same definition as above and W" is a protecting group; $R_6$, W, X, Y, X', Y', Z' A, A', D, D', L and $=$ have the same definition as above.

In vitro Cytotoxicity of Compounds

The in vitro cytotoxicity of the cytotoxic compounds (e.g., indolinobenzodiazepine or oxazolidinobenzodiazepine), derivatives thereof, dimers thereof or conjugates thereof of the present invention can be evaluated for their ability to suppress proliferation of various cancerous cell lines in vitro (Tables 1, 2 in FIGS. 31, 32.). For example, cell lines such as the human breast carcinoma line SK—Br-3, or the human epidermoid carcinoma cell line KB, can be used for the assessment of cytotoxicity of these new compounds. Cells to be evaluated can be exposed to the compounds for 72 hours and the surviving fractions of cells measured in direct assays by known methods. $IC_{50}$ values can then be calculated from the results of the assays.

Examples of in vitro cytotoxicity of compounds of the present invention that were tested on a panel of cancer cell lines and their data is shown in Table 1. All the indolinobenzodiazepine dimer compounds tested were highly potent with $IC_{50}$ values in the low picomolar range. IGN-09 retained most of its potency on multi-drug resistant cell lines such as COL0205-MDR (only 4-fold higher $IC_{50}$ than COL0205). Compounds of the invention are 1000 to 10,000-fold more cytotoxic than other DNA interacting drugs used in cancer treatment, such as doxorubicin, melphalan and cis-platin. In a direct comparison, the potency of the non-linker bearing compounds IGN1 (compound 18) and IGN09 (compound 15) was compared to the linker-bearing compounds IGN03 (compound 34) and IGN05 (compound 36) was tested towards a representative cell line Ramos. As shown in Table2, all four compounds are highly potent with $IC_{50}$ values less than 1 picomolar, demonstrating that the incorporation of linker does not affect potency.

Cell-Binding Agents

The effectiveness of the compounds (e.g., indolinobenzodiazepine or oxazolidinobenzodiazepine), derivatives thereof, dimers thereof or conjugates thereof of the invention as therapeutic agents depends on the careful selection of an appropriate cell-binding agent. Cell-binding agents may be of any kind presently known, or that become known and includes peptides and non-peptides. Generally, these can be antibodies (especially monoclonal antibodies), lymphokines, hormones, growth factors, vitamins, nutrient-transport molecules (such as transferrin), or any other cell-binding molecule or substance.

More specific examples of cell-binding agents that can be used include:

polyclonal antibodies;
monoclonal antibodies;
fragments of antibodies such as Fab, Fab', and F(ab')$_2$, Fv (Parham, *J. Immunol.* 131:2895-2902 (1983); Spring et al. *J. Immunol.* 113:470-478 (1974); Nisonoff et al. *Arch. Biochem. Biophys.* 89:230-244 (1960));
interferons (e.g. .alpha., .beta., .gamma.);
lymphokines such as IL-2, IL-3, IL-4, IL-6;
hormones such as insulin, TRH (thyrotropin releasing hormone), MSH (melanocyte-stimulating hormone), steroid hormones, such as androgens and estrogens;
growth factors and colony-stimulating factors such as EGF, TGF-alpha, FGF, VEGF, G-CSF, M-CSF and GM-CSF (Burgess, *Immunology Today* 5:155-158 (1984));
transferrin (O'Keefe et al. *J. Biol. Chem.* 260:932-937 (1985)); and
vitamins, such as folate.

Monoclonal antibody techniques allow for the production of extremely specific cell-binding agents in the form of specific monoclonal antibodies. Particularly well known in the art are techniques for creating monoclonal antibodies produced by immunizing mice, rats, hamsters or any other mammal with the antigen of interest such as the intact target cell, antigens isolated from the target cell, whole virus, attenuated whole virus, and viral proteins such as viral coat proteins. Sensitized human cells can also be used. Another method of creating monoclonal antibodies is the use of phage libraries of scFv (single chain variable region), specifically human scFv (see e.g., Griffiths et al., U.S. Pat. Nos. 5,885,793 and 5,969,108; McCafferty et al., WO 92/01047; Liming et al., WO 99/06587). In addition, resurfaced antibodies disclosed in U.S. Pat. No. 5,639,641 may also be used, as may chimeric antiobodies and humanized antibodies. Selection of the appropriate cell-binding agent is a matter of choice that depends upon the particular cell population that is to be targeted, but in general human monoclonal antibodies are preferred if an appropriate one is available.

For example, the monoclonal antibody MY9 is a murine IgG$_i$ antibody that binds specifically to the CD33 Antigen {J. D. Griffin et al 8 Leukemia Res., 521 (1984)} and can be used if the target cells express CD33 as in the disease of acute myelogenous leukemia (AML). Similarly, the monoclonal antibody anti-B4 is a murine IgG$_1$, that binds to the CD19 antigen on B cells {Nadler et al, 131 J. Immunol. 244-250 (1983)} and can be used if the target cells are B cells or diseased cells that express this antigen such as in non-Hodgkin's lymphoma or chronic lymphoblastic leukemia HuB4 is a resurfaced antibody derived from the murine anti-B4 antibody (Roguska et al., 1994, Proc. Natl. Acad. Sci., 91, pg 969-973). HuN901 is a humanized antibody that binds to the CD56 antigen expressed on small cell lung cancer, multiple myeloma, ovarian cancer and other solid tumors including neuroendocrine cancers (Roguska et al., 1994, Proc. Natl. Acad. Sci., 91, pg 969-973). B38.1 is a chimeric antibody targeting EpCAM. Fully human antibodies such as panitumumab targeting the EGF receptor expressed on several solid tumors may also be used (Van Cutsem et al., J Clin Oncol. 2007;25(13):1658-1664). The cell-binding agent that comprises the conjugates and the modified cell-binding agents of the present invention may be of any kind presently known, or that become known, and includes peptides and non-peptides. The cell-binding agent may be any compound that can bind a cell, either in a specific or non-specific manner. Generally, these can be antibodies (especially monoclonal antibodies and antibody fragments), interferons, lymphokines, hormones, growth factors, vitamins, nutrient-transport molecules (such as transferrin), or any other cell-binding molecule or substance.

Where the cell-binding agent is an antibody, it binds to an antigen that is a polypeptide and may be a transmembrane molecule (e.g. receptor) or a ligand such as a growth factor. Exemplary antigens include molecules such as renin; a growth hormone, including human growth hormone and bovine growth hormone; growth hormone releasing factor; parathyroid hormone; thyroid stimulating hormone; lipoproteins; alpha- 1-antitrypsin; insulin A-chain; insulin B-chain; proinsulin; follicle stimulating hormone; calcitonin; luteinizing hormone; glucagon; clotting factors such as factor vmc, factor IX, tissue factor (TF), and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin, such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA-4; inhibin; activin; vascular endothelial growth factor (VEGF); receptors for hormones or growth factors; protein A or D; rheumatoid factors; a neurotrophic factor such as bone-derived neurotrophic factor (BDNF), neurotrophin-3, -4, -5, or -6 (NT-3, NT4, NT-5, or NT-6), or a nerve growth factor such as NGF-13; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins, EpCAM, GD3, FLT3, PSMA, PSCA, MUC1, MUC16, STEAP, CEA, TENB2, EphA receptors, EphB receptors, folate receptor, FOLR1, mesothelin, cripto, alpha$_v$beta$_6$, integrins, VEGF, VEGFR, tarnsferrin receptor, IRTA1, IRTA2, IRTA3, IRTA4, IRTA5; CD proteins such as CD2, CD3, CD4, CD5, CD6, CD8, CD11, CD14, CD19, CD20, CD21, CD22, CD25, CD26, CD28, CD30, CD33, CD36, CD37, CD38, CD40, CD44, CD52, CD55, CD56, CD59, CD70, CD79, CD80. CD81, CD103, CD105, CD134, CD137, CD138, CD152 or an antibody which binds to one or more tumor-associated antigens or cell-surface receptors disclosed in US Publication No. 20080171040 or US Publication No. 20080305044 and are incorporated in their entirety by reference; erythropoietin; osteoinductive factors; immunotoxins; a bone morphogenetic protein (BMP); an interferon, such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor; viral antigen such as, for example, a portion of the HIV envelope; transport proteins; homing receptors; addressins; regulatory proteins; integrins, such as CD11a, CD11b, CD11c, CD18, an ICAM, VLA-4 and VCAM; a tumor associated antigen such as HER2, HER3 or HER4 receptor; and fragments of any of the above-listed polypeptides.

Additionally, GM-CSF, which binds to myeloid cells can be used as a cell-binding agent to diseased cells from acute myelogenous leukemia. IL-2 which binds to activated T-cells can be used for prevention of transplant graft rejection, for therapy and prevention of graft-versus-host disease, and for treatment of acute T-cell leukemia. MSH, which binds to melanocytes, can be used for the treatment of melanoma. Folic acid can be used to target the folate receptor expressed on ovarian and other tumors. Epidermal growth factor can be used to target squamous cancers such as lung and head and neck. Somatostatin can be used to target neuroblastomas and other tumor types.

Cancers of the breast and testes can be successfully targeted with estrogen (or estrogen analogues) or androgen (or androgen analogues) respectively as cell-binding agents.

Production of Cytotoxic Conjugates

The present invention also provides cytotoxic compound-cell-binding agent conjugates comprising a cell binding agent linked to one or more cytotoxic compounds via a variety of linkers, including, but not limited to, disulfide linkers, thioether linkers, amide bonded linkers, peptidase—labile linkers, acid-labile linkers, esterase-labile linkers. Representational cytotoxic conjugates of the invention are antibody/cytotoxic compound, antibody fragment/cytotoxic compound, epidermal growth factor (EGF)/ cytotoxic compound, melanocyte stimulating hormone (MSH)/ cytotoxic compound, thyroid stimulating hormone (TSH)/ cytotoxic compound, somatostatin/cytotoxic compound, folate/cytotoxic compound, estrogen/cytotoxic compound, estrogen analogue/cytotoxic compound, androgen/cytotoxic compound, and androgen analogue/cytotoxic compound.

In a preferred embodiment, the present invention provides an indolinobenzodiazepine dimer-cell-binding agent conjugate comprising the cytotoxic agent and the cell binding agent linked through a covalent bond. The linker can be cleaved at the site of the tumor/unwanted proliferating cells to deliver the cytotoxic agent to its target in a number of ways. The linker can be cleaved, for example, by low pH (hydrazone), reductive environment (disulfide), proteolysis (amide/peptide link), or through an enzymatic reaction (esterase/glycosidase).

In a preferred aspect, representatative cytotoxic conjugates of the invention are antibody/indolinobenzodiazepine dimer, antibody fragment/indolinobenzodiazepine dimer, epidermal growth factor (EGF)/indolinobenzodiazepine dimer, melanocyte stimulating hormone (MSH)/indolinobenzodiazepine dimer, thyroid stimulating hormone (TSH)/indolinobenzodiazepine dimer, somatostatin/indolinobenzodiazepine dimer, folate/indolinobenzodiazepine dimer, estrogen/indolinobenzodiazepine dimer, estrogen analogue/indolinobenzodiazepine dimer, prostate specific membrane antigen (PSMA) inhibitor/indolinobenzodiazepine dimer, matriptase inhibitor/indolinobenzodiazepine dimer, designed ankyrin repeat proteins (DARPins)/indolinobenzodiazepine dimer, androgen/indolinobenzodiazepine dimer, and androgen analogue/indolinobenzodiazepine dimer.

Disulfide containing cytotoxic conjugates can be made by reacting a thiol-containing cytotoxic agent such as 49 with an appropriately modified cell-binding agent. These conjugates may be purified to remove non-linked cytotoxic agent by using gel-filtration, ion exchange chromatography, ceramic hydroxyappetite (CHT) chromatography, hydrophobic interaction chromatography (CHT), tangential flow filtration (TFF), or by HPLC.

A solution of an antibody in aqueous buffer may be incubated with a molar excess of an antibody modifying agent such as N-succinimidyl-3-(2-pyridyldithio)propionate (SPDP) or with N-succinimidyl-4-(2-pyridyldithio)butanoate (SPDB) to introduce dithiopyridyl groups. The modified antibody is then reacted with the thiol-containing cytotoxic agent such as compound 49 to produce a disulfide-linked antibody- indolinobenzodiazepine dimer conjugate. The cytotoxic-cell binding conjugate may then be purified using any of the above mentioned methods.

Alternatively, the antibody may be incubated with a molar excess of an antibody modifying agent such as 2-iminothiolane, L-homocysteine thiolactone (or derivatives), or N-Succinimidyl-S-acetylthioacetate (SATA) to introduce sulfhydryl groups. The modified antibody is then reacted with the appropriate disulfide-containing cytotoxic agent, such as, compound 51 to produce a disulfide-linked antibody-cytotoxic agent conjugate. The antibody-cytotoxic agent conjugate may then be purified by gel-filtration or other methods mentioned above.

The number of cytotoxic molecules bound per antibody molecule can be determined spectrophotometrically by measuring the ratio of the absorbance at 280 nm and 330 nm. An average of 1-10 cytotoxic molecules/antibody molecule(s) can be linked by this method. The preferred average number of linked cytotoxic molecules per antibody molecule is 2-5, and the most preferred is 3-4.5.

Alternatively, a solution of an antibody in aqueous buffer may be incubated with a molar excess of an antibody-modifying agent such as N-succinimidyl-4-(N-maleimidomethyl)-cyclohexane-1-carboxylate to introduce maleimido groups, or with N-succinimidyl-4-(iodoacetyl)-aminobenzoate (SIAB) to introduce iodoacetyl groups. The modified antibody is then reacted with the thiol-containing cytotoxic agent to produce a thioether-linked antibody-cytotoxic conjugate. The antibody-cytotoxic conjugate may then be purified by gel-filtration or other methods mentioned above or by methods known to one of skill in the art.

Cytotoxic agents containing linkers terminating in an N-Hydroxy succinimidyl (NHS) ester, such as compounds 43, 44, and 46, can be reacted with the antibody to produce direct amide linked conjugates such as huN901-IGN-03 and huN901-IGN-07. The antibody-cytotoxic agent conjugate may then be purified by gel-filtration or other methods mentioned above.

The following cell-binding agent/cytotoxic agent conjugates can be prepared using the appropriate linkers. Dimer 1 and 2 with peptide cleavable linkers can be prepared from the corresponding NHS esters, Dimer 3 can be made by reacting the appropriate thiol-containing cytotoxic agent with SMCC modified cell binding agent, and acid-labile hydrazone Dimer 4 can be prepared through condensation of a cytotoxic agent containing an alkyl, aryl ketone with a hydrazide modified cell binding agent.

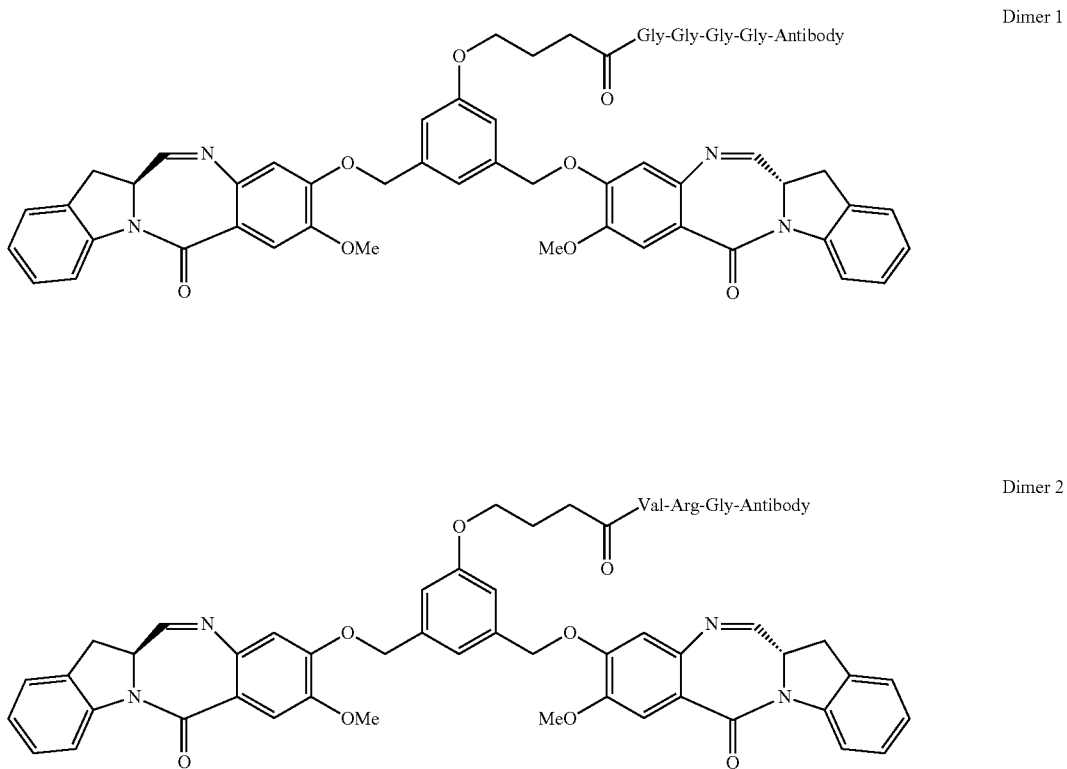

Dimer 3
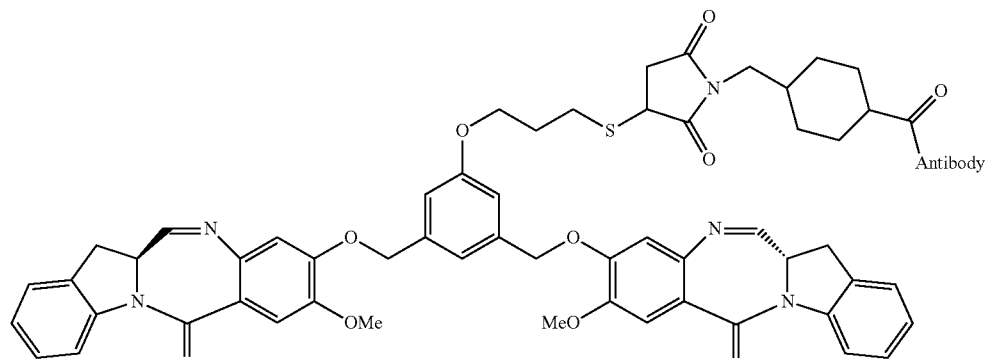
Dimer 4
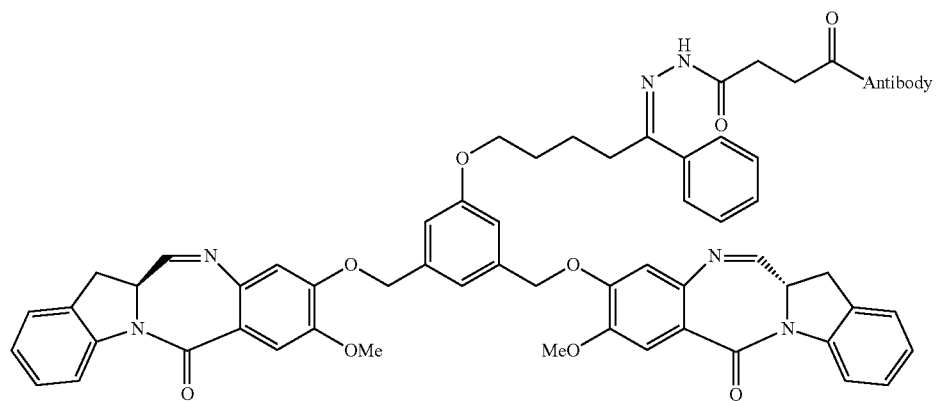
Asymmetric indolinobenzodiazepine dimer conjugates such as Dimers 5-8 can also be prepared using similar methods to those described above.
Dimer 5
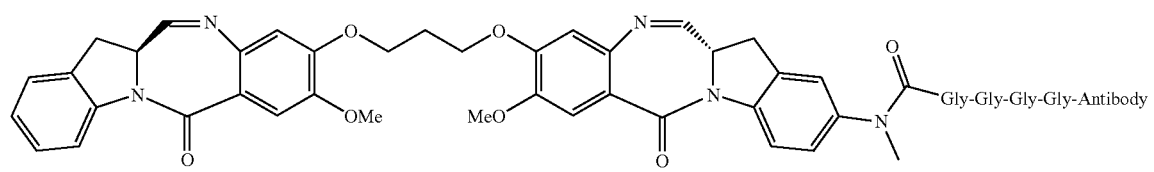
Dimer 6
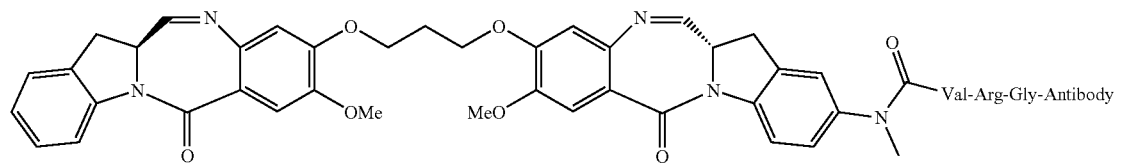
Dimer 7
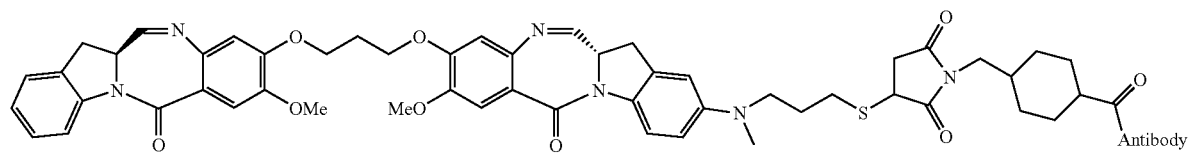

-continued

Dimer 8

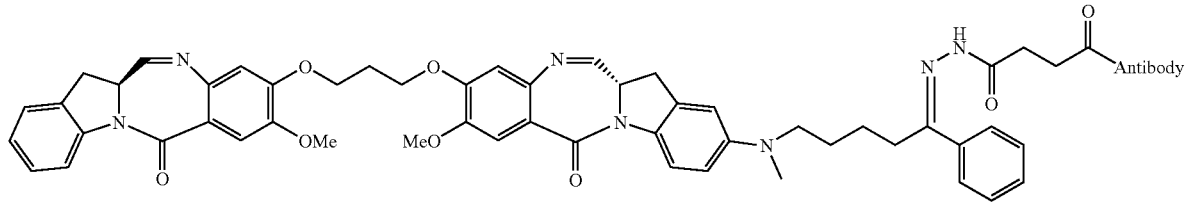

Conjugates of cell-binding agents with cytotoxic agents of the invention can be evaluated for their ability to suppress proliferation of various unwanted cell lines in vitro. For example, cell lines such as the human colon carcinoma line COLO 205, the rhabdomyosarcoma cell line RH-30, and the multiple myeloma cell line MOLP-8 can be used for the assessment of cytotoxicity of these conjugates. Cells to be evaluated can be exposed to the compounds for 1-5 days and the surviving fractions of cells measured in direct assays by known methods. $IC_{50}$ values can then be calculated from the results of the assays.

Examples of in vitro potency and target specificity of antibody-cytotoxic agent conjugates of the present invention are shown in FIG. 21-26. All of the conjugates with cytotoxic agent/antibody ratios of 1-3 are extremely cytotoxic on the antigen positive cancer cells with an $IC_{50}$ in the low picomolar range. Antigen negative cell lines remained viable when exposed to the same conjugates. The target specificity of conjugates of the indolinobenzodiazepine dimers are >1000 with the antibodies huN901 (anti-CD56) and muB38.1 (anti-EpCAM). For example, the B38.1-IGN-3 conjugate killed antigen positive COLO 205 cells with an $IC_{50}$ value of 1.86 pM, while the antigen negative Namalwa cell line was about 200-fold less sensitive with an $IC_{50}$ value of 336.3 pM, demonstrating antigen specificity. In addition, the conjugate is also highly potent towards the multidrug resistant COLO 205 MDR cell line with an $IC_{50}$ value of 16 pM. Similarly, the huN901-IGN3 conjugate was highly potent, with an $IC_{50}$ value of 15 pM for antigen positive RH30 cells (FIG. 22). Addition of an excess of unconjugated huN901 antibody abolished this cytotoxic effect ($IC_{50}$>3 nM), demonstrating antigen-specificity. Another huN901-IGN conjugate (huN901-IGN-07) also showed high potency towards antigen expressing RH-30 cells, with drug load dependent cytotoxicity and $IC_{50}$ values of 16 pm, 3 pM and 2 pM respectively for conjugates bearing 1.2, 2.0 and 3.0 linked drugs per antibody molecule (FIG. 23). Similar results were obtained with huN901-IGN07 and huN901-IGN03 towards antigen-positive Molp-8 cells. Hu901-IGN07 gave $IC_{50}$ values of 5 pM, 3 pM and 2 pM respectively for IGN07 loads of 1.2, 2.0 and 3.0 (FIG. 24). The huN901-IGN07 and IGN03 conjugates were much less potent towards antigen negative Namalwa cells with $IC_{50}$ values ranging from 1000 pM to >3000 pM (FIG. 25). The B38.1-IGN10 conjugate was also specifically potent killing antigen positive COLO 205 cells, with an $IC_{50}$ of 17 pM, and less potent (170 pM) for antigen-negative Ramos cells (FIG. 26).

In one example, in vivo efficacy of a cell binding agent/cytotoxic agent conjugate was measured. Nude mice bearing human MOLP-8 tumors were treated with huN901-IGN-07 conjugate and significant tumor regression was observed compared while untreated mice tumors grew rapidly (FIG. 27).

The indolinobenzodiazepine dimers of the present invention bind and alkylate double-stranded DNA (dsDNA) containing guanine residues on opposite strands spaced 4 base pairs apart. FIGS. 28-30 present data from reverse-phase ion pair chromatography assays showing rate of IGN-01, IGN-02, and IGN-09 binding and crosslinking to dsDNA. The indolino group (IGN-01) is preferred to the oxazole group (IGN-02) for rapid DNA binding and interstrand crosslinking (ICL). Initial rate of IGN1-DNA adduct formation is dependent on DNA sequence. IGN1 binds faster to DNA containing an internal GATC motif than DNA with a GTAC sequence. DNA probe substituted with deoxyInosine (I) (containing no C-2 amino group) in place of guanine (G) showed no reaction with IGN-1 (FIG. 29).

The $IC_{50}$ values of various compounds of the present invention towards a panel of cell lines is listed in FIG. 31. Comparative in vitro potency of linkable and non-linkable compounds of the present invention are shown in FIG. 32. Incorporation of a linker does not significantly affect potency of the parent compounds.

Compositions and Methods of Use

The present invention includes a composition (e.g., a pharmaceutical composition) comprising novel benzodiazepine compounds (e.g., indolinobenzodiazepine or oxazolidinobenzodiazepine), derivatives thereof, or conjugates thereof, (and/or solvates, hydrates and/or salts thereof) and a carrier (a pharmaceutically acceptable carrier). The present invention also includes a composition (e.g., a pharmaceutical composition) comprising novel benzodiazepine compounds, derivatives thereof, or conjugates thereof, (and/or solvates, hydrates and/or salts thereof) and a carrier (a pharmaceutically acceptable carrier), further comprising a second therapeutic agent. The present compositions are useful for inhibiting abnormal cell growth or treating a proliferative disorder in a mammal (e.g., human). The present compositions are also useful for treating depression, anxiety, stress, phobias, panic, dysphoria, psychiatric disorders, pain, and inflammatory diseases in a mammal (e.g., human).

The present invention includes a method of inhibiting abnormal cell growth or treating a proliferative disorder in a mammal (e.g., human) comprising administering to said mammal a therapeutically effective amount of novel benzodiazepine compounds (e.g., indolinobenzodiazepine or oxazolidinobenzodiazepine), derivatives thereof, or conjugates thereof, (and/or solvates and salts thereof) or a composition thereof, alone or in combination with a second therapeutic agent.

The present invention also provides methods of treatment comprising administering to a subject in need of treatment an effective amount of any of the conjugates described above.

Similarly, the present invention provides a method for inducing cell death in selected cell populations comprising contacting target cells or tissue containing target cells with an effective amount of a cytotoxic agent comprising any of the cytotoxic compound-cell-binding agents (e.g., indolinobenzodiazepine or oxazolidinobenzodiazepine dimer linked to a cell binding agent) of the present invention, a salt or solvate thereof. The target cells are cells to which the cell-binding agent can bind.

If desired, other active agents, such as other anti-tumor agents, may be administered along with the conjugate.

Suitable pharmaceutically acceptable carriers, diluents, and excipients are well known and can be determined by those of ordinary skill in the art as the clinical situation warrants.

Examples of suitable carriers, diluents and/or excipients include: (1) Dulbecco's phosphate buffered saline, pH about 7.4, containing or not containing about 1 mg/ml to 25 mg/ml human serum albumin, (2) 0.9% saline (0.9% w/v NaCl), and (3) 5% (w/v) dextrose; and may also contain an antioxidant such as tryptamine and a stabilizing agent such as Tween 20.

The method for inducing cell death in selected cell populations can be practiced in vitro, in vivo, or ex vivo.

Examples of in vitro uses include treatments of autologous bone marrow prior to their transplant into the same patient in order to kill diseased or malignant cells: treatments of bone marrow prior to their transplantation in order to kill competent T cells and prevent graft-versus-host-disease (GVHD); treatments of cell cultures in order to kill all cells except for desired variants that do not express the target antigen; or to kill variants that express undesired antigen.

The conditions of non-clinical in vitro use are readily determined by one of ordinary skill in the art.

Examples of clinical ex vivo use are to remove tumor cells or lymphoid cells from bone marrow prior to autologous transplantation in cancer treatment or in treatment of autoimmune disease, or to remove T cells and other lymphoid cells from autologous or allogenic bone marrow or tissue prior to transplant in order to prevent GVHD. Treatment can be carried out as follows. Bone marrow is harvested from the patient or other individual and then incubated in medium containing serum to which is added the cytotoxic agent of the invention, concentrations range from about 10 μM to 1 pM, for about 30 minutes to about 48 hours at about 37° C. The exact conditions of concentration and time of incubation, i.e., the dose, are readily determined by one of ordinary skill in the art. After incubation the bone marrow cells are washed with medium containing serum and returned to the patient intravenously according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

For clinical in vivo use, the cytotoxic agent of the invention will be supplied as a solution or a lyophilized powder that are tested for sterility and for endotoxin levels. Examples of suitable protocols of conjugate administration are as follows. Conjugates are given weekly for 4 weeks as an intravenous bolus each week. Bolus doses are given in 50 to 1000 ml of normal saline to which 5 to 10 ml of human serum albumin can be added. Dosages will be 10 μg to 2000 mg per administration, intravenously (range of 100 ng to 20 mg/kg per day). After four weeks of treatment, the patient can continue to receive treatment on a weekly basis. Specific clinical protocols with regard to route of administration, excipients, diluents, dosages, times, etc., can be determined by one of ordinary skill in the art as the clinical situation warrants.

Examples of medical conditions that can be treated according to the in vivo or ex vivo methods of inducing cell death in selected cell populations include malignancy of any type including, for example, cancer of the lung, breast, colon, prostate, kidney, pancreas, ovary, and lymphatic organs; autoimmune diseases, such as systemic lupus, rheumatoid arthritis, and multiple sclerosis; graft rejections, such as renal transplant rejection, liver transplant rejection, lung transplant rejection, cardiac transplant rejection, and bone marrow transplant rejection; graft versus host disease; viral infections, such as CMV infection, HIV infection, AIDS, etc.; and parasite infections, such as giardiasis, amoebiasis, schistosomiasis, and others as determined by one of ordinary skill in the art.

Cancer therapies and their dosages, routes of administration and recommended usage are known in the art and have been described in such literature as the Physician's Desk Reference (PDR). The PDR discloses dosages of the agents that have been used in treatment of various cancers. The dosing regimen and dosages of these aforementioned chemotherapeutic drugs that are therapeutically effective will depend on the particular cancer being treated, the extent of the disease and other factors familiar to the physician of skill in the art and can be determined by the physician. The contents of the PDR are expressly incorporated herein in its entirety by reference. One of skill in the art can review the PDR, using one or more of the following parameters, to determine dosing regimen and dosages of the chemotherapeutic agents and conjugates that can be used in accordance with the teachings of this invention. These parameters include:

Comprehensive index
By Manufacturer
Products (by company's or trademarked drug name)
Category index
Generic/chemical index (non-trademark common drug names)
Color images of medications
Product information, consistent with FDA labeling
Chemical information
Function/action
Indications & Contraindications
Trial research, side effects, warnings
Analogues and derivatives One skilled in the art of cytotoxic agents will readily understand that each of the cytotoxic agents described herein can be modified in such a manner that the resulting compound still retains the specificity and/or activity of the starting compound. The skilled artisan will also understand that many of these compounds can be used in place of the cytotoxic agents described herein. Thus, the cytotoxic agents of the present invention include analogues and derivatives of the compounds described herein.

All references cited herein and in the examples that follow are expressly incorporated by reference in their entireties.

EXAMPLES

The invention will now be illustrated by reference to non-limiting examples. Unless otherwise stated, all percents, ratios, parts, etc. are by weight. All reagents were purchased from the Aldrich Chemical Co., New Jersey, or other commercial sources. Nuclear Magnetic Resonance ($^1$H NMR) spectra were acquired on a Bruker 400 MHz instrument and mass spectra were acquired on a Bruker Daltonics Esquire 3000 instrument using electrospray ionization.

Example 1

(2S)-1-[5-methoxy-2-nitro-4-(phenylmethoxy)-benzoyl]-2-indolinecarboxylic acid methyl ester 5:

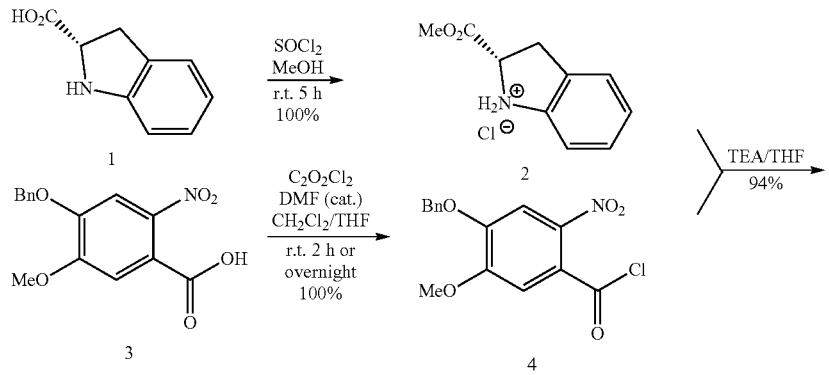

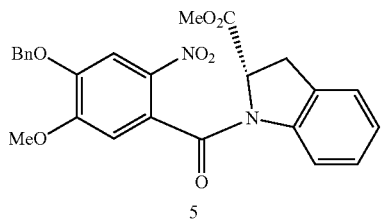

To a stirred solution of 4-benzyloxy-5-methoxy-2-nitrobenzoic acid 3 (7.01 g, 23.1 mmol) in anhydrous dichloromethane (100 mL) and THF (10 mL) was added oxalyl chloride (4.1 mL, 46.2 mmol) and DMF (30 μt, 0.38 mmol) at room temperature. Large amounts of bubbles formed after the addition of the DMF. The mixture was stirred overnight (the reaction usually finished within 3 hours) and then the solvents were removed by rotary evaporation in vacuo. The residue was co-evaporated one more time by addition of anhydrous dichloromethane and high vacuumed to give the acetyl chloride 4 as a yellow solid, which was directly used for the next step.

To a stirred solution of (s)-(−)-Indoline-2-carboxylic acid 1 (3.43 g, 21.0 mmol) in anhydrous methanol (42 mL) was added thionyl chloride (3.1 mL, 42.0 mmol) dropwise at 0° C. The ice bath was removed after 30 minutes and the mixture continued to be stirred at room temperature for 5 hours. The solvent was removed under reduced pressure and the residue was further dried on high vacuum to give methyl ester 2, which was dissolved in anhydrous THF ((70 mL) in a 500 mL round bottom flask. The solution was cooled to 0° C. and triethylamine (9.7 mL, 69.3 mmol) was added, followed quickly by addition of freshly prepared acetyl chloride 4 in anhydrous THF (70 mL) via canula at 0° C. The mixture was stirred at 0~5° C. for another 1.5 hours then at room temperature for 30 minutes. The reaction was quenched by addition of cold 5% HCl and then diluted with ethyl acetate and water. The aqueous layer was extracted with ethyl acetate three times. The combined organic layers were washed subsequently with brine, saturated sodium bicarbonate and brine, dried over anhydrous sodium sulfate and filtered. The solvents were evaporated under reduced pressure and the residue was purified via silica gel chromatography (Hexanes/Ethyl acetate, 2:1, 1.5:1) to give (2S)-1-[5-methoxy-2-nitro-4-(phenylmethoxy)-benzoyl]-2-indolinecarboxylic acid methyl ester 5 as a yellow solid (9.1 g, y=94%). $^1$H NMR (400 Hz, CDCl$_3$): the compound appears as three distinct rotomers. δ 8.27 (d, J=8.4 Hz, 0.3H), 7.90 (s, 0.1H), 7.82 (s, 0.6H), 7.79 (s, 0.3H), 7.50-7.28 (m, 5.4H), 7.20-7.09 (m, 1.3H), 7.05 (s, 0.6H), 6.97-6.81 (m, 1.6H), 6.76 (s, 0.1H), 5.85 (d, J=8.0 Hz, 0.1H), 5.70 (d, J=8.0 Hz, 0.6H), 5.45-5.41 (m, 0.6H), 5.33-5.21 (m, 2.1H), 4.55 (dd, J$_1$=10.8 Hz, J$_2$=2.8 Hz, 0.3H), 3.98 (s, 1.8H), 3.94 (s, 0.9H), 3.83-3.81 (m, 2.4H), 3.62 (dd, J$_1$=16.4 Hz, J$_2$11.4 Hz, 1H), 3.56 (s, 0.9H), 3.27-3.13 (m, 1H); $^{13}$C NMR (400 Hz, CDCl$_3$): 171.5, 164.7, 154.4, 148.6, 148.3, 140.3, 137.4, 135.11, 135.05, 130.5, 129.2, 128.7, 128.4, 127.9, 127.6, 127.5, 126.7, 125.5, 124.8, 124.3, 123.9, 117.6, 112.4, 110.1, 109.2, 108.8, 71.3, 71.2, 61.5, 60.2, 60.1, 56.7, 56.5, 52.5, 52.4, 33.6, 31.4; HRMS (ESI, m/z): calc. 463.1505 (M +H)$^+$, found 463.1516.

(2S)-1-[5-methoxy-2-nitro-4-(phenylmethoxy)-benzoyl]-2-indolinealdehyde 6:

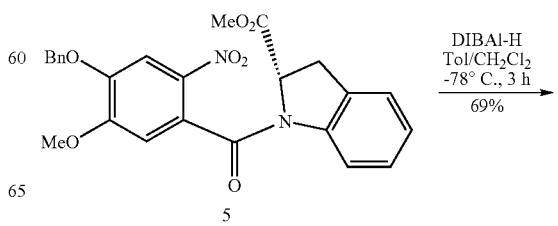

-continued

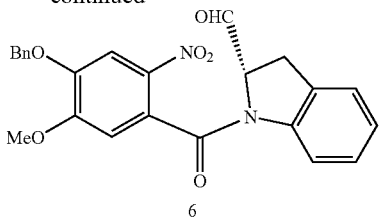

6

To a stirred solution of the methyl ester 5 (4.4 g, 9.5 mmol) in anhydrous dichloromethane (11 mL) and toluene (33 mL) was added dibal-H (19 mL, 1.0 M in toluene) dropwise via a syringe pump in 30 minutes at −78° C. The mixture continued to be stirred at −78° C. for 3 hours and TLC (hexanes/AcOEt, 1:1.5) showed that the starting material was almost consumed. The reaction was quenched with methanol (0.4 mL) and 5% HCl (30 mL) at −78° C. Ethyl acetate (100 mL) was added and the dry ice/acetone bath was removed. The mixture was stirred at room temperature for 30 minutes and then transferred to a separatory funnel. The aqueous layer was extracted with AcOEt twice and the combined organic layers were washed with brine, saturated sodium bicarbonate and brine, and dried over anhydrous sodium sulfate. It was filtered through celite and the solvents were removed under reduced pressure (temperature<35° C.). The residue was purified by flash chromatography (Hexanes/AcOEt, 1.5:1, 1:1, 1:1.5) to give the aldehyde 6 as a yellow solid (2.85 g, y=69%). $^1$H NMR (400 Hz, CDCl$_3$): the compound appears as three distinct rotomers. δ 10.02 (s, 0.3H), 9.85 (s, 0.5H), 9.45 (s, 0.2H), 8.32-8.31 (m, 0.2H), 7.93 (s, 0.3H), 7.83 (s, 0.5H), 7.79 (s, 0.2H), 7.53-7.34 (m, 5.2H), 7.26-7.14 (m, 1.3H), 7.08 (s, 0.5H), 7.01-6.94 (m, 1H), 6.91-6.82 (m, 1H), 5.78 (d, J=8.4 Hz, 0.3H), 5.71 (d, J=8.4 Hz, 0.5H), 5.52-5.48 (m, 0.5H), 5.35-5.21 (m, 2.3H), 4.53-4.50 (m, 0.2H), 4.06 (s, 1.5H), 3.98 (s, 0.6H), 3.94 (s, 0.9H), 3.63-3.17 (m, 2H); HRMS (ESI, m/z): calc. 433.1400 (M+H)$^+$, found 433.1387. Compound 7:

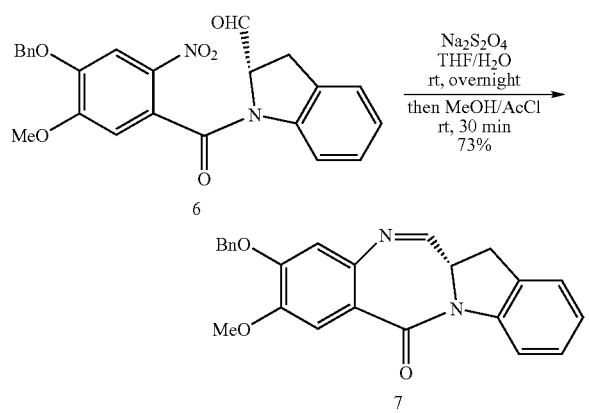

To a stirred solution of aldehyde 6 (2.16 g, 5 mmol) in THF (230 mL) was added deioned water (150 mL) and sodium dithionite (85%, 4.61 g, 22.5 mmol). The obtained slightly cloudy solution became clear after addition of another 5 mL of deioned water. The clear mixture was stirred at room temperature for 16 hours and 30 mL of MeOH was added. After stirring for another 2 hours, the solvents were removed under reduced pressure (bath temperature below 35° C.). The residue was suspended in acetonitrile and evaporated to help remove any remaining water. The obtained white solid was further completely dried by leaving on a high vacuum for a few hours. The residue was suspended in dichloromethane/methanol (1:1) and filtered through celite. The flask and the solid were thoroughly washed with dichloromethane/methanol (1:1). The filtrate was stripped under reduced pressure. The residue was dissolved in methanol (50 mL) followed by addition of acetyl chloride (1.8 mL, 25 mmol) dropwise. The mixture was stirred at room temperature for 30 minutes and concentrated under reduced pressure (bath temperature below 35° C.) to remove half of the methanol. The remainder was quenched with saturated sodium bicarbonate followed by addition of dichloromethane (150 mL) and water (100 mL). The aqueous layer was extracted with dichloromethane (2×100 mL) and the combined organic layers were washed with brine, dried over anhydrous sodium sulfate and filtered. The solvents were removed under reduced pressure and the residue was purified by silica gel chromatography (Hexanes/AcOEt, 1:1, 1:1.3, 1:1.5) to give compound 7 as a yellow solid (1.41 g, y=73%). $^1$H NMR (400 Hz, CDCl$_3$): δ 8.26 (d, J=8.0 Hz, 1H), 7.83 (d, J=4.4 Hz, 1H), 7.57 (s, 1H), 7.46-7.23 (m, 7H), 7.11-7.08 (m, 1H), 6.86 (s, 1H), 5.23 (d, J=12 Hz, 1H), 5.18 (d, J=12 Hz, 1H), 4.44 (ddd, J$_1$=11.2 Hz, J$_2$=4.4 Hz, J$_3$=4.0 Hz, 1H), 3.97 (s, 3H), 3.67 (dd, J$_1$=16.4 Hz, J$_2$=11.2 Hz, 1H), 3.46 (dd, J$_1$=16.4 Hz, J$_2$=4.0 Hz, 1H); $^{13}$C NMR (400 Hz, CDCl$_3$): δ 163.8, 163.0, 150.9, 148.3, 141.96, 139.97, 136.0, 129.4, 128.6, 128.1, 128.08, 127.3, 124.7, 124.69, 120.7, 116.8, 111.9, 111.3, 70.8, 56.2, 54.9, 32.5; HRMS(ESI, m/z): calc. 385.1552 (M+H)$^+$, found 385.1592.

Indolinobenzodiazepine (IBD) Monomer 8

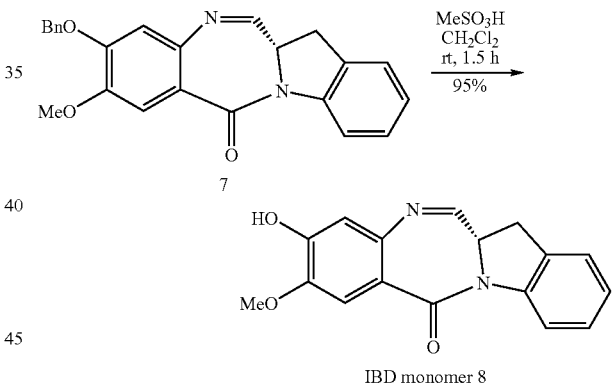

IBD monomer 8

To a stirred solution of the starting material 7 (1.41 g, 3.67 mmol) in dichloromethane (26 mL) was added a freshly mixed solution of methanesulfonic acid (26 mL) in dichloromethane (52 mL) at room temperature. The mixture was stirred at room temperature for 1.5 hours and diluted with dichloromethane (100 mL). The mixture was poured on ice (~200 g)/MeOH (10 mL). The pH of the obtained solution was adjusted to 7 with saturated NaHCO$_3$, solid NaHCO$_3$ and water. The mixture was separated and the dichloromethane layer was washed with brine. The combined aqueous layers were extracted with ethyl acetate (3×80 mL). The ethyl acetate layers were combined and washed with brine. The dichloromethane and ethyl acetate were combined, dried over anhydrous sodium sulfate and filtered. The solvents were removed and the residue (1.26 g) was purified by silica gel chromatography (CH$_2$Cl$_2$/MeOH, 20:1, 15:1) to give the IBD monomer 8 as a yellow solid (1.02 g, y=95%). $^1$H NMR (400 Hz, CDCl$_3$): δ 8.29 (d, J=8.0 Hz, 1H), 7.91 (d, J=4.8 Hz, 1H), 7.59 (s, 1H), 7.32-7.28 (m, 2H), 7.13 (t, J=7.2 Hz, 1H), 6.94

(s, 1H), 6.02 (s, —OH), 4.50 (dt, J$_1$=10.8 Hz, J$_2$=4.4 Hz, 1H), 4.02 (s, 3H), 3.73 (dd, J$_1$=16.8 Hz, J$_2$=10.8 Hz, 1H), 3.52 (dd, J$_1$=16.8 Hz, J$_2$=3.6 Hz, 1H); HRMS (ESI, m/z): calc. 295.1083 (M+H)$^+$, found 295.1076.

Example 2

(s)-(−)-3-(Benzyloxycarbonyl)-4-oxazolidinecarboxylic methyl ester 10

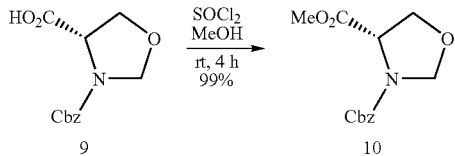

To a stirred solution of (s)-(−)-3-(Benzyloxycarbonyl)-4-oxazolidinecarboxylic acid 9 (1.75 g, 6.96 mmol) in anhydrous methanol (15 mL) was added thionyl chloride (1.02 mL, 13.9 mmol) at 0° C. After 30 minutes, the ice/water bath was removed and the reaction mixture continued to be stirred at room temperature for 3.5 hours. The reaction was quenched by addition of saturated sodium bicarbonate and diluted with dichloromethane (100 mL) and water (50 mL). The mixture was separated and the aqueous layer was extracted with dichloromethane (2×50 mL). The combined organic layers were washed with brine, dried over anhydrous sodium sulfate and filtered. The solvents were removed under reduced pressure and the residue was purified by silica gel chromatography (Hexanes/AcOEt, 1.5:1) to give (s)-(−)-3-(Benzyloxycarbonyl)-4-oxazolidinecarboxylic methyl ester 10 as colorless oil (1.84 g, y=99%). $^1$H NMR (400 Hz, CDCl$_3$): the compound appears as a pair of distinct rotomers. δ 7.35 (bs, 5H), 5.22-4.99 (m, 4H), 4.53-4.45 (m, 1H), 4.22-4.09 (m, 2H), 3.76 (s, 1.5H), 3.65 (s, 1.5H); MS (m/z): found 288.0 (M+Na)$^+$.
Compound 11:

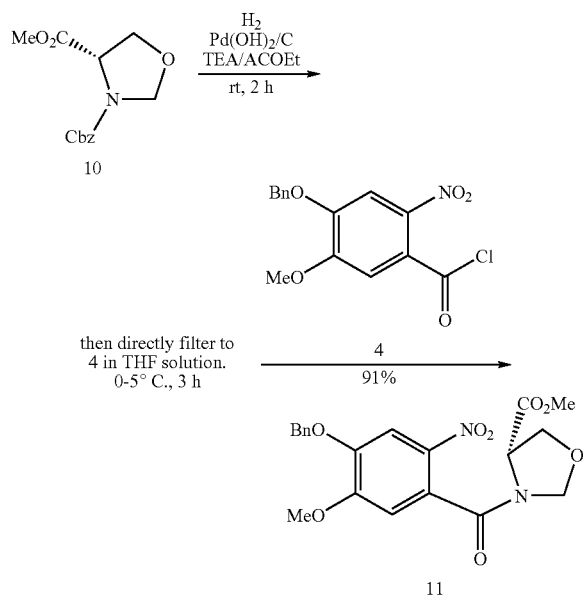

To a stirred solution of (s)-(−)-3-(Benzyloxycarbonyl)-4-oxazolidinecarboxylic methyl ester 10 (1.04 g, 3.92 mmol) in ethyl acetate (16 mL) was added triethyl amine (1.4 mL, 10 mmol) and palladium hydroxide on carbon (20%, 267 mg, 0.337 mmol). The air in the reaction flask was removed by vacuum, then a hydrogen balloon was applied and the mixture was stirred under hydrogen atmosphere at room temperature for 2 hours. To a solution of acetyl chloride 4 (prepared from 1.3 g, 4.3 mmol of 4-benzyloxy-5-methoxy-2-nitrobenzoic acid 2 following the procedures described above) in anhydrous THF (15 mL) was added triethyl amine (1.1 mL, 7.9 mmol) at 0° C., followed by addition of the above hydrogenation reaction mixture by filtration through celite. The palladium catalyst/celite was washed with anhydrous THF (15 mL). The obtained mixture was stirred at 0° C. for 3 hours. It was diluted with ethyl acetate and saturated ammonium chloride. The pH of the mixture was adjusted to 6~7 by addition of 5% hydrochloric acid. The mixture was separated and the aqueous layer was extracted with ethyl acetate (2×80 mL). The combined organic layers were washed with brine, dried over anhydrous sodium sulfate and filtered. The solvents were removed under reduced pressure and the residue was purified by silica gel chromatography (Hexanes/AcOEt, 1:2, 1:3) to give compound 11 as a pale yellow solid (1.49 g, y=91%). $^1$H NMR (400 Hz, CDCl$_3$): the compound appears as a pair of distinct rotomers. δ 7.78 (s, 0.5H), 7.75 (s, 0.5H), 7.48-7.37 (m, 5H), 6.97 (s, 0.5H), 6.91 (s, 0.5H), 5.39 (d, J=4.8 Hz, 0.5H), 5.26-5.23 (m, 2.5H), 4.95 (dd, J1=7.2 Hz, J2=4.4 Hz, 0.5H), 4.81 (d, J=3.6 Hz, 0.5H), 4.67 (d, J=3.6 Hz, 0.5H), 4.37-4.30 (m, 1H), 4.25-4.11 (m, 1.5H), 4.02 (s, 1.5H), 3.97 (s, 1.5H), 3.87 (s, 1.5H), 3.67 (s, 1.5H); HRMS (ESI, m/z): calc. 417.1298 (M+H)$^+$, found 417.1305.
Aldehyde 12:

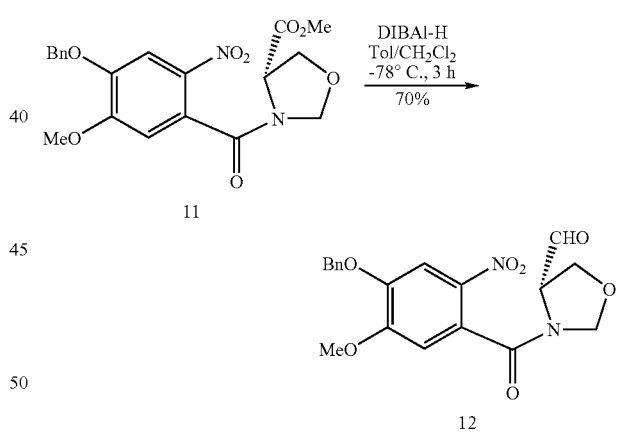

To a stirred solution of the methyl ester 11 (1.49 g, 3.6 mmol) in anhydrous dichloromethane (4 mL) and toluene (12 mL) was added dibal-H (6.5 mL, 1.0 M in toluene) dropwise via a syringe pump in 30 minutes at −78° C. The mixture continued to be stirred at −78° C. for 2 hours. The reaction was quenched with methanol (146 ₜA, 3.6 mmol) and 5% HCl (30 mL) at −78° C. Ethyl acetate (100 mL) was added and the dry ice/acetone bath was removed. The mixture was stirred at room temperature for 30 minutes and then transferred to a separatory funnel. The aqueous layer was extracted with AcOEt twice. All the organic layers were combined, washed with brine, saturated sodium bicarbonate and brine. It was dried over anhydrous sodium sulfate and filtered through celite. The filtrate was evaporated under reduced pressure and the residue was purified by silica gel chromatography (Hexanes/AcOEt, 1:5, 1:10) to give the aldehyde 12 as a pale yellow solid (980 mg, y=70%). $^1$H NMR (400 Hz, CDCl$_3$): the compound appears as a pair of distinct rotomers. δ 9.83 (s, 0.67H), 9.45 (s, 0.33H), 7.77 (s, 0.67H), 7.72 (s, 0.33H), 7.45-7.37 (m, 5H), 6.90 (s, 1H), 5.31-5.19 (m, 3H), 4.77 (bs, 1H), 4.67-4.56 (m, 1H), 4.36-3.94 (m, 5H); HRMS (ESI, m/z): calc. 387.1192 (M+H)$^+$, found 387.1184.

Compound 13:

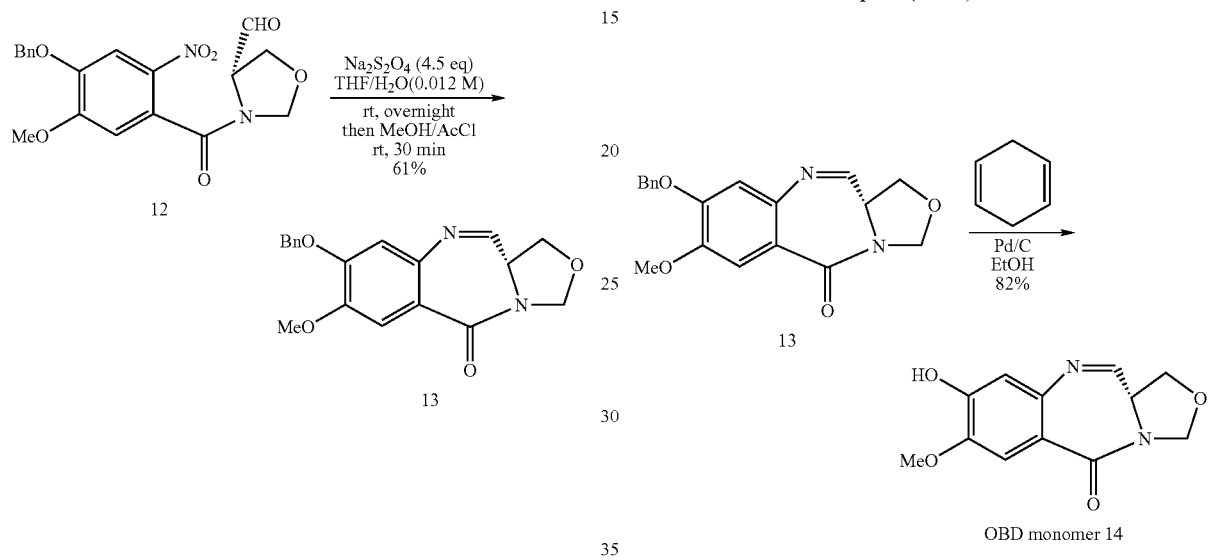

To a stirred solution of aldehyde 12 (154 mg, 0.4 mmol) in THF (21 mL) was added deioned water (14 mL) and sodium dithionite (85%, 369 mg, 1.8 mmol). The clear mixture was stirred at room temperature for 16 hours and 5 mL of MeOH was added. After being stirred another 2 hours, the solvents were removed under reduced pressure (bath temperature below 35° C.). The residue was suspended in acetonitrile and evaporated to help remove the remaining water. The obtained white solid was further completely dried by leaving on a high vacuum for a few hours. The residue was suspended in dichloromethane/methanol (2:1) and filtered through celite. The flask and the solid were thoroughly washed with dichloromethane/methanol (1:1). The filtrate was stripped under reduced pressure. The residue was dissolved in methanol (5 mL) and a freshly prepared acetyl chloride (0.15 mL)/MeOH (5 mL) solution was added quickly. The mixture was stirred at room temperature for 30 minutes and quenched by addition of saturated sodium bicarbonate. It was diluted with dichloromethane and water. The two layers were separated and the aqueous layer was extracted with dichloromethane. The combined dichloromethane layers were washed with brine and dried over anhydrous sodium sulfate. The solvents were removed under reduced pressure to give 127 mg crude product. The aqueous layer and the washing solution were combined and acidified to pH 2~3 with KHSO$_4$. It was concentrated to half under reduced pressure (temperature<40° C.) and extracted with dichloromethane. The combined dichloromethane was washed with saturated sodium bicarbonate and brine, dried over anhydrous sodium sulfate. It was filtered and the filtrate was evaporated under reduced pressure. The residue was combined with above 127 mg crude product and purified by silica gel chromatography (Hexanes/AcOEt, 1:3, 1:5, 1:8) to give compound 13 as a colorless foam (80 mg, y=61%). $^1$H NMR (400 Hz, CDCl$_3$): δ 7.77 (d, J=4.0 Hz, 1H), 7.52 (s, 1H), 7.46-7.28 (m, 5H), 6.88 (s, 1H), 5.28 (d, J=5.2 Hz, 1H), 5.23 (d, J=12 Hz, 1H), 5.17 (d, J=12 Hz, 1H), 5.05 (d, J=5.2 Hz, 1H), 4.49 (dd, J1=9.6 Hz, J2=3.2 Hz, 1H), 4.33 (dd, J1=9.6 Hz, J2=6.4 Hz, 1H), 3.96 (s, 3H), 3.83 (dd, J1=6.4 Hz, J2=3.2 Hz, 1H); MS (m/z): found 361.1 (M+Na)$^+$, 379.1 (M+H$_2$O+Na)$^-$, 339.1 (M+H)$^+$.

Oxazolidinobenzodiazepine (OBD) Monomer 14

A solution of compound 13 (90 mg, 0.27 mmol) and Pd/C (10%, 90 mg) in absolute ethanol (1.5 mL) was bubbled with argon. 1,4-Cyclohexadiene (496 μl, 5.3 mmol) was added and the argon bubble was continued for 3 hours until the starting material disappeared (TLC, dichloromethane/methanol 10:1). The mixture was then filtered through celite and the celite was washed with methanol. The filtrate was evaporated under reduced pressure to give 63 mg of the crude product as colorless foam, which was purified by silica gel chromatography (dichloromethane/methanol, 20:1) to give OBD monomer 14 (55 mg, y=82%) as a white solid.

$^1$H NMR (400 Hz, CDCl$_3$): it appears as a mixture of imine and its methyl ethers, C11(R) and C11(S) (2:3:1). δ 7.71 (bs, 1H), 7.43 (s, 0.5H), 7.41 (s, 1H), 7.18 (s, 1.5H), 6.83 (s, 1H), 6.36 (s, 1.5H), 6.13 (s, 0.5H), 5.25 (d, J=4.8 Hz, 0.5H), 5.22-5.20 (m, 1H), 5.14 (d, J=5.2 Hz, 1.5H), 5.10 (d, J=4.8 Hz, 0.5H), 5.05 (d, J=5.2 Hz, 1.5H), 5.00-4.97 (m, 1H), 4.47 (d, J=8.8 Hz, 1.5H), 4.44-4.41 (m, 1H), 4.32 (apt, J=8.0 Hz, 0.5H), 4.28-4.25 (m, 1H), 4.18-4.00 (m, 2×1.5H+2× 0.5H=4H), 3.84 (bs, 3×1H+0.5H=3.5H), 3.76 (bs, 3×1.5H+ 1H=5.5H), 3.73 (s, 3×0.5H=1.5H), 3.56 (dt, J1=8.8 Hz, J2=2.8 Hz, 1.5H), 3.34 (s, 3×1.5H=4.5H), 3.22 (s, 3×0.5H=1.5H); MS (m/z): found 303.1 (M+MeOH+Na)$^+$, 271.1 (M+Na)$^+$.

Example 3

Dimer 15 (IGN-09):

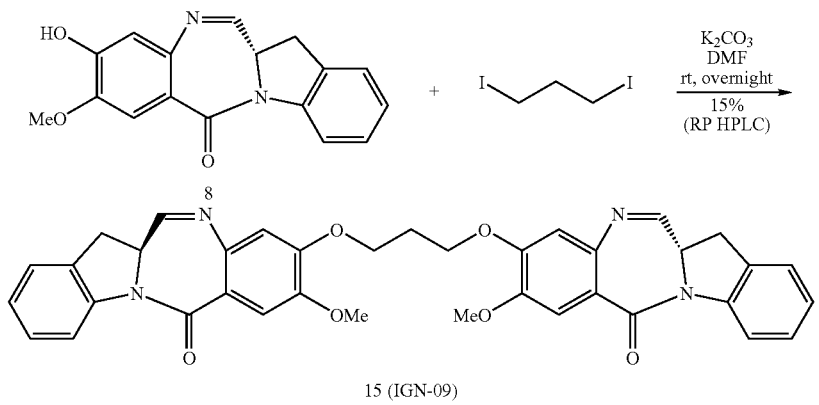

15 (IGN-09)

To a solution of IBD monomer 8 (147 mg, 0.5 mmol) and 1,3-diiodopropane (23 μl, 0.2 mmol) in anhydrous DMF (1.0 mL) was added potassium carbonate (111 mg, 0.8 mmol). The mixture was stirred at room temperature overnight (16 hours) and diluted with dichloromethane. It was washed with saturated ammonium chloride and brine, dried over anhydrous sodium sulfate and filtered. The filtrate was evaporated under reduced pressure and the residue was purified through preparative reverse phase HPLC (C18 column, acetonitrile/water) to give dimer 15 (IGN-09) (18.9 mg, y=15%) as a white solid. $^1$H NMR (400 Hz, CDCl$_3$): δ 8.26 (d, J=8.0 Hz, 2H), 7.87 (d, J=4.4 Hz, 2H), 7.55 (s, 2H), 7.26 (s, 4H), 7.12-7.08 (m, 2H), 6.88 (s, 2H), 4.45 (ddd, J1=10.8 Hz, J2=4.4 Hz, J3=4.0 Hz, 2H), 4.36-4.26 (m, 4H), 3.94 (s, 6H), 3.70 (dd, J1=16.8 Hz, J2=10.8 Hz, 2H), 3.50 (dd, J1=16.8 Hz, J2=4.0 Hz, 2H), 2.45 (p, J=6.0 Hz, 2H); HRMS (ESI, m/z): calc. 629.2400 (M+H)$^+$, found 629.2400.

Example 4

Dimer 18 (IGN-01):

minutes and was quenched with ice/water, diluted with cold ethyl acetate. The mixture was separated and the organic layer was washed with cold water, dried over anhydrous sodium sulfate. It was filtered and the filtrate was evaporated by rotary evaporation in vacuo (temperature<35° C.). The residue 17 was high vacuumed for a few hours before being dissolved in anhydrous DMF (1.5 mL). IBD monomer 7 (94 mg, 0.32 mmol), anhydrous potassium carbonate (50 mg, 0.36 mmol) and potassium iodide (27 mg, 0.16 mmol) were added subsequently. The mixture was stirred at room temperature for 17 hours (checked by mass spectrum) and diluted with dichloromethane. It was washed with brine, dried over anhydrous sodium sulfate and filtered. The filtrate was evaporated under reduced pressure and the residue was purified by reverse phase HPLC (C18 column, CH$_3$CN/H$_2$O, loaded column with CH$_3$CN/H$_2$O, 3:1, stirred for 30 min and centrifuged before injection) to furnish dimer 18 (IGN-01, 6.6 mg) as a white solid. $^1$H NMR (400 Hz, CDCl$_3$): δ 8.21 (d, J=8.0 Hz, 2H), 7.79 (d, J=4.4 Hz, 2H), 7.51 (s, 2H), 7.46 (s, 1H), 7.36 (bs, 3H), 7.23-7.18 (m, 4H), 7.06-7.03 (m, 2H), 6.79 (s, 2H),

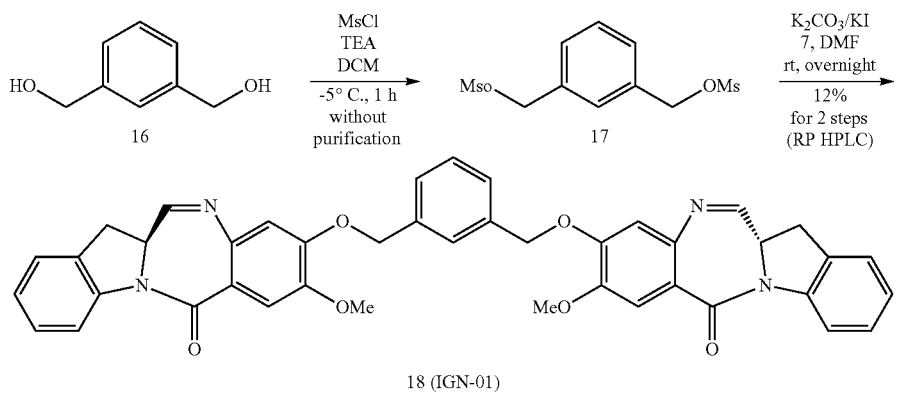

18 (IGN-01)

To a stirred solution of 1,3-Benzenedimethanol 16 (11 mg, 0.08 mmol) in anhydrous dichloromethane (0.8 mL) was added triethylamine (33 μl, 0.24 mmol) then methanesulfonyl chloride (16 μL, 0.21 mmol) dropwise in 15 minutes at −5~−10° C. The solution was stirred at −5~−10° C. for another 60

5.20 (d, J=12.4 Hz, 2H), 5.14 (d, J=12.4 Hz, 2H), 4.41 (ddd, J1=10.8 Hz, J2=4.4 Hz, J3=4.0 Hz, 2H), 3.92 (s, 6H), 3.64 (dd, J1=17.2 Hz, J2=11.2 Hz, 2H), 3.42 (dd, J1=16.8 Hz, J2=4.0 Hz, 2H); HRMS (ESI, m/z): calc. 691.2557 (M+H)$^+$, found 691.2570.

Example 5

Dimer 19 (IGN-02):

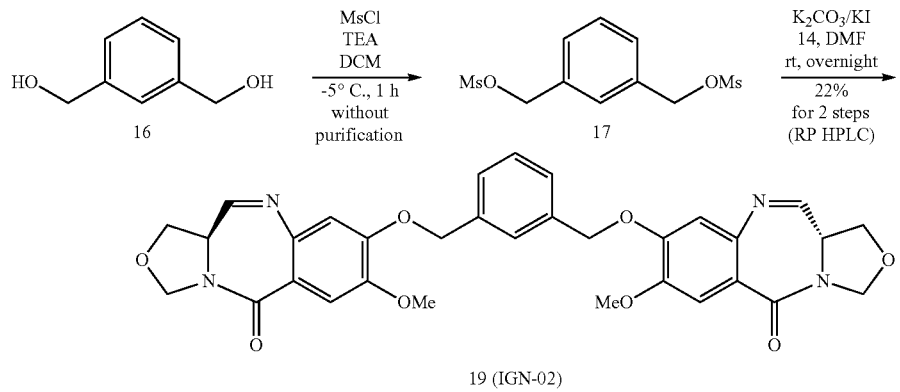

To a stirred solution of 1,3-Benzenedimethanol 16 (10 mg, 0.074 mmol) in anhydrous dichloromethane (0.8 mL) was added triethylamine (31 µl, 0.22 mmol) then methanesulfonyl chloride (15 µL, 0.19 mmol) dropwise in 15 minutes at −5~−10° C. The solution was stirred at −5~−10° C. for another 60 minutes and was quenched with ice/water, diluted with cold ethyl acetate. The mixture was separated and the organic layer was washed with cold water, dried over anhydrous sodium sulfate. It was filtered and the filtrate was evaporated by rotary evaporation in vacuo (temperature<35° C.). The residue 17 was high vacuumed before dissolving in anhydrous DMF (1.5 mL). OBD monomer 14 (70 mg, 0.28 mmol), anhydrous potassium carbonate (51 mg, 0.37 mmol) and potassium iodide (25 mg, 0.15 mmol) were added subsequently. The mixture was stirred at room temperature for 17 hours (checked by mass spectrum) and diluted with dichloromethane. It was washed with brine, dried over anhydrous sodium sulfate and filtered. The filtrate was evaporated under reduced pressure and the residue was purified by reverse phase HPLC (C18 column, CH$_3$CN/H$_2$O, loaded column with CH$_3$CN/H$_2$O, 3:1, stirred for 30 min and centrifuged before injection) to furnish dimer 19 (IGN-02, 10.0 mg) as a white solid. $^1$H NMR (400 Hz, CDCl$_3$): δ 7.75 (d, J=4.0 Hz, 2H), 7.50-7.48 (bs, 3H), 7.38 (bs, 3H), 6.83 (s, 2H), 5.26 (d, J=5.2 Hz, 2H), 5.21 (d, J=14.4 Hz, 2H), 5.15 (d, J=14.0 Hz, 2H), 5.03 (d, J=5.6 Hz, 2H), 4.34-4.30 (m, 2H), 3.94 (s, 6H), 3.86-3.76 (m, 2H); HRMS (ESI, m/z): calc. 599.2142 (M+H)$^+$, found 599.2184.

Example 6

Triol 21:

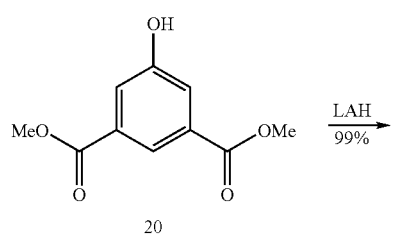

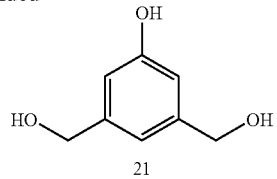

To a stirred solution of dimethyl 5-hydroxyisophthalate 20 (2.1 g, 10 mmol) in anhydrous THF (50 mL) was added lithium aluminum hydride (2.0 M in THF, 10 mL, 20 mmol) at −20~−30° C. via a syringe pump in 30 minutes. The cooling bath was removed after 30 minutes and the mixture continued to be stirred at room temperature for 4 hours. It was cooled to 0~−10° C. and quenched with saturated sodium sulfate. The mixture was diluted with acetonitrile and 5% hydrochloric acid (20 mL) was added. It was stirred for 30 minutes and dried over anhydrous sodium sulfate. The mixture was filtered through celite and the filtrate was evaporated under reduced pressure. The residue was purified through silica gel chromatography (Dichloromethane/Methanol, 10:1, 8:1, 5:1) to give triol 21 (1.5 g, y=99%) as a colorless oil which became white solid after stocking $^1$H NMR (400 Hz, MeOD): δ 6.78, (s, 1H), 6.69 (s, 2H), 4.50 (s, 4H). $^{13}$C NMR (400 Hz, MeOD): δ 158.7, 144.4, 117.8, 113.8, 65.2; MS (m/z): found 153.0 (M−H)$^-$.

Compound 22:

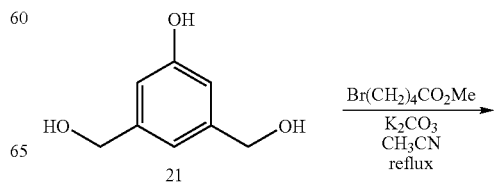

-continued

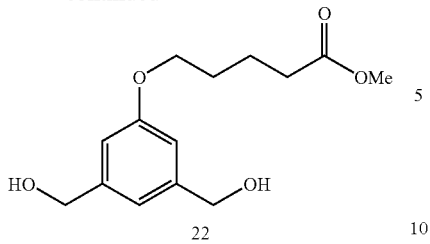
22

To a solution of triol 21 (827 mg, 5.37 mmol) and methyl 5-bromovalerate (998 mg, 5.12 mmol) in acetonitrile (40 mL) was added potassium carbonate (3.71 g, 26.9 mmol). The mixture was put in a 86° C. oil bath and refluxed for 6 hours. The reaction mixture was removed from the oil bath, cooled to room temperature and the solvents were evaporated under reduced pressure (temperature<35° C.). The residue was diluted with dichloromethane and filtered. The filtrate was washed with brine, dried over anhydrous sodium sulfate and filtered. The filtrate was stripped under reduced pressure and the residue was purified through silica gel chromatography (Hexanes/Ethyl acetate, 1:2, 1:3) to give compound 22 (1.15 g, y=84%) as a white solid. $^1$H NMR (400 Hz, CDCl$_3$): δ 6.89 (s, 1H), 6.80 (s, 2H), 4.62 (s, 4H), 3.98-3.95 (m, 2H), 3.67 (s, 3H), 2.41-2.37 (m, 2H), 2.23 (bs, —OH×2), 1.84-1.78 (m, 4H); MS (m/z): found 291.1 (M+Na)$^+$.

Compound 23:

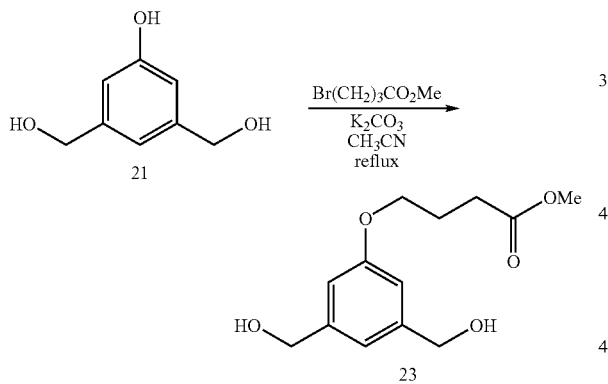
23

Following the procedure to prepare compound 22, compound 23 (1.43 g, y=75%) was synthesized as a white solid from triol 21 (1.16 g, 7.53 mmol), methyl 4-bromobutyrate (1.52 g, 8.39 mmol) and potassium carbonate (5.2 g, 37.6 mmol). $^1$H NMR (400 Hz, CDCl$_3$): δ 6.90 (s, 1H), 6.80 (s, 2H), 4.62 (s, 4H), 4.00 (t, J=6.0 Hz, 2H), 3.68 (s, 3H), 2.51 (t, J=7.2 Hz, 2H), 2.19 (s, —OH×2), 2.13-2.06 (m, 2H); MS (m/z): found 277.1 (M+Na)$^+$.

Compound 24:

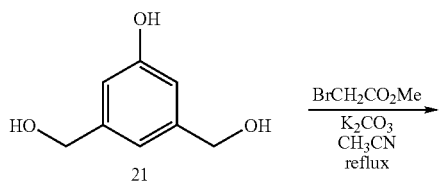
21

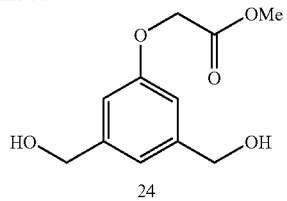
24

Following the procedure to prepare compound 22, compound 24 (515 mg, y=37%) was synthesized as a white sticky solid from triol 21 (953 mg, 6.19 mmol), methyl bromoacetate (587 µl, 6.19 mmol) and potassium carbonate (4.3 g, 31 mmol). $^1$H NMR (400 Hz, CDCl$_3$): δ 6.95 (s, 1H), 6.81 (s, 2H), 4.64 (s, —OH×2), 4.61 (s, 4H), 3.81 (s, 3H), 2.41 (s, 2H); $^{13}$C NMR (400 Hz, CDCl$_3$): δ 169.4, 158.1, 143.0, 118.5, 112.1, 65.2, 64.8, 52.3; MS (m/z): found 249.0 (M+Na)$^+$.

Compound 27:

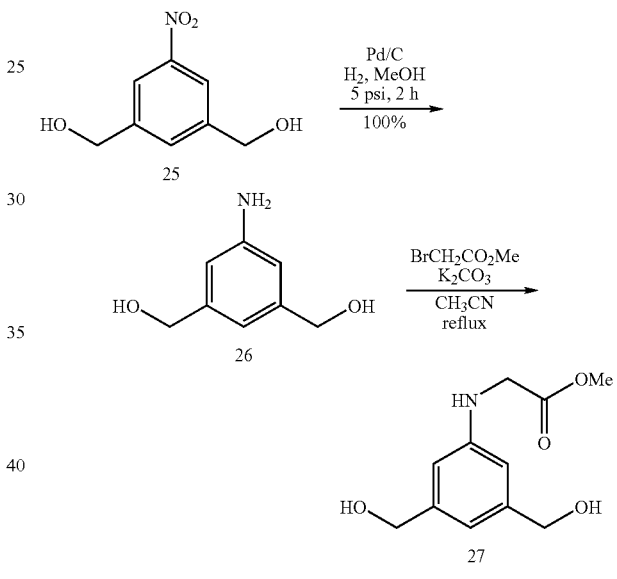

To a solution of 5-nitro-m-xylene-α,α'-diol 25 (1.07 g, 5.84 mmol) in methanol (50 mL) was added Pd/C (10%, 311 mg, 0.29 mmol). Hydrogen was introduced to replace the air then the mixture was hydrogenated (H$_2$, 5 psi) for 2 hours at room temperature. The solution was filtered through celite and the filtrate was evaporated by rotary evaporation in vacuo to give compound 26 as a white solid (900 mg, y=100%). $^1$H NMR (400 Hz, MeOD): δ 6.71 (s, 1H), 6.66 (s, 2H), 4.51 (s, 4H); $^{13}$C NMR (400 Hz, MeOD): δ 148.9, 143.8, 116.7, 114.3, 65.5; It was dissolved in anhydrous acetonitrile (30 mL) and ethyl bromoacetate (443 µl, 4.67 mmol) and potassium carbonate (807 mg, 5.84 mmol) were added. The mixture was put in a 86° C. oil bath and refluxed for 17 hours. The reaction mixture was removed from the oil bath, cooled to room temperature and diluted with dichloromethane. It was filtered through celite and the solid was washed with dichloromethane. White precipitate appeared in the filtrate. It was collected by filtration to give compound 27 (414 mg, y=39%) as a white solid. $^1$H NMR (400 Hz, MeOD): δ 6.67 (s, 1H), 6.53 (s, 2H), 4.51 (s, 4H), 3.94 (s, 2H), 3.73 (s, 3H); $^{13}$C NMR (400 Hz, MeOD): δ 174.0, 149.7, 143.9, 116.2, 111.6, 65.6, 52.6, 46.5; MS (m/z): found 248.0 (M+Na)$^+$.

Compound 28:

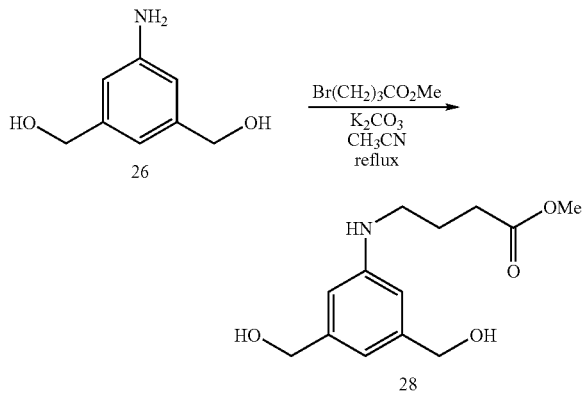

To a solution of 5-nitro-m-xylene-α,α'-diol 25 (564 mg, 3.08 mmol) in methanol (35 mL) was added Pd/C (10%, 164 mg, 0.154 mmol). Hydrogen was introduced to replace the air then the mixture was hydrogenated (H$_2$, 5 psi) for 2 hours at room temperature. The solution was filtered through celite and the filtrate was evaporated by rotary evaporation in vacuo to give compound 26, which was dissolved in anhydrous acetonitrile (15 mL) and methyl 4-bromobutyrate (557 mg, 3.08 mmol) and potassium carbonate (426 mg, 3.08 mmol) were added. The mixture was put in a 86° C. oil bath and refluxed for 18 hours. The reaction mixture was removed from the oil bath, cooled to room temperature and diluted with dichloromethane. It was filtered through celite and the solid was washed with dichloromethane/acetonitrile (1:1). The filtrate was evaporated under reduced pressure and the residue was purified through silica gel chromatography (Combiflash, dichloromethane/methanol) to give compound 28 (292 mg, y=37%) as a white solid. $^1$H NMR (400 Hz, MeOD): δ 6.62 (s, 1H), 6.55 (s, 2H), 4.50 (s, 4H), 3.65 (s, 3H), 3.13 (d, J=7.2 Hz, 2H), 2.43 (d, J=7.2 Hz, 2H), 1.89 (p, J=7.2 Hz, 2H); $^{13}$C NMR (400 Hz, MeOD): δ 175.9, 150.5, 143.7, 115.5, 111.7, 65.7, 52.2, 44.3, 32.5, 25.8; MS (m/z): found 276.0 (M+Na)$^+$.

Compound 29:

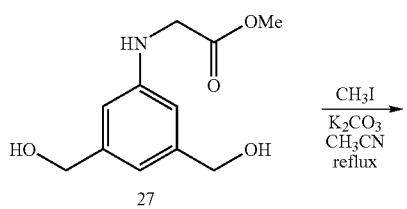

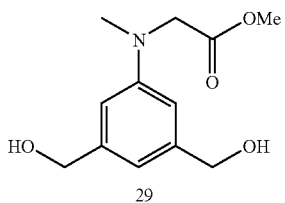

To a solution of compound 27 (230 mg, 1.02 mmol) in anhydrous acetonitrile (7 mL) was added methyl iodide (70 μl, 1.12 mmol) and potassium carbonate (155 mg, 1.12 mmol). The mixture was put in a 86° C. oil bath and refluxed for 17 hours. The reaction mixture was removed from the oil bath, cooled to room temperature and diluted with dichloromethane. It was filtered through celite and the solid was washed with dichloromethane/methanol (10:1). The filtrate was evaporated under reduced pressure and the residue was purified through silica gel chromatography (Combiflash, dichloromethane/methanol) to give compound 29 (98 mg, y=40%) as a white solid. $^1$H NMR (400 Hz, MeOD): δ 6.70 (s, 1H), 6.63 (s, 2H), 4.84 (s, 2×-OH), 4.54 (s, 4H), 4.16 (s, 2H), 3.69 (s, 3H), 3.05 (s, 3H); $^{13}$C NMR (400 Hz, MeOD): δ 173.6, 150.9, 143.8, 115.6, 111.0, 65.7, 54.9, 52.4, 39.8; MS (m/z): found 262.0 (M+Na)$^+$.

Compound 30:

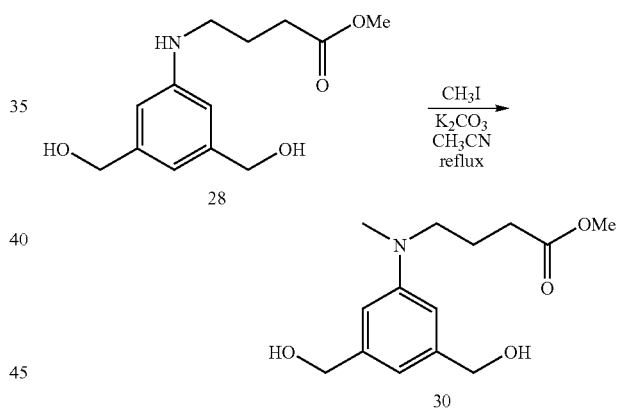

To a solution of compound 28 (151 mg, 0.597 mmol) in anhydrous acetonitrile (4 mL) was added methyl iodide (74 μl, 1.19 mmol) and potassium carbonate (99 mg, 0.716 mmol). The mixture was put in an 86° C. oil bath and refluxed for 17 hours. The reaction mixture was removed from the oil bath, cooled to room temperature and diluted with dichloromethane. It was filtered through celite and the solid was washed with dichloromethane/methanol (10:1). The filtrate was evaporated under reduced pressure and the residue was purified through silica gel chromatography (Combiflash, dichloromethane/methanol) to give compound 30 (63 mg, y=39%) as a colorless oil. $^1$H NMR (400 Hz, MeOD): δ 6.67 (s, 2H), 6.65 (s, 1H), 4.54 (s, 4H), 3.65 (s, 3H), 3.36 (t, J=7.2 Hz, 2H), 2.92 (s, 3H), 2.36 (t, J=7.2 Hz, 1H), 1.87 (p, J=7.2 Hz, 2H); $^{13}$C NMR (400 Hz, MeOD): δ 175.7, 151.3, 143.7, 115.0, 111.4, 65.9, 53.0, 52.2, 38.9, 32.2, 23.3; MS (m/z): found 290.0 (M+Na)$^+$.

Compound 34 (IGN-03):

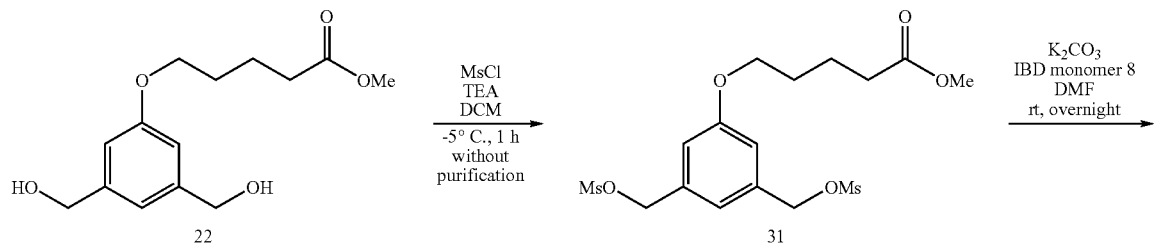

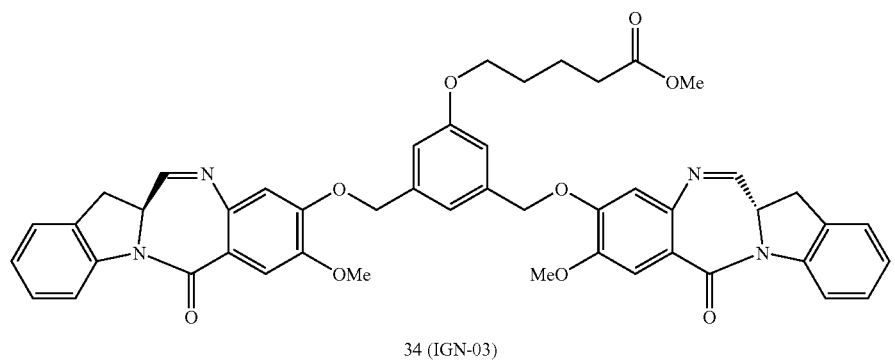

34 (IGN-03)

To a stirred solution of compound 22 (80.4 mg, 0.3 mmol) in anhydrous dichloromethane (2 mL) was added triethylamine (125 μl, 0.9 mmol) then methanesulfonyl chloride (60 μL, 0.78 mmol) dropwise in 15 minutes at −5~−10° C. The solution was stirred at −5~−10° C. for another 60 minutes and was quenched with ice/water, diluted with cold ethyl acetate. The mixture was separated and the organic layer was washed with cold water, dried over anhydrous sodium sulfate. It was filtered and the filtrate was evaporated by rotary evaporation in vacuo (temperature<35° C.). The residue 31 was high vacuumed before dissolving in anhydrous DMF (3 mL). IBD monomer 7 (221 mg, 0.75 mmol) and anhydrous potassium carbonate (207 mg, 1.5 mmol) were added. The mixture was stirred at room temperature for 20 hours (checked by mass spectrum) and diluted with dichloromethane. It was washed with water and brine, dried over anhydrous sodium sulfate and filtered. The filtrate was evaporated under reduced pressure and the residue was purified through silica gel chromatography (hexanes/ethyl acetate, 1:3, 1:4, 1:6, 1:10, then ethylacetate/methanol, 10:1) to give compound 34 (169 mg, y=68%, 86% purity based on analytical reverse phase HPLC) as a yellowish solid. Fractions that contained impurities and compound 34 were also collected and the solvents were evaporated to give 70 mg of yellowish solid. The two yellowish solids were combined and further purified through reverse phase HPLC (C18 column, $CH_3CN/H_2O$, loaded column with $CH_3CN/H_2O$, 3:1, stirred for 30 min and centrifuged before injection) to furnish dimer 34 (IGN-03, 103 mg, y=41%) as a white solid. $^1$H NMR (400 Hz, $CDCl_3$): δ 8.27 (d, J=8.0 Hz, 2H), 7.85 (d, J=3.2 Hz, 2H), 7.58 (s, 2H), 7.29-7.24 (m, 4H), 7.12-7.07 (m, 3H), 6.94 (s, 2H), 6.83 (s, 2H), 5.22 (d, J=12.8 Hz, 2H), 5.16 (d, J=12.8 Hz, 2H), 4.47 (dt, J1=11.2 Hz, J2=4.4 Hz, 2H), 3.98 (bs, 8H), 3.73-3.64 (m, 2H), 3.68 (s, 3H), 3.48 (dd, J1=16.8 Hz, J2=3.6 Hz, 2H), 2.42-2.38 (m, 2H), 1.83-1.80 (m, 4H); HRMS (ESI, m/z): calc. 821.3187 (M+H)$^+$, found 821.3188.

Compound 35 (IGN-04):

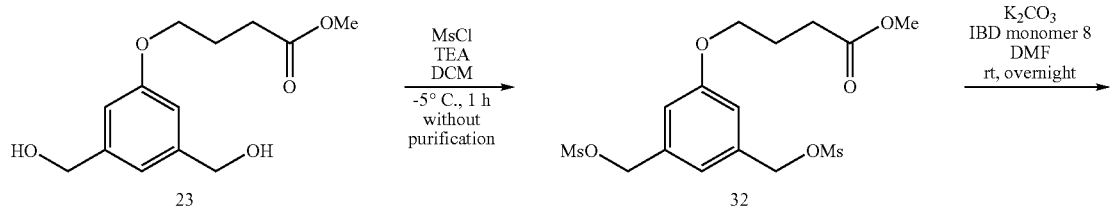

-continued

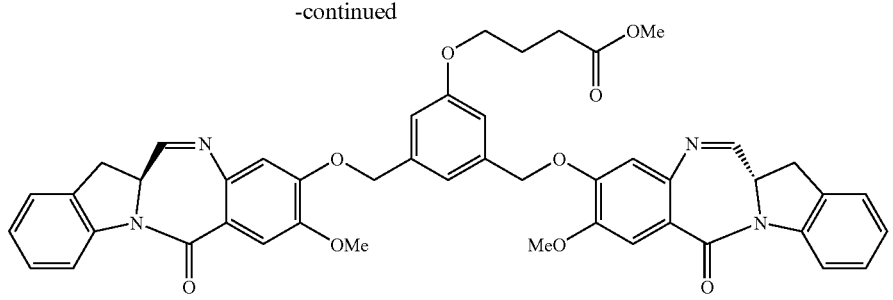

35 (IGN-04)

Following the procedure to prepare compound 34, compound 35 (IGN-04) was synthesized (151 mg, y=62%, 88% purity based on analytical reverse phase HPLC) as a yellowish solid. Part of it was further purified by reverse phase HPLC for $^1$H NMR analysis. $^1$H NMR (400 Hz, CDCl$_3$): δ 8.17 (d, J=8.0 Hz, 2H), 7.74 (d, J=5.2 Hz, 2H), 7.48 (s, 2H), 7.20-7.15 (m, 4H), 7.03-6.99 (m, 3H), 6.85 (s, 2H), 6.75 (s, 2H), 5.12 (d, J=12.8 Hz, 2H), 5.06 (d, J=12.8 Hz, 2H), 4.37 (dt, J1=11.2 Hz, J2=4.4 Hz, 2H), 3.93 (t, J=6.0 Hz, 2H), 3.86 (s, 6H), 3.64-3.57 (m, 2H), 3.60 (s, 3H), 3.39 (dd, J1=16.8 Hz, J2=3.6 Hz, 2H), 2.44 (t, J=7.2 Hz, 2H), 2.02 (p, J=6.4 Hz, 2H); HRMS (ESI, m/z): calc. 807.3030 (M+H)$^+$, found 807.3008.

Compound 36 (IGN-05):

Following the procedure to prepare compound 34, compound 36 (IGN-05) was synthesized (84.5 mg, y=18%) as a white solid after preparative reverse phase HPLC. $^1$H NMR (400 Hz, CDCl$_3$): δ 8.24 (d, J=8.0 Hz, 2H), 7.79 (d, J=4.4 Hz, 2H), 7.55 (s, 2H), 7.26-7.22 (m, 4H), 7.12-7.07 (m, 3H), 6.96 (s, 2H), 6.81 (s, 2H), 5.18 (d, J=12.8 Hz, 2H), 5.12 (d, J=12.8 Hz, 2H), 4.64 (s, 2H), 4.44 (dt, J1=10.8 Hz, J2=4.4 Hz, 2H), 3.95 (s, 6H), 3.77 (s, 3H), 3.73-3.62 (m, 2H), 3.44 (dd, J1=16.8 Hz, J2=3.6 Hz, 2H); HRMS (ESI, m/z): calc. 779.2717 (M+H)$^+$, found 779.2703.

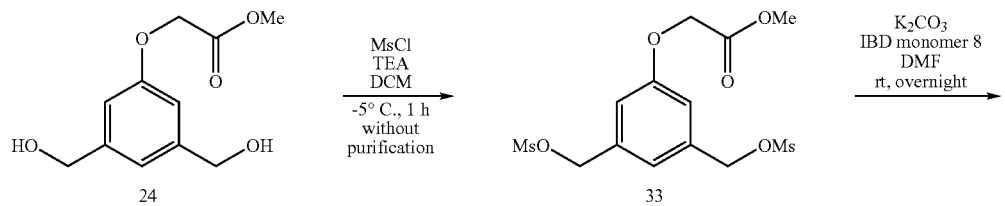

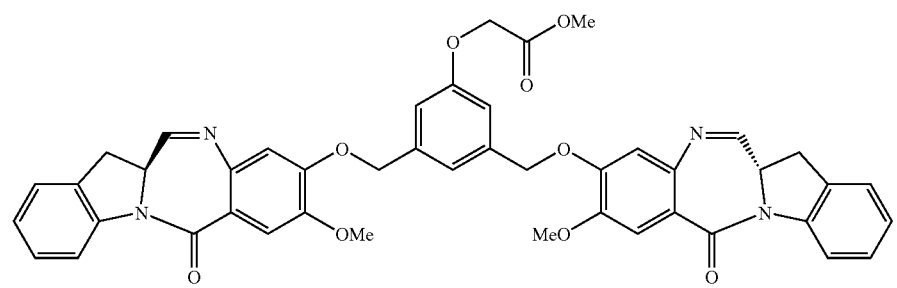

36 (IGN-05)

Compound 39 (IGN-06):

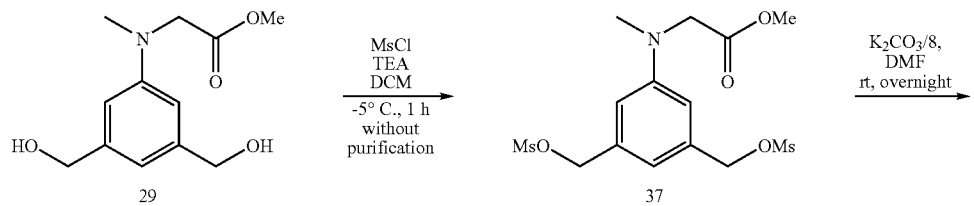

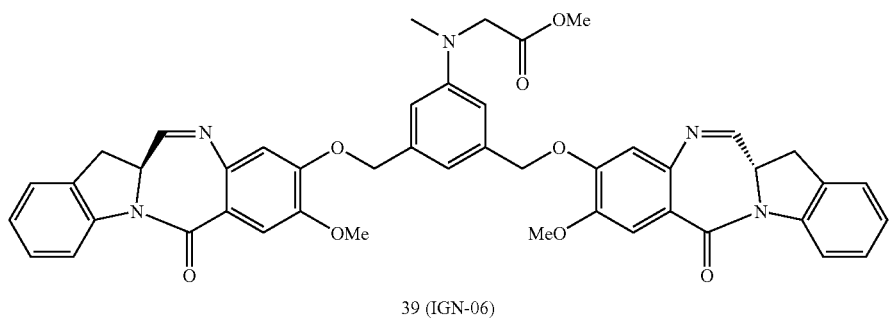

39 (IGN-06)

Following the procedure to prepare compound 34, compound 39 (IGN-06) was synthesized in 6% yield as a white solid after preparative reverse phase HPLC. $^1$H NMR (400 Hz, CDCl$_3$): δ 8.28 (d, J=8.0 Hz, 2H), 7.86 (d, J=4.0 Hz, 2H), 7.58 (s, 2H), 7.31-7.26 (m, 4H), 7.12 (t, J=7.2 Hz, 2H), 6.90-6.86 (m, 3H), 6.72 (s, 2H), 5.22 (d, J=12.4 Hz, 2H), 5.13 (d, J=12.4 Hz, 2H), 4.51-4.46 (m, 2H), 3.99 (s, 6H), 3.74-3.68 (m, 2H), 3.71 (s, 3H), 3.49 (dd, J$_1$=16.8 Hz, J$_2$=3.6 Hz, 2H), 3.09 (s, 3H); HRMS (ESI, m/z): calc. 792.3033 (M+H)$^+$, found 792.3013.

Compound 40 (IGN-07):

Following the procedure to prepare compound 34, compound 40 (IGN-07) was synthesized in 21% yield as a white solid after preparative reverse phase HPLC. $^1$H NMR (400 Hz, CDCl$_3$): δ 8.27 (d, J=8.0 Hz, 2H), 7.84 (d, J=4.4 Hz, 2H), 7.58 (s, 2H), 7.30-7.23 (m, 4H), 7.21-7.02 (m, 3H), 6.88 (s, 2H), 6.74 (s, 2H), 5.23-5.13 (m, 4H), 4.50-4.42 (m, 2H), 3.99 (s, 6H), 3.74-3.70 (m, 2H), 3.67 (s, 3H), 3.51-3.33 (m, 4H), 2.92 (s, 3H), 2.36-2.30 (m, 2H), 1.93-1.84 (m, 2H); HRMS (ESI, m/z): calc. 820.3346 (M+H), found 820.3329.

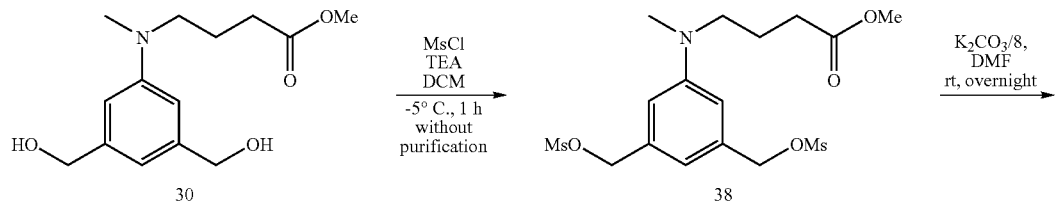

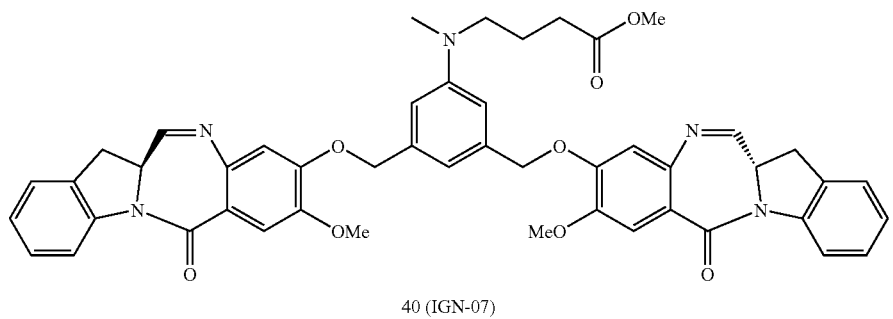

40 (IGN-07)

Example 7

Compound 41:

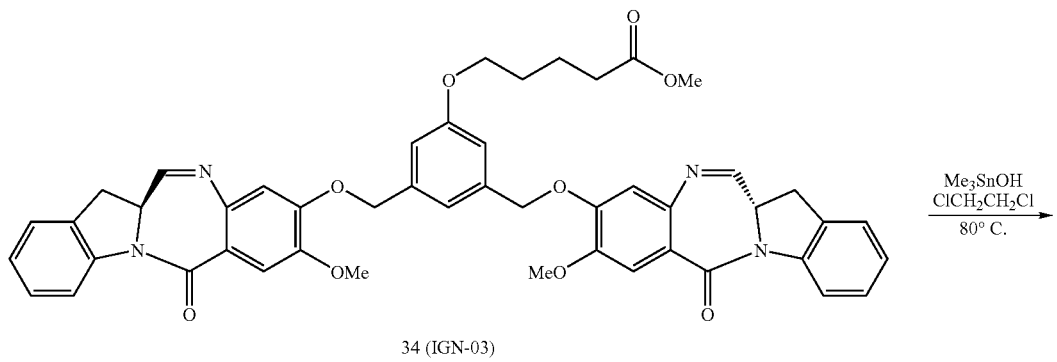

34 (IGN-03)

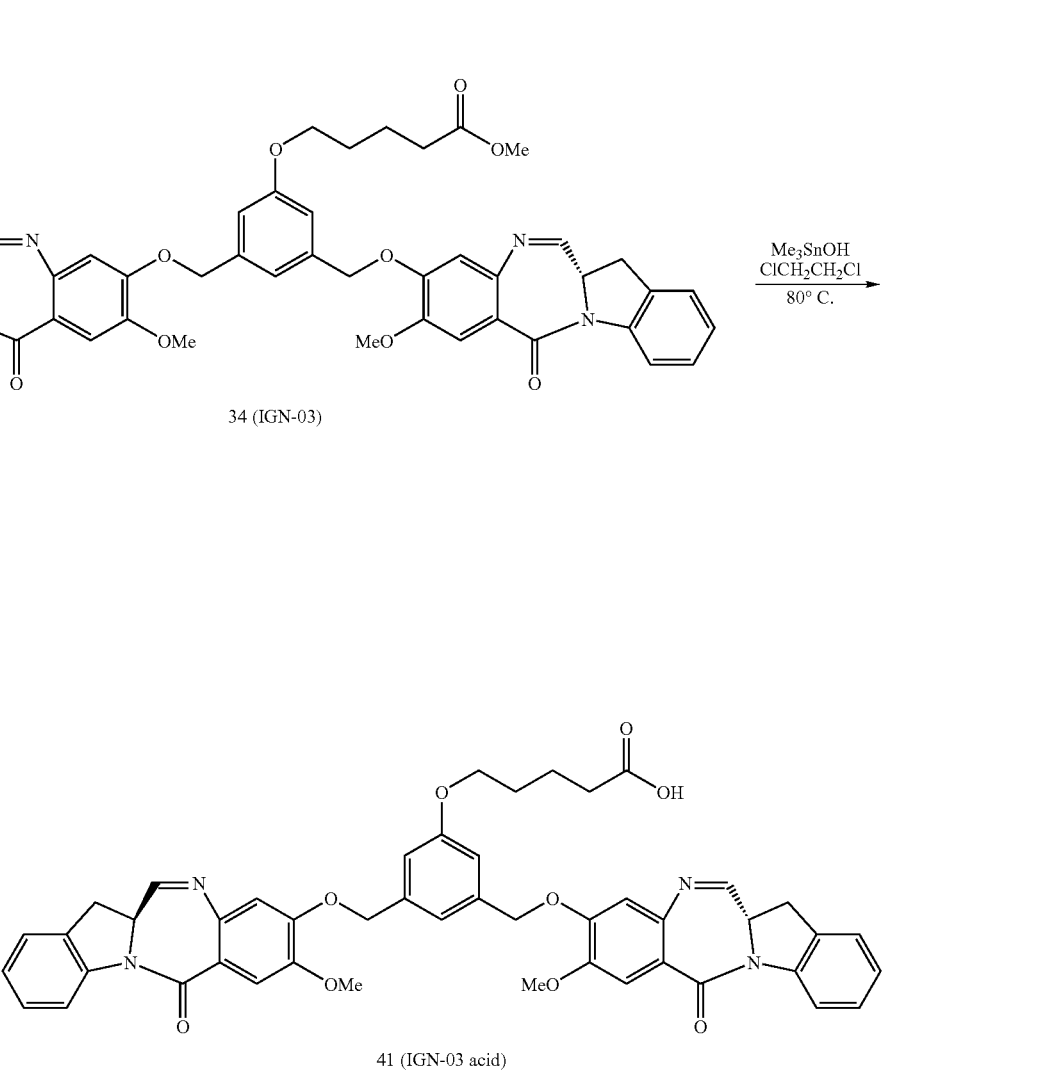

41 (IGN-03 acid)

To a solution of compound 34 (42 mg, 0.051 mmol) in anhydrous 1,2-dichloroethane (1 mL) was added trimethyltin hydroxide (139 mg, 0.77 mmol). The mixture was heated at 78~82° C. (80° C. oil bath) and stirred overnight. The TLC (CH$_2$Cl$_2$/MeOH, 10:1) showed the disappearance of the starting material. The reaction mixture was cooled to room temperature and diluted with dichloromethane. It was washed with drops of 5% hydrochloric acid in brine, saturated ammonium chloride and brine, dried over anhydrous sodium sulfate, filtered and evaporated. The residue was purified by silica gel chromatography (combiflash, CH$_2$Cl$_2$/MeOH, from 1:0 to 5:1) to give IGN-03 acid 41 (33.8 mg, y=82%) as a yellowish solid. The residue can also be used for next step without purification. MS (m/z): found 805.1 (M−H)$^-$, 823.0 (M+H$_2$O−H)$^-$, 829.2 (M+Na)$^+$, 847.2 (M+H$_2$O+Na)$^+$.

Compound 42:

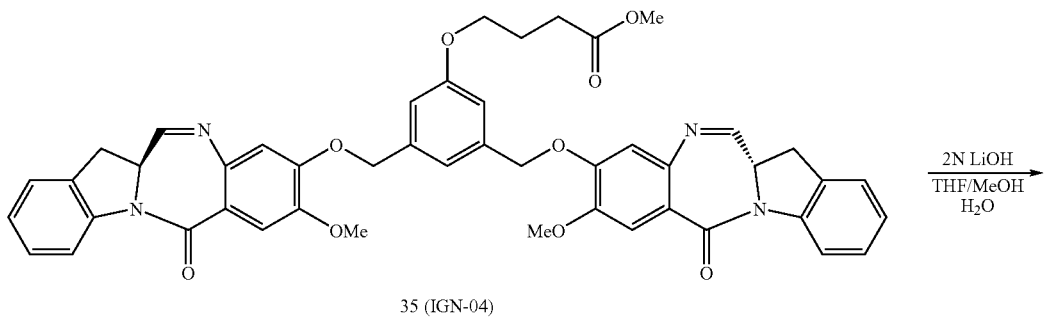

35 (IGN-04)

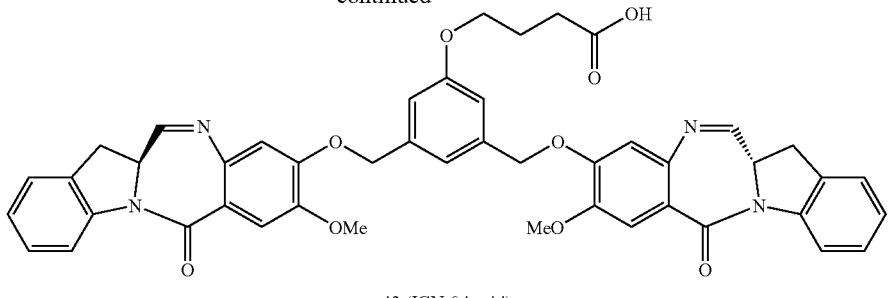

42 (IGN-04 acid)

To a stirred solution of compound 35 (32 mg, 0.040 mmol) in a mixture of THF (0.4 mL), methanol (0.1 mL) and deionized water (0.1 ml) was added freshly prepared 2N LiOH (24 μl, 0.048 mmol) at 0° C. The cooling bath was removed and the mixture was stirred at room temperature for 8 hours. The reaction mixture was diluted with ethyl acetate and water. The pH of the mixture was adjusted to 4~5 with 5% hydrochloric acid. It was washed with brine, dried over anhydrous sodium sulfate and filtered. The filtrate was evaporated under reduced pressure and the residue was purified by preparative reverse phase HPLC (C18 column, acetonitrile/$H_2O$) to give the IGN-04 acid 42 (4.2 mg, y=13%) as a white solid. MS (m/z): found 791.0 (M−H)$^-$, 809.0 (M+$H_2O$−H)$^-$, 815.2 (M+Na)$^+$, 833.1 (M+$H_2O$+Na)$^+$.

Compound 43:

dine. The mixture was stirred at room temperature overnight and diluted with dichloromethane. It was washed with saturated ammonium chloride and brine, dried over anhydrous sodium sulfate and filtered. The filtrate was evaporated under reduced pressure. The residue was purified through silica gel chromatography (Combiflash, $CH_2Cl_2$/MeOH, from 1:0 to 10:1) to give IGN-03 NHS eater 43 (7.9 mg, y=79%) as a yellowish solid. Reverse phase preparative HPLC (C18 column, $CH_3CN$/$H_2O$, extracted the product fractions with dichloromethane) purification gave 3.2 mg white solid for $^1$H NMR analysis. $^1$H NMR (400 Hz, $CDCl_3$): δ 8.28 (d, J=8.0 Hz, 2H), 7.87 (d, J=4.0 Hz, 2H), 7.59 (s, 2H), 7.31-7.27 (m, 4H), 7.15-7.10 (m, 3H), 6.97 (s, 2H), 6.86 (s, 2H), 5.25 (d, J=12.4 Hz, 2H), 5.18 (d, J=12.4 Hz, 2H), 4.49 (dt, $J_1$=10.8 Hz,

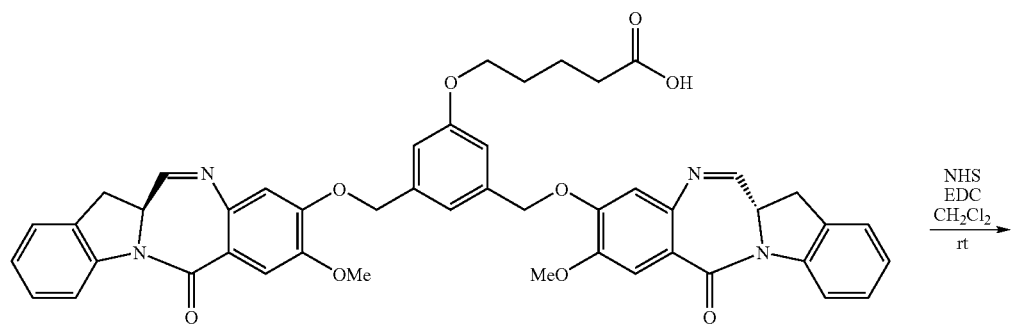

41 (IGN-03 acid)

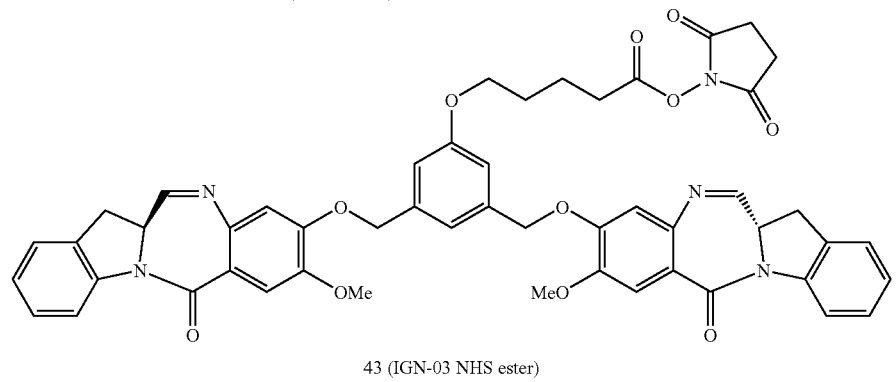

43 (IGN-03 NHS ester)

To a stirred solution of IGN-03 acid 41 (8.9 mg, 0.011 mmol) in anhydrous dichloromethane (0.2 mL) was added N-hydroxysuccinimide (2.6 mg, 0.022 mmol), N-(3-dimethylaminopropyl)-N'-ethylcarbodiimide hydrochloride (4.2 mg, 0.022 mmol) and a tiny particle of dimethylaminopyri- $J_2$=4.0 Hz, 2H), 4.04 (t, J=5.6 Hz, 2H), 4.01 (s, 6H), 3.72 (dd, $J_1$=16.8 Hz, $J_2$=10.8 Hz, 2H), 3.51 (dd, $J_1$=16.8 Hz, $J_2$=4.0 Hz, 2H), 2.85 (bs, 4H), 2.72 (t, J=6.8 Hz, 2H), 1.99-1.91 (m, 4H); HRMS (ESI, m/z): calc. 904.3194 (M+H)$^+$, found 904.3182.

2Compound 44:

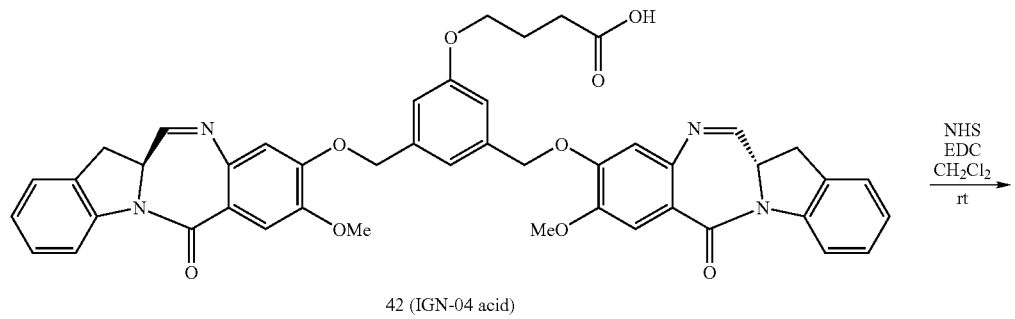
42 (IGN-04 acid)

NHS
EDC
CH₂Cl₂
rt

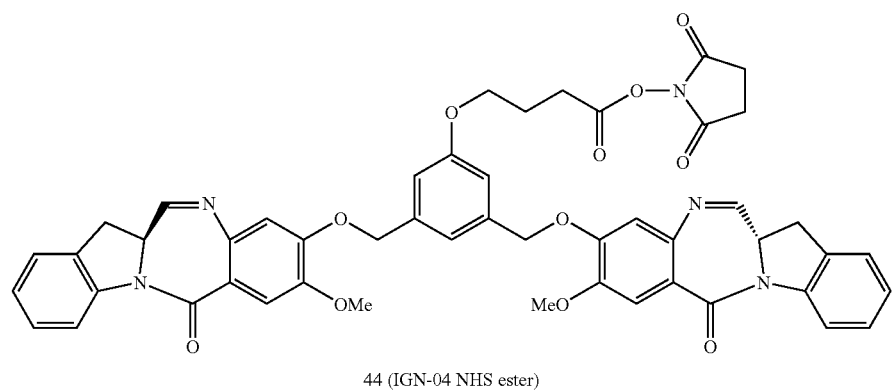
44 (IGN-04 NHS ester)

Following the procedure to prepare compound 43, compound 44 was synthesized in 86% yield as a yellowish solid. MS (m/z): found 944.2 (M+MeOH+Na)⁺, 976.2 (M+2MeOH+Na)⁺.

Compound 45 (IGN-07 Acid):

To a solution of compound 40 (14 mg, 0.017 mmol) in anhydrous 1,2-dichloroethane (0.5 mL) was added trimethyltin hydroxide (62 mg, 0.34 mmol). The mixture was heated at 78~82° C. (80° C. oil bath) and stirred overnight. The TLC (CH₂Cl₂/MeOH, 10:1) showed the disappearance of the start-

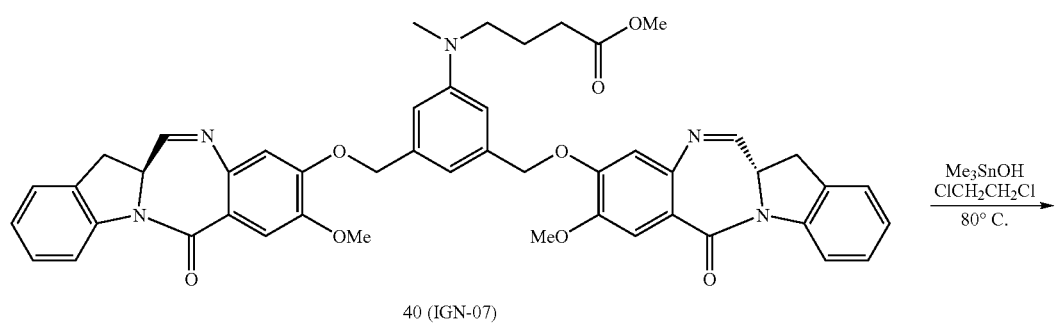
40 (IGN-07)

Me₃SnOH
ClCH₂CH₂Cl
80° C.

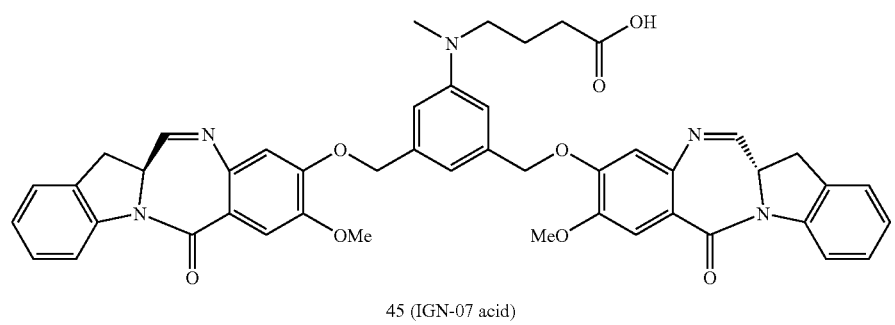
45 (IGN-07 acid)

ing material. The reaction mixture was cooled to room temperature and diluted with dichloromethane. It was washed with saturated ammonium chloride and brine, dried over anhydrous sodium sulfate, filtered and evaporated to give IGN-07 acid 45 as a pale yellowish solid (29.2 mg, contaminated with trimethyltin hydroxide). MS (m/z): found 804.1 (M−H)⁻, 822.1 (M+H$_2$O−H)⁻, 828.2 (M+Na)⁺, 846.2 (M+H$_2$O+Na)⁺. It was used for next step without purification. Compound 46:

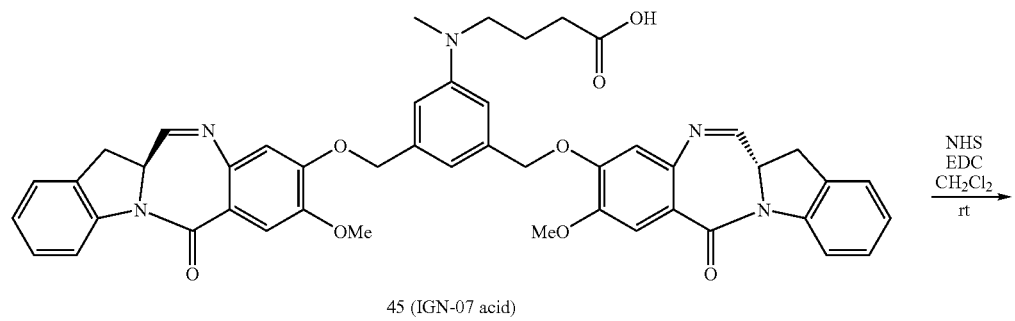

45 (IGN-07 acid)

MeOH, from 1:0 to 10:1) to give IGN-07 NHS eater 46 (9.1 mg, y=59% for two steps from IGN-07) as a yellowish solid. ¹H NMR (400 Hz, CDCl$_3$): δ 8.25 (d, J=7.6 Hz, 2H), 7.82 (d, J=4.4 Hz, 2H), 7.55 (s, 2H), 7.26-7.18 (m, 5H), 7.09 (t, J=7.6 Hz, 2H), 6.84 (s, 2H), 6.74 (s, 2H), 5.21 (d, J=12.4 Hz, 2 H), 5.15 (d, J=12.4 Hz, 2H), 4.46-4.42 (m, 2H), 3.98 (s, 6H), 3.72-3.64 (m, 2H), 3.44-3.37 (m, 4H), 2.95 (s, 3H), 2.74 (bs, 4H), 2.57 (t, J=7.2 Hz, 2H), 1.95 (t, J=7.2 Hz, 2H); HRMS (ESI, m/z): calc. 903.3354 (M+H)⁺, found 903.3347.

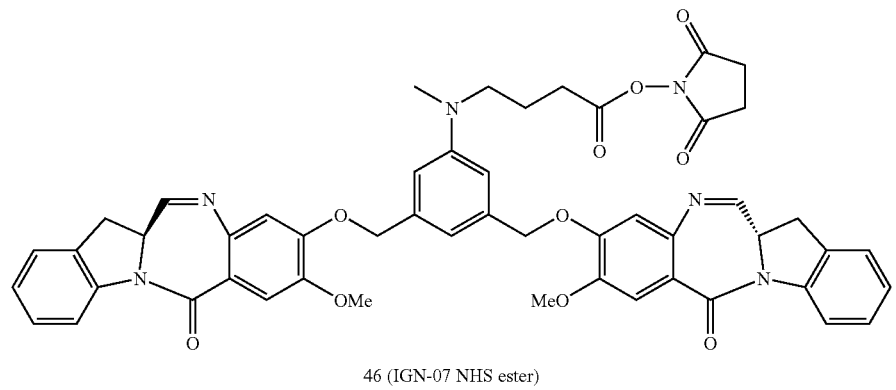

46 (IGN-07 NHS ester)

To a stirred solution of IGN-07 acid 45 from above reaction (0.017 mmol) in anhydrous dichloromethane (0.5 mL) was added N-hydroxysuccinimide (6.1 mg, 0.051 mmol), N-(3-dimethylaminopropyl)-N'-ethylcarbodiimide hydrochloride (9.8 mg, 0.051 mmol) and a tiny particle of dimethylaminopyridine. The mixture was stirred at room temperature overnight and diluted with dichloromethane. It was washed with saturated ammonium chloride and brine, dried over anhydrous sodium sulfate and filtered. The filtrate was evaporated under reduced pressure. The residue was purified through silica gel chromatography (Combiflash, CH$_2$Cl$_2$/

Example 8

Compound 47:

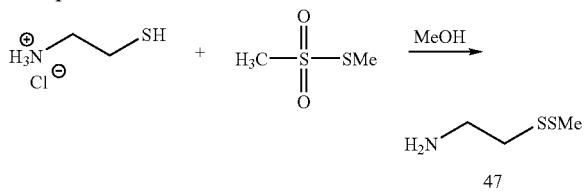

To a stirred solution of cysteamine hydrochloride (568 mg, 5 mmol) in anhydrous methanol (15 mL) was added S-methyl methanethiosulfonate (519 μl, 5.5 mmol) at 0° C. The mixture was stirred at room temperature overnight. Triethylamine (1.4 mL, 10 mmol) was added and the solvents were removed under reduced pressure. The residue was dissolved in 50 mL of anhydrous dichloromethane and gave a 0.1 M solution of compound 47 in dichloromethane (assuming 100% yield). An aliquot of the solution (0.2 mL) was used for next step reaction. The rest of the solution was diluted with dichloromethane, washed with saturated sodium bicarbonate and brine, dried over anhydrous sodium sulfate and filtered. The filtrate was evaporated under reduced pressure and the residue was purified through silica gel chromatography (dichloromethane/methanol, 10:1 with 1% triethylamine) to give compound 47 (82 mg, y=13%, product lost in the aqueous work up due to its good water solubility) as a colorless oil. $^1$H NMR (400 Hz, CDCl$_3$): δ 3.02 (t, J=6.4 Hz, 2H), 2.77 (t, J=6.4 Hz, 2H), 2.41 (s, 3H), 1.34 (bs, 2H).

Compound 48 (IGN-08):

pyl)-N'-ethylcarbodiimide hydrochloride (3.8 mg, 0.02 mmol), triethylamine (1.4 μl, 0.01 mmol) and a tiny particle of dimethylaminopyridine were added. The mixture was stirred at room temperature overnight and diluted with dichloromethane. It was washed with saturated ammonium chloride and brine, dried over anhydrous sodium sulfate and filtered. The filtrate was evaporated under reduced pressure and the residue was purified through preparative reverse phase HPLC (C18 column, acetonitrile/H$_2$O) to give compound 48 (4.0 mg, y=44%) as a white solid. $^1$H NMR (400 Hz, CDCl$_3$): δ 8.25 (d, J=8.0 Hz, 2H), 7.84 (d, J=4.4 Hz, 2H), 7.57 (s, 2H), 7.29-7.24 (m, 4H), 7.10 (t, J=7.6 Hz, 2H), 7.06 (s, 1H), 6.92 (s, 2H), 6.82 (s, 2H), 5.22 (d, J=12.8 Hz, 2H), 5.17 (d, J=12.4 Hz, 2H), 4.46 (dt, J$_1$=11.2 Hz, J$_2$=4.4 Hz, 2H), 3.98 (bs, 8H), 3.69 (dd, J$_1$=16.8 Hz, J$_2$=10.8 Hz, 2H), 3.62 (d, J=6.4 Hz, 1H), 3.58 (d, J=6.0 Hz, 1H), 3.48 (dd, J$_1$=17.2 Hz, J$_2$=3.6 Hz, To a flask containing IGN-03 acid 41 (8.1 mg, 0.01 mmol) was added above 0.1 M solution of compound 47 in anhydrous dichloromethane (0.2 mL). N-(3-dimethylaminopro- 2H), 2.82 (t, J=6.4 Hz, 2H), 2.39 (s, 3H), 2.23 (t, J=6.8 Hz, 2H), 1.80-1.78 (m, 4H); HRMS (ESI, m/z): calc. 912.3101 (M+H)$^+$, found 912.3118.

Compound 49:

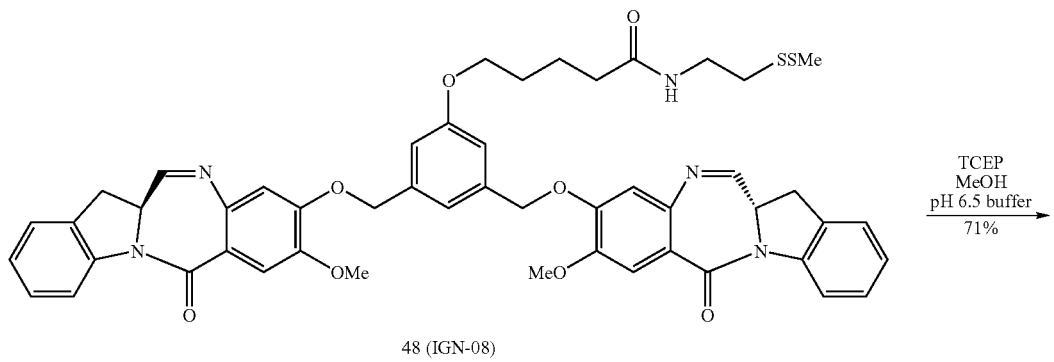

48 (IGN-08)

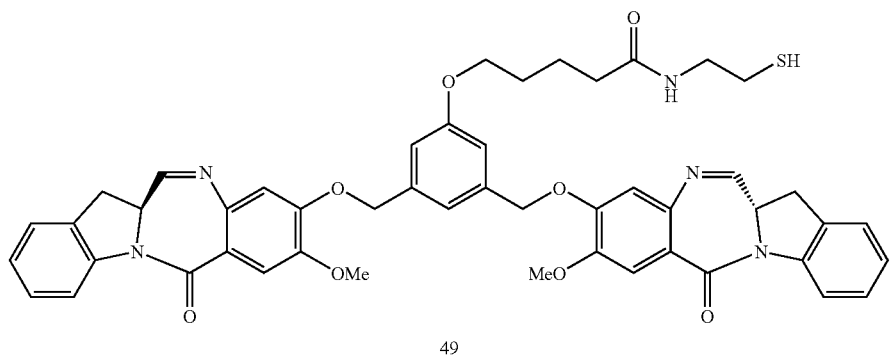

49

To a suspension of tris(2-carboxyethyl) phosphine hydrochloride (TCEP.HCl, 3.8 mg, 0.013 mmol) in a drop of deionized water (~50 μL) was added saturated sodium bicarbonate dropwise (~25 μL) to adjust the pH to about 6~7, followed by addition of pH 6.5 buffer solution (0.1 M phosphate buffer, 0.3 mL). The obtained mixture was added to the solution of compound 48 (IGN-08, 4.0 mg, 0.0044 mmol) in methanol (1.0 mL) and acetonitrile (1.0 mL). The solution was stirred at room temperature for 1.5 hours and diluted with pH 6.5 buffer and dichloromethane (the reaction was checked by mass spectra, which showed only the product signals). It was separated and the organic layer was washed with brine, dried over anhydrous sodium sulfate and filtered. The filtrate was evaporated under reduced pressure and the residue was purified by silica gel chromatography (Combiflash, dichloromethane/MeOH) to give product 49 as a pale yellow solid (2.7 mg, y=71%). MS (m/z): found 864.0 (M−H)⁻, 932.0 (M+MeOH+2H$_2$O−H)⁻, 888.1 (M+Na)⁺, 920.2 (M+MeOH+Na)⁺, 952.2 (M+2MeOH+Na)⁺.

Example 9

Compound 50:

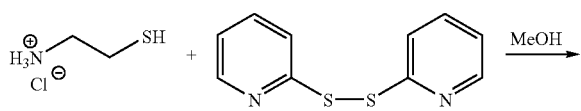

-continued

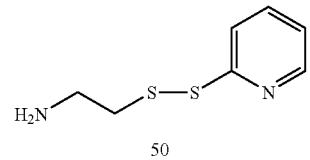

50

To a stirred solution of cysteamine hydrochloride (227 mg, 2 mmol) in anhydrous methanol (10 mL) was added aldrithiol (661 mg, 3 mmol). Reaction solution became clear yellow from clear colorless after the addition of aldrithiol. The mixture was stirred at room temperature for 21 hours. Triethylamine (279 μl, 2 mmol) was added and the solvents were removed under reduced pressure. The residue was purified through silica gel chromatography (Combiflash, dichloromethane/methanol, 1:0 to 15:1 with 0.1% triethylamine) to give compound 50 (301 mg, y=81%) as a colorless oil. ¹H NMR (400 Hz, CDCl$_3$): δ 8.52-8.49 (m, 1H), 7.69-7.60 (m, 2H), 7.15-7.10 (m, 1H), 3.04 (t, J=6.0 Hz, 2H), 2.92 (t, J=6.0 Hz), 1.92 (bs, 2H).

Compound 51 (IGN-10):

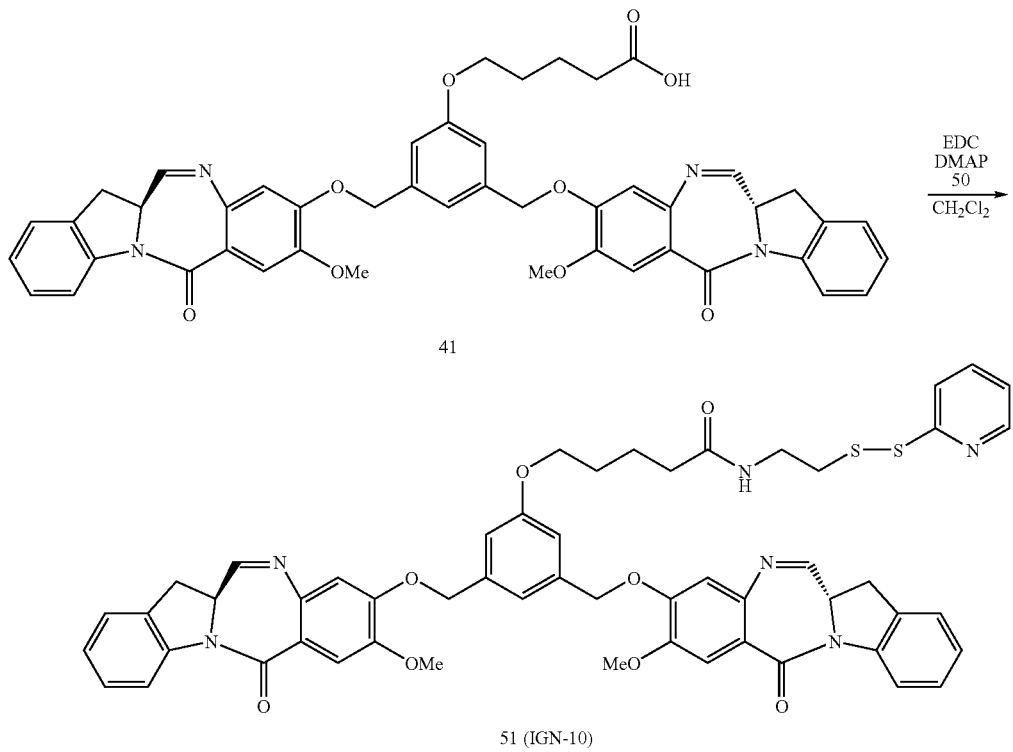

To a solution of IGN-03 acid 41 (from 0.05 mmol of IGN-03 without purification) in anhydrous dichloromethane (1 mL) was added compound 50 (37 mg, 0.2 mmol), N-(3-dimethylaminopropyl)-N'-ethylcarbodiimide hydrochloride (38 mg, 0.2 mmol) and a tiny particle of dimethylaminopyridine. The mixture was stirred at room temperature overnight and diluted with dichloromethane. It was washed with saturated ammonium chloride and brine, dried over anhydrous sodium sulfate and filtered. The filtrate was evaporated under reduced pressure. The residue was purified through silica gel chromatography (Combiflash, dichloromethane/methanol, 1:0 to 5:1) to give 51 mg of yellow foam, which was further purified through preparative reverse phase HPLC (C18 column, acetonitrile/H$_2$O) to give compound 51 (7.4 mg, y=15%) as a yellowish solid. $^1$H NMR (400 Hz, CDCl$_3$): δ 8.50 (d, J=4.4 Hz, 1H), 8.28 (d, J=8.0 Hz, 2H), 7.87 (d, J=4.4 Hz, 2H), 7.63-7.59 (m, 3H), 7.52 (d, J=8.0 Hz, 1H), 7.31-7.21 (m, 4H), 7.14-7.09 (m, 4H), 6.96 (s, 2H), 6.85 (s, 2H), 5.23 (d, J=12.8 Hz, 2H), 5.18 (d, J=12.4 Hz, 2H), 4.49 (dt, J$_1$=11.2 Hz, J$_2$=4.4 Hz, 2H), 4.03-4.00 (m, 8H), 3.72 (dd, J$_1$=16.8 Hz, J$_2$=11.2 Hz, 2H), 3.60 (d, J=5.6 Hz, 1H), 3.57 (d, J=5.6 Hz, 1H), 3.50 (dd, J$_1$=16.8 Hz, J$_2$=3.6 Hz, 2H), 2.95 (t, J=5.6 Hz, 2H), 2.30 (t, J=6.4 Hz, 2H), 1.85-1.84 (m, 4H); HRMS (ESI, m/z): calc. 975.3210 (M+H)$^+$, found 975.3190.

Compound 53:

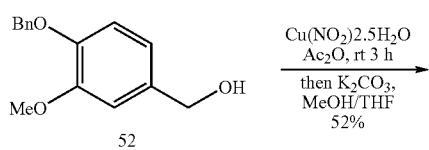

-continued

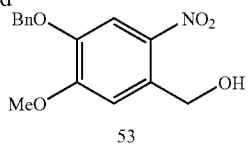

To a stirred solution of 4-benzyloxy-3-methoxybenzyl alcohol 52 (2.5 g, 10 mmol) in acetic anhydride (30 mL) was added copper(II) nitrate hydrate (2.7 g, 11 mmol) slowly in portion at 0° C. The obtained suspension continued to be stirred at 0° C. for 1 hour and at room temperature for 3 hours. The reaction mixture was poured on ice/water and stirred for 1 hour. It was filtered to collect the yellow solid, which was subsequently dissolved in MeOH/THF(1:1, V/V, 30 mL). Potassium carbonate (2.1 g, 15 mmol) was added and the obtained mixture was stirred at room temperature for 3 hours. It was concentrated under reduced pressure and the residue was diluted with dichloromethane, washed with water and brine, dried over anhydrous sodium sulfate and filtered. The filtrate was evaporated under reduced pressure and the residue was purified through silica gel chromatography (CH$_2$Cl$_2$/MeOH, 20:1, 18:1, 15:1) to give compound 53 (1.50 g, y=52%) as yellow solid. $^1$H NMR (400 Hz, CDCl$_3$): δ 7.78 (s, 1H), 7.48-7.33 (m, 5H), 7.20 (s, 1H), 5.18 (s, 2H), 4.96 (s, 2H), 4.01 (s, 3H).

Example 10

Compound 123:

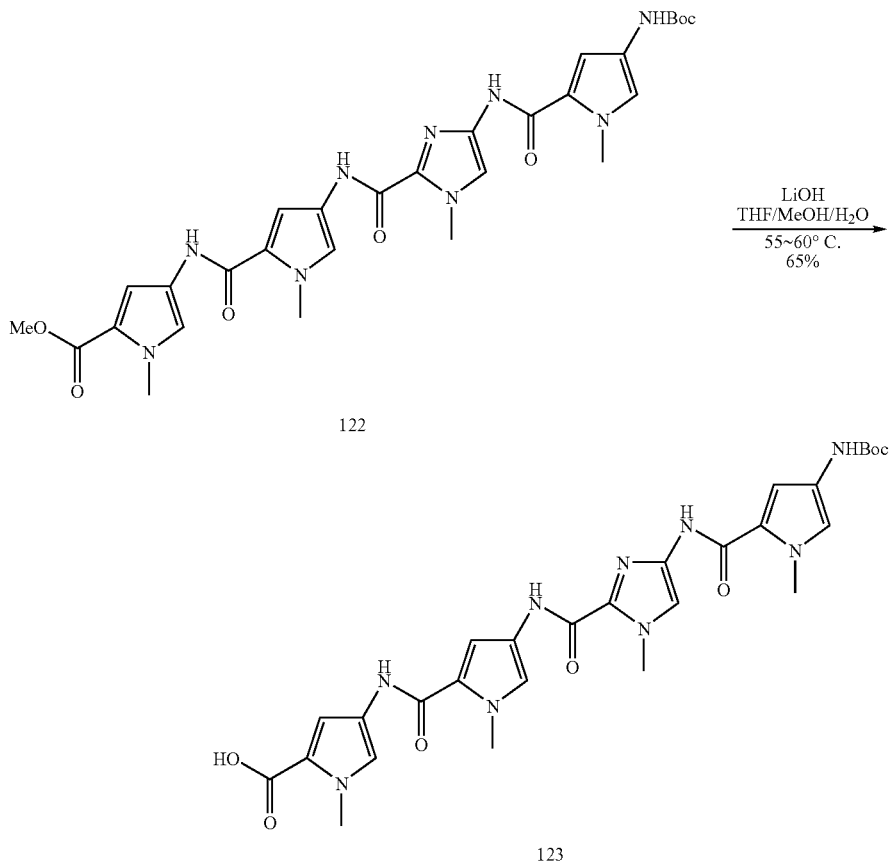

To a stirred solution of compound 122 (137 mg, 0.22 mmol) in THF (1.5 mL) and MeOH (0.5 mL) was added a solution of lithium hydroxide monohydrate (46 mg, 1.1 mmol) in deioned water (0.5 mL). The mixture was stirred in a 60° C. oil bath for 6 hours. It was cooled to room temperature and diluted with ethyl acetate and water. The pH was adjusted to 4~5 with 5% hydrochloric acid. The aqueous layer was extracted with ethyl acetate. The combined organic layers were washed with saturated sodium bicarbonate and brine, dried over anhydrous sodium sulfate and filtered. The filtrate was striped to give compound 123 (87.5 mg, y=65%). MS (m/z): found 606.1 $(M-H)^-$.

Compound 124:

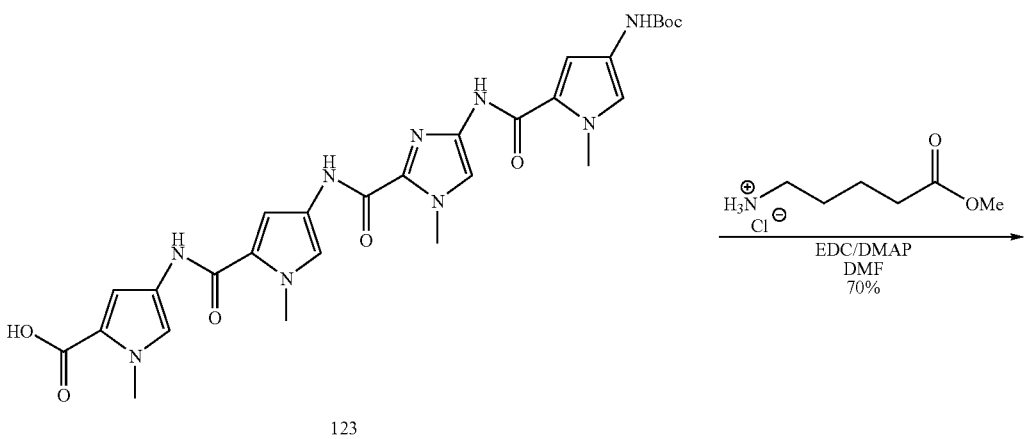

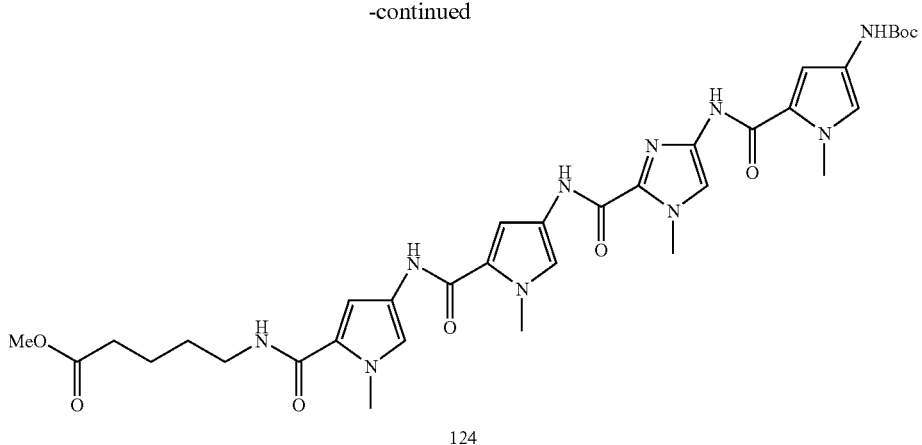

124

To a solution of acid 123 (87.5 mg, 0.14 mmol) in anhydrous DMF (1 mL) was added DMAP (21 mg, 0.17 mmol), methyl 5-aminovalerate hydrochloride (26 mg, 0.15 mmol) and EDC (40 mg, 0.21 mmol). The mixture was stirred at room temperature overnight and diluted with ethyl acetate. It was washed with saturated ammonium chloride, brine, saturated sodium bicarbonate and brine, dried over anhydrous sodium sulfate and filtered. The filtrate was striped and the residue was purified through silica gel chromatography (Combiflash, dhchloromethane/MeOH) to give compound 124 (71 mg, y=70%) as a yellow foam. $^1$H NMR (400 Hz, CDCl$_3$): δ 9.07 (s, 1H), 8.62 (s, 1H), 8.40 (s, 1H), 7.19 (s, 1H), 7.17 (s, 1H), 7.09 (s, 1H), 7.00 (s, 1H), 6.74 (s, 1H), 6.62 (s, 3H), 6.46 (s, 1H), 3.94 (s, 3H), 3.85 (bs, 12H), 3.34-3.31 (m, 2H), 2.32 (t, J=7.2 Hz, 2H), 1.68-1.55 (m, 4H), 1.48 (s, 9H); MS (ESI, m/z): found 721.0 (M+H)$^+$.

Compound 125:

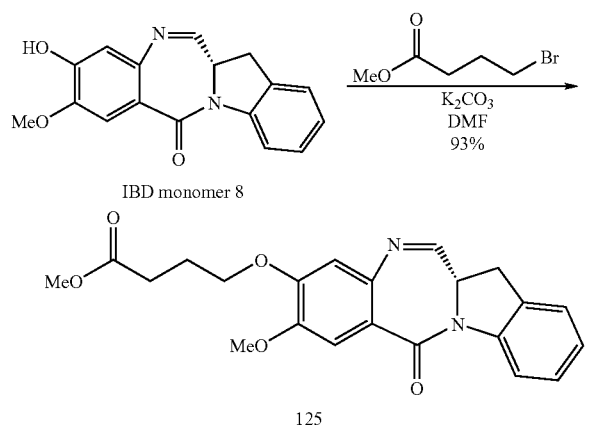

125

To a solution of IBD monomer 8 (118 mg, 0.4 mmol) and methyl 4-bromobutyrate (109 mg, 0.6 mmol) in anhydrous DMF (1.5 mL) was added potassium carbonate (111 mg, 0.8 mmol). The mixture was stirred at room temperature overnight and diluted with ethyl acetate, washed with saturated ammonium chloride and brine. It was dried over anhydrous sodium sulfate and filtered. The filtrate was striped under reduced pressure to give compound 125 (146 mg, y=93%) as a yellow foam. $^1$H NMR (400 Hz, CDCl$_3$): δ 8.25 (d, J=8.0 Hz, 1H), 7.84 (d, J=4.4 Hz, 1H), 7.52 (s, 1H), 7.26-7.22 (m, 2H), 7.10-7.06 (m, 1H), 6.81 (s, 1H), 4.44 (dt, J$_1$=10.8 Hz, J$_2$=4.0 Hz, 1H), 4.15-4.07 (m, 2H), 3.92 (s, 3H), 3.68 (s, 3H), 3.67-3.64 (m, 1H), 3.46-3.43 (m, 1H), 2.55 (t, J=7.2 Hz, 2H), 2.22-2.15 (m, 2H); MS (ESI, m/z): found 465.2 (M+MeOH+K)$^+$.

Compound 126:

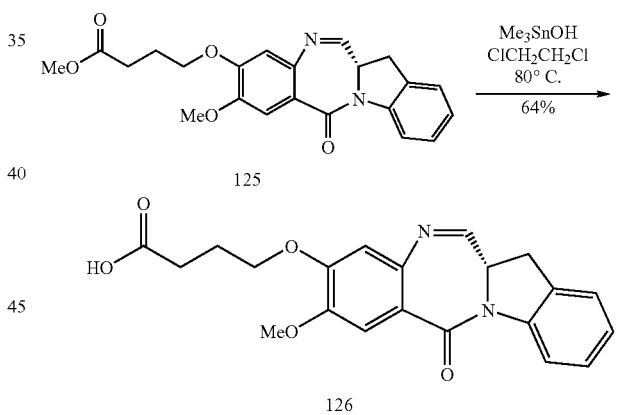

The mixture of compound 125 (146 mg, 0.37 mmol) and trimethyltin hydroxide (669 mg, 3.7 mmol) in anhydrous 1,2-dichloroethane (2 mL) was heated to 80° C. (oil bath temperature) and stirred at that temperature for 18 hours. The oil bath was removed and the mixture was diluted with dichloromethane, washed with brine/5% HCl (0.5 mL), saturated sodium bicarbonate and brine, dried over anhydrous sodium sulfate and filtered. The filtrate was striped and the residue was purified through silica gel chromatography (Combiflash, dichloromethane/MeOH) to give compound 126 (90 mg, y=64%) as a yellow solid. $^1$H NMR (400 Hz, CDCl$_3$): δ 8.26 (d, J=8.0 Hz, 1H), 7.83 (bs, 1H), 7.54 (s, 1H), 7.30-7.25 (m, 2H), 7.11 (t, J=7.6 Hz, 1H), 6.88 (s, 1H), 4.48 (dt, J$_1$=11.2 Hz, J$_2$=4.0 Hz, 1H), 4.16-4.13 (m, 2H), 3.94 (s, 3H), 3.71 (dd, J$_1$=16 Hz, J$_2$=11.2 Hz, 1H), 3.47 (d, J=16 Hz, 1H), 2.60 (t, J=6.4 Hz, 2H), 2.22-2.18 (m, 2H).

Compound 127 (IGN-11):

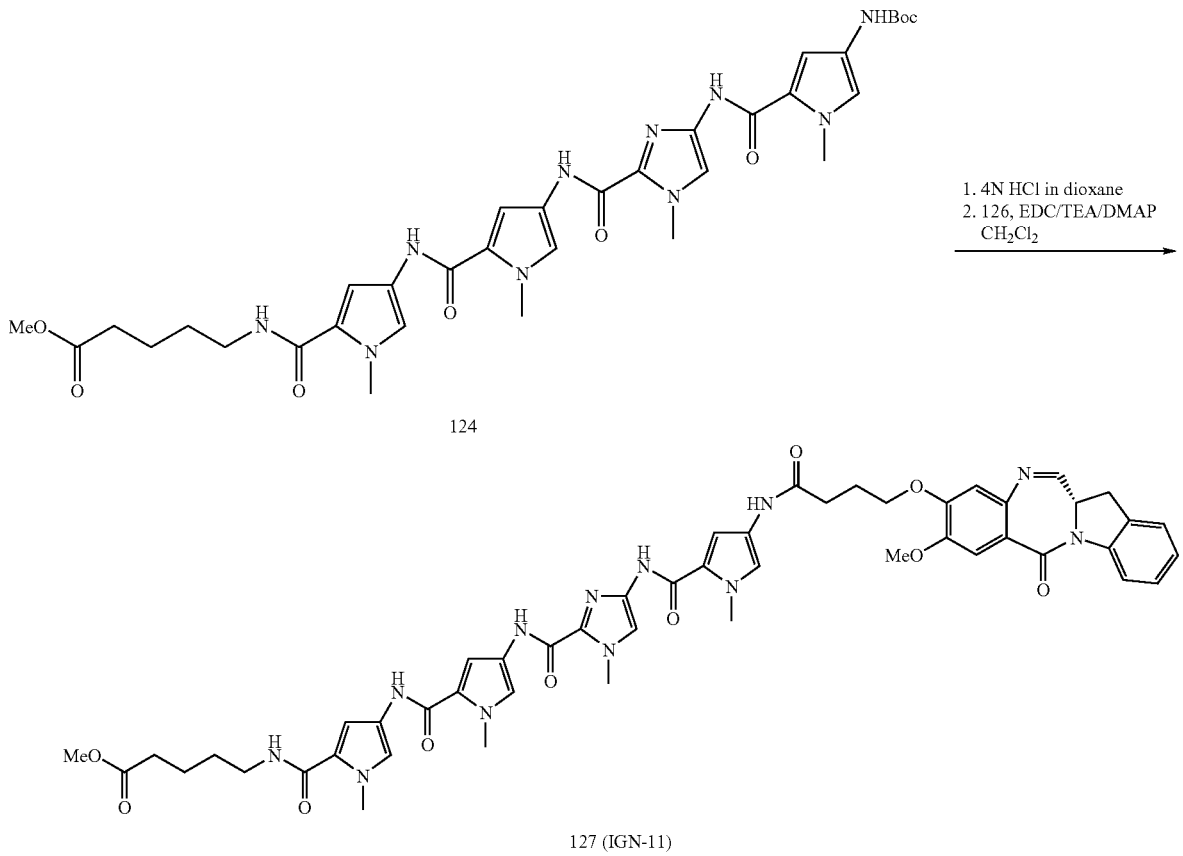

To a flask containing compound 124 (71 mg, 0.099 mmol) was added 4N HCl in dioxane (4 mL). The mixture was stirred at room temperature for 2 hours and striped under reduced pressure. The residue was dissolved in anhydrous dichloromethane (1.5 mL). Compound 126 (42 mg, 0.11 mmol), triethylamine (14 µl, 0.1 mmol), EDC (38 mg, 0.2 mmol) and DMAP (1 mg, 0.0099 mmol) were added subsequently. The reaction mixture was stirred at room temperature for 22 hours and diluted with dichloromethane, washed with saturated ammonium chloride and brine. It was dried over anhydrous sodium sulfate and filtered. The filtrate was striped under reduced pressure and the residue was purified through silica gel chromatography (Combiflash, dichloromethane/MeOH) to furnish compound 127 (14 mg, y=49%) as a yellow solid. HRMS (ESI, m/z): calc. 983.4164 (M+H)$^+$, found 983.4167.

Example 11

Preparation of IGN-03 NHS Ester (Compound 43) and IGN-07 NHS Ester (Compound 46) Stock Solution:

Solutions of IGN-03 NHS ester and IGN-07 NHS ester are made fresh to a 0.006 M stock based on a molecular weight of 903.93 g/mole (IGN-03 NHS ester) or 902.95 (IGN-07 NHS ester) in dimethylacetamide (DMA). The stock solution is assayed spectrophotometrically using a reference extinction coefficient determined at 330 nm ($\epsilon_{330\ nm}$=15,231 M$^{-1}$cm$^{-1}$).

Example 12

4-(tert-Butoxycarbonylamino)-1-methyl-1H-pyrrole-2-carboxylic acid

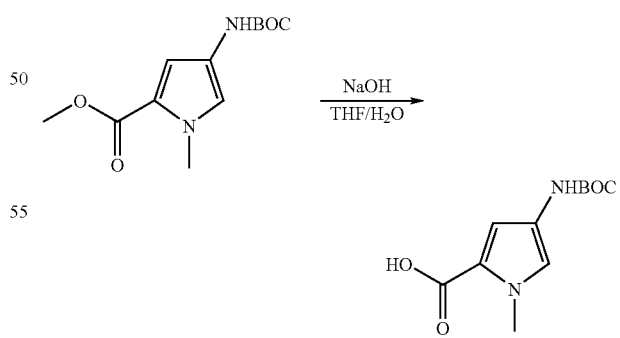

Methyl 4-(tert-butoxycarbonylamino)-1-methyl-1H-pyrrole-2-carboxylate (Eldon E. Baird and Peter B. Dervan, J. Am. Chem. Soc. 1996, 118, 6141-6146) (5.0 g, 19.67 mmol) in 120 ml of 1:1 THF/H$_2$O was added 8 g of NaOH in 30 ml of water. The mixture was stirred overnight, concentrated, diluted with water, extracted with EtAc/Hexane (1:1). The aqueous solution was adjusted to pH 4.0 with 20% $H_3PO_4$ and extracted with EtAc (4×60 ml). The organic solutions were combined, dried over $MgSO_4$, filtered, evaporated and crystallized with ethanol/EtAc/Hexane to afford 3.81 g (81%) of the title product. $^1$H NMR ($CD_3OD$) 12.79 (s, 1H), 10.48 (br, 1H), 7.51 (s, 1H), 6.99 (s, 1H), 3.78 (s, 3H), 1.49 (s, 9H); $^{13}$C NMR 158.47, 153.82, 123.64, 121.56, 109.58, 79.52, 37.06, 28.42; MS m/z– 239.2 (M–H).

4-(tert-butoxycarbonylamino)-1-methyl-1H-imidazole-2-carboxylic acid

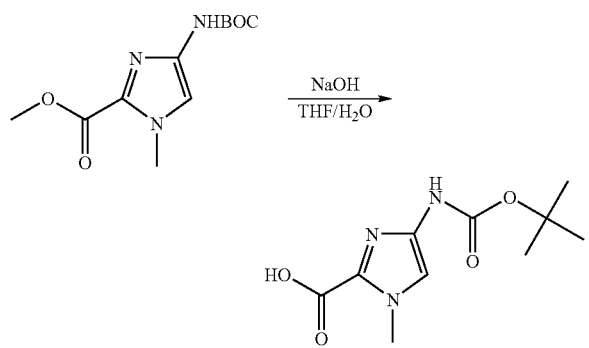

Methyl 4-(tert-butoxycarbonylamino)-1-methyl-1H-imidazole-2-carboxylate (5.0 g, 19.59 mmol) in 120 ml of 1:1 THF/$H_2O$ was added 8 g of NaOH in 30 ml of water. The mixture was stirred overnight, concentrated, diluted with water, extracted with EtAc/Hexane (1:1). The aqueous solution was adjusted to pH 4.0 with 20% $H_3PO_4$ and extracted with EtAc (4×60 ml). The organic solutions were combined, dried over $MgSO_4$, filtered, evaporated and crystallized with ethanol/EtAc/Hexane to afford 3.85 g (81%) of the title product. $^1$H NMR (DMSO) 9.32 (s, 1H), 7.29 (s, 1H), 3.57 (s, 3H), 1.42 (s, 9H); $^{13}$C NMR 172.45, 159.78, 136.93, 135.44, 132.85, 79.50, 35.57, 28.07; MS m/z– 240.8 (M–H).

1-Methyl-4-nitro-1H-pyrrole-2-carboxylic acid

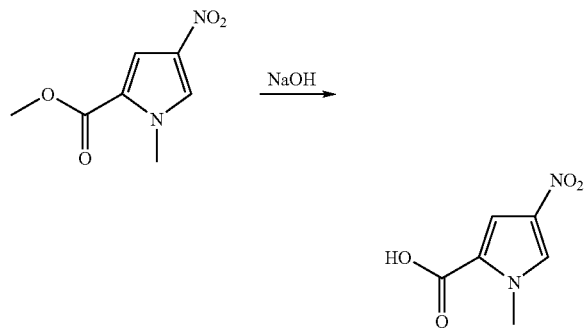

Methyl 1-methyl-4-nitro-1H-pyrrole-2-carboxylate (5.0 g, 27.17 mmol) in 120 ml of 1:1 THF/$H_2O$ was added 8 g of NaOH in 30 ml of water. The mixture was stirred overnight, concentrated, diluted with water, extracted with EtAc/Hexane (1:1). The aqueous solution was adjusted to pH 3~4 with 20% $H_3PO_4$ and extracted with EtAc (4×60 ml). The organic solutions were combined, dried over $MgSO_4$, filtered, evaporated and crystallized with ethanol/EtAc/Hexane to afford 4.06 g (88%) of the title product. $^1$H NMR (DMSO) 13.12 (s, 1H), 8.21 (s, 1H), 7.25 (s, 1H), 3.91 (s, 3H); $^{13}$C NMR 160.97, 134.01, 129.16, 123.81, 111.38, 37.47; MS m/z– 169.1 (M–H).

Methyl 1-methyl-4-(1-methyl-4-nitro-1H-pyrrole-2-carboxamido)-1H-pyrrole-2-carboxylate

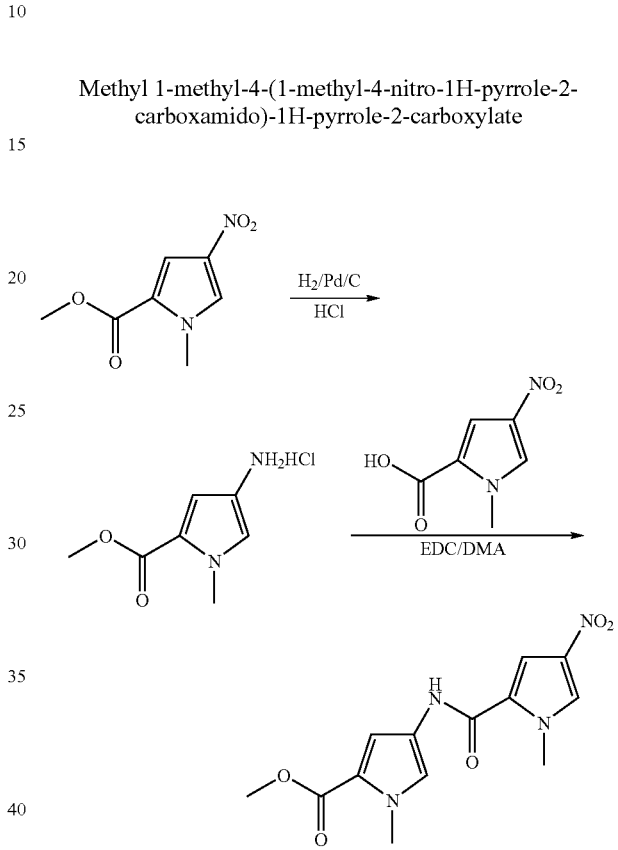

In a hydrogenation bottle was added methyl 1-methyl-4-nitro-1H-pyrrole-2-carboxylate (3.0 g, 16.30 mmol), 80 ml of THF, 405 mg of 10% Pd/C and 1.3 ml of HCl (conc.). After evacuation under vacuum the bottle was placed under 30 psi hydrogen and shaken for 5 hours. The mixture was filtered through celites, evaporated to dryness without further purification. To the dry mixture was added 1-methyl-4-nitro-1H-pyrrole-2-carboxylic acid (2.75 g, 16.18 mmol), 80 ml of DMA, EDC (8.51 g, 44.27 mmol) and DIPEA (2.80 ml, 16.10 mmol). The mixture was stirred under Ar overnight, concentrated, diluted with THF/EtAc (1:2, 150 ml), and washed 1M $NaH_2PO_4$/NaCl (conc) and $NaHCO_3$ (conc) separately. The organic layer was separated and dried over $MgSO_4$, filtered concentrated and crystallized with THF/$H_2O$ to afford 3.74 g (75%) of the title product. $^1$H NMR (DMSO) 10.25 (s, 1H), 8.17 (s, 1H), 7.25 (s, 1H), 6.52 (s, 1H), 6.08 (s, 1H), 3.90 (s, 3H), 3.78 (s, 3H), 3.56 (s, 3H); $^{13}$C NMR 157.87, 156.84, 133.76, 128.16, 123.39, 119.13, 118.18, 111.83, 107.50, 104.17, 51.55, 37.41, 36.03; MS m/z+ 329.1 (M+Na).

139
Methyl 4-(4-(tert-butoxycarbonylamino)-1-methyl-1H-pyrrole-2-carboxamido)-1-methyl-1H-imidazole-2-carboxylate

140
Methyl 4-(4-(tert-butoxycarbonylamino)-1-methyl-1H-imidazole-2-carboxamido)-1-methyl-1H-imidazole-2-carboxylate

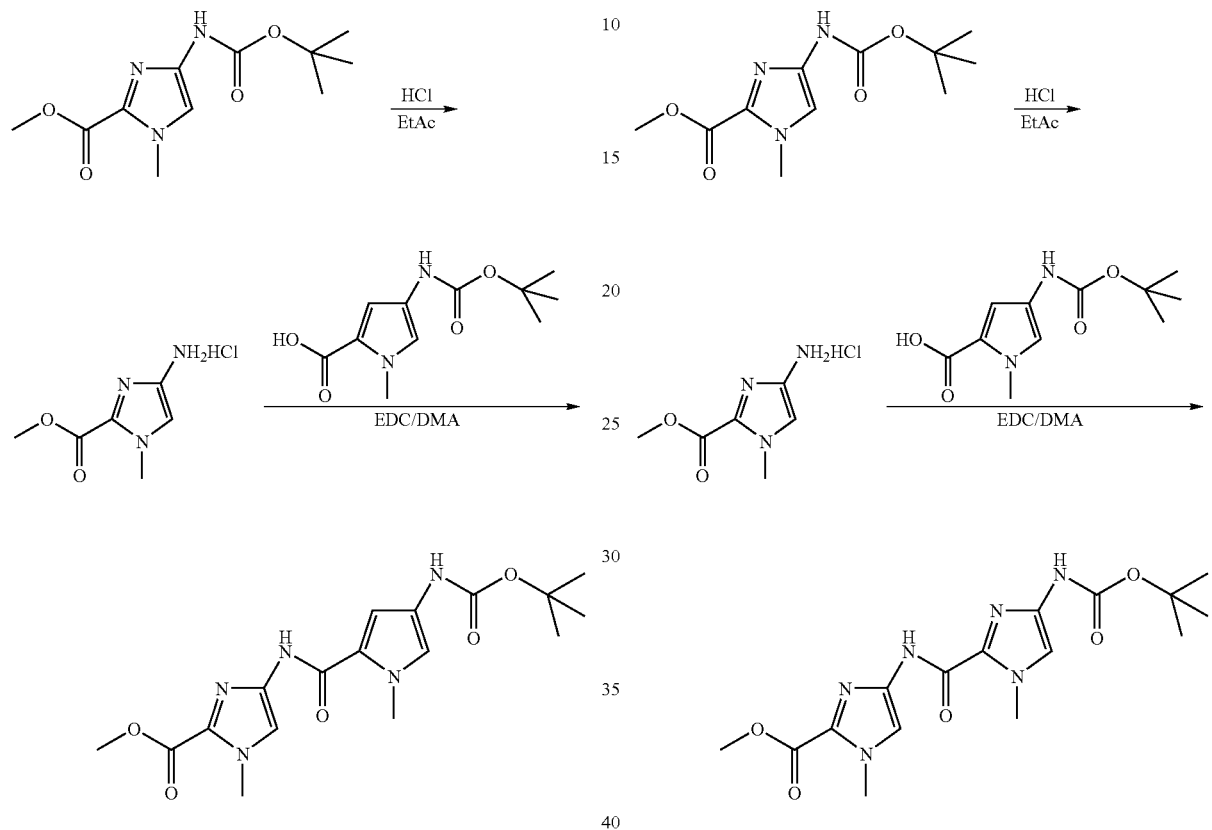

Methyl 4-(tert-butoxycarbonylamino)-1-methyl-1H-imidazole-2-carboxylate (2.50 g, 9.80 mmol) in 30 ml of EtAc was added 6 ml of HCl (conc.). After stirring for 45 min, the mixture was diluted with ethanol and toluene, concentrated and co-evaporated with ethanol/toluene (1:1, 3×50 ml) to dryness without further purification. To the dry compound was added 4-(tert-butoxycarbonylamino)-1-methyl-1H-pyrrole-2-carboxylic acid (2.35 g, 9.8 mmol), EDC (5.60 g, 29.1 mmol), DIPEA (1.70 ml, 9.8 mmol) and 80 ml of DMA. The mixture was stirred under Ar overnight, concentrated, diluted with THF/EtAc (1:2, 150 ml), and washed 1M NaH$_2$PO$_4$/NaCl (conc) and NaHCO$_3$ (conc) separately. The organic solvent layer was separated and dried over MgSO$_4$, filtered, concentrated and purified on SiO2 chromatography eluted with EtAc/DCM (1:25 to 1:15) to afford 2.72 g (73%) of the title product. $^1$H NMR (DMF-d7) 10.27 (s, 1H), 9.08 (s, 1H), 7.41 (s, 1H), 7.32 (s, 1H), 7.07 (s, 1H), 4.10 (s, 3H), 3.93 (s, 3H), 3.84 (s, 3H), 1.47 (s, 9H); $^{13}$C NMR 162.62, 161.20, 153.82, 145.32, 144.12, 132.56, 128.46, 124.39, 119.83, 79.51, 52.75, 36.06, 35.83, 28.88; MS m/z+ 400.2 (M+Na).

Methyl 4-(tert-butoxycarbonylamino)-1-methyl-1H-imidazole-2-carboxylate (2.50 g, 9.80 mmol) in 30 ml of EtAc was added 6 ml of HCl (conc.). After stirred for 30 min, the mixture was diluted with ethanol and toluene, concentrated and co-evaporated with ethanol/toluene (1:1, 3×50 ml) to dryness compound without further purification. To the dryness compound was added 4-(tert-butoxycarbonylamino)-1-methyl-1H-imidazole-2-carboxylic acid (2.36 g, 9.8 mmol), EDC (5.90 g, 30.7 mmol), DIPEA (1.70 ml, 9.8 mmol) and 80 ml of DMA. The mixture was stirred under Ar overnight, concentrated, diluted with THF/EtAc (1:2, 150 ml), and washed 1M NaH$_2$PO$_4$/NaCl (conc) and NaHCO$_3$ (conc) separately. The organic solvent layer was separated and dried over MgSO$_4$, filtered, concentrated and purified on SiO2 chromatography eluted with EtAc/DCM (1:25 to 1:15) to afford 2.65 g (71.5%) of the title product. $^1$H NMR (DMSO) 11.17 (s, 1H), 10.48 (s, 1H), 7.58 (s, 1H), 7.32 (s, 1H), 4.01 (s, 3H), 3.94 (s, 3H), 3.92 (s, 3H), 1.45 (s, 9H); $^{13}$C NMR 160.60, 157.30, 135.92, 135.45, 132.86, 126.12, 114.83, 79.50, 52.70, 35.58, 34.92, 28.08; MS m/z+401.8 (M+Na).

141

1-Methyl-4-(1-methyl-4-nitro-1H-pyrrole-2-carboxamido)-1H-pyrrole-2-carboxylic acid

142

4-(4-(tert-Butoxycarbonylamino)-1-methyl-1H-pyrrole-2-carboxamido)-1-methyl-1H-imidazole-2-carboxylic acid

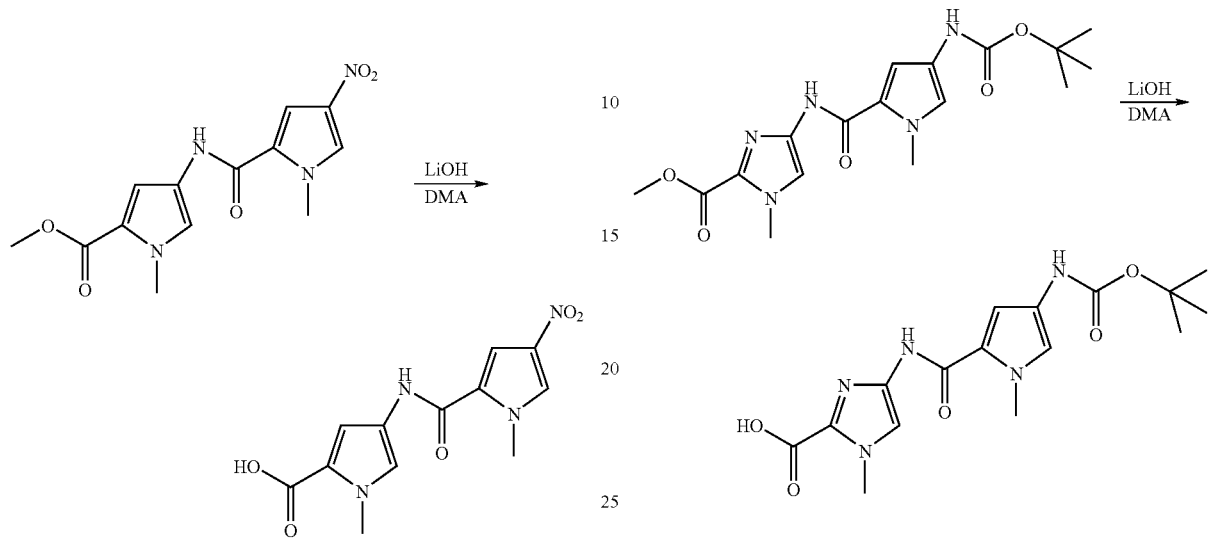

Methyl 1-methyl-4-(1-methyl-4-nitro-1H-pyrrole-2-carboxamido)-1H-pyrrole-2-carboxylate (2.0 g, 6.53 mmol) in 50 ml of DMA was added 2 g of LiOH in 30 ml of water. The mixture was stirred overnight, concentrated, diluted with water, extracted with EtAc/Hexane (1:1). The aqueous solution was adjusted to pH 4.0 with 20% $H_3PO_4$ to form precipitates. The precipitates were filtered, washed with water and dried over $P_2O_5$ with vaccum to afford 1.4 g (73%) of the title product. $^1$H NMR (DMF-d7) 10.34 (br, 1H), 8.17 (s, 1H), 7.62 (s, 1H), 7.51 (s, 1H), 7.00 (s, 1H), 4.09 (s, 1H), 3.91 (s, 1H); $^{13}$C NMR 158.47, 135.61, 129.11, 127.77, 123.65, 121.57, 121.50, 109.48, 108.52, 38.38, 37.05; MS m/z– 291.0 (M–H).

Methyl 4-(4-(tert-butoxycarbonylamino)-1-methyl-1H-pyrrole-2-carboxamido)-1-methyl-1H-imidazole-2-carboxylate (2.0 g, 5.30 mmol) in 50 ml of DMA was added 2 g of LiOH in 30 ml of water. The mixture was stirred overnight, concentrated, diluted with water, extracted with EtAc/Hexane (1:1). The aqueous solution was adjusted to pH 4.0 with 20% $H_3PO_4$ to form precipitates. The precipitates were filtered, washed with water and dried over $P_2O_5$ with vaccum to afford 1.44 g (75%) of the title product. $^1$H NMR (DMSO) 10.41 (br, 1H), 9.07 (s, 1H), 7.48 (s, 1H), 6.97 (s, 1H), 6.88 (s, 1H), 3.92 (s, 1H), 3.81 (s, 1H), 1.47 (s, 9H); $^{13}$C NMR 160.46, 158.42, 152.85, 145.21, 135.81, 129.11, 127.77, 122.39, 121.57, 113.58, 79.81, 36.06, 35.25, 28.17; MS m/z– 362.1 (M–H).

Methyl 4-(4-(4-(4-(tert-butoxycarbonylamino)-1-methyl-1H-pyrrole-2-carboxamido)-1-methyl-1H-imidazole-2-carboxamido)-1-methyl-1H-pyrrole-2-carboxamido)-1-methyl-1H-pyrrole-2-carboxylate

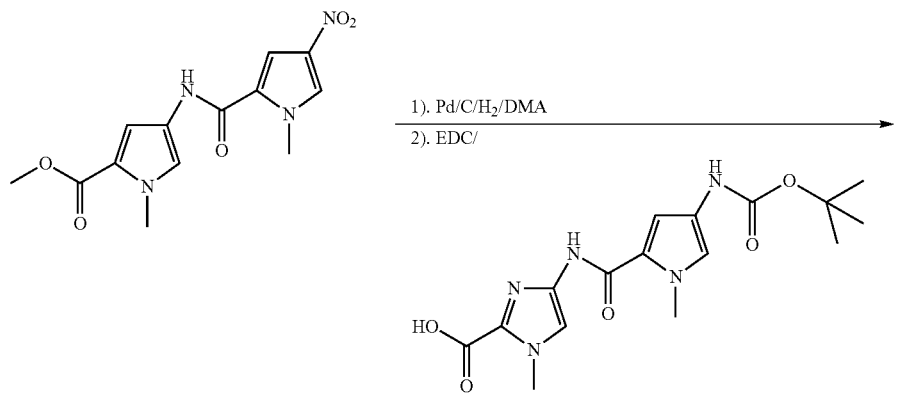

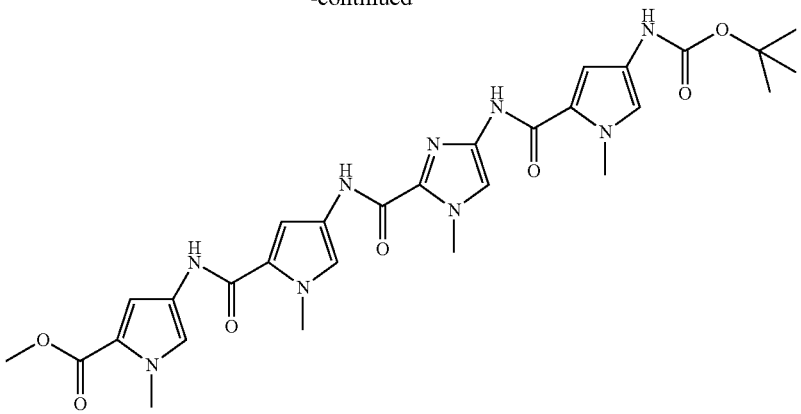

In a hydrogenation bottle was added methyl 1-methyl-4-(1-methyl-4-nitro-1H-pyrrole-2-carboxamido)-1H-pyrrole-2-carboxylate (1.0 g, 3.27 mmol), 20 ml of THF, 305 mg of 10% Pd/C (50% wet) and 0.25 ml of HCl (conc.). After evacuation under vacuum the bottle wasplaced under 50 psi hydrogen and shaken for 4 hours. The mixture was filtered through celite, evaporated to dryness without further purification. To the dried mixture was added 4-(4-(tert-butoxycarbonylamino)-1-methyl-1H-pyrrole-2-carboxamido)-1-methyl-1H-imidazole-2-carboxylic acid (1.15 g, 3.16 mmol), 10 ml of DMA, EDC (2.0 g, 10.4 mmol) and DIPEA (0.70 ml, 4.02 mmol). The mixture was stirred under Ar overnight, concentrated, diluted with Hexane/EtAc (1:1, 10 ml) and water 10 ml to form precipitates. The precipitates were filtered, washed 1M $NaH_2PO_4$, 1 M $NaHCO_3$ and water, dried over $P_2O_5$ with vacuum to afford 1.61 g (82%) of the title product. $^1$H NMR (DMF-d7) 10.29 (s, 1H), 10.20 (s, 1H), 10.12 (s, 1H), 9.08 (s, 1H), 7.58 (s, 1H), 7.47 (d, 1H, J=1.7 Hz), 7.26 (d, 1H, J=1.5 Hz), 7.15 (d, 1H, J=1.5 Hz), 6.98 (s, 1H), 6.91 (d, 1H, J=1.8 Hz), 6.86 (s, 1H), 3.97 (s, 3H), 3.82 (s, 3H), 3.73 (s, 3H), 3.56 (s, 3H), 1.45 (s, 9H); $^{13}$C NMR 162.16, 160.05, 159.90, 157.20, 154.31, 137.88, 135.35, 124.56, 124.39, 124.24, 123.09, 120.09, 119.82, 115.32, 105.58, 102.27, 79.31, 51.51, 38.13, 36.01, 35.80, 35.08, 28.79; MS m/z+ 644.2 (M+Na).

Methyl 1-methyl-4-(1-methyl-4-(1-methyl-4-(1-methyl-4-nitro-1H-pyrrole-2-carboxamido-1H-pyrrole-2-carboxamido)-1H-pyrrole-2-carboxamido)-1H-pyrrole-2-carboxylate

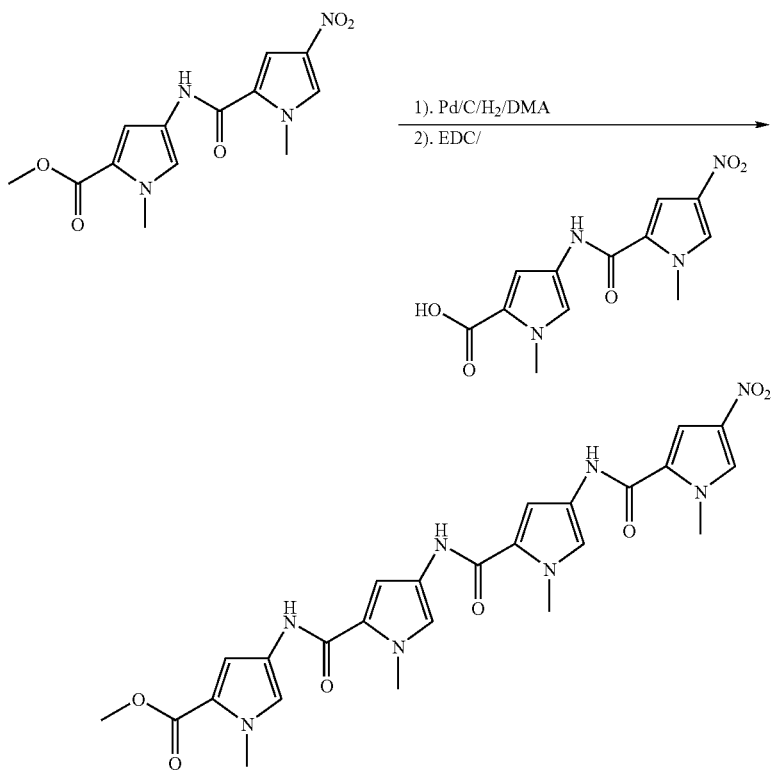

In a hydrogenation bottle was added methyl 1-methyl-4-(1-methyl-4-nitro-1H-pyrrole-2-carboxamido)-1H-pyrrole-2-carboxylate (2.0 g, 6.53 mmol), 80 ml of DMA, 500 mg of 10% Pd/C (50% wet) and 0.4 ml of HCl (conc.). After evacuation under vacuum, the bottle was placed under 50 psi hydrogen and shaken for 4 hours. The mixture was filtered through celite, evaporated to dryness without further purification. To the dry mixture was added 1-methyl-4-(1-methyl-4-nitro-1H-pyrrole-2-carboxamido)-1H-pyrrole-2-carboxylic acid (1.49 g, 5.10 mmol), 30 ml of DMA, EDC (4.0 g, 20.8 mmol) and DIPEA (1.0 ml, 5.75 mmol). The mixture was stirred under Ar overnight, concentrated, diluted with Hexane/EtAc (1:1, 10 ml) and water 10 ml to form precipitates. The precipitates were filtered, washed 1M $NaH_2PO_4$, 1 M $NaHCO_3$ and water, dried over $P_2O_5$ under vacuum to afford 2.13 g (76%) of the title product. $^1$H NMR (DMSO) 10.28 (s, 1H), 10.25 (s, 1H), 9.78 (s, 1H), 8.18 (s, 1H), 7.86 (s, 1H), 7.52 (s, 1H), 7.31 (d, 1H, J=1.7 Hz), 7.25 (s, 1H), 7.23 (s, 1H), 7.17 (d, 1H, J=1.5 Hz), 6.98 (s, 1H), 6.71 (s, 1H), 4.02 (s, 3H), 3.94 (s, 3H), 3.83 (s, 3H), 3.73 (s, 3H), 3.56 (s, 3H), 1.47 (s, 9H); $^{13}$C NMR 160.78, 158.93, 158.06, 157.81, 135.25, 127.28, 126.36, 123.78, 122.57, 121.91, 121.40, 120.94, 119.65, 110.73, 108.39, 107.34, 103.75, 80.81, 51.57, 39.74, 38.52, 38.22, 37.08, 28.63; MS m/z+ 573.2 (M+Na).

4-(4-(4-(4-(tert-butoxycarbonylamino)-1-methyl-1H-pyrrole-2-carboxamido)-1-methyl-1H-imidazole-2-carboxamido)-1-methyl-1H-pyrrole-2-carboxamido)-1-methyl-1H-pyrrole-2-carboxylic acid Methyl 4-(4-(4-(4-(tert-butoxycarbonylamino)-1-methyl-1H-pyrrole-2-carboxamido)-1-methyl-1H-imidazole-2-carboxamido)-1-methyl-1H-pyrrole-2-carboxamido)-1-methyl-1H-pyrrole-2-carboxylate (510 mg, 0.82 mmol) in 10 ml of DMA was added 0.8 g of LiOH in 10 ml of water. The mixture was stirred overnight, concentrated, diluted with water, extracted with EtAc/Hexane (1:1). The aqueous solution was adjusted to pH 4.0 with 20% $H_3PO_4$ to form precipitates. The precipitates were filtered, washed with water and dried over $P_2O_5$ under vaccum to afford 363 mg (73%) of the title product. $^1$H NMR (DMF-d7) 10.31 (s, 1H), 10.18 (s, 1H), 10.11 (s, 1H), 9.10 (s, 1H), 7.58 (s, 1H), 7.54 (s, 1H), 7.41 (s, 1H), 7.33 (s, 1H), 7.21 (s, 1H), 7.10 (s, 1H), 7.06 (s, 1H), 4.10 (s, 1H), 3.98 (s, 1H), 3.95 (s, 1H), 3.93 (s, 1H), 1.47 (s, 9H); $^{13}$C NMR 162.16, 160.05, 159.90, 157.20, 154.31, 137.88, 135.35, 124.56, 124.39, 123.51, 123.09, 121.76, 120.09, 119.83, 118.96, 115.32, 109.53, 105.58, 102.27, 79.32, 38.13, 36.02, 35.81, 34.88, 28.79; MS m/z− 606.2 (M−H).

S-3-(tert-butoxycarbonylamino)propyl ethanethioate

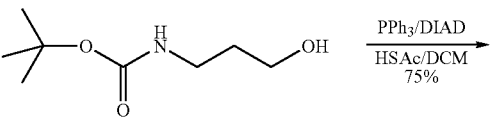

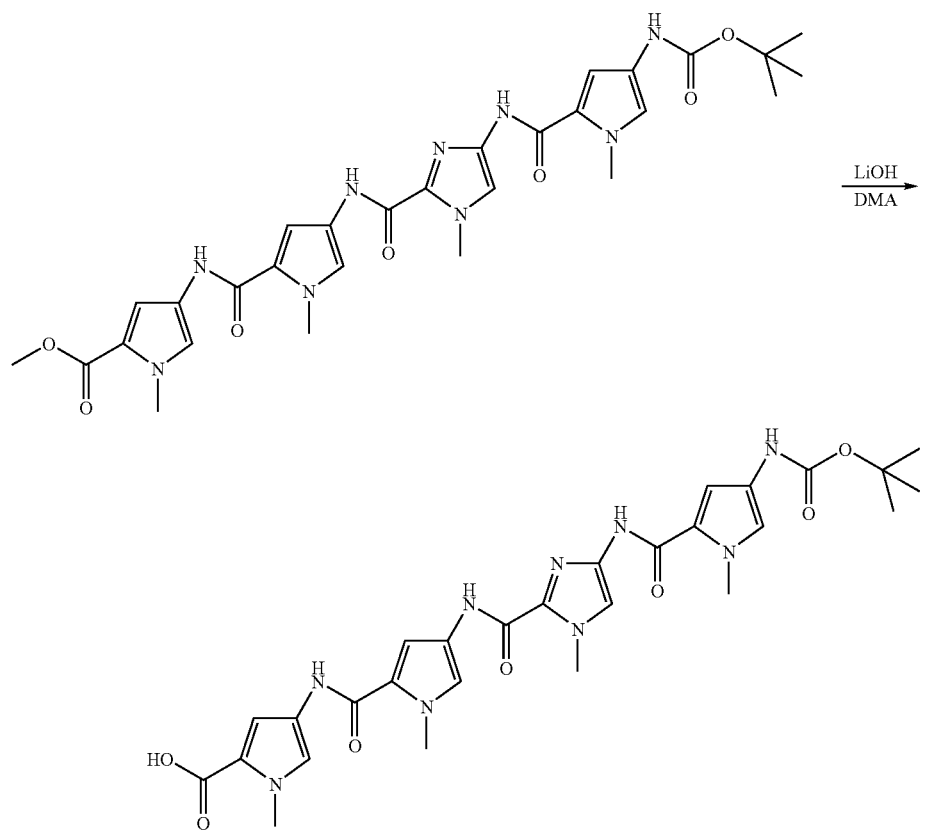

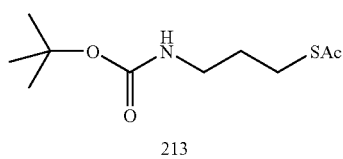

213 tert-Butyl 3-hydroxypropylcarbamate (3.22 g, 18.37 mmol) in 100 ml of DCM at 0° C. was added thiolacetic acid (2.0 ml, 26.73 mmol) and triphenylphosphine (7.0 g, 26.73 mmol) under Ar. After stirred at 0° C. for 15 min, DIAD (6.0 ml, 28.93) was added. The mixture was stirred at 0° C. for 2 h then RT overnight. The mixture was concentrated, diluted with 120 ml of EtAc/Hexane (1:2), filtered through celite. The solution was washed with NaHCO$_3$ (conc.)/NaCl (conc.) and 1 M NaH$_2$PO$_4$ respectively, dried over MgSO$_4$, filtered, evaporated and purified on SiO$_2$ chromatography eluted with EtAc/Hexane (1:7 to 1:6) to afford 3.22 g (75%) of the title compound. $^1$H NMR (CDCl$_3$) 3.09 (t, 2H, J=6.5 Hz), 2.84 (t, 2H, J=6.9 Hz), 2.27 (s, 3H), 1.69 (dt, 2H, J=6.8, 13.5 Hz),1.38 (s, 9H); $^{13}$C NMR 196.35, 156.16, 79.50, 39.26, 30.79, 30.24, 28.61, 26.44; MS m/z+ 256.0 (M+Na).

S-3-(tert-butoxycarbonyl(methyl)amino)propyl ethanethioate

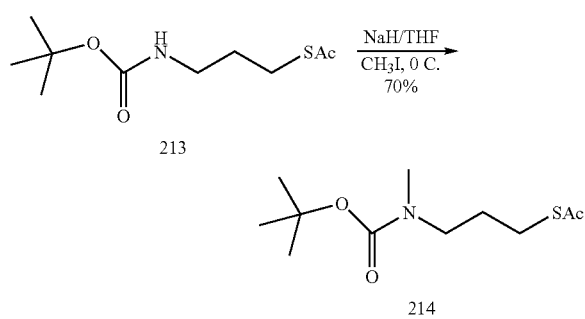

To a solution of NaH (0.57 g, 60%, 14.25 mmol) in 20 ml of THF at 0° C. was added S-3-(tert-butoxycarbonylamino)propyl ethanethioate (1.25 g, 5.36 mmol) under Ar. After stirring at 0° C. for 30 min, MeI (1.0 ml, 16.06 mmol) was added to the mixture. Stirring was continued at 0° C. for 2 h then RT overnight. The mixture was concentrated, redissolved in 120 ml of EtAc/Hexane (1:2), washed with 1 M NaH$_2$PO$_4$ NaCl (conc.), dried over MgSO$_4$, filtered, evaporated and purified on SiO$_2$ chromatography eluted with EtAc/Hexane (1:7) to afford 1.121 g (85%) of the title compound. $^1$H NMR (CDCl$_3$) 3.69 (t, 2H, J=7.3 Hz), 2.41 (t, 2H, J=7.3 Hz), 2.39 (s, 3H), 2.03 (s, 3H), 1.76 (m, 2H),1.47 (s, 9H); $^{13}$C NMR 173.21, 153.39, 83.28, 43.67, 31.84, 28.26, 28.19, 27.11, 15.65; MS m/z+ 270.0 (M+Na).

S-3-(Methylamino)propyl ethanethioate hydrogen chloride salt

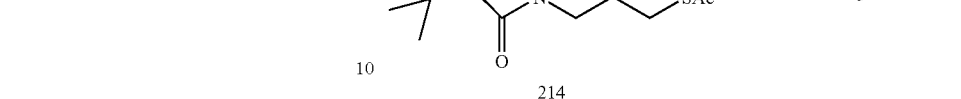

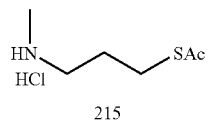

S-3-(tert-Butoxycarbonyl(methyl)amino)propyl ethanethioate (206 mg, 0.834 mmol) in 4 ml of EtAc was added 1.0 ml of HCl (conc.) at RT. The mixture was stirred at RT for 1 h, diluted with ethanol/toluene (6 ml, 1:1), evaporated and co-evaporated with ethanol/toluene (3×10 ml), crystallized with ethanol/EtAc/Hexane, filtered, and dried over a vaccum to afford 135 mg (88%) of the title compound. $^1$H NMR (CDCl$_3$) 9.70 (br, 1H), 8.56 (br, 1H), 3.42 (m, 2H), 2.52 (m, 2H), 2.35 (s, 3H), 2.05 (s, 3H), 1.88 (m, 2H); $^{13}$C NMR 174.64, 40.57, 31.57, 27.69, 20.94, 15.62; MS m/z+ 170.0 (M+Na), 148.10 (M+H).

tert-Butyl 2-(pyridin-2-yldisulfanyl)ethylcarbamate (217)

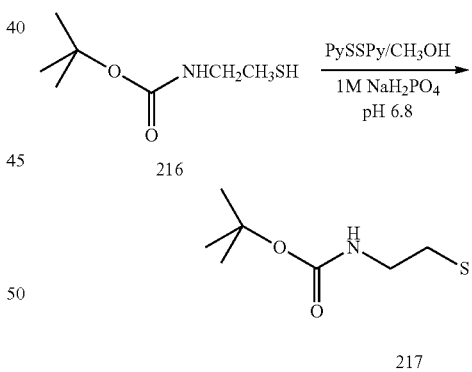

To the solution of 2,2'-dithiolpyridine (3.97 g, 18.02 mmol) in 100 ml of methanol and 80 ml of 1 M NaH$_2$PO$_4$, pH 6.8 was added tert-Butyl 2-mercaptoethylcarbamate (1.00 g, 5.65 mmol) in 50 ml of methanol. The mixture was stirred under Ar overnight, concentrated, extracted with dichloromethane, dried over MgSO$_4$, filtered, evaporated and purified on SiO$_2$ chromatography eluted with EtAc/Hexane (1:10 to 1:6) to afford 1.341 g (83%) of the title compound. $^1$H NMR (CDCl$_3$) 8.39 (m, 1H), 7.56 (m, 1H), 7.49 (m, 1H), 7.03 (m, 1H), 7.00 (m, 1H), 3.34 (m, 2H), 2.84 (m, 2H),1.37 (s, 9H); $^{13}$C NMR 160.05, 159.39, 159.07, 149.87, 137.21, 120.78, 79.48, 39.58, 38.96, 28.57; MS m/z+ 309.2 (M+Na).

2-(pyridin-2-yldisulfanyl)ethanamine

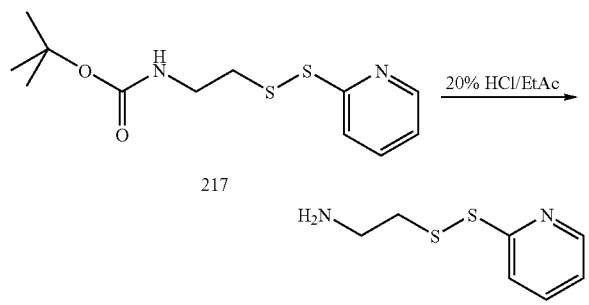

217

218 tert-Butyl 2-(pyridin-2-yldisulfanyl)ethylcarbamate (1.06 g, 3.70 mmol) in 16 ml of EtAc was added 4.0 ml of HCl (conc.) at RT. The mixture was stirred at RT for 0.5 h, diluted with ethanol/toluene (6 ml, 1:1), evaporated and co-evaporated with ethanol/toluene (3×10 ml), crystallized with ethanol/EtAc/Hexane, filtered, and dried over a vaccum to afford 135 mg (88%) of the title compound. $^1$H NMR (CD$_3$OD) 7.58 (m, 1H), 7.47 (m, 1H), 7.06 (m, 1H), 6.83 (m, 1H), 3.34 (m, 2H), 3.02 (m, 2H); $^{13}$C NMR 158.69, 149.07, 137.81, 122.48, 120.98, 39.52, 36.94; MS m/z+ 187.10 (M+H).

Methyl 4-bromobutanoate (223)

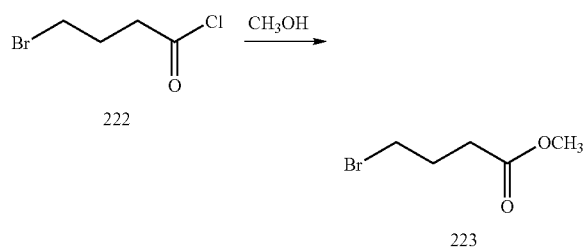

222

223

4-Bromobutanoyl chloride (3.1 ml, 25.28 mmol) was added to 15 ml of dry metanol at 0° C. Stirring was continued at 0° C. under Ar for 2 h then at RT overnight. The mixture was evaporated, diluted with EtAc/Hexane (1:5), filtered through SiO$_2$ gel, and evaporated to afford 4.50 g (99%) of the title compound. $^1$H NMR (CDCl$_3$) 3.65 (s, 3H), 3.43 (t, 2H, J=6.5 Hz), 2.47 (t, 2H, J=7.1 Hz), 2.13 (dt, 2H, J=6.7, 13.6 Hz); $^{13}$C NMR 173.08, 51.84, 32.82, 32.34, 27.89; MS m/z+ 203.0 (M+Na).

(Z)-methyl 4-(7-methoxy-2',3'-benzo[e]-5-oxo-5,11a-dihydro-1H-benzo[e]pyrrolo[1,2-a][1,4]diazepin-8-yloxy)butanoate

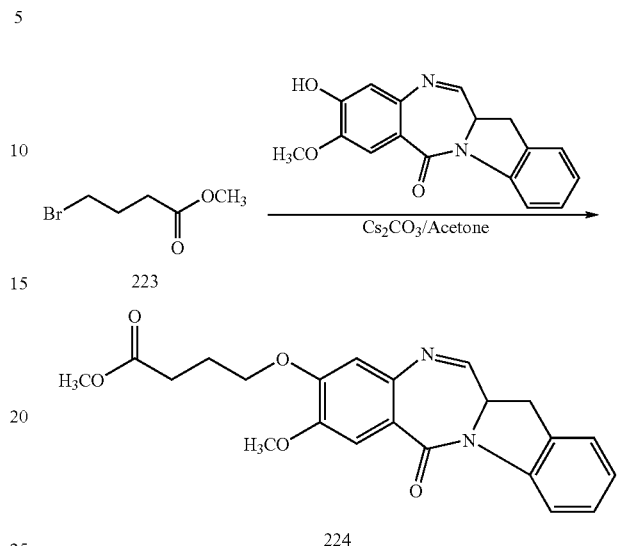

223

224

(Z)-2,3-Benzo-8-hydroxy-7-methoxy-1H-benzo[e]pyrrolo[1,2-a][1,4]diazepin-5(11aH)-one (60 mg, 0.20 mmol) in 4 ml of acetone was added Cs$_2$CO$_3$ (90 mg, 0.28 mmol), follwed added methyl 4-bromobutanoate (50 mg, 0.27 mmol). The mixture was stirred under Ar over night, evaporated, and purified on SiO$_2$ chromatography eluted with EtAc/DCM (1:5 to 1:3) to afford 50.1 mg (63%) of the title compound. $^1$H NMR (CDCl$_3$) 8.19 (d, 1H, J=7.9 Hz), 7.80 (d, 1H, J=4.2 Hz), 7.48 (s, 1H), 7.19 (m, 2H), 7.03 (d, 1H, J=7.4 Hz), 6.77 (s, 1H), 4.41 (m, 1H), 3.88 (s, 3H), 3.64 (m, 2H), 3.62 (s, 3H), 3.42 (dd, 1H, J=3.4, 13.7 Hz), 2.50 (t, 2H, J=7.2 Hz), 2.12 (t, 2H, J=6.8 Hz); $^{13}$C NMR, 173.64, 164.12, 163.24, 152.25, 148.41, 142.28, 140.34, 129.69, 128.39, 124.97, 120.85, 117.15, 112.15, 110.68, 68.08, 56.40, 55.18, 51.90, 32.84, 30.64, 24.50; MS m/z+ 187.10 (M+H). MS m/z+ 417.2 (M+Na), 435.2 (M+Na+H$_2$O).

4-(7-methoxy-2,3-benzo[e]-5-oxo-5,11a-dihydro-1H-benzo[e]pyrrolo[1,2-a][1,4]diazepin-8-yloxy)butanoic acid

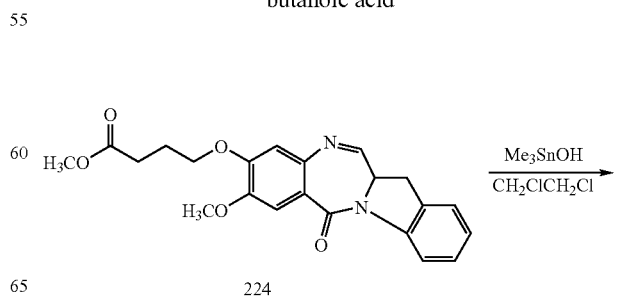

224

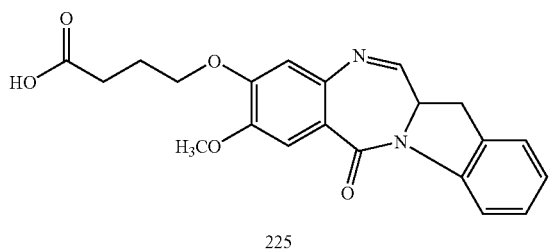

225

(Z)-methyl 4-(7-methoxy-2',3'-benzo[e]-5-oxo-5,11a-dihydro-1H-benzo[e]pyrrolo[1,2-a][1,4]diazepin-8-yloxy)butanoate (41 mg, 0.104 mmol) and trimethyltin hydroxide (302 mg, 1.67 mmol) in 15 ml of dichloroethane was refluxed at 85° C. under Ar overnight. The mixture was washed with 1 M NaH$_2$PO$_4$, pH 3.5, dried over MgSO$_4$, filtered, evaporated and purified on SiO$_2$ chromatography eluted with EtAc/DCM/HCl (1:25:0.01%) to afford 30 mg (76%) of the title compound. $^1$H NMR (CDCl$_3$) 8.18 (d, 1H, J=7.9 Hz), 7.85 (m, 1H), 7.46 (s, 1H), 7.20 (m, 2H), 7.04 (d, 1H, J=7.4 Hz), 6.81 (s, 1H), 4.40 (m, 1H), 3.86 (s, 3H), 3.63 (m, 2H), 3.23 (dd, 1H, J=10.2, 16.3 Hz), 2.52 (t, 2H, J=7.2 Hz), 2.12 (t, 2H, J=6.8 Hz); $^{13}$C NMR, 173.64, 164.12, 163.24, 152.25, 148.41, 142.28, 140.34, 129.69, 128.39, 125.10, 120.85, 117.19, 112.15, 110.68, 67.94, 56.43, 55.18, 31.81, 30.64, 24.21; MS m/z– 397.0 (M+H$_2$O–H).

4-{[4-({4-[4-(7-methoxy-2',3'-benzo[e]-5-oxo-5,11a-dihydro-1H-benzo[e]pyrrolo[1,2-a][1,4]diazepin-8-yloxy)butyrylamino]-1-methyl-1H-pyrrole-2-carbonyl}amino)-1-methyl-1H-imidazole-2-carbonyl]amino}-1-methyl-1H-pyrrole-2-carbonyl]-amino}-1-methyl-1H-pyrrole-2-carboxylic acid methyl ester (226)

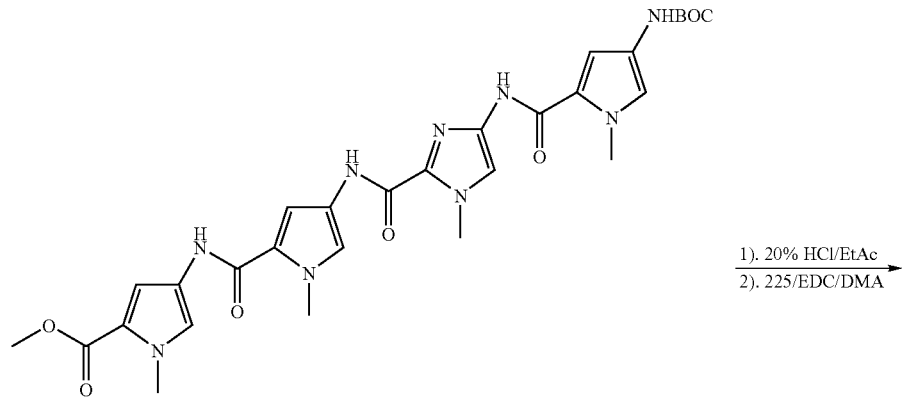

181

1). 20% HCl/EtAc
2). 225/EDC/DMA

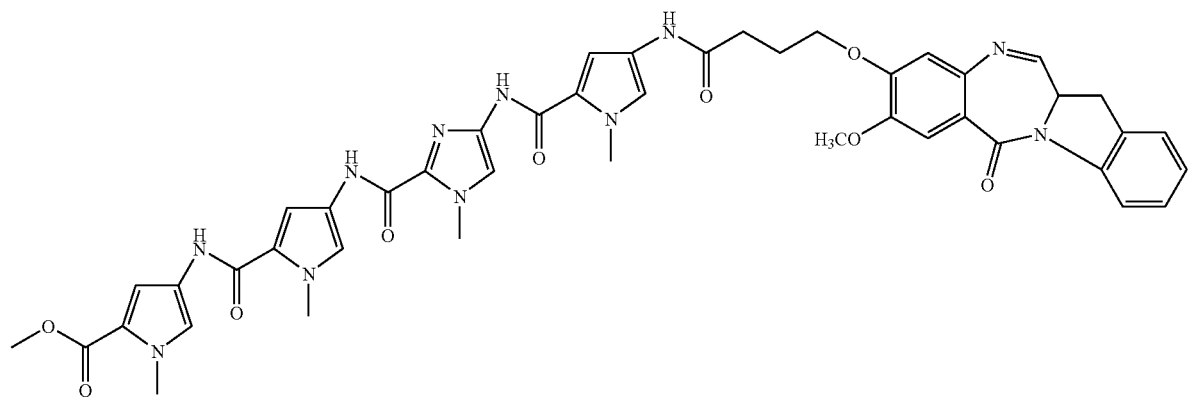

226

To methyl 4-(4-(4-(4-(tert-butoxycarbonylamino)-1-methyl-1H-pyrrole-2-carboxamido)-1-methyl-1H-imidazole-2-carboxamido)-1-methyl-1H-pyrrole-2-carboxamido)-1-methyl-1H-pyrrole-2-carboxylate (15 mg, 0.024 mmol) in 4 ml of EtAc was added 1.0 ml of HCl (conc.). The mixture was stirred at RT for 0.5 h, diluted with ethanol/toluene (6 ml, 1:1), evaporated and co-evaporated with ethanol/toluene (3×10 ml), and dried over a vacuum. The solid compound was philized to afford a white solid (4.2 mg (30%) of the title compound). MS m/z– 900.3 (M+H₂O–H).

S-3-(4-(4-(4-(4-(tert-butoxycarbonylamino)-1-methyl-1H-pyrrole-2-carboxamido)-1-methyl-1H-imidazole-2-carboxamido)-1-methyl-1H-pyrrole-2-carboxamido)-N,1-dimethyl-1H-pyrrole-2-carboxamido)propyl ethanethioate (227)

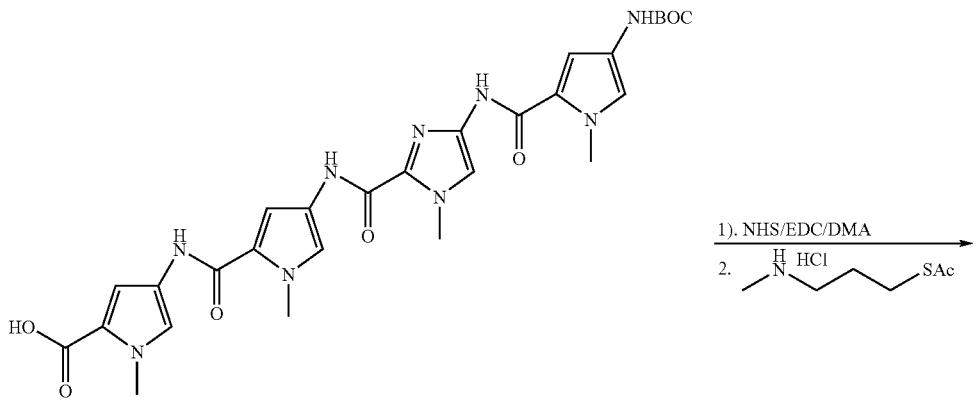

197

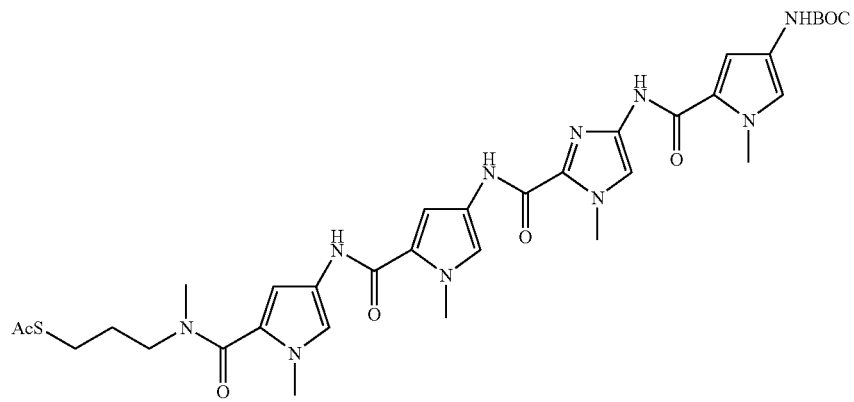

227 used directly without further purification. To the solid was added 4-(7-methoxy-2',3'-benzo[e]-5-oxo-5,11a-dihydro-1H-benzo[e]pyrrolo[1,2-a][1,4]diazepin-8-yloxy)butanoic acid (6 mg, 0.015 mmol), EDC (40 mg, 0.21 mmol), DIPEA (4 ul, 0.023 mmol) and 1 ml of DMA. The mixture was stirred under Ar over night, evaporated, and purified on HPLC preparative C-18 column (Φ10 mm×200 mm column, flow rate 9 mL/min and a gradient solvent system going from 75:25 solvent A:B at time 0-5 min to 40:60 A:B at 15 min then to 20:80 A:B at 25 min until to 10:90 A:B at 30 min. Solvent A—water, solvent B—acetonitrile/dioxane (1:2)) and lyo- 4-(4-(4-(4-(tert-butoxycarbonylamino)-1-methyl-1H-pyrrole-2-carboxamido)-1-methyl-1H-imidazole-2-carboxamido)-1-methyl-1H-pyrrole-2-carboxamido)-1-methyl-1H-pyrrole-2-carboxylic acid (256 mg, 0.42 mmol), NHS (60 mg, 0.52 mmol) and EDC (500 mg, 2.60 mmol) in 4 ml of DMA were stirred under Ar for 2 h, then S-3-(methylamino)propyl ethanethioate hydrogen chloride salt (76.5 mg, 0.42 mmol) was added and the mixture was kept stirring for 24 h, evaporated and purified on SiO₂ chromatography eluted with THF/DCM (1:5 to 1:4) to afford 198 mg (64%) of the title compound. ¹H NMR (DMSO) 10.21 (s, 1H), 10.09 (s, 1H), 10.06 (s, 1H), 9.08 (s, 1H), 7.76 (d, 1H, J=1.7 Hz), 7.52 (s, 1H), 7.28 (s, 1H), 7.21 (d, 1H, J=1.7 Hz), 6.97 (s, 1H), 6.87 (s, 1H), 3.98 (s, 1H), 3.86 (s, 3H), 3.75 (s, 3H), 3.73 (s, 3H), 3.66 (m, 2H), 2.85 (s, 3H), 2.60 (m, 2H), 2.01 (s, 3H), 1.45 (s, 9H); $^{13}$C NMR 173.31, 162.16, 160.05, 159.90, 157.20, 154.31, 137.88, 135.35, 124.56, 124.39, 123.51, 123.09, 121.76, 120.09, 119.83, 118.96, 115.32, 109.53, 105.58, 102.27, 79.32, 43.67, 38.13, 36.02, 35.81, 34.88, 31.84, 28.79, 28.26, 28.21, 27.01; MS m/z+ 759.2 (M+Na).

(Z)—S-3-(4-(4-(4-(4-(4-(7-methoxy-2,3-benzo[e]-5-oxo-5,11a-dihydro-1H-benzo[e]pyrrolo[1,2-a][1,4]diazepin-8-yloxy)butanamido)-1-methyl-1H-pyrrole-2-carboxamido)-1-methyl-1H-imidazole-2-carboxamido)-1-methyl-1H-pyrrole-2-carboxamido)-N,1-dimethyl-1H-pyrrole-2-carboxamido)propyl ethanethioate (27 mg, 0.037 mmol) was stirred in 2 ml of dioxane and 0.5 ml of HCl (conc) for 15 min, diluted with ethanol/toluene (6 ml, 1:1), evaporated and co-evaporated with ethanol/toluene (4×10 ml), crystallized with EtOH/DCM/Hexane and dried over a vacuum to afford 21 mg of solid. The solid compound was used directly without further purification. To the solid was added 4-(7-methoxy-2,3-benzo[e]-5-oxo-5,11a-dihydro-1H-benzo[e]pyrrolo[1,2-a][1,4]diazepin-8-yloxy) butanoic acid (10 mg, 0.026 mmol), EDC (101 mg, 0.52 mmol), DIPEA (5 ul, 0.028 mmol) and 2 ml of DMA. The mixture was stirred overnight, evaporated, diluted with DCM, washed with 1 M NaH$_2$PO$_4$/NaCl (conc), pH 4.0, dried over MgSO$_4$, filtered, evaporated and purified on HPLC preparative C-18 column (Φ10 mm×200 mm column, flow rate 9 mL/min and a gradient solvent system going from 75:25 solvent A:B at time 0-5 min to 40:60 A:B at 15 min then to 20:80 A:B at 25 min until to 10:90 A:B at 30 min.

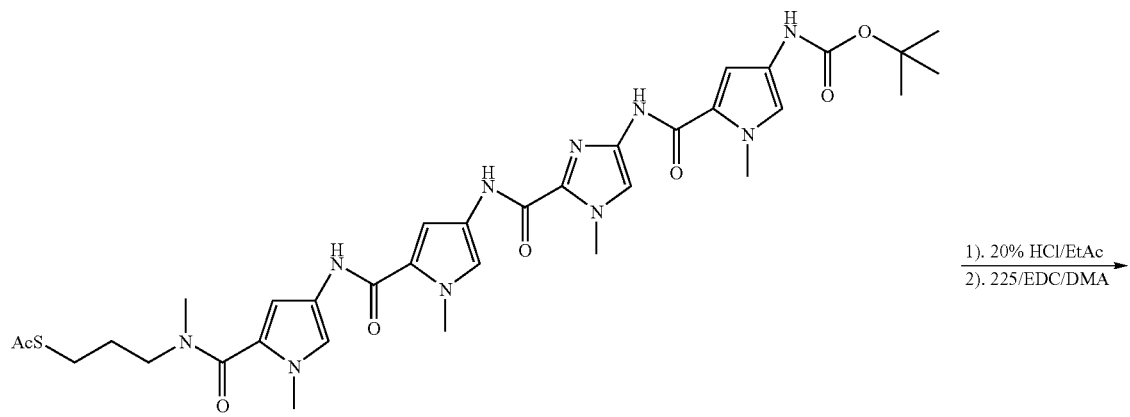

227

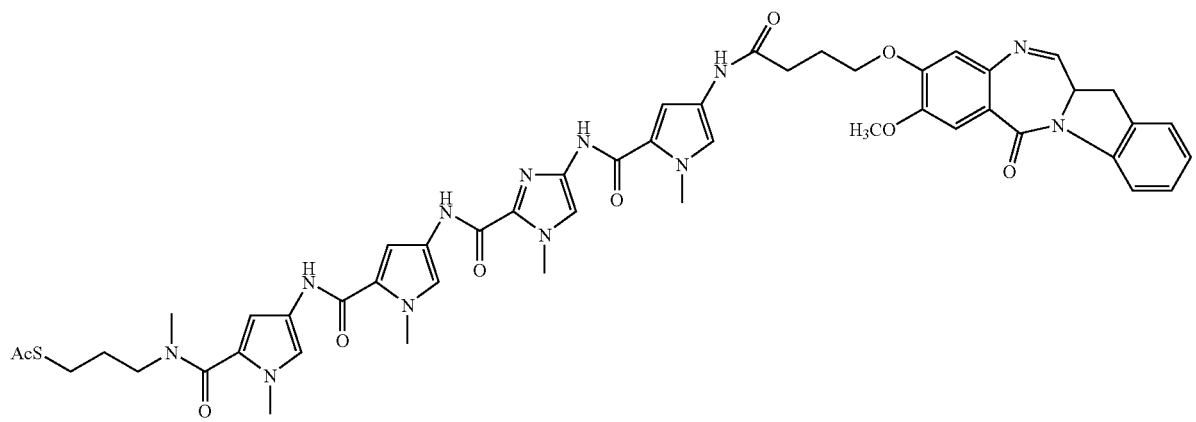

228

S-3-(4-(4-(4-(4-(tert-butoxycarbonylamino)-1-methyl-1H-pyrrole-2-carboxamido)-1-methyl-1H-imidazole-2-carboxamido)-1-methyl-1H-pyrrole-2-carboxamido)-N,1-dimethyl-1H-pyrrole-2-carboxamido)propyl ethanethioate (227)

Solvent A—water, solvent B—acetonitrile/dioxane(1:2)) and lyophilized to afford a white solid 8.2 mg (32%) of the title compound. MS m/z− 1015.1 (M+H$_2$O−H), UV $\epsilon_{(\lambda=305\ nm)}$=32800 M$^{-1}$cm$^{-1}$.

tert-Butyl 1-methyl-5-(1-methyl-2-(1-methyl-5-(1-methyl-5-(2-(pyridin-2-yldisulfanyl)ethylcarbamoyl)-1H-pyrrol-3-ylcarbamoyl)-1H-pyrrol-3-ylcarbamoyl)-1H-imidazol-4-ylcarbamoyl)-1H-pyrrol-3-ylcarbamate (229)

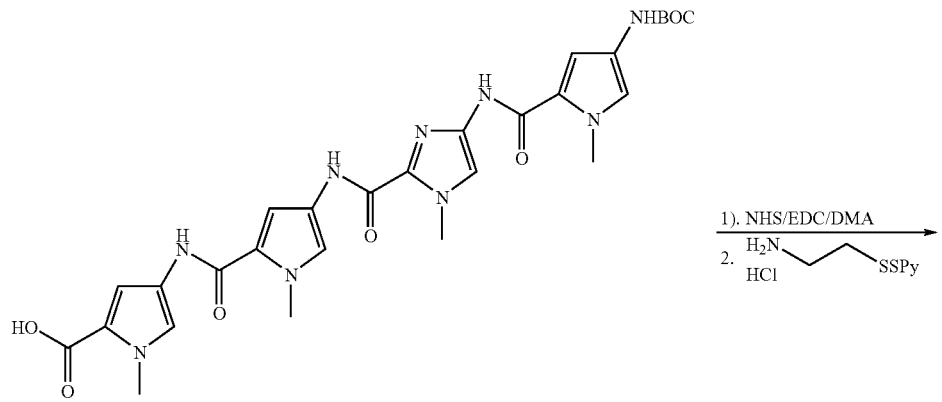

0.18 mmol), DIPEA (30 ul, 0.17 mmol) and EDC (200 mg, 1.04 mmol) in 2 ml of DMA were stirred under Ar for 24 h, evaporated and purified on $SiO_2$ chromatography eluted with THF/DCM (1:5 to 1:4) to afford 90 mg (68%) of the title compound. $^1$H NMR (DMSO) 10.93 (s, 1H), 10.19 (s, 1H),

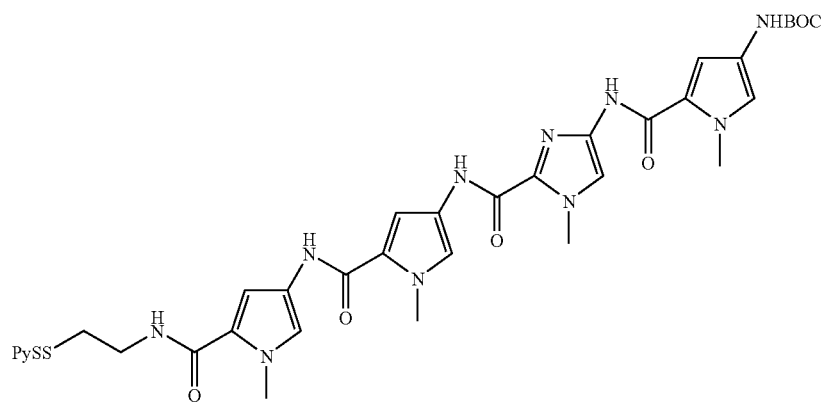

4-(4-(4-(4-(tert-butoxycarbonylamino)-1-methyl-1H-pyrrole-2-carboxamido)-1-methyl-1H-imidazole-2-carboxamido)-1-methyl-1H-pyrrole-2-carboxamido)-1-methyl-1H-pyrrole-2-carboxylic acid (102 mg, 0.17 mmol), 2-(pyridin-2-yldisulfanyl)ethanamine hydrogen chloride salt (40 mg, 10.06 (s, 1H), 9.03 (s, 1H), 8.81 (m 1H), 8.29 (m, 1H), 8.03 (m, 1H), 7.68 (s, 1H), 7.47 (s, 1H), 7.28 (s, 1H), 7.24 (s, 1H), 7.18 (m, 1H), 6.87 (s, 1H), 3.96 (s, 1H), 3.86 (s, 3H), 3.75 (s, 3H), 3.73 (s, 3H), 3.58 (m, 2H), 2.48 (m, 2H), 1.45 (s, 9H); MS m/z+ 798.0 (M+Na), 776.0 (M+H).

4-(4-(4-(7-methoxy-2,3-benzo[e]-1-5-oxo-5,11a-dihydro-1H-benzo[e]pyrrolo[1,2-a][1,4]diazepin-8-yloxy)butanamido)-1-methyl-1H-pyrrole-2-carboxamido)-1-methyl-N-(1-methyl-5-(1-methyl-5-(methyl (2-(pyridin-2-yldisulfanyl)ethyl)carbamoyl)-1H-pyrrol-3-ylcarbamoyl)-1H-pyrrol-3-yl)-1H-imidazole-2-carboxamide (Φ10 mm×200 mm column, flow rate 9 mL/min and a gradient solvent system going from 75:25 solvent A:B at time 0-5 min to 40:60 A:B at 15 min then to 20:80 A:B at 25 min until to 10:90 A:B at 30 min. Solvent A—water, solvent B—acetonitrile/dioxane (1:2)) and lyophilized to afford a white solid 7.5 mg (27%) of the title compound. MS m/z– 1050.0 (M+H$_2$O–H), UV δ$_{(\lambda=305\ nm)}$=32855 M$^{-1}$cm$^{-1}$.

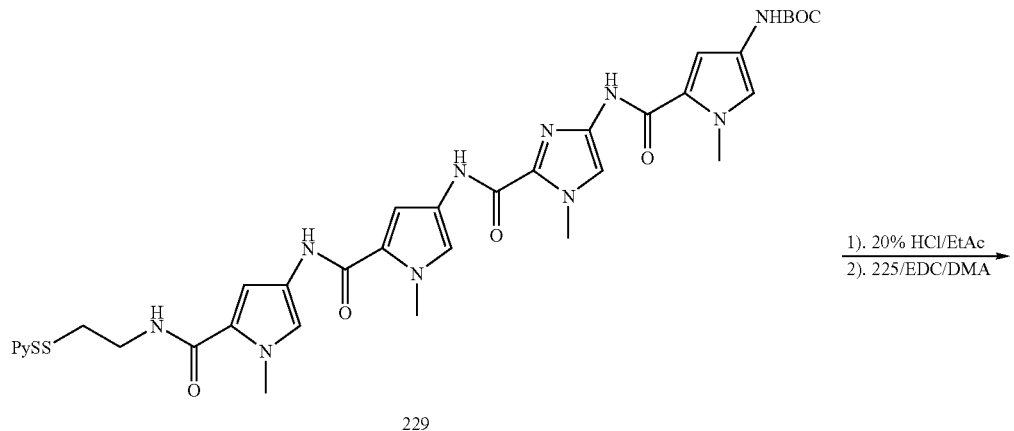

229

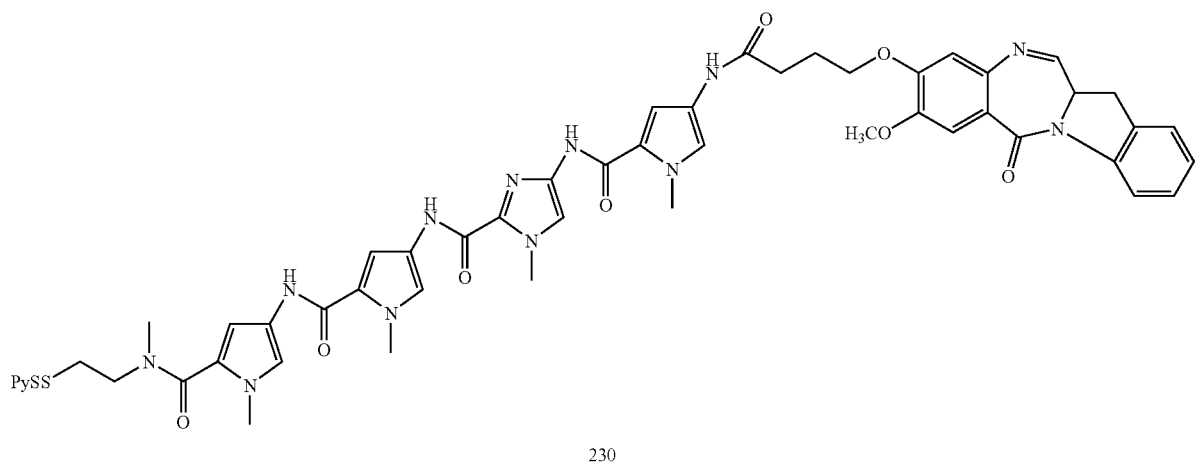

230 tert-Butyl 1-methyl-5-(1-methyl-2-(1-methyl-5-(1-methyl-5-(2-(pyridin-2-yldisulfanyl)ethylcarbamoyl)-1H-pyrrol-3-ylcarbamoyl)-1H-pyrrol-3-ylcarbamoyl)-1H-imidazol-4-ylcarbamoyl)-1H-pyrrol-3-ylcarbamate (229) (30 mg, 0.038 mmol) was stirred in 2 ml of dioxane and 0.5 ml of HCl (conc) for 15 min, diluted with ethanol/toluene (6 ml, 1:1), evaporated and co-evaporated with ethanol/toluene (4×10 ml), crystallized with EtOH/DCM/Hexane and dried over vacuum to afford 19.5 mg of solid. The solid compound was used directly without further purification. To the solid was added 4-(7-methoxy-2,3-benzo[e]-5-oxo-5,11a-dihydro-1H-benzo[e]pyrrolo[1,2-a][1,4]diazepin-8-yloxy) butanoic acid (10 mg, 0.026 mmol), EDC (102 mg, 0.52 mmol), DIPEA (5 ul, 0.028 mmol) and 2 ml of DMA. The mixture was stirred overnight, evaporated, diluted with DCM, washed with 1 M NaH$_2$PO$_4$/NaCl (conc), pH 4.0, dried over MgSO$_4$, filtered, evaporated and purified on HPLC preparative C-18 column

1-(4-(2-bromoethoxy)phenyl)ethanone

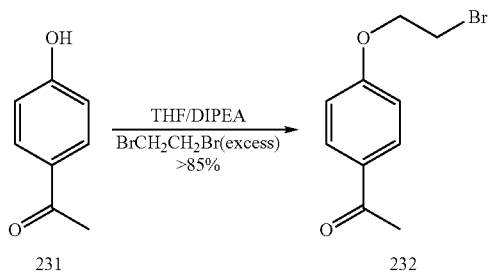

1-(4-hydroxyphenyl)ethanone (8.2 g, 60.2 mmol), potassium carbonate (15.2 g, 110.1 mmol), and KI (1.0 g, 6.0 mmol) in 100 DMF was stirred for 5 min, then 1,2-dibromoethane (60 ml, 696.2 mmol) was added. The mixture was stirred overnight, evaporated, diluted with EtAc/Hexane (1:1), washed with 0.1 M HCl/NaCl (conc), dried over MgSO$_4$, filtered, evaporated and purified by SiO$_2$ chrmatography eluted with EtAc/Hexane (1:3 to 2:3) to afford 12.41 g (85.2%) of the title compound. $^1$H NMR (CDCl$_3$) 7.87 (ddd, 2H, J=2.8, 4.9, 9.7 Hz), 6.88 (ddd, 2H, J=2.8, 4.9, 9.6 Hz), 4.29 (t, 2H, J=6.2 Hz), 3.59 (t, 2H, J=6.2 Hz); $^{13}$C NMR 196.88, 162.11, 131.15, 130.54, 113.80, 68.06, 29.50, 26.62; MS m/z+ 264.80 (M+Na), 266.80 (M+2+Na).

(5-hydroxy-1,3-phenylene)dimethanol

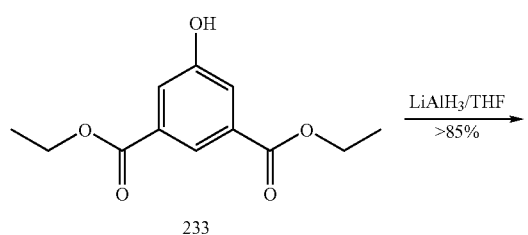

To a solution of 100 ml of 2.0 M LiAlH$_4$ in THF at 0° C. was added dimethyl 5-hydroxy isophthalate (12.3 g, 58.5 mmol) in 120 ml of THF in 15 mim under Ar. The mixture was stirred at 0° C. for 30 min then at RT overnight. The mixture was quenched with 20 ml of methanol at 0° C., and the mixture was adjusted to pH 5.0 with addition of H$_3$PO$_4$, filtered through celite, evaporated and crystallized with ether/hexane to afford 76.6 (85%) of the title compound. $^1$H NMR (DMSO) 6.68 (s, 1H), 6.61 (s, 2H), 4.69 (s, 4H); MS m/z+ 177.0 (M+Na).

1-(4-(2-(3,5-bis(hydroxymethyl)phenoxy)ethoxy)phenyl)ethanone (235)

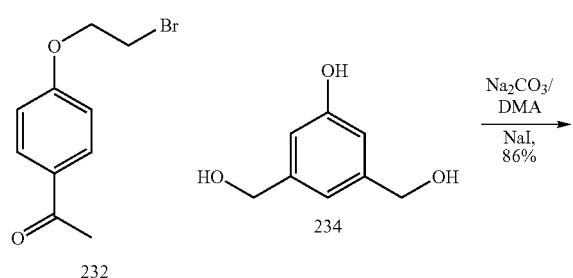

To a stirred solution of (5-hydroxy-1,3-phenylene)dimethanol (3.0, 20.0 mmol), sodium carbonate (2.5 g, 29.0 mmol) and sodium iodide (0.45 g, 2.9 mmol) in 60 ml of DMA was added 1-(4-(2-bromoethoxy)phenyl)ethanone (5.0, 20.57 mmol). The mixture was stirred overnight, evaporated and purified on SiO$_2$ chromatography eluted with EtAc/Hexane (4:1 to 5:1) to afford 5.41 g (86%) of the title compound. $^1$H NMR (CD$_3$OD) 7.99 (ddd, 2H, J=2.8, 4.8, 9.8 Hz), 7.07 (ddd, 2H, J=2.8, 4.7, 9.8 Hz), 6.94 (s, 1H), 6.89 (s, 2H), 4.58 (s, 4H), 4.42 (dd, 2H, J=2.2, 6.1 Hz), 4.37 (m, 2H), 2.55 (s, 3H); $^{13}$C NMR 199.55, 164.66, 160.59, 144.72, 132.03, 131.74, 119.16, 115.64, 113.11, 68.36, 67.87, 65.20, 26.53; MS m/z+ 339.2 (M+Na).

1-(4-(2-(3,5-bis(bromomethyl)phenoxy)ethoxy)phenyl)ethanone (236)

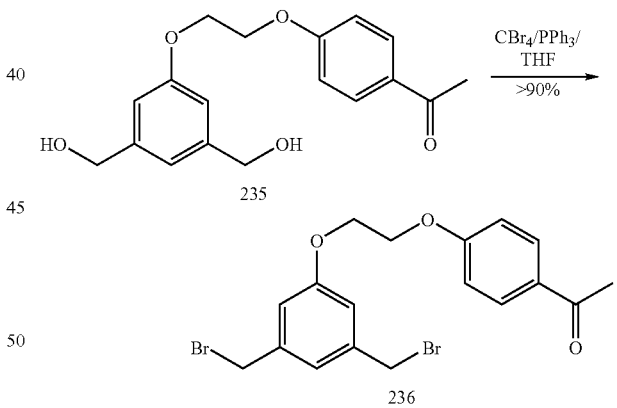

1-(4-(2-(3,5-bis(hydroxymethyl)phenoxy)ethoxy)phenyl)ethanone (0.216g, 0.68 mmol), carbon tetrabromide (0.50g, 1.50 mmol) and PPh3 (0.40g, 1.52 mmol) was stirred in 18 ml of THF under Ar overnight and filtered. The solution was concentrated, purified on SiO$_2$ chromatography eluted with EtAc/Hexane (1:4) and crystallized with ether/hexane to afford 277 mg (92%) of the title compound. $^1$H NMR (CDCl$_3$) 7.94 (ddd, 2H, J=2.7, 4.6, 9.6 Hz), 7.02 (s, 1H), 6.98 (ddd, 2H, J=2.7, 4.6, 9.6 Hz), 6.91 (d, 2H, J=1.2 Hz), 4.62 (s, 4H), 4.35 (m, 4H), 2.55 (s, 3H); $^{13}$C NMR 197.05, 162.63, 159.14, 139.98, 130.96, 130.85, 122.57, 155.60, 114.52, 66.78, 66.73, 32.88, 26.57; MS m/z+ 462.9 (M+Na), 464.9 (M+2+Na).

(R)-Methyl piperidine-2-carboxylate (238)

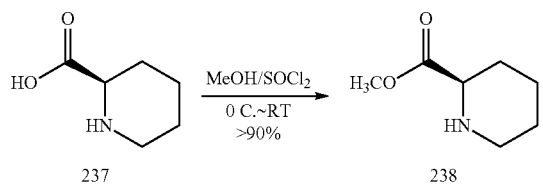 [SMILES: O=C(O)[C@H]1CCCCN1 ; COC(=O)[C@H]1CCCCN1]

To (R)-Piperidine-2-carboxylic acid (5.00 g, 38.73) in 150 ml of dry methanol at 0° C. was added thionyl chloride (5.2 ml, 71.28 mmol) under Ar. The mixture was stirred at 0° C. for 30 min, then at RT overnight, evaporated and crystallized with EtOH/hexane to afford 4.96 g (92%) of the title product. $^1$H NMR (CD$_3$OD) 3.67 (s, 3H), 3.57 (m, 1H), 2.79 (m, 1H), 2.69 (m, 1H), 2.01 (m, 1H), 1.98 (m, 1H), 1.73 (m, 1H), 1.55-1.45 (m, 4H); $^{13}$C NMR 171.22, 62.50, 51.35, 45.35, 29.52, 28.41, 23.82; MS m/z+ 144.0 (M+H).

(R)-Methyl 1-(4-(benzyloxy)-5-methoxy-2-nitrobenzoyl)piperidine-2-carboxylate (239)

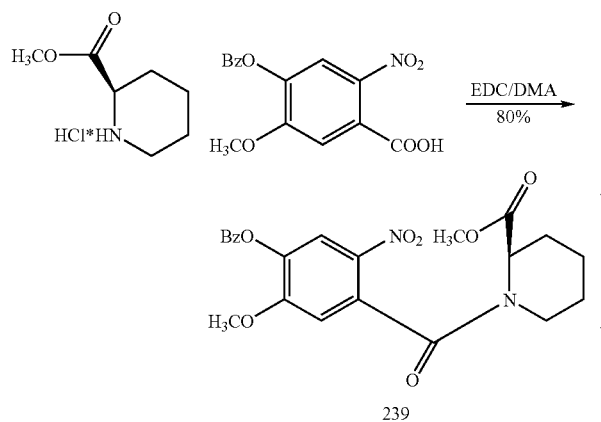

4-(benzoyloxy)-5-methoxy-2-nitrobenzoic acid (1.70 g, 5.61 mmol), (R)-methyl piperidine-2-carboxylate (1.05 g, 5.84 mmol), EDC (3.90 g, 20.31 mmo) and DIPEA (1.0 ml, 5.75 mmol) was stirred in 20 ml of DMA over night. The mixture was evaporated, diluted with DCM, washed with washed 1M NaH$_2$PO$_4$/NaCl (conc) and 0.1 M NaHCO$_3$/NaCl (conc) separately. The organic solvent layer was separated and dried over MgSO$_4$, filtered, concentrated and purified on SiO$_2$ chromatography eluted with EtAc/DCM (1:15) to afford 1.772 g (74%) of the title product. $^1$H NMR (CDCl$_3$) 7.69 (s, 1H), 7.40- 7.38 (m, 2H), 7.35-7.27 (m, 3H), 6.76 (d, 1H), 5.15 (s, 2H), 3.91 (s, 3H), 3.83 (s, 1H), 3.73 (s, 3H), 3.18 (m, 2H), 1.70 (m 2H), 1.47 (m, 4H); $^{13}$C NMR 171.89, 171.33, 155.10, 154.78, 148.32, 135.59, 129.05, 128.74, 127.80, 109.66, 109.58, 109.41, 71.63, 56.92, 52.70, 52.19, 45.70, 39.92, 27.29, 26.35, 21.63; MS m/z+ 451.2 (M+Na).

(R)-1-(4-(benzyloxy)-5-methoxy-2-nitrobenzoyl) piperidine-2-carbaldehyde

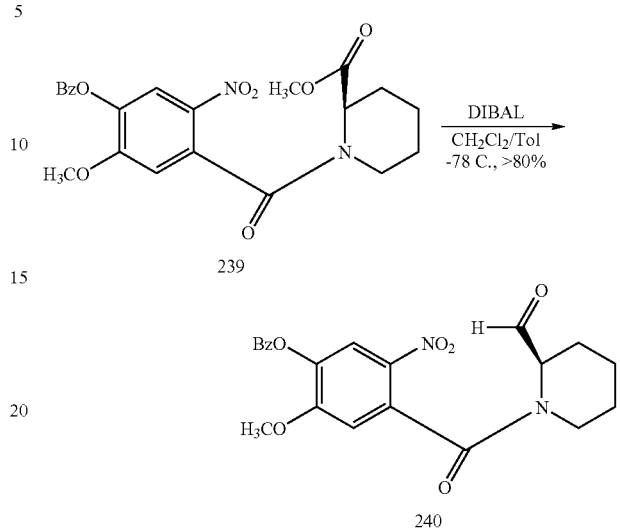

(R)-Methyl 1-(4-(benzoyloxy)-5-methoxy-2-nitrobenzoyl)piperidine-2-carboxylate (1.50 g, 3.50 mmol) in 30 ml of 1:1 DCM/benzene at −78° C. was added 7.5 ml of 1.0 M DIBAL in toluene under Ar in 10 min. The mixture was stirred at −78° C. for 1 hr and the reaction was quenched with 0.5 ml of methanol. The mixture was diluted with 150 ml of EtAc and 100 ml of 0.2 M HCl. The organic solvent layer was separated and was separated and the aqueous layer was extracted with EtOAc (3×80 ml). The organics were combined, dried over MgSO$_4$, filtered, concentrated and purified on SiO2 chromatography eluted with EtAc/hexane (3:2) to afford 1.52 g (90%) of the title product. $^1$H NMR (CDCl$_3$), 9.60 (s, 1H), 7.70 (s, 1H), 7.65-7.28 (m, 5H), 6.78 (m, 1H), 5.16 (s, 2H), 3.92 (s, 3H), 3.22, (m, 1H), 3.01 (m, 1H), 2.20 (m, 1H), 1.84 (m, 1H), 1.65-1.40 (m, 4H); $^{13}$C NMR 200.24, 171.31, 155.13, 154.78, 148.41, 146.20, 137.57, 135.47, 129.03, 128.73, 127.31, 109.83, 109.41, 71.61, 64.50, 56.96, 45.98, 25.25, 23.42, 18.70; MS m/z+ 421.1 (M+Na).

(R,Z)-3-(benzyloxy)-2-methoxy-7,8,9,10-tetrahydrobenzo[e]pyrido[1,2-a][1,4]diazepin-12(6aH)-one

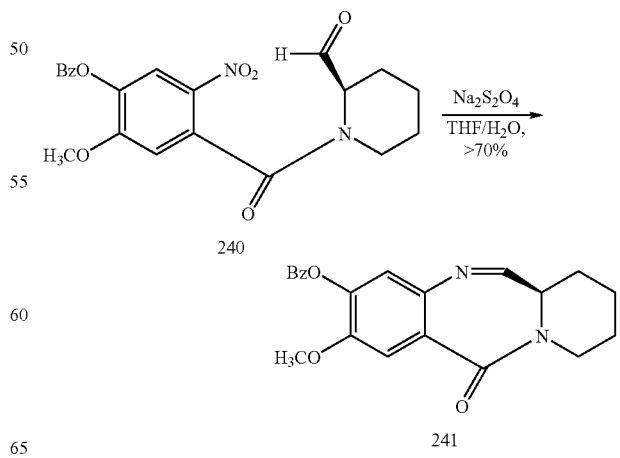

To (R)-1-(4-(benzyloxy)-5-methoxy-2-nitrobenzoyl)piperidine-2-carbaldehyde (1.0 g, 2.51 mmol) in a mixture solution of 25 ml of THF and 15 ml of water was added Na₂S₂O₄ (3.0 g, 17.25 mmol). The mixture was stirred for 4 h, diluted with methanol and dioxane, evaporated and co-evaporated with dioxane (3×60 ml) to dryness. The solid was sonicated with a mixture of CH₃OH/CH₂Cl₂ (1:1, 80 ml), filtered and evaporated to solid. The yield solid was dissolved in CH₃OH (100 ml) and 0.4 ml of HCl (conc) was added. The mixture was stirred for 1 h, neutralized to pH 3.0 with 0.1 M NaHCO₃, concentrated, and extracted with CH₂Cl₂ (4×60 ml), The organic layers were combined, washed with 1M NaHCO₃/NaCl (conc.), dried over Na₂SO₄, filtered, evaporated and purified on SiO₂ chromatography eluted with EtAc/CH₂Cl₂ (1:3) to afford 615 mg (70%) of the title product. ¹H NMR (CDCl₃), 7.81 (d, 1H, J=5.7 Hz), 7.38~7.23 (m, 6H), 6.74 (s, 1H), 5.12 (dd, 2H, J=2.3, 21.8 Hz), 4.18 (m, 1H), 3.88 (d, 3H), 3.69 (m, 1H), 3.15 (m, 1H), 1.99 (m, 1H), 1.87 (m, 1H), 1.79-1.65 (m, 4H); ¹³C NMR 167.76, 163.31, 150.72, 148.48, 140.09, 136.46, 128.87, 128.28, 127.53, 121.77, 111.01, 71.02, 56.41, 49.84, 39.93, 24.76, 23.21, 18.62; MS m/z+ 373.2 (M+Na), 391.2 (M+Na+H₂O), 405.3 (M+Na+CH₃OH).

(R,Z)-3-Hydroxy-2-methoxy-7,8,9,10-tetrahydrobenzo[e]pyrido[1,2-a][1,4]diazepin-12(6aH)-one (242)

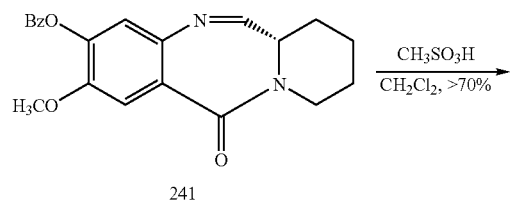

To (R,Z)-3-(benzyloxy)-2-methoxy-7,8,9,10-tetrahydrobenzo[e]pyrido[1,2-a][1,4]diazepin-12(6aH)-one (241) (215 mg, 0.614 mmol) in 25 ml of CH₂Cl₂ at 0° C. was added 25 ml of CH₂SO₃H. The mixture was stirred at 0° C. for 10 min and then at RT for 2 h, diluted with CH₂Cl₂, neutralized with cold 1.0 M NaHCO₃, extracted with CH₂Cl₂, dried over Na₂SO₄, filtered, evaporated and purified on SiO₂ chromatography eluted with CH₃OH/CH₂Cl₂ (1:15) to afford 122 mg (70%) of the title product. ¹H NMR (CDCl₃), 7.75 (d, 1H, J=5.7 Hz), 7.28 (s, 1H), 6.70 (s, 1H), 4.08 (m, 1H), 3.83 (d, 3H), 3.61 (m, 1H), 3.08 (m, 1H), 1.91 (m, 1H), 1.81 (m, 1H), 1.71~1.55 (m, 4H); ¹³C NMR 167.81, 163.46, 148.53, 145.71, 140.84, 121.23, 111.89, 111.39, 56.45, 49.83, 39.96, 24.71, 23.22, 18.60; MS m/z+ 283.7 (M+Na).

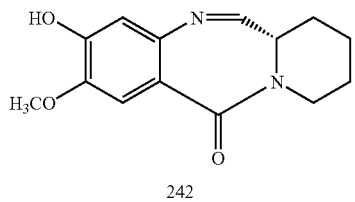

(5Z,5'Z,6aR,6a'R)-3,3'-(5-(2-(4-Acetylphenoxy) ethoxy)-1,3-phenylene)bis(methylene)bis(oxy)bis(2-methoxy-7,8,9,10-tetrahydrobenzo[e]pyrido[1,2-a][1,4]diazepin-12(6aH)-one) (243)

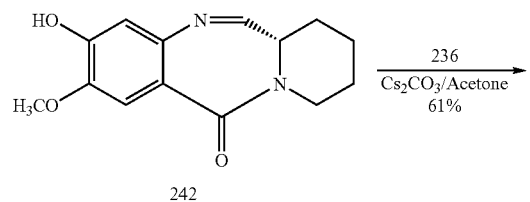

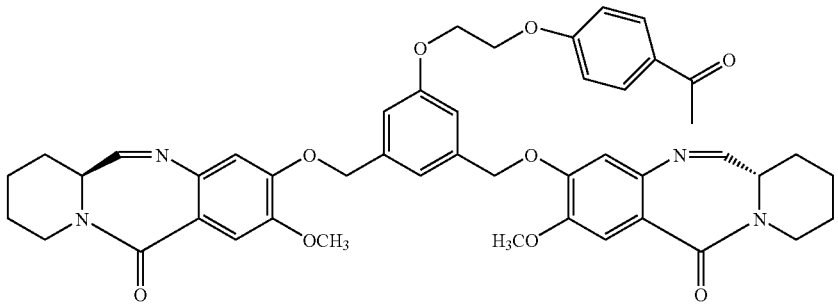

To a stirring solution of (R,Z)-3-hydroxy-2-methoxy-7,8,9,10-tetrahydrobenzo[e]pyrido[1,2-a][1,4]diazepin-12(6aH)-one (242) (42 mg, 0.16 mmol), Cs₂CO₃ (100 mg, 0.307 mmol), KI (3.2 mg, 0.018 mmol) in 5 ml of acetone was added 1-(4-(2-(3,5-bis(bromomethyl)phenoxy)ethoxy)phenyl) ethanone (236) (36 mg, 0.081 mmol). The mixture was stirred over night, evaporated and purified on HPLC preparative C-18 column (Φ10 mm×200 mm column, flow rate 9 mL/min and a gradient solvent system going from 80:20 solvent A:B at time 0-5 min to 50:50 A:B at 15 min then to 30:70 A:B at 25 min until to 10:90 A:B at 30 min. Solvent A—water, solvent B—dioxane) and lyophilized to afford a white solid 39.1 mg (61%) of the title compound. ¹H NMR (DMF-d₇), 8.30 (m, 2H), 7.75 (d, 2H, J=5.7 Hz), 7.30 (s, 2H), 7.01 (m, 2H), 6.71 (s, 2H), 6.68 (s, 1H), 6.63 (s, 2H), 5.21 (s, 4H), 4.43 (m, 2H), 4.32 (m, 2H), 4.08 (m, 2H), 3.83 (s, 6H), 3.61 (m, 2H), 3.08

(m, 2H), 2.56 (s, 3H), 1.91 (m, 2H), 1.81 (m, 2H), 1.71~1.55 (m, 8H); MS m/z+ 823.2 (M+Na), 839.3 (M+K), 857.3 (M+K+H₂O); MS m/z− 799.2 (M−H).

tert-Butyl 2-(4-(2,5-dioxo-2,5-dihydro-1H-pyrrol-1-yl)butanoyl)hydrazinecarboxylate (245)

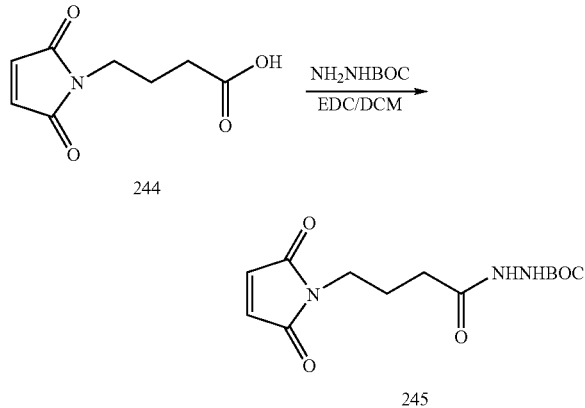

4-Maleimidobutyric acid (245 mg, 1.33 mmol), tert-butyl hydrazinecarboxylate (201 mg, 1.52 mmol) and EDC (400 mg, 2.08 mmol) in 5 ml of CH₂Cl₂, were stirred overnight under Ar, washed with 1 M NaH₂PO₄/NaCl (conc), dried over MgSO₄, filtered, evaporated and purified on SiO₂ chromatography eluted with MeOH/DCM (1:25) to afford 335 mg (85%) of the title compound. ¹H NMR (CDCl₃), 7.83 (br, 1H), 6.65 (s, 2H), 6.50 (br, 1H), 3.58 (t, 2H, J=6.3 Hz), 2.15 (t, 2H, J=7.0 Hz), 1.90 (dt, 2H, J=6.8, 13.4 Hz), 1.40 (s, 9H); ¹³C NMR 171.30, 155.61, 134.41, 82.00, 37.13, 31.38, 28.36, 24.95; MS m/z+ 320.2 (M+Na).

4-(2,5-Dioxo-2,5-dihydro-1H-pyrrol-1-yl)butanehydrazide trifluoroacetic acid salt (246)

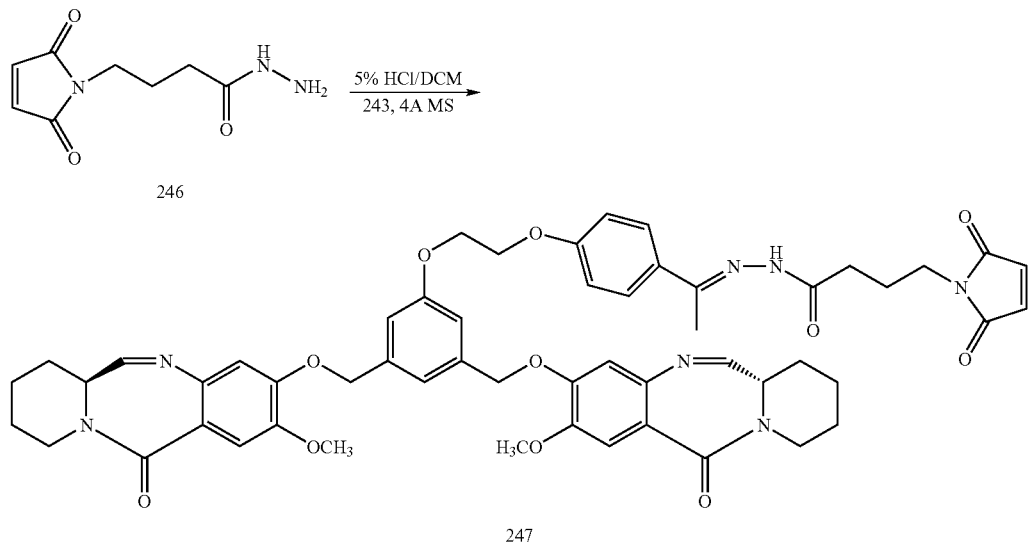

To tert-Butyl 2-(4-(2,5-dioxo-2,5-dihydro-1H-pyrrol-1-yl)butanoyl)-hydrazinecarboxylate (245) (200 mg, 0.673 mmol) in 8 ml of DCM was added 2 ml of TFA. The mixture was stirred for 45 min, diluted with ethanol/toluene (8 ml, 1:1), evaporated and co-evaporated with ethanol/toluene (3×10 ml), crystallized with ethanol/EtAc/Hexane, filtered, and dried under vaccum to afford 188 mg (90%) of the title compound. ¹H NMR (CD₃OD) 6.72 (s, 2H), 5.39 (s, 0.6H), 3.47 (t, 2H, J=6.6 Hz), 2.20 (m, 2H), 1.85 (m, 2H); ¹³C NMR 172.72, 135.56, 54.93, 39.20, 37.99, 25.20; MS m/z+ 197.9 (M+H).

(E)-N'-(1-(4-(2-(3,5-bis(((S,Z)-2-methoxy-12-oxo-6a,7,8,9,10,12-hexahydrobenzo[e]pyrido[1,2-a][1,4]diazepin-3-yloxy)methyl)phenoxy)ethoxy)phenyl)ethylidene)-4-(2,5-dioxo-2,5-dihydro-1H-pyrrol-1-yl)butanehydrazide (247)

4-(2,5-Dioxo-2,5-dihydro-1H-pyrrol-1-yl)butanehydrazide trifluroacetic acid salt (246) (3 mg, 0.0096 mmol), (5Z,5'Z,6aR,6a'R)-3,3'-(5-(2-(4-Acetylphenoxy)ethoxy)-1, 3-phenylene)bis(methylene)bis(oxy)bis(2-methoxy-7,8,9,10-tetrahydrobenzo[e]pyrido[1,2-a][1,4]diazepin-12(6aH)-one) (243) (7.5 mg, 0.0093 mmol) and 50 mg 4 Å molecular sieves was stirred in 2 ml of dry 5% HAc in DCM (one day earlier dried by 4 Å molecular sieves) for 2 h, neutralized with 0.5 ml of DIPEA, evaporated and purified on HPLC preparative C-18 column (Φ10 mm×200 mm column, flow rate 9 mL/min and a gradient solvent system going from 80:20 solvent A:B at time 0-5 min to 50:50 A:B at 15 min then to 30:70 A:B at 25 min until to 10:90 A:B at 30 min. Solvent A—water, solvent B—methanol/dioxane (2:1)) and lyophilized to afford a white solid 5.6 mg (61%) of the title compound. MS m/z+ 1066.3 (M+2CH$_3$OH+Na).

Example 13

Preparation of huN901-IGN-07 Conjugate:

huN901 antibody that binds to the CD56 antigen was selected for conjugation of IGN derivatives. A solution of huN901 antibody at a concentration of 3 mg/mL in an aqueous buffer containing 0.05 M N-(2-hydroxyethyl)-piperazine-N'-2-ethanesulfonic acid (HEPES) and 2 mM ethylenediaminetetra-acetic acid (EDTA), pH 8 was treated with a 20-fold molar excess of a solution of IGN-07 NHS ester in dimethylacetamide (DMA) such that the final concentration of DMA in the buffer was 10% v/v. The reaction mixture was stirred at room temperature for 120 min and then loaded onto a Sephadex G25 gel filtration column (HiPrep™ 26/10 Desalting Column GE#17-5087-01) that has been previously equilibrated into an aqueous buffer containing 0.01 M sodium citrate, 0.135 M sodium chloride, pH 5.5. The conjugated antibody-containing fractions are collected and pooled to yield product. The pooled sample was dialyzed overnight against the same elution buffer (0.01 M sodium citrate, 0.135 M sodium chloride, pH 5.5) to further purify the product.

The final conjugate was assayed spectrophotometrically using the extinction coefficients that were determined for IGN-07 ($\delta_{330\ nm}$=15,231 M-1 cm-1 and $\epsilon_{280\ nm}$=26,864 M-1 cm-1) and huN901 antibody ($\epsilon_{280\ nm}$=225,000 M-1cm-1). An average of 3.1 IGN molecules per molecule of antibody were linked.

Preparation of IGN-10 (Compound 51) Stock Solution:

A solution of IGN-10 was made fresh to a 0.004 M stock based on a molecular weight of 975.14 g/mole in dimethylacetamide (DMA). The stock solution was assayed spectrophotometrically using a reference extinction coefficient determined at 330 nm ($\epsilon_{330\ nm}$=15,500 M-1 cm-1).

Example 14

Preparation of muB38.1-IGN-10 Conjugate:

muB38.1 antibody that binds to the EpCAM antigen was selected for conjugation of IGN derivatives through a disulfide bond. A solution of muB38.1 antibody at a concentration of 2.5 mg/mL in an aqueous buffer containing phosphate buffered saline (PBS) pH 7.4 was treated with 120 molar excess of 1-homocysteine thiolactone for 12 hr at 37° C. The reaction mixture was loaded onto a Sephadex G25 gel filtration column (HiPrep™ 26/10 Desalting Column GE#17-5087-01) that was previously equilibrated in PBS pH 7.4. Fractions containing antibody are collected and pooled and assayed for reactive thiol content using the Ellman's assay. The modified antibody was then treated with a 4-fold molar excess of IGN-10 (in DMA) per free thiol and allowed to react at room temperature for 8 hr. The reaction mixture was loaded onto a Sephadex G25 gel filtration column (HiPrep™ 26/10 Desalting Column GE#17-5087-01) that has been previously equilibrated into an aqueous buffer containing 0.01 M sodium citrate, 0.135 M sodium chloride, pH 5.5. The conjugated antibody-containing fractions are collected and pooled to yield product. The pooled sample was dialyzed overnight against the same elution buffer (0.01 M sodium citrate, 0.135 M sodium chloride, pH 5.5) to further purify the product.

The final conjugate was assayed spectrophotometrically using the extinction coefficients that were determined for IGN-10 ($\epsilon_{330\ nm}$=15,500 M-1 cm-1 and $\epsilon_{280\ nm}$=26,864 M-1 cm-1) and muB38.1 antibody ($\epsilon_{280\ nm}$=215,525 M-1cm-1). An average of 0.7 IGN molecules per molecule of antibody was linked.

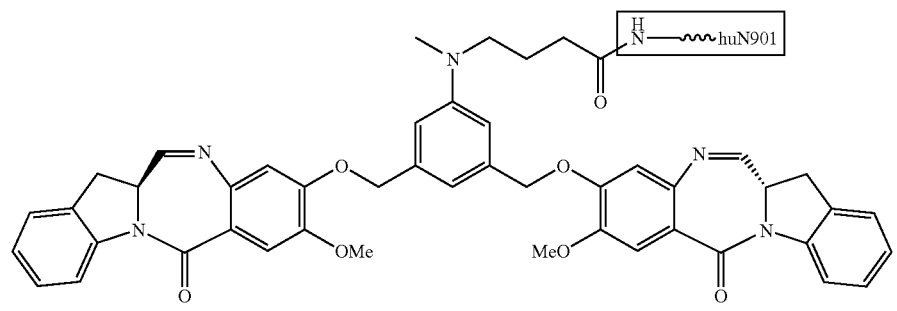

huN901-IGN-07

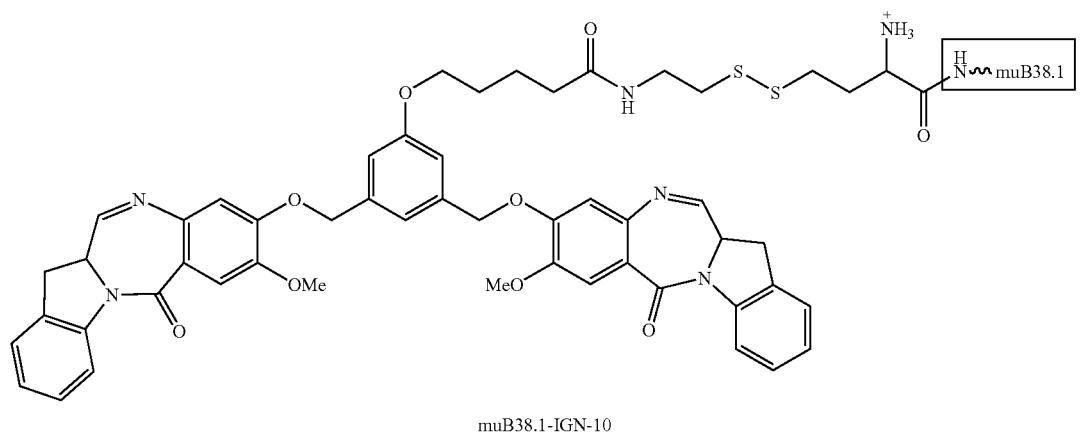

muB38.1-IGN-10

Example 15

DNA Probe Assay for Measuring IGN Dimer Binding and Alkylation to Double Stranded DNA (dsDNA):

Reaction conditions: dsDNA (25 µM final concentration) in 100 mM TRIS, 1 mM EDTA, pH 8 was mixed with 3.7 molar equivalents of IGN-01 (compound 18), IGN-02 (compound 19), or IGN-09 (compound 15) dissolved in acetonitrile (final acetonitrile concentration<2% by volume). The reaction was incubated at 15° C. (below TM of the dsDNA) and 10 µl aliquots are injected on reverse phase-HPLC at various time points after mixing HPLC conditions: Waters Xbridge C8 2.1×50 mm column, Buffer A: 100 mM hexafluoroisopropanol, 16.3 mM triethylamine, in water, Buffer B: Methanol; 98% A→100% B over 32 min, 0.25 ml/min flow, 60° C. column heat, 260 nm detection. Areas under the curve (AUC) for the probe DNA peak and the resulting IGN/DNA adduct peak are used to determine the % crosslinking at each time point of incubation.

DNA annealing: single stranded DNA (Invitrogen) was annealed into dsDNA using a Peltier thermal cycler (PTC-200, MJ Research). 1 mM DNA in 100 mM TRIS, 1 mM EDTA pH 8 was heated to 80° C. and then gradually cooled to 4° C. over 90 min in 15 degree steps. The resulting dsDNA was kept at 4° C. until used in the assay. IGN-01, IGN-02, and IGN-09 did not form covalent adducts with single stranded DNA (ssDNA) in control experiments.

Example 16

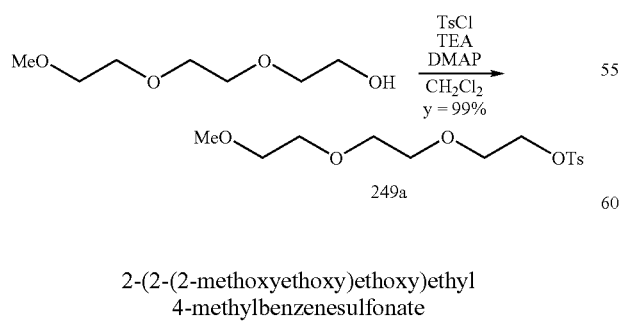

2-(2-(2-methoxyethoxy)ethoxy)ethyl 4-methylbenzenesulfonate

To a stirred solution of 2-(2-(2-methoxyethoxy)ethoxy)ethanol (1.64 g, 10 mmol) in anhydrous dichloromethane (30 mL) was added triethylamine (2.53 g, 25 mmol), tosyl chloride (3.81 g, 20 mmol) and DMAP (0.061 g, 0.5 mmol) subsequently at room temperature. The mixture continued to be stirred overnight and worked up by diluted with ethyl acetate and filtered to remove the triethylamine hydrochloride solid. The solid was washed with ethyl acetate and the filtrate was evaporated. The residue was diluted with ethyl acetate and filtered to remove the additional precipitate. The filtrate was evaporated to give the crude product as liquid. It was purified by silica gel chromatography (dichloromethane/methanol) to give compound 249a as an oil (3.16 g, yield =99%). $^1$H NMR (400 Hz, CDCl$_3$): δ 7.81 (d, J=8.0 Hz, 2H), 7.35 (d, J=8.0 Hz, 2H), 4.17 (t, J=3.2 Hz, 2H), 3.70 (t, J=4.8 Hz, 2H), 3.64-3.60 (m, 6H), 3.54 (t, J=4.8 Hz, 2H), 3.38 (s, 3H), 2.46 (s, 3H); $^{13}$C NMR (400 Hz, CDCl$_3$): 67 144.7, 133.0, 129.8, 127.9, 71.9, 70.7, 70.52, 70.50, 69.2, 68.6, 59.0, 21.6; MS (m/z): found 341.1 (M+Na)$^+$.

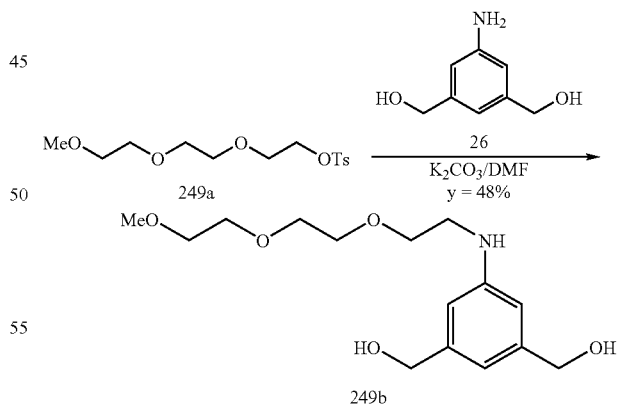

(5-(2-(2-(2-methoxyethoxy)ethoxy)ethylamino)-1,3-phenylene)dimethanol

To the mixture of the tosylate 249a (1.85 g, 5.81 mmol) and aniline compound 26 (1.78 g, 11.6 mmol) in anhydrous DMF (9 mL) was added anhydrous potassium carbonate (1.61 g, 11.6 mmol). The mixture was heated to 85° C. and stirred at that temperature overnight. The solution was cooled to room temperature and diluted with dichloromethane. It was filtered through celite and the solid was washed with dichloromethane. The filtrate was evaporated and the residue was diluted with dichloromethane and filtered again to remove the additional solid. The filtrate was evaporated and the residue was purified by silica gel chromatography (dichloromethane/methanol) to give compound 249b as a light yellowish oil (835 mg, yield=48%). $^1$H NMR (400 Hz, CDCl$_3$): δ 6.60 (s, 1H), 6.47 (s, 2H), 4.48 (s, 4H), 4.31 (bs, 1H), 3.66-3.59 (m, 8H), 3.55-3.52 (m, 2H), 3.36 (s, 3H), 3.24 (t, J=4.8 Hz, 2H); $^{13}$C NMR (400 Hz, CDCl$_3$): δ 148.5, 142.4, 114.6, 110.7, 71.8, 70.4, 70.3, 70.1, 69.4, 64.9, 58.9, 43.5; MS (m/z): found 322.2 (M+Na)$^+$.

Compound 249c (IGN-14 Linker):

To the solution of compound 249b (319 mg, 1.07 mmol) and methyl 4-bromobutyrate (248 mg, 1.37 mmol) in anhydrous acetonitrile (5 mL) was added anhydrous potassium carbonate (177 mg, 1.28 mmol). The mixture was stirred and heated at reflux (86° C. oil bath) overnight. It was cooled to room temperature and diluted with dichloromethane. The mixture was filtered through celite and the filtrate was evaporated. The residue was purified by silica gel chromatography (dichloromethane/methanol) to give compound 249c (IGN-14 linker) as colorless oil (246 mg, yield=58%). $^1$H NMR (400 Hz, CDCl$_3$): δ 6.69 (s, 2H), 6.66 (s, 1H), 4.64 (s, 4H), 3.71 (s, 3H), 3.64-3.62 (m, 8H), 3.57-3.54 (m, 4H), 3.40-3.38 (m, 5H), 2.38 (t, J=7.2 Hz, 2H), 1.93 (p, J=7.2 Hz, 2H); MS (m/z): found 422.3 (M+Na)$^+$.

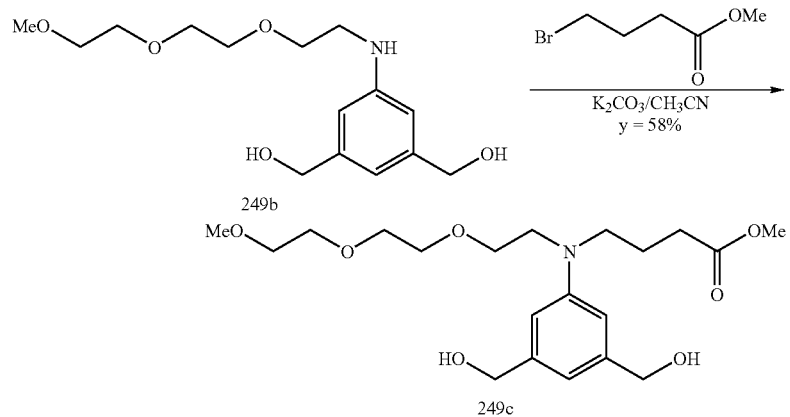

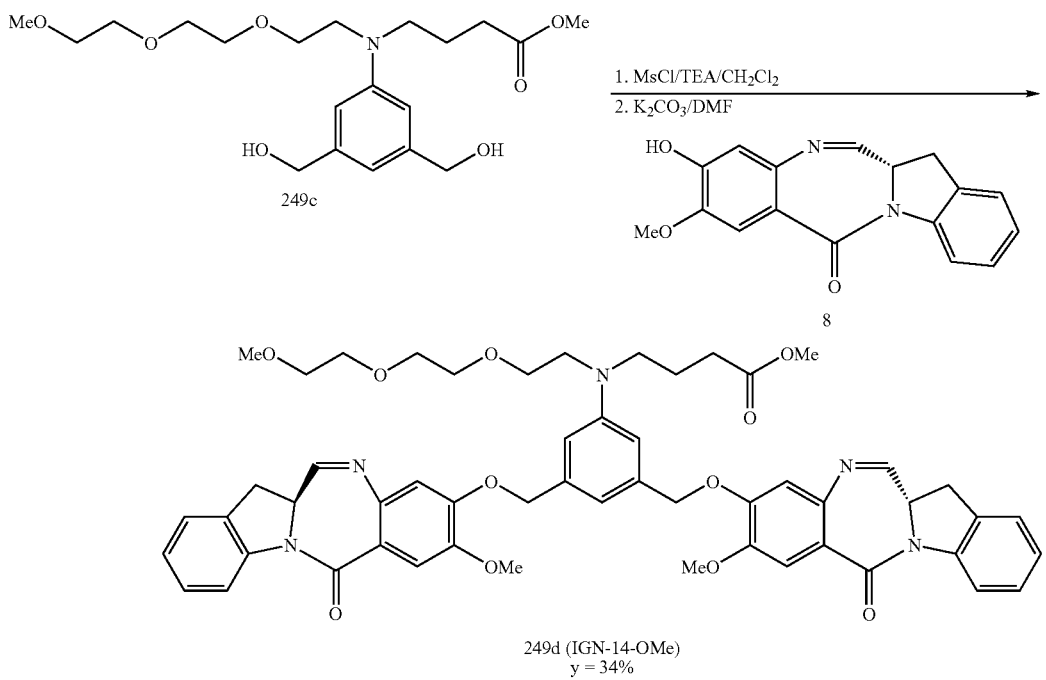

Compound 249d (IGN-14-OMe):

To a stirred solution of compound 249c (120 mg, 0.3 mmol) in anhydrous dichloromethane (3 mL) was added triethylamine (146 µl, 1.05 mmol). The mixture was cooled to −10° C. and methanesulfonyl chloride (70 µl, 0.9 mmol) was added slowly in 15 minutes. The solution continued to be stirred between −10° C. to −5° C. for 60 minutes and quenched by addition of ice/water. It was diluted with ethyl acetate and washed with cold water. The organic layer was dried over anhydrous sodium sulfate, filtered, evaporated and high vacuumed to give the mesylate as colorless oil. The mesylate was transferred to a 10 mL round bottom flask with ethyl acetate, evaporated and high vacuumed. Compound 8 (221 mg, 0.75 mmol) was added followed by addition of anhydrous DMF (2 mL) and anhydrous potassium carbonate (207 mg, 1.5 mmol). The mixture was stirred at room temperature overnight. It was diluted with dichloromethane and washed with brine. The organic layer was dried over anhydrous sodium sulfate, filtered and evaporated. The residue was purified by preparative reverse phase HPLC (C18 column, eluted with $CH_3CN/H_2O$) to give compound 249d (IGN-14-OMe) as a light yellowish solid (98 mg, yield=34%). $^1$H NMR (400 Hz, $CDCl_3$): δ 8.29 (d, J=8.0 Hz, 2H), 7.86 (d, J=4.4 Hz, 2H), 7.58 (s, 2H), 7.31-7.26 (m, 4H), 7.12 (t, J=8.0 Hz, 2H), 6.88 (s, 2H), 6.83 (s, 1H), 6.76 (s, 2H), 5.18 (dd, $J_1$=23.2 Hz, $J_2$=12.4 Hz, 4H), 4.49 (dt, $J_1$=10.8 Hz, $J_2$=4.4 Hz, 2H), 3.99 (s, 6H), 3.73-3.52 (m, 19H), 3.40-3.37 (m, 5H), 2.35 (t, J=7.2 Hz, 2H), 1.90 (p, J=7.2 Hz, 2H); $^{13}$C NMR (400 Hz, $CDCl_3$): δ 173.7, 164.9, 163.2, 151.1, 148.5, 148.4, 142.1, 140.2, 137.8, 129.7, 128.2, 124.9, 120.7, 117.0, 113.8, 112.0, 111.4, 110.4, 72.0, 71.3, 70.7, 70.6, 68.6, 59.1, 56.3, 55.0, 51.7, 50.7, 32.7, 31.3, 22.4; MS (m/z): found 974.6 $(M+Na)^+$, 992.7 $(M+H_2O+Na)^+$, 1010.7 $(M+2H_2O+Na)^+$, 950.3 $(M-H)^-$, 1022.3 $(M+4H_2O-H)^-$.

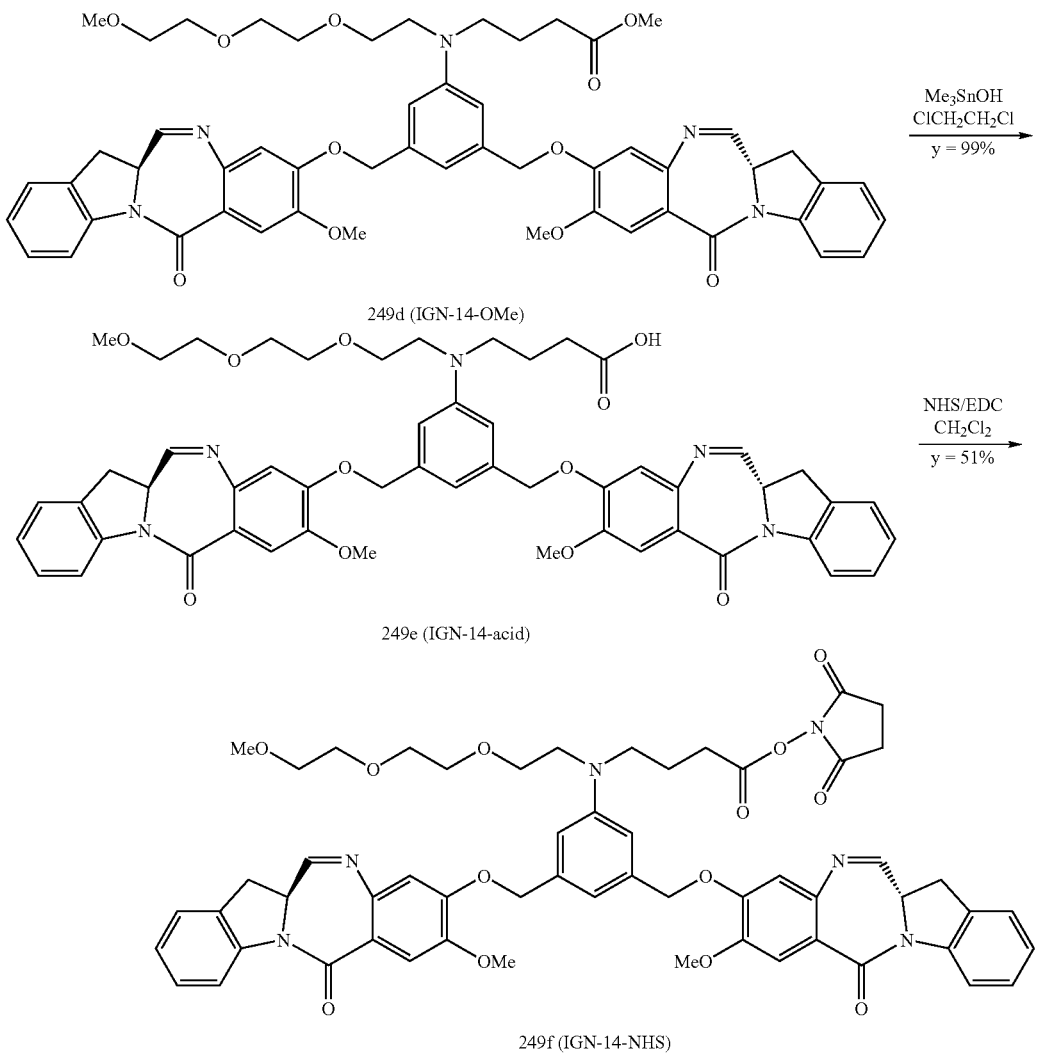

249d (IGN-14-OMe)

249e (IGN-14-acid)

249f (IGN-14-NHS)

Compound 249f (IGN-14-NHS):

To the solution of compound 249d (105 mg, 0.11 mmol) in anhydrous 1,2 dichloroethane (2 mL) was added trimethyltin hydroxide (299 mg, 1.65 mmol). The mixture was heated to 80° C. and stirred overnight. It was cooled to room temperature, diluted with dichloromethane and washed with mixed solution of saturated sodium chloride and 5% hydrochloric acid (~1 mL), then brine. The organic layer was dried over anhydrous sodium sulfate, filtered and evaporated. The residue was passed a short silica gel column and eluted with dichloromethane/methanol to remove the extra trimethyltin hydroxide. The product fractions were evaporated and high vacuumed to give the acid 249e as a yellowish solid (102 mg, yield=99%). MS (m/z): found 936.1 (M−H)⁻, 960.3 (M+Na)⁺. Compound 249e was then dissolved in anhydrous dichloromethane (1 mL). N-hydroxysuccinimide (NHS, 37.5 mg, 0.326 mmol) and N-(3-dimethylaminopropyl)-N'-ethyl-carbodiimide hydrochloride (EDC, 62.5 mg, 0.326 mmol) was added subsequently. The mixture was stirred at room temperature overnight and diluted with dichloromethane, washed with brine and dried over anhydrous sodium sulfate. It was filtered, evaporated and the residue was purified by preparative reverse phase HPLC (C18 column, eluted with acetonitrile/water). The product fractions were combined and extracted with dichloromethane. The organic layers were dried over anhydrous sodium sulfate, filtered, evaporated and high vacuumed to give compound 249f (IGN-14-NHS) as a light yellowish solid (57.8 mg, yield=51%). $^1$H NMR (400 Hz, CDCl$_3$): δ 8.28 (d, J=7.6 Hz, 2H), 7.86 (d, J=4.4 Hz, 2H), 7.58 (s, 2H), 7.31-7.27 (m, 4H), 7.12 (t, J=7.6 Hz, 2H), 6.87 (s, 2H), 6.81 (s, 1H), 6.74 (s, 2H), 5.23 (dd, J$_1$=26.4 Hz, J$_2$=12.4 Hz, 4H), 4.49 (dt, J$_1$=10.8 Hz, J$_2$=4.4 Hz, 2H), 4.00 (s, 6H), 3.73-3.47 (m, 18H), 3.37 (s, 3H), 2.79-2.74 (m, 4H), 2.59 (t, J=7.2 Hz, 2H), 1.97 (p, J=7.2 Hz, 2H); MS (m/z): found 1057.4 (M+Na)⁺.

Example 17

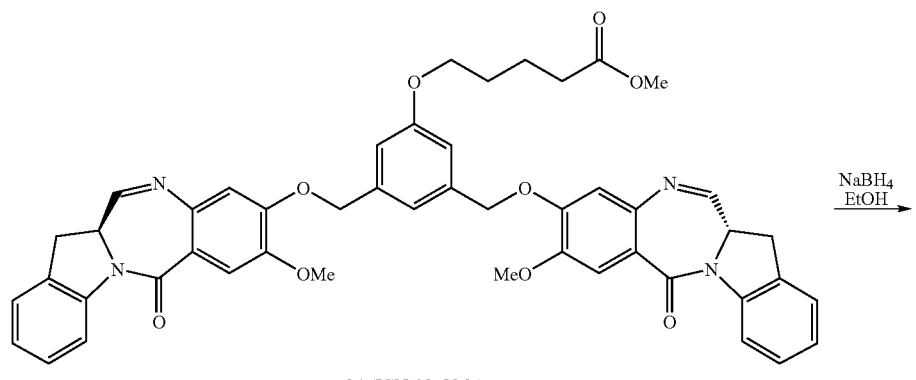

34 (IGN-03-OMe)

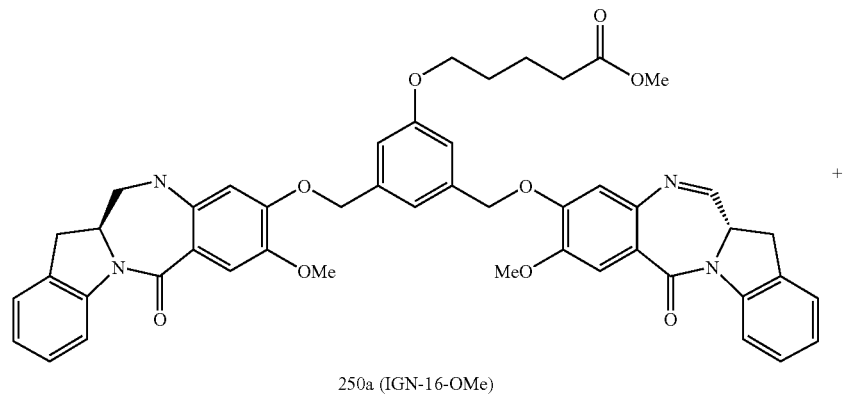

250a (IGN-16-OMe)

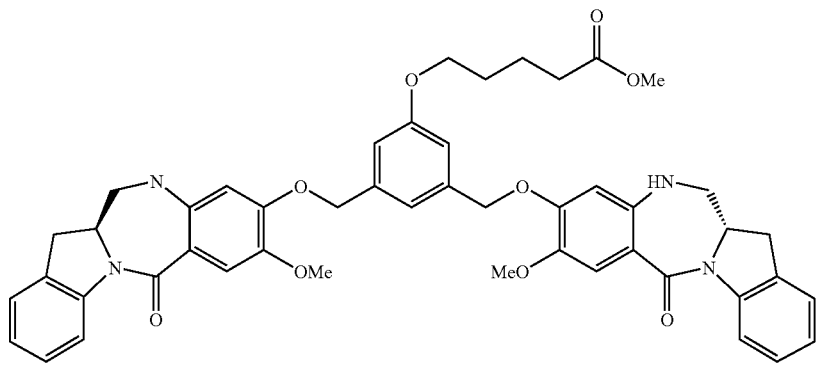

250b (IGN-18-OMe)

Compounds 250a (IGN-16-OMe) and 250b (IGN-18-OMe):

To a stirred solution of compound 34 (111 mg, 0.135 mmol) in absolute ethanol (1.0 mL) and anhydrous dichloromethane (0.5 mL) was added sodium borohydride (1.0 mg, 0.027 mmol) at 0° C. After 30 minutes, the ice/water bath was removed and the reaction mixture continued to be stirred at room temperature for 3 hours. The reaction was quenched by addition of saturated ammonium chloride and diluted with dichloromethane. The mixture was separated and the organic layer was washed with brine, dried over anhydrous sodium sulfate and filtered. The solvents were removed under reduced pressure and the residue was purified by preparative reverse phase HPLC (C 18 column, eluted with acetonitrile/water) to give compounds 250a (IGN-16-OMe, 6.6 mg) and 250b (8.0 mg) as white solid. 250a: MS (m/z), found 845.3 (M+Na)$^+$, 863.3 (M+H$_2$O+Na)$^+$. 250b: $^1$H NMR (400 Hz, CDCl$_3$), δ 8.34 (d, J=8.0 Hz, 2H), 7.49 (s, 2H), 7.27-7.03 (m, 6H), 6.89-6.87 (m, 3H), 6.05 (s, 2H), 4.96 (dd, J$_1$=20.8 Hz, J$_2$=12.8 Hz, 4H), 4.40-4.34 (m, 2H), 3.94-3.91 (m, 2H), 3.87 (s, 6H), 3.67 (s, 3H), 3.53-3.42 (m, 6H), 2.78 (dd, J$_1$=16.8 Hz, J$_2$=4.0 Hz, 2H), 2.38-2.37 (m, 2H), 1.79-1.77 (m, 4H); MS (m/z), found 847.3 (M+Na)$^+$.

Example 18

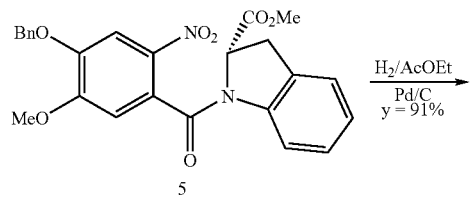

5

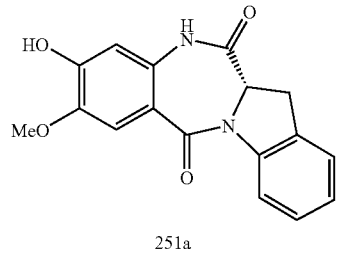

251a

Compound 251a:

To a stirred solution of compound 5 (840 mg, 1.82 mmol) in ethyl acetate (10 mL) was added palladium on charcoal (10%, 193 mg, 0.182 mmol). The flask was briefly vacuumed and replaced with H$_2$ in a balloon. The mixture continued to be hydrogenated for overnight and filtered through celite. The solid was washed with methanol and the filtrate was treated with 5% hydrochloric acid (0.1 mL). The solution was stripped under reduce pressure and the residue was purified by silica gel chromatography (dichloromethane/methanol) to give compound 251a as a white solid (512 mg, yield=91%). $^1$H NMR (400 Hz, CDCl$_3$), δ 8.21 (d, J=8.0 Hz, 1H), 8.09 (bs, NH), 7.53 (s, 1H), 7.31-7.25 (m, 2H), 7.12 (t, J=7.6 Hz, 1H), 6.61 (s, 1H), 6.22 (bs, 1H), 4.73 (dd, J$_1$=10.4 Hz, J$_2$=2.8 Hz, 1H), 4.07 (dd, J$_1$=16.4 Hz, J$_2$=2.4 Hz, 1H), 3.98 (s, 3H), 3.34 (dd, J$_1$=16.4 Hz, J$_2$=10.4 Hz, 1H); MS (m/z), found 333.1 (M+Na)$^+$, 308.9 (M−H)$^-$.

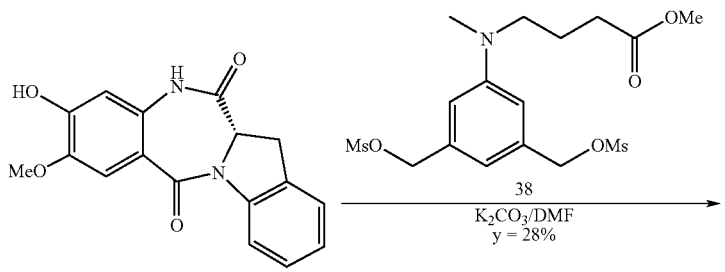

251a

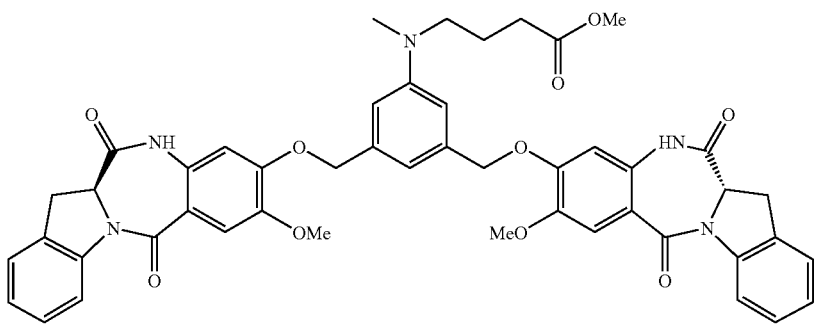

251b (IGN-17-OMe)

181

Compound 251b (IGN-17-OMe):

To a solution of compound 38 (0.165 mmol, prepared from 44 mg of compound 30 following the procedure described in example 6) and 251a (128 mg, 0.413 mmol) in anhydrous DMF (1.5 mL) was added anhydrous potassium carbonate (114 mg, 0.825 mmol). The mixture was stirred at room temperature overnight and diluted with dichloromethane, washed with brine and dried over anhydrous sodium sulfate and magnesium sulfate. It was filtered, evaporated and part of the residue was purified by preparative reverse phase HPLC (C18 column, eluted with acetonitrile/water) to give 1.9 mg of compound 251b as a white solid. The rest of the residue was purified by preparative thin layer chromatography (dichloromethane/methanol, 12:1) to give 36.8 mg of product as a white solid. Total 38.7 mg of compound 251b (IGN-17-OMe) was isolated (yield=28%). $^1$H NMR (400 Hz, CDCl$_3$): δ 8.61 (s, 2H), 8.15 (d, J=8.0 Hz, 7.48 (s, 2H), 7.25 (d, J=7.6 Hz, 2H), 7.20 (t, J=7.6 Hz, 2H), 7.07 (t, J=7.6 Hz, 2H), 7.07 (t, J=7.6 Hz, 2H), 6.73 (s, 1H), 6.69 (s, 2H), 6.58 (s, 2H), 5.02 (dd, J$_1$=17.6 Hz, J$_2$=13.2 Hz, 4H), 4.66 (dd, J$_1$=10.4 Hz, J$_2$=2.8 Hz, 2H), 4.00 (dd, J$_1$=16.4 Hz, J$_2$=2.4 Hz, 2H), 3.90 (s, 6H), 3.68 (s, 3H), 3.39-3.23 (m, 4H), 2.89 (s, 3H), 2.44-2.30 (m, 2H), 1.91-1.92 (m, 2H); $^{13}$C NMR (400 Hz, CDCl$_3$): δ 174.5, 169.1, 164.2, 151.6, 149.6, 146.9, 141.2, 137.3, 130.6, 129.4, 127.5, 124.9, 124.8, 119.6, 117.1, 114.2, 112.5, 110.9, 106.0, 71.4, 58.0, 56.2, 51.9, 51.7, 38.3, 31.1, 28.2, 21.8; MS (m/z), found 874.3 (M+Na)$^+$, 850.2 (M−H)$^−$.

Example 19

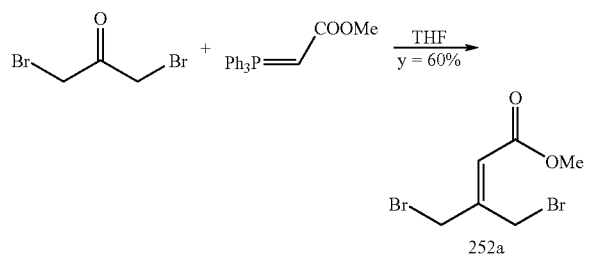

Compound 252a:

The mixture of 1,3-dibromoaceton (0.863 g, purity 75%, 3.0 mmol) and methyl (triphenylphosphoranylidene)acetate (1.505 g, 4.5 mmol) in anhydrous THF (15 mL) was heated to reflux for 4.5 hours. The solution was cooled to room temperature and evaporated. The residue was purified by silica gel chromatography (hexanes/ethyl acetate) to give compound 252a as colorless liquid (485 mg, yield=60%). $^1$H NMR (400 Hz, CDCl$_3$): δ 6.06 (s, 1H), 4.76 (s, 2H), 4.19 (s, 2H), 3.79 (s, 3H); $^{13}$C NMR (400 Hz, CDCl$_3$): δ 165.1, 150.4, 121.3, 51.8, 33.6, 25.5.

182

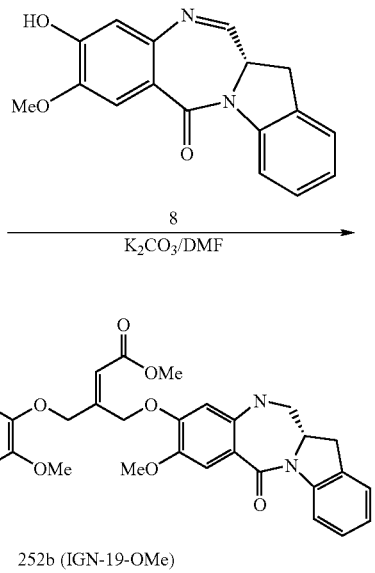

Compound 252b (IGN-19-OMe):

The mixture of compound 252a (32 mg, 0.118 mmol), monomer 8 (87 mg, 0.294 mmol) and anhydrous potassium carbonate (49 mg, 0.353 mmol) in anhydrous DMF (1 mL) was stirred at room temperature overnight. It was diluted with dichloromethane, washed with brine and dried over anhydrous sodium sulfate. The solution was filtered, evaporated and purified by silca gel chromatography (dichloromethane/methanol) to give 105 mg of compound 252b mixed with side products as yellowish foam. Part of the produxts was further purified by preparative reverse phase HPLC (C18 column, eluted with acetonitrile/water) to give 10 mg of compound 252b (IGN-19-OMe) as a white solid. MS (m/z): found 721.2 (M+Na)$^+$, 739.2 (M+H$_2$O+Na)$^+$, 757.2 (M+2H$_2$O+Na)$^+$, 697.1 (M−H)$^−$, 769.1 (M+4H$_2$O−H)$^−$.

Example 20

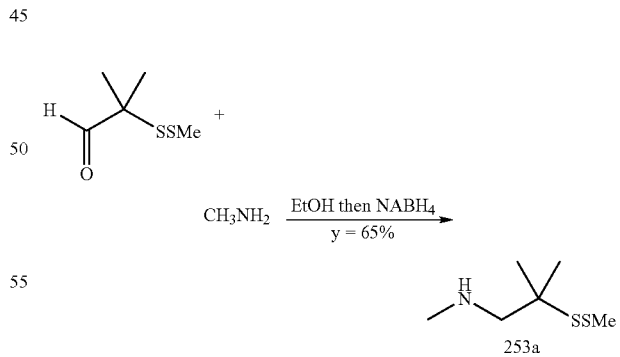

Compound 253a:

To a solution of 2-(methyldithio)-isobutyraldehyde (690 mg, 4.59 mmol) in absolute ethanol (15 mL) was added methylamine (629 μl, 33% wt, 5.05 mmol). The mixture was stirred at room temperature for four hours and cooled to 0° C. followed by addition of sodium borohydride (174 mg, 4.59 mmol). After one hour, the reaction was quenched with a few drops of cold 5% hydrochloric acid and then basified with saturated sodium bicarbonate. The mixture was diluted with dichloromethane and washed with brine. The organic layer was dried over anhydrous sodium sulfate, filtered and evaporated under reduce pressure. The residue was purified by silica gel chromatography (0.2% triethylamine in dichloromethane/methanol) to give volatile compound 253a as light yellowish liquid (491 mg, yield=65%). $^1$H NMR (400 Hz, CDCl$_3$): δ 2.61 (s, 2H), 2.45 (s, 3H), 2.39 (s, 3H), 1.32 (s, 6H), 1.20 (s, NH); $^{13}$C NMR (400 Hz, CDCl$_3$): δ 61.2, 51.7, 37.2, 26.5, 25.3; MS (m/z): found 166.0 (M+H)$^+$.

then brine. The organic layer was dried over anhydrous sodium sulfate, filtered and evaporated. The residue was purified by silica gel chromatography (dichloromethane/methanol) to give the acid 253b as a colorless oil (93.9 mg, yield=99%). $^1$H NMR (400 Hz, CDCl$_3$): δ 6.62 (s, 2H), 6.57 (s, 1H), 4.50 (s, 4H), 3.63-3.54 (m, 8H), 3.53-3.46 (m, 4H), 3.36-3.31 (m, 5H), 2.29 (t, J=6.8 Hz, 2H), 1.83 (p, J=6.8 Hz, 2H); $^{13}$C NMR (400 Hz, CDCl$_3$): δ 177.0, 148.2, 142.4, 113.8, 110.1, 71.9, 70.7, 70.6, 70.4, 68.8, 65.2, 59.0, 50.8, 50.7, 31.4, 22.3; MS (m/z): found 384.2 (M−H)$^-$, 408.4 (M+Na)$^+$.

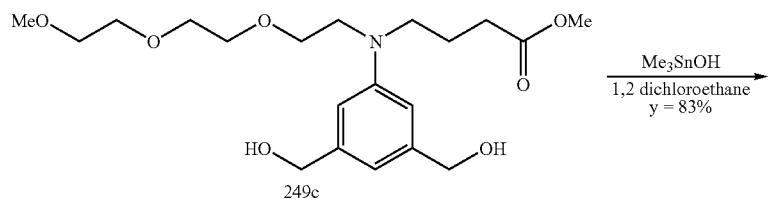

Compound 253b:

The mixture of compound 249c (117 mg, 0.293 mmol) and trimethyltin hydroxide (794 mg, 4.39 mmol) in anhydrous 1,2-dichloroethane (1.5 mL) was heated to 80° C. and stirred overnight. It was cooled to room temperature, diluted with dichloromethane and washed with mixed solution of saturated sodium chloride and 5% hydrochloric acid (~1 mL),

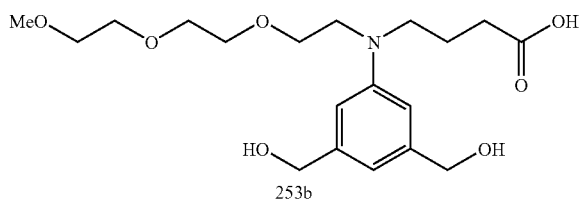

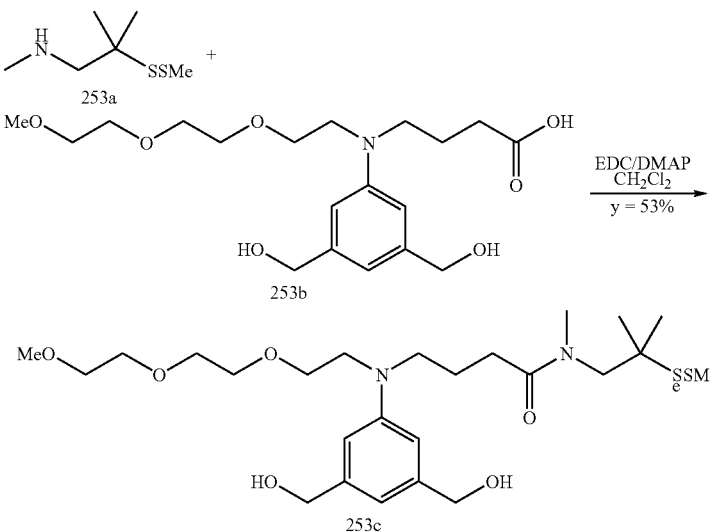

Compound 253c:

To a solution of amine 253a (44.3 mg, 0.268 mmol) and carboxylic acid 253b (93.3, 0.244 mmol) in anhydrous dichloromethane (1.5 mL) was added N-hydroxysuccinimide (NHS, 70.1 mg, 0.365 mmol) and DMAP (5.95 mg, 0.049 mmol). The mixture was stirred at room temperature overnight and diluted with dichloromethane, washed with saturated ammonium chloride and brine, dried over anhydrous sodium sulfate, filtered and evaporated. The residue was purified by silica gel chromatography (dichloromethane/methanol) to give compound 253c as colorless oil (69.1 mg, yield=53%). $^1$H NMR (400 Hz, CDCl$_3$): δ 6.71 (s, 2H), 6.64 (s, 1H), 4.57 (s, 4H), 3.63-3.59 (m, 8H+2OH), 3.54-3.51 (m, 4H), 3.38-3.34 (m, 3.08 (s, 2.35H), 3.00 (s, 0.65H), 2.86 (bs, 2H), 2.43 (s, 3H), 2.34 (t, J=6.8 Hz, 2H), 1.95-1.88 (m, 2H), 1.36 (s, 1.3H), 1.31 (s, 4.7H); $^{13}$C NMR (400 Hz, CDCl$_3$): δ 173.7, 148.5, 142.7, 113.2, 109.8, 72.0, 70.8, 70.7, 70.6, 68.9, 65.6, 59.1, 56.5, 53.0, 52.2, 51.0, 50.8, 38.8, 30.6, 26.6, 25.6, 22.3; MS (m/z): found 555.5 (M+Na)$^+$.

triethylamine (63 µl, 0.454 mmol). The mixture was cooled to −10° C. and methanesulfonyl chloride (30 µl, 0.389 mmol) was added slowly in 15 minutes. The solution continued to be stirred between −10° C. to −5° C. for 60 minutes and quenched by addition of ice/water. It was diluted with ethyl acetate and washed with cold water. The organic layer was dried over anhydrous sodium sulfate, filtered, evaporated and high vacuumed to give the mesylate as colorless oil. The mesylate was transferred to a 10 mL round bottom flask with ethyl acetate, evaporated and high vacuumed. Compound 8 (99 mg, 0.338 mmol) was added followed by addition of anhydrous DMF (1 mL) and anhydrous potassium carbonate (90 mg, 0.65 mmol). The mixture was stirred at room temperature overnight. It was diluted with dichloromethane and washed with brine. The organic layer was dried over anhydrous sodium sulfate, filtered and evaporated. The residue was purified by silica gel chromatography (dichloromethane/methanol) to give 150 mg yellowish foam, which was further purified by preparative reverse phase HPLC (C18 column, eluted with CH$_3$CN/H$_2$O) to give compound 253d as a light

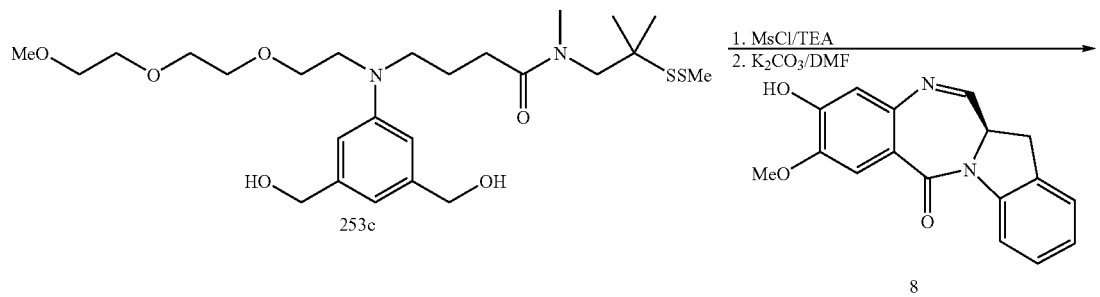

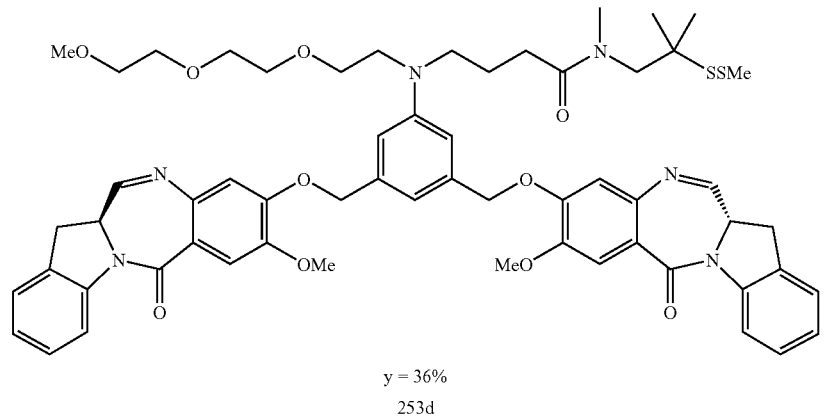

Compound 253d:

To a stirred solution of compound 253c (69.1 mg, 0.13 mmol) in anhydrous dichloromethane (1.5 mL) was added yellowish solid (50.7 mg, yield=36%). MS (m/z): found 1107.7 (M+Na)$^+$, 1125.7 (M+H$_2$O+Na)$^+$, 1143.7 (M+2H$_2$O+Na)$^+$, 1083.4 (M−H)$^-$, 1155.5 (M+4H$_2$O−H)$^-$.

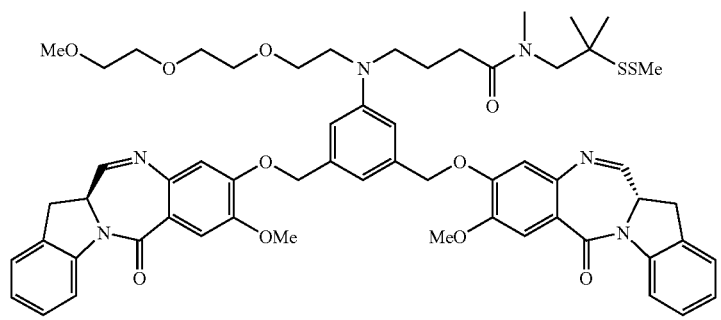 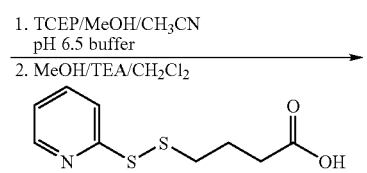

y = 36%
253d

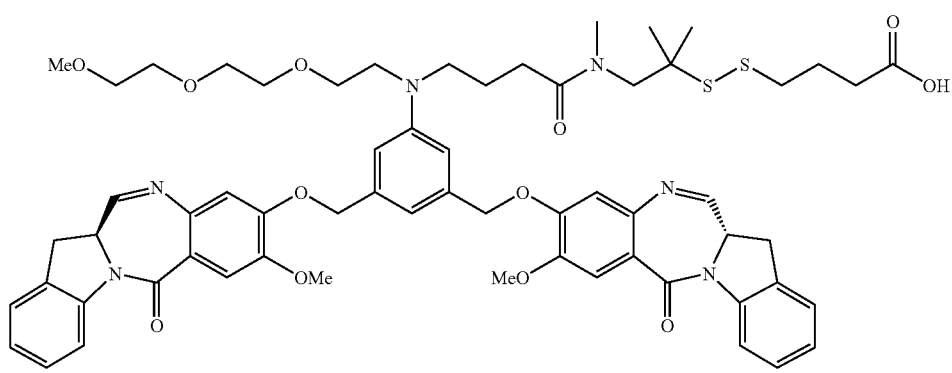

y = 30%
253e

Compound 253e:

To a small vial containing tris(2-carboxyethyl)phosphine hydrochloride (TCEP, 19.1 mg, 0.067 mmol) was added a few drops of deioned water. Saturated sodium bicarbonate was added dropwise until pH is about 7 indicated by a pH test paper. It was then diluted with pH 6.5 phosphate buffer (0.4 mL) to give a fresh TCEP solution. To a stirred solution of compound 253d (24.1 mg, 0.022 mmol) in methanol (3 mL) and acetonitrile (1 mL) was added the TCEP solution and stirred at room temperature for 1.5 hours. It was diluted with dichloromethane and washed with brine, dried over anhydrous sodium sulfate, filtered and evaporated to give the thiol as a yellowish solid (21.9 mg) which was directly used for next step (the thiol is not able to be purified due to aggregation). To a solution of the thiol (21.9 mg, 0.021 mmol) in anhydrous dichloromethane (0.1 mL) and methanol (0.4 mL) was added 4-(2-pyridyldithio)butanoic acid (24.2 mg, 0.105 mmol) and triethyl amine (29 µl, 0.211 mmol). The mixture was stirred at room temperature for five hours and quenched by saturated ammonium chloride. It was diluted with dichloromethane, separated and the organic layer was washed with brine, dried over anhydrous sodium sulfate, filtered and evaporated. The residue was purified by preparative reverse phase HPLC (C18 column, eluted with acetonitrile/water) to give compound 253e as a white solid (7.3 mg, yield=30%). $^1$H NMR (400 Hz, CDCl$_3$): δ 8.28 (d, J=7.6 Hz, 2H), 7.89 (bs, 2H), 7.60 (bs, 2H), 7.31-7.26 (m, 4H), 7.12 (t, J=7.6 Hz, 2H), 6.91-6.78 (m, 5H), 5.22-5.13 (m, 4H), 4.54-4.49 (m, 2H), 3.99 (s, 6H), 3.68-3.41 (m, 20H), 3.38 (s, 3H), 3.07 (s, 3H), 2.78-2.77 (m, 2H), 2.47 (bs, 2H), 2.35 (bs, 2H), 2.01-1.95 (m, 4H), 1.31 (s, 6H); MS (m/z): found 1179.7 (M+Na)$^+$, 1197.7 (M+H$_2$O+Na)$^+$, 1073.6 (M+H$_2$O–H)$^-$, 1191.5 (M+2H$_2$O–H)$^-$.

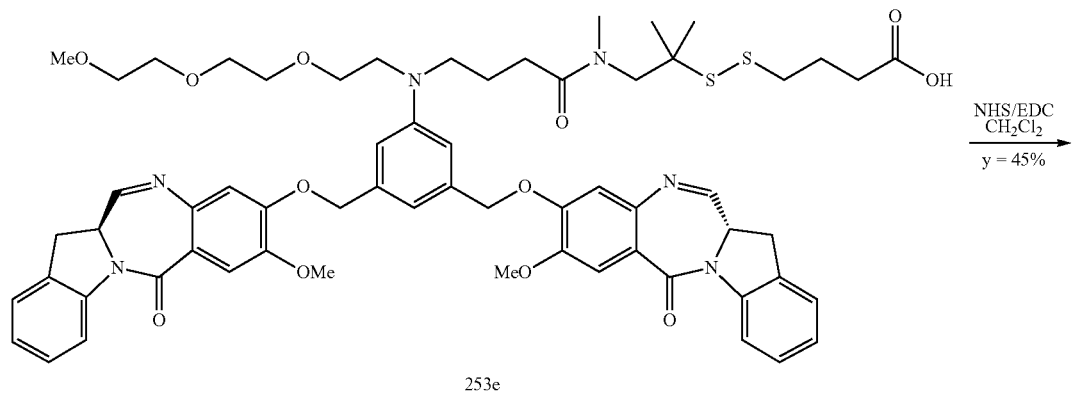

253e

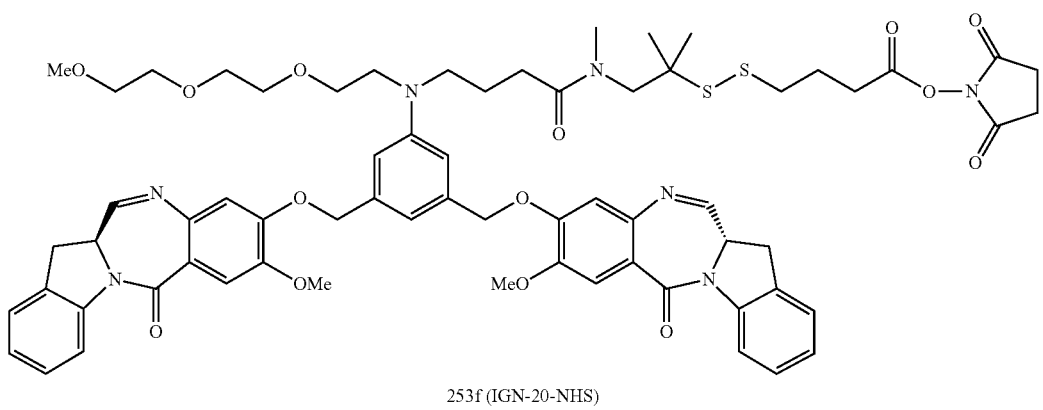

253f (IGN-20-NHS)

Compound 253f:

To a solution of compound 253e (9.0 mg, 0.00778 mmol) in anhydrous dichloromethane (0.5 mL) was added N-hydroxysuccinimide (NHS, 2.68 mg, 0.023 mmol) and N-(3-dimethylaminopropyl)-N'-ethylcarbodiimide hydrochloride (EDC, 4.47 mg, 0.023 mmol) subsequently. The mixture was stirred at room temperature overnight and diluted with dichloromethane, washed with brine and dried over anhydrous sodium sulfate. It was filtered, evaporated and the residue was purified by preparative reverse phase HPLC (C18 column, eluted with acetonitrile/water). The product fractions were combined and extracted with dichloromethane. The organic layers were dried over anhydrous sodium sulfate, filtered, evaporated and high vacuumed to give compound 253f (IGN-20-NHS) as a yellowish foam (4.4 mg, yield=45%). MS (m/z): found 1276.7 (M+Na)$^+$.

Example 21

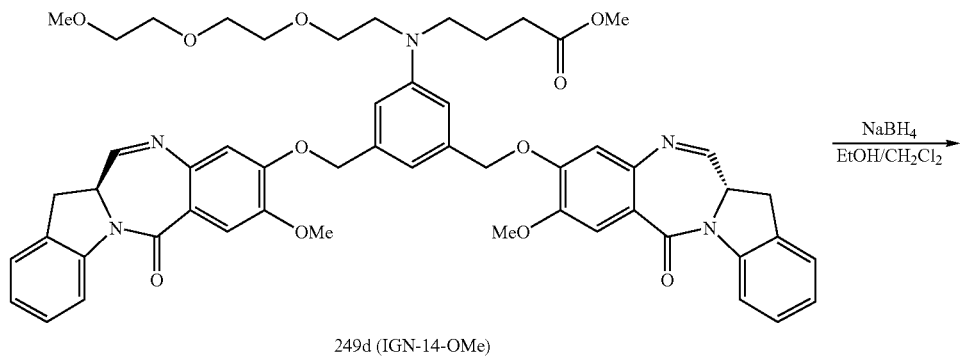

249d (IGN-14-OMe)

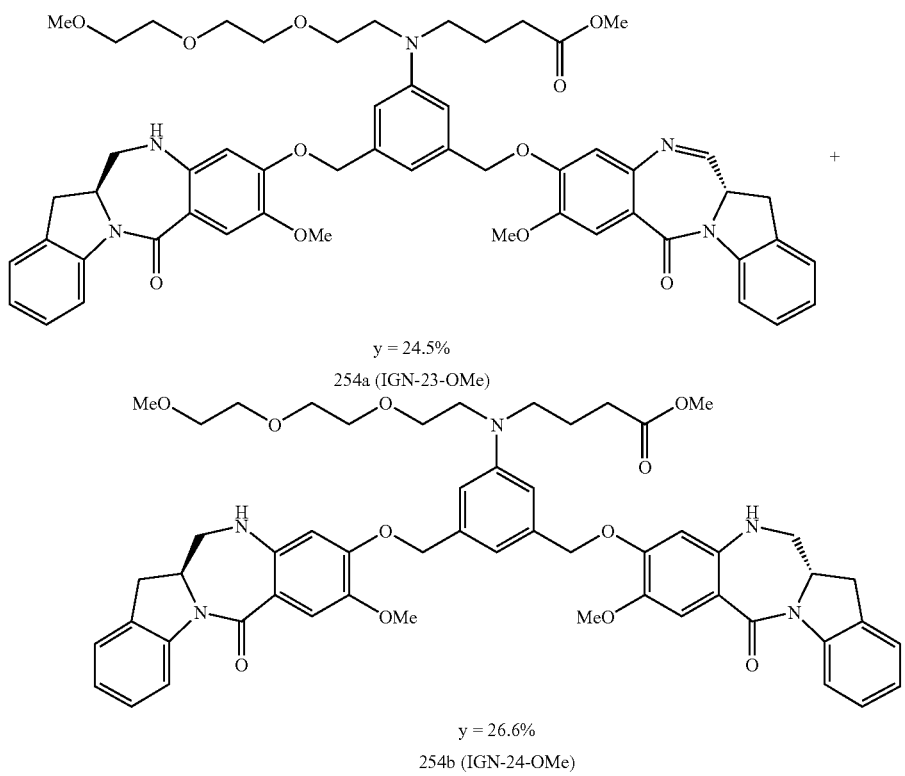

y = 24.5%
254a (IGN-23-OMe)

y = 26.6%
254b (IGN-24-OMe)

Compound 254a (IGN-23-OMe) and 254b (IGN-24-OMe):

To a stirred solution of compound 249d (91.8 mg, 0.103 mmol) in absolute ethanol (1.0 mL) and anhydrous dichloromethane (0.4 mL) was added sodium borohydride (0.4 mg, 0.0106 mmol) at 0° C. After 30 minutes, the ice/water bath was removed and the reaction mixture continued to be stirred at room temperature for 3 hours. The reaction was quenched by addition of saturated sodium ammonium chloride and diluted with dichloromethane. The mixture was separated and the organic layer was washed with brine, dried over anhydrous sodium sulfate and filtered. The solvents were removed under reduced pressure and the residue was purified by preparative reverse phase HPLC (C18 column, eluted with acetonitrile/water) to give compounds 254a (IGN-23-OMe, 24.2 mg, yield=24.5%) and 254b (IGN-24-OMe, 26.3 mg, yield=26.6%) as a yellowish solid. 254a: $^1$H NMR (400 Hz, $CDCl_3$): δ 8.34 (d, J=8.0 Hz, 1H), 8.27 (d, J=7.6 Hz, 1H), 7.83 (d, J=4.4 Hz, 1H), 7.57 (s, 1H), 7.46 (s, 1H), 7.29-7.02 (m, 6H), 6.87 (s, 1H), 6.75 (s, 1H), 6.70-6.66 (m, 2H), 6.10 (s, 1H), 5.21-5.02 (m, 4H), 4.49-4.39 (m, 2H), 3.99 (s, 3H), 3.89 (s, 3H), 3.66 (s, 3H), 3.64-3.41 (m, 19H), 3.39-3.34 (m, 4H), 2.78 (dd, $J_1$=16.4 Hz, $J_2$=3.6 Hz, 1H), 2.33 (t, J=7.2 Hz, 2H), 1.90-1.84 (m, 2H); $^{13}$C NMR (400 Hz, $CDCl_3$): δ 173.8, 166.8, 164.0, 163.5, 152.3, 151.2, 148.7, 148.5, 143.0, 142.1, 140.7, 140.2, 138.5, 137.8, 129.8, 129.7, 128.3, 127.9, 125.0, 124.7, 123.9, 120.9, 117.5, 117.0, 114.6, 113.4, 113.2, 112.1, 111.6, 110.2, 110.1, 104.2, 72.1, 71.4, 71.2, 70.80, 70.76, 70.70, 68.7, 59.2, 57.3, 56.5, 56.4, 55.1, 54.8, 51.8, 50.9, 50.7, 33.3, 32.7, 31.3, 22.4; MS (m/z), found 976.7 (M+Na)$^+$, 994.6 (M+$H_2O$+Na)$^+$; 254b: MS (m/z), found 978.7 (M+Na)$^+$.

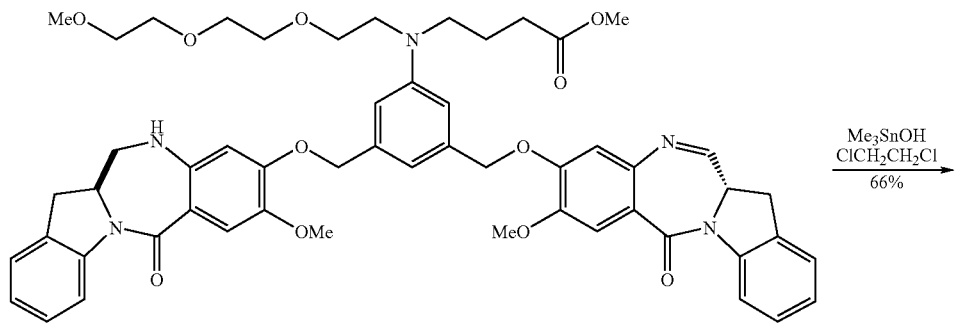

254a

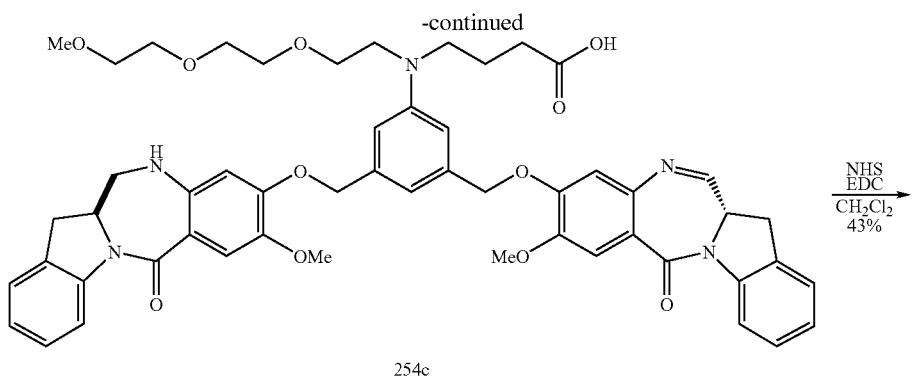

254c

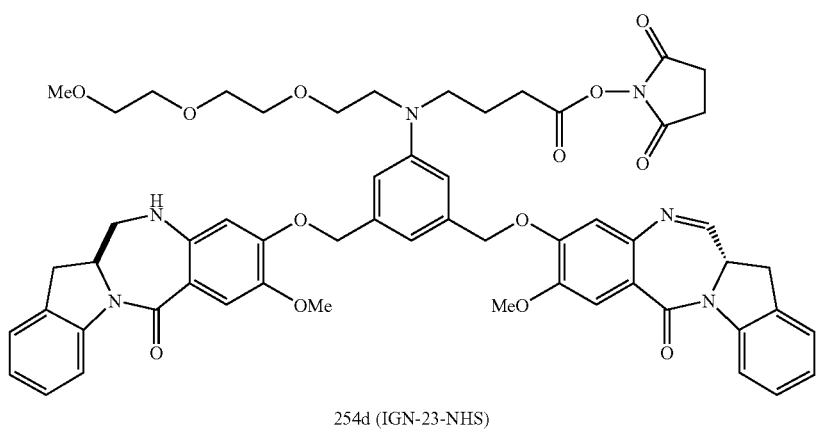

254d (IGN-23-NHS)

Compound 254c and 254d (IGN-23-NHS):

To the solution of compound 254a (31.8 mg, 0.033 mmol) in anhydrous 1,2 dichloroethane (1 mL) was added trimethyltin hydroxide (90 mg, 0.5 mmol). The mixture was heated to 80° C. and stirred overnight. It was cooled to room temperature, diluted with dichloromethane and washed with mixed solution of saturated sodium chloride and 5% hydrochloric acid (~1 mL), then brine. The organic layer was dried over anhydrous sodium sulfate, filtered and evaporated. The residue was passed a short silica gel column and eluted with dichloromethane/methanol to remove the extra trimethyltin hydroxide. The product fractions were evaporated and high vacuumed to give the acid 254c as a yellowish solid (20.8 mg, yield=66%). MS (m/z): found 938.2 (M–H)$^-$, 962.3 (M+Na)$^+$. Compound 254c (20.8 mg, 0.022 mmol) was then dissolved in anhydrous dichloromethane (1 mL). The reaction flask was briefly vacuumed and replaced with argon. N-hydroxysuccinimide (NHS, 5.09 mg, 0.044 mmol) and N-(3-dimethylaminopropyl)-N'-ethylcarbodiimide hydrochloride (EDC, 8.48 mg, 0.044 mmol) was added subsequently. The mixture was stirred at room temperature overnight and diluted with dichloromethane, washed with brine and dried over anhydrous sodium sulfate. It was filtered, evaporated and the residue was purified by preparative reverse phase HPLC (C18 column, eluted with acetonitrile/water). The product fractions were combined and extracted with dichloromethane. The organic layers were dried over anhydrous sodium sulfate, filtered, evaporated and high vacuumed to give compound 254d (IGN-23-NHS) as a light yellowish solid (9.8 mg, yield=43%). MS (m/z): found 1059.6 (M+Na)$^+$, 1077.6 (M+H$_2$O+Na)$^+$.

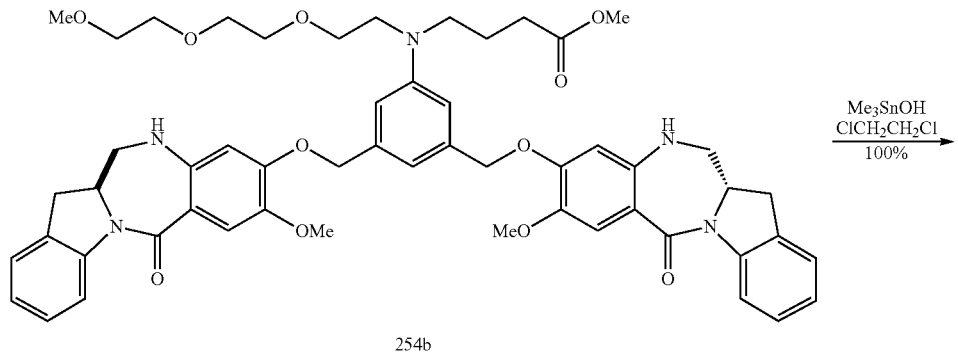

254b

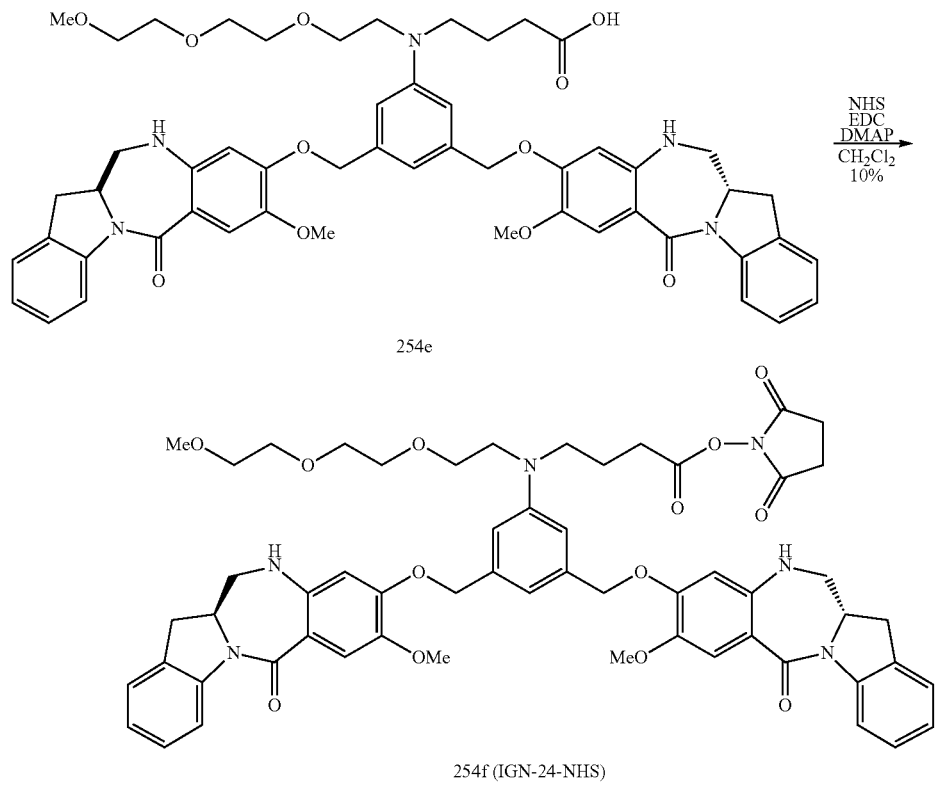

254e 254f (IGN-24-NHS)

Compound 254e and 254f (IGN-24-NHS):

To the solution of compound 254b (26.3 mg, 0.028 mmol) in anhydrous 1,2 dichloroethane (1 mL) was added trimethyltin hydroxide (74.6 mg, 0.413 mmol). The mixture was heated to 80° C. and stirred overnight. It was cooled to room temperature, diluted with dichloromethane and washed with mixed solution of saturated sodium chloride and 5% hydrochloric acid (~1 mL), then brine. The organic layer was dried over anhydrous sodium sulfate, filtered and evaporated. The residue was passed a short silica gel column and eluted with dichloromethane/methanol to remove the extra trimethyltin hydroxide. The product fractions were evaporated and high vacuumed to give the acid 254e as a yellowish solid (26 mg, yield=100%). MS (m/z): found 940.5 (M–H)⁻, 964.6 (M+Na)⁺. Compound 2542 (26 mg, 0.028 mmol) was then dissolved in anhydrous dichloromethane (1 mL). N-hydroxysuccinimide (NHS, 9.57 mg, 0.083 mmol), N-(3-dimethylaminopropyl)-N'-ethylcarbodiimide hydrochloride (EDC, 15.9 mg, 0.083 mmol) and DMAP (0.34 mg, 0.0028 mmol) was added subsequently. The mixture was stirred at room temperature overnight and diluted with dichloromethane, washed with saturated ammonium chloride and brine, dried over anhydrous sodium sulfate. It was filtered, evaporated and the residue was purified by preparative reverse phase HPLC (C18 column, eluted with acetonitrile/water). The product fractions were combined and extracted with dichloromethane. The organic layers were dried over anhydrous sodium sulfate, filtered, evaporated and high vacuumed to give compound 254f (IGN-24-NHS) as a light yellowish solid (3.0 mg, yield=10%). MS (m/z): found 1061.7 (M+Na)⁺. Note: DMAP should not have been added and it may be the cause of the low yield.

Example 22

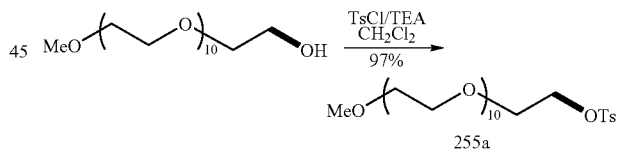

255a

Compound 255a:

To a stirred solution of O-methyl-undecaethylene glycol (500 mg, 0.968 mmol) in anhydrous dichloromethane (3 mL) was added triethylamine (270 μl, 1.94 mmol), tosyl chloride (277 mg, 1.45 mmol) and DMAP (5.91 mg, 0.048 mmol) subsequently at room temperature. The mixture continued to be stirred overnight and worked up by diluted with ethyl acetate and filtered to remove the triethylamine hydrochloride solid. The solid was washed with ethyl acetate and the filtrate was evaporated. The residue was diluted with ethyl acetate and filtered to remove the additional precipitate. The filtrate was evaporated to give the crude product as liquid. It was purified by silica gel chromatography (dichloromethane/methanol) to give compound 255a as a light yellowish oil (630 mg, yield=97%). $^1$H NMR (400 Hz, CDCl$_3$): δ 7.81 (d, J=8.0 Hz, 2H), 7.35 (d, J=8.0 Hz, 2H), 4.17 (t, J=4.8 Hz, 2H), 3.72-3.54 (m, 42H), 3.39 (s, 3H), 2.46 (s, 3H); MS (m/z): found 693.6 (M+Na)$^+$.

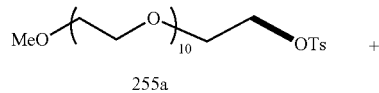

celite and the solid was washed with dichloromethane. The filtrate was evaporated and the residue was diluted with dichloromethane and filtered again to remove the additional solid. The filtrate was evaporated and the residue was purified by silica gel chromatography (hexanes/10% methanol in THF) to give compound 255b as a colorless oil (41.8 mg, yield=5.9%). $^1$H NMR (400 Hz, CDCl$_3$): δ 6.66 (s, 2H), 6.65 (s, 1H), 4.60 (s, 4H), 3.69 (s, 3H), 3.66-3.58 (m, 42H), 3.56-3.53 (m, 2H), 3.39-3.36 (m, 5H), 2.52 (broad s, 2OH), 2.36 (t, J=7.2 Hz, 2H), 1.91 (p, J=7.2 Hz, 2H); $^{13}$C NMR (400 Hz, CDCl$_3$): δ 173.9, 148.5, 142.8, 113.4, 109.9, 72.1, 70.8, 70.7, 68.9, 65.7, 59.2, 51.8, 50.9, 50.7, 31.3, 22.4; MS (m/z): found 774.3 (M+Na)$^+$.

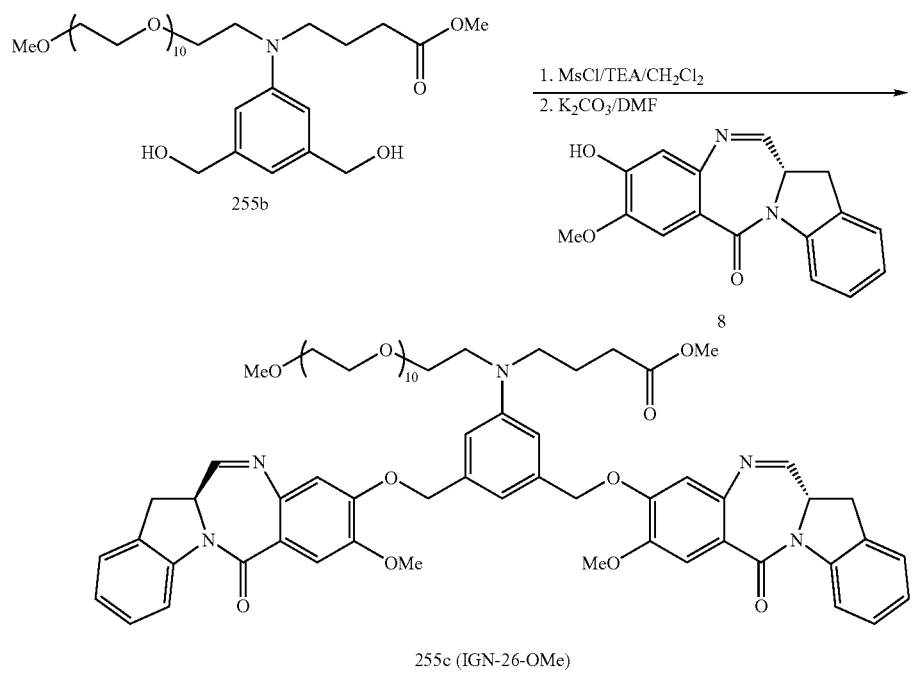

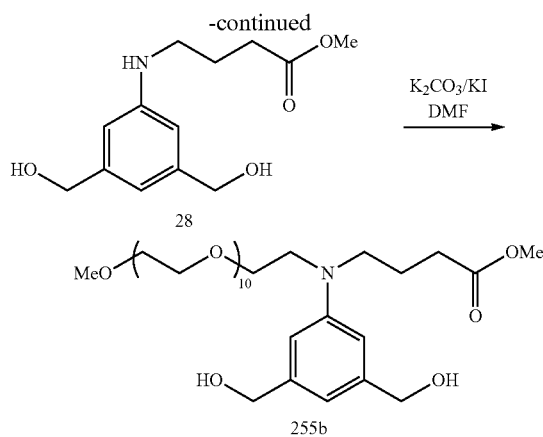

Compound 255b:

To the mixture of the tosylate 255a (630 mg, 0.939 mmol) and aniline 28 (238 mg, 0.939 mmol) in anhydrous DMF (3 mL) was added anhydrous potassium carbonate (195 mg, 1.409 mmol) and potassium iodide (31.2 mg, 0.188 mmol). The mixture was heated to 85° C. and stirred at that temperature overnight. The solution was cooled to room temperature and diluted with dichloromethane. It was filtered through

Compound 255c (IGN-26-OMe):

To a stirred solution of compound 255b (41.8 mg, 0.056 mmol) in anhydrous dichloromethane (1 mL) was added triethylamine (27 µl, 0.196 mmol). The mixture was cooled to −10° C. and methanesulfonyl chloride (12.9 µl, 0.167 mmol) was added slowly in 15 minutes. The solution continued to be stirred between −10° C. to −5° C. for 60 minutes and quenched by addition of ice/water. It was diluted with ethyl acetate and washed with cold water. The organic layer was dried over anhydrous sodium sulfate, filtered, evaporated and high vacuumed to give the mesylates as colorless oil. MS (m/z): found 930.3 (M+Na)$^+$. The mesylates (30 mg, 0.033 mmol) was transferred to a 5 mL round bottom flask with ethyl acetate, evaporated and high vacuumed. Compound 8 (29.2 mg, 0.099 mmol) was added followed by addition of anhydrous DMF (0.5 mL), anhydrous potassium carbonate (22.8 mg, 0.165 mmol) and potassium iodide (5.5 mg, 0.033 mmol). The mixture was stirred at room temperature overnight. It was diluted with dichloromethane and washed with brine. The organic layer was dried over anhydrous sodium sulfate, filtered and evaporated. The residue was purified by silica gel chromatography (hexanes/10% methanol in THF) to give 20.5 mg of a mixture which contained compound 255c. It was dissolved in anhydrous dichloromethane (0.3 mL). Triethylamine (4 µl, 0.03 mmol), tosyl chloride (3.8 mg, 0.02 mmol) and DMAP (0.2 mg, 0.002 mmol) were added subsequently at room temperature. The mixture continued to be stirred at room temperature overnight and then was evaporated. The residue was purified by silica gel chromatography (dichloromethane/methanol) to give 11 mg of light yellowish foam. It was further purified by preparative reverse phase HPLC (C18 column, eluted with CH$_3$CN/H$_2$O) to give compound 255c (IGN-26-OMe) as colorless foam (1.6 mg, yield=2.2%). MS (m/z): found 1326.5 (M+Na)$^+$, 1344.6 (M+H$_2$O+Na)$^+$, 1362.5 (M+2H$_2$O+Na)$^+$.

Example 23

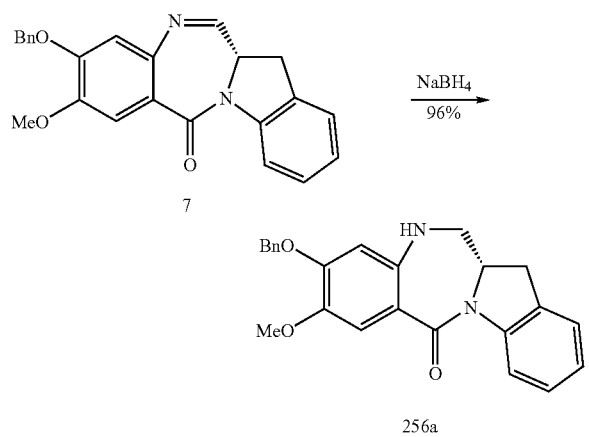

Compound 256a:

To a stirred solution of compound 7 (384 mg, 1.0 mmol) in absolute ethanol (6 mL) and anhydrous dichloromethane (2 mL) was added sodium borohydride (37.8 mg, 1.0 mmol) at 0° C. After 30 minutes, the ice/water bath was removed and the reaction mixture continued to be stirred at room temperature overnight. The reaction was quenched by addition of saturated ammonium chloride and diluted with dichloromethane. The mixture was separated and the organic layer was washed with brine, dried over anhydrous sodium sulfate and filtered. The solvents were removed under reduced pressure to give compound 256a as a white solid (369 mg, yield=96%). $^1$H NMR (400 Hz, CDCl$_3$): δ 8.37 (d, J=8.0 Hz, 1H), 7.50 (s, 1H), 7.40-7.24 (m, 6H), 7.18 (d, J=7.2 Hz, 1H), 7.05 (t, J=7.2 Hz, 1H), 6.12 (s, 1H), 5.06 (s, 2H), 4.40 (tt, J$_1$=10.0 Hz, J$_2$=3.6 Hz, 1H), 3.87 (s, 3H), 3.52-3.41 (m, 3H), 2.78 (dd, J$_1$=16.8 Hz, J$_2$=3.6 Hz, 1H); $^{13}$C NMR (400 Hz, CDCl$_3$): δ 166.5, 152.1, 142.73, 142.70, 140.4, 136.3, 129.5, 128.5, 127.9, 127.7, 127.1, 124.5, 123.8, 117.2, 114.5, 112.7, 103.4, 70.5, 57.1, 56.2, 54.5, 33.1; MS (m/z), found 409.2 (M+Na)$^+$.

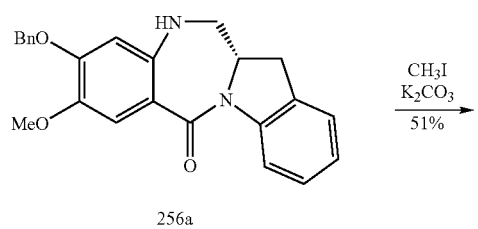

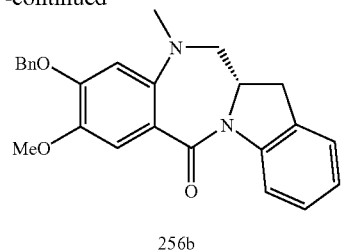

Compound 256b:

To a solution of compound 256a (369 mg, 0.955 mmol) in anhydrous acetonitrile (9 mL) was added iodomethane (65 μl, 1.05 mmol) and potassium carbonate (158 mg, 1.15 mmol). The mixture was stirred, heated to 82° C. and refluxed overnight. The reaction mixture was removed from the oil bath, cooled to room temperature and diluted with dichloromethane. It was filtered through celite and the filtrate was evaporated under reduced pressure. The residue was purified through silica gel chromatography (hexanes/ethyl acetate) to give compound 256b as a colorless foam (195 mg, yield=51%). Also 123 mg of starting material 256a was recovered. $^1$H NMR (400 Hz, CDCl$_3$): δ 8.29 (d, J=8.0 Hz, 1H), 7.46 (s, 1H), 7.44 (s, 1H), 7.39-7.24 (m, 5H), 7.16 (d, J=7.2 Hz, 1H), 7.04 (t, J=7.6 Hz, 1H), 6.46 (s, 1H), 5.19 (dd, J$_1$=15.2 Hz, J$_2$=12.4 Hz, 2H), 4.36-4.29 (m, 1H), 3.89 (s, 3H), 3.38-3.31 (m, 2H), 3.02 (dd, J$_1$=10.8 Hz, J$_2$=4.0 Hz, 1H), 2.70 (dd, J$_1$=16.8 Hz, J$_2$=2.8 Hz, 1H), 2.65 (s, 3H); $^{13}$C NMR (400 Hz, CDCl$_3$): δ 166.9, 151.2, 144.2, 142.1, 141.9, 136.7, 129.8, 128.6, 128.0, 127.8, 127.3, 125.1, 123.9, 121.7, 117.1, 113.5, 104.7, 71.1, 64.2, 57.2, 56.3, 40.2, 32.0; MS (m/z): found 423.2 (M+Na)$^+$.

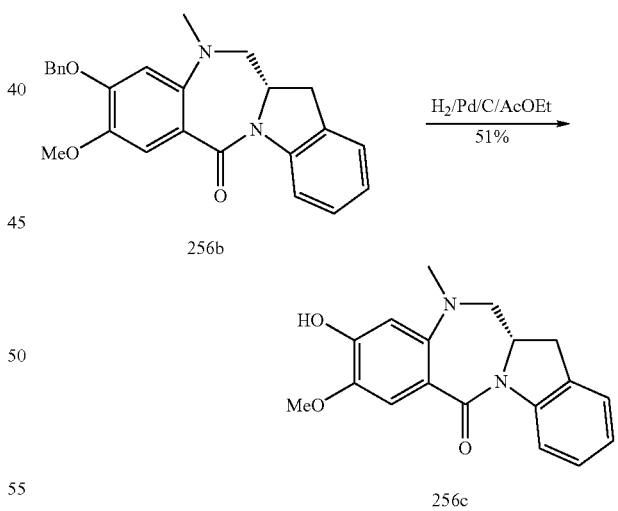

Compound 256c:

To a stirred solution of compound 256b (195 mg, 0.487 mmol) in ethyl acetate (2.5 mL) was added palladium on charcoal (10%, 25.9 mg, 0.024 mmol). The flask was briefly vacuumed and replaced with H$_2$ in a balloon. The mixture continued to be hydrogenated for overnight and filtered through celite. The filtrate was stripped under reduce pressure and the residue was purified by silica gel chromatography (dichloromethane/methanol) to give compound 256c as a white solid (126 mg, yield=83%). $^1$H NMR (400 Hz, MeOD):

δ 8.14 (d, J=8.0 Hz, 1H), 7.30-7.23 (m, 2H), 7.22 (s, 1H), 7.10 (t, J=7.6 Hz, 1H), 6.56 (s, 1H), 4.46-4.38 (m, 1H), 3.88 (s, 3H), 3.48-3.37 (m, 2H), 3.12 (dd, J₁=10.8 Hz, J₂=4.4 Hz, 1H), 2.84 (dd, J₁=16.8 Hz, J₂=2.8 Hz, 1H), 2.80 (s, 3H).

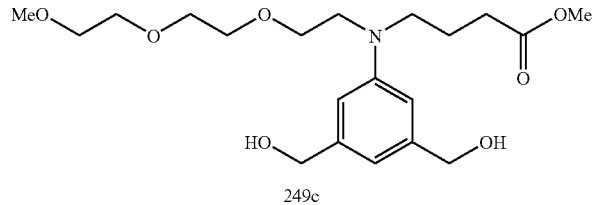

249c

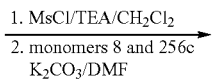

1. MsCl/TEA/CH₂Cl₂
2. monomers 8 and 256c
   K₂CO₃/DMF

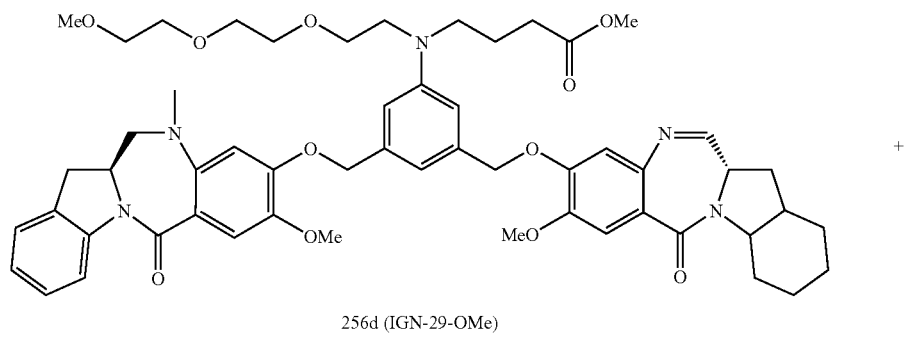

256d (IGN-29-OMe)

+

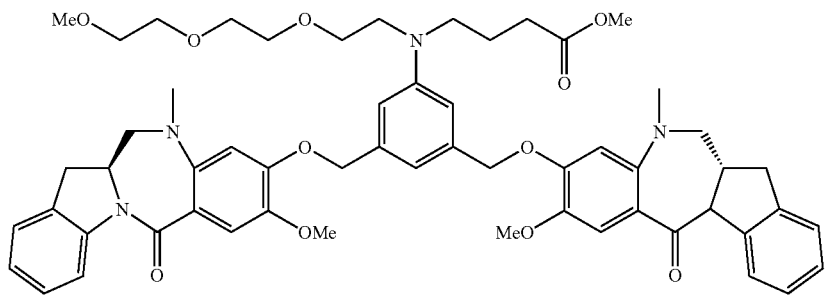

256e

Compound 256d (IGN-29-OMe):

To a stirred solution of compound 249c (136 mg, 0.34 mmol) in anhydrous dichloromethane (2 mL) was added triethylamine (142 µl, 1.02 mmol). The mixture was cooled to −10° C. and methanesulfonyl chloride (66 µl, 0.85 mmol) was added slowly in 15 minutes. The solution continued to be stirred between −10° C. to −5° C. for 60 minutes and quenched by addition of ice/water. It was diluted with ethyl acetate and washed with cold water. The organic layer was dried over anhydrous sodium sulfate, filtered, evaporated and high vacuumed to give the mesylate as colorless oil. The mesylate was transferred to a 10 mL round bottom flask with ethyl acetate, evaporated and high vacuumed. Compound 8 (120 mg, 0.41 mmol) and 256c (106 mg, 0.34 mmol) were added to it followed by addition of anhydrous DMF (1.5 mL), anhydrous potassium carbonate (235 mg, 1.7 mmol). The mixture was stirred at room temperature overnight. It was diluted with dichloromethane and washed with brine. The organic layer was dried over anhydrous sodium sulfate, filtered and evaporated. The residue was purified by preparative reverse phase HPLC (C18 column, eluted with CH₃CN/H₂O) to give compound 256d (IGN-29-OMe) as a light yellowish solid (46 mg, yield=14%) and compound 256e. 256d: ¹H NMR (400 Hz, CDCl₃), δ 8.27 (d, J=8.0 Hz, 2H), 7.84 (d, J=4.8 Hz, 1H), 7.57 (s, 1H), 7.32-7.04 (m, 7H), 6.87 (s, 1H), 6.82 (s, 1H), 6.76-6.70 (m, 2H), 6.50 (s, 1H)5.18-5.12 )m, 4H), 4.49-4.43 (m, 1H), 4.40-4.35 (m, 1H), 3.98 (s, 3H), 3.89 (s, 3H), 3.68-3.52 (m, 18H), 3.41-3.36 (m, 6H), 3.08 (dd, J₁=10.8 Hz, J₂=4.4 Hz, 1H), 2.56 (dd, J₁=16.8 Hz, J₂=2.8 Hz, 1H), 2.70 (s, 3H), 2.34 (t, J=7.2 Hz, 2H), 1.92-1.85 (m, 2H); MS (m/z): found 990.6 (M +Na)⁺, 1008.6 (M+H₂O+Na)⁺. 256e: MS (m/z): found 1006.6 (M+Na)⁺.

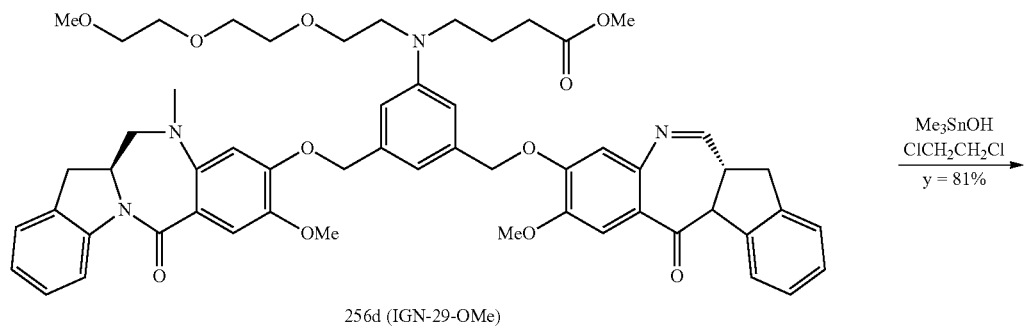

256d (IGN-29-OMe)

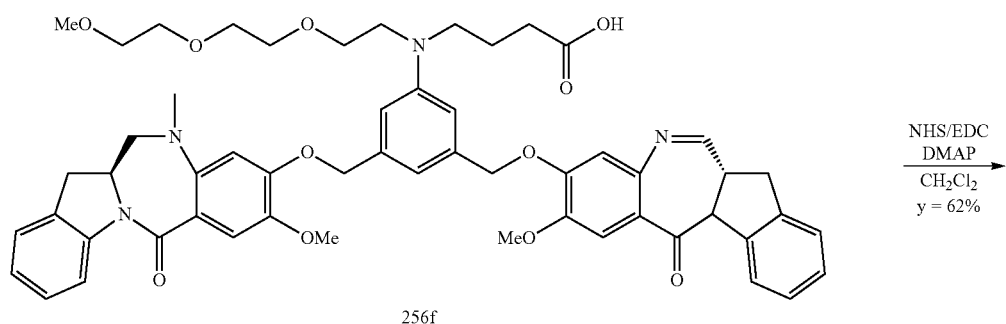

256f

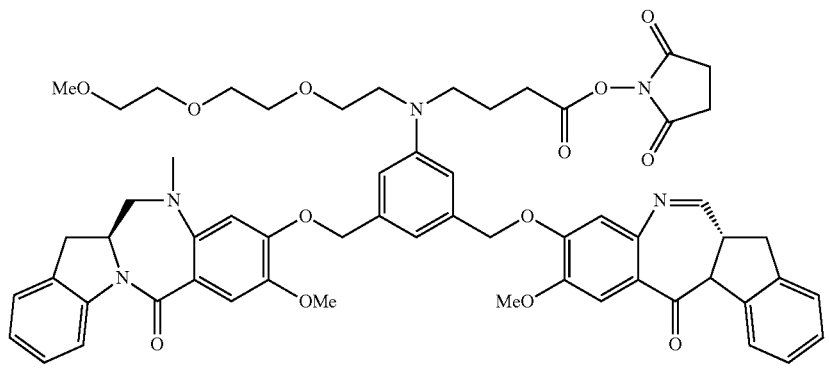

256g (IGN-29-NHS)

Compound 256f and Compound 256g (IGN-29-NHS):

To the solution of compound 256d (46 mg, 0.048 mmol) in anhydrous 1,2 dichloroethane (1.5 mL) was added trimethyltin hydroxide (129 mg, 0.71 mmol). The mixture was heated to 80° C. and stirred overnight. It was cooled to room temperature, diluted with dichloromethane and washed with mixed solution of saturated sodium chloride and 5% hydrochloric acid (~1 mL), then brine. The organic layer was dried over anhydrous sodium sulfate, filtered and evaporated. The residue was passed a short silica gel column and eluted with dichloromethane/methanol to remove the extra trimethyltin hydroxide. The product fractions were evaporated and high vacuumed to give the acid 256f as a yellowish solid (36.9 mg, yield=81%). MS (m/z): found 952.8 (M−H)⁻. Compound 256f (36.9 mg, 0.039 mmol) was then dissolved in anhydrous dichloromethane (0.8 mL). N-hydroxysuccinimide (NHS, 13.4 mg, 0.12 mmol) and N-(3-dimethylaminopropyl)-N'-ethylcarbodiimide hydrochloride (EDC, 22.2 mg, 0.12 mmol) was added subsequently. The mixture was stirred at room temperature overnight and diluted with dichloromethane, washed with brine and dried over anhydrous sodium sulfate. It was filtered, evaporated and the residue was purified by preparative reverse phase HPLC (C18 column, eluted with acetonitrile/water). The fractions containing product were combined and extracted with dichloromethane. The organic layers were dried over anhydrous sodium sulfate, filtered, evaporated and high vacuumed to give compound 256g (IGN-29-NHS) as a light yellowish solid (25.4 mg, yield=62%). MS (m/z): found 1073.4 (M+Na)⁺, 1091.4 (M+H$_2$O+Na)⁺, 1103.3 (M+3H$_2$O−H)⁻.

Example 24

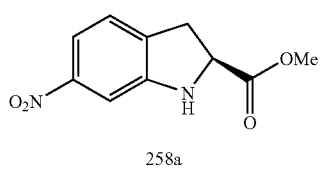

258a

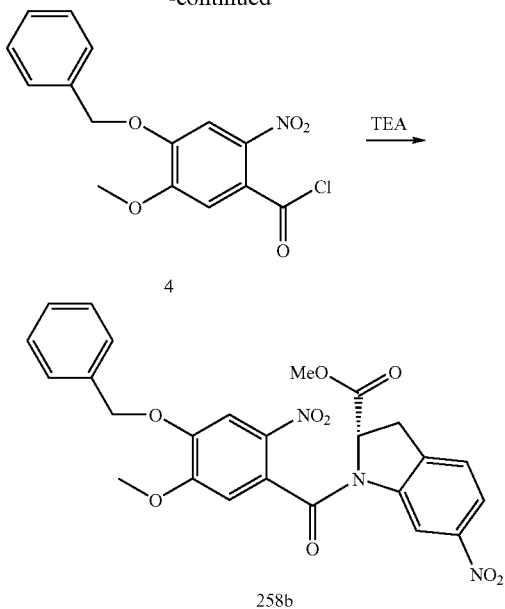

methyl 1-(4-(benzyloxy)-5-methoxy-2-nitrobenzoyl)-6-nitroindoline-2-carboxylate (258b)

Methyl 6-nitroindoline-2-carboxylate (258a) (0.233 g, 1.048 mmol) was dissolved in anhydrous tetrahydrofuran (4 ml) in a separate flask and cooled to 0° C. an ice bath. In another flask 4-(benzyloxy)-5-methoxy-2-nitrobenzoyl chloride (4) (0.371 g, 1.153 mmol) was dissolved in anhydrous tetrahydrofuran (4 ml) and cooled to 0° C. in an ice bath. To the flask containing the indoline was added triethylamine (0.438 ml, 3.15 mmol) via syringe and the acetyl chloride 4 was added quickly to the reaction mixture via cannula at 0° C. The reaction was stirred for 90 minutes at 0° C. and then at room temperature for an additional 1 hour. The reaction was then quenched with 5% HCl and extracted with ethyl acetate (3×). The combined organic layers were washed with brine, dried over anhydrous sodium sulfate, and concentrated in vacuo. The residue was purified by silica gel chromatography using 30% Acetone in hexane to give methyl 1-(4-(benzyloxy)-5-methoxy-2-nitrobenzoyl)-6-nitroindoline-2-carboxylate (258b) (0.220 g, 0.434 mmol, 41.4% yield) as a yellowish foam. $^1$H NMR (400 Hz, CDCl$_3$): δ 3.30 (m, 1H), 3.60 (s, 3H), 3.69 (m, 1H), 3.86 (s, 3H), 4.64 (dd, 1 H, J=2.4 Hz, 10.8), 5.23 (s, 2H), 7.31 (m, 1H), 7.46 (m, 6H), 7.99 (dd, 1H, J=2.0, 8.0 Hz), 9.04 (d, 1H, J=2.0 Hz). MS (m/z), found 530.1 ([M]$^+$+Na).

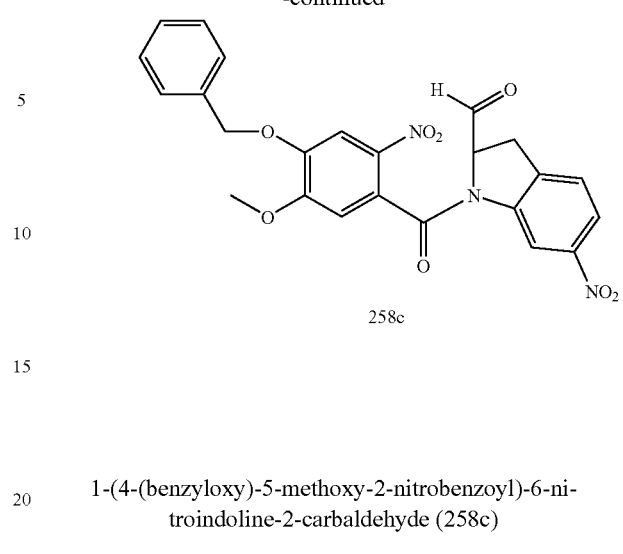

1-(4-(benzyloxy)-5-methoxy-2-nitrobenzoyl)-6-nitroindoline-2-carbaldehyde (258c)

Methyl 1-(4-(benzyloxy)-5-methoxy-2-nitrobenzoyl)-6-nitroindoline-2-carboxylate (258b) (1.023 g, 2.016 mmol) was dissolved in a mixture of anhydrous dichloromethane (2.5 mL) and toluene (7.5 mL) and cooled to −78° C. in a dry ice and acetone bath. After 15 minutes DIBAL-H (1.0M in THF) (4.03 mL, 4.03 mmol) was added via a syringe pump over about a 20 minute period. The resulting solution was stirred for 2 hrs at −78° C. after which methanol (1 ml) was added dropwise to quench the reaction at −78° C. The reaction was then diluted with 5% HCl and ethyl acetate and warmed to room temperature. The aqueous layer was washed with additional ethyl acetate and the combined organic layers were washed with brine and dried over anhydrous sodium sulfate. The reaction mixture was passed through a layer of celite and concentrated in vacuo. The crude residue was purified by silica gel chromatography using 40% acetone in hexane to give 1-(4-(benzyloxy)-5-methoxy-2-nitrobenzoyl)-6-nitroindoline-2-carbaldehyde (258c) (621 mg, 1.301 mmol, 64.5% yield). $^1$H NMR (400 Hz, CDCl$_3$): δ 3.15-3.60 (m, 2H), 3.90 (s, 0.6H), 3.92 (s, 1.2H), 3.97 (s, 1.2H), 4.57 (d, 0.2H, J=4.8 Hz), 5.21 (m, 7.19-7.41 (m, 5.6H), 7.60-7.77 (m, 1.6H), 7.86-7.91 (m, 0.8H), 8.94 (s, 0.4H), 9.34 (s, 0.4H), 9.74 (s, 0.4H), 9.90 (s, 0.2H). MS (m/z), found 500.1 ([M]$^+$+Na).

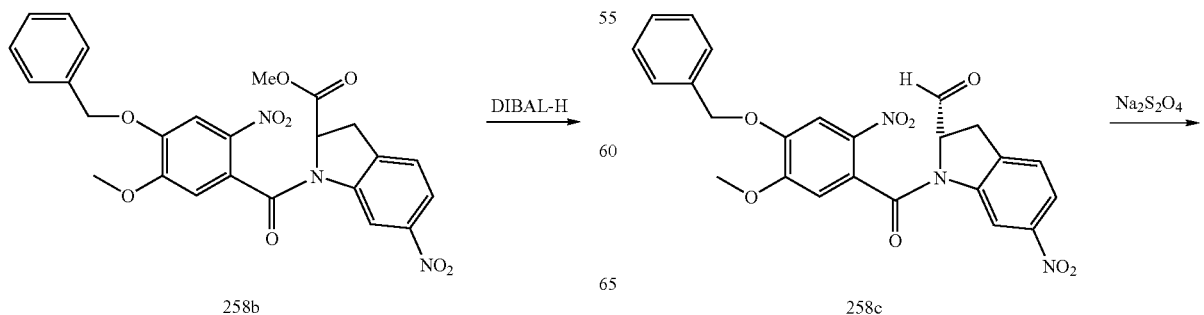

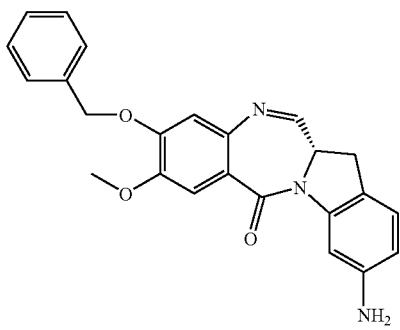

258d

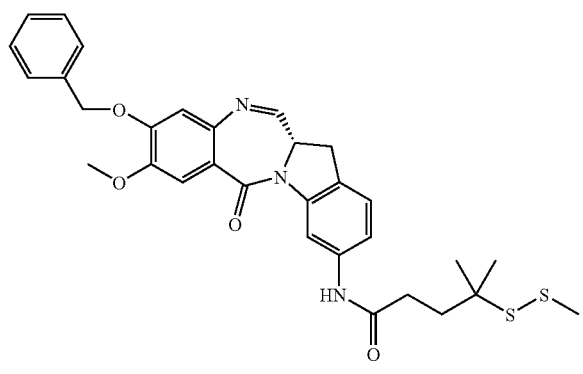

258e

Compound 258e:

1-(4-(benzyloxy)-5-methoxy-2-nitrobenzoyl)-6-nitroindoline-2-carbaldehyde (258c) (0.125 g, 0.262 mmol) was dissolved in tetrahydrofuran (8 mL) and water (5.33 mL). To this solution was added sodium hydrosulfite (0.456 g, 2.62 mmol) and the reaction was capped with a septa and vented with a needle (no nitrogen/argon needed) and stirred overnight. Methanol was added to the reaction mixture and stirred an additional 30 minutes at which point the reaction was concentrated in vacuo to remove all solvents. The residue was dissolved in a 1:1 mixture of methanol and dichloromethane (20 mL) which left a residue which did not dissolve. The mixture was passed through a short pad of silica on top of a short pad of celite and rinsed thoroughly with the 1:1 mixture of methanol and dichloromethane. The filtrate was filtered again through celite and then a solution of HCl in dioxane (4M) was added with stirring until a pH of ~3-4 was obtained. The reaction was then stirred for an additional 30 minutes and then aqueous sodium bicarbonate was added until the reaction became basic (~pH 8-9) at which time additional dichloromethane was added and the organic layer removed. The aqueous layer was washed with additional dichloromethane and the resulting organic layers were combined and washed with brine, dried over anhydrous sodium sulfate and concentrated in vacuo. The residue containing compound 258d (0.105 g, 0.263 mmol, 100% yield) was used in the next step without further treatment. MS (m/z), found 454.2 ([M]$^+$+Na+CH3OH).

To a small vial containing 4-methyl-4-(methyldisulfanyl) pentanoic acid (0.061 g, 0.313 mmol), EDC (0.060 g, 0.313 mmol), and DMAP (0.038 g, 0.313 mmol) were dissolved in dichloromethane (1 mL) with stirring. To this mixture compound 258d (0.125 g, 0.313 mmol) dissolved in dichloromethane (1.5 mL) was added and the mixture was stirred at room temperature overnight. Water was added and the layers were seperated. The organic layer was washed with brine, dried over anhydrous sodium sulfate, and concentrated in vacuo. The residue was purified on a silica gel column using 50% ethyl acetate in hexane to give compound 258e (0.037 g, 0.064 mmol, 20.54% yield). $^1$H NMR (400 Hz, CDCl$_3$): δ 1.27 (s, 6H), 1.97 (t, 2H, J=8.0 Hz), 2.06 (t, 2H, J=8.0 Hz), 2.45 (s, 3H), 3.48 (m, 1H), 3.67 (m, 1H), 3.99 (s, 3H), 4.49 (m, 1H), 5.24 (q, 2H, J=8.4 Hz), 6.90 (s, 1H), 7.22 (d, 1H, J=8.0 Hz), 7.39 (m, 5H), 7.55 (s, 1H), 7.82 (d, 1H, J=8.0 Hz), 7.87 (d, 1H, J=4.0 Hz), 8.07 (s, 1H). MS (m/z), found 630.3 ([M]$^+$+Na+MeOH).

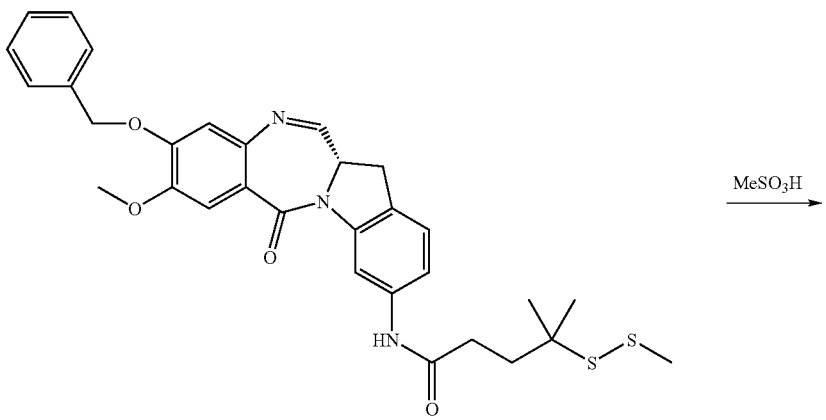

258e

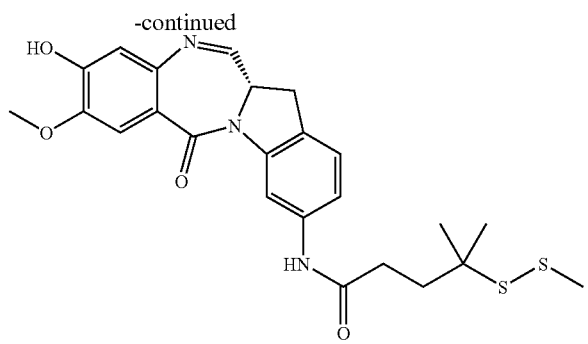

258f

Compound 258f:

Compound 258e (0.0185 g, 0.032 mmol) was dissolved in anhydrous dichloromethane (0.5 ml) and to this solution was added methanesulfonic acid (0.021 ml, 0.321 mmol) dissolved in anhydrous dichloromethane (0.500 ml) and the resulting mixture was stirred at room temperature for three hours. The reaction was poured over a mixture of ice and methanol and neutralized to pH 7 with aqueous sodium bicarbonate. The reaction was then diluted with dichloromethane and the layers were separated. The organic layer was washed with brine, dried over anhydrous sodium sulfate, and concentrated in vacuo. The residue was purified by silica ptlc using 3% methanol in dichloromethane to give NH(4-methyl-4-methyldithio-pentanoate)-indole IGN monomer (0.007 g, 0.014 mmol, 44.9% yield). MS (m/z), found 484.0 ([M]$^+$−1).

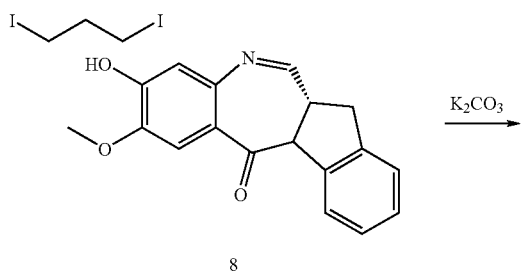

8

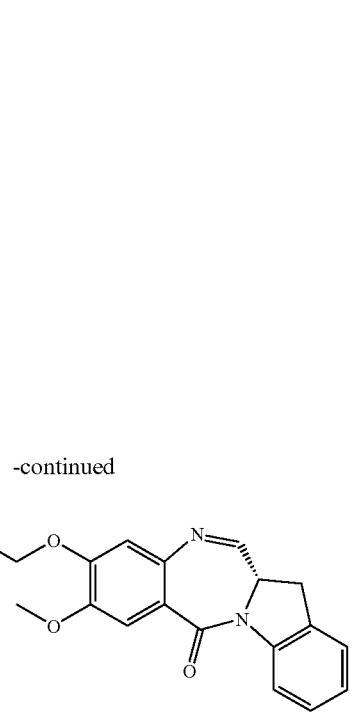

258g

Compound 258g:

In a small vial dissolved Compound 8 (0.033 g, 0.112 mmol) in DMF (1.5 ml) with stirring at room temperature. 1,3-diiodopropane (0.065 ml, 0.561 mmol) was added followed by the addition of potassium carbonate (0.023 g, 0.168 mmol). The reaction was covered in foil and stirred at room temperature overnight. The reaction was diluted with dichloromethane and washed with aqueous ammonium chloride and brine. The organic layer was dried over anhydrous sodium sulfate, filtered, and concentrated in vacuo. The residue was purified by silica ptlc using 50% ethyl acetate in hexane to give Compound 258g (0.018 g, 0.039 mmol, 34.7% yield). MS (m/z), found 533.0 ([M]$^+$+K).

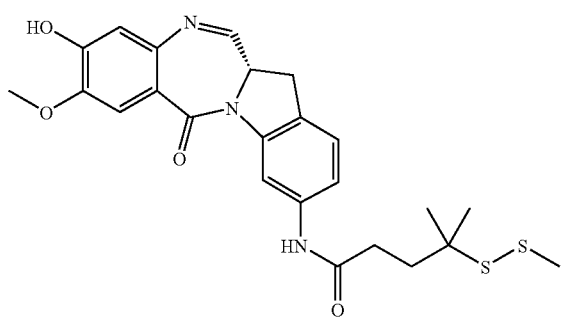

258f

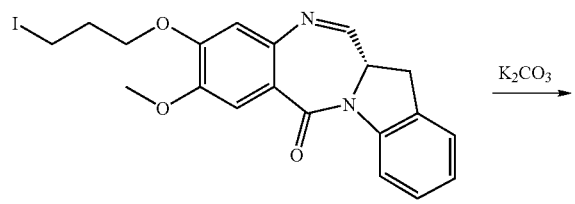

258g

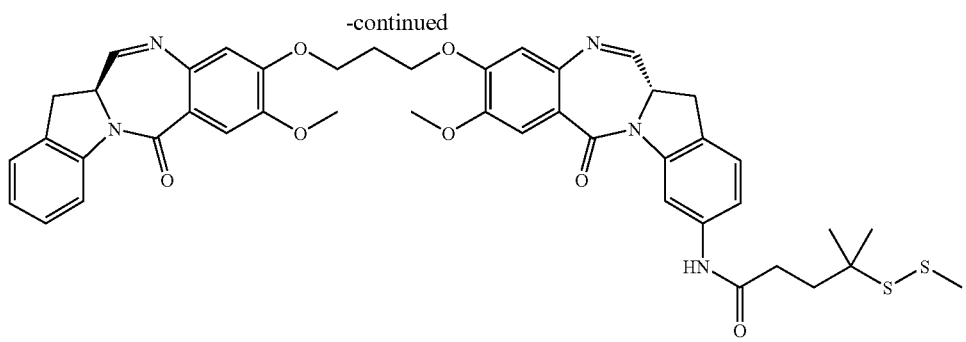

258h

Compound 258 h (IGN-15-SMe):

In a small vial dissolved Compound 258f (0.007 g, 0.014 mmol) in dimethylformamide (1 ml) with stirring at room temperature. Compound 8 (6.66 mg, 0.014 mmol) was added followed by the addition of potassium carbonate (1.992 mg, 0.014 mmol). The reaction was covered in foil and stirred at room temperature overnight. Reaction was diluted with dichloromethane and washed with aqueous ammonium chloride and brine. The organic layer was dried over anhydrous sodium sulfate, filtered, and concentrated in vacuo. The residue was purified by silica ptlc plate in 5% methanol in dichloromethane to give Compound 258h (IGN-15-SMe) (0.005 g, 7.32 µmol, 50.8% yield). MS (m/z), found 906.3 ([M]$^+$+Na+2CH3OH).

Example 25

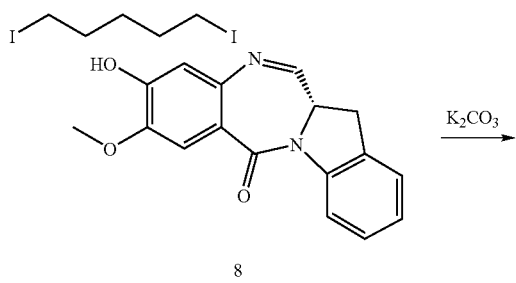

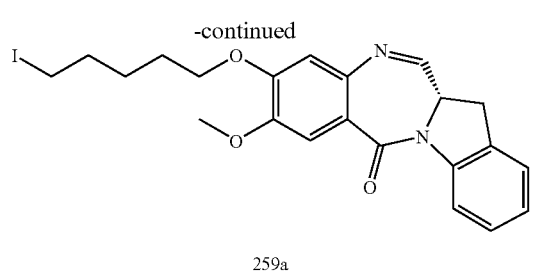

259a

Compound 259a:

In a small vial dissolved Compound 8 (0.100 g, 0.340 mmol) in DMF (5 ml) with stirring at room temperature. 1,5-diiodopentane (0.506 ml, 3.40 mmol) was added followed by the addition of potassium carbonate (0.070 g, 0.510 mmol). The reaction was covered in foil and stirred at room temperature overnight. The reaction was diluted with dichloromethane and washed with aqueous ammonium chloride and brine. The organic layer was dried over anhydrous sodium sulfate, filtered, and concentrated in vacuo. The residue was purified by silica ptlc using 50% ethyl acetate in hexane to give Compound 259a (0.045 g, 7.32 µmol, 27% yield). $^1$H NMR (400 Hz, CDCl$_3$): δ 1.64 (m, 2H), 1.94 (M, 4H), 3.24 (t, 2H, J=6.5 Hz), 3.52 (dd, 1H, J=4.0, 16.6 Hz), 3.73 (dd, 1H, J=10.5, 16.6 Hz), 3.98 (s, 3H), 4.12 (m, 2H), 4.50 (dt, 1H, J=4.0, 11.2 Hz), 6.84 (s, 1H), 7.13 (t, 1H, J=6.0 Hz), 7.29 (m, 2H), 7.57 (s, 1H), 7.90 (d, 1H, J=4.4 Hz), 8.29 (d, 1H, J=8.0 Hz). MS (m/z), found 533.3 ([M]$^+$+K).

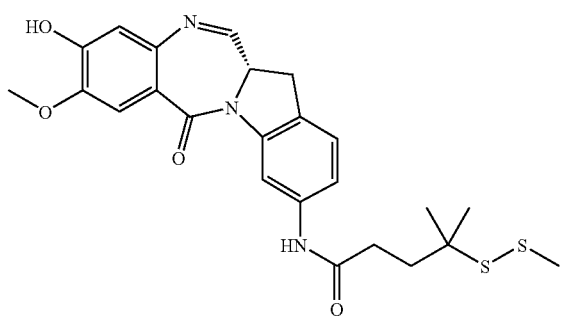

258f

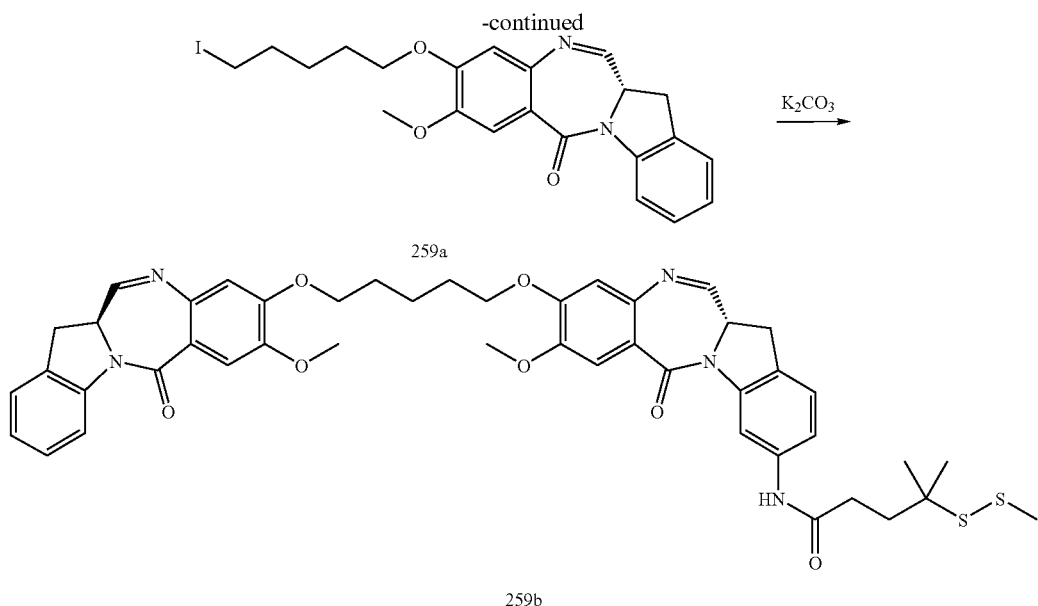

Compound 259b (IGN-21-SMe):

In a small vial dissolved Compound 258f (15 mg, 0.031 mmol) in dimethylformamide (1 ml) with stirring at room temperature. Compound 259a (17.42 mg, 0.036 mmol) was added followed by the addition of potassium carbonate (4.27 mg, 0.031 mmol). The reaction was covered in foil and stirred at room temperature overnight. Reaction was diluted with dichloromethane and washed with aqueous ammonium chloride and brine. The organic layer was dried over anhydrous sodium sulfate, filtered, and concentrated in vacuo. The residue was purified by silica ptlc plate in 5% methanol in dichloromethane to give Compound 259a (IGN-15-SMe) (0.006 g, 7.32 μmol, 22% yield). MS (m/z), found 934.1 ([M]$^+$+Na+ 2CH3OH).

Example 26

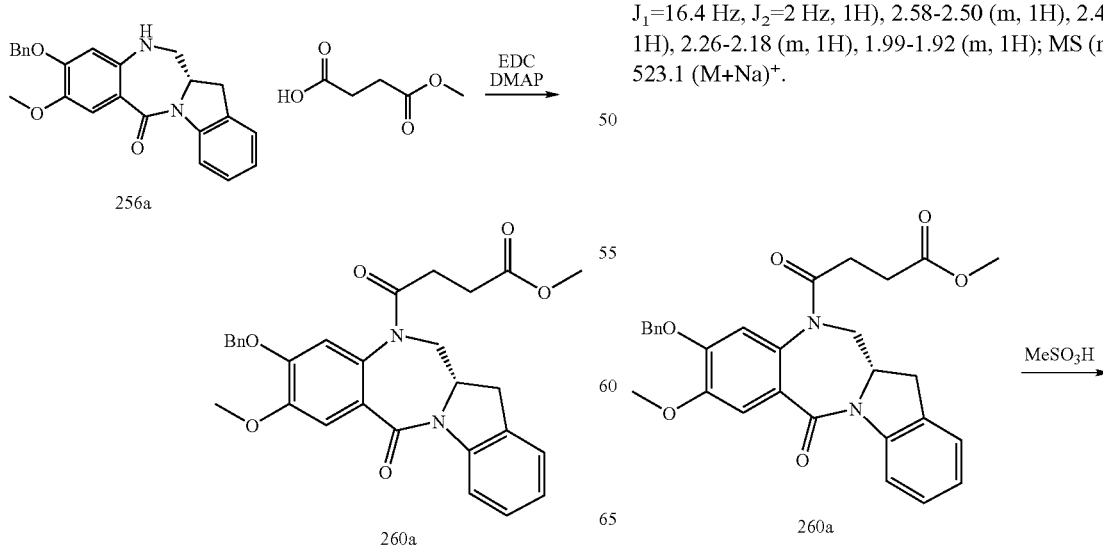

Compound 260a:

Compound 256a (55 mg, 0.142 mmol) was dissolved in anhydrous dichloromethane and then 4-methoxy-4-oxobutanoic acid (76 mg, 0.575 mmol), EDC (70 mg, 0.365 mmol), and DMAP (8.69 mg, 0.071 mmol) were added sequentially. The mixture was stirred overnight at room temperature and was checked by TLC to ensure no starting material remained. The reaction was then diluted with water and ethyl acetate. After further extraction with ethyl acetate, the organic was washed with brine, dried over sodium sulfate, filtered and concentrated in vacuo. The crude residue was purified by silica gel chromatography using 50% ethyl acetate in hexane to give compound 260a (54 mg, yield=76%). $^1$H NMR (400 Hz, CDCl$_3$): δ 8.21 (d, J=8.0 Hz, 1H), 7.45-7.25 (m, 7H), 7.20 (d, J=7.2 Hz, 1H), 7.08 (t, J=7.4 Hz, 1H), 6.825 (s, 1H), 5.27 (q, J=15.1 Hz, 2H), 4.56 (t, J=12.6 Hz, 1H), 4.35-4.29 (m, 1H), 3.99 (s, 3H), 3.65 (s, 3H), 3.44-3.38(m, 2H), 2.88 (dd, J$_1$=16.4 Hz, J$_2$=2 Hz, 1H), 2.58-2.50 (m, 1H), 2.40-2.33 (m, 1H), 2.26-2.18 (m, 1H), 1.99-1.92 (m, 1H); MS (m/z), found 523.1 (M+Na)$^+$.

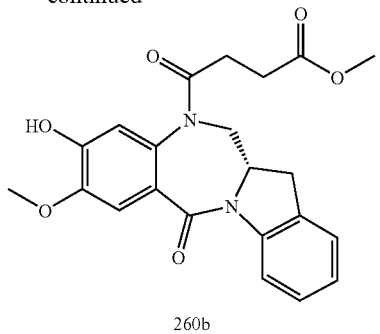

260b

Compound 260b:
To a solution of compound 260a (50 mg, 0.100 mmol) in anhydrous dichloromethane (11.5 ml) was added drop wise methanesulfonic acid (0.389 ml, 5.99 mmol) resulting in a yellow solution. The reaction stirred at room temperature and was monitored by TLC until completion beginning at 30 minutes. It was diluted with water and methanol then neutralized to pH 7 using saturated sodium bicarbonate. The aqueous layer was extracted with dichloromethane and the organic layer dried over sodium sulfate. The crude product was purified by silica gel chromatography using 6% methanol in dichloromethane to give compound 260b (40 mg, yield=98%). $^1$H NMR (400 Hz, CDCl$_3$): δ 8.22 (d, J=8.0 Hz, 1H), 7.35 (s, 1H), 7.28 (t, J=7.8 Hz, 1H), 7.22 (d, J=7.2 Hz, 1H), 7.09 (t, J=7.4 Hz, 1H), 6.90 (s, 1H), 6.06 (s, 1H), 4.63 (t, J=12.6 Hz, 1H), 4.38-4.30 (m, 1H), 4.00 (s, 3H), 3.66 (s, 3H), 3.47-3.39 (m, 2H), 2.90 (dd, J$_1$=16.2 Hz, J$_2$=2.2 Hz, 1H), 2.69-2.59 (m, 2H), 2.52-2.45 (m, 1H), 2.22-2.14 (m, 1H); MS (m/z), found 433 (M+Na)$^+$.

Compound 260c:
Compound 260b (20 mg, 0.049 mmol) and compound 259a (30 mg, 0.061 mmol) were dissolved in anhydrous N,N-dimethylformamide (1 ml). Potassium carbonate (20.20 mg, 0.146 mmol) was added and the reaction stirred overnight at room temperature. It was quenched with water and extracted with dichloromethane. The organic was washed with brine and dried over sodium sulfate. The crude product was purified by silica gel chromatography using 5% methanol in dichloromethane to give compound 260c (25 mg, yield=66%). MS (m/z), found 813.5 (M+Na+H$_2$O)$^+$.

Example 27

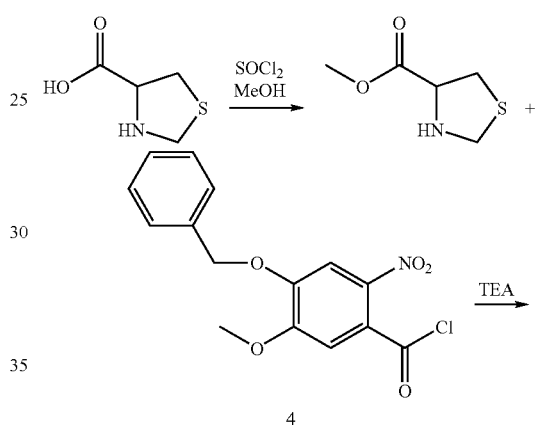

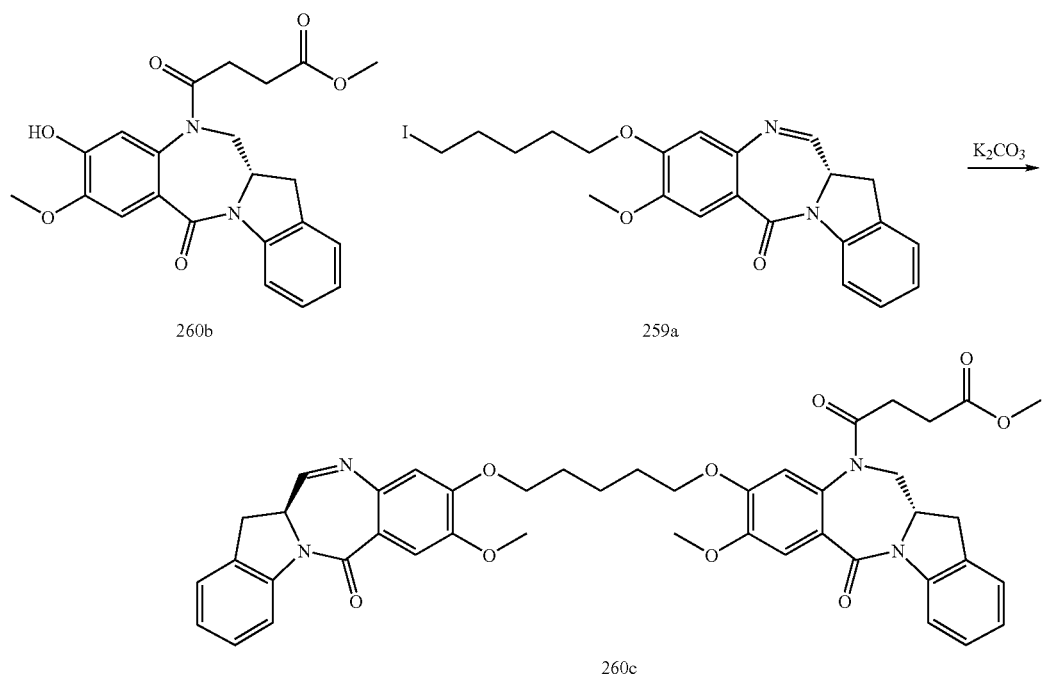

260c

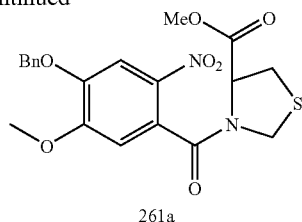
261a

Compound 261a:

The commercially available starting material, thiazolidine-4-carboxylic acid (1.3 g, 9.59 mmol) was dissolved in anhydrous methanol (19.18 mL) and cooled to 0° C. in an ice bath. Thionyl chloride (1.40 mL, 19.18 mmol) was added drop wise and the reaction stirred for 30 minutes. The ice bath was removed and stirring continued either for 4-5 hours or overnight. The solvent was stripped and the product placed on the high vacuum to give 4-(methoxycarbonyl)thiazolidin-3-ium chloride. Without further purification and assuming 100% yield, the 4-(methoxycarbonyl)thiazolidin-3-ium chloride (1.761 g, 9.59 mmol) and compound 4 (3.39 g, 10.55 mmol) were each dissolved separately in tetrahydrofuran (32.0 mL) and cooled to 0° C. Triethylamine (4.41 mL, 31.6 mmol) was added to the solution with 4-(methoxycarbonyl)thiazolidin-3-ium chloride and then compound 4 was added quickly via canula. After 20 minutes, the pH of the solution was checked to ensure it was basic. The reaction stirred at 0° C. for 1.5 hours and then at room temperature for 30 minutes and was checked by MS. It was quenched with cold 5% hydrochloric acid and diluted with cold ethyl acetate and water. The solution was extracted with ethyl acetate three times and the combined organic washed with brine, saturated sodium bicarbonate and then brine again. It was dried over sodium sulfate, filtered and stripped. The crude material was purified by silica gel chromatography using a gradient of 50% to 75% ethyl acetate in hexanes to give compound 261a (4.1 g, yield=99%). $^1$H NMR (400 Hz, CDCl$_3$): the compound appears as a pair of distinct rotomers. δ 7.78 (s, 0.6H), 7.74 (s, 0.4H), 7.48-7.35 (m, 5H), 6.96 (s, 0.4H), 6.92 (s, 0.6H), 5.40 (dd, J$_1$=7.0 Hz, J$_2$=3.4 Hz, 0.6H), 5.31-5.22 (m, 2H), 5.13 (d, 9.6Hz, 0.4H), 4.60 (d, J=9.6 Hz, 0.4H), 4.46 (dd, J$_1$=4.4 Hz, J$_2$=3.2 Hz, 0.4 H), 4.36 (d, J=8.4 Hz, 0.6H), 4.26 (d, J=8.4 Hz, 0.6H), 4.02 (s, 1.8H), 3.96 (s, 1.2H), 3.86 (s, 1.8H), 3.71 (s, 1.2H), 3.48-3.43 (m, 0.6H), 3.36-3.29 (m, 1.4H); MS (m/z), found 455.3 (M+Na)$^+$.

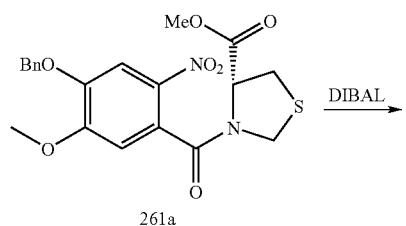
261a

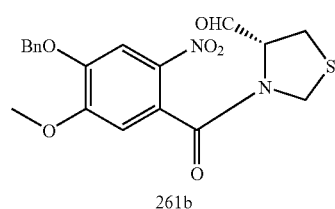
261b

Compound 261b:

Compound 261a (4.1 g, 9.48 mmol) was dissolved in dichloromethane (11 mL) and toluene (33 mL) then cooled to –78° C. in an acetone/dry ice bath. Diisobutylaluminium hydride (18.96 mL, 18.96 mmol) was added very slowly, over at least 30 minutes, using a syringe pump. The reaction stirred at –78° C. for 3 hours and was quenched with methanol (0.4 mL) and then 5% hydrochloric acid (30 mL). Ethyl acetate (100 ml) was added and the ice bath removed. The mixture continued to stir at room temperature for 30 minutes. It was extracted using ethyl acetate and the combined organic washed with brine, saturated sodium bicarbonate, and then brine again. It was dried over anhydrous sodium sulfate and filtered through celite. The crude material was purified by silica gel chromatography using 75% ethyl acetate in hexanes to give compound 261b (2.3 g, yield=60%). $^1$H NMR (400 Hz, CDCl$_3$): the compound appears as a pair of rotomers. δ 9.80 (s, 0.8H), 9.41 (s, 0.2H), 7.80 (s, 0.8H), 7.73 (s, 0.2H), 7.49-7.36 (m, 5H), 6.91 (s, 0.2H), 6.84 (s, 0.8H), 5.25-5.22 (m, 2H), 4.85-4.73 (m, 1H), 4.35-4.30 (m, 1H), 4.22-4.17 (m, 1H), 4.04-3.97 (m, 3H), 3.40-3.26 (m, 2H); MS (m/z), found 425.0 (M+Na)$^+$.

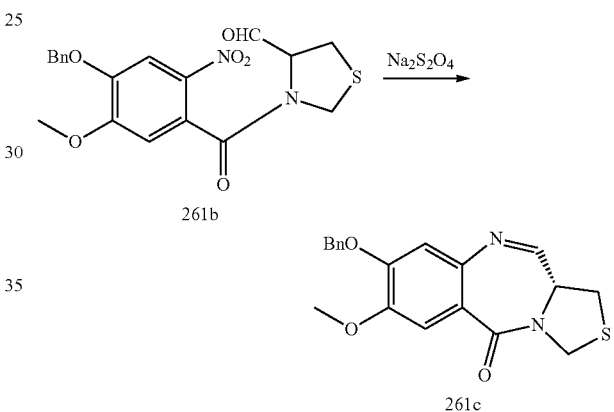

Compound 261c:

Compound 261b was dissolved in tetrahydrofuran (230 mL) then water (150 mL). Sodium hydrosulfite (5.27 g, 25.7 mmol) was added slowly, in small portions. If the solution remained cloudy, additional water was added drop wise until the solution cleared. The reaction was capped with a septa and needle to allow release of the SO$_2$ gas and was stirred overnight. The solution changed from a yellow to very pale, almost colorless solution. The following morning, water was added until the solution cleared and then methanol (30 mL) was added. It stirred for an additional 2 hours and the solvents were then evaporated and the residue re-evaporated with acetonitrile at least twice. The white residue was placed on the high vacuum for a few hours. It was re-dissolved in methanol:dichloromethane [1:1], filtered through celite, and stripped. The filter step was repeated until dilution in methanol appeared clear with no particles. The intermediate was placed on the high vacuum until completely dry then dissolved in anhydrous methanol (50 ml). Acetyl chloride (1.9 ml, 26.7 mmol) was added drop wise at room temperature, causing a yellow precipitate to form. It stirred at room temperature for 30 minutes and was quenched with saturated sodium bicarbonate. The mixture was diluted with dichloromethane and water (130 mL/85 mL) and extracted with dichloromethane. The aqueous layer was acidified with sodium hydrogensulfate, concentrated to a reduced volume, and then re-extracted.

The combined organic was washed with saturated sodium bicarbonate and brine and dried over sodium sulfate. The stripped residue was purified by silica gel chromatography using 60% ethyl acetate in hexanes to give compound 261c (1.2 g, yield=59%). $^1$H NMR (400 Hz, CDCl$_3$): δ 7.69 (d, J=4.4Hz, 1H), 7.52-7.28 (m, 6H), 6.87 (s, 1H), 5.22 (q, J=12.3 Hz, 2H), 4.85, (d, J=10.4 Hz, 1H), 4.58 (d, J=10.4 Hz, 1H), 4.03-4.02 (m, 1H), 3.98 (s, 3H), 3.51-3.47 (m, 1H), 3.45-3.23 (m, 1H); MS (m/z), found 377.3 (M+Na)$^+$.

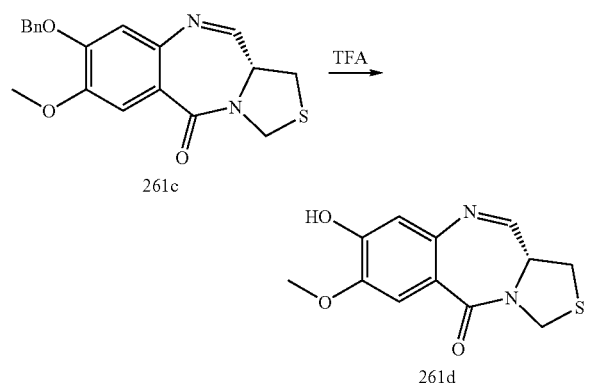

Compound 261d:

Compound 261c (75 mg, 0.212 mmol) was dissolved in neat trifluoroacetic acid (0.4 ml, 5.19 mmol). It refluxed for approximately 1 hour at 50° C. and then the temperature was increased to 80° C. After 3 hours total, the solvent was evaporated. The residue was directly purified by PTLC using 5% methanol in dichloromethane to give compound 261d (19.4 mg, 35%). $^1$H NMR (400 Hz, CDCl$_3$): δ 7.72 (d, J=4.4 Hz, 1H), 7.51 (s, 1H), 6.91(s, 1H), 6.18 (s, 1H), 4.85 (d, J=10.4 Hz, 1H), 4.58 (J=10.4 Hz, 1H), 4.05-4.02 (m, 1H), 3.99 (s, 3H), 3.50 (dd, J$_1$=12.4 Hz, J$_2$=6 Hz, 1H), 3.32, (dd, J$_1$=12.4 H, J$_2$=2 Hz, 1H); MS (m/z), found 319.0 (M+Na+MeOH)$^+$.

Example 28

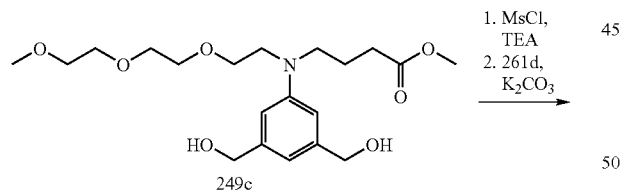

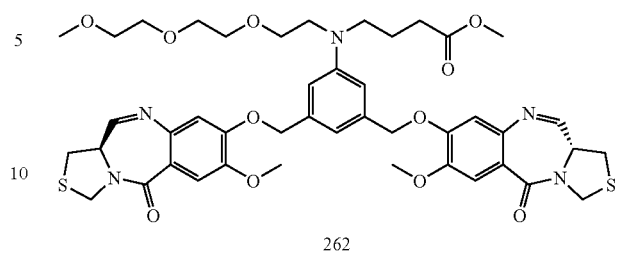

Compound 262:

Compound 249c (18 mg, 0.045 mmol) was dissolved in anhydrous dichloromethane (0.45 mL) and then cooled in an ice/brine bath. First, triethylamine (0.022 ml, 0.158 mmol) and then methanesulfonyl chloride (10.46 µl, 0.135 mmol) were added; the second very slowly. The mixture continued to stir in the bath for 1 hour. The reaction was quenched with ice/water and diluted with cold ethyl acetate. After separation, the organic layer was washed again with cold water and dried over sodium sulfate. It was filtered and evaporated under reduced pressure, keeping the temperature below 20° C., and then placed on the high vacuum to be used directly. Once completely dry, the product, and compound 261d (28.5 mg, 0.108 mmol) were dissolved in anhydrous N,N-dimethylformamide (350 µL). Potassium carbonate (29.8 mg, 0.216 mmol) was added. After stirring overnight at room temperature, the reaction was diluted with dichloromethane, washed with brine, dried over sodium sulfate, filtered and stripped. The crude product was first purified by silica gel chromatography using 4% methanol in dichloromethane to remove baseline residue. The recovered material was then purified using reverse phase HPLC (C18 column, CH$_3$CN/H$_2$O, loaded column with 3:1, centrifuged before injection) to give compound 262 as a solid. $^1$H NMR (400 Hz, CDCl$_3$): δ 7.68 (dd, J$_1$=4.4 Hz, J$_2$=1.6 Hz, 2H), 7.51 (s, 2H), 6.86 (s, 2H), 6.78 (s, 1H), 6.71 (s, 2H), 5.16 (dq, J$_1$=8.4 Hz, J$_2$=2.2, 4H), 4.85 (d, J=10.4 Hz, 2H), 4.58 (J=10.4 Hz, 2H), 4.04-3.97 (m, 7H), 3.68-3.38 (m, 18H), 3.40-3.29 (m. 7H), 2.33 (t, 7.2 Hz, 2H), 1.89-1.35 (m, 2H) MS (m/z), found 914.1 (M+Na)$^+$.

Example 29 (IGN-13)

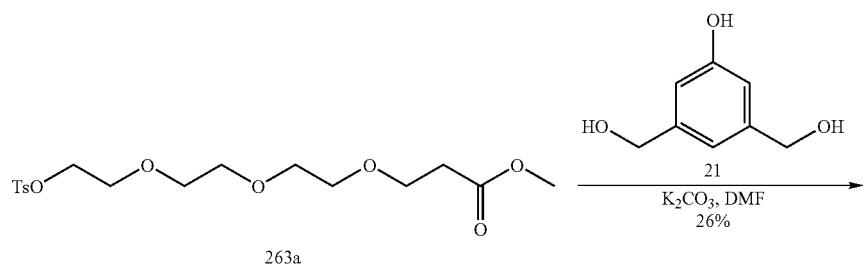

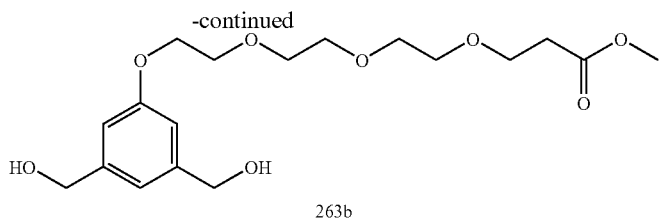

263b methyl 3-(2-(2-(2-(3,5-bis(hydroxymethyl)phenoxy)ethoxy)ethoxy)ethoxy)propanoate (263b)

To a stirred mixture of methyl 3-(2-(2-(2-(tosyloxy)ethoxy)ethoxy)ethoxy)propanoate (263a) (1.504 g, 3.85 mmol) and (5-hydroxy-1,3-phenylene)dimethanol (21) (0.54 g, 3.50 mmol) in anhydrous DMF (7.8 ml) was added potassium carbonate (0.726 g, 5.25 mmol). The reaction was stirred at room temperature for 18 hours at 75° C. The mixture was allowed to cool to room temperature, quenched with water, and extracted with ethyl acetate. The organic extracts were washed with brine, dried over anhydrous magnesium sulfate, filtered and concentrated. Purification by silica gel chromatography (5% MeOH/CH$_2$Cl$_2$) yielded methyl 3-(2-(2-(2-(3,5-bis(hydroxymethyl)phenoxy)ethoxy)ethoxy)ethoxy)propanoate (263b)(340 mg, 26%). $^1$H NMR (400 Hz, CDCl$_3$): δ 6.83 (s, 1H), 6.75 (s, 2H), 4.52 (s, 4H), 4.05 (t, J=4.8 Hz, 2), 3.79 (t, J=4.8 Hz, 2H), 3.70 (t, J=6.4 Hz, 2H), 3.65 (s, 3H), 3.70-3.56 (m, 8H), 3.26 (s, 2H), 2.55 (t, J=6.4 Hz, 2H); $^{13}$C NMR (400 Hz, CDCl$_3$): δ 172.31, 159.1, 143.0, 117.7, 112.1, 70.8, 70.7, 70.5, 70.4, 69.8, 67.5, 66.6, 64.7, 51.8, 34.9; MS (m/z), found 395.2 (M+Na)$^+$.

ride (0.076 ml, 0.973 mmol) was added slowly. After stirring for one hour at −5° C. the reaction was quenched with cold water and extracted with cold ethyl acetate. The organic extracts were washed with cold water, dried over anhydrous sodium sulfate, filtered and concentrated under reduced pressure to give methyl 3-(2-(2-(2-(3,5-bis((methylsulfonyloxy)methyl)pehoxy)ethoxy)ethoxy)ethoxy)propanoate. MS (m/z), found 551.1 (M+Na)$^+$. To a stirred mixture of methyl 3-(2-(2-(2-(3,5-bis((methylsulfonyloxy)methyl)phenoxy)ethoxy)ethoxy)ethoxy)propanoate (206 mg, 0.390 mmol) and compound 8 (287 mg, 0.974 mmol) in anhydrous DMF (3.9 ml) was added potassium carbonate (269 mg, 1.949 mmol). The reaction was allowed to stir at room temperature for 18 hours. The mixture was quenched with water and extracted three times with dichloromethane. The organic extracts were washed with water and brine, dried over anhydrous sodium sulfate, filtered and concentrated in vacuo. Purification by flash silica gel chromatography (5% MeOH/CH$_2$Cl$_2$) followed by preparative reverse phase HPLC (C18 column, eluted with CH$_3$CN/H$_2$O) gave compound 263c (110 mg, 30%) as a white solid. $^1$H NMR (400 Hz, CDCl$_3$): δ 8.18

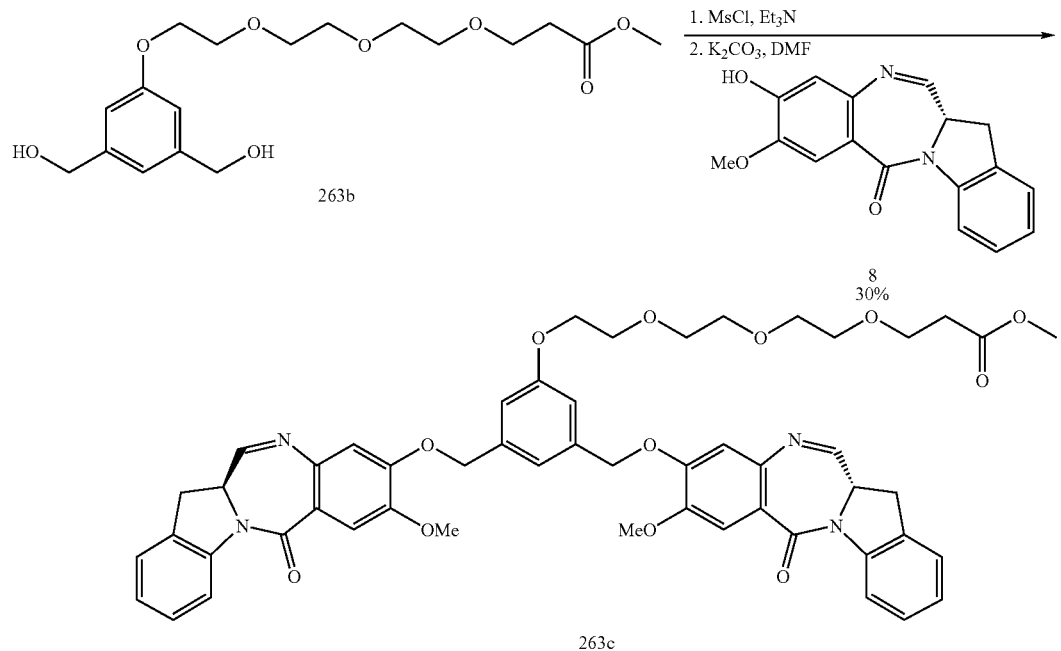

263c

Compound 263c:

To a stirred solution of methyl 3-(2-(2-(2-(3,5-bis(hydroxymethyl)phenoxy)ethoxy)ethoxy)ethoxy)propanoate (263b) (145 mg, 0.389 mmol) in anhydrous dichloromethane (5.5 ml) was added triethylamine (0.163 ml, 1.168 mmol). The mixture was cooled to −5° C. and methanesulfonyl chlo- (d, J=8.0 Hz, 2H), 7.77 (m, 2H), 7.49 (s, 2H), 7.19 (m, 4H), 7.02 (m, 2H), 6.89 (s, 2H), 6.87 (s, 1H), 6.75 (s, 2H), 5,10 (m, 4H), 4.39 (m, 2H), 4.05 (m, 2H), 3.90 (s, 6H), 3.77 (m, 2H), 3.67 (t, J=6.4 Hz, 2H), 3.64 (m, 2H), 3.59 (s, 3H), 3.70-3.54 (m, 8H), 3.40 (m, 2H), 2.51 (t, J=6.4 Hz, 2H); MS (m/z), found 965.3 (M+H$_2$O+Na)$^+$, 983.3 (M+2H$_2$O+Na)$^+$.

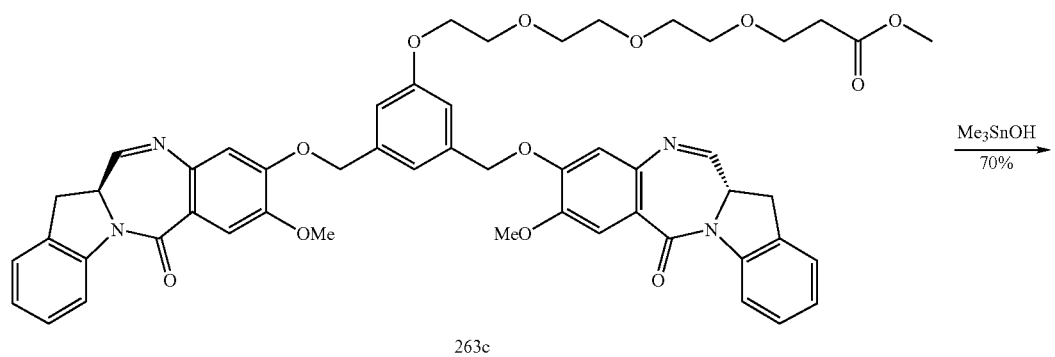

263c

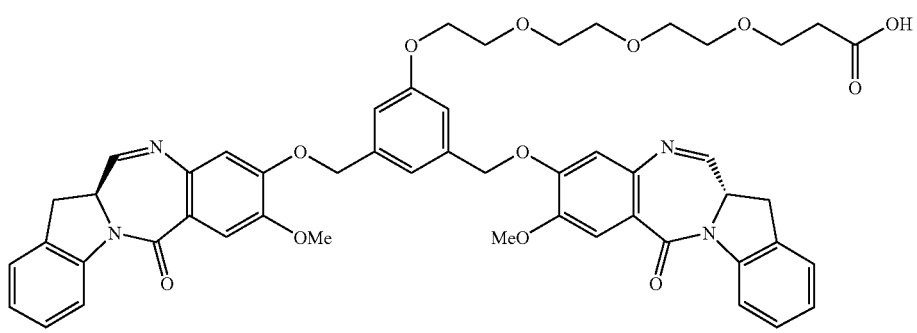

263d

Compound 263d:

To a solution of compound 263c (51 mg, 0.055 mmol) in 1,2-Dichloroethane (2.2 ml) was added trimethyl tin hydroxide (199 mg, 1.103 mmol). The reaction was stirred for 18 hours at 80° C., then cooled to room temperature, and quenched with saturated ammonium chloride. The mixture was extracted with dichloromethane. The organic layer was washed with brine, dried over anhydrous sodium sulfate, filtered and concentrated. Purification by silica gel chromatography (10% MeOH/CH$_2$Cl$_2$) yielded compound 263d (35 mg, 70%). $^1$H NMR (400 Hz, CDCl$_3$): δ 8.26 (d, J=8.0 Hz, 2H), 7.88 (m, 2H), 7.58 (s, 2H), 7.28 (m, 4H), 7.11 (m, 3H), 7.00 (s, 2H), 6.88 (s, 2H), 5.21 (m, 4H), 4.49 (m, 2H), 4.18 (m, 2H), 4.00 (s, 6H), 3.89 (m, 2H), 3.79 (m, 2H), 3.70 (m,10H), 3.51 (m, 2H), 2.62 (m, 2H); MS (m/z), found 909.2 (M−1)$^−$, 927.2 (M−1+H$_2$O)$^−$, 945.2 (M−1+2H$_2$O)$^−$.

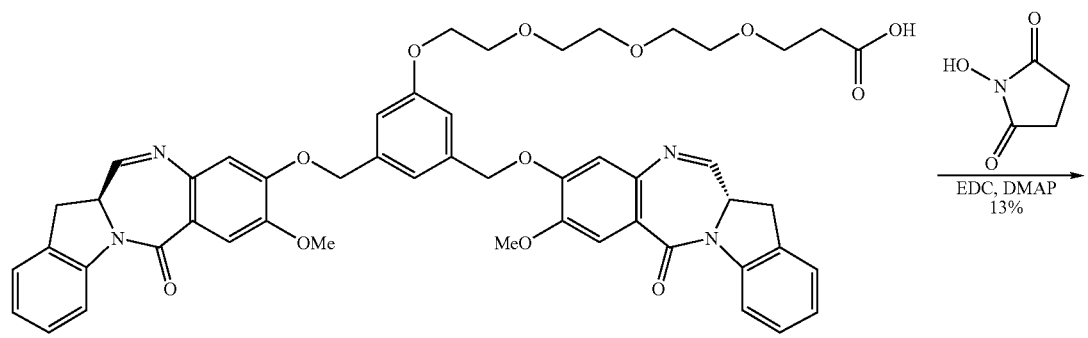

263d

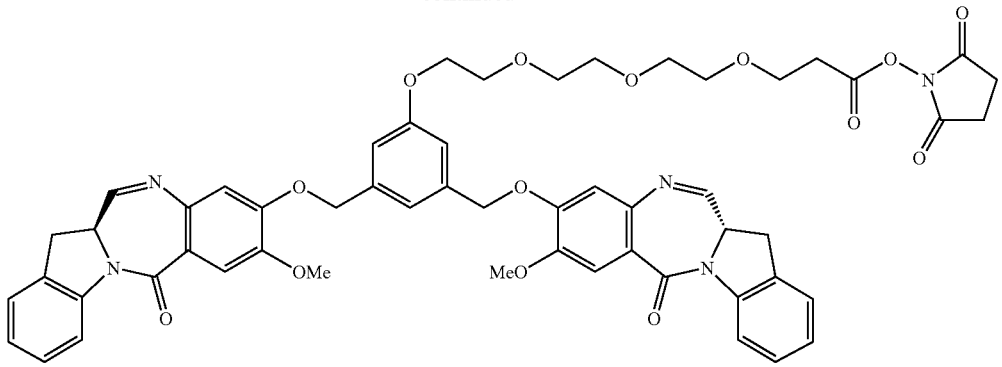

263e

Compound 263e:

To a solution of compound 263d (30 mg, 0.033 mmol) in anhydrous dichloromethane (2.5 mL) was added N-hydroxy succinimide (9.77 mg, 0.082 mmol), EDC (15.78 mg, 0.082 mmol), and DMAP (0.406 mg, 3.29 μmol). The reaction was stirred for 18 hours at room temperature and then diluted with dichloromethane. The mixture was washed with saturated ammonium chloride and brine. The organic layer was dried over anhydrous sodium sulfate, filtered and concentrated in vacuo. The crude material was purified by preparative reverse phase HPLC (C18 column, eluted with $CH_3CN/H_2O$). Fractions containing product were extracted with dichloromethane, dried over anhydrous sodium sulfate, filtered and co-evaporated with acetonitrile under reduced pressure to give compound 263e (4.5 mg, 13%) as a white solid; MS (m/z), found 1030.4 $(M+Na)^+$, 1046.3 $(M+K)^+$.

Example 30 (IGN-27)

methyl 3-(2-(2-(2-(3,5-bis(hydroxymethyl)phenylamino)ethoxy)ethoxy)ethoxy)propanoate (264a)

To a mixture of methyl 3-(2-(2-(2-(tosyloxy)ethoxy)ethoxy)ethoxy)propanoate (263a) (250 mg, 0.640 mmol) and (5-amino-1,3-phenylene)dimethanol (26)(108 mg, 0.704 mmol) in anhydrous DMF (1.4 ml) was added potassium carbonate (133 mg, 0.960 mmol). The reaction stirred for 18 hours at 80° C. and then was allowed to cool to room temperature. The mixture was quenched with water and extracted two times with ethyl acetate. The organic extracts were washed with brine, dried over anhydrous magnesium sulfate, filtered and concentrated. Purification by silica gel chromatography (5% Methanol/methylene chloride) yielded methyl 3-(2-(2-(2-(3,5-bis(hydroxymethyl)phenylamino)ethoxy)ethoxy)ethoxy)propanoate (264a) (61 mg, 25%); $^1H$ NMR (400 Hz, $CDCl_3$): δ 6.58 (s, 1H), 6.47 (s, 2H), 4.49 (s, 4H), 3.67 (t, J=6.4 Hz, 2H), 3.62 (s, 3H), 3.64-3.54 (m, 10H), 3.21 (t, J=5.2 Hz, 2H), 2.51 (t, J=6.4 Hz, 2H); MS (m/z), found 394.3 $(M+Na)^+$.

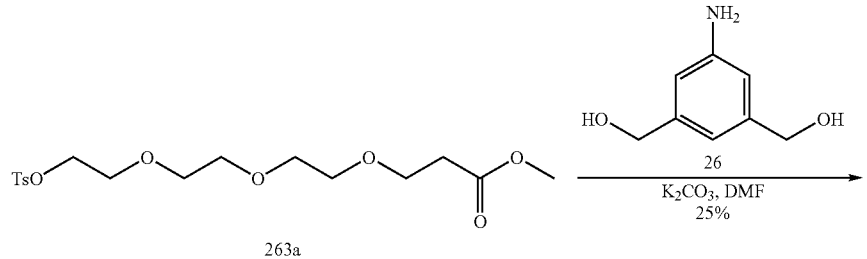

263a

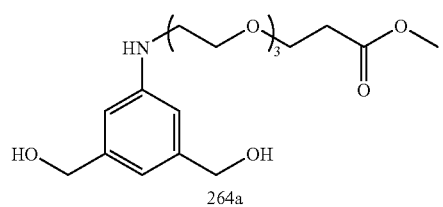

264a

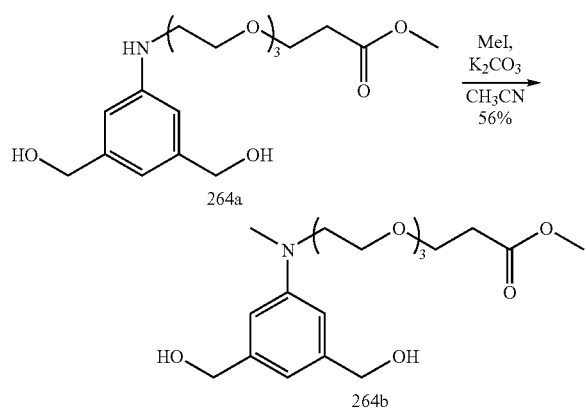

Compound 264b:

To a solution of methyl 3-(2-(2-(2-(3,5-bis(hydroxymethyl)phenylamino)ethoxy)ethoxy)ethoxy)propanoate (264a) (60 mg, 0.162 mmol) in acetonitrile (1.6 ml) was added iodomethane (0.013 ml, 0.210 mmol) and potassium carbonate (26.8 mg, 0.194 mmol). The reaction stirred at 82° C. for 18 hours. The mixture was cooled to room temperature and then the solvent was removed under reduced pressure. The crude material was diluted with 3:1 $CH_2Cl_2$/MeOH and filtered through Celite. The filtrate was concentrated and purified by silica gel chromatography eluting with 5% Methanol/dichloromethane to give Compound 264b (35 mg, 56%). $^1$H NMR (400 Hz, $CDCl_3$): δ 6.58 (s, 3H), 4.52 (s, 4H), 3.64 (t, J=6.4 Hz, 2H), 3.60 (s, 3H), 3.53 (m, 12H), 2.91 (s, 3H), 2.51 (t, J=6.4 Hz, 2H), 2.28 (s, 2H); $^{13}$C NMR (400 Hz, $CDCl_3$): δ 172.1, 149.8, 142.4, 113.4, 109.9, 70.7, 70.6, 70.4, 70.3, 68.6, 66.5, 65.6, 52.3, 51.7, 38.9, 34.8; MS (m/z), found 408.4 $(M+Na)^+$.

Compound 264c:

To a stirred solution of compound 246b (60 mg, 0.156 mmol) in anhydrous dichloromethane (2.8 mL) was added triethylamine (0.065 mL, 0.467 mmol). The mixture was cooled to −5° C. and methanesulfonyl chloride (0.030 mL, 0.389 mmol) was added slowly. After stirring for one hour at −5° C. the reaction was quenched with cold water and extracted with cold ethyl acetate. The organic layer was washed with cold water, dried over anhydrous sodium sulfate, filtered and concentrated under reduced pressure to give the dimesylate intermediate. MS (m/z), found 564.0 $(M+Na)^+$.

To a mixture of the dimesylate linker (49 mg, 0.090 mmol) and compound 8 (66.6 mg, 0.226 mmol) in anhydrous DMF (0.9 mL) was added potassium carbonate (62.5 mg, 0.452 mmol). The reaction was stirred for 18 hours at room temperature, quenched reaction with water and extracted three times with dichloromethane. The organic extracts were washed with water and brine, dried over anhydrous sodium sulfate, filtered and concentrated in vacuo. Purification by flash silica gel chromatography (5% MeOH/$CH_2Cl_2$) followed by preparative reverse phase HPLC (C18 column, eluted with $CH_3CN/H_2O$) gave compound 264c (16 mg, 19%) as a white solid. $^1$H NMR (400 Hz, $CDCl_3$): δ 8.18 (d, J=8.0 Hz, 2H), 7.76 (m, 2H), 7.48 (s, 2H), 7.18 (m, 4H), 7.02 (t, J=7.2 Hz, 2H), 6.79 (m, 2H), 6.74 (s, 1H), 6.65 (s, 2H), 5.08 (m, 4H), 4.39 (m, 2H), 3.89 (s, 6H), 3.66 (t, J=6.4 Hz, 2H), 3.62 (m, 2H), 3.60 (s, 3H), 3.53 (m, 12H), 3.40 (m, 2H), 2.91 (s, 3H), 2.51 (t, J=6.4 Hz, 2H); MS (m/z), found 978.3 $(M+H_2O+Na)^+$, 996.3 $(M+2H_2O+Na)^+$.

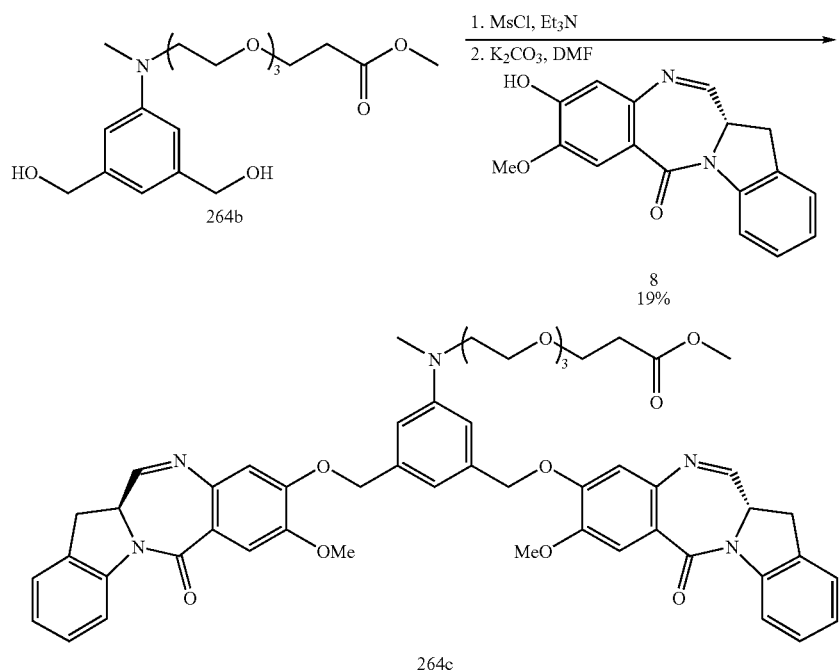

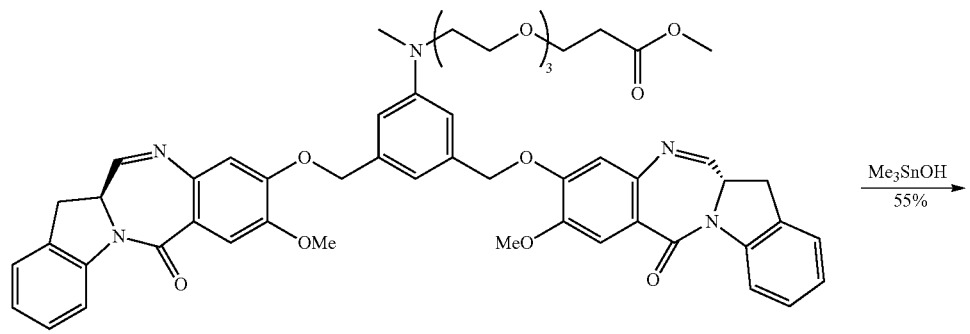

264c

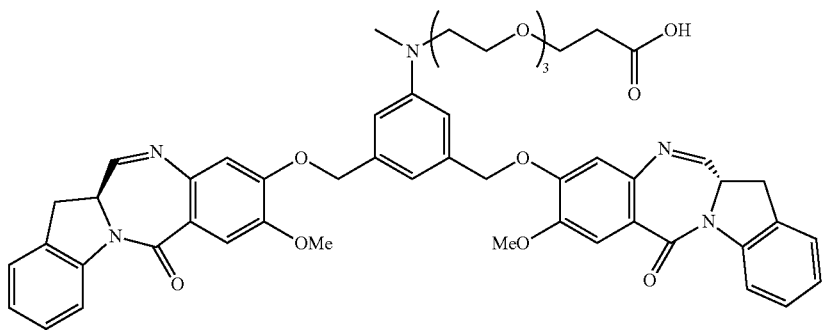

264d

Compound 264d:

To a solution of Compound 264c (26 mg, 0.028 mmol) in anhydrous 1,2-Dichloroethane (1.1 ml) was added trimethyl tin hydroxide (100 mg, 0.554 mmol). The reaction was stirred for 18 hours at 80° C. The mixture was allowed to cool to room temperature and extracted with dichloromethane and saturated ammonium chloride. The organic extracts were washed with brine, dried over anhydrous sodium sulfate, filtered and concentrated in vacuo. Purification by preparative TLC in 5% Methanol/methylene chloride yielded compound 264d (14 mg, 55%). MS (m/z), found 922.1 (M−1)⁻, 940.0 (M−1+H$_2$O)⁻, 958.1 (M−1+2H$_2$O)⁻.

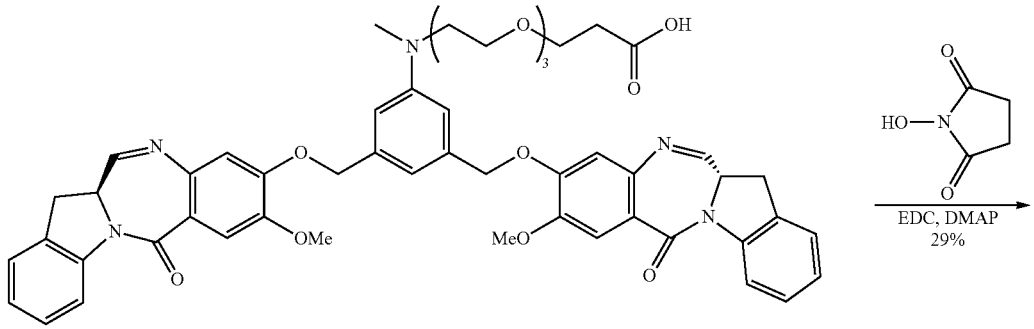

264d

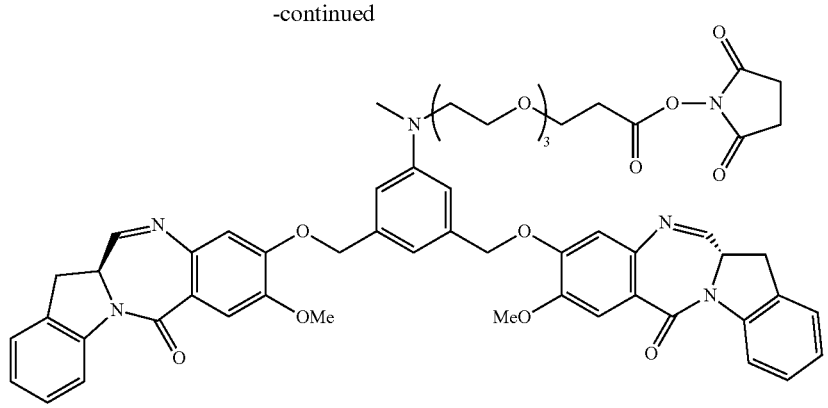

264e

Compound 264e:

To a stirred solution of compound 264d (13 mg, 0.014 mmol) in anhydrous dichloromethane (1.0 mL) was added N-hydroxysuccinimide (5.01 mg, 0.042 mmol), EDC (8.09 mg, 0.042 mmol), and DMAP (0.172 mg, 1.407 μmol). The reaction stirred for 18 hours at room temperature. The mixture was extracted with dichloromethane and saturated ammonium chloride. The organic layer was washed with brine, dried over anhydrous sodium sulfate, filtered and concentrated in vacuo. The crude material was purified by preparative reverse phase HPLC (C18 column, eluted with $CH_3CN/H_2O$). Fractions containing product were combined and extracted with dichloromethane, dried over anhydrous sodium sulfate, filtered and co-evaporated with acetonitrile under reduced pressure to obtain compound 264e (4.1 mg, 29%). MS (m/z), found 1021.3 $(M+H)^+$, 1043.2 $(M+Na)^+$, 1061.2 $(M+H_2O+Na)^+$, 1079.2 $(M+2H_2O+Na)^+$.

Example 31 (IGN-28)

methyl 1-(tosyloxy)-3,6,9,12,15,18,21,24,27,30,33, 36-dodecaoxanonatriacontan-39-oate (265b)

To a stirred solution of methyl 1-hydroxy-3,6,9,12,15,18, 21,24,27,30,33,36-dodecaoxanonatriacontan-39-oate (265a) (1.2 g, 1.897 mmol) in dichloromethane (9.48 mL) at 0° C. was added triethylamine (0.529 mL, 3.79 mmol), toluene sulfonylchloride (0.542 g, 2.84 mmol) and DMAP (0.023 g, 0.190 mmol). The mixture was stirred for one hour at 0° C. and then three hours at ambient temperature, after which it was quenched with water and extracted twice with dichloromethane. The organic extracts were washed with brine, dried over anhydrous magnesium sulfate, filtered and concentrated in vacuo. Purification by silica gel chromatography (5% $MeOH/CH_2Cl_2$) gave methyl 1-(tosyloxy)-3,6,9,12, 15,18,21,24,27,30,33,36-dodecaoxanonatriacontan-39-oate (265b)(1.0 g, 67%) as a light yellow oil. $^1H$ NMR (400 Hz, $CDCl_3$): δ 7.80 (d, J=8.4 Hz, 2H), 7.35 (d, J=8.0 Hz, 2H), 4.16 (t, J=4.8 Hz, 2H), 3.75 (t, J=6.4 Hz, 2H), 3.69 (s, 3H), 3.64 (m, 46H), 2.60 (t, J=6.4 Hz, 2H), 2.45 (s, 3H).

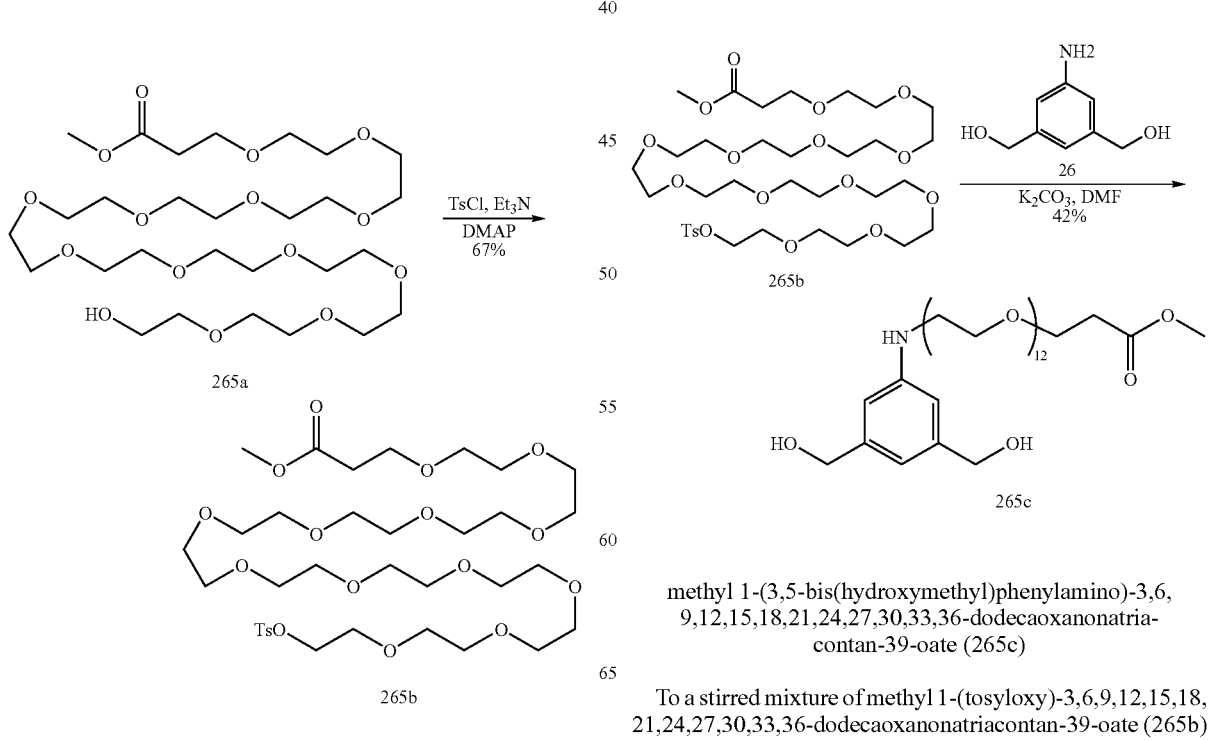

methyl 1-(3,5-bis(hydroxymethyl)phenylamino)-3,6, 9,12,15,18,21,24,27,30,33,36-dodecaoxanonatriacontan-39-oate (265c)

To a stirred mixture of methyl 1-(tosyloxy)-3,6,9,12,15,18, 21,24,27,30,33,36-dodecaoxanonatriacontan-39-oate (265b)

(700 mg, 0.890 mmol) and (5-amino-1,3-phenylene) dimethanol (26) (150 mg, 0.978 mmol) in anhydrous DMF (2.0 ml) was added potassium carbonate (184 mg, 1.334 mmol). The reaction was stirred at 80° C. overnight. The mixture was cooled to room temperature, quenched with water and extracted with 10% Methanol/Methylene chloride. The organic layer was washed with brine, dried over anhydrous magnesium sulfate, filtered and concentrated in vacuo. The crude product was purified by silica gel chromatography (eluted with 5→15% MeOH/CH2Cl2) to give methyl 1-(3,5-bis(hydroxymethyl)phenylamino)-3,6,9,12,15,18,21,24,27,30,33,36-dodecaoxanonatriacontan-39-oate (265c) (285 mg, 42%). $^1$H NMR (400 Hz, CDCl$_3$): δ 6.62 (s, 1H), 6.51 (s, 2H), 4.52 (s, 4H), 3.72 (t, J=6.4 Hz, 2H), 3.65 (s, 3H), 3.61 (m, 48H), 2.94 (s, 2H), 2.63 (s, 1H), 2.57 (t, J=6.4 Hz, 2H); MS (m/z), found 790.4 (M+Na)⁻.

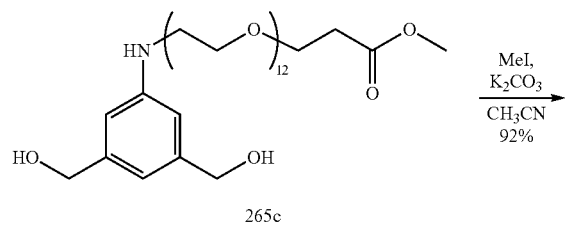

265c

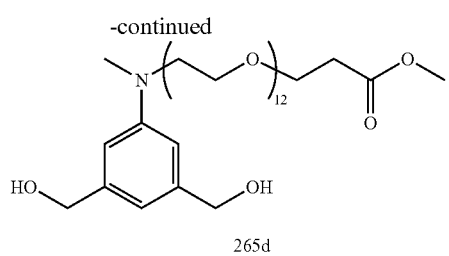

265d methyl 2-(3,5-bis(hydroxymethyl)phenyl)-5,8,11,14,17,20,23,26,29,32,35,38-dodecaoxa-2-azahentetracontan-41-oate (265d)

To a stirred solution of methyl 1-(3,5-bis(hydroxymethyl)phenylamino)-3,6,9,12,15,18,21,24,27,30,33,36-dodecaoxanonatriacontan-39-oate (265c) (67 mg, 0.087 mmol) in anhydrous DMF (1.0 ml) was added iodomethane (7.06 μl, 0.113 mmol) and potassium carbonate (14.47 mg, 0.105 mmol). The reaction was stirred at 82° C. for 18 hours. The mixture was cooled to room temperature, diluted with water and extracted with dichloromethane. The organic layer was dried over anhydrous sodium sulfate, filtered and concentrated in vacuo. Purification by preparative TLC (10% MeOH/CH$_2$Cl$_2$) gave methyl 2-(3,5-bis(hydroxymethyl)phenyl)-5,8,11,14,17,20,23,26,29,32,35,38-dodecaoxa-2-azahentetracontan-41-oate (265d) (62 mg, 92%). $^1$H NMR (400 Hz, CDCl$_3$): δ 6.65 (s, 3H), 4.59 (d, J=5.6 Hz, 4H), 3.74 (t, J=6.4 Hz, 2H), 3.67 (s, 3H), 3.61 (m, 46H), 3.54 (t, J=6.0 Hz, 2H) 2.98 (s, 3H), 2.59 (t, J=6.4 Hz, 2H), 2.55 (m, 2H); MS (m/z), found 820.5 (M+K)⁺.

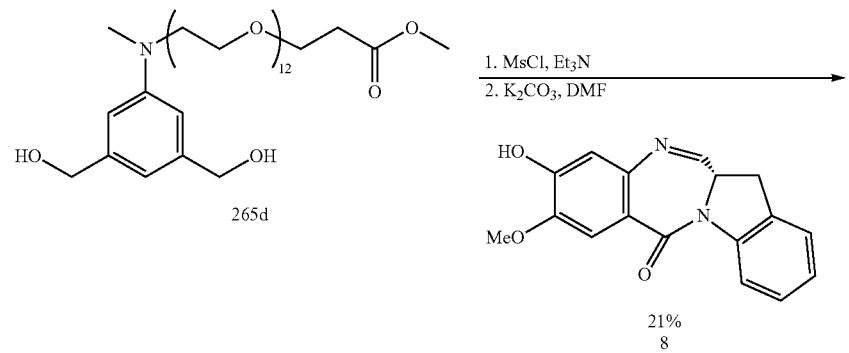

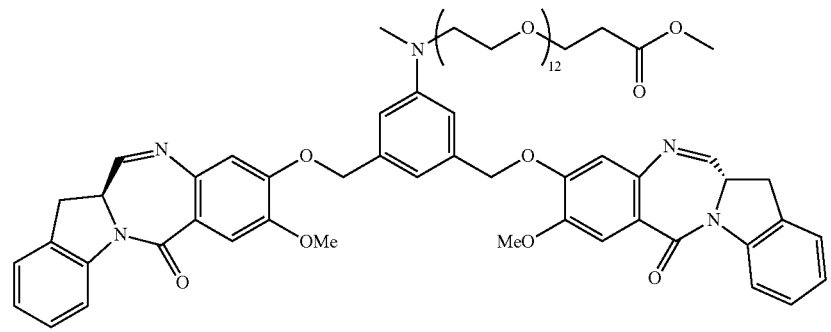

265e

Compound 265e:

To a stirred solution of methyl 2-(3,5-bis(hydroxymethyl)phenyl)-5,8,11,14,17,20,23,26,29,32,35,38-dodecaoxa-2-azahentetracontan-41-oate (265d) (71 mg, 0.091 mmol) in anhydrous dichloromethane (1.4 mL) was added triethylamine (0.038 mL, 0.272 mmol). The mixture was cooled to −5° C. and methanesulfonyl chloride (0.018 mL, 0.227 mmol) was added slowly. After stirring for one hour at −5° C. the reaction was quenched with cold water and extracted with cold ethyl acetate. The organic extracts were washed with cold water, dried over anhydrous sodium sulfate, filtered and concentrated under reduced pressure to give methyl 2-(3,5-bis((methylsulfonyloxy)methyl)phenyl)-5,8,11,14,17,20,23,26,29,32,35,38-dodecaoxa-2-azahentetracontan-41-oate. MS (m/z), found 960.2 (M+Na)$^+$. To a mixture of methyl 2-(3,5-bis((methylsulfonyloxy)methyl)phenyl)-5,8,11,14,17,20,23,26,29,32,35,38-dodecaoxa-2-azahentetracontan-41-oate (69 mg, 0.074 mmol) and compound 8 (54.1 mg, 0.184 mmol) in anhydrous DMF (0.8 mL) was added potassium carbonate (50.8 mg, 0.368 mmol). The reaction was allowed to stir for 18 hours at room temperature. The reaction was quenched with water and extracted twice with dichloromethane. The remaining aqueous layer was extracted twice with 50% MeOH/CH$_2$Cl$_2$. The combined organic extracts were washed with brine, dried over anhydrous sodium sulfate, filtered and concentrated in vacuo. Purification by flash silica gel chromatography (5% MeOH/CH$_2$Cl$_2$) followed by preparative reverse phase HPLC (C18 column, eluted with CH$_3$CN/H$_2$O) gave compound 265e (23 mg, 23%). MS (m/z), found 1375.4 (M+Na+H$_2$O)$^+$, 1393.4 (M+Na+2H$_2$O)$^+$.

Compound 265f:

To a stirred solution of compound 265e (22 mg, 0.016 mmol) in anhydrous 1,2-dichloroethane (300 μL) was added trimethyl tin hydroxide (44.7 mg, 0.247 mmol). The reaction stirred at 90° C. for 18 hours. The mixture was allowed to cool to room temperature and then diluted with dichloromethane. The organic layer was washed with brine containing a few drops 5% concentrated hydrochloric acid and then with brine alone, dried over anhydrous sodium sulfate, filtered and concentrated in vacuo. Purification by preparative TLC (2×5% MeOH/CH2Cl2) gave compound 265f (7.5 mg, 34%). MS (m/z), found 1318.4 (M−1)$^-$, 1336.4 (M−1+H$_2$O)$^-$, 1354.4 (M−1+2H$_2$O)$^-$.

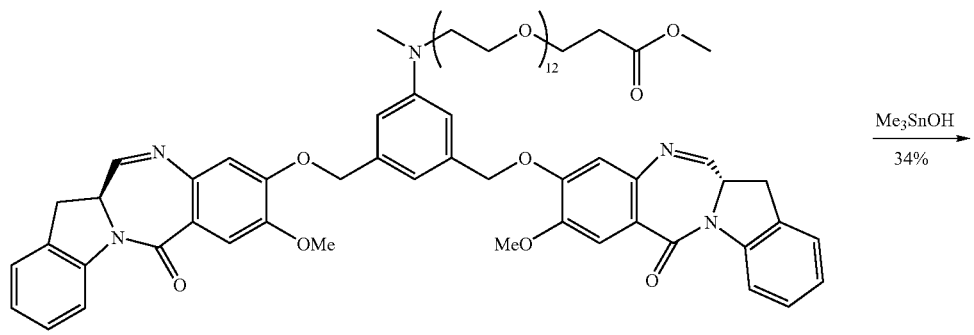

265e

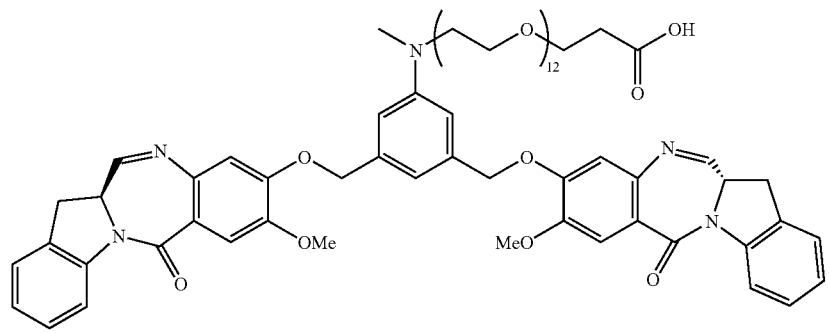

265f

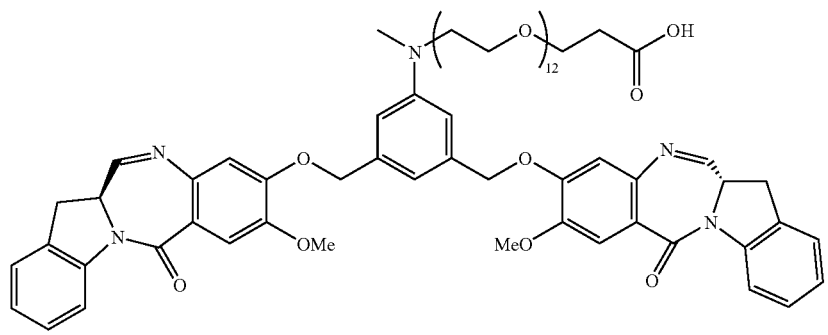
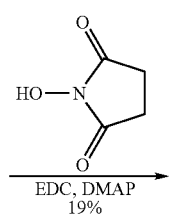

265f

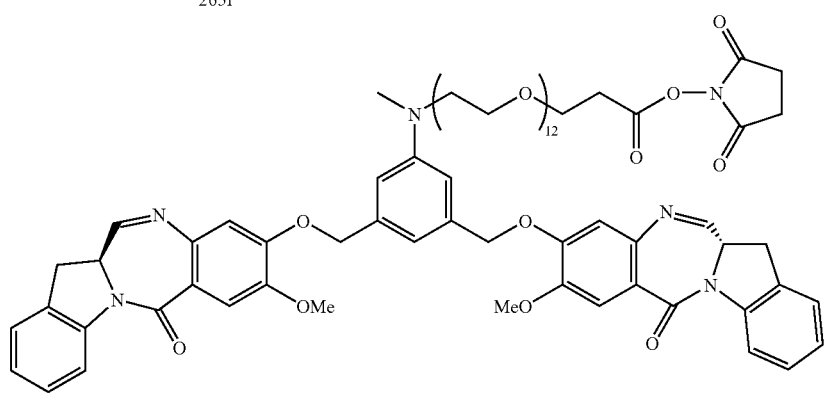

265g

Compound 265g:

To a stirred solution of compound 265f (7.5 mg, 5.68 μmol) in anhydrous dichloromethane (400 μL) was added N-hydroxy succinimide (1.961 mg, 0.017 mmol), EDC (3.27 mg, 0.017 mmol), and DMAP (0.069 mg, 0.568 μmol). The reaction stirred for 18 hours at room temperature. The mixture was extracted with dichloromethane and saturated ammonium chloride. The organic layer was washed with brine, dried over anhydrous sodium sulfate, filtered and the solvent was removed under reduced pressure. The crude material was purified by preparative reverse phase HPLC (C18 column, eluted with $CH_3CN/H_2O$). Fractions containing product were extracted with dichloromethane, dried over anhydrous sodium sulfate, filtered and co-evaporated with acetonitrile to give compound 265g (1.5 mg, 19%). MS (m/z), found 1439.9 $(M+Na)^+$, 1457.9 $(M+Na+H_2O)^+$.

Example 32 (IGN-22)

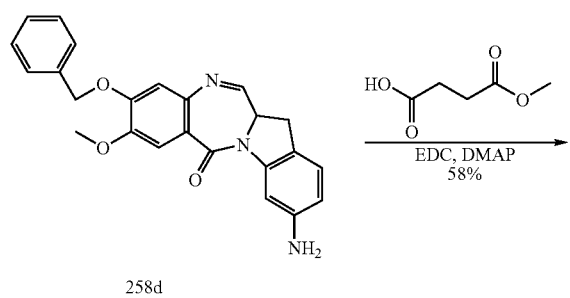

258d

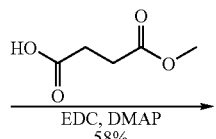

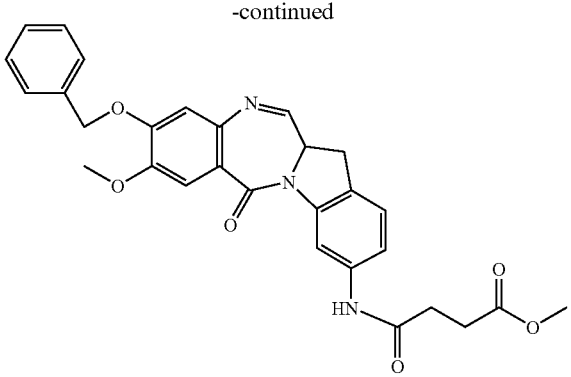

266a

Compound 266a:

To a solution of compound 258d (20 mg, 0.050 mmol) in dichloromethane (1.0 mL) was added mono-methyl succinate (13.23 mg, 0.100 mmol), EDC (19.20 mg, 0.100 mmol), and DMAP (3.06 mg, 0.025 mmol) was added. The reaction stirred at room temperature for 18 hours. The mixture was diluted with water and extracted with ethyl acetate. The organic extracts were washed with brine, filtered and concentrated under reduced pressure. Purification by silica gel chromatography (3% $MeOH/CH_2Cl_2$) gave compound 266a (15mg, 58%). MS (m/z), found 568.4$(M+Na+MeOH)^+$.

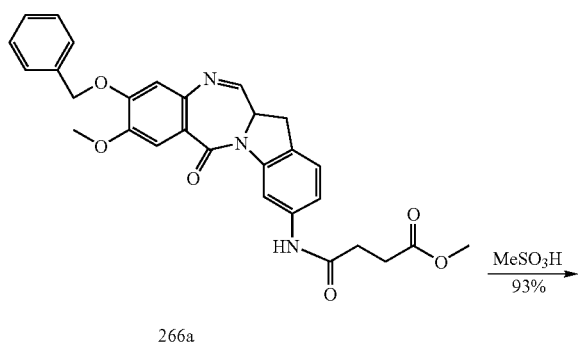

266a

Compound 266b:

To a solution of compound 266a (15 mg, 0.029 mmol) in dichloromethane (3.5 ml) was added methanesulfonic acid (0.114 ml, 1.753 mmol). The reaction was stirred for one hour at room temperature then diluted with methanol and water. The mixture was neutralized with saturated sodium bicarbonate to pH=7 and extracted three times with dichloromethane. The organic layer was dried over anhydrous sodium sulfate, filtered and concentrated in vacuo. Purification by preparative TLC (2×5% MeOH/CH$_2$Cl$_2$) gave compound 266b (11.5 mg, 93%). MS (m/z), found 446.4(M+Na)$^+$, 478.4 (M+Na+ MeOH)$^+$.

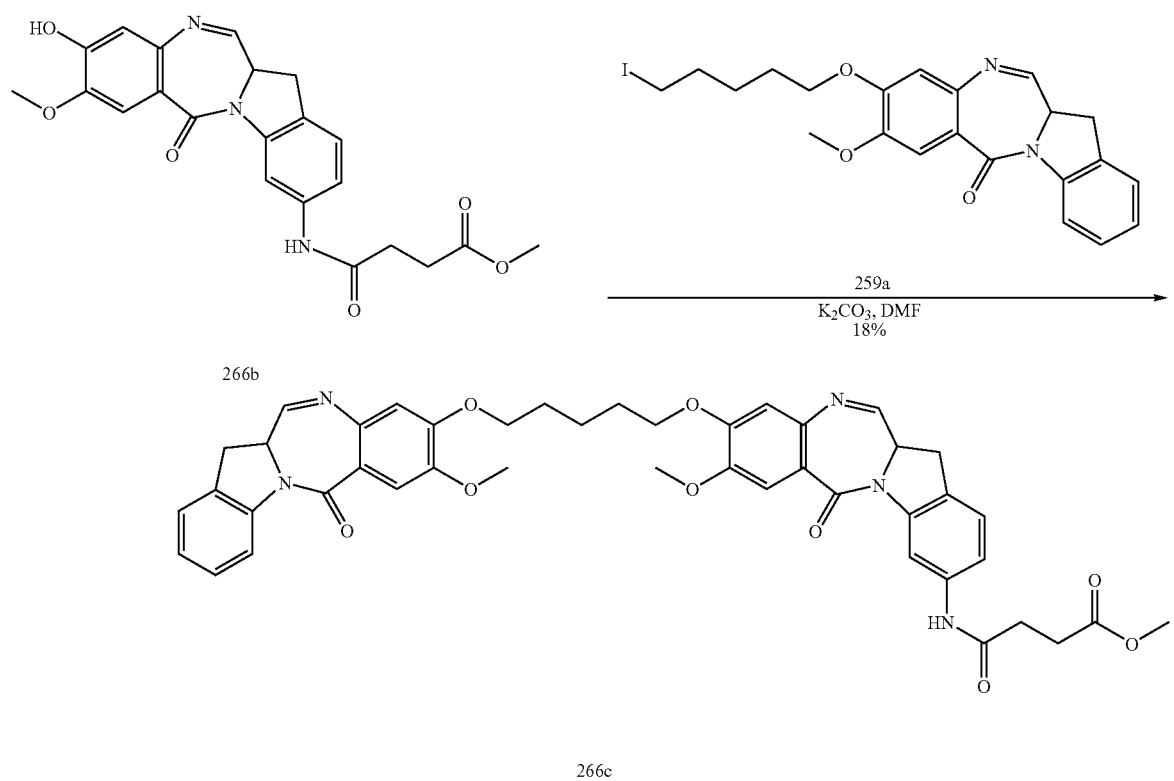

266c

Compound 266c:

To a mixture of compound 266b (11.5 mg, 0.027 mmol) and compound 259a (19.98 mg, 0.041 mmol) in anhydrous DMF (0.5 ml) was added potassium carbonate (11.26 mg, 0.081 mmol). The reaction was stirred for 18 hours at room temperature. The mixture was quenched with water and extracted three times with dichloromethane. The organic layer was washed with brine, dried over anhydrous sodium sulfate, filtered and concentrated under reduced pressure. Purification by preparative TLC (5% MeOH/CH$_2$Cl$_2$) followed by preparative reverse phase HPLC (C18 column, eluted with CH$_3$CN, H$_2$O) yielded compound 266c (4 mg, 18%). $^1$H NMR (400 Hz, CDCl$_3$): δ 8.27 (d, J=8.0 Hz, 1H), 8.06 (s, 1H), 7.87 (m, 2H), 7.74 (m, 1H), 7.55 (s, 1H), 7.52 (s, 1H), 7.49 (m, 1H), 7.26 (m, 1H) 7.19 (d, J=8.8 Hz, 1H), 7.10 (m, 1H), 6.82 (m, 2H), 4.49 (m, 2H), 4.12 (m, 4H), 3.95 (s, 6H), 3.71 (s, 3H), 3.48 (m, 4H), 2.75 (m, 2H), 2.66 (m, 2H), 1.98 (m, 4H), 1.70 (m, 2H); MS (m/z), found 824.1(M+K)$^+$.

-continued

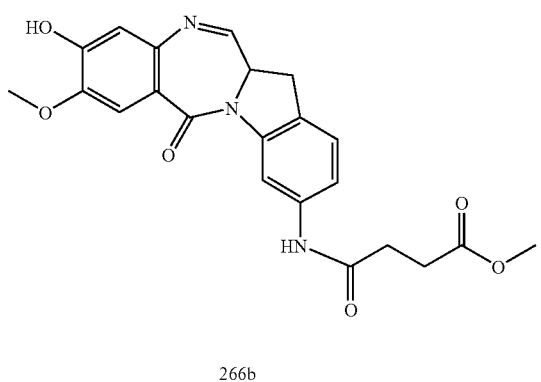

266b

Example 33 (IGN-31)

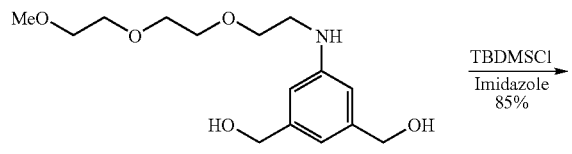

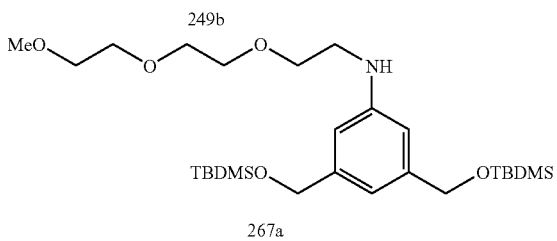

3,5-bis((tert-butyldimethylsilyloxy)methyl)-N-(2-(2-(2-methoxyethoxy)ethoxy)ethyl)aniline (267a)

To a solution of (5-(2-(2-(2-methoxyethoxy)ethoxy)ethylamino)-1,3-phenylene)dimethanol (249b)(0.4 g, 1.336 mmol) in dichloromethane (6.68 mL) was added t-butyldimethylsilyl chloride (0.604 g, 4.01 mmol) and imidazole (0.318 g, 4.68 mmol). The reaction stirred at room temperature for 90 minutes. The mixture was diluted with dichloromethane and filtered through Celite. The filtrated was concentrated and purified by silica gel chromatography eluting with 20% Ethyl acetate/Hexanes to yield 3,5-bis((tert-butyldimethylsilyloxy)methyl)-N-(2-(2-(2-methoxyethoxy)ethoxy)ethyl)aniline (267a) (600 mg, 85%). MS (m/z), found 550.3 (M+Na)$^+$.

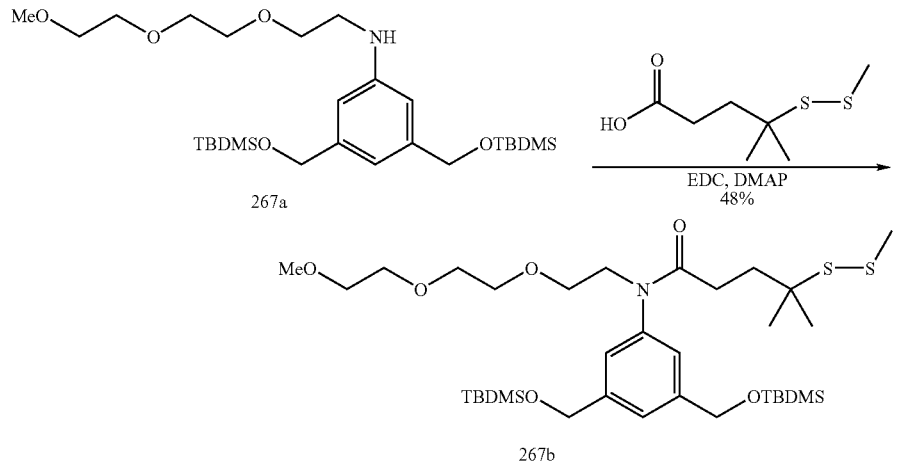

N-(3,5-bis((tert-butyldimethylsilyloxy)methyl)phenyl)-N-(2-(2-(2-methoxyethoxy)ethoxy)ethyl)-4-methyl-4-(methyldisulfanyl)pentanamide (267b)

To a mixture of 3,5-bis((tert-butyldimethylsilyloxy)methyl)-N-(2-(2-(2-methoxyethoxy)ethoxy)ethyl)aniline (267a) (525 mg, 0.995 mmol) and 4-methyl-4-(methyldisulfanyl)pentanoic acid (232 mg, 1.193 mmol) in anhydrous dichloromethane (9.0 mL) was added EDC (229 mg, 1.193 mmol) and DMAP (12.15 mg, 0.099 mmol). The reaction was stirred at room temperature for five hours. The mixture was diluted with dichloromethane and water. The organic layer was washed with brine, dried over anhydrous sodium sulfate, filtered and concentrated under reduced pressure. Purification by silica gel chromatography (30% Ethyl acetate/Hexanes) gave N-(3,5-bis((tert-butyldimethylsilyloxy)methyl)phenyl)-N-(2-(2-(2-methoxyethoxy)ethoxy)ethyl)-4-methyl-4-(methyldisulfanyl)pentanamide (267b) (335 mg, 48%).

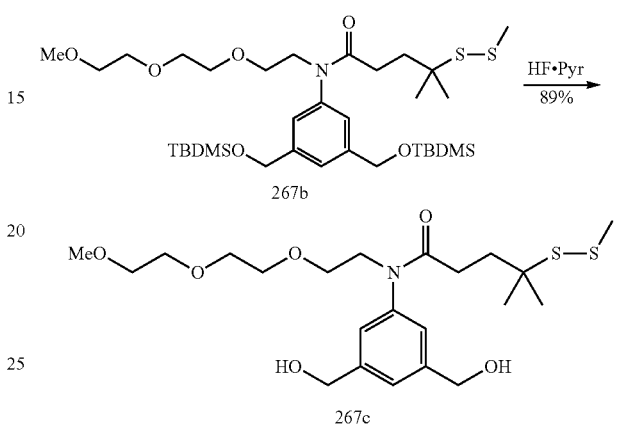

N-(3,5-bis(hydroxymethyl)phenyl)-N-(2-(2-(2-methoxyethoxy)ethoxy)ethyl)-4-methyl-4-(methyldisulfanyl)pentanamide (267c)

To a stirred solution of N-(3,5-bis((tert-butyldimethylsilyloxy)methyl)phenyl)-N-(2-(2-(2-methoxyethoxy)ethoxy)ethyl)-4-methyl-4-(methyldisulfanyl)pentanamide (267b)(315 mg, 0.447 mmol) in anhydrous acetonitrile (7.0 mL) at 0° C. was added anhydrous pyridine (7.00 mL) followed by dropwise addition of HF.Pyridine (3.1 mL, 1 mL/100 mg). The reaction stirred at 0° C. for two hours. It was diluted with ethyl acetate and slowly quenched with saturated sodium bicarbonate. The mixture was extracted three times with ethyl acetate. The organic layer was washed with water and brine, dried over sodium sulfate, filtered and concentrated. Purification by silica gel chromatography, eluting with 5% MeOH/CH$_2$Cl$_2$, yielded N-(3,5-bis(hydroxymethyl)phenyl)-N-(2-(2-(2-methoxyethoxy)ethoxy)ethyl)-4-methyl-4-(methyldisulfanyl)pentanamide (267c)(190 mg, 89%). $^1$H NMR (400 Hz, CDCl$_3$): δ 7.21 (s, 1H), 7.16 (s, 2H), 4.63 (s, 4H), 3.79 (t, J=5.2,5.6 Hz, 2H), 3.53 (m, 6H), 3.48 (m, 4H), 3.29 (s, 3H), 2.53 (s, 2H), 2.27 (s, 3H), 2.07 (m, 2H), 1.84 (m, 2H), 1.08 (s, 6H); MS (m/z), found 498.2 (M+Na)$^+$.

dimethanesulfonate. MS (m/z), found 654.1 (M+Na)$^+$. To a mixture of (5-(N-(2-(2-(2-methoxyethoxy)ethoxy)ethyl)-4-methyl-4-(methyldisulfanyl)pentanamido)-1,3-phenylene)bis(methylene)dimethanesulfonate (89 mg, 0.141 mmol) and compound 8 (83 mg, 0.282 mmol) in anhydrous DMF (1.5 mL) was added potassium carbonate (97 mg, 0.704 mmol). The reaction stirred for 18 hours at room temperature. The

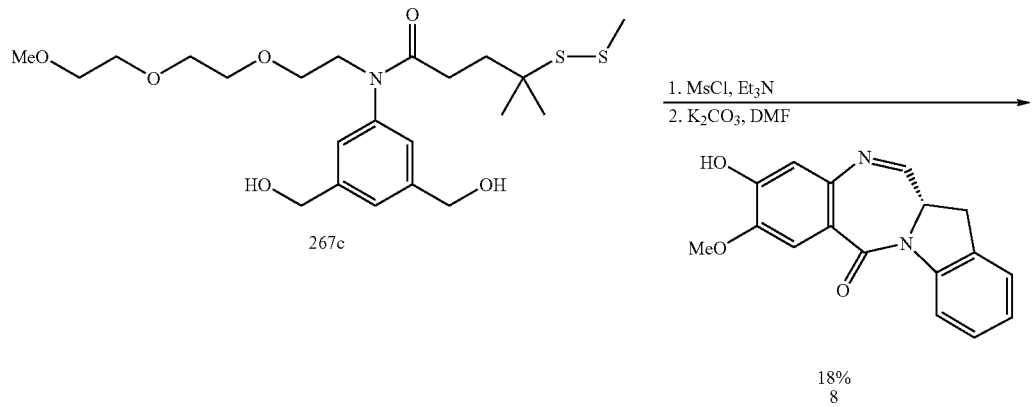

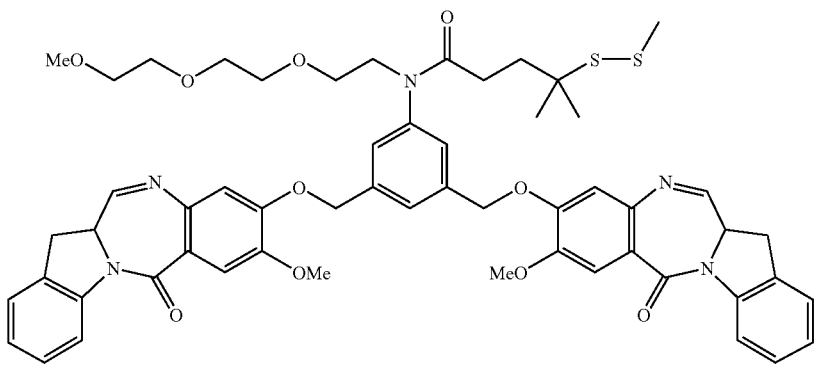

Compound 267d:

To a stirred solution of N-(3,5-bis(hydroxymethyl)phenyl)-N-(2-(2-(2-methoxyethoxy)ethoxy)ethyl)-4-methyl-4-(methyldisulfanyl)pentanamide (267c) (72 mg, 0.151 mmol) in anhydrous dichloromethane (3.0 mL) was added triethylamine (0.063 mL, 0.454 mmol). The mixture was cooled to −5° C. and methanesulfonyl chloride (0.029 mL, 0.378 mmol) was added slowly. After stirring for one hour at −5° C. the reaction was quenched with cold water and extracted with cold ethyl acetate. The organic layer was washed with cold water, dried over anhydrous sodium sulfate, filtered and concentrated under reduced pressure to give (5-(N-(2-(2-(2-methoxyethoxy)ethoxy)ethyl)-4-methyl-4-(methyldisulfanyl)pentanamido)-1,3-phenylene)bis(methylene)

mixture was quenched with water and extracted twice with dichloromethane. The organic layer was washed with brine, dried over anhydrous sodium sulfate, filtered and concentrated in vacuo. Purification by silica gel chromatography (5% MeOH/CH$_2$Cl$_2$) and preparative reverse phase HPLC (C18 column, eluted with CH$_3$CN/H$_2$O) yielded compound 267d (27 mg, 18%). $^1$H NMR (400 Hz, CDCl$_3$): δ 8.28 (d, J=4.8 Hz, 2H), 7.87 (m, 2H), 7.61 (s, 2H), 7.37-7.27 (m, 7H), 7.13 (t, J=7.2, 7.6 Hz, 2H), 6.88 (s, 2H), 5.25 (m, 4H), 4.50 (m, 2H), 4.00 (s, 6H), 3.90 (m, 2H), 3.73 (m, 2H), 3.60 (m, 6H), 3.51 (m, 6H), 3.30 (s, 3H), 2.32 (s, 3H), 2.15 (m, 2H), 1.90 (m, 2H), 1.13 (s, 6H); MS (m/z), found 1050.3 (M+Na)$^+$, 1068.3 (M+H$_2$O+Na)$^+$, 1086.3 (M+2H$_2$O+Na)$^+$.

Example 34 (IGN-32)

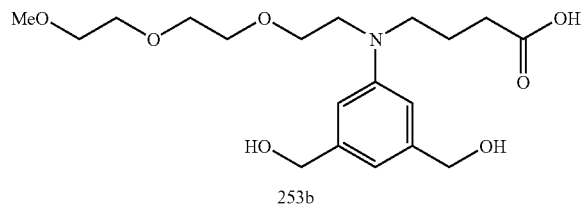

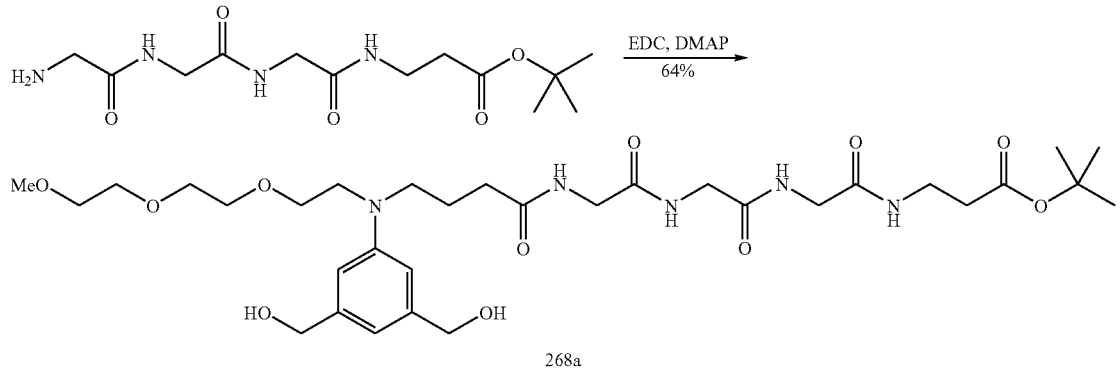

Compound 268a:

To a mixture of compound 253b (150 mg, 0.389 mmol) and tert-butyl 3-(2-(2-(2-aminoacetamido)acetamido)acetamido)propanoate (148 mg, 0.467 mmol) in anhydrous DMF (1.5 ml) was added EDC (90 mg, 0.467 mmol) and DMAP (4.75 mg, 0.039 mmol). The reaction stirred for 18 hours at room temperature. The mixture was directly purified by preparative reverse phase HPLC (C18 column, eluted with CH₃CN/H₂O+0.1% formic acid). Further purification by preparative TLC (15% MeOH/CH₂Cl₂) yielded compound 268a (170 mg, 64%). $^1$H NMR (400 Hz, CDCl$_3$): δ 7.62 (m, 1H), 7.56 (m, 1H), 7.38 (m, 1H), 7.11 (m, 1H), 6.55 (s, 2H), 6.52 (s, 1H), 4.45 (s, 4H), 4.17 (s, 2H), 3.63 (m, 6H), 3.55-3.40 (m, 12H), 3.28 (m, 7H), 2.33 (t, J=6.4 Hz, 2H), 2.16 (m, 2H), 1.79 (m, 2H), 1.36 (s, 9H); MS (m/z), found 706.3 (M+Na)$^+$.

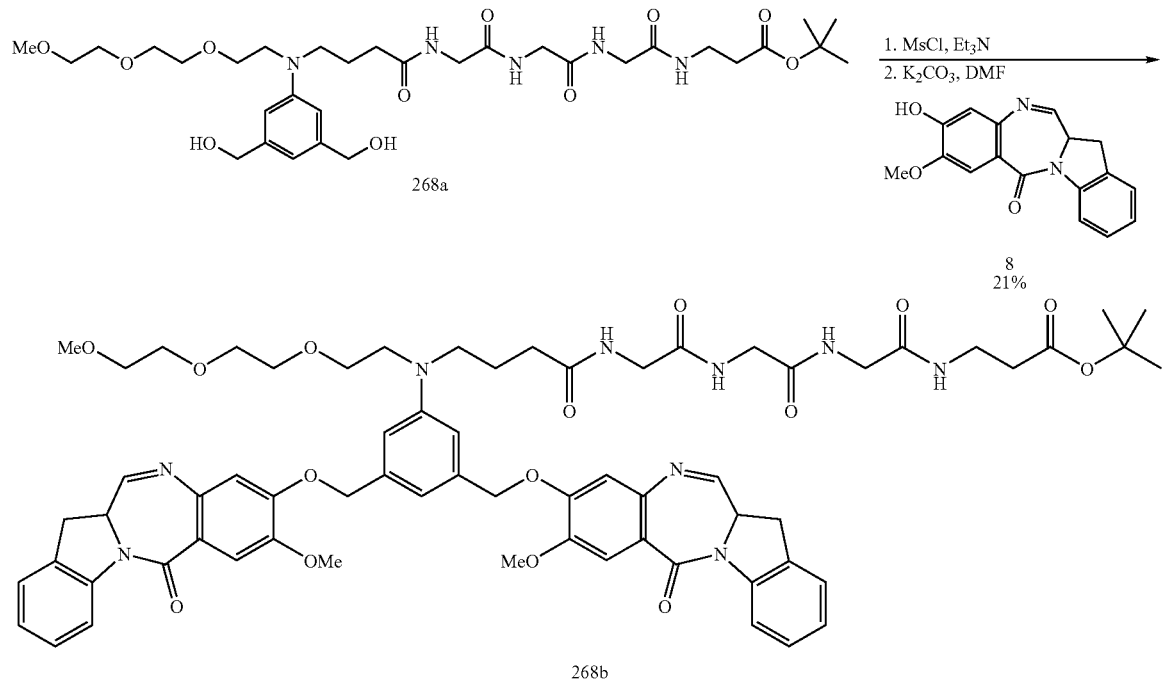

Compound 268b:

To a stirred solution of compound 268a (59 mg, 0.086 mmol) in anhydrous dichloromethane (1.75 ml) was added triethylamine (0.036 ml, 0.259 mmol). The mixture was cooled to −5° C. and methanesulfonyl chloride (0.017 ml, 0.216 mmol) was added slowly. After stirring for one hour at −5° C. the reaction was quenched with cold water and extracted with cold ethyl acetate. The organic extracts were washed with cold water, dried over anhydrous sodium sulfate, filtered and concentrated under reduced pressure to give the desired dimesylate intermediate. MS (m/z), found 862.3 (M+Na)$^+$.

To a solution of the dimesylate intermediate (65 mg, 0.077 mmol) and compound 8 (114 mg, 0.387 mmol) in anhydrous DMF (1.0 mL) was added potassium carbonate (86 mg, 0.619 mmol). The reaction was stirred for 18 hours at room temperature, then quenched with water and extracted three times with dichloromethane. The organic layer was washed with brine, dried over anhydrous sodium sulfate, filtered and concentrated under reduced pressure. Purification by silica gel chromatography (2%→10% MeOH/CH$_2$Cl$_2$) yielded compound 268b (22 mg, 21%). $^1$H NMR (400 Hz, CDCl$_3$): δ 8.26 (d, J=8.0 Hz, 2H), 7.88 (m, 2H), 7.58 (s, 2H), 7.28 (m, 4H), 7.13 (t, J=7.2 Hz, 2H), 6.89 (s, 2H), 6.81 (s, 1H), 6.73 (s, 2H), 5.19 (m, 4H), 4.48 m, 2H), 3.99 (s, 6H), 3.7-3.4 (m, 26H), 3.34 (s, 3H), 2.45 (t, J=6.4 Hz, 2H), 2.30 (m, 2H), 1.81 (m, 2H), 1.44 (s, 9H).

Example 35

Preparation of chB38.1-IGN14 Conjugate:

A solution of chB38.1 antibody at a concentration of 2 mg/mL in an aqueous buffer containing 0.05 M N-(2-hydroxyethyl)-piperazine-N'-2-ethanesulfonic acid (HEPES) and 2 mM ethylenediaminetetra-acetic acid (EDTA), pH 8 was treated with a 10-fold molar excess of a solution of IGN14-NHS in dimethylacetamide (DMA) such that the final concentration of DMA in the buffer was 10% v/v. The reaction mixture was stirred at room temperature for 120 min and then loaded onto a Sephadex G25 gel filtration column (HiPrep™ 26/10 Desalting Column GE#17-5087-01) that had been previously equilibrated into an aqueous buffer containing 10 mM histidine, 250 mM glycine, 1% sucrose pH 5.5. The conjugated antibody-containing fractions were collected and pooled to yield product. The pooled sample was dialyzed overnight against the same elution buffer to further purify the product. The final conjugate was assayed spectrophotometrically using the extinction coefficients that were determined for IGN-14 ($\epsilon_{330}$=15,231 M$^{-1}$ cm$^{-1}$ and $\epsilon_{280}$=26,864 M$^{-1}$ cm$^{-1}$) and chB38.1 antibody ($\epsilon_{280\ nm}$=204,000 M$^{-1}$ cm$^{-1}$). An average of 3.3 IGN14 molecules per molecule of antibody were linked.

Example 36

Preparation of huMy9-6-IGN23 Conjugate

A solution of huMy9-6 antibody at a concentration of 2 mg/mL in an aqueous buffer containing 0.05 M N-(2-hydroxyethyl)-piperazine-N'-2-ethanesulfonic acid (HEPES) and 2 mM ethylenediaminetetra-acetic acid (EDTA), pH 8.5 was treated with a 12.5-fold molar excess of a solution of IGN23-NHS in dimethylacetamide (DMA), glycerol, and sucrose. The final concentration of DMA, glycerol and sucrose in the buffer was 15%, 5% and 5% (v/v) respectively. The reaction mixture was stirred at room temperature for 120 min and then loaded onto a Sephadex G25 gel filtration column (HiPrep™ 26/10 Desalting Column GE#17-5087-01) that had been previously equilibrated into an aqueous buffer containing 10 mM histidine, 250 mM glycine, 1% sucrose, pH 5.5. The conjugated antibody-containing fractions were collected and pooled to yield product. The pooled sample was concentrated using Millipore centrifugal filter devices, and then dialyzed overnight against the same elution buffer to further purify the product.

The final conjugate was assayed spectrophotometrically using the extinction coefficients that were determined for IGN-23 ($e_{330}$=15,231 M$^{-1}$ cm$^{-1}$ and $e_{280}$=26,864 M$^{-1}$ cm$^{-1}$) and huMy9-6 ($e_{280\ nm}$=206,460 M−1cm−1). An average of 2.2 IGN23 molecules per molecule of antibody were linked.

Example 37

Preparation of chB38.1-IGN27 Conjugate

A solution of chB38.1 antibody at a concentration of 2 mg/mL in an aqueous buffer containing 0.05 M N-(2-hydroxyethyl)-piperazine-N'-2-ethanesulfonic acid (HEPES) and 2 mM ethylenediaminetetra-acetic acid (EDTA), pH 8.5 was treated with a 12-fold molar excess of a solution of IGN27-NHS in dimethylacetamide (DMA, 5 mM stock) such that the final concentration of DMA in the buffer was 15% v/v. The reaction mixture was stirred at room temperature for 4 hr and then loaded on to a Sephadex G25 gel filtration column (HiPrep™ 26/10 Desalting Column GE#17-5087-01) that had been previously equilibrated into an aqueous buffer containing PBS pH 7.4. The conjugated antibody-containing fractions were collected and pooled to yield product. The pooled sample was dialyzed overnight against the same elution buffer to further purify the product.

The final conjugate was assayed spectrophotometrically using the extinction coefficients that were determined for IGN-27 ($e_{330}$=15,231 M$^{-1}$ cm$^{-1}$ and $e_{280}$=26,864 M$^{-1}$ cm$^{-1}$) and chB38.1 antibody ($e_{280\ nm}$=204,000 M−1 cm−1). An average of 2.9 IGN27 molecules per molecule of antibody were linked.

Example 38

In Vitro Potency IGN Free Drugs and IGN Conjugates:

General Procedure Used: Samples of IGN Free Drugs or IGN Conjugates were added to 96-well flat bottomed tissue culture plates and titrated using serial dilutions to cover the desired molar range. Antigen positive (Ag+) or Antigen negative (Ag−) cells were added to the wells in specific cell densities in such a way that there were triplicate samples for each drug concentration for each corresponding cell line. The plates were then incubated at 37° C. in an atmosphere of 5% CO$_2$ for 4-5 days depending on the cell line. COLO 205 (1,000 cells/well), Namalwa (3,000 cells/well)—4 days; RH30(1,000 cells/well), Ramos (10,000 cells/well), KB (1,000 cells/well)—5 days)

At the end of the incubation period cytotoxic potencies were then assessed using a WST-based cell viability assay and surviving cells were measured by developing with WST (2-7 hours). The absorbance in each well was measured and the surviving fraction of cells at each concentration was plotted to reveal the cytotoxicity and antigen specificity (of the conjugates).

The cytotoxicity of the IGN Free Drugs and the potency and specificity of the IGN conjugates were measured against a panel of human cancer cell lines selected from COLO 205, NB-4, LOVO, Namalwa, RH30, Ramos, KB, and/or LOVO. Results are illustrated in FIGS. 51-58.

FIG. 51: Table which demonstrates the high potency (in nM) of the IGN Free Drugs against multiple cell lines. In general the IGN Free Drugs are found to be potent in the low picomolar range against this panel of cell lines.

FIG. 52: (A) chB38.1-IGN13 conjugate (3.8 IGN/Ab) was found to be potent at sub-picomolar levels against COLO 205 (Ag+) cells and the activity was significantly diminished (0.26 nM) when the antigen binding sites were blocked with 1 μM unconjugated chB38.1 antibody indicating the high specificity of this conjugate (>260 fold). (B) chB38.1-IGN13 conjugate (3.8 IGN/Ab) was found to be potent picomolar levels (0.002 pM) against LOVO (Ag+) cells in a clonogenic assay.

FIG. 53: huMy9-6-IGN13 conjugate (3.4 IGN/Ab) was found to be potent at picomolar levels against NB-4 (Ag+) cells (0.077 nM) and the activity was significantly diminished (1.0 nM) when the antigen binding sites were blocked with 1 μM huMy9-6 antibody indicating that this conjugate is specific.

FIG. 54: (A) chB38.1-IGN14 conjugate (3.1 IGN/Ab) was found to be potent at sub-picomolar levels against COLO 205 (Ag+) cells and the activity was significantly less towards Namalwa (Ag−) cells (0.9 nM) indicating the high specificity of this conjugate (>900 fold). (B) chB38.1-IGN14 conjugate (2.6 IGN/Ab) was found to be very potent towards LOVO (Ag+) cells (0.012 nM) and the activity was significantly less towards Namalwa (Ag−) cells (>3.0 nM) indicating the high specificity of this conjugate (>250 fold).

FIG. 55: huMy9-6-IGN14 conjugate (3.3 IGN/Ab) was found to be highly potent against NB-4 (Ag+) cells (0.033 nM) and the activity was significantly less towards Namalwa (Ag−) cells (0.6 nM) indicating the high specificity of this conjugate.

FIG. 56: (A) chB38.1-IGN23 conjugate (2.5 IGN/Ab) was found to be potent at picomolar levels against LOVO (Ag+) cells (0.063 nM) and the activity was significantly less towards Namalwa (Ag−) cells (>3.0 nM) indicating the high specificity of this conjugate. (B) chB38.1-IGN23 conjugate (2.0 IGN/Ab) was found to be potent at picomolar levels against COLO 205 (Ag+) cells (0.006 nM) and the activity was significantly diminished (2.5 nM) when the antigen binding sites were blocked with 1 μM chB38.1 indicating that this conjugate is specific.

FIG. 57: chB38.1-IGN29 conjugate (2.8 IGN/Ab) was found to be potent at sub-nanomolar levels against COLO 205 (Ag+) cells (0.410 nM) and the activity was significantly diminished (18 nM) when the antigen binding sites were blocked with 1 μM chB38.1 indicating that this conjugate is specific.

Example 39

In Vivo Efficacy of chB38.1-IGN14 Conjugate in COLO 205 Tumor Bearing Nude Mice:

In this study, the anti-tumor activity of chB38.1-IGN14 was investigated in female nude mice bearing COLO 205 tumors, a human colon carcinoma model. COLO 205 tumor cells, 2×10⁶ cells/mouse were subcutaneously inoculated at a volume of 0.1 mL/mouse in the area over the right shoulder of female athymic nude mice, 5 weeks of age. Eight days after tumor cell inoculation mice were randomized into groups (n=6 per group) by tumor volume. Treatment was initiated the day of randomization, and groups included a control group dosed with PBS (200 μL/injection), naked chB38.1 antibody (2.8 mg/kg), non-targeting chKTI-IGN14 (50 μg/kg) conjugate and chB38.1-IGN14 (50 μg/kg IGN14 dose; 2.5 mg/kg antibody dose). All treatments were administered twice on a weekly schedule (day 8 and 15, post-cell inoculation). Arrows indicate dosing times post inoculation. All treatments were well tolerated with the mean body weight losses comparable to loss seen in PBS control mice. Median tumor volume vs time is shown (FIG. 58) with the data demonstrating the anti-tumor activity of the chB38.1-IGN14 conjugate. Both the non-targeting and the naked antibody show no activity beyond that seen with the vehicle control, suggesting that the anti-tumor activity observed with the chB38.1-IGN-14 conjugate is antigen-specific.

Example 40

FIG. 59 shows the mass spectrum of chB38.1-IGN14 (deglycosylated antibody). Peaks are labeled D1-D7 to indicate the number of IGN14 molecules attached per antibody. The average number of IGN14 molecules per antibody was calculated to be 3.5 (matching drug load calculated by UV-vis).

We claim:
1. A compound selected from formula (IV) or (V):

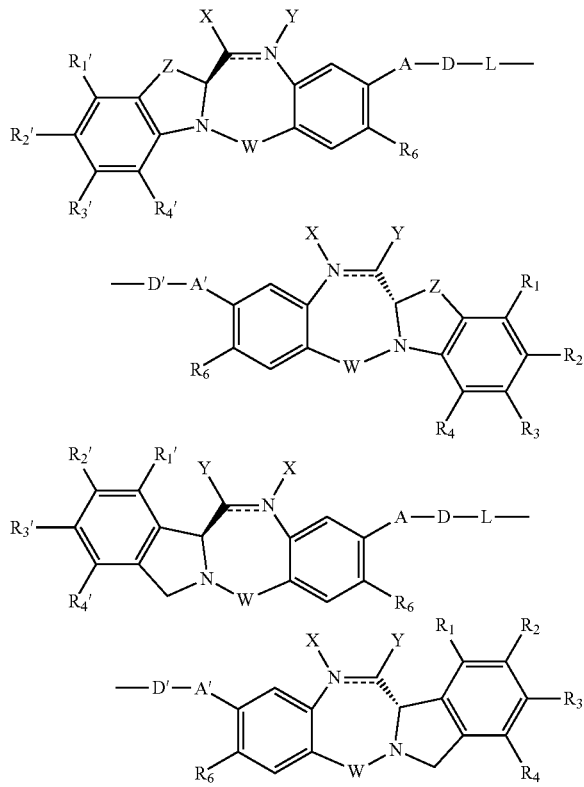

or a pharmaceutically acceptable salt, optical isomer, racemate, diastereomer, or enantiomer thereof, wherein:

the double line $=\!=$ between N and C represents a single bond or a double bond, provided that when it is a double bond X is absent and Y is —H, and when it is a single bond, X is —H; and Y is selected from —OR, —OCOR', —OCOOR', —OCONR'R", —NR'R", —NRCOR', —NRCOP, wherein P is an amino acid or a polypeptide containing between 2 to 20 amino acid units, —SR', —SOR', —SO₂R', —SO₃, —OSO₃, a halogen, a cyano, or an azido, wherein R, R' and R" are the same or different and are selected from —H, an optionally substituted linear, branched or cyclic alkyl, alkenyl or alkynyl having from 1 to 10 carbon atoms, a polyethylene glycol unit (—OCH$_2$CH$_2$)$_n$, wherein n is an integer from 1 to 2000, a 5- or 6-membered heteroaryl ring containing one or more heteroatoms independently selected from nitrogen, oxygen, and sulfur, a 5- to 18-membered fused ring system, wherein at least one of the rings is aromatic, containing one or more heteroatoms independently selected from nitrogen, oxygen, and sulfur, an aryl having from 6 to 18 carbon atoms, a 3- to 18-membered heterocyclic ring having 1 to 6 heteroatoms selected from O, S, N and P, wherein the optional substituent is selected from halogen, —OR$_7$, —NR$_8$R$_9$, —NO$_2$, —NRCOR', —SR$_{10}$, —SOR', —SO$_2$R', —SO$_3$, —OSO$_3$, —SO$_2$NRR', a cyano, an azido, —COR$_{11}$, —OCOR$_{11}$ or —OCONR$_{11}$R$_{12}$, wherein R$_7$, R$_8$, R$_9$, R$_{10}$, R$_{11}$ and R$_{12}$ are each independently selected from —H, a linear, branched or cyclic alkyl, alkenyl or alkynyl having from 1 to 10 carbon atoms, a polyethylene glycol unit (—OCH$_2$CH$_2$)$_n$, wherein n is an integer from 1 to 2000, a 5- or 6-membered heteroaryl ring containing one or more heteroatoms independently selected from nitrogen, oxygen, and sulfur, a 5- to 18-membered fused ring system, wherein at least one of the rings is aromatic, containing one or more heteroatoms independently selected from nitrogen, oxygen, and sulfur, an aryl having from 6 to 18 carbon atoms, a 3- to 10-membered heterocyclic ring having 1 to 6 heteroatoms selected from O, S, N and P, and R$_{10}$ is optionally —SR$_{13}$ or —COR$_{13}$, wherein R$_{13}$ is selected from a linear, branched or cyclic alkyl, alkenyl or alkynyl having from 1 to 10 carbon atoms, a 5- or 6-membered heteroaryl ring containing one or more heteroatoms independently selected from nitrogen, oxygen, and sulfur, a 5- to 18-membered fused ring system, wherein at least one of the rings is aromatic, containing one or more heteroatoms independently selected from nitrogen, oxygen, and sulfur, an aryl having from 6 to 18 carbon atoms, a 3- to 18-membered heterocyclic ring having 1 to 6 heteroatoms selected from O, S, N and P, optionally R$_{11}$ is —OR$_{14}$, wherein R$_{14}$ has the same definition as R, optionally R" is —OH;

W is C=O;

R$_1$, R$_2$, R$_3$, R$_4$, R$_1$', R$_2$', R$_3$' and R$_4$' are each independently selected from —H, an optionally substituted linear, branched or cyclic alkyl, alkenyl or alkynyl having from 1 to 10 carbon atoms, a polyethylene glycol unit (—OCH$_2$CH$_2$)$_n$, wherein n is an integer from 1 to 2000, wherein the optional substituent is selected from halogen, —OR$_7$, —NR$_8$R$_9$, —NO$_2$, —NRCOR', —SR$_{10}$, —SOR', —SO$_2$R', —SO$_3$, —OSO$_3$, —SO$_2$NRR', a cyano, an azido, —COR$_{11}$, —OCOR$_{11}$, —OCONR$_{11}$R$_{12}$, or a polyethylene glycol unit (—OCH$_2$CH$_2$)$_n$, wherein n is an integer from 1 to 2000, or a substituent selected from a halogen, guanidinium [—NH(C=NH)NH$_2$], —OR$_7$, —NR$_8$R$_9$, —NO$_2$, —NRCOR', —SR$_{10}$, —SOR', —SO$_2$R', —SO$_3$, —OSO$_3$, —SO$_2$NRR', a cyano, an azido, —COR$_{11}$, —OCOR$_{11}$ or —OCONR$_{11}$R$_{12}$, optionally, any one of R$_1$, R$_2$, R$_3$, R$_4$, R$_1$', R$_2$', R$_3$', or R$_4$' is a linking group that enables linkage to a cell binding agent via a covalent bond or is selected from a polypyrrolo, poly-indolyl, poly-imidazolyl, polypyrrolo-imidazolyl, poly-pyrrolo-indolyl or polyimidazolo-indolyl unit optionally bearing the linking group, Z is CR$_{15}$R$_{16}$, wherein R$_{15}$ and R$_{16}$ are each independently selected from —H, a linear, branched or cyclic alkyl having from 1 to 10 carbon atoms, or a polyethylene glycol unit (—OCH$_2$CH$_2$)$_n$, wherein n is an integer from 1 to 2000;

R$_6$ is —OR, —SR or —NRR', optionally R$_6$ is the linking group;

A and A' are the same or different and are selected from O, CRR'O, S, CRR'S, NR$_{15}$ or CRR'NHR$_{15}$, wherein R$_{15}$ has the same definition as R;

D and D' are the same or different and are independently selected from a linear, branched or cyclic alkyl, alkenyl or alkynyl having 1 to 10 carbon atoms, optionally substituted with any one of halogen, —OR$_7$, —NR$_8$R$_9$, —NO$_2$, —NRCOR', —SR$_{10}$, —SOR', —SO$_2$R', —SO$_3$, —OSO$_3$, —SO$_2$NRR', a cyano, an azido, —COR$_{11}$, —OCOR$_{11}$ or —OCONR$_{11}$R$_{12}$, or a polyethylene glycol unit (—OCH$_2$CH$_2$)$_n$, wherein n is an integer from 1 to 2000;

L is absent, or is a phenyl group or 3- to 18-membered heterocyclic ring having 1 to 6 heteroatoms selected from O, S, N and P, wherein said phenyl group or 3- to 18-membered heterocyclic ring represented by L is optionally substituted, wherein the substituent is the linking group, or is selected from a linear, branched or cyclic alkyl, alkenyl or alkynyl having from 1 to 10 carbon atoms, optionally substituted with any one of halogen, —OR$_7$, —NR$_8$R$_9$, —NO$_2$, —NRCOR', —SR$_{10}$, SOR', —SO$_2$R', —SO$_3$, —OSO$_3$, —SO$_2$NRR', a cyano, an azido, —COR$_{11}$, —OCOR$_{11}$ or —OCONR$_{11}$R$_{12}$, or a polyethylene glycol unit (—OCH$_2$CH$_2$)$_n$, wherein n is an integer from 1 to 2000; optionally, L itself is the linking group;

provided that the compound has no more than one linking group.

2. The compounds of claim 1, wherein:

Y is selected from —OR, —NR'R", —SO$_3$, or —OSO$_3$, wherein R is selected from —H, a linear, branched or cyclic alkyl, alkenyl or alkynyl having from 1 to 10 carbon atoms, a polyethylene glycol unit (—OCH$_2$CH$_2$)$_n$, wherein n is an integer from 1 to 2000, an aryl having from 6 to 10 carbon atoms, or, a heterocyclic ring having from 3 to 10 carbon atoms;

R$_1$, R$_2$, R$_3$, R$_4$, R$_1$', R$_2$', R$_3$' and R$_4$' are each independently selected from —H, —NO$_2$ or the linking group;

R$_6$ is —OR$_{18}$, wherein R$_{18}$ has the same definition as R;

A and A' are each O;

D and D' are the same or different and are independently selected from a linear, branched or cyclic alkyl, alkenyl or alkynyl having 1 to 10 carbon atoms;

L is absent, or is a phenyl group or a heterocyclic ring having from 3 to 10 carbon atoms, wherein said phenyl group or heterocyclic ring represented by L is optionally substituted, wherein the substituent is the linking group, or is selected from a linear, branched or cyclic alkyl, alkenyl or alkynyl having from 1 to 10 carbon atoms, optionally substituted with any one of halogen, —OR$_7$, —NR$_8$R$_9$, —NO$_2$, —NRCOR', —SR$_{10}$, —SOR', —SO$_2$R', —SO$_3$, —OSO$_3$, —SO$_2$NRR', a cyano, an azido, —COR$_{11}$, —OCOR$_{11}$ or —OCONR$_{11}$R$_{12}$, or a polyethylene glycol unit (—OCH$_2$CH$_2$)$_n$, wherein n is an integer from 1 to 2000; optionally, L itself is the linking group.

3. The compound of claim 1 selected from formulae (XII) and (XIII):

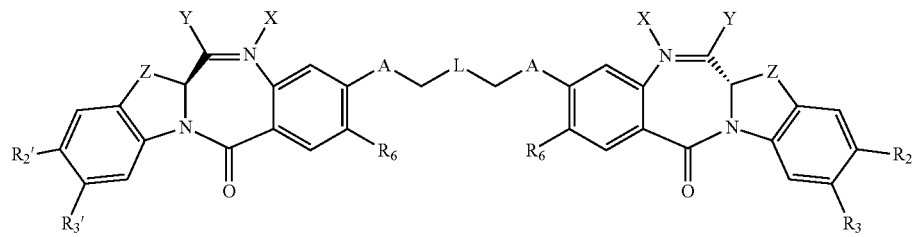

(XII)

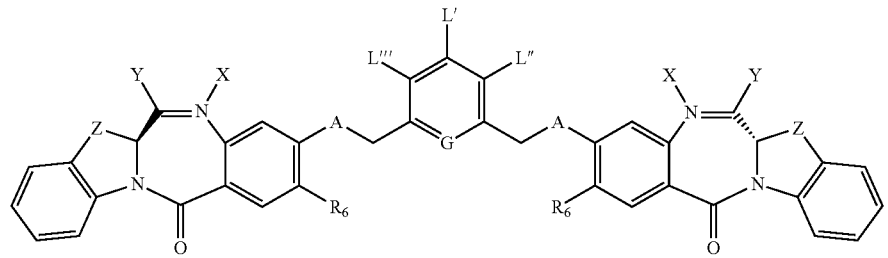

(XIII)

or a pharmaceutically acceptable salt, optical isomer, racemate, diastereomer, or enantiomer thereof, wherein Y is selected from —OH, —OR, —NR'R", —SO$_3$, or —OSO$_3$, wherein R, R' and R" are selected from a linear, branched or cyclic alkyl, alkenyl or alkynyl having from 1 to 10 carbon atoms;

one of R$_2$, R$_3$, R$_2$' and R$_3$' is the linking group and the others are —H or —NO$_2$;

—OSO$_3$, —SO$_2$NRR', a cyano, an azido, —COR$_{11}$, —OCOR$_{11}$ or —OCONR$_{11}$R$_{12}$, optionally, L itself is the linking group;

one of L', L" or L'" is the linking group, while the others are —H; preferably L' is the linking group; and G is CH or N.

4. The compound of claim 1, selected from formulae (XIV) and (XV):

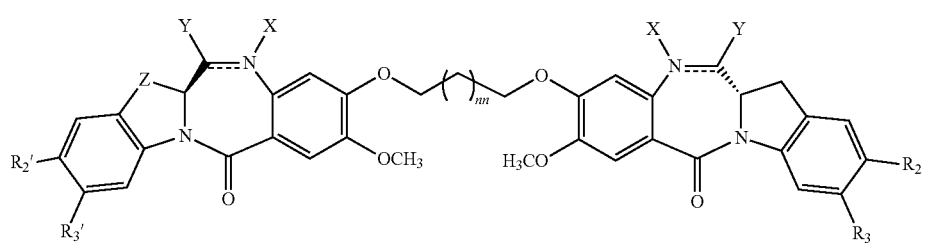

(XIV)

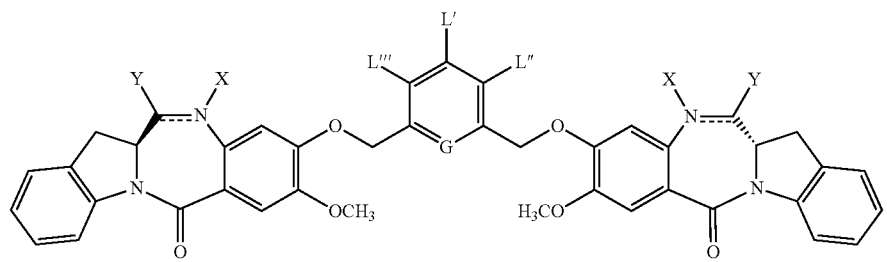

(XV)

R$_6$ is —OR;

Z is CH$_2$;

A is O or NR$_{15}$;

L is (CH$_2$)$_{nn}$, wherein nn is 0 or an integer between 1 and 5, or a substituted or unsubstituted alkyl or alkenyl having from 2 to 4 carbon atoms, wherein the substituent is selected from halogen, —OR$_7$, —NR$_8$R$_9$, —NO$_2$, —NRCOR', —SR$_{10}$, —SOR', —SO$_2$R', —SO$_3$, or a pharmaceutically acceptable salt, optical isomer, racemate, diastereomer, or enantiomer thereof, wherein Y is selected from —OH, —OR, —SO$_3$, or —OSO$_3$, wherein R is selected from a linear, branched or cyclic alkyl, alkenyl or alkynyl having from 1 to 10 carbon atoms;

nn is 0 or an integer from 1 to 5;

one of R$_2$, R$_3$, R$_2$' and R$_3$' in formula (XIV) is the linking group and the others are —H or —NO$_2$;

one of L', L" or L'" in formula (XV) is the linking group, and the others are —H; and G is CH or N.

5. The compound of any one of claims 1-4, wherein one of $R_1$, $R_2$, $R_3$, $R_4$, $R_1'$, $R_2'$, $R_3'$, $R_4'$, L', L", L'" is independently selected from:

—O(CR$_{20}$R$_{21}$)$_m$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X",

—O(CR$_{20}$R$_{21}$)$_m$(CR$_{26}$=CR$_{27}$)$_{m'}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X",

—O(CR$_{20}$R$_{21}$)$_m$(alkynyl)$_n$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —O(CR$_{20}$R$_{21}$)$_m$(piperazino)$_t$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —O(CR$_{20}$R$_{21}$)$_m$(Pyrrolo)$_t$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —O(CR$_{20}$R$_{21}$)$_m$A"$_{m''}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —S(CR$_{20}$R$_{21}$)$_m$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —S(CR$_{20}$R$_{21}$)$_m$(CR$_{26}$=CR$_{27}$)$_{m'}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —S(CR$_{20}$R$_{21}$)$_m$(alknyl)$_n$(CR$_{22}$R$_{23}$)$_n$(OCH$_2$CH$_2$)$_p$(CR$_{40}$R$_{41}$)$_{p''}$Y' (CR$_{24}$R$_{25}$)$_q$(CO)$_t$X", —S(CR$_{20}$R$_{21}$)$_m$(piperazino)$_t$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —S(CR$_{20}$R$_{21}$)$_m$(pyrrolo)$_t$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —S(CR$_{20}$R$_{21}$ )$_m$A"$_{m''}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —NR$_{33}$(C=O)$_{p'}$(CR$_{20}$R$_{21}$)$_m$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —NR$_{33}$(C=O)$_{p'}$(CR$_{20}$R$_{21}$)$_m$(CR$_{26}$=CR$_{27}$)$_{m'}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —NR$_{33}$(C=O)$_{p'}$(CR$_{20}$R$_{21}$)$_m$(alkynyl)$_n$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —NR$_{33}$(C=O)$_{p'}$(CR$_{20}$R$_{21}$)$_m$(piperazino)$_t$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —NR$_{33}$(C=O)$_{p'}$(CR$_{20}$R$_{21}$)$_m$(pyrrolo)$_t$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —NR$_{33}$(C=O)$_{p'}$(CR$_{20}$R$_{21}$)$_m$A"$_{m''}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —(CR$_{20}$R$_{21}$)$_m$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —(CR$_{20}$R$_{21}$)$_m$(CR$_{26}$=CR$_{27}$)$_{m'}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —(CR$_{20}$R$_{21}$)$_m$(alkynyl)$_n$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —(CR$_{20}$R$_{21}$)$_m$(piperazino)$_t$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —(CR$_{20}$R$_{21}$)$_m$A"$_{m''}$(CR$_{22}$R$_{23}$)$_n$(OCH$_2$CH$_2$)$_p$(CR$_{50}$R$_{41}$)$_{p''}$Y"(CR$_{24}$R$_{25}$)$_q$(CO)$_t$X", —(CR$_{20}$R$_{21}$)$_m$(CR$_{29}$=N—NR$_{30}$)$_{n''}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —(CR$_{20}$R$_{21}$)$_m$(CR$_{29}$=N—NR$_{30}$)$_{n''}$(CR$_{26}$=CR$_{27}$)$_{m'}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", —(CR$_{20}$R$_{21}$)$_m$(CR$_{29}$=N—NR$_{30}$)$_{n''}$(alkynyl)$_n$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", or, —(CR$_{20}$R$_{21}$)$_m$(CR$_{29}$=N—NR$_{30}$)$_{n''}$A"$_{m''}$(CR$_{22}$R$_{23}$)$_n$(OCH$_2$CH$_2$)$_p$(CR$_{40}$R$_{41}$)$_{p''}$Y"(CR$_{24}$R$_{25}$)$_q$(CO)$_t$X", wherein:

m, n, p, q, m', n', t' are integer from 1 to 10, or are optionally 0;

t, m", n" and p" are 0 or 1;

X" is selected from —OR$_{36}$, —SR$_{37}$, —NR$_{38}$R$_{39}$, wherein R$_{36}$, R$_{37}$, R$_{38}$, R$_{39}$ are —H, a linear, branched or cyclic alkyl, alkenyl or alkynyl having from 1 to 20 carbon atoms, or, a polyethylene glycol unit —(OCH$_2$CH$_2$)$_n$, R$_{37}$, optionally, is a thiol protecting group, or when t=1, COX" forms a reactive ester selected from N-hydroxysuccinimide esters, N-hydroxyphthalimide esters, N-hydroxy sulfo-succinimide esters, para-nitrophenyl esters, dinitrophenyl esters, pentafluorophenyl esters and their derivatives, wherein said derivatives facilitate amide bond formation;

Y" is absent or is selected from O, S, S—S or NR$_{32}$, wherein R$_{32}$ has the same definition as given above for R, provided that when Y" is not S—S and t=0, X" is selected from a maleimido group, a haloacetyl group or —SR$_{37}$;

A" is an amino acid selected from glycine, alanine, leucine, valine, lysine, citrulline, glutamate or a polypeptide containing between 2 to 20 amino acid units;

R$_{20}$, R$_{21}$, R$_{22}$, R$_{23}$, R$_{24}$, R$_{25}$, R$_{26}$, and R$_{27}$ are the same or different and are —H or a linear or branched alkyl having from 1 to 5 carbon atoms;

R$_{29}$ and R$_{30}$ are the same or different and are —H or alkyl from 1 to 5 carbon atoms;

R$_{33}$ is —H or linear, branched or cyclic alkyl, alkenyl or alkynyl having from 1 to 12 carbon atoms, a polyethylene glycol unit —(OCH$_2$CH$_2$)$_n$, or R$_{33}$ is —COR$_{34}$, —CSR$_{34}$, —SOR$_{34}$, or —SO$_2$R$_{34}$, wherein R$_{34}$ is —H or linear, branched or cyclic alkyl, alkenyl or alkynyl having from 1 to 20 carbon atoms or, a polyethylene glycol unit —(OCH$_2$CH$_2$)$_n$; and one of R$_{40}$ and R$_{41}$ is optionally a negatively or positively charged functional group and the other is —H or alkyl, alkenyl, alkynyl having 1 to 4 carbon atoms.

6. A compound selected from formula (I) or (II)

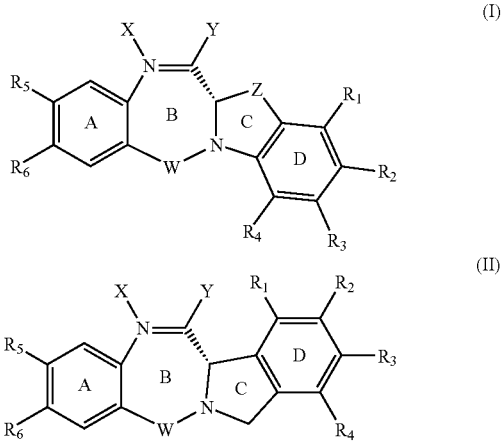

or a pharmaceutically acceptable salt, optical isomer, racemate, diastereomer, or enantiomer thereof, wherein:

the double line == between N and C represents a single bond or a double bond, provided that when it is a double bond X is absent and Y is —H, and when it is a single bond, X is —H; and Y is selected from —OR, —OCOR', —OCOOR', —OCONR'R", —NR'R", —NRCOR', —NRCOP, wherein P is an amino acid or a polypeptide containing between 2 to 20 amino acid units, —SR', —SOR', —SO$_2$R', —SO$_3$, —OSO$_3$, a halogen, a cyano, or an azido, wherein R, R' and R" are the same or different and are selected from —H, an optionally substituted linear, branched or cyclic alkyl, alkenyl or alkynyl having from 1 to 20 carbon atoms, a polyethylene glycol unit (—OCH$_2$CH$_2$)$_n$, wherein n is an integer from 1 to 2000, a 5- or 6-membered heteroaryl ring containing one or more heteroatoms independently selected from nitrogen, oxygen, and sulfur, a 5- to 18-membered fused ring system, wherein at least one of the rings is aromatic, containing one or more heteroatoms independently selected from nitrogen, oxygen, and sulfur, an aryl having from 6 to 18 carbon atoms, a 3- to 18-membered heterocyclic ring having 1 to 6 heteroatoms selected from O, S, N and P, wherein the optional substituent is selected from halogen, —OR$_7$, —NR$_8$R$_9$, —NO$_2$, —NRCOR', —SR$_{10}$, —SOR', —SO$_2$R', —SO$_3$, —OSO$_3$, —SO$_2$NRR', a cyano, an azido, —COR$_{11}$, —OCOR$_{11}$ or —OCONR$_{11}$R$_{12}$, wherein R$_7$, R$_8$, R$_9$, R$_{10}$, R$_{11}$ and R$_{12}$ are each independently selected from —H, a linear, branched or cyclic alkyl, alkenyl or alkynyl having from 1 to 10 carbon atoms, a polyethylene glycol unit (—OCH$_2$CH$_2$)$_n$, wherein n is an integer from 1 to 2000, a 5- or 6-membered heteroaryl ring containing one or more heteroatoms independently selected from nitrogen, oxygen, and sulfur, a 5- to 18-membered fused ring system, wherein at least one of the rings is aromatic containing one or more heteroatoms independently selected from nitrogen, oxygen, and sulfur, an aryl having from 6 to 18 carbon atoms, a 3- to 18-membered heterocyclic ring having 1 to 6 heteroatoms selected from O, S, N and P, and R$_{10}$ optionally is —SR$_{13}$ or —COR$_{13}$, wherein R$_{13}$ is selected from a linear, branched or cyclic alkyl, alkenyl or alkynyl having from 1 to 10 carbon atoms, a polyethylene glycol unit (—OCH$_2$CH$_2$)$_n$, wherein n is an integer from 1 to 2000, a 5- or 6-membered heteroaryl ring containing one or more heteroatoms independently selected from nitrogen, oxygen, and sulfur, a 5- to 18-membered fused ring system, wherein at least one of the rings is aromatic, containing one or more heteroatoms independently selected from nitrogen, oxygen, and sulfur, a 3- to 18- —membered heterocyclic ring having 1 to 6 heteroatoms selected from O, S, N and P, and R$_{11}$ can also be —OR$_{14}$, wherein R$_{14}$ is —H or has the same definition as R, optionally, R" is —OH;

W is C=O;

R$_1$, R$_2$, R$_3$, R$_4$, are each independently selected from —H, an optionally substituted linear, branched or cyclic alkyl, alkenyl or alkynyl having from 1 to 10 carbon atoms, a polyethylene glycol unit (—OCH$_2$CH$_2$)$_n$, wherein n is an integer from 1 to 2000, wherein the optional substituent is selected from halogen, —OR$_7$, —NR$_8$R$_9$, —NO$_2$, —NRCOR', —SR$_{10}$, —SOR', —SO$_2$R', —SO$_3$, —OSO$_3$, —SO$_2$NRR', a cyano, an azido, —COR$_{11}$, —OCOR$_{11}$, —OCONR$_{11}$R$_{12}$, or a polyethylene glycol unit (—OCH$_2$CH$_2$)$_n$, wherein n is an integer from 1 to 2000, or a substituent selected from a halogen, —OR$_7$, —NR$_8$R$_9$, —NO$_2$, —NRCOR', —SR$_{10}$, —SOR', —SO$_2$R', —SO$_3$, —OSO$_3$, —SO$_2$NRR', a cyano, an azido, guanidinium [—NH(C=NH)NH$_2$], —COR$_{11}$, —OCOR$_{11}$ or —OCONR$_{11}$R$_{12}$, optionally, any one of R$_1$, R$_2$, R$_3$, R$_4$ is a linking group that enables linkage to a cell binding agent via a covalent bond, or is selected from a polypyrrolo, poly-indolyl, poly-imidazolyl, polypyrrolo-imidazolyl, poly-pyrrolo-indolyl or polyimidazolo-indolyl unit optionally bearing the linking group;

R$_5$ is selected from —OR$_{15}$, —CRR'OH, —SH, —CRR'SH, —NHR$_{15}$ or —CRR'NHR$_{15}$, wherein R$_{15}$ has the same definition as R; optionally, R$_5$ is the linking group or is selected from a polypyrrolo, poly-indolyl, poly-imidazolyl, polypyrrolo-imidazolyl, poly-pyrrolo-indolyl or polyimidazolo-indolyl unit optionally bearing the linking group;

R$_6$ is —OR, —SR, —NRR', or optionally R$_6$ is the linking group;

Z is —CR$_{15}$R$_{16}$, wherein R$_{15}$ and R$_{16}$ are each independently selected from —H, a linear, branched or cyclic alkyl having from 1 to 10 carbon atoms, or a polyethylene glycol unit (—OCH$_2$CH$_2$)$_n$, wherein n is an integer from 1 to 2000;

provided that the compound has no more than one linking group.

7. The compound of claim 6, or a pharmaceutically acceptable salt, optical isomer, racemate, diastereomer, or enantiomer thereof, wherein:

the double line = between N and C represents a double bond and X is absent and Y is —H, or the double line = between N and C represents a single bond wherein X is —H and Y is selected from —OR, a sulfite —SO$_3$, or the amine protecting moiety;

R$_1$, R$_2$, R$_3$, R$_4$, are each —H; optionally, independently, any one of R$_1$, R$_2$, R$_3$ and R$_4$ is the linking group;

R$_5$ is selected from —OR$_{15}$, —CRR'OH, —SH, —CRR'SH, —NHR$_{15}$ or —CRR'NHR$_{15}$, wherein R$_{15}$ is —H or has the same definition as given above for R, or is selected from a polypyrrolo, poly-indolyl, poly-imidazolyl, polypyrrollo-imidazolyl, poly-pyrrolo-indolyl or polyimidazolo-indolyl unit optionally bearing the linking group;

R$_6$ is —OCH$_3$;

Z is —CH$_2$—.

8. The compound of claim 6 selected from formulae (VII), (VIII) and (IX):

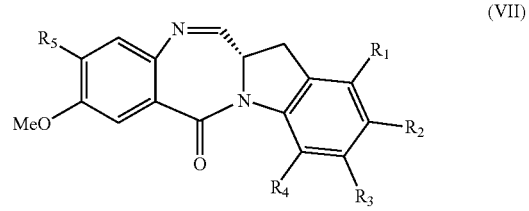

(VII)

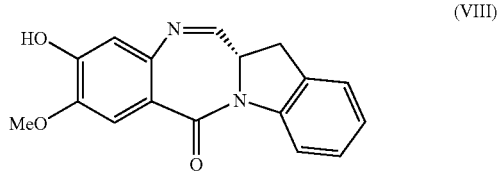

(VIII)

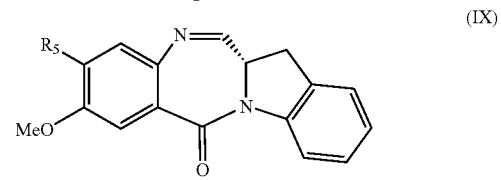

(IX)

or a pharmaceutically acceptable salt, optical isomer, racemate, diastereomer, or enantiomer thereof.

9. The compound of any one of claims 6-8, wherein $R_5$ is:
—OH,
—O$(CR_{20}R_{21})_m(CR_{22}R_{23})_n(OCH_2CH_2)_p(CR_{40}R_{41})_{p''}Y''(CR_{24}R_{25})_q(CO)_tX''$,
—O$(CR_{20}R_{21})_m(CR_{26}=CR_{27})_{m'}(CR_{22}R_{23})_n(OCH_2CH_2)_p(CR_{40}R_{41})_{p''}Y''(CR_{24}R_{25})_q(CO)_tX''$,
—O$(CR_{20}R_{21})_m(alkynyl)_n(CR_{22}R_{23})_n(OCH_2CH_2)_p(CR_{40}R_{41})_{p''}Y''(CR_{24}R_{25})_1(CO)_tX''$,
—O$(CR_{20}R_{21})_m(indolo)_{p'}(CR_{22}R_{23})_n(OCH_2CH_2)_p(CR_{40}R_{41})_{p''}Y''(CR_{24}R_{25})_q(CO)_tX''$,
—O$(CR_{20}R_{21})_m(pyrrolo)_{q'}(CR_{22}R_{23})_n(OCH_2CH_2)_p(CR_{40}R_{41})_{p''}Y''(CR_{24}R_{25})_q(CO)_tX''$,
—O$(CR_{20}R_{21})_m(pyrrolo)_{q'}(imidazolo)_{q''}(CR_{22}R_{23})_n(OCH_2CH_2)_p(CR_{40}R_{41})_{p''}Y''(CR_{24}R_{25})_q(CO)_tX''$,
—O$(CR_{20}R_{21})_m(imidazolo)_{q'}(CR_{22}R_{23})_n(OCH_2CH_2)_p(CR_{40}R_{41})_{p''}Y''(CR_{24}R_{25})_q(CO)_tX''$,
—O$(CR_{20}R_{21})_m(pyrrolo)_{q'}(indolo)_{q''}(CR_{22}R_{23})_n(OCH_2CH_2)_p(CR_{40}R_{41})_{p''}Y''(CR_{24}R_{25})_q(CO)_tX''$,
—O$(CR_{20}R_{21})_m(indolo)_{q'}(imidazolo)_{q''}(CR_{22}R_{23})_n(OCH_2CH_2)_p(CR_{40}R_{41})_{p''}Y''(CR_{24}R_{25})_q(CO)_tX''$,
—O$(CR_{20}R_{21})_m(piperazino)_t(CR_{22}R_3)_n(OCH_2CH_2)_p(CR_{40}R_{41})_{p''}Y''(CR_{24}R_{25})_q(CO)_tX''$,
—O$(CR_{20}R_{21})_mA''_{m''}(CR_{22}R_{23})_n(OCH_2CH_2)_p(CR_{40}R_{41})_{p''}Y''(CR_{24}R_{25})_q(CO)_tX''$,
—SH,
—S$(CR_{20}R_{21})_m(CR_{22}R_{23})_n(OCH_2CH_2)_p(CR_{40}R_{41})_{p''}Y''(CR_{24}R_{25})_q(CO)_tX''$,
—S$(CR_{20}R_{21})_m(CR_{26}=CR_{27})_{m'}(CR_{22}R_{23})_n(OCH_2CH_2)_p(CR_{40}R_{41})_{p''}Y''(CR_{24}R_{25})_q(CO)_tX''$,
—S$(CR_{20}R_{21})_m(alkynyl)_n(CR_{22}R_{23})_n(OCH_2CH_2)_p(CR_{40}R_{41})_{p''}Y''(CR_{24}R_{25})_q(CO)_tX''$,
—S$(CR_{20}R_{21})_m(indolo)_{p'}(CR_{22}R_{23})_n(OCH_2CH_2)_p(CR_{40}R_{41})_{p''}Y''(CR_{24}R_{25})_q(CO)_tX''$,
—S$(CR_{20}R_{21})_m(pyrrolo)_{q'}(CR_{22}R_{23})_n(OCH_2CH_2)_p(CR_{40}R_{41})_{p''}Y''(CR_{24}R_{25})_q(CO)_tX''$,
—S$(CR_{20}R_{21})_m(imidazolo)_{q'}(CR_{22}R_3)_n(OCH_2CH_2)_p(CR_{40}R_{41})_{p''}Y''(CR_{24}R_{25})_q(CO)_tX''$,
—S$(CR_{20}R_{21})_m(pyrrolo)_{q'}(imidazolo)_{q''}(CR_{22}R_{23})_n(OCH_2CH_2)_p(CR_{40}R_{41})_{p''}Y''(CR_{24}R_{25})_q(CO)_tX''$,
—S$(CR_{20}R_{21})_m(pyrrolo)_{q'}(indolo)_{q''}(CR_{22}R_{23})_n(OCH_2CH_2)_p(CR_{40}R_{41})_{p''}Y''(CR_{24}R_{25})_q(CO)_tX''$,
—S$(CR_{20}R_{21})_m(indolo)_{q'}(imidazolo)_{q''}(CR_{22}R_{23})_n(OCH_2CH_2)_p(CR_{40}R_{41})_{p''}Y''(CR_{24}R_{25})_q(CO)_tX''$,
—S$(CR_{20}R_{21})_m(piperazino)_t(CR_{22}R_3)_n(OCH_2CH_2)_p(CR_{40}R_{41})_{p''}Y''(CR_{24}R_{25})_q(CO)_tX''$,
—S$(CR_{20}R_{21})_mA''_{m''}(CR_{22}R_{23})_n(OCH_2CH_2)_p(CR_{40}R_{41})_{p''}Y''(CR_{24}R_{25})_q(CO)_tX''$,
—NH$_2$,
—NR$_{28}(CR_{20}R_{21})_m(CR_{22}R_{23})_n(OCH_2CH_2)_p(CR_{40}R_{41})_{p''}Y''(CR_{24}R_{25})_q(CO)_tX''$,
—NR$_{28}(CR_{20}R_{21})_m(CR_{26}=CR_{27m'}(CR_{22}R_{23})_n(OCH_2C_2)_p(CR_{40}R_{41})_{p''}Y''(CR_{24}R_{25})_q(CO)_tX''$,
—NR$_{28}(CR_{20}R_{21})_m(alkynyl)_n(CR_2R_{23})_n(OCH_2CH_2)_p(CR_{40}R_{41})_{p''}Y''(CR_{24}R_{25})_q(CO)_tX''$,
—NR$_{28}(CR_{20}R_{21})_m(indolo)_{p'}(CR_{22}R_{23})_n(OCH_2CH_2)_p(CR_{40}R_{41})_{p''}Y''(CR_{24}R_{25})_q(CO)_tX''$,
—NR$_{28}(CR_{20}R_{21})_m(pyrrolo)_{q'}(CR_{22}R_{23})_n(OCH_2CH_2)_p(CR_{40}R_{41})_{p''}Y''(CR_{24}R_{25})_q(CO)_tX''$,
—NR$_{28}(CR_{20}R_{21})_m(imidazole)_{q'}(CR_2R_{23})_n(OCH_2CH_2)_p(CR_{40}R_{41})_{p''}Y''(CR_{24}R_{25})_q(CO)_tX''$,
—NR$_{28}(CR_{20}R_{21})_m(pyrrolo)_{q'}imidazolo)_{q''}(CR_{22}R_{23})_n(OCH_2CH_2)_p(CR_{40}R_{41})_{p''}Y''(CR_{24}R_{25})_q(CO)_tX''$,
—NR$_{28}(CR_{20}R_{21})_m(pyrrolo)_{q'}indolo)_{q''}(CR_{22}R_{23})_n(OCH_2CH_2)_p(CR_{40}R_{41})_{p''}Y''(CR_{24}R_{25})_q(CO)_tX''$,
—NR$_{28}(CR_{20}R_{21})_m(indolo)_{q'}imidazolo)_{q''}(CR_{22}R_{23})_n(OCH_2CH_2)_p(CR_{40}R_{41})_{p''}Y''(CR_{24}R_{25})_q(CO)_tX''$,
—NR$_{28}(CR_{20}R_{21})_m(piperazino)_t(CR_2R_{23})_n(OCH_2CH_2)_p(CR_{40}R_{41})_{p''}Y''(CR_{24}R_{25})_q(CO)_tX''$,
—NR$_{28}(CR_{20}R_{21})_mA''_{m''}(CR_{22}R_{23})_n(OCH_2CH_2)_p(CR_{40}R_{41})_{p''}Y''(CR_{24}R_{25})_q(CO)_tX''$,
—$(CR_{20}R_{21})_m(CR_{22}R_{23})_n(OCH_2CH_2)_p(CR_{40}R_{41})_{p''}Y''(CR_{24}R_{25})_q(CO)_tX''$,
—$(CR_{20}R_{21})_m(CR_{26}=CR_{27})_{m'}(CR_{22}R_{23})_n(OCH_2CH_2)_p(CR_{40}R_{41})_{p''}Y''(CR_{24}R_{25})_q(CO)_tX''$,
—$(CR_{20}R_{21})_m(alkynyl)_n(CR_{22}R_{23})_n(OCH_2CH_2)_p(CR_{40}R_{41})_{p''}Y''(CR_{24}R_{25})_q(CO)_tX''$,
—$(CR_{20}R_{21})_m(indolo)_{p'}(CR_{22}R_{23})_n(OCH_2CH_2)_p(CR_{40}R_{41})_{p''}Y''(CR_{24}R_{25})_q(CO)_tX''$,
—$(CR_{20}R_{21})_m(pyrrolo)_{q'}(CR_{22}R_{23})_n(OCH_2CH_2)_p(CR_{40}R_{41})_{p''}Y''(CR_{24}R_{25})_q(CO)_tX''$,
—$(CR_{20}R_{21})_m(piperazino)_t(CR_{22}R_{23})_n(OCH_2CH_2)_p(CR_{40}R_{41})_{p''}Y''(CR_{24}R_{25})_q(CO)_tX''$,
—$(CR_{20}R_{21})_m(pyrrolo)_{q'}(indolo)_{q''}CR_{22}R_{23})_n(OCH_2CH_2)_p(CR_{40}R_{41})_{p''}Y''(CR_{24}R_{25})_q(CO)_tX''$,
$(CR_{20}R_{21})_m(imidazolo)_{q'}(CR_{22}R_{23})_n(OCH_2CH_2)_p(CR_{40}R_{41})_{p''}Y''(CR_{24}R_{25})_q(CO)_tX''$,
$(CR_{20}R_{21})_m(pyrrolo)_{q'}(imidazolo)_{q''}(CR_{22}R_{23})_n(OCH_2CH_2)_p(CR_{40}R_{41})_{p''}Y''(CR_{24}R_{25})_q(CO)_tX''$,
$(CR_{20}R_{21})_m(imidazolo)_{q'}(indolo)_{q''}CR_{22}R_{23})_n(OCH_2CH_2)_p(CR_{40}R_{41})_{p''}Y''(CR_{24}R_{25})_q(CO)_tX''$,
—$(CR_{20}R_{21})_mA''_{m''}(CR_{22}R_{23})_n(OCH_2CH_2)_p(CR_{40}R_{41})_{p''}Y''(CR_{24}R_{25})_q(CO)_tX''$,
—$(CR_{20}R_{21})_m(CR_{29}=N-NR_{30})_{n'}(CR_{22}R_{23})_n(OCH_2CH_2)_p(CR_{40}R_{41})_{p''}Y''(CR_{24}R_{25})_q(CO)_tX''$,
—$(CR_{20}R_{21})_m(CR_{29}=N-NR_{30})_{n'}(CR_{26}=CR_{27})_{m'}(CR_{22}R_{23})_n(OCH_2CH_2)_p(CR_{40}R_{41})_{p''}Y''(CR_{24}R_{25})_q(CO)_tX''$,
—$(CR_{20}R_{21})_m(CR_{29}=N-NR_{30})_{n'}(alkynyl)_n(CR_{22}R_{23})_n OCH_2CH_2)_p(CR_{40}R_{41})_{p''}Y''(CR_{24}R_{25})_q(CO)_tX''$,
—$(CR_{20}R_{21})_m(CR_{29}=N-NR_{30})_{n''l}A'''_{m''}(CR_{22}R_{23})_n(OCH_2CH_2)_p(CR_{40}R_{41})_{p''}Y''(CR_{24}R_{25})_q(CO)_tX''$, wherein:

m, n, p, q, m', n', p', q', q'', are integer from 1 to 10 and can be 0;

t, m'', n'' and p'' are 0 or 1;

X'' is selected from —OR$_{36}$, —SR$_{37}$, —NR$_{38}$R$_{39}$, wherein R$_{36}$, R$_{37}$, R$_{38}$, R$_{39}$ are —H, a linear, branched or cyclic alkyl, alkenyl or alkynyl having from 1 to 20 carbon atoms or, a polyethylene glycol unit —$(OCH_2CH_2)_n$, optionally R$_{37}$ is a thiol protecting group, or when t =1, COX'' forms a reactive ester selected from N-hydroxysuccinimide esters, N-hydroxyphthalimide esters, N-hydroxy sulfo-succinimide esters, para-nitrophenyl esters, dinitrophenyl esters, pentafluorophenyl esters and their derivatives, wherein said derivatives facilitate amide formation;

Y'' is absent or is selected from O, S, S—S or NR$_{32}$, wherein R$_{32}$ has the same definition as given above for R, or when Y'' is not S—S and t =0, X'' is selected from a maleimido group, a haloacetyl group or SR$_{37}$;

A'' is an amino acid selected from glycine, alanine, leucine, valine, lysine, citrulline, glutamate, or a polypeptide containing between 2 to 20 amino acid units;

R$_{20}$, R$_{21}$, R$_{22}$, R$_{23}$, R$_{24}$, R$_{25}$, R$_{26}$, R$_{27}$ are the same or different and are —H or a linear or branched alkyl having from 1 to 5 carbon atoms;

R$_{28}$ is —H or alkyl;

R$_{29}$ and R$_{30}$ are the same or different and are —H or an alkyl from 1 to 5 carbon atoms;

optionally, one of R$_{40}$ and R$_{41}$ is a negatively or positively charged functional group and the other is —H or alkyl, alkenyl, alkynyl having 1 to 4 carbon atoms.

10. A compound selected from the group consisting of:
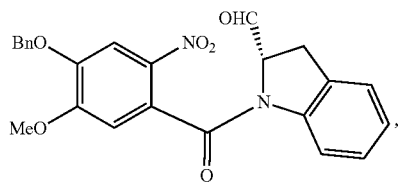
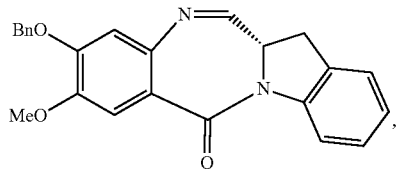
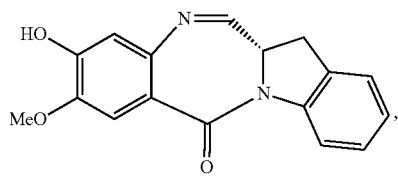
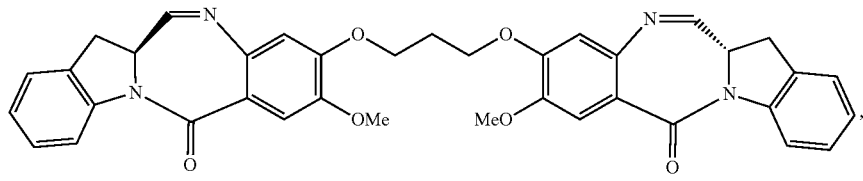
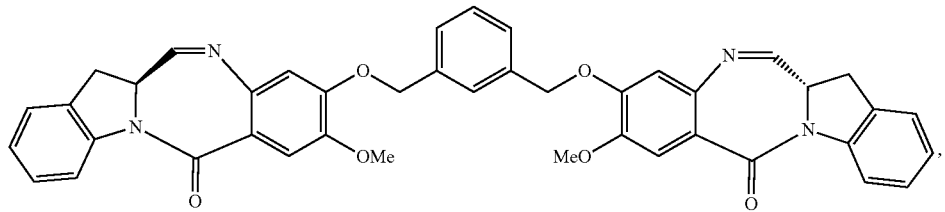
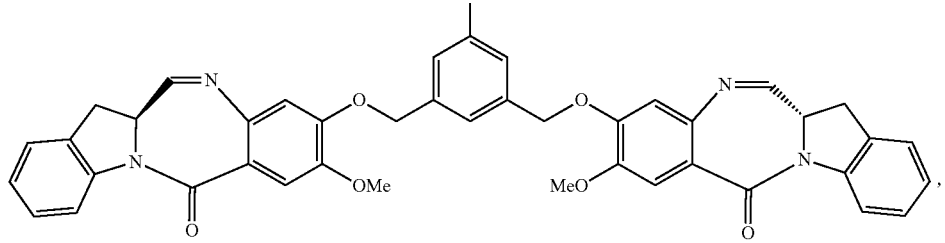
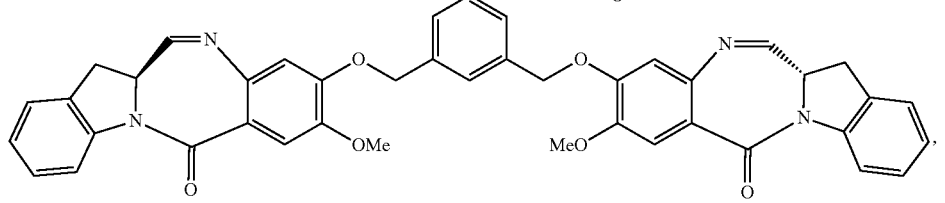
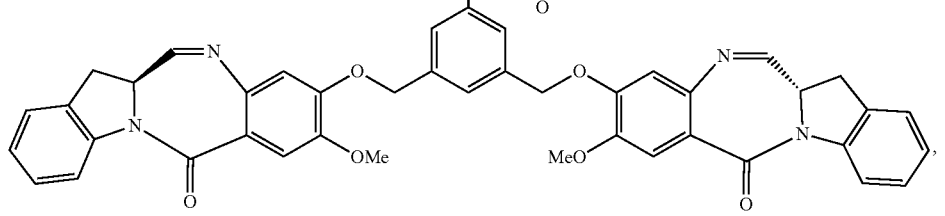

-continued
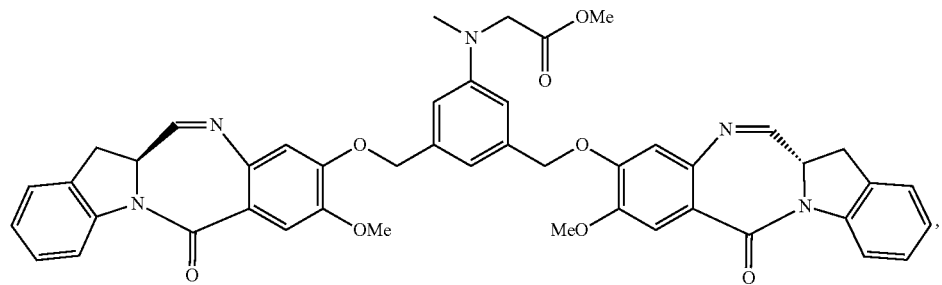
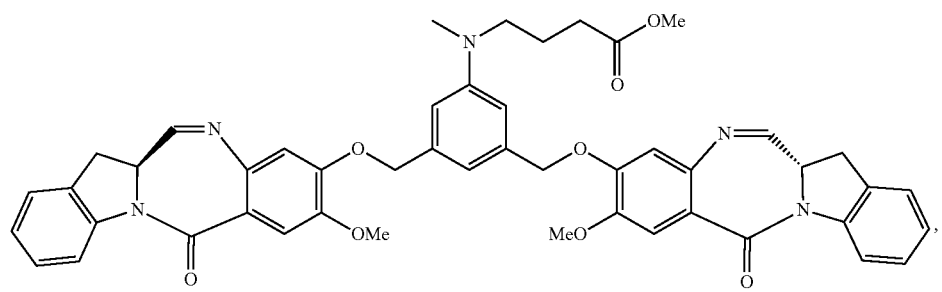
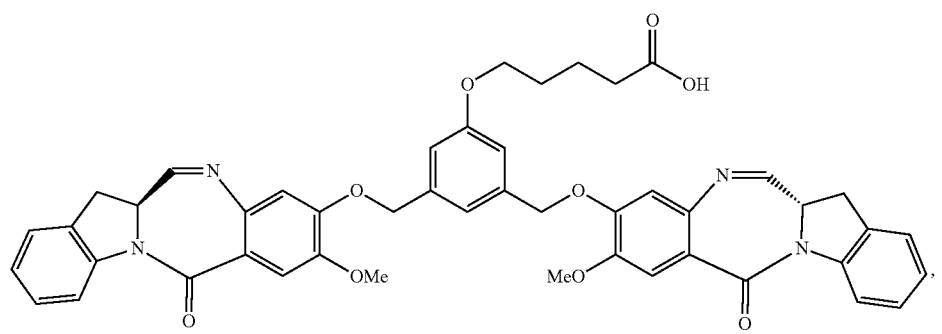
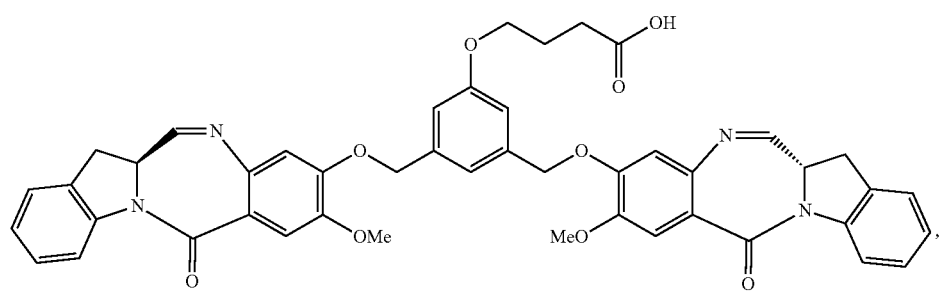
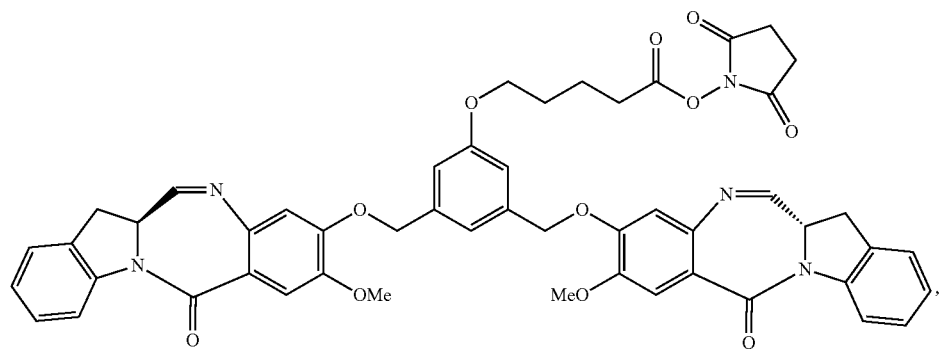

-continued
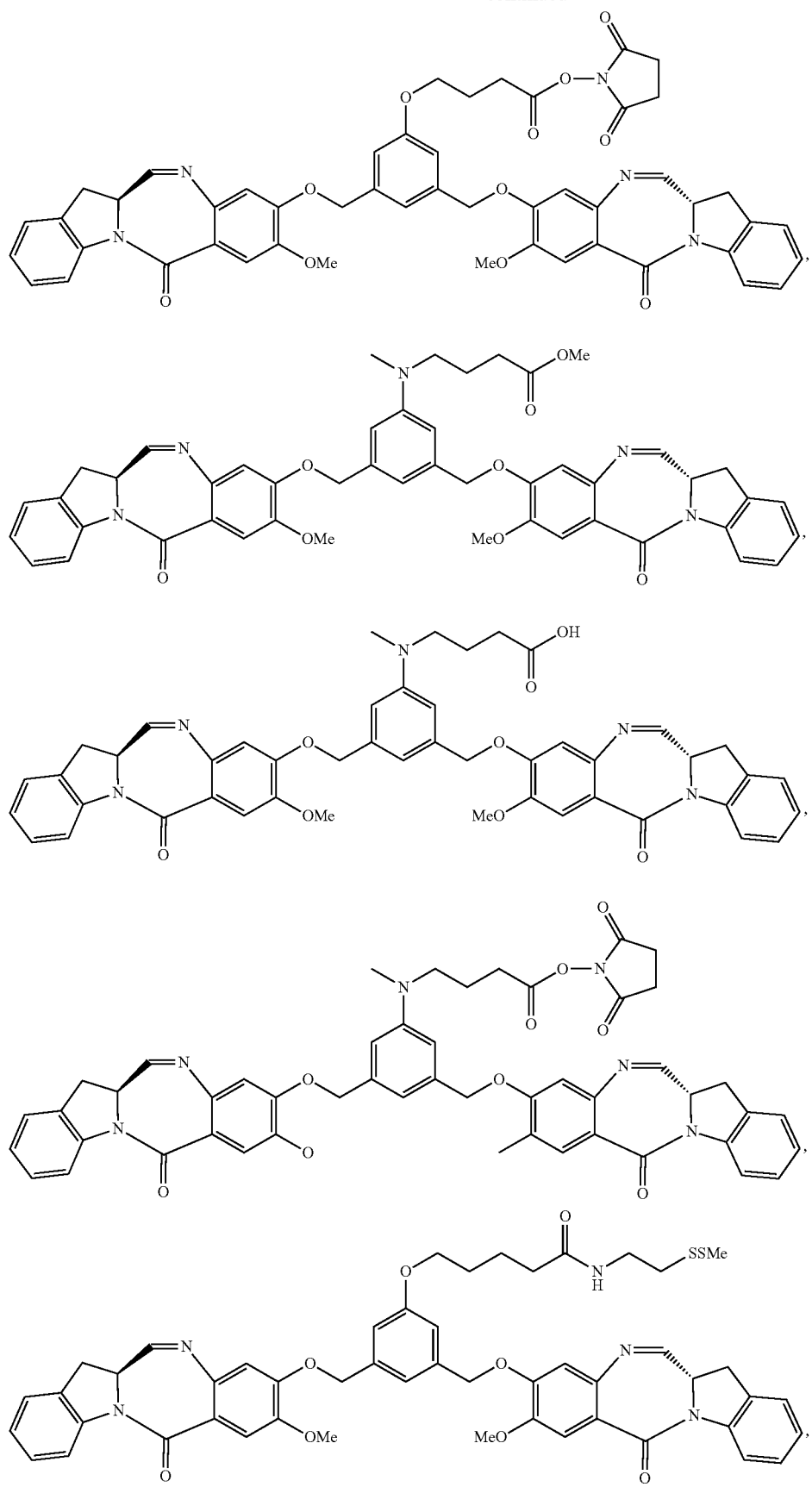

-continued
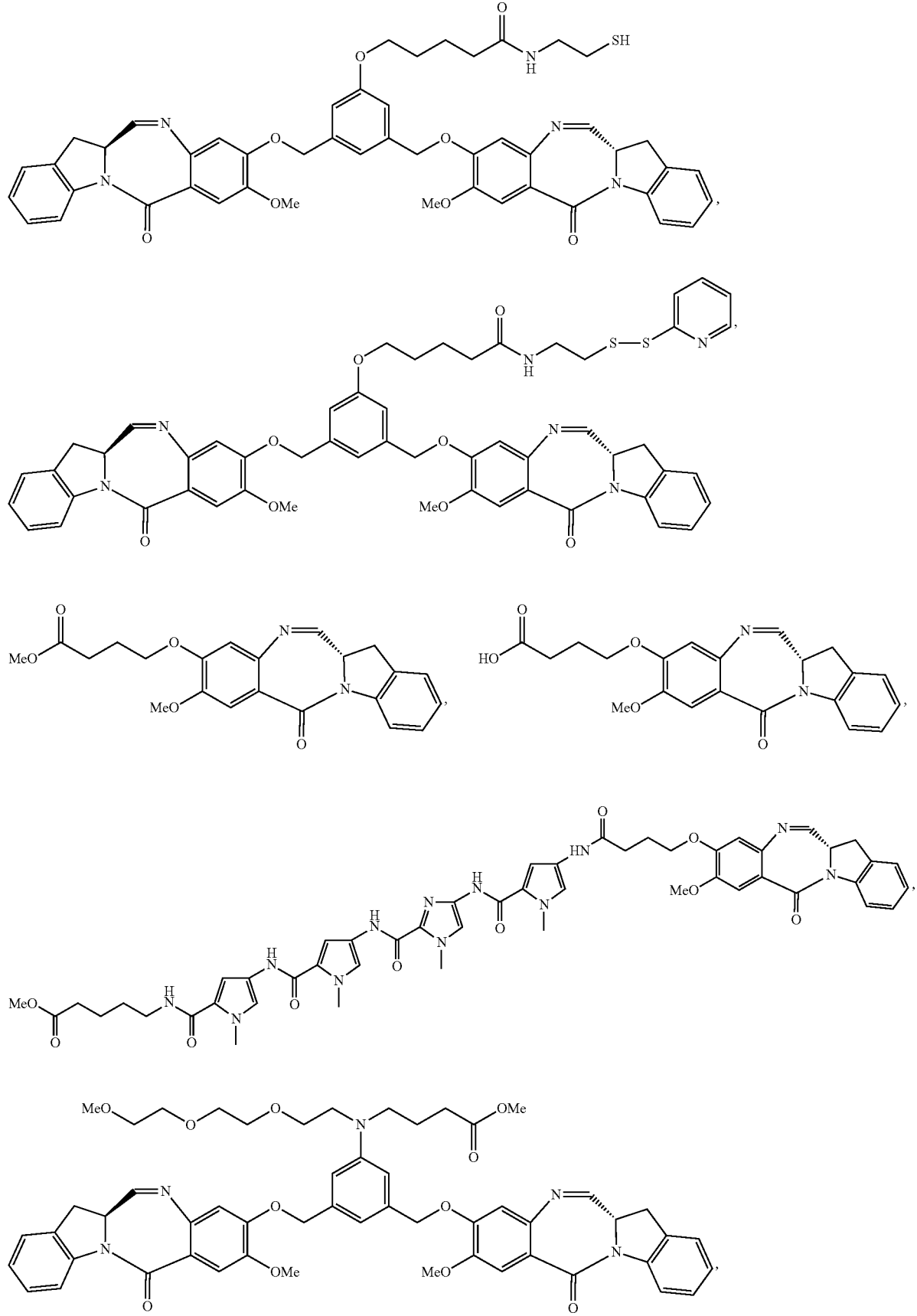

269 270
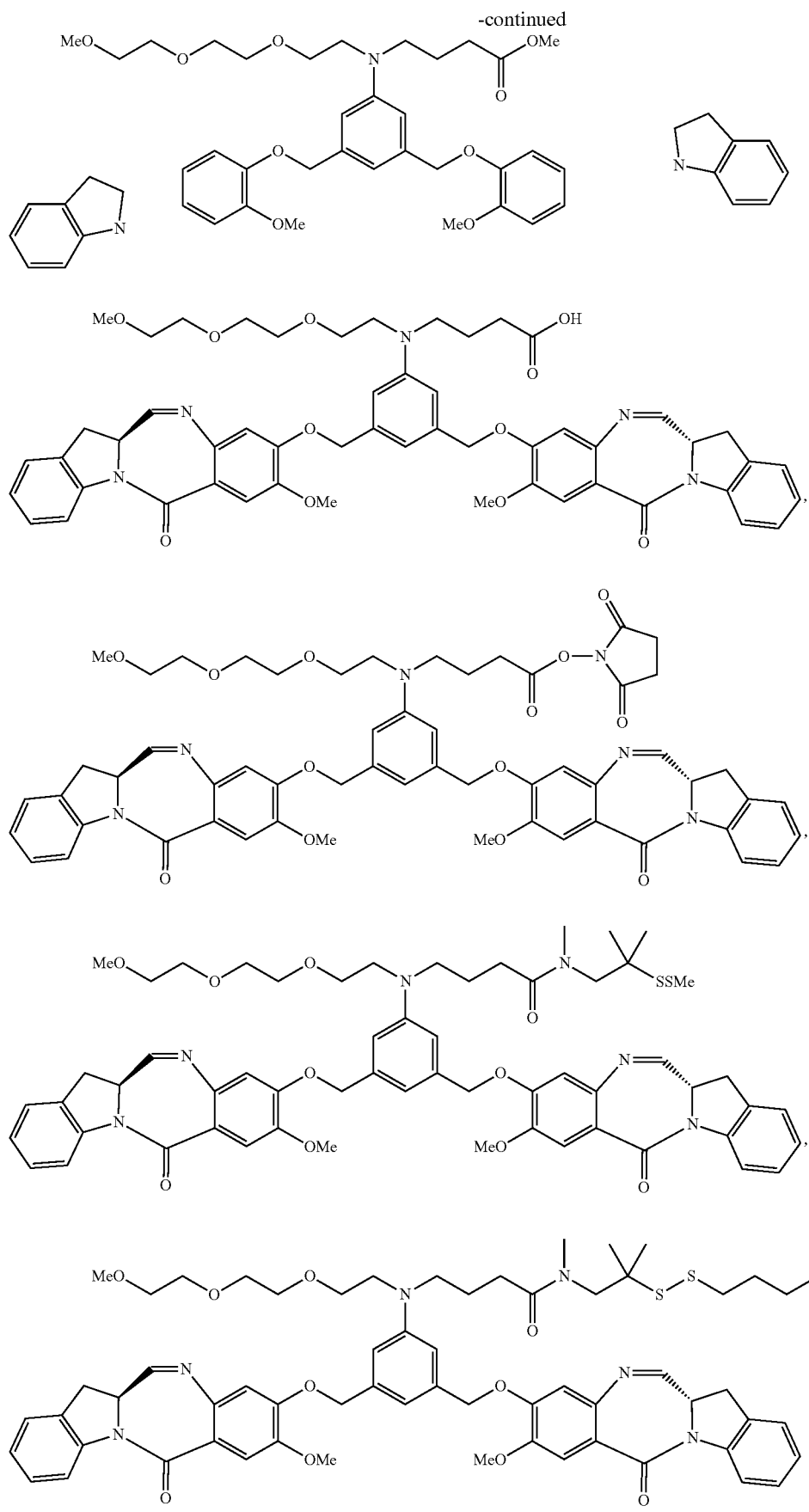

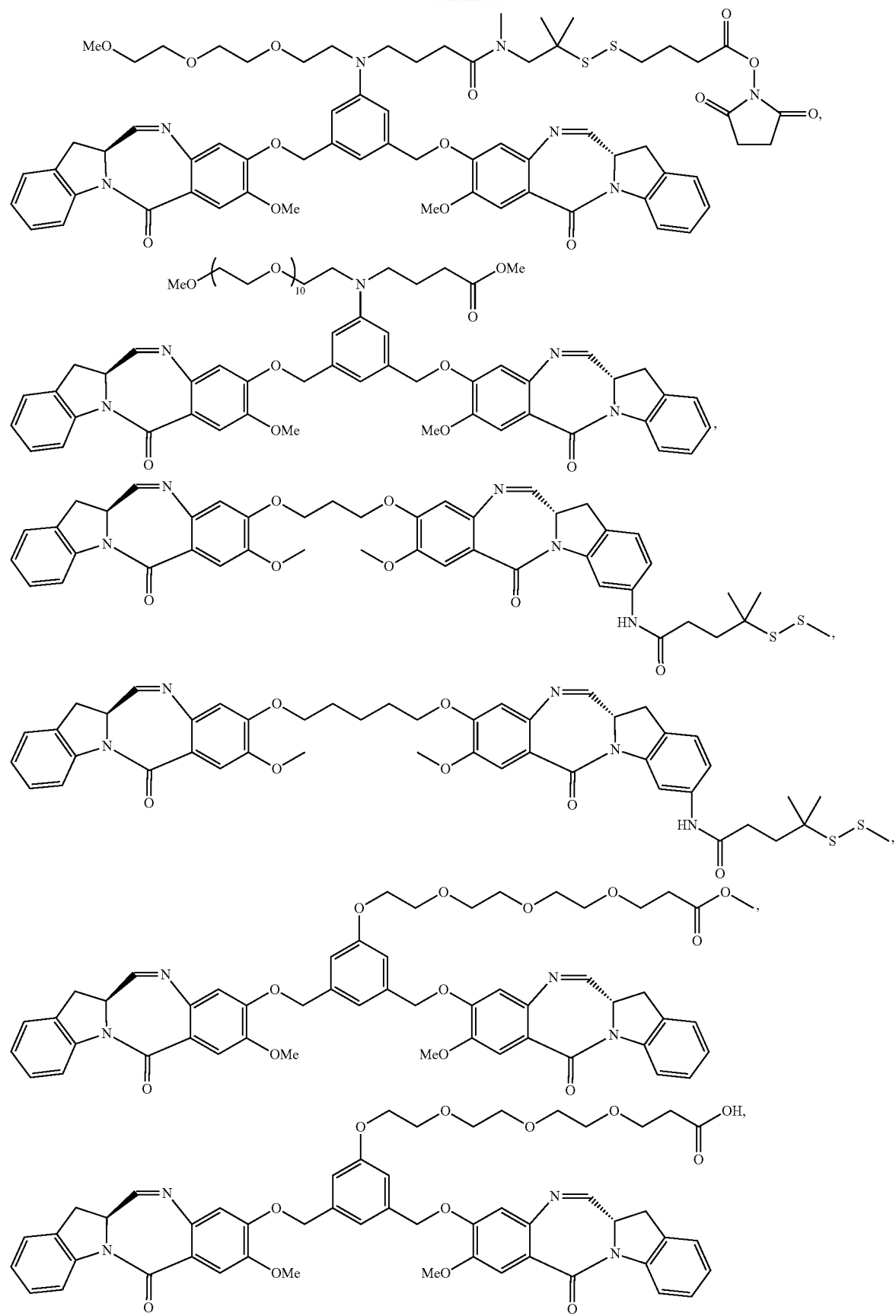

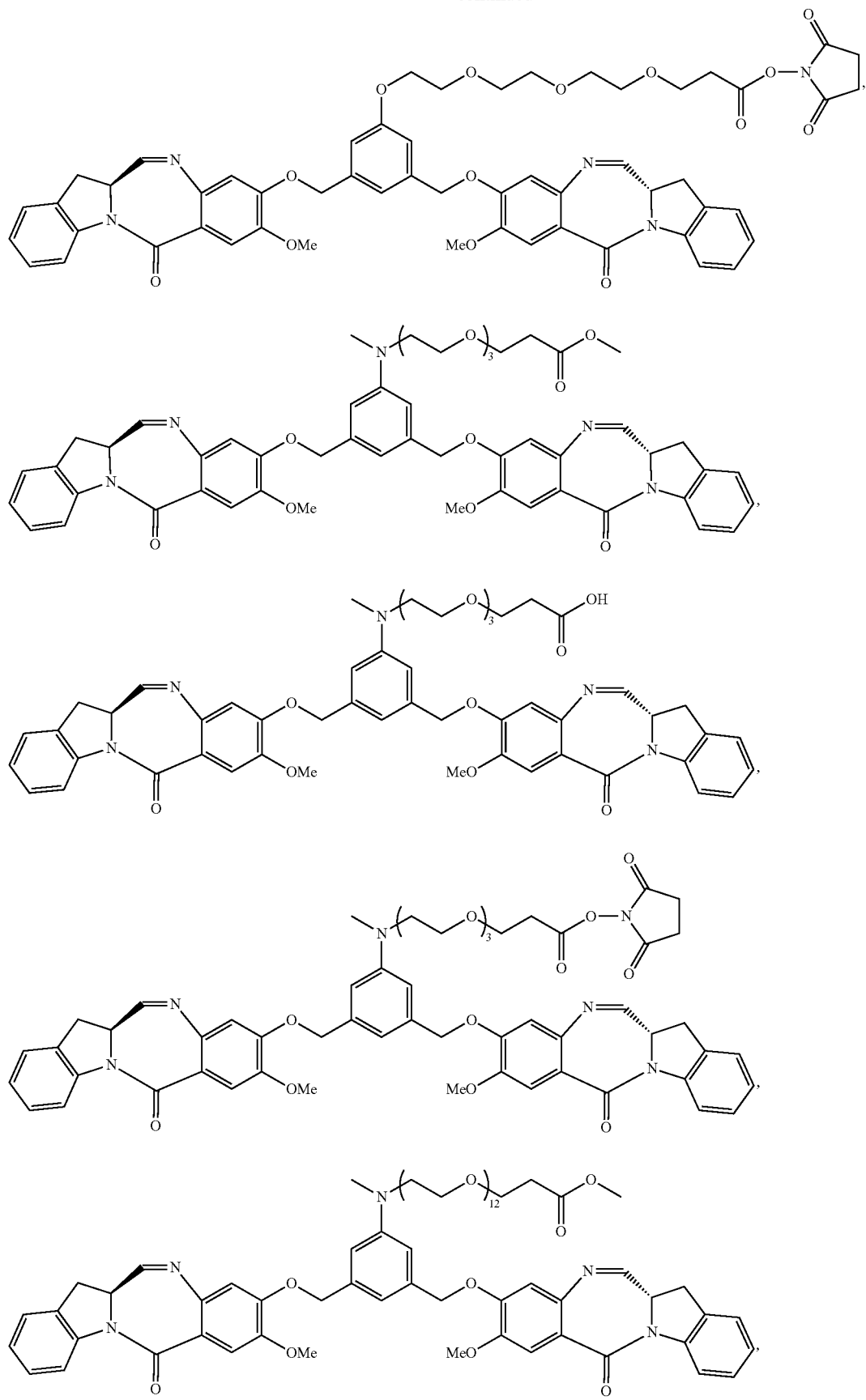

-continued

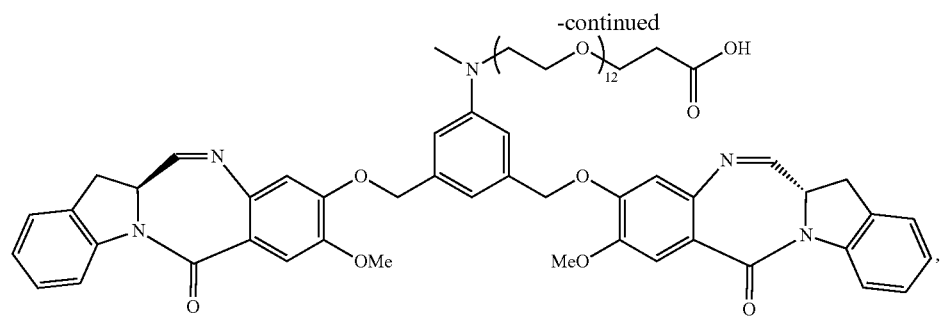

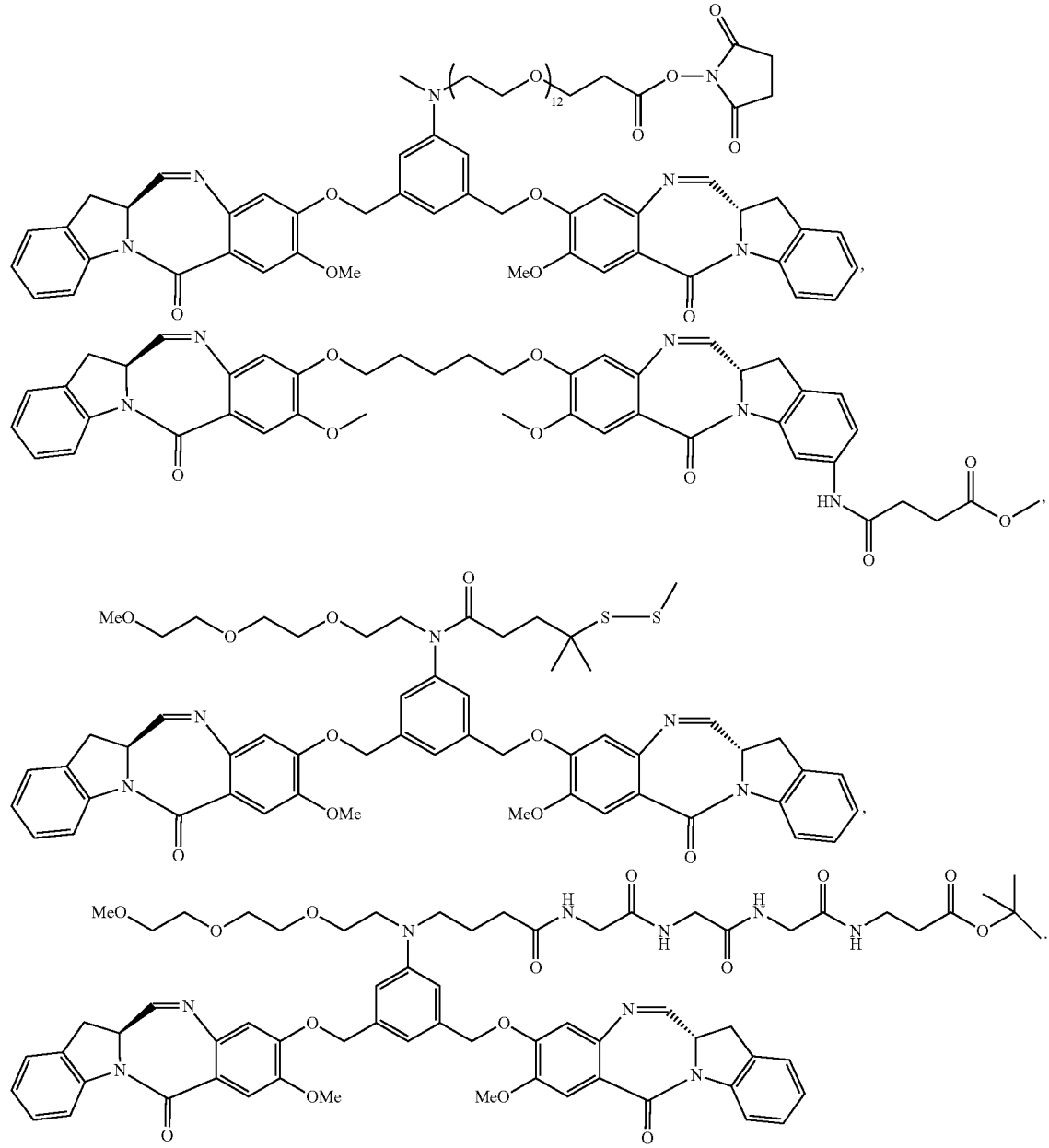

11. A pharmaceutical composition comprising a compound of claim 1 or 6, and a pharmaceutically acceptable carrier.

12. The pharmaceutical composition of claim 11, further comprising a second compound, which is a chemotherapeutic agent.

13. A method of inhibiting abnormal cell growth or treating a proliferative disorder in a mammal, comprising administering to said mammal a therapeutically effective amount of the compound of claim 1 or 6, wherein the proliferative disorder is Burkitt's lymphoma, colon cancer, rhabdomyosarcoma, acute promyelocytic leukemia, epidermoid carcinoma, multiple myeloma, breast cancer, acute lymphoblastic leukemia (ALL), or melanoma.

14. A process for the preparation of a compound of formula (I), or a pharmaceutically acceptable salt, optical isomer, racemate, diastereomer, or enantiomer thereof, the process comprising:

a) coupling compound of formula (1) and compound of formula (2) to give compound of formula (3);

b) converting compound of formula (3) into aldehyde of formula (4); and c) converting compound of formula (4) into compound of formula (I),

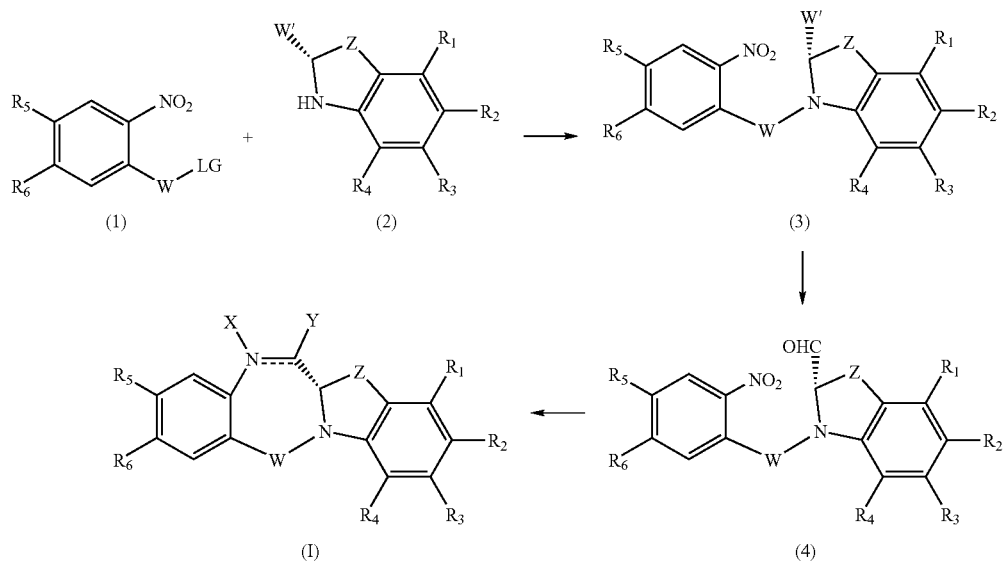

wherein:
the double line = between N and C represents a single bond or a double bond, provided that when it is a double bond X is absent and Y is —H, and when it is a single bond, X is —H; and
Y is selected from —OR, —OCOR', —OCOOR', —OCONR'R", —NR'R", —NRCOR', —NRCOP, wherein P is an amino acid or a polypeptide containing between 2 to 20 amino acid units, —SR', —SOR', —$SO_2R'$, —$SO_3$, —$OSO_3$, a halogen, a cyano, or an azido, wherein R, R' and R" are the same or different and are selected from —H, an optionally substituted linear, branched or cyclic alkyl, alkenyl or alkynyl having from 1 to 20 carbon atoms, a polyethylene glycol unit (—$OCH_2CH_2$)$_n$, wherein n is an integer from 1 to 2000, a 5- or 6-membered heteroaryl ring containing one or more heteroatoms independently selected from nitrogen, oxygen, and sulfur, a 5- to 18-membered fused ring system, wherein at least one of the rings is aromatic, containing one or more heteroatoms independently selected from nitrogen, oxygen, and sulfur, an aryl having from 6 to 18 carbon atoms, a 3- to 18-membered heterocyclic ring having 1 to 6 heteroatoms selected from O, S, N and P, wherein the optional substituent is selected from halogen, —$OR_7$, —$NR_8R_9$, —$NO_2$, —$NRCOR'$, —$SR_{10}$, —SOR', —$SO_2R'$, a sulfite —$SO_3$, —$OSO_3$, —$SO_2NRR'$, a cyano, an azido, —$COR_{11}$, —$OCOR_{11}$ or —$OCONR_{11}R_{12}$, wherein $R_7$, $R_8$, $R_9$, $R_{10}$, $R_{11}$ and $R_{12}$ are each independently selected from —H, a linear, branched or cyclic alkyl, alkenyl or alkynyl having from 1 to 10 carbon atoms, a polyethylene glycol unit (—$OCH_2CH_2$)$_n$, wherein n is an integer from 1 to 2000, a 5- or 6-membered heteroaryl ring containing one or more heteroatoms independently selected from nitrogen, oxygen, and sulfur, a 5- to 18-membered fused ring system, wherein at least one of the rings is aromatic, containing one or more heteroatoms independently selected from nitrogen, oxygen, and sulfur, an aryl having from 6 to 18 carbon atoms, a 3- to 18-membered heterocyclic ring having 1 to 6 heteroatoms selected from O, S, N and P, and $R_{10}$ optionally is —$SR_{13}$ or —$COR_{13}$, wherein $R_{13}$ is selected from a linear, branched or cyclic alkyl, alkenyl or alkynyl having from 1 to 10 carbon atoms, a polyethylene glycol unit (—$OCH_2CH_2$)$_n$, wherein n is an integer from 1 to 2000, a 5- or 6-membered heteroaryl ring containing one or more heteroatoms independently selected from nitrogen, oxygen, and sulfur, a 5- to 18-membered fused ring system, wherein at least one of the rings is aromatic, containing one or more heteroatoms independently selected from nitrogen, oxygen, and sulfur, a 3- to 18-membered heterocyclic ring having 1 to 6 heteroatoms selected from O, S, N and P, and $R_{11}$ can also be —$OR_{14}$, wherein $R_{14}$ is —H or has the same definition as R, optionally, R" is an —OH;

W is C=O;

$R_1$, $R_2$, $R_3$, $R_4$, are each independently selected from —H, a substituted or unsubstituted an optionally substituted linear, branched or cyclic alkyl, alkenyl or alkynyl having from 1 to 10 carbon atoms, a polyethylene glycol unit (—$OCH_2CH_2$)$_n$, wherein n is an integer from 1 to 2000, wherein the optional substituent is selected from halogen, —$OR_7$, —$NR_8R_9$, —$NO_2$, —$NRCOR'$, —$SR_{10}$, —SOR', —$SO_2R'$, —$SO_3$, —$OSO_3$, —$SO_2NRR'$, a cyano, an azido, —$COR_{11}$, —$OCOR_{11}$, —$OCONR_{11}R_{12}$, or a polyethylene glycol unit (—$OCH_2CH_2$)$_n$, wherein n is an integer from 1 to 2000, or a substituent selected from a halogen, —$OR_7$, —$NR_8R_9$, —$NO_2$, —$NRCOR'$, —$SR_{10}$, —SOR', —$SO_2R'$, —$SO_3$, —$OSO_3$, —$SO2NRR'$, a cyano, an azido, guanidinium [—NH (C=NH)NH$_2$], —COR$_{11}$, —OCOR$_{11}$ or —OCONR$_{11}$R$_{12}$, optionally, any one of R$_1$, R$_2$, R$_3$, R$_4$ is a linking group that enables linkage to a cell binding agent via a covalent bond or is selected from a polypyrrolo, poly-indolyl, poly-imidazolyl, polypyrrolo-imidazolyl, poly-pyrrollo-indolyl or polyimidazolo-indolyl unit optionally bearing the linking group;

R$_5$ is selected from —OR$_{15}$, —CRR'OH, —SH, —CRR'SH, —NHR$_{15}$ or —CRR'NHR$_{15}$, wherein R$_{15}$ has the same definition as R; optionally, R$_5$ is the linking group or is selected from a polypyrrolo, polyindolyl, poly-imidazolyl, polypyrrollo-imidazolyl, poly-pyrrollo- indolyl or polyimidazolo-indolyl unit optionally bearing the linking group;

R$_6$ is —OR, —SR, —NRR', or optionally R$_6$ is the linking group;

Z is $_{CR15}$R$_{16}$, wherein R$_{15}$ and R$_{16}$ are each independently selected from —H, a linear, branched or cyclic alkyl having from 1 to 10 carbon atoms, or a polyethylene glycol unit (—OCH$_2$CH$_2$)$_n$, wherein n is an integer from 1 to 2000;

provided that the compound has no more than one linking group,

LG is a leaving group;

W' is COOR or CH$_2$OW", and

W" is a protecting group.

15. A process for the preparation of compound of formula (II), or a pharmaceutically acceptable salt, optical isomer, racemate, diastereomer, or enantiomer thereof, the process comprising:
   a) coupling compound of formula (1) and compound of formula (5) to give compound of formula (6);
   b) converting compound of formula (6) into aldehyde of formula (7); and
   c) converting compound of formula (7) into compound of formula (II), Y is selected from —OR, —OCOR', —OCOOR', —OCONR'R", —NR'R", —NRCOR', —NRCOP, wherein P is an amino acid or a polypeptide containing between 2 to 20 amino acid units, —SR', —SOR', —SO$_2$R', —SO$_3$, —OSO$_3$, a halogen, a cyano, or an azido, wherein R, R' and R" are the same or different and are selected from —H, an optionally substituted linear, branched or cyclic alkyl, alkenyl or alkynyl having from 1 to 20 carbon atoms, a polyethylene glycol unit (—OCH$_2$CH$_2$)$_n$, wherein n is an integer from 1 to 2000, a 5- or 6-membered heteroaryl ring containing one or more heteroatoms independently selected from nitrogen, oxygen, and sulfur, a 5- to 18-membered fused ring system, wherein at least one of the rings is aromatic, containing one or more heteroatoms independently selected from nitrogen, oxygen, and sulfur, an aryl having from 6 to 18 carbon atoms, a 3- to 18-membered heterocyclic ring having 1 to 6 heteroatoms selected from O, S, N and P, wherein the optional substituent is selected from halogen, —OR$_7$, —NR$_8$R$_9$, —NO$_2$, —NRCOR', —SR$_{10}$, —SOR', —SO$_2$R', —SO$_3$, —OSO$_3$, —SO$_2$NRR', a cyano, an azido, —COR$_{11}$, —OCOR$_{11}$ or —OCONR$_{11}$R$_{12}$, wherein R$_7$, R$_8$, R$_9$, R$_{10}$, R$_{11}$ and R$_{12}$ are each independently selected from —H, a linear, branched or cyclic alkyl, alkenyl or alkynyl having from 1 to 10 carbon atoms, a polyethylene glycol unit (—OCH$_2$CH$_2$)$_n$, wherein n is an integer from 1 to 2000, a 5- or 6-membered heteroaryl ring containing one or more heteroatoms independently selected from nitrogen, oxygen, and sulfur, a 5- to 18-membered fused ring system, wherein at least one of the rings is aromatic containing one or more heteroatoms independently selected from nitrogen, oxygen, and sulfur, an aryl having from 6 to 18 carbon atoms, a 3- to 18-membered heterocyclic ring having 1 to 6 heteroa-

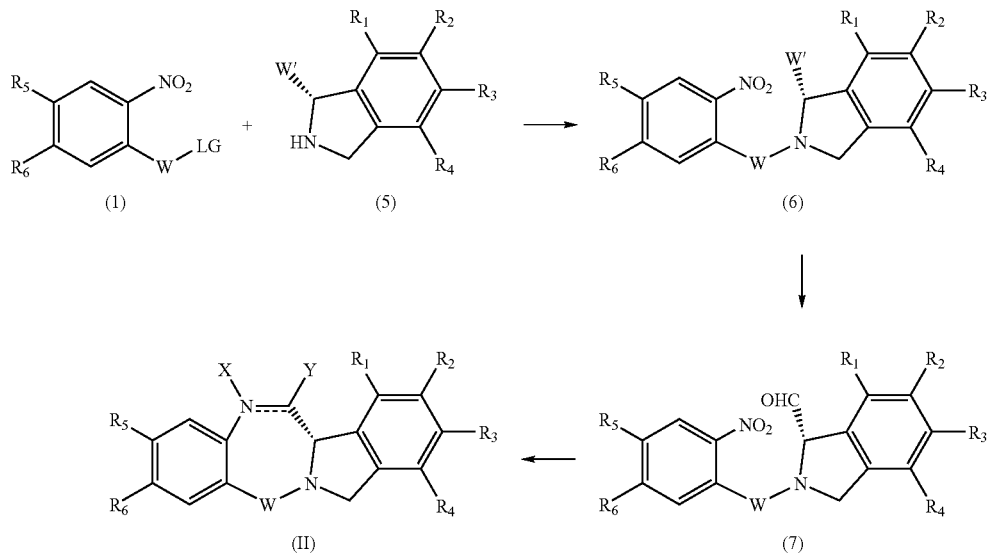

wherein:
   the double line = between N and C represents a single bond or a double bond, provided that when it is a double bond X is absent and Y is —H, and when it is a single bond, X is —H; and toms selected from O, S, N and P, and R$_{10}$ optionally is —SR$_{13}$ or —COR$_{13}$, wherein R$_{13}$ is selected from a linear, branched or cyclic alkyl, alkenyl or alkynyl having from 1 to 10 carbon atoms, a polyethylene glycol unit (—OCH$_2$CH$_2$)$_n$, wherein n is an integer from 1 to 2000, a 5- or 6-membered heteroaryl ring containing one or more heteroatoms independently selected from nitrogen, oxygen, and sulfur, a 5- to 18-membered fused ring system, wherein at least one of the rings is aromatic, containing one or more heteroatoms independently selected from nitrogen, oxygen, and sulfur, a 3- to 18-membered heterocyclic ring having 1 to 6 heteroatoms selected from O, S, N and P, and $R_{11}$ can also be —$OR_{14}$, wherein $R_{14}$ is -H or has the same definition as R, optionally, R" is —OH;

W is C=O;

$R_1$, $R_2$, $R_3$, $R_4$, are each independently selected from —H, an optionally substituted linear, branched or cyclic alkyl, alkenyl or alkynyl having from 1 to 10 carbon atoms, a polyethylene glycol unit (—$OCH_2CH_2$)$_n$, wherein n is an integer from 1 to 2000, wherein the optional substituent is selected from halogen, —$OR_7$, —$NR_8R_9$, —$NO_2$, —NRCOR', —$SR_{10}$, —SOR', —$SO_2R'$, —$SO_3$, —$OSO_3$, —$SO_2NRR'$, a cyano, an azido, —$COR_{11}$, —$OCOR_{11}$, —$OCONR_{11}R_{12}$, or a polyethylene glycol unit (—$OCH_2CH_2$)$_n$, wherein n is an integer from 1 to 2000, or a substituent selected from a halogen, —$OR_7$, —$NR_8R_9$, —$NO_2$, —NRCOR', —$SR_{10}$, —SOR', —$SO_2R'$, —$SO_3$, —$OSO_3$, —$SO_2NRR'$, a cyano, an azido, guanidinium [—NH(C=NH)$NH_2$], —$COR_{11}'$, —$OCOR_{11}$ or —$OCONR_{11}R_{12}$, optionally, any one of $R_1$, $R_2$, $R_3$, $R_4$ is a linking group that enables linkage to a cell binding agent via a covalent bond or is selected from a polypyrrolo, poly-indolyl, poly-imidazolyl, polypyrrolo-imidazolyl, poly-pyrrollo-indolyl or polyimidazolo-indolyl unit optionally bearing the linking group;

$R_5$ is selected from —$OR_{15}$, —CRR'OH, —SH, —CRR'SH, —$NHR_{15}$ or —CRR'$NHR_{15}$, wherein $R_{15}$ has the same definition as R; optionally, $R_5$ is the linking group or is selected from a polypyrrolo, poly-indolyl, poly-imidazolyl, polypyrrolo-imidazolyl, poly-pyrollo- indolyl or polyimidazolo-indolyl unit optionally bearing the linking group;

$R_6$ is —OR, —SR, —NRR', or optionally $R_6$ is the linking group;

Z is $CR_{15}R_{16}$, wherein $R_{15}$ and $R_{16}$ are each independently selected from —H, a linear, branched or cyclic alkyl having from 1 to 10 carbon atoms, a polyethylene glycol unit (—$OCH_2CH_2$)$_n$, wherein n is an integer from 1 to 2000;

provided that the compound has no more than one linking group;

LG is a leaving group;

W' is COOR or $CH_2OW''$, and

W" is a protecting group.

16. A process for the preparation of compound of formula (IV), or a pharmaceutically acceptable salt, optical isomer, racemate, diastereomer, or enantiomer thereof, the process comprising: coupling compound of formula (11), compound of formula (11)' and compound of formula (12) to give compound of formula (IV),

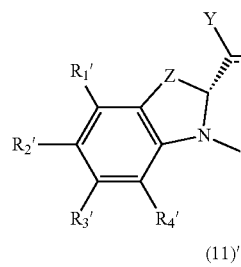

(11)'

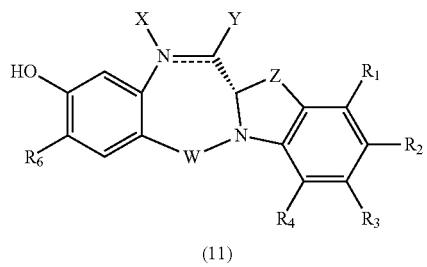

LG—D—L—D'—LG (12)

(11)

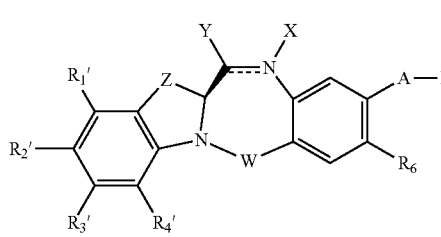

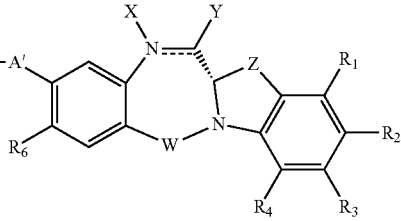

(IV)

wherein:

the double line == between N and C represents a single bond or a double bond, provided that when it is a double bond X is absent and Y is —H, and when it is a single bond, X is —H; and Y is selected from —OR, —OCOR', —OCOOR', —OCONR'R", —NR'R", —NRCOR', —NRCOP, wherein P is an amino acid or a polypeptide containing between 2 to 20 amino acid units, —SR', —SOR', —$SO_2R'$, —$SO_3$, —$OSO_3$, a halogen, a cyano, or an azido, wherein R, R' and R" are the same or different and are selected from —H, an optionally substituted linear, branched or cyclic alkyl, alkenyl or alkynyl having from 1 to 10 carbon atoms, a polyethylene glycol unit (—$OCH_2CH_2$)$_n$, wherein n is an integer from 1 to 2000, a 5- or 6-membered heteroaryl ring containing one or more heteroatoms independently selected from nitrogen, oxygen, and sulfur, a 5- to 18-membered fused ring system, wherein at least one of the rings is aromatic, containing one or more heteroatoms independently selected from nitrogen, oxygen, and sulfur, an aryl having from 6 to 18 carbon atoms, a 3- to 18-membered heterocyclic ring having 1 to 6 heteroatoms selected from O, S, N and P, wherein the optional substituent is selected from halogen, —OR$_7$, —NR$_8$R$_9$, —NO$_2$, —NRCOR', —SR$_{10}$, —SOR', —SO$_2$R', —OS$_3$, —OSO$_3$, —SO$_2$NRR', a cyano, an azido, —COR$_{11}$, —OCOR$_{11}$ or —OCONR$_{11}$R$_{12}$, wherein R$_7$, R$_8$, R$_9$, R$_{10}$, R$_{11}$ and R$_{12}$ are each independently selected from —H, a linear, branched or cyclic alkyl, alkenyl or alkynyl having from 1 to 10 carbon atoms, a polyethylene glycol unit (—OCH$_2$CH$_2$)$_n$, wherein n is an integer from 1 to 2000, a 5- or 6-membered heteroaryl ring containing one or more heteroatoms independently selected from nitrogen, oxygen, and sulfur, a 5- to 18-membered fused ring system, wherein at least one of the rings is aromatic, containing one or more heteroatoms independently selected from nitrogen, oxygen, and sulfur, an aryl having from 6 to 18 carbon atoms, a 3- to 10-membered heterocyclic ring having 1 to 6 heteroatoms selected from O, S, N and P, and R$_{10}$ is optionally —SR$_{13}$ or —COR$_{13}$, wherein R$_{13}$ is selected from a linear, branched or cyclic alkyl, alkenyl or alkynyl having from 1 to 10 carbon atoms, a 5- or 6-membered heteroaryl ring containing one or more heteroatoms independently selected from nitrogen, oxygen, and sulfur, a 5- to 18-membered fused ring system, wherein at least one of the rings is aromatic, containing one or more heteroatoms independently selected from nitrogen, oxygen, and sulfur, an aryl having from 6 to 18 carbon atoms, a 3- to 18-membered heterocyclic ring having 1 to 6 heteroatoms selected from O, S, N and P, optionally R$_{11}$ is —OR$_{14}$, wherein R$_{14}$ has the same definition as R, optionally R" is —OH;

W is C=O;

R$_1$, R$_2$, R$_3$, R$_4$, R$_1$', R$_2$', R$_3$' and R$_4$' are each independently selected from —H, an optionally substituted linear, branched or cyclic alkyl, alkenyl or alkynyl having from 1 to 10 carbon atoms, a polyethylene glycol unit (—OCH$_2$CH$_2$)$_n$, wherein n is an integer from 1 to 2000, wherein the optional substituent is selected from halogen, —OR$_7$, —NR$_8$R$_9$, —NO$_2$, —NRCOR', —SR$_{10}$, —SOR', —SO$_2$R', —SO$_3$, —OSO$_3$, —SO$_2$NRR', a cyano, an azido, —COR$_{11}$, —OCOR$_{11}$, —OCONR$_{11}$R$_{12}$, or a polyethylene glycol unit (—OCH$_2$CH$_2$)$_n$, wherein n is an integer from 1 to 2000, or a substituent selected from a halogen, guanidinium [—NH(C=NH)NH$_2$], —OR$_7$, —NR$_8$R$_9$, —NO$_2$, —NRCOR', —SR$_{10}$, —SOR', —SO$_2$R', —SO$_3$, —OSO$_3$, —SO$_2$NRR', a cyano, an azido, —COR$_{11}$, —OCOR$_{11}$ or —OCONR$_{11}$R$_{12}$, optionally, any one of R$_1$, R$_2$, R$_3$, R$_4$, R$_1$', R$_2$', R$_3$', or R$_4$' is a linking group that enables linkage to a cell binding agent via a covalent bond or is selected from a polypyrrolo, poly-indolyl, poly-imidazolyl, polypyrrollo-imidazolyl, poly-pyrrollo-indolyl or polyimidazolo-indolyl unit optionally bearing the linking group, Z is CR$_{15}$R$_{16}$, wherein R$_{15}$ and R$_{16}$ are each independently selected from —H, a linear, branched or cyclic alkyl having from 1 to 10 carbon atoms, a polyethylene glycol unit (—OCH$_2$CH$_2$)$_n$, wherein n is an integer from 1 to 2000;

R$_6$ is —OR, —SR or —NRR', optionally R$_6$ is the linking group;

A and A' are the same or different and are selected from O, CRR'O, S, CRR'S, NR$_{15}$ or CRR'NHR$_{15}$, and wherein R$_{15}$ has the same definition as R;

D and D' are the same or different and are independently selected from a linear, branched or cyclic alkyl, alkenyl or alkynyl having 1 to 10 carbon atoms, optionally substituted with any one of halogen, —OR$_7$, —NR$_8$R$_9$, —NO$_2$, —NRCOR', —SR$_{10}$, —SOR', —SO$_2$R', —SO$_3$, —OSO$_3$, —SO$_2$NRR', a cyano, an azido, —COR$_{11}$, —OCOR$_{11}$ or —OCONR$_{11}$R$_{12}$, or a polyethylene glycol unit (—OCH$_2$CH$_2$)$_n$, wherein n is an integer from 1 to 2000;

L is absent, or is a phenyl group or a 3- to 18-membered heterocyclic ring having 1 to 6 heteroatoms selected from O, S, N and P, wherein said phenyl group or heterocyclic ring represented by L is optionally substituted, wherein the substituent is a linking group that enables linkage to a cell binding agent via a covalent bond, or is selected from linear, branched or cyclic alkyl, alkenyl or alkynyl having from 1 to 10 carbon atoms, optionally substituted with any one of halogen, —OR$_s$, —NR$_8$R$_9$, —NO$_2$, —NRCOR', —SR$_{10}$, —SOR', —SO$_2$R', —SO$_3$, —OSO$_3$, —SO$_2$NRR', a cyano, an azido, —COR$_{11}$, —OCOR$_{11}$ or —OCONR$_{11}$R$_{12}$, a polyethylene glycol unit (—OCH$_2$CH$_2$)$_n$, wherein n is an integer from 1 to 2000; optionally, L itself is the linking group; provided that the compound has no more than one linking group; and LG is a leaving group.

17. A process for the preparation of compound of formula (IV), or a pharmaceutically acceptable salt, optical isomer, racemate, diastereomer, or enantiomer thereof, the process comprising:
a) converting compound of formula (15) into aldehyde of formula (16); and
b) converting compound of formula (16) into compound of formula (N),

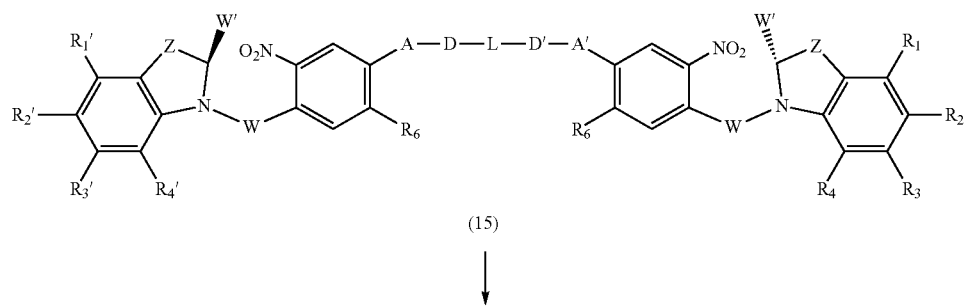

(15)

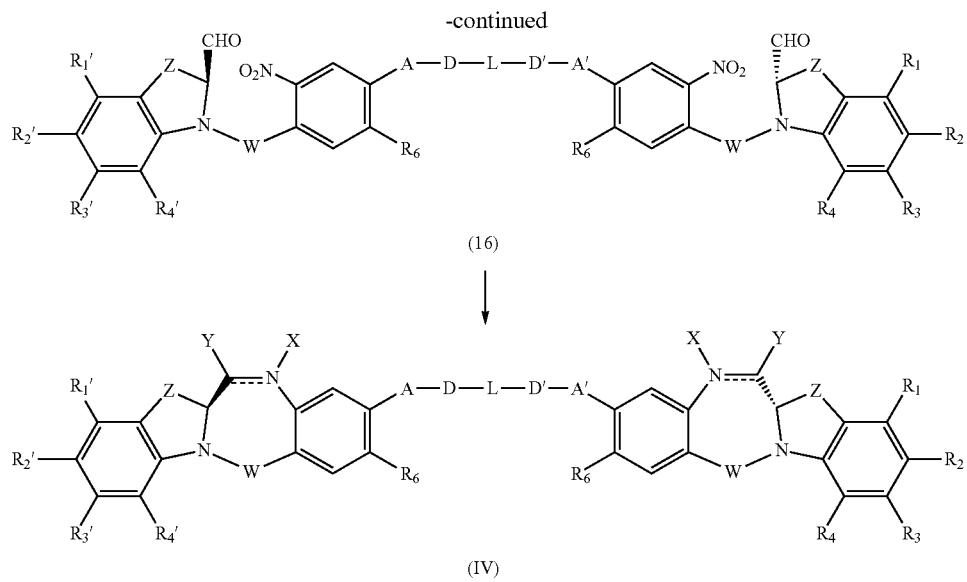

(IV)

wherein:
the double line ═ between N and C represents a single bond or a double bond, provided that when it is a double bond X is absent and Y is —H, and when it is a single bond, X is —H; and Y is selected from —OR, —OCOR', —OCOOR', —OCONR'R", —NR'R", —NRCOR', —NRCOP, wherein P is an amino acid or a polypeptide containing between 2 to 20 amino acid units, —SR', —SOR', —SO$_2$R', —SO$_3$, —OSO$_3$, a halogen, a cyano, or an azido, wherein R, R' and R" are the same or different and are selected from —H, an optionally substituted linear, branched or cyclic alkyl, alkenyl or alkynyl having from 1 to 10 carbon atoms, a polyethylene glycol unit (—OCH$_2$CH$_2$)$_n$, wherein n is an integer from 1 to 2000, a 5- or 6-membered heteroaryl ring containing one or more heteroatoms independently selected from nitrogen, oxygen, and sulfur, a 5- to 18-membered fused ring system, wherein at least one of the rings is aromatic, containing one or more heteroatoms independently selected from nitrogen, oxygen, and sulfur, an aryl having from 6 to 18 carbon atoms, a 3- to 18-membered heterocyclic ring having 1 to 6 heteroatoms selected from O, S, N and P, wherein the optional substituent is selected from halogen, —OR$_7$, —NR$_8$R$_9$, —NO$_2$, —NRCOR', —SR$_{10}$, —SOR', —SO$_2$R', —SO$_3$, —OSO$_3$, —SO$_2$NRR', a cyano, an azido, —COR$_{11}$, —OCOR$_{11}$ or —OCONR$_{11}$R$_{12}$, wherein the definitions of R$_7$, R$_8$, R$_9$, R$_{10}$, R$_{11}$ and R$_{12}$ are each independently selected from —H, a linear, branched or cyclic alkyl, alkenyl or alkynyl having from 1 to 10 carbon atoms, a polyethylene glycol unit (—OCH$_2$CH$_2$)$_n$, wherein n is an integer from 1 to 2000, a 5- or 6-membered heteroaryl ring containing one or more heteroatoms independently selected from nitrogen, oxygen, and sulfur, a 5- to 18-membered fused ring system, wherein at least one of the rings is aromatic, containing one or more heteroatoms independently selected from nitrogen, oxygen, and sulfur, an aryl having from 6 to 18 carbon atoms, a 3- to 10-membered heterocyclic ring having 1 to 6 heteroatoms selected from O, S, N and P, and R$_{10}$ is optionally —SR$_{13}$ or —COR$_{13}$, wherein R$_{13}$ is selected from a linear, branched or cyclic alkyl, alkenyl or alkynyl having from 1 to 10 carbon atoms, a 5- or 6-membered heteroaryl ring containing one or more heteroatoms independently selected from nitrogen, oxygen, and sulfur, a 5- to 18-membered fused ring system, wherein at least one of the rings is aromatic, containing one or more heteroatoms independently selected from nitrogen, oxygen, and sulfur, an aryl having from 6 to 18 carbon atoms, a 3- to 18-membered heterocyclic ring having 1 to 6 heteroatoms selected from O, S, N and P, optionally R$_{11}$ is —OR$_{14}$, wherein R$_{14}$ has the same definition as R, optionally R" is —OH;

W is C═O;

R$_1$, R$_2$, R$_3$, R$_4$, R$_1$', R$_2$', R$_3$' and R$_4$' are each independently selected from —H, an optionally substituted linear, branched or cyclic alkyl, alkenyl or alkynyl having from 1 to 10 carbon atoms, a polyethylene glycol unit (—OCH$_2$CH$_2$)$_n$, wherein n is an integer from 1 to 2000, wherein the optional substituent is selected from halogen, —OR$_7$, —NR$_8$R$_9$, —NO$_2$, —NRCOR', —SR$_{10}$, —SOR', —SO$_2$R', —SO$_3$, —OSO$_3$, —SO$_2$NRR', a cyano, an azido, —COR$_{11}$, —OCOR$_{11}$, —OCONR$_{11}$R$_{12}$, or a polyethylene glycol unit (—OCH$_2$CH$_2$)$_n$, wherein n is an integer from 1 to 2000, or a substituent selected from a halogen, guanidinium [—NH(C═NH)NH$_2$], —OR$_7$, —NR$_8$R$_9$, —NO$_2$, —NRCOR', —SR$_{10}$, —SOR', —SO$_2$R', —SO$_3$, —OSO$_3$, —SO$_2$NRR', a cyano, an azido, —COR$_{11}$, —OCOR$_{11}$ or —OCONR$_{11}$R$_{12}$, optionally, any one of R$_1$, R$_2$, R$_3$, R$_4$, R$_1$', R$_2$', R$_3$', or R$_4$' is a linking group that enables linkage to a cell binding agent via a covalent bond or is selected from a polypyrrolo, poly-indolyl, poly-imidazolyl, polypyrrollo-imidazolyl, poly-pyrollo-indolyl or polyimidazolo-indolyl unit optionally bearing the linking group, Z is CR$_{15}$R$_{16}$, wherein R$_{15}$ and R$_{16}$ are each independently selected from —H, a linear, branched or cyclic alkyl having from 1 to 10 carbon atoms, a polyethylene glycol unit (—OCH$_2$CH$_2$)$_n$, wherein n is an integer from 1 to 2000;

$R_6$ is —OR, —SR or —NRR', optionally $R_6$ is the linking group;

A and A' are the same or different and are selected from O, CRR'O, S, CRR'S, $NR_{15}$ or CRR'$NHR_{15}$, and wherein $R_{15}$ has the same definition as R;

D and D' are the same or different and independently selected from a linear, branched or cyclic alkyl, alkenyl or alkynyl having 1 to 10 carbon atoms, optionally substituted with any one of halogen, —$OR_7$, —$NR_8R_9$, —$NO_2$, —NRCOR', —$SR_{10}$, —SOR', —$SO_2R'$, —$SO_3$, —$OSO_3$, —$SO_2NRR'$, a cyano, an azido, —$COR_{11}$, —$OCOR_{11}$ or —$OCONR_{11}R_{12}$, or a polyethylene glycol unit (—$OCH_2CH_2$)$_n$, wherein n is an integer from 1 to 2000;

L is absent, or is a phenyl group or a 3- to 18-membered heterocyclic ring having 1 to 6 heteroatoms selected from O, S, N and P, wherein said phenyl group or heterocyclic ring represented by L is optionally substituted, wherein the substituent is the linking group, or is selected from linear, branched or cyclic alkyl, alkenyl or alkynyl having from 1 to 10 carbon atoms, optionally substituted with any one of halogen, —$OR_7$, —$NR_8R_9$, —$NO_2$, —NRCOR', —$SR_{10}$, —SOR', —$SO_2R'$, —$SO_3$, —$OSO_3$, —$SO_2NRR'$, a cyano, an azido, —$COR_{11}$, —$OCOR_{11}$ or —$OCONR_{11}R_{12}$, a polyethylene glycol unit (—$OCH_2CH_2$)$_n$, wherein n is an integer from 1 to 2000; optionally, L itself is the linking group;

provided that the compound has no more than one linking group;

W' is COOR or $CH_2OW''$, and W'' is a protecting group.

18. A process for the preparation of compound of formula (V), or a pharmaceutically acceptable salt, optical isomer, racemate, diastereomer, or enantiomer thereof, the process comprising coupling compound of formula (13), compound of formula (13)' and compound of formula (12) to give compound of formula (V),

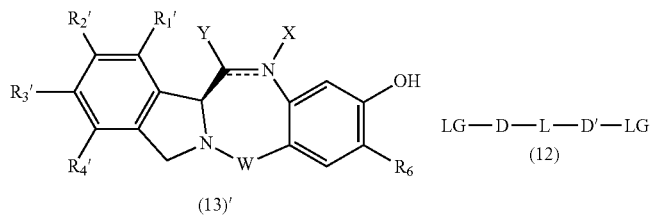
(13)'

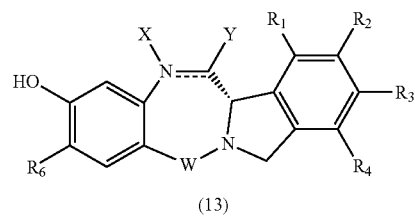
(13)

LG—D—L—D'—LG
(12)

↓

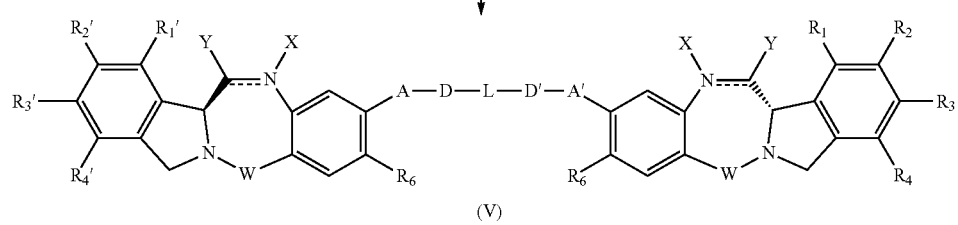

(V)

wherein:
the double line = between N and C represents a single bond or a double bond, provided that when it is a double bond X is absent and Y is —H, and when it is a single bond, X is —H; and Y is selected from —OR, —OCOR', —OCOOR', —OCONR'R'', —NR'R'', —NRCOR', —NRCOP, wherein P is an amino acid or a polypeptide containing between 2 to 20 amino acid units, —SR', —SOR', —$SO_2R'$, —$SO_3$, —$OSO_3$, a halogen, a cyano, or an azido, wherein R, R' and R'' are the same or different and are selected from —H, an optionally substituted linear, branched or cyclic alkyl, alkenyl or alkynyl having from 1 to 10 carbon atoms, a polyethylene glycol unit (—$OCH_2CH_2$)$_n$, wherein n is an integer from 1 to 2000, a 5- or 6-membered heteroaryl ring containing one or more heteroatoms independently selected from nitrogen, oxygen, and sulfur, a 5- to 18-membered fused ring system, wherein at least one of the rings is aromatic, containing one or more heteroatoms independently selected from nitrogen, oxygen, and sulfur, an aryl having from 6 to 18 carbon atoms, a 3- to 18-membered heterocyclic ring having 1 to 6 heteroatoms selected from O, S, N and P, wherein the optional substituent is selected from halogen, —$OR_7$, —$NR_8R_9$, —$NO_2$, —NRCOR', —$SR_{10}$, —SOR', —$SO_2R'$, —$SO_3$, —$OSO_3$, —$SO_2NRR'$, a cyano, an azido, —$COR_{11}$, —$OCOR_{11}$ or —$OCONR_{11}R_{12}$, wherein the definitions of $R_7$, $R_8$, $R_9$, $R_{10}$, $R_{11}$ and $R_{12}$, are each independently selected from —H, a linear, branched or cyclic alkyl, alkenyl or alkynyl having from 1 to 10 carbon atoms, a polyethylene glycol unit (—$OCH_2CH_2$)$_n$, wherein n is an integer from 1 to 2000, a 5- or 6-membered heteroaryl ring containing one or more heteroatoms independently selected from nitrogen, oxygen, and sulfur, a 5- to 18-membered fused ring system, wherein at least one of the rings is aromatic, containing one or more heteroatoms independently selected from nitrogen, oxygen, and sulfur, an aryl having from 6 to 18 carbon atoms, a 3- to 10-membered heterocyclic ring having 1 to 6 heteroatoms selected from O, S, N and P, and $R_{10}$ is optionally —$SR_{13}$ or —$COR_{13}$, wherein $R_{13}$ is selected from a linear, branched or cyclic alkyl, alkenyl or alkynyl having from 1 to 10 carbon atoms, a 5- or 6-membered heteroaryl ring containing one or more heteroatoms independently selected from nitrogen, oxygen, and sulfur, a 5- to 18-membered fused ring system, wherein at least one of the rings is aromatic, containing one or more heteroatoms independently selected from nitrogen, oxygen, and sulfur, an aryl having from 6 to 18 carbon atoms, a 3- to 18-membered heterocyclic ring having 1 to 6 heteroatoms selected from O, S, N and P, optionally $R_{11}$ is $OR_{14}$, wherein $R_{14}$ has the same definition as R, optionally R" is —OH;

W is C=O;

$R_1$, $R_2$, $R_3$, $R_4$, $R_1'$, $R_2'$, $R_3'$ and $R_4'$ are each independently selected from —H, an optionally substituted linear, branched or cyclic alkyl, alkenyl or alkynyl having from 1 to 10 carbon atoms, a polyethylene glycol unit $(—OCH_2CH_2)_n$, wherein n is an integer from 1 to 2000, wherein the optional substituent is selected from halogen, —$OR_7$, —$NR_8R_9$, —$NO_2$, —NRCOR', —$SR_{10}$, —SOR', —$SO_2R'$, —$SO_3$, —$OSO_3$, —$SO_2NRR'$, a cyano, an azido, —$COR_{11}$, —$OCOR_{11}$, —$OCONR_{11}R_{12}$, or a polyethylene glycol unit $(—OCH_2CH_2)_n$, wherein n is an integer from 1 to 2000, or a substituent selected from a halogen, guanidinium [—NH(C=NH)$NH_2$], —$OR_7$, —$NR_8R_9$, —$NO_2$, —NRCOR', —$SR_{10}$, —SOR', —$SO_2R'$, —$SO_3$, —$OSO_3$, —$SO_2NRR'$, a cyano, an azido, —$COR_{11}$, —$OCOR_{11}$ or —$OCONR_{11}R_{12}$, optionally, any one of $R_1$, $R_2$, $R_3$, $R_4$, $R_1'$, $R_2'$, $R_3'$, or $R_4'$ is a linking group that enables linkage to a cell binding agent via a covalent bond or is selected from a polypyrrolo, poly-indolyl, poly-imidazolyl, polypyrollo-imidazolyl, poly-pyrollo-indolyl or polyimidazolo-indolyl unit optionally bearing the linking group, Z is $CR_{15}R_{16}$, wherein $R_{15}$ and $R_{16}$ are each independently selected from —H, a linear, branched or cyclic alkyl having from 1 to 10 carbon atoms, a polyethylene glycol unit $(—OCH_2CH_2)_n$, wherein n is an integer from 1 to 2000;

$R_6$ is —OR, —SR or —NRR', optionally $R_6$ is the linking group;

A and A' are the same or different and are selected from O, CRR'O, S, CRR'S, $NR_{15}$ or CRR'$NHR_{15}$, wherein $R_{15}$ has the same definition as R;

D and D' are the same or different and independently selected from a linear, branched or cyclic alkyl, alkenyl or alkynyl having 1 to 10 carbon atoms, optionally substituted with any one of halogen, —$OR_7$, —$NR_8R_9$, —$NO_2$, —NRCOR', —$SR_{10}$, —SOR', —$SO_2R'$, —$SO_3$, —$OSO_3$, —$SO_2NRR'$, a cyano, an azido, —$COR_{11}$, —$OCOR_{11}$ or —$OCONR_{11}R_{12}$, or a polyethylene glycol unit $(—OCH_2CH_2)_n$, wherein n is an integer from 1 to 2000;

L is absent, or is a phenyl group or a 3- to 18-membered heterocyclic ring having 1 to 6 heteroatoms selected from O, S, N and P, wherein said phenyl group or heterocyclic ring represented by L is optionally substituted, wherein the substituent is the linking group, or is selected from linear, branched or cyclic alkyl, alkenyl or alkynyl having from 1 to 10 carbon atoms, optionally substituted with any one of halogen, —$OR_7$, —$NR_8R_9$, —$NO_2$, —NRCOR', —$SR_{10}$, —SOR', —$SO_2R'$, —$SO_3$, —$OSO_3$, —$SO_2NRR'$, a cyano, an azido, —$COR_{11}$, —$OCOR_{11}$ or —$OCONR_{11}R_{12}$, a polyethylene glycol unit $(—OCH_2CH_2)_n$, wherein n is an integer from 1 to 2000; optionally, L itself is the linking group;

provided that the compound has no more than one linking group; and

LG is a leaving group.

19. A process for the preparation of compound of formula (V), or a pharmaceutically acceptable salt, optical isomer, racemate, diastereomer, or enantiomer thereof, the process comprising:

a) converting compound of formula (17) into aldehyde of formula (18); and b) converting compound of formula (18) into compound of formula (V),

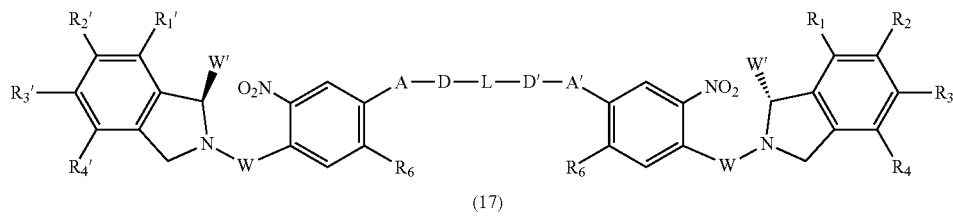

(17)

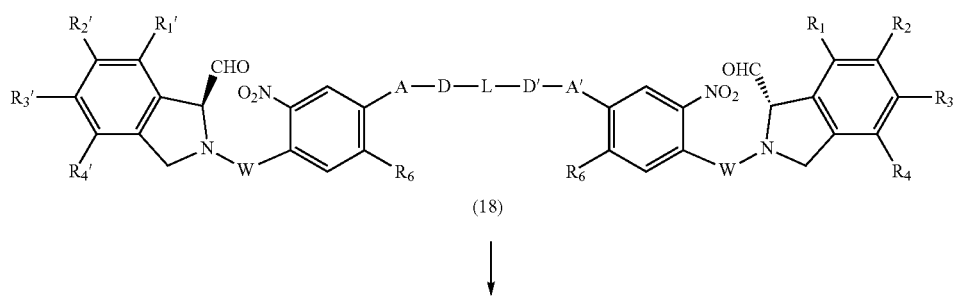

(18)

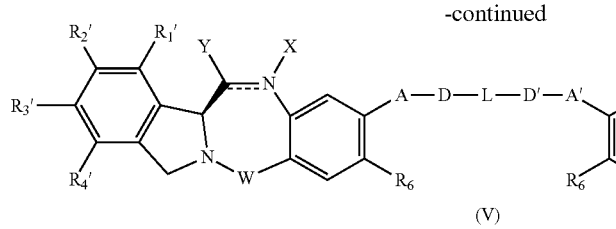
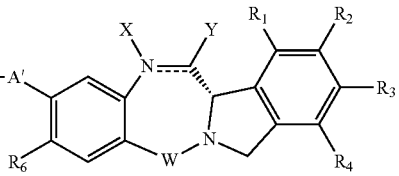

(V)

wherein:
the double line == between N and C represents a single bond or a double bond, provided that when it is a double bond X is absent and Y is —H, and when it is a single bond, X is —H; and Y is selected from —OR, —OCOR', —OCOOR', —OCONR'R", —NR'R", —NRCOR', —NRCOP, wherein P is an amino acid or a polypeptide containing between 2 to 20 amino acid units, —SR', a sulfoxide represented by —SOR', —SO$_2$R', —SO$_3$, —OSO$_3$, a halogen, a cyano, an or azido, wherein R, R' and R" are the same or different and are selected from —H, an optionally substituted linear, branched or cyclic alkyl, alkenyl or alkynyl having from 1 to 10 carbon atoms, a polyethylene glycol unit (—OCH$_2$CH$_2$)$_n$, wherein n is an integer from 1 to 2000, a 5- or 6-membered heteroaryl ring containing one or more heteroatoms independently selected from nitrogen, oxygen, and sulfur, a 5- to 18-membered fused ring system, wherein at least one of the rings is aromatic, containing one or more heteroatoms independently selected from nitrogen, oxygen, and sulfur, an aryl having from 6 to 18 carbon atoms, a 3- to 18-membered heterocyclic ring having 1 to 6 heteroatoms selected from O, S, N and P, wherein the optional substituent is selected from halogen, —OR$_7$, —NR$_8$R$_9$, —NO$_2$, —NRCOR', —SR$_{10}$, —SOR', —SO$_2$R', —SO$_3$, —OSO$_3$, —SO$_2$NRR', a cyano, an azido, —COR$_{11}$, —OCOR$_{11}$ or —OCONR$_{11}$R$_{12}$, wherein the definitions of R$_7$, R$_8$, R$_9$, R$_{10}$, R$_{11}$ and R$_{12}$ are each independently selected from —H, a linear, branched or cyclic alkyl, alkenyl or alkynyl having from 1 to 10 carbon atoms, a polyethylene glycol unit (—OCH$_2$CH$_2$)$_n$, wherein n is an integer from 1 to 2000, a 5- or 6-membered heteroaryl ring containing one or more heteroatoms independently selected from nitrogen, oxygen, and sulfur, a 5- to 18-membered fused ring system, wherein at least one of the rings is aromatic, containing one or more heteroatoms independently selected from nitrogen, oxygen, and sulfur, an aryl having from 6 to 18 carbon atoms, a 3- to 10-membered heterocyclic ring having 1 to 6 heteroatoms selected from O, S, N and P, and R$_{10}$ is optionally —SR$_{13}$ or —COR$_{13}$, wherein R$_{13}$ is selected from a linear, branched or cyclic alkyl, alkenyl or alkynyl having from 1 to 10 carbon atoms, a 5- or 6-membered heteroaryl ring containing one or more heteroatoms independently selected from nitrogen, oxygen, and sulfur, a 5- to 18-membered fused ring system, wherein at least one of the rings is aromatic, containing one or more heteroatoms independently selected from nitrogen, oxygen, and sulfur, an aryl having from 6 to 18 carbon atoms, a 3- to 18-membered heterocyclic ring having 1 to 6 heteroatoms selected from O, S, N and P, optionally R$_{11}$ is —OR$_{14}$, wherein R$_{14}$ has the same definition as R, optionally R" is —OH;

W is C=O;

R$_1$, R$_2$, R$_3$, R$_4$, R$_1$', R$_2$', R$_3$' and R$_4$' are each independently selected from —H, an optionally substituted linear, branched or cyclic alkyl, alkenyl or alkynyl having from 1 to 10 carbon atoms, a polyethylene glycol unit (—OCH$_2$CH$_2$)$_n$, wherein n is an integer from 1 to 2000, wherein the optional substituent is selected from halogen, —OR$_7$, —NR$_8$R$_9$, —NO$_2$, —NRCOR', —SR$_{10}$, —SOR', —SO$_2$R', —SO$_3$, —OSO$_3$, —SO$_2$NRR', a cyano, an azido, —COR$_{11}$, —OCOR$_{11}$, —OCONR$_{11}$R$_{12}$, or a polyethylene glycol unit (—OCH$_2$CH$_2$)$_n$, wherein n is an integer from 1 to 2000, or a substituent selected from a halogen, guanidinium [—NH(C=NH)NH$_2$], —OR$_7$, —NR$_8$R$_9$, —NO$_2$, —NRCOR', —SR$_{10}$, —SOR', —SO$_2$R', —SO$_3$, —OSO$_3$, —SO$_2$NRR', a cyano, an azido, —COR$_{11}$, —OCOR$_{11}$ or —OCONR$_{11}$R$_{12}$, optionally, any one of R$_1$, R$_2$, R$_3$, R$_4$, R$_1$', R$_2$', R$_3$', or R$_4$' is a linking group that enables linkage to a cell binding agent via a covalent bond or is selected from a polypyrrolo, poly-indolyl, poly-imidazolyl, polypyrollo-imidazolyl, poly-pyrollo-indolyl or polyimidazolo-indolyl unit optionally bearing the linking group, Z is CR$_{15}$R$_{16}$, wherein R$_{15}$ and R$_{16}$ are each independently selected from —H, a linear, branched or cyclic alkyl having from 1 to 10 carbon atoms, a polyethylene glycol unit (—OCH$_2$CH$_2$)$_n$, wherein n is an integer from 1 to 2000;

R$_6$ is —OR, —SR or —NRR', optionally R$_6$ is the linking group;

A and A' are the same or different and are selected from O, CRR'O, S, CRR'S, NR$_{15}$ or CRR'NHR$_{15}$, wherein R$_{15}$ has the same definition as R;

D and D' are the same or different and are independently selected from a linear, branched or cyclic alkyl, alkenyl or alkynyl having 1 to 10 carbon atoms, optionally substituted with any one of halogen, —OR$_7$, —NR$_8$R$_9$, —NO$_2$, —NRCOR', —SR$_{10}$, —SOR', —SO$_2$R', —SO$_3$, —OSO$_3$, —SO$_2$NRR', a cyano, an azido, —COR$_{11}$, —OCOR$_{11}$ or —OCONR$_{11}$R$_{12}$, or a polyethylene glycol unit (—OCH$_2$CH$_2$)$_n$, wherein n is an integer from 1 to 2000;

L is absent, or is a phenyl group or a 3- to 18-membered heterocyclic ring having 1 to 6 heteroatoms selected from O, S, N and P, wherein said phenyl group or heterocyclic ring represented by L is optionally substituted, wherein the substituent is linking group, or is selected from linear, branched or cyclic alkyl, alkenyl or alkynyl having from 1 to 10 carbon atoms, optionally substituted with any one of halogen, —OR$_7$, —NR$_8$R$_9$, —NO$_2$, —NRCOR', —SR$_{10}$, —SOR', —$SO_2R'$, —$SO_3$, —$OSO_3$, —$SO_2NRR'$, a cyano, an azido, —$COR_{11}$, —$OCOR_{11}$ or —$OCONR_{11}R_{12}$, a polyethylene glycol unit (—$OCH_2CH_2)_n$, wherein n is an integer from 1 to 2000; optionally, L itself is the linking group;

provided that the compound has no more than one linking group;

W' is COOR or $CH_2OW''$; and

W" is a protecting group.

20. The method of claim 13, further comprising administering to said mammal a second compound, which is a chemotherapeutic agent.

21. The method of claim 13, wherein the colon cancer is a multi-drug resistant (MDR) colon cancer.

22. The method of claim 13, wherein the Burkitt's lymphoma is a multi-drug resistant (MDR) Burkitt's lymphoma.

23. The method of claim 20, wherein said chemotherapeutic agent is administered to said mammal sequentially or consecutively.

* * * * *

UNITED STATES PATENT AND TRADEMARK OFFICE
CERTIFICATE OF CORRECTION

PATENT NO. : 8,426,402 B2
APPLICATION NO. : 12/700131
DATED : April 23, 2013
INVENTOR(S) : Wei Li et al.

Page 1 of 1

It is certified that error appears in the above-identified patent and that said Letters Patent is hereby corrected as shown below:

In the Claims:

Claim 10, Column 269/270, please replace the first chemical structure

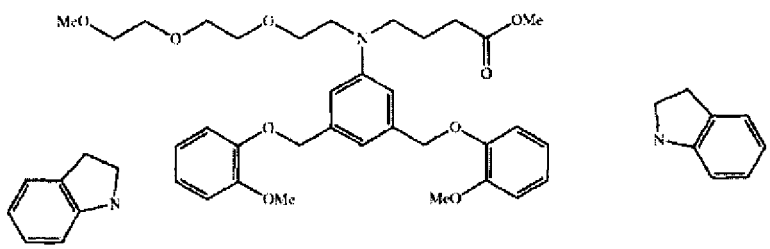

with the structure

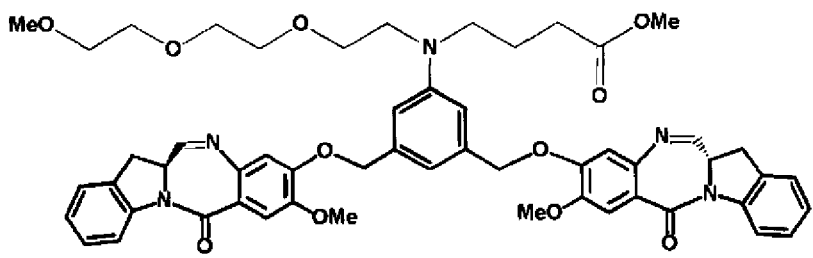

Signed and Sealed this
Nineteenth Day of August, 2014

Michelle K. Lee
*Deputy Director of the United States Patent and Trademark Office*